(12) United States Patent
Durley

(10) Patent No.: US 7,795,271 B2
(45) Date of Patent: Sep. 14, 2010

(54) SUBSTITUTED PYRIMIDINONES

(75) Inventor: Richard C. Durley, Chesterfield, MO (US)

(73) Assignee: Pharmacia Corporation, Chesterfield, MO (US)

( * ) Notice: Subject to any disclaimer, the term of this patent is extended or adjusted under 35 U.S.C. 154(b) by 0 days.

(21) Appl. No.: 12/434,906

(22) Filed: May 4, 2009

(65) Prior Publication Data

US 2009/0306108 A1 Dec. 10, 2009

Related U.S. Application Data

(63) Continuation of application No. 11/457,493, filed on Jul. 14, 2006, now abandoned, which is a continuation-in-part of application No. 10/808,146, filed on Mar. 24, 2004, now Pat. No. 7,183,287.

(60) Provisional application No. 60/460,124, filed on Apr. 3, 2003.

(51) Int. Cl.
| | | |
|---|---|---|
| A61K 31/513 | (2006.01) |
| A61K 31/506 | (2006.01) |
| A61K 31/5375 | (2006.01) |
| A61K 31/541 | (2006.01) |
| C07D 239/46 | (2006.01) |
| C07D 239/52 | (2006.01) |
| C07D 403/06 | (2006.01) |
| C07D 417/06 | (2006.01) |
| C07D 413/06 | (2006.01) |
| A61P 29/00 | (2006.01) |

(52) U.S. Cl. ............... 514/269; 514/275; 514/227.8; 514/231.5; 544/319; 544/320; 544/321; 544/60; 544/123

(58) Field of Classification Search ............ 514/269, 514/272; 544/319, 320, 321
See application file for complete search history.

(56) References Cited

U.S. PATENT DOCUMENTS 7,183,287 B2 * 2/2007 Durley ............... 514/269

FOREIGN PATENT DOCUMENTS

| JP | 61205261 | 9/1986 |
| WO | WO 2004014868 | 2/1984 |
| WO | WO 9511235 | 4/1995 |
| WO | WO 9824780 | 6/1998 |
| WO | WO 9964400 | 12/1999 |
| WO | WO 0129010 | 4/2001 |

OTHER PUBLICATIONS

Trends in Cell Biology; 7; 353-361; 1997.
Mol. Cell Biology; 19; 21-30; 1999.
Embo J.; 20; 466-479; 2001.
Paul, et al.; Cell Signal; 9; 403-410 (1997).
Lee, et al., Nature; 372; 376; 1994.
J. Biol. Chem., 274, 6272; 1999.
JPET; 293; 281; 2000.
Boehm, et al; Ex. Opin. Ther. Patents; 10; 25; 2000.
Rev. Infect. Disease; 6; 51; 1984.
Lymphokien Cytokien Res.; 11; 253-256; 1992.
Clin. Exp. Immunol.; 989; 244-250; 1992.
Perretti, M., et al., Br. J. Pharmacol; 110; 868-874; 1993.
J.M. Stuart; Collagen Autoimmune Arthritis; Annual Rev. Immunol; 2; 199; 1984.
Database WPI; Section Ch, Week 198643; Derwent Publications Ltd., London, GB; AN 1986-281625 XP002294127.
Database Chemabs 'Online!' Chemical Abstracts Service, Columbus, OH, US; XP002294080, retrieved from STN Database accession No. 1966:104220 abstract; and XP002294078.

* cited by examiner

*Primary Examiner*—Venkataraman Balasubramanian
(74) *Attorney, Agent, or Firm*—Jennifer A. Kispert; J. Michael Dixon

(57) ABSTRACT

Disclosed are compounds Formula I

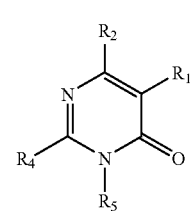

and pharmaceutically acceptable salts thereof, wherein $R_1$, $R_2$, $R_4$, and $R_5$ are defined herein. These compounds are useful for treating diseases and conditions caused or exacerbated by unregulated p38 MAP Kinase and/or TNF activity. Pharmaceutical compositions containing the compounds, methods of preparing the compounds and methods of treatment using the compounds are also disclosed.

12 Claims, No Drawings

SUBSTITUTED PYRIMIDINONES

This application is a continuation of U.S. patent application Ser. No. 11/457,493, filed on Jul. 14, 2006; U.S. patent application Ser. No. 11/457,493 now abandoned, which is a continuation-in-part of U.S. patent application Ser. No. 10/808,146 (now U.S. Pat. No. 7,183,287), filed Mar. 24, 2004, which claims the benefit of U.S. Provisional Application 60/460,124 filed Apr. 3, 2003.

BACKGROUND

1. Field

This invention relates to substituted pyrimidinones that are useful for treating diseases and conditions caused or exacerbated by unregulated p38 MAP kinase activity. It also relates to Pharmaceutical compositions containing the pyrimidinone compounds, methods of preparing the pyrimidinone compounds and methods of treatment using these compounds.

2. Description Of The Related Art

Numerous cell surface receptors use one or more of the mitogen-activated protein kinase (MAP kinase) cascades during signal transduction. MAP kinases are a family of protein-directed serine/threonine kinases that are activated by dual phosphorylation. One subgroup of the MAP kinases is p38 MAP kinase, which is activated by a variety of signals including proinflammatory cytokines such as tumor necrosis factor (TNF) and interleukin-1 (IL-1), as well as bacterial lipopolysaccharides and environmental stress such as osmotic shock and ultraviolet radiation (Ono, K. and J. Han, Cell Signal. 12: 1, 2000). Within the p38 kinase family, there are four distinct isozymes: p38 alpha, p38 beta, p38 gamma, and p38 delta. The p38 kinase family function downstream of an activating stimulus by phosphorylating and activating transcription factors (e.g. ATF2, CHOP and MEP2C) as well as other kinases (e.g. MAPKAP-2 and MAPKAP-3) (Trends in Cell biology 7, 353-361, 1997; Mol Cell Biology 19, 21-30, 1999; EMBO J 20, 466-479, 2001) Upon activation, the p38 kinase cascade leads to the induction of gene expression of several factors involved in inflammation and immunity including TNF, interleukin-6, granulocyte-macrophage colony stimulating factor (GM-CSF), and HIV long terminal repeat (Paul et al., Cell Signal. 9: 403-410, 1997). The products of the p38 phosphorylation stimulate the production of inflammatory cytokines and other proteins, including TNF and IL-1, and cyclooxygenase-2, and also possibly modulate the effects of these cytokines on their target cells, and thus stimulate inflammation processes (Lee, J. C. et al, Nature, 372: 376, 1994).

P38 MAP kinases have also been shown to promote apoptosis during ischemia in cardiac myocytes, which suggests that p38 MAP kinase inhibitors can be used to treat ischemic heart disease (J. Biol. Chem. 274, 6272, 1999). They are also required for T-cell HIV-1 replication and may be useful targets for AIDS therapy. P38 pathway inhibitors have been used to increase cancer cell sensitivity to cancer therapy also find use in the treatment of asthma (JPET 293, 281, 2000).

TNF is a cytokine and a potent proinflammatory mediator implicated in inflammatory conditions such as arthritis, asthma, septic shock, non-insulin dependent diabetes mellitus, multiple sclerosis, asthma, and inflammatory bowel disease. Thus inhibitors of p38 MAP kinases (required for TNF production) may be useful for the treatment of inflammatory conditions resulting from excessive cytokine production such as arthritis. (Boehm, J. C. and J. L. Adams, Exp. Opin. Ther. Patents 10: 25, 2000, and references cited therein). TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpesvirus-6 (HHV-6), human herpesvirus-7 (HHV-7), human herpesvirus-8 (HHV-8), pseudorabies and rhinotracheitis, among others.

Excessive or unregulated TNF production has also been shown to produce elevated levels of IL-1. Inhibition of TNF, therefore, should reduce levels of IL-1 (European Cytokine Netw 6, 225, 1995) and ameliorate disease states caused by unregulated IL-1 synthesis. Such disease states include rheumatoid arthritis, rheumatoid spondylitis, osteoarthritis, gouty arthritis, sepsis, septic shock, endotoxic shock, gram negative sepsis, toxic shock syndrome, adult respiratory distress syndrome, cerebral malaria, chronic pulmonary inflammatory disease, silicosis, pulmonary sarcosis, bone resorption diseases, reperfusion injury, graft versus host reaction, alallograft rejections, fever and myalgias due to infection, cachexia secondary to infection or malignancy, cachexia secondary to acquired immune deficiency syndrome (AIDS), AIDS related complex (ARC), keloid formation, scar tissue formation, Crohn's disease, ulcerative colitis, and pyresis.

IL-1 has also been shown to mediate a variety of biological activities such as the activation of T-helper cells, induction of fever, stimulation of prostaglandin or collagenase production, neutrophil chemotaxis, and the suppression of plasma iron levels (Rev. Infect. Disease, 6, 51 (1984)). Elevated levels of IL-1 have also been implicated in mediating or exacerbating a number of disease states including rheumatoid arthritis, osteoarthritis, rheumatoid spondylitis, gouty arthritis, inflammatory bowel disease, adult respiratory distress syndrome (ARDS), psoriasis, Crohn's disease, ulcerative colitis, anaphylaxis, muscle degeneration, cachexia, Reiter's syndrome, type I and type II diabetes, bone resorption diseases, ischemia reperfusion injury, arteriosclerosis, brain trauma, multiple sclerosis, sepsis, septic shock, and toxic shock syndrome. Viruses sensitive to TNF inhibition, such as HIV-1, HIV-2, HIV-3, are also affected by IL-1 production. In rheumatoid arthritis, both IL-1 and TNF induce collagenase synthesis and ultimately lead to tissue destruction within arthritic joints (Lymphokine Cytokine Res. (11): 253-256, (1992) and Clin. Exp. Immunol. 989:244-250, (1992)).

IL-6 is another pro-inflammatory cytokine, which is associated with many conditions including inflammation. Consequently, TNF, IL-1 and IL-6 affect a wide variety of cells and tissues and are important inflammatory mediators of a wide variety of disease states and conditions. The inhibition of these cytokines by inhibition or modulation of p38 kinase is of benefit in controlling, reducing and alleviating many of these disease states and conditions. Therefore, the invention concerns finding small molecule inhibitors or modulators of p38 kinase and the p38 kinase pathway.

SUMMARY

In a broad aspect, the invention provides compounds of Formula I (Embodiment I):

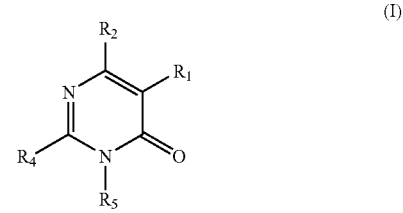

(I)

and pharmaceutically acceptable salts thereof, wherein $R_1$ is H, halogen, $NO_2$, alkyl, carboxaldehyde, hydroxyalkyl, dihydroxyalkyl, arylalkoxy, arylalkyl, alkenyl, alkynyl, arylalkynyl, —CN, aryl, alkanoyl, alkoxy, alkoxyalkyl, haloalkyl, haloalkoxy, carboxyl, or arylalkanoyl, wherein the aryl portion of arylalkoxy, arylalkyl, and arylalkanoyl is unsubstituted or substituted with 1, 2, 3, 4, or 5 groups that are independently halogen, $C_1$-$C_4$ alkyl, $C_1$-$C_4$ alkoxy, nitro, CN, haloalkyl, haloalkoxy or $CO_2R$;

wherein the alkyl portion of the alkyl, hydroxyalkyl, dihydroxyalkyl, arylalkoxy, arylalkyl, alkanoyl, alkoxy, alkoxyalkyl and arylalkanoyl groups is unsubstituted or substituted with 1, 2, or 3 groups that are independently halogen, $C_1$-$C_4$ alkoxy, $C_1$-$C_4$ alkoxycarbonyl, or $C_3$-$C_7$ cycloalkyl;

$R_2$ is H, OH, halogen, —$OSO_2$—($C_1$-$C_6$)alkyl, —$OSO_2$-aryl, arylalkoxy, aryloxy, arylthio, arylthioalkoxy, arylalkynyl, alkoxy, aryloxy($C_1$-$C_6$)alkyl, alkyl, alkynyl, —OC(O)NH($CH_2$)$_n$aryl, —OC(O)N(alkyl)($CH_2$)$_n$aryl, alkoxyalkyl, dialkylamino, alkyl, alkoxy, aryl, arylalkyl, heteroaryl, heteroarylalkyl, arylalkenyl, heterocycloalkyl, heterocycloalkylalkyl, alkoxyalkyl, $NR_8R_9$, dialkylamino, or $CO_2R$, wherein n is 0, 1, 2, 3, 4, 5 or 6;

each of which groups is unsubstituted or substituted with 1, 2, 3, 4, or 5 groups that are independently halogen, —($C_1$-$C_6$)alkyl-N(R)—$CO_2R_{30}$, haloalkyl, heteroaryl, heteroarylalkyl, —$NR_6R_7$, $R_6R_7N$—($C_1$-$C_6$ alkyl)-, —C(O)$NR_6R_7$, —($C_1$-$C_4$)alkyl-C(O)$NR_6R_7$, —($C_1$-$C_4$ alkyl)-NRC(O)$NR_{16}R_{17}$, haloalkoxy, alkyl, CN, hydroxyalkyl, dihydroxyalkyl, alkoxy, alkoxycarbonyl, phenyl, —$SO_2$-phenyl wherein the phenyl and —$SO_2$-phenyl groups are optionally substituted with 1, 2, or 3 groups that are independently halogen or $NO_2$, or —OC(O)$NR_6R_7$, wherein $R_{16}$ and $R_{17}$ are independently H or $C_1$-$C_6$ alkyl; or $R_{16}$, $R_{17}$ and the nitrogen to which they are attached form a morpholinyl ring;

$R_6$ and $R_7$ are independently at each occurrence H, alkyl, hydroxyalkyl, dihydroxyalkyl, alkoxy, alkanoyl, arylalkyl, arylalkoxy, alkoxycarbonyl, —$SO_2$-alkyl, OH, alkoxy, alkoxyalkyl, arylalkoxycarbonyl, —($C_1$-$C_4$)alkyl-$CO_2$-alkyl, heteroarylalkyl, or arylalkanoyl, wherein each is unsubstituted or substituted with 1, 2, or 3 groups that are independently, halogen, OH, SH, heterocycloalkyl, heterocycloalkylalkyl, $C_3$-$C_7$ cycloalkyl, alkoxy, $NH_2$, NH(alkyl), N(alkyl)(alkyl), —O-alkanoyl, alkyl, haloalkyl, carboxaldehyde, or haloalkoxy; or $R_6$, $R_7$, and the nitrogen to which they are attached form a morpholinyl, pyrrolidinyl, thiomorpholinyl, thiomorpholinyl S-oxide, thiomorpholinyl S,S-dioxide, piperidinyl, pyrrolidinyl, or piperazinyl ring which is optionally substituted with 1 or 2 groups that are independently $C_1$-$C_4$ alkyl, alkoxycarbonyl, $C_1$-$C_4$ alkoxy, hydroxyl, hydroxyalkyl, dihydroxyalkyl, or halogen;

R at each occurrence is independently hydrogen or $C_1$-$C_6$ alkyl optionally substituted with 1 or 2 groups that are independently OH, SH, halogen, amino, monoalkylamino, dialkylamino or $C_3$-$C_6$ cycloalkyl;

$R_{30}$ is $C_1$-$C_6$ alkyl optionally substituted with 1 or 2 groups that are independently OH, SH, halogen, amino, monoalkylamino, dialkylamino or $C_3$-$C_6$ cycloalkyl;

each $R_8$ is independently hydrogen, alkyl, alkanoyl, arylalkyl and arylalkanoyl, wherein each of the above is optionally substituted with 1, 2, 3, 4, or 5 groups that are independently alkyl, alkoxy, alkoxycarbonyl, halogen, or haloalkyl;

each $R_9$ is hydrogen, alkyl, alkanoyl, arylalkyl, cycloalkyl, cycloalkylalkyl, alkenyl, heteroaryl, aminoalkyl, monoalkylaminoalkyl, dialkylaminoalkyl, arylalkanoyl, —$SO_2$-phenyl, and aryl wherein each of the above is optionally substituted with 1, 2, 3, 4, or 5 groups that are independently alkyl, alkoxy, alkoxycarbonyl, halogen, or haloalkyl;

$R_4$ is hydrogen or $R_4$ is alkyl unsubstituted or substituted with one or two groups that are independently $CO_2R$, —$CO_2$—($C_1$-$C_6$)alkyl, —C(O)$NR_6R_7$, —C(O)$R_6$, —N($R_{30}$)C(O)$NR_{16}R_{17}$, —N($R_{30}$)C(O)—($C_1$-$C_6$)alkoxy, or —$NR_6R_7$, arylalkoxy, arylalkyl, heteroaryl, heteroarylalkyl, hydroxyalkyl, dihydroxyalkyl, haloalkyl, $R_6R_7N$—($C_1$-$C_6$ alkyl)-, —$NR_6R_7$, alkoxy, hydroxyalkoxy-, ($R_6R_7N$)-alkoxy-, $R_6R_7NC(O)$-alkoxy-, $R_6C(O)N(R_7)$alkoxy-, carboxaldehyde, —C(O)$NR_6R_7$, $CO_2R$, alkoxyalkyl, or alkoxyalkoxy, wherein the heteroaryl or aryl portions of is the above are unsubstituted or substituted with 1, 2, 3, 4, or 5 groups that are independently halogen, hydroxy, alkoxy, alkyl, —$CO_2$—($C_1$-$C_6$)alkyl, —$CONR_6R_7$, —$NR_6R_7$, $R_6R_7N$—($C_1$-$C_6$)alkyl-, nitro, haloalkyl, or haloalkoxy; and $R_5$ is H, aryl, arylalkyl, arylthioalkyl, alkyl optionally substituted with 1, 2, or 3 groups that are independently arylalkoxycarbonyl, —$NR_8R_9$, halogen, —C(O)$NR_8R_9$, alkoxycarbonyl, $C_3$-$C_7$ cycloalkyl, or alkanoyl, alkoxy, alkoxyalkyl optionally substituted with one trimethylsilyl group, amino, alkoxycarbonyl, hydroxyalkyl, dihydroxyalkyl, alkynyl, —$SO_2$-alkyl, alkoxy optionally substituted with one trimethylsilyl group, heterocycloalkylalkyl, cycloalkyl, cycloalkylalkyl, -alkyl-S-aryl, -alkyl-$SO_2$-aryl, heteroarylalkyl, heterocycloalkyl, heteroaryl, or alkenyl optionally substituted with alkoxycarbonyl, wherein each of the above is unsubstituted or substituted with 1, 2, 3, 4, or 5 groups that are independently alkyl, halogen, alkoxy, hydroxyalkyl, dihydroxyalkyl, arylalkoxy, thioalkoxy, alkoxycarbonyl, arylalkoxycarbonyl, $CO_2R$, CN, OH, hydroxyalkyl, dihydroxyalkyl, amidinooxime, —$NR_6R_7$, —$NR_8R_9$, $R_6R_7N$—($C_1$-$C_6$ alkyl)-, carboxaldehyde, $SO_2$alkyl, —$SO_2H$, —$SO_2NR_6R_7$, alkanoyl wherein the alkyl portion is optionally substituted with OH, halogen or alkoxy, —C(O)$NR_6R_7$, —($C_1$-$C_4$ alkyl)-C(O)$NR_6R_7$, amidino, haloalkyl, —($C_1$-$C_4$ alkyl)-$NR_{15}C(O)NR_{16}R_{17}$, —($C_1$-$C_4$ alkyl)-$NR_{15}C(O)R_{18}$, —O—$CH_2$—O—, —O—$CH_2CH_2$—O—, or haloalkoxy; wherein $R_{15}$ is H or $C_1$-$C_6$ alkyl; and $R_{18}$ is $C_1$-$C_6$ alkyl optionally substituted with —O—($C_2$-$C_6$ alkanoyl, $C_1$-$C_6$ hydroxyalkyl, $C_1$-$C_6$ dihydroxyalkyl, $C_1$-$C_6$ alkoxy, $C_1$-$C_6$ alkoxy $C_1$-$C_6$ alkyl; amino $C_1$-$C_6$ alkyl, mono or dialkylamino $C_1$-$C_6$ alkyl.

The invention also includes intermediates that are useful in making the compounds of the invention.

The compounds and salts of the invention bind and/or interact with p38 kinase and/or TNF. Preferably, they inhibit the activity of p38 kinase and/or TNF. They are therefore used in treating p38 map kinase or TNF mediated disorders. Preferably they are used in treating p38 alpha or TNF mediated disorders.

The invention also includes pharmaceutical compositions comprising at least one compound or salt of formula I and at least one pharmaceutically acceptable carrier, solvent, adjuvant or excipient.

The invention also includes methods of treating a TNF mediated disorder, a p38 kinase mediated disorder, inflammation and/or arthritis in a subject, the method comprising treating a subject having or susceptible to such disorder or condition with a therapeutically-effective amount of a compound or salt of Formula I.

DETAILED DESCRIPTION

In a preferred aspect, the invention provides compounds of formula I wherein:
no more than two of $R_1$, $R_2$, $R_4$, and $R_5$ are simultaneously hydrogen;
$R_6$ and $R_7$ are not simultaneously OH;
when $R_2$ is OH, $R_4$ is methyl and $R_5$ is phenyl, $R_1$ is not acetyl; and
$R_4$ and $R_5$ are not simultaneously hydrogen.

In other aspects and embodiments, the invention provides:
Embodiment 2. Compounds of the formula:

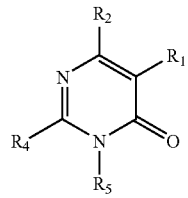

and the pharmaceutically acceptable salts thereof, wherein
$R_1$ is H, halogen, alkyl, carboxaldehyde, hydroxyalkyl, dihydroxyalkyl, arylalkoxy, arylalkyl, alkenyl, alkynyl, arylalkynyl, CN, alkanoyl, alkoxy, alkoxyalkyl, haloalkyl, carboxyl, or arylalkanoyl,
wherein the aryl portion of arylalkoxy, arylalkyl, and arylalkanoyl is unsubstituted or substituted with 1, 2, 3, 4, or 5 groups that are independently halogen, $C_1$-$C_4$ alkyl, $C_1$-$C_4$ alkoxy, nitro, CN, haloalkyl, haloalkoxy or $CO_2R$;
wherein the alkyl portion of the alkyl, hydroxyalkyl, dihydroxyalkyl, arylalkoxy, arylalkyl, alkanoyl, alkoxy, alkoxyalkyl and arylalkanoyl groups is unsubstituted or substituted with 1, 2, or 3 groups that are independently halogen, $C_1$-$C_4$ alkoxy, $C_1$-$C_4$ alkoxycarbonyl, or cyclopropyl;
$R_2$ is H, OH, halogen, —$OSO_2$—($C_1$-$C_6$)alkyl, —$OSO_2$-aryl, arylalkoxy, aryloxy, arylthioalkoxy, arylalkynyl, alkoxy, phenyloxy($C_1$-$C_6$)alkyl, —OC(O)NH($CH_2$)$_n$aryl, —OC(O)N(alkyl)($CH_2$)$_n$aryl, alkyl, alkynyl, alkoxyalkyl, dialkylamino, heteroaryl, heterocycloalkyl, aryloxyalkyl, or $CO_2R$, wherein
each of the above is unsubstituted or substituted with 1, 2, 3, 4, or 5 groups that are independently halogen, —$NR_6R_7$, haloalkyl, haloalkoxy, alkyl, heteroaryl, heteroarylalkyl, —($C_1$-$C_4$)alkyl-C(O)$NR_6R_7$, $R_6R_7$N—($C_1$-$C_6$ alkyl)-, —C(O)$NR_6R_7$, —($C_1$-$C_4$ alkyl)-NRC(O)$NR_{16}R_{17}$, CN, hydroxyalkyl, dihydroxyalkyl, —OC(O)$NR_6R_7$, or —($C_1$-$C_6$)alkyl-N(R)—$CO_2R_{30}$, wherein $R_{16}$ and $R_{17}$ are independently H or $C_1$-$C_6$ alkyl; or
$R_{16}$, $R_{17}$ and the nitrogen to which they are attached form a morpholinyl ring;

$R_6$ and $R_7$ are independently at each occurrence H, alkyl, hydroxyalkyl, dihydroxyalkyl, alkoxy, alkoxyalkyl, alkanoyl, arylalkyl, arylalkoxy, arylalkoxycarbonyl, or arylalkanoyl, wherein each of the above is unsubstituted or substituted with 1, 2, or 3 groups that are independently, halogen, alkoxy, alkyl, OH, SH, carboxaldehyde, haloalkyl, or haloalkoxy; or
$R_6$, $R_7$, and the nitrogen to which they are attached form a morpholinyl, thiomorpholinyl, thiomorpholinyl S-oxide, thiomorpholinyl S,S-dioxide, piperidinyl, pyrrolidinyl, or piperazinyl ring which is optionally substituted with 1 or 2 groups that are independently $C_1$-$C_4$ alkyl, alkoxycarbonyl, hydroxyl, hydroxyalkyl, dihydroxyalkyl, or halogen;

n is 0, 1, 2, 3, 4, 5 or 6;
R at each occurrence is independently H or $C_1$-$C_6$ alkyl optionally substituted with 1 or 2 groups that are independently OH, SH, halogen, amino, monoalkylamino, dialkylamino or $C_3$-$C_6$ cycloalkyl;
$R_{30}$ is $C_1$-$C_6$ alkyl optionally substituted with 1 or 2 groups that are independently OH, SH, halogen, amino, monoalkylamino, dialkylamino or $C_3$-$C_6$ cycloalkyl;
$R_4$ is H, alkyl optionally substituted with one or two groups that are independently $CO_2R$, —$CO_2$alkyl, —C(O)$NR_6R_7$, —C(O)$R_6$, —N($R_{30}$)C(O)$NR_{16}R_{17}$, —N($R_{30}$)C(O)—($C_1$-$C_6$)alkoxy, or —$NR_6R_7$, arylalkoxy, heteroaryl, arylalkyl, hydroxyalkyl, dihydroxyalkyl, haloalkyl, —$NR_6R_7$, —C(O)$NR_6R_7$, alkoxy, hydroxyalkoxy-, ($R_6R_7$N)-alkoxy-, $R_6R_7$NC(O)-alkoxy-, $R_6$C(O)N($R_7$)alkoxy-, alkoxyalkyl, or alkoxyalkoxy, wherein
the heteroaryl or aryl portions of the above are unsubstituted or substituted with 1, 2, 3, 4, or 5 groups that are independently halogen, hydroxy, alkoxy, alkyl, —$CO_2$—($C_1$-$C_6$)alkyl, —$CONR_6R_7$, —$NR_6R_7$, $R_6R_7$N—($C_1$-$C_6$)alkyl-, nitro, haloalkyl, or haloalkoxy; and
$R_5$ is H, arylalkyl, alkyl optionally substituted with 1, 2, or 3 groups that are independently arylalkoxycarbonyl, —$NR_8R_9$, halogen, —C(O)$NR_8R_9$, alkoxycarbonyl, or alkanoyl, alkoxyalkyl optionally substituted with one trimethylsilyl group, alkoxycarbonyl, amino, hydroxyalkyl, dihydroxyalkyl, alkenyl optionally substituted with alkoxycarbonyl, alkynyl, —$SO_2$-alkyl, aryl, alkoxy optionally substituted with one trimethylsilyl group, heterocycloalkylalkyl, heteroarylalkyl, heterocycloalkyl, or heteroaryl, wherein
each of the above is unsubstituted or substituted with 1, 2, 3, 4, or 5 groups that are independently alkyl, halogen, alkoxy, arylalkoxy, hydroxyalkyl, dihydroxyalkyl, thioalkoxy, —$SO_2$alkyl, alkoxycarbonyl, arylalkoxycarbonyl, $CO_2R$, CN, OH, amidinooxime, $NR_8R_9$, $R_6R_7$N—($C_1$-$C_6$ alkyl)-, —C(O)$NR_6R_7$, amidino, hydroxyalkyl, dihydroxyalkyl, carboxaldehyde, —$NR_6R_7$, haloalkyl, —($C_1$-$C_4$ alkyl)-C(O)$NR_6R_7$, —($C_1$-$C_4$ alkyl)-$CO_2R$, —($C_1$-$C_4$ alkyl)-$C_1$-$C_6$ alkoxycarbonyl, —($C_1$-$C_4$ alkyl)-CN, —($C_1$-$C_4$ alkyl)-$NR_{15}C(O)R_{18}$, —O—$CH_2$—O—, —O—$CH_2CH_2$—O—, phenyl or haloalkoxy;
$R_8$ is hydrogen, alkyl, alkanoyl, arylalkyl and arylalkanoyl;
$R_9$ is alkyl, alkanoyl, arylalkyl, heteroaryl, aminoalkyl, monoalkylaminoalkyl, dialkylaminoalkyl, and arylalkanoyl.

Embodiment 3. Compounds according to embodiment 2 wherein
$R_1$ is H, halogen, alkyl optionally substituted with $C_1$-$C_4$ alkoxycarbonyl, carboxaldehyde, hydroxyalkyl, dihydroxyalkyl, phenyl($C_1$-$C_6$)alkoxy, phenyl($C_1$-$C_6$)alkyl, CN, alkanoyl, alkoxy, $C_2$-$C_4$ alkynyl, $C_2$-$C_6$ alkenyl optionally substituted with $C_1$-$C_4$ alkoxycarbonyl, alkoxyalkyl, haloalkyl, or phenyl($C_1$-$C_6$)alkanoyl,
  wherein the phenyl groups are unsubstituted or substituted with 1, 2, 3, 4, or 5 groups that are independently halogen, $C_1$-$C_4$ alkyl, $C_1$-$C_4$ alkoxy, nitro, CN, $CF_3$, $OCF_3$ or $CO_2R$;
wherein the alkyl groups are unsubstituted or substituted with 1, 2, or 3 groups that are independently halogen, methoxy, or ethoxy;
$R_2$ is OH, phenyl($C_1$-$C_6$)alkoxy, phenyloxy, phenyloxy($C_1$-$C_6$)alkyl, phenyl($C_1$-$C_4$)thioalkoxy, $C_1$-$C_8$ alkoxy, alkoxyalkoxy, —O—$SO_2$phenyl, alkynyl, phenyl($C_2$-$C_4$)alkynyl, alkyl, —OC(O)NH($CH_2$)$_n$phenyl, —OC(O)N(alkyl)($CH_2$)$_n$phenyl, dialkylamino, pyridyl, pyrimidyl, pyridazyl, pyrazolyl, imidazolyl, pyrrolyl, tetrahydroquinolinyl, tetrahydroisoquinolinyl, tetrazolyl, pyrazinyl, benzimidazolyl, triazinyl, tetrahydrofuryl, piperidinyl, hexahydropyrimidinyl, thiazolyl, thienyl, or $CO_2R$, wherein
  n is 0, 1, 2, 3, 4, 5 or 6;
  each of the above is unsubstituted or substituted with 1, 2, 3, 4, or 5 groups that are independently halogen, $NR_6R_7$, haloalkyl, haloalkoxy, hydroxyalkyl, dihydroxyalkyl, alkyl, phenyl, pyridyl, piperidinyl, piperazinyl, —($C_1$-$C_6$)alkyl-N(R)—$CO_2R_{30}$, $R_6R_7N$—($C_1$-$C_6$ alkyl)-, —C(O)$NR_6R_7$, —($C_1$-$C_4$)alkyl-C(O)$NR_6R_7$, —($C_1$-$C_4$ alkyl)-NRC(O)$NR_{16}R_{17}$, or —OC(O)$NR_6R_7$, wherein
    $R_6$ and $R_7$ are independently at each occurrence H, alkyl, ($C_1$-$C_4$)hydroxyalkyl, ($C_1$-$C_4$) dihydroxyalkyl, ($C_1$-$C_4$) alkoxy, ($C_1$-$C_4$)alkoxy ($C_1$-$C_4$)alkyl, ($C_1$-$C_4$)alkanoyl, phenyl($C_1$-$C_4$) alkyl, phenyl($C_1$-$C_4$)alkoxy, phenyl($C_1$-$C_4$) alkoxycarbonyl, or phenyl($C_1$-$C_4$)alkanoyl, wherein each of the above is unsubstituted or substituted with 1, 2, or 3 groups that are independently, halogen, OH, SH, $C_3$-$C_6$ cycloalkyl, ($C_1$-$C_4$) alkoxy, ($C_1$-$C_4$)alkyl, $CF_3$, carboxaldehyde, $NH_2$, NH($C_1$-$C_6$)alkyl, N($C_1$-$C_6$)alkyl($C_1$-$C_6$)alkyl, $OCF_3$; or
    $R_6$, $R_7$, and the nitrogen to which they are attached form a morpholinyl, thiomorpholinyl; piperidinyl, pyrrolidinyl, or piperazinyl ring which is optionally substituted with 1 or 2 groups that are independently $C_1$-$C_4$ alkyl, hydroxy, hydroxy $C_1$-$C_4$ alkyl, $C_1$-$C_4$ dihydroxyalkyl, $C_1$-$C_4$ alkoxycarbonyl, or halogen; and
$R_4$ is H, alkyl optionally substituted with one or two groups that are independently $CO_2R$, —$CO_2$alkyl, —C(O)$NR_6R_7$, —C(O)$R_6$, —N($R_{30}$)C(O)$NR_{16}R_{17}$, —N($R_{30}$)C(O)—($C_1$-$C_6$)alkoxy, or —$NR_6R_7$, arylalkoxy, heteroaryl, arylalkyl, hydroxyalkyl, dihydroxyalkyl, haloalkyl, —$NR_6R_7$, —C(O)$NR_6R_7$, alkoxy, hydroxyalkoxy-, ($R_6R_7$N)-alkoxy-, $R_6R_7$NC(O)-alkoxy-, $R_6$C(O)N($R_7$)alkoxy-, alkoxyalkyl, or alkoxyalkoxy, wherein
  the heteroaryl or aryl portions of the above are unsubstituted or substituted with 1, 2, 3, 4, or 5 groups that are independently halogen, hydroxy, alkoxy, alkyl, —$CO_2$—($C_1$-$C_6$)alkyl, —CON$R_6R_7$, —$NR_6R_7$, $R_6R_7$N—($C_1$-$C_6$)alkyl-, nitro, haloalkyl, or haloalkoxy; and
$R_5$ is phenyl($C_1$-$C_6$)alkyl, ($C_1$-$C_6$)alkyl optionally substituted with 1, 2, 3, 4, or 5 groups that are independently phenyl $C_1$-$C_4$ alkoxycarbonyl, —$NR_8R_9$, halogen, —C(O)$NR_8R_9$, alkoxycarbonyl, or alkanoyl, phenyl, alkoxy, $C_2$-$C_6$ alkynyl, $C_2$-$C_6$ alkenyl optionally substituted with alkoxycarbonyl, indolyl, quinolinyl, isoquinolinyl, isoindolyl, dihydroindolyl, pyrazolyl, imidazolyl, dihydroisoindolyl, indolon-2-yl, indazolyl, benzimidazolyl, pyridyl, imidazolidine dione, pyrazolyl($C_1$-$C_6$ alkyl), imidazolyl($C_1$-$C_6$ alkyl), piperidinyl($C_1$-$C_6$)alkyl, pyrrolidinyl($C_1$-$C_6$)alkyl, imidazolidinyl($C_1$-$C_6$)alkyl, tetrahydroisoquinolinyl($C_1$-$C_6$)alkyl, 1H-indazolyl($C_1$-$C_6$)alkyl, dihydroindolon-2-yl($C_1$-$C_6$ alkyl), indolinyl($C_1$-$C_6$ alkyl), dihydrobenzimidazolyl($C_1$-$C_6$ alkyl), or dihydrobenzoimidazolonyl($C_1$-$C_6$ alkyl), pyridyl($C_1$-$C_6$) alkyl, pyridazinyl($C_1$-$C_6$)alkyl, pyrimidinyl($C_1$-$C_6$) alkyl, pyrazinyl($C_1$-$C_6$)alkyl, tetrahydrofuryl($C_1$-$C_6$)alkyl, naphthyl($C_1$-$C_6$)alkyl, morpholinyl($C_1$-$C_6$)alkyl, tetrahydrofuryl($C_1$-$C_6$)alkyl, thienyl($C_1$-$C_6$)alkyl, piperazinyl ($C_1$-$C_6$)alkyl, indolyl($C_1$-$C_6$)alkyl, quinolinyl($C_1$-$C_6$) alkyl, isoquinolinyl($C_1$-$C_6$)alkyl, isoindolyl($C_1$-$C_6$)alkyl, dihydroindolyl($C_1$-$C_6$)alkyl, pyrazolyl($C_1$-$C_4$)alkyl, imidazolyl($C_1$-$C_4$)alkyl, dihydroisoindolyl($C_1$-$C_6$)alkyl, indoon-2-yl($C_1$-$C_6$)alkyl, indolon-2-yl($C_1$-$C_6$)alkyl, or morpholinyl $C_1$-$C_6$ alkyl, wherein
  each of the above is unsubstituted or substituted with 1, 2, 3, 4, or 5 groups that are independently $C_1$-$C_6$ alkyl, halogen, $C_1$-$C_6$ alkoxy, phenyl $C_1$-$C_6$ alkoxy, $C_1$-$C_6$ thioalkoxy, $C_1$-$C_6$ alkoxycarbonyl, $CO_2R$, CN, —$SO_2$($C_1$-$C_6$)alkyl, amidinooxime, $NR_8R_9$, —$NR_6R_7$, $NR_6R_7$ $C_1$-$C_6$ alkyl, —C(O)$NR_6R_7$, —($C_1$-$C_4$)alkyl-C(O)$NR_6R_7$, amidino, $C_1$-$C_4$ haloalkyl, hydroxy $C_1$-$C_6$ alkyl, $C_1$-$C_6$ dihydroxyalkyl, or $C_1$-$C_4$ haloalkoxy; wherein
    $R_8$ is hydrogen, $C_1$-$C_6$ alkyl, $C_1$-$C_6$ alkanoyl, phenyl $C_1$-$C_6$ alkyl and phenyl $C_1$-$C_6$ alkanoyl; and
    $R_9$ is aminoalkyl, mono $C_1$-$C_6$ alkylamino $C_1$-$C_6$ alkyl, di $C_1$-$C_6$ alkylamino $C_1$-$C_6$ alkyl, $C_1$-$C_6$ alkyl, $C_1$-$C_6$ alkanoyl, phenyl $C_1$-$C_6$ alkyl, indazolyl, and phenyl $C_1$-$C_6$ alkanoyl.

Embodiment 4. Compounds according to embodiment 3, wherein
$R_1$ is H, halogen, $C_1$-$C_4$ alkyl optionally substituted with $C_1$-$C_4$ alkoxycarbonyl, $C_2$-$C_4$ alkenyl optionally substituted with $C_1$-$C_4$ alkoxycarbonyl, $C_2$-$C_4$ alkynyl, or carboxaldehyde;
$R_2$ is benzyloxy, OH, phenyloxy, phenyloxy($C_1$-$C_6$)alkyl, phenyl ($C_1$-$C_4$)thioalkoxy, or pyridyl; wherein each of the above is optionally substituted with 1, 2, 3, 4, or 5 groups that are independently halogen, —($C_1$-$C_6$)alkyl-N(R)—$CO_2R_{30}$, $NR_6R_7$, —($C_1$-$C_4$)alkyl-C(O)$NR_6R_7$, ($C_1$-$C_4$)haloalkyl, —C(O)$NR_6R_7$, —($C_1$-$C_4$ alkyl)-NRC(O)$NR_{16}R_{17}$, ($C_1$-$C_4$)haloalkoxy, hydroxyalkyl, $C_1$-$C_6$ dihydroxyalkyl, ($C_1$-$C_6$)alkyl, pyridyl, or $R_6R_7N$—($C_1$-$C_6$ alkyl)-.

Embodiment 4a. Compounds according to embodiment 4, wherein $R_1$ is H.
Embodiment 4b. Compounds according to embodiment 4, wherein $R_1$ is halogen.
Embodiment 4c. Compounds according to embodiment 4, wherein $R_1$ is $C_1$-$C_4$ alkyl optionally substituted with $C_1$-$C_4$ alkoxycarbonyl.
Embodiment 5. Compounds according to embodiment 4, wherein
$R_5$ is indolyl, pyridyl, pyridazinyl, pyrimidinyl, indazolyl, tetrahydroquinolyl, tetrahydroisoquinolyl, pyrazolyl, imidazolyl, furanyl, quinolinyl, isoquinolinyl, isoindolyl, dihydroindolyl, dihydroisoindolyl, indolon-2-yl, or pyrazinyl, each of which is unsubstituted or substituted with 1, 2, 3, 4 or 5 groups that are independently $C_1$-$C_4$ alkyl, halogen, $CF_3$, $OCF_3$, —$CO_2CH_3$, $C_1$-$C_4$ hydroxyalkyl, dihydroxyalkyl, $C_1$-$C_4$ alkoxy, —$CO_2$($C_1$-$C_5$ alkyl), benzyloxy, —$NR_6R_7$, —($C_1$-$C_4$)alkyl-C(O)$NR_6R_7$, —$NR_8R_9$, $NR_6R_7$—($C_1$-$C_4$ alkyl), —C(O)$NR_6R_7$, or amidinooxime; wherein $R_6$ and $R_7$ are independently at each occurrence H, $C_1$-$C_4$ alkyl, $C_1$-$C_4$ hydroxyalkyl, $C_1$-$C_4$ dihydroxyalkyl, $C_1$-$C_4$ alkoxy, $C_1$-$C_4$ alkoxy $C_1$-$C_4$ alkyl, $C_1$-$C_4$ alkanoyl, phenyl $C_1$-$C_4$ alkyl, phenyl $C_1$-$C_4$ alkoxy, or phenyl $C_1$-$C_4$ alkanoyl, wherein each is unsubstituted or substituted with 1, 2, or 3 groups that are independently, halogen, OH, SH, $C_3$-$C_6$ cycloalkyl, aryl, $C_1$-$C_4$ alkoxy, $C_1$-$C_4$ alkyl, OH, $CF_3$, or $OCF_3$; or $R_6$, $R_7$, and the nitrogen to which they are attached form a morpholinyl, thiomorpholinyl, pyrrolidinyl, or piperazinyl ring which is optionally substituted with 1 or 2 groups that are independently $C_1$-$C_4$ alkyl, hydroxy, hydroxy $C_1$-$C_4$ alkyl, $C_1$-$C_4$ dihydroxyalkyl, or halogen.

Embodiment 6. Compounds according to embodiment 5, wherein $R_5$ is indolyl, pyridyl, pyrimidinyl, pyrazolyl, furanyl, indazolyl, dihydroindolyl, dihydroisoindolyl, indolon-2-yl, or pyrazinyl, each of which is unsubstituted or substituted with 1, 2, 3, or 4 groups that are independently $C_1$-$C_4$ alkyl, halogen, $CF_3$, $OCF_3$, —$CO_2CH_3$, $C_1$-$C_4$ hydroxyalkyl, $C_1$-$C_4$ dihydroxyalkyl, $C_1$-$C_4$ alkoxy, —$CO_2$($C_1$-$C_5$ alkyl), benzyloxy, —C(O)$NR_6R_7$, —$NR_8R_9$, —($C_1$-$C_4$)alkyl-C(O)$NR_6R_7$, —$NR_6R_7$, $NR_6R_7$—($C_1$-$C_4$ alkyl)-, and amidinooxime.

Embodiment 7. Compounds according to embodiment 6, wherein $R_5$ is indolyl, pyridyl, pyrimidinyl, dihydroindolyl, dihydroisoindolyl, pyrazolyl, or pyrazinyl, each of which is unsubstituted or substituted with 1, 2, 3, or 4 groups that are independently $C_1$-$C_4$ alkyl, halogen, $CF_3$, $OCF_3$, —$CO_2CH_3$, $C_1$-$C_4$ hydroxyalkyl, $C_1$-$C_4$ dihydroxyalkyl, $C_1$-$C_4$ alkoxy, —$CO_2$($C_1$-$C_5$ alkyl), benzyloxy, —C(O)$NR_6R_7$, $NR_8R_9$, —($C_1$-$C_4$)alkyl-C(O)$NR_6R_7$, —$NR_6R_7$, $NR_6R_7$—($C_1$-$C_4$ alkyl)-, or amidinooxime; wherein $R_6$ and $R_7$ are independently at each occurrence H, $C_1$-$C_4$ alkyl, $C_1$-$C_4$ hydroxyalkyl, $C_1$-$C_4$ dihydroxyalkyl, $C_1$-$C_4$ alkoxy, $C_1$-$C_4$ alkanoyl, $C_1$-$C_4$ alkoxy $C_1$-$C_4$ alkyl, each of which is optionally substituted with 1, 2, or 3 groups that are independently halogen, OH, SH, $C_3$-$C_6$ cycloalkyl, $C_1$-$C_4$ alkoxy, $C_1$-$C_4$ alkyl, OH, $CF_3$, or $OCF_3$.

Embodiment 8. Compounds according to embodiment 7, wherein $R_5$ is indolyl, pyridyl, pyrimidinyl, dihydroindolyl, dihydroisoindolyl, pyrazolyl, or pyrazinyl, each of which is unsubstituted or substituted with 1, 2, or 3 groups that are independently $C_1$-$C_4$ alkyl, halogen, $CF_3$, $OCF_3$, $C_1$-$C_4$ hydroxyalkyl, $C_1$-$C_4$ dihydroxyalkyl, $C_1$-$C_4$ alkoxy, —C(O)$NR_6R_7$, —($C_1$-$C_4$)alkyl-C(O)$NR_6R_7$, $NR_8R_9$, —$NR_6R_7$, or $NR_6R_7$—($C_1$-$C_4$ alkyl)-; wherein $R_6$ and $R_7$ are independently at each occurrence H, $C_1$-$C_4$ alkyl, $C_1$-$C_4$ hydroxyalkyl, $C_1$-$C_4$ dihydroxyalkyl, $C_1$-$C_4$ alkanoyl, or $C_1$-$C_4$ alkoxy, each of which is optionally substituted with 1, 2, or 3 groups that are independently halogen, OH, SH, $C_3$-$C_6$ cycloalkyl, $C_1$-$C_4$ alkoxy, $C_1$-$C_4$ alkyl, OH, $CF_3$, or $OCF_3$.

Embodiment 9. Compounds according to embodiment 4, wherein $R_5$ is phenyl, phenyl($C_1$-$C_6$)alkyl, or ($C_1$-$C_6$)alkyl, wherein each of the above is unsubstituted or substituted with 1, 2, 3, 4, or 5 groups that are independently alkyl, halogen, alkoxy, benzyloxy, hydroxyalkyl, dihydroxyalkyl, thioalkoxy, —$CO_2$($C_1$-$C_5$ alkyl), $CO_2R$, CN, amidinooxime, —$NR_8R_9$, —$NR_6R_7$, $R_6R_7N$—($C_1$-$C_6$ alkyl)-, —C(O)$NR_6R_7$, —($C_1$-$C_4$)alkyl-C(O)$NR_6R_7$, amidino, $CF_3$, or $OCF_3$;

$R_8$ is hydrogen, $C_1$-$C_6$ alkyl, $C_1$-$C_6$ alkanoyl, phenyl $C_1$-$C_6$ alkyl and phenyl $C_1$-$C_6$ alkanoyl; and $R_9$ is aminoalkyl, mono $C_1$-$C_6$ alkylamino $C_1$-$C_6$ alkyl, di $C_1$-$C_6$ alkylamino $C_1$-$C_6$ alkyl, $C_1$-$C_6$ alkyl, $C_1$-$C_6$ alkanoyl, phenyl $C_1$-$C_4$ alkyl, indazolyl, and phenyl $C_1$-$C_4$ alkanoyl.

Embodiment 10. Compounds according to embodiment 4, wherein $R_5$ is phenyl, phenyl($C_1$-$C_6$)alkyl, which is unsubstituted or substituted with 1, 2, 3, 4, or 5 groups that are independently alkyl, halogen, alkoxy, benzyloxy, thioalkoxy, —$CO_2$($C_1$-$C_5$ alkyl), $CO_2R$, CN, amidinooxime, —$NR_8R_9$, —$NR_6R_7$, $R_6R_7N$—($C_1$-$C_6$ alkyl)-, $R_6R_7NC(O)$—($C_1$-$C_4$ alkyl)-, $R_6R_7NC(O)$—($C_5$-$C_6$ alkyl)-, —C(O)$NR_6R_7$, amidino, $CF_3$, or $OCF_3$; wherein $R_6$ and $R_7$ are independently at each occurrence H, $C_1$-$C_4$ alkyl, $C_1$-$C_4$ hydroxyalkyl, $C_1$-$C_4$ dihydroxyalkyl, $C_1$-$C_4$ alkoxy, $C_1$-$C_4$ alkoxy $C_1$-$C_4$ alkyl, $C_1$-$C_4$ alkanoyl, phenyl $C_1$-$C_4$ alkyl, phenyl $C_1$-$C_4$ alkoxy, or phenyl $C_1$-$C_4$ alkanoyl, wherein each is unsubstituted or substituted with 1, 2, or 3 groups that are independently, halogen, OH, SH, $C_3$-$C_6$ cycloalkyl, $C_1$-$C_4$ alkoxy, $C_1$-$C_4$ alkyl, $CF_3$, or $OCF_3$; or $R_6$, $R_7$, and the nitrogen to which they are attached form a morpholinyl, thiomorpholinyl, or piperazinyl ring which is optionally substituted with 1 or 2 groups that are independently $C_1$-$C_4$ alkyl, hydroxy, hydroxy $C_1$-$C_4$ alkyl, $C_1$-$C_4$ dihydroxyalkyl, or halogen;

$R_8$ is hydrogen, $C_1$-$C_6$ alkyl, $C_1$-$C_6$ alkanoyl, phenyl $C_1$-$C_6$ alkyl and phenyl $C_1$-$C_6$ alkanoyl; and $R_9$ is aminoalkyl, mono $C_1$-$C_6$ alkylamino $C_1$-$C_6$ alkyl, di $C_1$-$C_6$ alkylamino $C_1$-$C_6$ alkyl, $C_1$-$C_6$ alkyl, $C_1$-$C_6$ alkanoyl, phenyl $C_1$-$C_4$ alkyl, indazolyl, and phenyl $C_1$-$C_4$ alkanoyl.

Embodiment 11. Compounds according to embodiment 10, wherein $R_5$ is phenyl, benzyl or phenethyl, wherein each is optionally substituted with 1, 2, 3, 4, or 5 groups that are independently $C_1$-$C_6$ alkyl, —$NR_6R_7$, —C(O)$NR_6R_7$, —($C_1$-$C_4$ alkyl)-C(O)$NR_6R_7$, —$NR_3R_9$, halogen, $C_1$-$C_6$ alkoxy, $CO_2R$, —($C_1$-$C_4$ alkyl)-$CO_2R$, $C_1$-$C_6$ thioalkoxy, amidinooxime, $C_1$-$C_6$ alkoxycarbonyl, —($C_1$-$C_4$ alkyl)-$C_1$-$C_6$ alkoxycarbonyl, $C_1$-$C_6$ hydroxyalkyl, $C_1$-$C_6$ dihydroxyalkyl, —($C_1$-$C_4$ alkyl)-CN, CN, phenyl $C_1$-$C_6$ alkoxy, OH, $C_1$-$C_4$ haloalkyl, $C_1$-$C_4$ haloalkoxy, $R_6R_7N$—($C_1$-$C_6$ alkyl)-, —($C_1$-$C_4$ alkyl)-$NR_{15}C(O)R_{18}$, amidinooxime, —$SO_2$($C_1$-$C_6$ alkyl), —O—$CH_2$—O—, —O—$CH_2CH_2$—O—, phenyl $C_1$-$C_4$ alkoxy, or phenyl; wherein $R_6$ and $R_7$ are independently at each occurrence H, $C_1$-$C_4$ alkyl, $C_1$-$C_4$ hydroxyalkyl, $C_1$-$C_4$ dihydroxyalkyl, $C_1$-$C_4$ alkanoyl, or $C_1$-$C_4$ alkoxy, each of which is optionally substituted with 1, 2, or 3 groups that are independently halogen, OH, SH, $C_3$-$C_6$ cycloalkyl, $C_1$-$C_4$ alkoxy, $C_1$-$C_4$ alkyl, OH, $CF_3$, or $OCF_3$.

Embodiment 12. Compounds according to embodiment 11, wherein $R_5$ is phenyl, benzyl or phenethyl, each of which is unsubstituted or substituted with 1, 2, 3, 4, or 5 groups that are independently CN, halogen, $C_1$-$C_4$ alkoxy, $CF_3$, $OCF_3$, $C_1$-$C_4$ alkyl, —$NR_8R_9$, —$NR_6R_7$, $R_6R_7N$—($C_1$-$C_6$ alkyl)-, or —C(O)$NR_6R_7$, wherein $R_6$ and $R_7$ are independently at each occurrence H, $C_1$-$C_4$ alkyl, $C_1$-$C_4$ hydroxyalkyl, $C_1$-$C_4$ dihydroxyalkyl, $C_1$-$C_4$ alkanoyl, or $C_1$-$C_4$ alkoxy, each of which is optionally substituted with 1, 2, or 3 groups that are independently halogen, OH, SH, $C_3$-$C_6$ cycloalkyl, $C_1$-$C_4$ alkoxy, $C_1$-$C_4$ alkyl, OH, $CF_3$, or $OCF_3$.

Embodiment 13. Compounds according to embodiment 4, wherein
the $R_5$ group is of the formula:

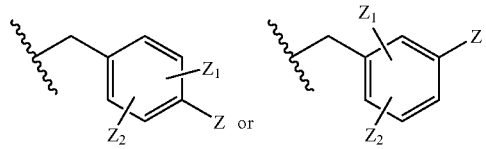

wherein
$Z_1$ and $Z_2$ are independently H, halogen, $C_1$-$C_4$ alkyl, or $CO_2R$; and Z is —C(O)$NR_6R_7$, —($C_1$-$C_4$)alkyl-C(O)$NR_6R_7$, —($C_1$-$C_4$ alkyl)-$NR_{15}$C(O)$R_{18}$, —$NR_6R_7$, $R_6R_7$N—($C_1$-$C_6$ alkyl)-, —$NR_8R_9$, $C_1$-$C_6$ hydroxyalkyl, $C_1$-$C_6$ dihydroxyalkyl, $C_1$-$C_6$ alkyl, $CO_2R$, or halogen; wherein $R_6$ and $R_7$ at each occurrence are independently H, OH, $C_1$-$C_6$ alkyl, amino $C_1$-$C_4$ alkyl, NH($C_1$-$C_6$ alkyl)alkyl, N($C_1$-$C_6$ alkyl)($C_1$-$C_6$ alkyl)$C_1$-$C_6$ alkyl, $C_1$-$C_6$ hydroxyalkyl, $C_1$-$C_6$ dihydroxyalkyl, $C_1$-$C_6$ alkoxy $C_1$-$C_6$ alkyl, or —$SO_2$($C_1$-$C_6$ alkyl) each of which is optionally substituted with 1, 2, or 3 groups that are independently halogen, OH, SH, $C_3$-$C_6$ cycloalkyl, $C_1$-$C_4$ alkoxy, $C_1$-$C_4$ alkyl, OH, $CF_3$, or $OCF_3$;
or $R_6$, $R_7$, and the nitrogen to which they are attached form a piperidinyl, pyrrolidinyl, piperazinyl, or a morpholinyl, thiomorpholinyl, ring optionally substituted with 1 or 2 groups that are independently alkyl, hydroxy, hydroxy $C_1$-$C_4$ alkyl, $C_1$-$C_4$ dihydroxyalkyl, or halogen; and $R_{18}$ is $C_1$-$C_6$ alkyl optionally substituted with —O—($C_2$-$C_6$ alkanoyl, $C_1$-$C_6$ hydroxyalkyl, $C_1$-$C_4$ dihydroxyalkyl, $C_1$-$C_6$ alkoxy, $C_1$-$C_6$ alkoxy $C_1$-$C_6$ alkyl; amino $C_1$-$C_6$ alkyl, mono or dialkylamino $C_1$-$C_6$ alkyl.

Embodiment 14. Compounds according to embodiment 4, wherein
$R_5$ is pyrazolyl($C_1$-$C_6$ alkyl), imidazolyl($C_1$-$C_6$ alkyl), thienyl($C_1$-$C_6$ alkyl), furanyl($C_1$-$C_6$ alkyl), piperidinyl($C_1$-$C_6$) alkyl, pyrrolidinyl($C_1$-$C_6$)alkyl, imidazolidinyl($C_1$-$C_6$) alkyl, piperazinyl($C_1$-$C_6$)alkyl, pyridyl($C_1$-$C_6$)alkyl, pyrimidyl($C_1$-$C_6$)alkyl, pyridazyl($C_1$-$C_6$)alkyl, pyrazinyl ($C_1$-$C_6$)alkyl, isoquinolinyl($C_1$-$C_6$)alkyl, tetrahydroisoquinolinyl($C_1$-$C_6$)alkyl, indolyl($C_1$-$C_6$)alkyl, 1H-indazolyl($C_1$-$C_6$)alkyl, dihydroindolyl($C_1$-$C_6$ alkyl), dihydroindolon-2-yl($C_1$-$C_6$ alkyl), indolinyl($C_1$-$C_6$ alkyl), dihydroisoindolyl($C_1$-$C_6$ alkyl), dihydrobenzimidazolyl ($C_1$-$C_6$ alkyl), or dihydrobenzoimidazolonyl($C_1$-$C_6$ alkyl), wherein each of the above is unsubstituted or substituted with 1, 2, 3, 4, or 5 groups that are independently ($C_1$-$C_6$)alkyl, halogen, ($C_1$-$C_6$)alkoxy, ($C_1$-$C_6$)hydroxyalkyl, $C_1$-$C_6$ dihydroxyalkyl, phenyl($C_1$-$C_6$)alkoxy, ($C_1$-$C_6$)thioalkoxy, ($C_1$-$C_6$)alkoxycarbonyl, phenyl($C_1$-$C_6$)alkoxycarbonyl, OH, $CO_2R$, CN, amidinooxime, —$NR_8R_9$, —$NR_6R_7$, $R_6R_7$N—($C_1$-$C_6$ alkyl)-, —C(O)$NR_6R_7$, —($C_1$-$C_4$ alkyl)-C(O)$NR_6R_7$, amidino, piperazinyl, morpholinyl, —$SO_2$ ($C_1$-$C_6$)alkyl, —$SO_2NH_2$, —$SO_2NH(C_1$-$C_6$)alkyl, $SO_2N(C_1$-$C_6$)alkyl($C_1$-$C_6$)alkyl, ($C_1$-$C_4$)haloalkyl, —($C_1$-$C_4$ alkyl)-$NR_{15}$C(O) $NR_{16}R_{17}$, —($C_1$-$C_4$ alkyl)-$NR_{15}$C(O)$R_{18}$, —O—$CH_2$—O, —O—$CH_2CH_2$—O—, or ($C_1$-$C_4$)haloalkoxy; wherein $R_6$ and $R_7$ are independently at each occurrence H, ($C_1$-$C_6$)alkyl, ($C_1$-$C_6$)alkoxy, ($C_1$-$C_6$)alkoxy($C_1$-$C_6$) alkyl, ($C_1$-$C_6$)alkoxycarbonyl, ($C_1$-$C_6$)hydroxyalkyl, $C_1$-$C_6$ dihydroxyalkyl, —($C_1$-$C_4$)alkyl-$CO_2$—($C_1$-$C_6$)alkyl, ($C_1$-$C_6$)alkanoyl, phenyl($C_1$-$C_6$)alkyl, phenyl($C_1$-$C_6$)alkoxy, or phenyl($C_1$-$C_6$)alkanoyl, wherein each of the above is unsubstituted or substituted with 1, 2, or 3 groups that are independently, halogen, ($C_1$-$C_4$)alkoxy, OH, SH, $C_3$-$C_6$ cycloalkyl, $NH_2$, NH($C_1$-$C_6$ alkyl), N($C_1$-$C_6$ alkyl)($C_1$-$C_6$ alkyl), ($C_1$-$C_4$)alkyl, $CF_3$ or $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, hydroxy, hydroxy $C_1$-$C_4$ alkyl, $C_1$-$C_4$ dihydroxyalkyl, or halogen; and $R_{18}$ is $C_1$-$C_6$ alkyl optionally substituted with —O—($C_2$-$C_6$ alkanoyl, $C_1$-$C_6$ hydroxyalkyl, $C_1$-$C_6$ dihydroxyalkyl, $C_1$-$C_6$ alkoxy, $C_1$-$C_6$ alkoxy $C_1$-$C_6$ alkyl; amino $C_1$-$C_6$ alkyl, mono or dialkylamino $C_1$-$C_6$ alkyl.

In this embodiment, it is preferred that $R_6$ and $R_7$ are not simultaneously OH; and $R_6$ and $R_7$ are not simultaneously —$SO_2$($C_1$-$C_6$ alkyl).

Embodiment 15. Compounds according to embodiment 14, wherein $R_5$ is pyrazolyl($C_1$-$C_6$ alkyl), imidazolyl($C_1$-$C_6$ alkyl), benzimidazolyl($C_1$-$C_6$ alkyl), thienyl($C_1$-$C_6$ alkyl), pyrimidyl ($C_1$-$C_6$)alkyl, indolyl($C_1$-$C_6$ alkyl), dihydroindolyl($C_1$-$C_6$ alkyl), dihydroisoindolyl($C_1$-$C_6$ alkyl), dihydroindolon-2-yl($C_1$-$C_6$ alkyl), pyridinyl($C_1$-$C_6$ alkyl), piperazinyl($C_1$-$C_6$ alkyl), or pyrazinyl($C_1$-$C_6$ alkyl) each of which is optionally substituted with 1, 2, or 3 groups that are independently $C_1$-$C_4$ alkyl, $C_1$-$C_4$ hydroxyalkyl, $C_1$-$C_4$ dihydroxyalkyl, halogen, —C(O)$NR_6R_7$, —($C_1$-$C_4$ alkyl)-C(O) $NR_6R_7$, $C_1$-$C_6$ alkoxycarbonyl, —$NR_6R_7$, $R_6R_7$N—($C_1$-$C_6$ alkyl)-, haloalkyl, $C_1$-$C_6$ alkanoyl, $R_6$ and $R_7$ at each occurrence are independently H, —$C_1$-$C_6$ alkyl optionally substituted with 1, 2, or 3 groups that are independently $C_1$-$C_4$ alkoxycarbonyl, halogen, $C_3$-$C_6$ cycloalkyl, OH, SH, or $C_1$-$C_4$ alkoxy;
or $R_6$, $R_7$, and the nitrogen to which they are attached form a piperidinyl, pyrrolidinyl, piperazinyl, or a morpholinyl ring optionally substituted with 1 or 2 groups that are independently alkyl, hydroxy, hydroxy $C_1$-$C_4$ alkyl, $C_1$-$C_4$ dihydroxyalkyl, or halogen.

Embodiment 16. Compounds according to embodiment 15, wherein
$R_5$ is of the formula:

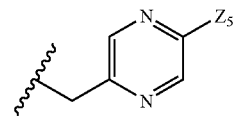

wherein
$Z_5$ is $C_1$-$C_4$ alkyl, $C_1$-$C_4$ hydroxyalkyl, $C_1$-$C_4$ dihydroxyalkyl, halogen, —C(O)$NR_6R_7$, —($C_1$-$C_4$ alkyl)-C(O)

NR$_6$R$_7$, C$_1$-C$_6$ alkoxycarbonyl, R$_6$R$_7$N—(C$_1$-C$_6$ alkyl)-, —NR$_6$R$_7$, CF$_3$, or C$_1$-C$_6$ alkanoyl, wherein R$_6$ and R$_7$ at each occurrence are independently H, C$_1$-C$_6$ alkyl optionally substituted with 1, 2, or 3 groups that are independently C$_1$-C$_4$ alkoxycarbonyl, halogen, C$_3$-C$_6$ cycloalkyl, OH, SH, or C$_1$-C$_4$ alkoxy;

or

R$_6$, R$_7$, and the nitrogen to which they are attached form a piperidinyl, pyrrolidinyl, piperazinyl, or a morpholinyl ring optionally substituted with 1 or 2 groups that are independently alkyl, hydroxy, hydroxy C$_1$-C$_4$ alkyl, C$_1$-C$_4$ dihydroxyalkyl, or halogen.

Embodiment 17. Compounds according to embodiment 15, wherein

R$_5$ is of the formula:

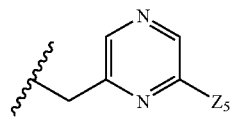

wherein

Z$_5$ is C$_1$-C$_4$ alkyl, C$_1$-C$_4$ hydroxyalkyl, C$_1$-C$_4$ dihydroxyalkyl, halogen, —C(O)NR$_6$R$_7$, —(C$_1$-C$_4$ alkyl)-C(O)NR$_6$R$_7$, C$_1$-C$_6$ alkoxycarbonyl, R$_6$R$_7$N—(C$_1$-C$_6$ alkyl)-, —NR$_6$R$_7$, CF$_3$, or C$_1$-C$_6$ alkanoyl, wherein R$_6$ and R$_7$ at each occurrence are independently H, C$_1$-C$_6$ alkyl optionally substituted with 1, 2, or 3 groups that are independently C$_1$-C$_4$ alkoxycarbonyl, halogen, C$_3$-C$_6$ cycloalkyl, OH, SH, or C$_1$-C$_4$ alkoxy;

or

R$_6$, R$_7$, and the nitrogen to which they are attached form a piperidinyl, pyrrolidinyl, piperazinyl, or a morpholinyl ring optionally substituted with 1 or 2 groups that are independently alkyl, hydroxy, hydroxy C$_1$-C$_4$ alkyl, C$_1$-C$_4$ dihydroxyalkyl, or halogen.

Embodiment 18. Compounds according to either embodiment 16 or 17, wherein

Z$_5$ is C$_1$-C$_4$ alkyl, C$_1$-C$_4$ hydroxyalkyl, C$_1$-C$_4$ dihydroxyalkyl, halogen, C$_1$-C$_6$ alkoxycarbonyl, CF$_3$, or C$_1$-C$_6$ alkanoyl.

Embodiment 19. Compounds according to either embodiment 16 or 17, wherein

Z$_5$ is C$_1$-C$_4$ alkyl, —C(O)NR$_6$R$_7$, —(C$_1$-C$_4$ alkyl)-C(O)NR$_6$R$_7$, R$_6$R$_7$N—(C$_1$-C$_6$ alkyl)-, or —NR$_6$R$_7$, CF$_3$, or C$_1$-C$_4$ alkanoyl, wherein R$_6$ and R$_7$ at each occurrence are independently H, C$_1$-C$_6$ alkyl optionally substituted with 1, 2, or 3 groups that are independently C$_1$-C$_4$ alkoxycarbonyl, halogen, C$_3$-C$_6$ cycloalkyl, OH, SH, or C$_1$-C$_4$ alkoxy;

or

R$_6$, R$_7$, and the nitrogen to which they are attached form a piperidinyl, pyrrolidinyl, piperazinyl, or a morpholinyl ring optionally substituted with 1 or 2 groups that are independently alkyl, hydroxy, hydroxy C$_1$-C$_4$ alkyl, C$_1$-C$_4$ dihydroxyalkyl, or halogen.

Embodiment 20. Compounds according to embodiment 19, wherein

Z$_5$ is —C(O)NR$_6$R$_7$, —(C$_1$-C$_4$ alkyl)-C(O)NR$_6$R$_7$, R$_6$R$_7$N—(C$_1$-C$_6$ alkyl)-, or —NR$_6$R$_7$, wherein R$_6$ and R$_7$ at each occurrence are independently H, C$_1$-C$_6$ alkyl optionally substituted with 1, 2, or 3 groups that are independently C$_1$-C$_4$ alkoxycarbonyl, halogen, cyclopropyl, OH, SH, or C$_1$-C$_4$ alkoxy.

Embodiment 21. Compounds according to embodiment 15, wherein

R$_5$ is of the formula:

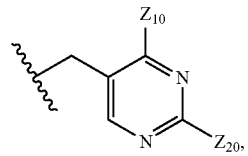

wherein

Z$_{10}$ is H or methyl; and

Z$_{20}$ is hydroxy(C$_1$-C$_4$)alkyl, C$_1$-C$_4$ dihydroxyalkyl, OH, halogen, haloalkyl, (C$_1$-C$_4$)alkyl, OCF$_3$, —NR$_6$R$_7$, R$_6$R$_7$N—(C$_1$-C$_6$ alkyl)-, —(C$_1$-C$_4$ alkyl)-C(O)NR$_6$R$_7$, or —C(O)NR$_6$R$_7$, wherein R$_6$ and R$_7$ at each occurrence are independently H, C$_1$-C$_6$ alkyl optionally substituted with 1, 2, or 3 groups that are independently C$_1$-C$_4$ alkoxycarbonyl, halogen, C$_3$-C$_6$ cycloalkyl, OH, SH, or C$_1$-C$_4$ alkoxy.

Embodiment 22. Compounds according to embodiment 15, wherein

R$_5$ is of the formula:

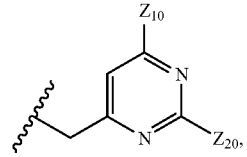

wherein

Z$_{10}$ is H or methyl; and

Z$_{20}$ is hydroxy(C$_1$-C$_4$)alkyl, C$_1$-C$_4$ dihydroxyalkyl, OH, halogen, CF$_3$, (C$_1$-C$_4$)alkyl, OCF$_3$, —NR$_6$R$_7$, R$_6$R$_7$N—(C$_1$-C$_6$ alkyl)-, —(C$_1$-C$_4$ alkyl)-C(O)NR$_6$R$_7$, or —C(O)NR$_6$R$_7$, wherein R$_6$ and R$_7$ at each occurrence are independently H, C$_1$-C$_6$ alkyl optionally substituted with 1, 2, or 3 groups that are independently C$_1$-C$_4$ alkoxycarbonyl, halogen, C$_3$-C$_6$ cycloalkyl, OH, SH, or C$_1$-C$_4$ alkoxy.

Embodiment 23. Compounds according to embodiment 15, wherein

R$_5$ is of the formula:

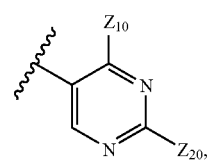

wherein

Z$_{10}$ is H or methyl; and

Z$_{20}$ is hydroxy(C$_1$-C$_4$)alkyl, C$_1$-C$_4$ dihydroxyalkyl, OH, halogen, haloalkyl, (C$_1$-C$_4$)alkyl, OCF$_3$, —NR$_6$R$_7$, R$_6$R$_7$N—(C$_1$-C$_6$ alkyl)-, —(C$_1$-C$_4$ alkyl)-C(O)NR$_6$R$_7$, or —C(O)NR$_6$R$_7$, wherein R$_6$ and R$_7$ at each occurrence are independently H, C$_1$-C$_6$ alkyl optionally substituted with 1, 2, or 3 groups that are independently C$_1$-C$_4$ alkoxycarbonyl, halogen, C$_3$-C$_6$ cycloalkyl, OH, SH, or C$_1$-C$_4$ alkoxy.

Embodiment 24. Compounds according to embodiment 15, wherein $R_5$ is of the formula:

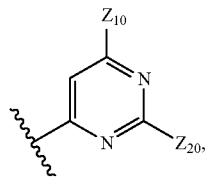

wherein $Z_{10}$ is H or methyl; and $Z_{20}$ is hydroxy($C_1$-$C_4$)alkyl, $C_1$-$C_4$ dihydroxyalkyl, OH, halogen, $CF_3$, ($C_1$-$C_4$)alkyl, $OCF_3$, —$NR_6R_7$, $R_6R_7N$—($C_1$-$C_6$ alkyl)-, —($C_1$-$C_4$ alkyl)-$C(O)NR_6R_7$, or —$C(O)NR_6R_7$, wherein $R_6$ and $R_7$ at each occurrence are independently H, $C_1$-$C_6$ alkyl optionally substituted with 1, 2, or 3 groups that are independently $C_1$-$C_4$ alkoxycarbonyl, halogen, $C_3$-$C_6$ cycloalkyl, OH, SH, or $C_1$-$C_4$ alkoxy.

Embodiment 25. Compounds according to embodiment 15, wherein $R_5$ is of the formula:

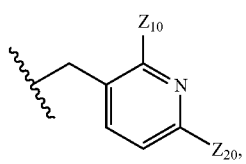

wherein $Z_{10}$ is H or methyl; and $Z_{20}$ is hydroxy($C_1$-$C_4$)alkyl, $C_1$-$C_4$ dihydroxyalkyl, OH, halogen, haloalkyl, ($C_1$-$C_4$)alkyl, $OCF_3$, —$NR_6R_7$, $R_6R_7N$—($C_1$-$C_6$ alkyl)-, —($C_1$-$C_4$ alkyl)-$C(O)NR_6R_7$, or —$C(O)NR_6R_7$, wherein $R_6$ and $R_7$ at each occurrence are independently H, $C_1$-$C_6$ alkyl optionally substituted with 1, 2, or 3 groups that are independently $C_1$-$C_4$ alkoxycarbonyl, halogen, $C_3$-$C_6$ cycloalkyl, OH, SH, or $C_1$-$C_4$ alkoxy.

Embodiment 26. Compounds according to embodiment 15, wherein $R_5$ is of the formula:

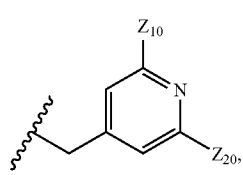

wherein $Z_{10}$ is H or methyl; and $Z_{20}$ is hydroxy($C_1$-$C_4$)alkyl, $C_1$-$C_4$ dihydroxyalkyl, OH, halogen, $CF_3$, ($C_1$-$C_4$)alkyl, $OCF_3$, —$NR_6R_7$, $R_6R_7N$—($C_1$-$C_6$ alkyl)-, —($C_1$-$C_4$ alkyl)-$C(O)NR_6R_7$, or —$C(O)NR_6R_7$, wherein $R_6$ and $R_7$ at each occurrence are independently H, $C_1$-$C_6$ alkyl optionally substituted with 1, 2, or 3 groups that are independently $C_1$-$C_4$ alkoxycarbonyl, halogen, $C_3$-$C_6$ cycloalkyl, OH, SH, or $C_1$-$C_4$ alkoxy.

Embodiment 27. Compounds according to embodiment 15, wherein $R_5$ is of the formula:

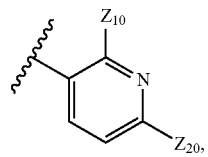

wherein $Z_{10}$ is H or methyl; and $Z_{20}$ is hydroxy($C_1$-$C_4$)alkyl, $C_1$-$C_4$ dihydroxyalkyl, OH, halogen, haloalkyl, ($C_1$-$C_4$)alkyl, $OCF_3$, —$NR_6R_7$, $R_6R_7N$—($C_1$-$C_6$ alkyl)-, —($C_1$-$C_4$ alkyl)-$C(O)NR_6R_7$, or —$C(O)NR_6R_7$, wherein $R_6$ and $R_7$ at each occurrence are independently H, $C_1$-$C_6$ alkyl optionally substituted with 1, 2, or 3 groups that are independently $C_1$-$C_4$ alkoxycarbonyl, halogen, $C_3$-$C_6$ cycloalkyl, OH, SH, or $C_1$-$C_4$ alkoxy.

Embodiment 28. Compounds according to embodiment 15, wherein $R_5$ is of the formula:

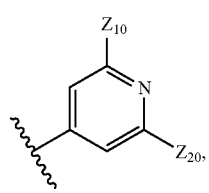

wherein $Z_{10}$ is H or methyl; and $Z_{20}$ is hydroxy($C_1$-$C_4$)alkyl, $C_1$-$C_4$ dihydroxyalkyl, OH, halogen, $CF_3$, ($C_1$-$C_4$)alkyl, $OCF_3$, —$NR_6R_7$, $R_6R_7N$—($C_1$-$C_6$ alkyl)-, —($C_1$-$C_4$ alkyl)-$C(O)NR_6R_7$, or —$C(O)NR_6R_7$, wherein $R_6$ and $R_7$ at each occurrence are independently H, $C_1$-$C_6$ alkyl optionally substituted with 1, 2, or 3 groups that are independently $C_1$-$C_4$ alkoxycarbonyl, halogen, $C_3$-$C_6$ cycloalkyl, OH, SH, or $C_1$-$C_4$ alkoxy.

Embodiment 29. Compounds according to embodiment 4, wherein $R_5$ is phenyl, which is optionally substituted with 1, 2, 3, 4, or 5 groups that are independently $C_1$-$C_4$ alkyl, —$C(O)NR_6R_7$, —($C_1$-$C_4$ alkyl)-$C(O)NR_6R_7$, —$NR_6R_7$, $NR_6R_7$ ($C_1$-$C_6$ alkyl), $C_1$-$C_6$ hydroxyalkyl, dihydroxyalkyl, halogen, $C_1$-$C_4$ alkoxy, $CO_2R$, OH, $C_1$-$C_6$ alkoxycarbonyl, $CF_3$, —($C_1$-$C_4$ alkyl)-$NR_{15}C(O)NR_{16}R_{17}$, —($C_1$-$C_4$ alkyl)-$NR_{15}C(O)R_{18}$; wherein $R_{15}$ is H or $C_1$-$C_6$ alkyl;

$R_{16}$ and $R_{17}$ are independently H or $C_1$-$C_6$ alkyl; or $R_{16}$, $R_{17}$, and the nitrogen to which they are attached form a morpholinyl ring; and $R_{18}$ is $C_1$-$C_6$ alkyl optionally substituted with —O—($C_2$-$C_6$ alkanoyl, $C_1$-$C_6$ hydroxyalkyl, $C_1$-$C_6$ dihydroxyalkyl, $C_1$-$C_6$ alkoxy, $C_1$-$C_6$ alkoxy $C_1$-$C_6$ alkyl; amino $C_1$-$C_6$ alkyl, mono or dialkylamino $C_1$-$C_6$ alkyl.

Embodiment 30. Compounds according to embodiment 29, wherein
$R_5$ is of the formula:

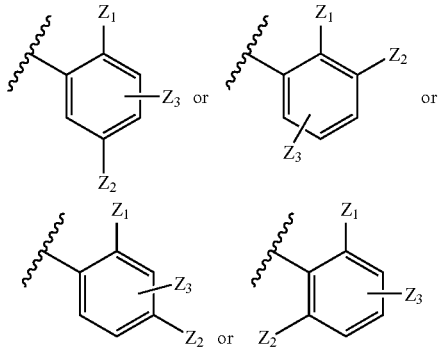

$Z_1$ is H, halogen, $C_1$-$C_4$ alkyl, $C_1$-$C_4$ haloalkyl, $C_1$-$C_4$ hydroxyalkyl, $C_1$-$C_4$ dihydroxyalkyl, or $C_1$-$C_4$ alkoxy; and
$Z_2$ is $C_1$-$C_4$ alkyl, —C(O)$NR_6R_7$, —($C_1$-$C_4$ alkyl)-C(O)$NR_6R_7$, —$NR_6R_7$, $NR_6R_7$($C_1$-$C_6$ alkyl), $C_1$-$C_6$ hydroxyalkyl, $C_1$-$C_6$ dihydroxyalkyl, halogen, $C_1$-$C_4$ alkoxy, $CO_2R$, OH, $C_1$-$C_6$ alkoxycarbonyl, or $C_1$-$C_4$ haloalkyl;
$Z_3$ is H, $C_1$-$C_4$ alkyl, —C(O)$NR_6R_7$, —($C_1$-$C_4$ alkyl)-C(O)$NR_6R_7$, —$NR_6R_7$, $NR_6R_7$($C_1$-$C_6$ alkyl), $C_1$-$C_6$ hydroxyalkyl, $C_1$-$C_6$ dihydroxyalkyl, halogen, $C_1$-$C_4$ alkoxy, $CO_2R$, OH, $C_1$-$C_6$ alkoxycarbonyl, or $C_1$-$C_4$ haloalkyl;
and wherein
$R_6$ and $R_7$ at each occurrence are independently H, OH, $C_1$-$C_6$ alkyl, amino $C_1$-$C_4$ alkyl, NH($C_1$-$C_6$ alkyl)alkyl, N($C_1$-$C_6$ alkyl)($C_1$-$C_6$ alkyl)$C_1$-$C_6$ alkyl, $C_1$-$C_6$ hydroxyalkyl, $C_1$-$C_6$ dihydroxyalkyl, $C_1$-$C_6$ alkoxy $C_1$-$C_6$ alkyl, —$SO_2$($C_1$-$C_6$ alkyl), —$SO_2NH_2$, —$SO_2NH$($C_1$-$C_6$ alkyl), —$SO_2N$($C_1$-$C_6$ alkyl)($C_1$-$C_6$ alkyl), or $C_1$-$C_6$ alkanoyl, each of which is optionally substituted with 1, 2, or 3 groups that are independently halogen, OH, SH, $C_3$-$C_6$ cycloalkyl, $C_1$-$C_4$ alkoxy, $C_1$-$C_4$ alkyl, OH, $CF_3$, or $OCF_3$.
In this embodiment, it is preferred that at least one of $Z_1$ $Z_2$, and $Z_3$ is not hydrogen.

Embodiment 31. Compounds according to embodiment 30, wherein
$R_5$ is of the formula:

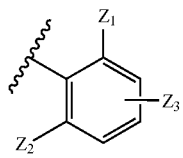

wherein
$Z_1$ is H, halogen, $C_1$-$C_4$ alkyl, $C_1$-$C_4$ haloalkyl, $C_1$-$C_4$ hydroxyalkyl, $C_1$-$C_4$ dihydroxyalkyl, or $C_1$-$C_4$ alkoxy; and
$Z_2$ is $C_1$-$C_4$ alkyl, —C(O)$NR_6R_7$, —($C_1$-$C_4$ alkyl)-C(O)$NR_6R_7$, —$NR_6R_7$, $NR_6R_7$($C_1$-$C_6$ alkyl), $C_1$-$C_6$ hydroxyalkyl, $C_1$-$C_6$ dihydroxyalkyl, halogen, $C_1$-$C_4$ alkoxy, $CO_2R$, OH, $C_1$-$C_6$ alkoxycarbonyl, or $C_1$-$C_4$ haloalkyl;
$Z_3$ is H, $C_1$-$C_4$ alkyl, —C(O)$NR_6R_7$, —($C_1$-$C_4$ alkyl)-C(O)$NR_6R_7$, —$NR_6R_7$, $NR_6R_7$($C_1$-$C_6$ alkyl), $C_1$-$C_6$ hydroxyalkyl, $C_1$-$C_6$ dihydroxyalkyl, halogen, $C_1$-$C_4$ alkoxy, $CO_2R$, OH, $C_1$-$C_6$ alkoxycarbonyl, or $C_1$-$C_4$ haloalkyl, and wherein
$R_6$ and $R_7$ at each occurrence are independently H, OH, $C_1$-$C_6$ alkyl, amino $C_1$-$C_4$ alkyl, NH($C_1$-$C_6$ alkyl)alkyl, N($C_1$-$C_6$ alkyl)($C_1$-$C_6$ alkyl)$C_1$-$C_6$ alkyl, $C_1$-$C_6$ hydroxyalkyl, $C_1$-$C_6$ dihydroxyalkyl, $C_1$-$C_6$ alkoxy $C_1$-$C_6$ alkyl, —$SO_2$($C_1$-$C_6$ alkyl), —$SO_2NH_2$, —$SO_2NH$($C_1$-$C_6$ alkyl), —$SO_2N$($C_1$-$C_6$ alkyl)($C_1$-$C_6$ alkyl), or $C_1$-$C_6$ alkanoyl, each of which is optionally substituted with 1, 2, or 3 groups that are independently halogen, OH, SH, $C_3$-$C_6$ cycloalkyl, $C_1$-$C_4$ alkoxy, $C_1$-$C_4$ alkyl, OH, $CF_3$, or $OCF_3$.
In this embodiment, it is preferred that at least one of $Z_1$, $Z_2$, and $Z_3$ is not hydrogen.

Embodiment 32. Compounds according to embodiment 30, wherein
$R_5$ is of the formula:

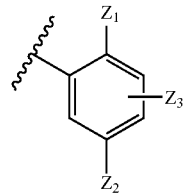

wherein
$Z_1$ is H, halogen, $C_1$-$C_4$ alkyl, $C_1$-$C_4$ haloalkyl, $C_1$-$C_4$ hydroxyalkyl, $C_1$-$C_4$ dihydroxyalkyl, or $C_1$-$C_4$ alkoxy; and
$Z_2$ is $C_1$-$C_4$ alkyl, —C(O)$NR_6R_7$, —($C_1$-$C_4$ alkyl)-C(O)$NR_6R_7$, —$NR_6R_7$, $NR_6R_7$($C_1$-$C_6$ alkyl), $C_1$-$C_6$ hydroxyalkyl, $C_1$-$C_6$ dihydroxyalkyl, halogen, $C_1$-$C_4$ alkoxy, $CO_2R$, OH, $C_1$-$C_6$ alkoxycarbonyl, or $C_1$-$C_4$ haloalkyl;
$Z_3$ is H, $C_1$-$C_4$ alkyl, —C(O)$NR_6R_7$, —($C_1$-$C_4$ alkyl)-C(O)$NR_6R_7$, —$NR_6R_7$, $NR_6R_7$($C_1$-$C_6$ alkyl), $C_1$-$C_6$ hydroxyalkyl, $C_1$-$C_6$ dihydroxyalkyl, halogen, $C_1$-$C_4$ alkoxy, $CO_2R$, OH, $C_1$-$C_6$ alkoxycarbonyl, or $C_1$-$C_4$ haloalkyl, and wherein
$R_6$ and $R_7$ at each occurrence are independently H, OH, $C_1$-$C_6$ alkyl, amino $C_1$-$C_4$ alkyl, NH($C_1$-$C_6$ alkyl)alkyl, N($C_1$-$C_6$ alkyl)($C_1$-$C_6$ alkyl)$C_1$-$C_6$ alkyl, $C_1$-$C_6$ hydroxyalkyl, $C_1$-$C_6$ dihydroxyalkyl, $C_1$-$C_6$ alkoxy $C_1$-$C_6$ alkyl, —$SO_2$($C_1$-$C_6$ alkyl), —$SO_2NH_2$, —$SO_2NH$($C_1$-$C_6$ alkyl), —$SO_2N$($C_1$-$C_6$ alkyl)($C_1$-$C_6$ alkyl), or $C_1$-$C_6$ alkanoyl, each of which is optionally substituted with 1, 2, or 3 groups that are independently halogen, OH, SH, $C_3$-$C_6$ cycloalkyl, $C_1$-$C_4$ alkoxy, $C_1$-$C_4$ alkyl, OH, $CF_3$, or $OCF_3$.
In this embodiment, it is preferred that at least one of $Z_1$, $Z_2$, and $Z_3$ is not hydrogen.

Embodiment 33. Compounds according to embodiment 29,
wherein
$R_5$ is either

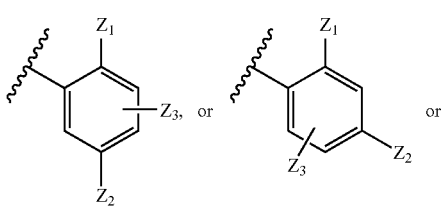

-continued

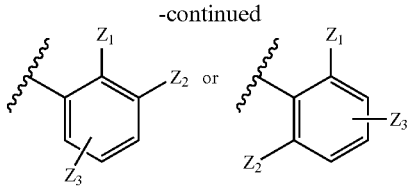

wherein
$Z_1$ is H, halogen, $C_1$-$C_4$ alkyl, $C_1$-$C_4$ haloalkyl, $C_1$-$C_4$ hydroxyalkyl, $C_1$-$C_4$ dihydroxyalkyl, or $C_1$-$C_4$ alkoxy; and
$Z_2$ is $C_1$-$C_4$ alkyl, —C(O)N$R_6R_7$, —($C_1$-$C_4$ alkyl)-C(O)N$R_6R_7$, —N$R_6R_7$, N$R_6R_7$($C_1$-$C_6$ alkyl), $C_1$-$C_6$ hydroxyalkyl, $C_1$-$C_6$ dihydroxyalkyl, halogen, $C_1$-$C_4$ alkoxy, $CO_2R$, $C_1$-$C_6$ alkoxycarbonyl, —($C_1$-$C_4$ alkyl)-N$R_{15}$C(O)N$R_{16}R_{17}$, or —($C_1$-$C_4$ alkyl)-N$R_{15}$C(O)$R_{18}$;
$Z_3$ is H, $C_1$-$C_4$ alkyl, —C(O)N$R_6R_7$, —($C_1$-$C_4$ alkyl)-C(O)N$R_6R_7$, —N$R_6R_7$, N$R_6R_7$($C_1$-$C_6$ alkyl), $C_1$-$C_6$ hydroxyalkyl, $C_1$-$C_6$ dihydroxyalkyl, halogen, $C_1$-$C_4$ alkoxy, $CO_2R$, $C_1$-$C_6$ alkoxycarbonyl, —($C_1$-$C_4$ alkyl)-N$R_{15}$C(O)N$R_{16}R_{17}$, or —($C_1$-$C_4$ alkyl)-N$R_{15}$C(O)$R_{18}$;
$R_6$, $R_7$, and the nitrogen to which they are attached form a piperidinyl, pyrrolidinyl, piperazinyl, or a morpholinyl ring optionally substituted with 1 or 2 groups that are independently alkyl, hydroxy, hydroxy $C_1$-$C_4$ alkyl, $C_1$-$C_4$ dihydroxyalkyl, or halogen;
$R_{15}$ is H or $C_1$-$C_6$ alkyl;
$R_{16}$ and $R_{17}$ are independently H or $C_1$-$C_6$ alkyl; or
$R_{16}$, $R_{17}$, and the nitrogen to which they are attached form a morpholinyl ring; and
$R_{18}$ is $C_1$-$C_6$ alkyl optionally substituted with —O—($C_2$-$C_6$ alkanoyl, $C_1$-$C_6$ hydroxyalkyl, $C_1$-$C_6$ dihydroxyalkyl, $C_1$-$C_6$ alkoxy, $C_1$-$C_6$ alkoxy $C_1$-$C_6$ alkyl; amino $C_1$-$C_6$ alkyl, mono or dialkylamino $C_1$-$C_6$ alkyl.
In this embodiment, it is preferred that at least one of $Z_1$, $Z_2$, and $Z_3$ is not hydrogen.

Embodiment 34. Compounds according to embodiment 33,
wherein
$R_5$ is of the formula:

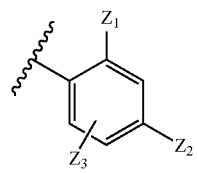

$Z_1$ is H, halogen, $C_1$-$C_4$ alkyl, $C_1$-$C_4$ haloalkyl, $C_1$-$C_4$ hydroxyalkyl, $C_1$-$C_4$ dihydroxyalkyl, or $C_1$-$C_4$ alkoxy; and
$Z_2$ is $C_1$-$C_4$ alkyl, —C(O)N$R_6R_7$, —($C_1$-$C_4$ alkyl)-C(O)N$R_6R_7$, —N$R_6R_7$, N$R_6R_7$($C_1$-$C_6$ alkyl), $C_1$-$C_6$ hydroxyalkyl, $C_1$-$C_6$ dihydroxyalkyl, halogen, $C_1$-$C_4$ alkoxy, $CO_2R$, $C_1$-$C_6$ alkoxycarbonyl, —($C_1$-$C_4$ alkyl)-N$R_{15}$C(O)N$R_{16}R_{17}$, or —($C_1$-$C_4$ alkyl)-N$R_{15}$C(O)$R_{18}$;
$Z_3$ is H, $C_1$-$C_4$ alkyl, —C(O)N$R_6R_7$, —($C_1$-$C_4$ alkyl)-C(O)N$R_6R_7$, —N$R_6R_7$, N$R_6R_7$($C_1$-$C_6$ alkyl), $C_1$-$C_6$ hydroxyalkyl, $C_1$-$C_6$ dihydroxyalkyl, halogen, $C_1$-$C_4$ alkoxy, $CO_2R$, $C_1$-$C_6$ alkoxycarbonyl, —($C_1$-$C_4$ alkyl)-N$R_{15}$C(O)N$R_{16}R_{17}$, or —($C_1$-$C_4$ alkyl)-N$R_{15}$C(O)$R_{18}$;
$R_6$, $R_7$, and the nitrogen to which they are attached form a piperidinyl, pyrrolidinyl, piperazinyl, or a morpholinyl ring optionally substituted with 1 or 2 groups that are independently alkyl, hydroxy, hydroxy $C_1$-$C_4$ alkyl, $C_1$-$C_4$ dihydroxyalkyl, or halogen;
$R_{15}$ is H or $C_1$-$C_6$ alkyl;
$R_{16}$ and $R_{17}$ are independently H or $C_1$-$C_6$ alkyl; or
$R_{16}$, $R_{17}$, and the nitrogen to which they are attached form a morpholinyl ring; and
$R_{18}$ is $C_1$-$C_6$ alkyl optionally substituted with —C—($C_2$-$C_6$ alkanoyl, $C_1$-$C_6$ hydroxyalkyl, $C_1$-$C_6$ dihydroxyalkyl, $C_1$-$C_6$ alkoxy, $C_1$-$C_6$ alkoxy $C_1$-$C_6$ alkyl; amino $C_1$-$C_6$ alkyl, mono or dialkylamino $C_1$-$C_6$ alkyl.
In this embodiment, it is preferred that at least one of $Z_1$, $Z_2$, and $Z_3$ is not hydrogen.

Embodiment 35. Compounds according to embodiment 33, wherein
$R_5$ is of the formula:

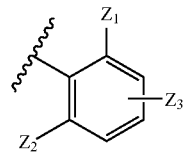

wherein
$Z_1$ is H, halogen, $C_1$-$C_4$ alkyl $C_1$-$C_4$ haloalkyl, $C_1$-$C_4$ hydroxyalkyl, $C_1$-$C_4$ dihydroxyalkyl, or $C_1$-$C_4$ alkoxy; and
$Z_2$ is $C_1$-$C_4$ alkyl, —C(O)N$R_6R_7$, —($C_1$-$C_4$ alkyl)-C(O)N$R_6R_7$, —N$R_6R_7$, N$R_6R_7$($C_1$-$C_6$ alkyl), $C_1$-$C_6$ hydroxyalkyl, $C_1$-$C_6$ dihydroxyalkyl, halogen, $C_1$-$C_4$ alkoxy, $CO_2R$, $C_1$-$C_6$ alkoxycarbonyl, —($C_1$-$C_4$ alkyl)-N$R_{15}$C(O)N$R_{16}R_{17}$, or —($C_1$-$C_4$ alkyl)-N$R_{15}$C(O)$R_{18}$;
$Z_3$ is H, $C_1$-$C_4$ alkyl, —C(O)N$R_6R_7$, —($C_1$-$C_4$ alkyl)-C(O)N$R_6R_7$, —N$R_6R_7$, N$R_6R_7$($C_1$-$C_6$ alkyl), $C_1$-$C_6$ hydroxyalkyl, $C_1$-$C_6$ dihydroxyalkyl, halogen, $C_1$-$C_4$ alkoxy, $CO_2R$, $C_1$-$C_6$ alkoxycarbonyl, —($C_1$-$C_4$ alkyl)-N$R_{15}$C(O)N$R_{16}R_{17}$, or —($C_1$-$C_4$ alkyl)-N$R_{15}$C(O)$R_{18}$;
$R_6$, $R_7$, and the nitrogen to which they are attached form a piperidinyl, pyrrolidinyl, piperazinyl, or a morpholinyl ring, each of which is optionally substituted with 1 or 2 groups that are independently alkyl, hydroxy, hydroxy $C_1$-$C_4$ alkyl, $C_1$-$C_4$ dihydroxyalkyl, or halogen;
$R_{15}$ is H or $C_1$-$C_6$ alkyl;
$R_{16}$ and $R_{17}$ are independently H or $C_1$-$C_6$ alkyl; or
$R_{16}$, $R_{17}$, and the nitrogen to which they are attached form a morpholinyl ring; and
$R_{18}$ is $C_1$-$C_6$ alkyl optionally substituted with —O—($C_2$-$C_6$ alkanoyl, $C_1$-$C_6$ hydroxyalkyl, $C_1$-$C_6$ dihydroxyalkyl, $C_1$-$C_6$ alkoxy, $C_1$-$C_6$ alkoxy $C_1$-$C_6$ alkyl; amino $C_1$-$C_6$ alkyl, mono or dialkylamino $C_1$-$C_6$ alkyl.
In this embodiment, it is preferred that at least one of $Z_1$, $Z_2$, and $Z_3$ is not hydrogen.

Embodiment 36. A compound of the formula

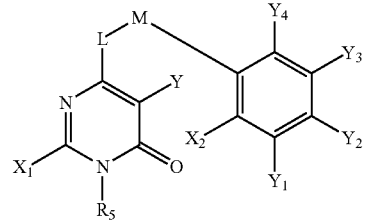

or a pharmaceutically acceptable salt thereof, wherein

L and M are independently selected from —O—, —CH$_2$—, —S—, —NR—, —N(R)—N(R)—, C(=O)—, —SO$_2$—;

R$_5$ is

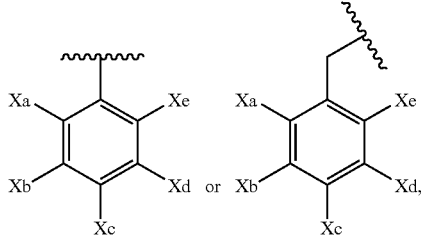

wherein

X$_1$, X$_2$, X$_a$, X$_b$, X$_c$, X$_d$, and X$_e$ at are independently selected from —C(O)NR$_6$R$_7$, —(C$_1$-C$_4$ alkyl)-C(O)NR$_6$R$_7$, —NR$_6$R$_7$, hydroxy(C$_1$-C$_4$)alkyl, C$_1$-C$_4$ dihydroxyalkyl, H, OH, halogen, haloalkyl, alkyl, haloalkoxy, heteroaryl, heterocycloalkyl, C$_3$-C$_7$ cycloalkyl, R$_6$R$_7$N—(C$_1$-C$_6$ alkyl)-, —CO$_2$—(C$_1$-C$_6$)alkyl, —N(R)C(O)NR$_6$R$_7$, —N(R)C(O)—(C$_1$-C$_6$)alkoxy, CO$_2$R—(C$_1$-C$_6$ alkyl)-, or —SO$_2$NR$_6$R$_7$; wherein the heteroaryl and heterocycloalkyl groups are optionally substituted with —NR$_6$R$_7$, —C(O)NR$_6$R$_7$, R$_6$R$_7$N—(C$_1$-C$_6$ alkyl)-, C$_1$-C$_6$ alkyl, C$_1$-C$_6$ alkoxy, or halogen; or R$_5$ is heteroaryl or heteroarylalkyl, wherein the heteroaryl and heteroaryl groups are optionally substituted with 1, 2, 3, or 4 groups that are independently —C(O)NR$_6$R$_7$, —(C$_1$-C$_4$ alkyl)-C(O)NR$_6$R$_7$, —NR$_6$R$_7$, hydroxy(C$_1$-C$_4$)alkyl, C$_1$-C$_4$ dihydroxyalkyl, H, OH, halogen, haloalkyl, alkyl, haloalkoxy, R$_6$R$_7$N—(C$_1$-C$_6$ alkyl)-, —CO$_2$—(C$_1$-C$_6$) alkyl, —N(R)C(O)NR$_6$R$_7$, or —N(R)C(O)—(C$_1$-C$_6$) alkoxy; wherein R$_6$ and R$_7$ are independently at each occurrence H, C$_1$-C$_6$ alkyl, C$_1$-C$_6$ alkoxy, C$_1$-C$_6$ alkoxy C$_1$-C$_6$ alkyl, C$_1$-C$_6$ alkoxycarbonyl, OH, C$_1$-C$_6$ hydroxyalkyl, C$_1$-C$_4$ dihydroxyalkyl, C$_1$-C$_6$ thiohydroxyalkyl, —(C$_1$-C$_4$)alkyl-CO$_2$-alkyl, pyridyl C$_1$-C$_6$ alkyl, C$_1$-C$_6$ alkanoyl, benzyl, phenyl C$_1$-C$_6$ alkoxy, or phenyl C$_1$-C$_6$ alkanoyl, wherein each of the above is unsubstituted or substituted with 1, 2, or 3 groups that are independently, halogen, C$_3$-C$_6$ cycloalkyl, C$_1$-C$_6$ alkoxy, piperidinyl C$_1$-C$_6$ alkyl, morpholinyl C$_1$-C$_6$ alkyl, piperazinyl C$_1$-C$_6$ alkyl, OH, SH, NH$_2$, NH(alkyl), N(alkyl)(alkyl), —O—C$_1$-C$_4$ alkanoyl, C$_1$-C$_4$ alkyl, CF$_3$, or OCF$_3$; or R$_6$, R$_7$, and the nitrogen to which they are attached form a morpholinyl, thiomorpholinyl, piperidinyl, pyrrolidinyl, or piperazinyl ring which is optionally substituted with 1 or 2 groups that are independently C$_1$-C$_4$ alkyl, C$_1$-C$_4$ alkoxy, hydroxy, hydroxy C$_1$-C$_4$ alkyl, C$_1$-C$_4$ dihydroxyalkyl, or halogen;

R at each occurrence is independently H or C$_1$-C$_6$ alkyl; and

Y, Y$_1$, Y$_2$, Y$_3$, and Y$_4$ are independently selected from H, halogen, alkyl, carboxaldehyde, hydroxyalkyl, dihydroxyalkyl, alkenyl, alkynyl, CN, alkanoyl, alkoxy, alkoxyalkyl, haloalkyl, and carboxyl.

Embodiment 37. Compounds according to embodiment 36 of the formula

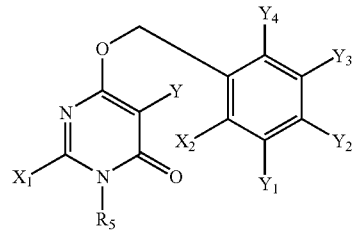

or a pharmaceutically acceptable salt thereof.

Embodiment 38. Compounds according to embodiment 37, wherein

R$_5$ is

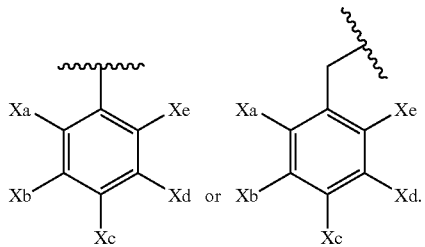

Embodiment 39. Compounds according to embodiment 31, wherein

Y$_2$, Y$_4$, and Y are independently halogen; and
Y$_1$ and Y$_3$ are both hydrogen.

Embodiment 40. Compounds according to embodiment 39, wherein

R$_5$ is

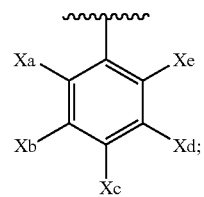

X$_1$ and X$_2$ are independently H, methyl, NR$_6$R$_7$, —(C$_1$-C$_4$ alkyl)-C(O)NR$_6$R$_7$, R$_6$R$_7$N—(C$_1$-C$_6$ alkyl)-, —C(O)NR$_6$R$_7$, C$_1$-C$_6$ hydroxyalkyl, C$_1$-C$_6$ dihydroxyalkyl, or —(C$_1$-C$_4$ alkyl)-morpholinyl; and X$_a$ and X$_e$ are independently halogen, NH$_2$, NH(C$_1$-C$_6$ alkyl), N(C$_1$-C$_6$ alkyl)(C$_1$-C$_6$ alkyl), methyl, or hydrogen.

In this embodiment, it is preferred that one of X$_a$ and X$_e$ is not hydrogen.

Embodiment 41. Compounds according to embodiment 40, wherein one of X$_b$ and X$_c$ is hydrogen and the other is —NR$_6$R$_7$, R$_6$R$_7$N—(C$_1$-C$_6$ alkyl)-, —C(O)NR$_6$R$_7$, —SO$_2$NR$_6$R$_7$, or halogen; where R$_6$ and R$_7$ are independently at each occurrence H, C$_1$-C$_6$ alkyl, C$_1$-C$_6$ alkoxy, C$_1$-C$_6$ alkoxy C$_1$-C$_6$ alkyl, C$_1$-C$_6$ alkoxycarbonyl, OH, C$_1$-C$_6$ hydroxyalkyl, C$_1$-C$_4$ dihydroxyalkyl, —(C$_1$-C$_4$)alkyl-CO$_2$-alkyl, pyridyl C$_1$-C$_6$ alkyl, C$_1$-C$_6$ alkanoyl, benzyl, phenyl C$_1$-C$_6$ alkoxy, or phenyl $C_1$-$C_6$ alkanoyl, wherein each of the above is unsubstituted or substituted with 1, 2, or 3 groups that are independently, halogen, $C_3$-$C_6$ cycloalkyl, $C_1$-$C_6$ alkoxy, piperidinyl $C_1$-$C_6$ alkyl, morpholinyl $C_1$-$C_6$ alkyl, piperazinyl $C_1$-$C_6$ alkyl, OH, SH, $NH_2$, NH(alkyl), N(alkyl)(alkyl), —O—$C_1$-$C_4$ alkanoyl, $C_1$-$C_4$ alkyl, $CF_3$, or $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, $C_1$-$C_4$ alkoxy, hydroxy, hydroxy $C_1$-$C_4$ alkyl, $C_1$-$C_4$ dihydroxyalkyl, or halogen.

Embodiment 42. Compounds according to embodiment 41, wherein $R_6$ and $R_7$ are independently at each occurrence H, $C_1$-$C_6$ alkyl, $C_1$-$C_6$ alkoxy, $C_1$-$C_6$ alkoxy $C_1$-$C_6$ alkyl, $C_1$-$C_6$ alkoxycarbonyl, OH, $C_1$-$C_6$ hydroxyalkyl, $C_1$-$C_6$ dihydroxyalkyl, —($C_1$-$C_4$)alkyl-$CO_2$-alkyl, pyridyl $C_1$-$C_6$ alkyl, $C_1$-$C_6$ alkanoyl, benzyl, phenyl $C_1$-$C_6$ alkoxy, or phenyl $C_1$-$C_6$ alkanoyl, wherein each of the above is unsubstituted or substituted with 1, 2, or 3 groups that are independently, halogen, $C_3$-$C_6$ cycloalkyl, $C_1$-$C_6$ alkoxy, piperidinyl $C_1$-$C_6$ alkyl, morpholinyl $C_1$-$C_6$ alkyl, piperazinyl $C_1$-$C_6$ alkyl, OH, $NH_2$, NH(alkyl), N(alkyl)(alkyl), —O—$C_1$-$C_4$ alkanoyl, $C_1$-$C_4$ alkyl, $CF_3$, or $OCF_3$.

Embodiment 43. Compounds according to embodiment 42, wherein $X_a$ is hydrogen, methyl, fluorine, or chlorine;
$X_c$ and $X_d$ are both hydrogen;
$X_b$ is —$NR_6R_7$, —($C_1$-$C_4$ alkyl)-C(O)$NR_6R_7$, $R_6R_7$N—($C_1$-$C_6$ alkyl)-, —C(O)$NR_6R_7$; wherein $R_6$ and $R_7$ are independently at each occurrence H, $C_1$-$C_6$ alkyl, $C_1$-$C_6$ hydroxyalkyl, $C_1$-$C_4$ dihydroxyalkyl, $C_1$-$C_6$ alkoxy, $C_1$-$C_6$ alkoxy $C_1$-$C_6$ alkyl, or $C_1$-$C_6$ alkanoyl, wherein each of the above is optionally substituted with 1, 2, or 3 groups that are independently OH, SH, halogen, or $C_3$-$C_6$ cycloalkyl.

Embodiment 44. Compounds according to embodiment 39, wherein $R_5$ is

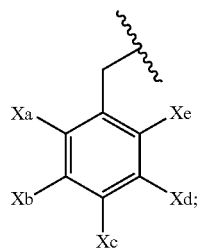

$X_a$ is H, fluoro, chloro, or methyl;
$X_e$ is hydrogen, halogen, or methyl; and
$X_b$ is H;
$X_d$ is H or halogen;

Embodiment 45. Compounds according to embodiment 44, wherein $X_c$ is —$SO_2NR_6R_7$, or halogen; wherein
$R_6$ and $R_7$ are independently at each occurrence H, $C_1$-$C_6$ alkyl, $C_1$-$C_6$ alkoxy, $C_1$-$C_6$ alkoxy $C_1$-$C_6$ alkyl, $C_1$-$C_6$ alkoxycarbonyl, OH, $C_1$-$C_6$ hydroxyalkyl, $C_1$-$C_6$ dihydroxyalkyl, —($C_1$-$C_4$)alkyl-$CO_2$-alkyl, pyridyl $C_1$-$C_6$ alkyl, $C_1$-$C_6$ alkanoyl, benzyl, phenyl $C_1$-$C_6$ alkoxy, or phenyl $C_1$-$C_6$ alkanoyl, wherein each of the above is unsubstituted or substituted with 1, 2, or 3 groups that are independently, halogen, $C_3$-$C_6$ cycloalkyl, $C_1$-$C_6$ alkoxy, piperidinyl $C_1$-$C_6$ alkyl, morpholinyl $C_1$-$C_6$ alkyl, piperazinyl $C_1$-$C_6$ alkyl, OH, SH, $NH_{21}$ NH(alkyl), N(alkyl)(alkyl), —O—$C_1$-$C_4$ alkanoyl, $C_1$-$C_4$ alkyl, $CF_3$, or $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, $C_1$-$C_4$ alkoxy, hydroxy, hydroxy $C_1$-$C_4$ alkyl, $C_1$-$C_4$ dihydroxyalkyl, or halogen; or $X_c$ is fluoro, chloro, —$NH_2$, —NH($C_1$-$C_6$ alkyl), —N($C_1$-$C_6$ alkyl)($C_1$-$C_6$ alkyl), —$SO_2NH_2$, —$SO_2NH$($C_1$-$C_6$ alkyl), —$SO_2N$($C_1$-$C_6$ alkyl)($C_1$-$C_6$ alkyl), or piperazinyl, wherein the piperazinyl group is optionally substituted with 1 or 2 groups that are independently $C_1$-$C_4$ alkyl, $C_1$-$C_4$ alkoxy, hydroxy, hydroxy $C_1$-$C_4$ alkyl, $C_1$-$C_4$ dihydroxyalkyl, or halogen.

Embodiment 46. Compounds according to embodiment 44, wherein $X_c$ is —C(O)$NR_6R_7$, —($C_1$-$C_6$ alkyl)-C(O)$NR_6R_7$, —$NR_6R_7$, or $R_6R_7$N—($C_1$-$C_6$ alkyl)-; wherein $R_6$ and $R_7$ are independently at each occurrence H, $C_1$-$C_6$ alkyl, $C_1$-$C_6$ alkoxy, $C_1$-$C_6$ alkoxy $C_1$-$C_6$ alkyl, $C_1$-$C_6$ alkoxycarbonyl, OH, $C_1$-$C_6$ hydroxyalkyl, $C_1$-$C_6$ dihydroxyalkyl, $C_1$-$C_6$ dihydroxyalkyl, —($C_1$-$C_4$)alkyl-$CO_2$-alkyl, pyridyl $C_1$-$C_6$ alkyl, $C_1$-$C_6$ alkanoyl, benzyl, phenyl $C_1$-$C_6$ alkoxy, or phenyl $C_1$-$C_6$ alkanoyl, wherein each of the above is unsubstituted or substituted with 1, 2, or 3 groups that are independently, halogen, $C_3$-$C_6$ cycloalkyl, $C_1$-$C_6$ alkoxy, piperidinyl $C_1$-$C_6$ alkyl, morpholinyl $C_1$-$C_6$ alkyl, piperazinyl $C_1$-$C_6$ alkyl, OH, —$NH_2$, —NH(alkyl), —N(alkyl)(alkyl), —O—$C_1$-$C_4$ alkanoyl, $C_1$-$C_4$ alkyl, $CF_3$, or $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, $C_1$-$C_4$ alkoxy, hydroxy, hydroxy $C_1$-$C_4$ alkyl, $C_1$-$C_4$ dihydroxyalkyl, or halogen.

Embodiment 47. Compounds according to embodiment 46, wherein $R_6$ is hydrogen; and
$R_7$ is $C_1$-$C_6$ alkyl or $C_1$-$C_6$ alkanoyl, each of which is optionally substituted with 1, 2, or 3 groups that are independently $NH_2$, NH($C_1$-$C_6$ alkyl), N($C_1$-$C_6$ alkyl)($C_1$-$C_6$ alkyl), OH, SH, cyclopropyl, or $C_1$-$C_4$ alkoxy;

Embodiment 48. Compounds according to embodiment 47, wherein $X_c$ is —C(O)$NR_6R_7$.

Embodiment 49. Compounds according to embodiment 47, wherein $X_c$ is $NR_6R_7$, or $R_6R_7$N—($C_1$-$C_6$ alkyl)-.

Embodiment 50. Compounds according to embodiment 38, wherein $X_a$ is hydrogen;
two of $X_b$, $X_c$, and $X_d$ are hydrogen and the other is —C(O)$NR_6R_7$, —($C_1$-$C_6$ alkyl)-C(O)$NR_6R_7$, —$NR_6R_7$, $R_6R_7$N—($C_1$-$C_6$ alkyl)- or —$CO_2$—($C_1$-$C_6$)alkyl; wherein $R_6$ and $R_7$ are independently at each occurrence H, $C_1$-$C_6$ alkyl, $C_1$-$C_6$ alkoxy, $C_1$-$C_6$ alkoxy $C_1$-$C_6$ alkyl, $C_1$-$C_6$ alkoxycarbonyl, OH, $C_1$-$C_6$ hydroxyalkyl, $C_1$-$C_6$ dihydroxyalkyl, —($C_1$-$C_4$)alkyl-$CO_2$-alkyl, pyridyl $C_1$-$C_6$ alkyl, $C_1$-$C_6$ alkanoyl, benzyl, phenyl $C_1$-$C_6$ alkoxy, or phenyl $C_1$-$C_6$ alkanoyl, wherein each of the above is unsubstituted or substituted with 1, 2, or 3 groups that are independently, halogen, $C_3$-$C_6$ cycloalkyl, $C_1$-$C_6$ alkoxy, piperidinyl $C_1$-$C_6$ alkyl, morpholinyl $C_1$-$C_6$ alkyl, piperazinyl $C_1$-$C_6$ alkyl, OH, $NH_2$, NH(alkyl), N(alkyl)(alkyl), —O—$C_1$-$C_4$ alkanoyl, $C_1$-$C_4$ alkyl, $CF_3$, or $OCF_3$; or $R_6$, $R_7$, and the nitrogen to which they are attached form a morpholinyl, piperidinyl, pyrrolidinyl, or piperazinyl ring which is optionally substituted with 1 or 2 groups that are independently $C_1$-$C_4$ alkyl, $C_1$-$C_4$ alkoxy, hydroxy, hydroxy $C_1$-$C_4$ alkyl, $C_1$-$C_4$ dihydroxyalkyl, or halogen; and $X_e$ is hydrogen, methyl, $C_1$-$C_2$ alkoxy, or halogen.

Embodiment 51. Compounds according to embodiment 50, wherein $X_b$ is —C(O)$NR_6R_7$, —($C_1$-$C_6$ alkyl)-C(O)$NR_6R_7$, —$NR_6R_7$, or $R_6R_7$N—($C_1$-$C_6$ alkyl)- wherein $R_6$ is hydrogen or $C_1$-$C_4$ alkyl;

$R_7$ is OH, $C_1$-$C_6$ alkyl or $C_1$-$C_6$ alkanoyl, wherein the alkyl and alkanoyl groups substituted with 1, 2, or 3 groups that are independently $NH_2$, NH($C_1$-$C_6$ alkyl), N($C_1$-$C_6$ alkyl)($C_1$-$C_6$ alkyl), $C_3$-$C_6$ cycloalkyl, OH, or $C_1$-$C_4$ alkoxy.

Embodiment 52. Compounds according to embodiment 38, wherein $X_a$ is halogen or methyl;

$X_b$ is H, —$NR_6R_7$, $R_6R_7$N—($C_1$-$C_6$ alkyl)-, —C(O)$NR_6R_7$, or —$CO_2$—($C_1$-$C_6$)alkyl;

$X_c$ is —$NR_6R_7$, $R_6R_7$N—($C_1$-$C_6$ alkyl)-, —C(O)$NR_6R_7$, halogen, —$CO_2$—($C_1$-$C_6$)alkyl, $NH_2$, NH($C_1$-$C_6$ alkyl), N($C_1$-$C_6$ alkyl)($C_1$-$C_6$ alkyl), —$SO_2NH_2$, —$SO_2$NH($C_1$-$C_6$ alkyl), —$SO_2$N($C_1$-$C_6$ alkyl)($C_1$-$C_6$ alkyl), or piperazinyl, wherein the piperazinyl group is optionally substituted with 1 or 2 groups that are independently $C_1$-$C_4$ alkyl, $C_1$-$C_4$ alkoxy, hydroxy, hydroxy $C_1$-$C_4$ alkyl, $C_1$-$C_4$ dihydroxyalkyl, or halogen;

$X_d$ is hydrogen;

$X_e$ is H, methyl, $NH_2$, NH($C_1$-$C_6$ alkyl) or N($C_1$-$C_6$ alkyl)($C_1$-$C_6$ alkyl).

Embodiment 53. Compounds according to embodiment 38, wherein $X_1$, $X_2$, $X_a$, $X_b$, $X_c$, $X_d$, and $X_e$ are independently selected from H, OH, halogen, $CF_3$, alkyl, $OCF_3$, pyridyl, pyridazinyl, pyrimidyl, pyrazinyl, thienyl, furyl, pyrrolyl, piperidinyl, piperazinyl, or $C_3$-$C_7$ cycloalkyl, wherein each of the above is optionally substituted with —$NR_6R_7$, —C(O)$NR_6R_7$, —($C_1$-$C_4$ alkyl)-C(O)$NR_6R_7$, $R_6R_7$N—($C_1$-$C_6$ alkyl)-, $C_1$-$C_6$ alkyl, $C_1$-$C_6$ alkoxy, or halogen.

Embodiment 54. Compounds according to embodiment 37, wherein $R_5$ is a heteroaryl or heteroarylalkyl group, where each heteroaryl is pyrazolyl, imidazolyl, furanyl, pyridyl, pyridazinyl, pyrimidinyl, pyrazinyl, pyrazolyl, imidazolyl, dihydroindolyl, dihydroisoindolyl, indolon-2-yl, quinolinyl, isoquinolinyl, tetrahydroisoquinolinyl, dihydroisoquinolinyl, or indolyl, each of which is optionally substituted with 1, 2, 3, or 4 groups that are independently —C(O)$NR_6R_7$, —($C_1$-$C_4$ alkyl)-C(O)$NR_6R_7$, —$NR_6R_7$, hydroxy($C_1$-$C_4$)alkyl, $C_1$-$C_4$ dihydroxyalkyl, hydrogen, hydroxy, halogen, haloalkyl, alkyl, haloalkoxy, $R_6R_7$N—($C_1$-$C_6$ alkyl)-, —$CO_2$—($C_1$-$C_6$)alkyl, —N(R)C(O)$NR_6R_7$, or —N(R)C(O)—($C_1$-$C_6$)alkoxy; wherein $R_6$ and $R_7$ are independently at each occurrence H, $C_1$-$C_6$ alkyl, $C_1$-$C_6$ alkoxy, $C_1$-$C_6$ alkoxy $C_1$-$C_6$ alkyl, $C_1$-$C_6$ alkoxycarbonyl, OH, $C_1$-$C_6$ hydroxyalkyl, $C_1$-$C_6$ dihydroxyalkyl, $C_1$-$C_6$ thiohydroxyalkyl, —($C_1$-$C_4$)alkyl-$CO_2$-alkyl, pyridyl $C_1$-$C_6$ alkyl, $C_1$-$C_6$ alkanoyl, benzyl, phenyl $C_1$-$C_6$ alkoxy, or phenyl $C_1$-$C_6$ alkanoyl, wherein each of the above is unsubstituted or substituted with 1, 2, or 3 groups that are independently, halogen, $C_3$-$C_6$ cycloalkyl, $C_1$-$C_6$ alkoxy, piperidinyl $C_1$-$C_6$ alkyl, morpholinyl $C_1$-$C_6$ alkyl, piperazinyl $C_1$-$C_6$ alkyl, OH, SH, $NH_2$, NH(alkyl), N(alkyl)(alkyl), —O—$C_1$-$C_4$ alkanoyl, $C_1$-$C_4$ alkyl, $CF_3$, or OCF.

Embodiment 55. Compounds according to embodiment 54, wherein $Y_2$, $Y_4$, and Y are independently halogen; and $Y_1$ and $Y_3$ are both hydrogen.

Embodiment 56. Compounds according to embodiment 55, wherein $X_1$ and $X_2$ are independently H, methyl, —$NR_6R_7$, $R_6R_7$N—($C_1$-$C_6$ alkyl)-, —C(O)$NR_6R_7$, —($C_1$-$C_4$ alkyl)-C(O)$NR_6R_7$, $C_1$-$C_6$ hydroxyalkyl, $C_1$-$C_6$ dihydroxyalkyl, or —($C_1$-$C_4$ alkyl)-morpholinyl.

Embodiment 57. Compounds according to embodiment 56, wherein $R_5$ is pyridyl $C_1$-$C_6$ alkyl, pyrimidinyl $C_1$-$C_6$ alkyl, or pyrazinyl $C_1$-$C_6$ alkyl, each of which is optionally substituted with 1, 2, or 3 groups that are independently hydroxy($C_1$-$C_4$)alkyl, $C_1$-$C_4$ dihydroxyalkyl, OH, halogen, $CF_3$, ($C_1$-$C_4$)alkyl, $OCF_3$, —$NR_6R_7$, —($C_1$-$C_4$ alkyl)-C(O)$NR_6R_7$, $R_6R_7$N—($C_1$-$C_6$ alkyl)-, or —C(O)$NR_6R_7$.

Embodiment 58. Compounds according to embodiment 57, wherein $R_5$ is of the formula:

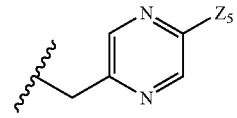

wherein $Z_5$ is hydroxy($C_1$-$C_4$)alkyl, $C_1$-$C_4$ dihydroxyalkyl, OH, halogen, $CF_3$, ($C_1$-$C_4$)alkyl, $OCF_3$, —$NR_6R_7$, $R_6R_7$N—($C_1$-$C_6$ alkyl)-, —($C_1$-$C_4$ alkyl)-C(O)$NR_6R_7$, or —C(O)$NR_6R_7$, wherein $R_6$ and $R_7$ at each occurrence are independently H, $C_1$-$C_6$ alkyl optionally substituted with 1, 2, or 3 groups that are independently $C_1$-$C_4$ alkoxycarbonyl, halogen, $C_3$-$C_6$ cycloalkyl, OH, SH, or $C_1$-$C_4$ alkoxy.

Embodiment 59. Compounds according to embodiment 57, wherein $R_5$ is of the formula:

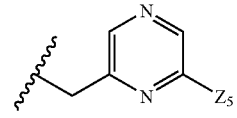

wherein $Z_5$ is hydroxy($C_1$-$C_4$)alkyl, $C_1$-$C_4$ dihydroxyalkyl, OH, halogen, $CF_3$, ($C_1$-$C_4$)alkyl, $OCF_3$, —$NR_6R_7$, $R_6R_7$N—($C_1$-$C_6$ alkyl)-, —($C_1$-$C_4$ alkyl)-C(O)$NR_6R_7$, or —C(O)$NR_6R_7$, wherein $R_6$ and $R_7$ at each occurrence are independently H, $C_1$-$C_6$ alkyl optionally substituted with 1, 2, or 3 groups that are independently $C_1$-$C_4$ alkoxycarbonyl, halogen, $C_3$-$C_6$ cycloalkyl, OH, SH, or $C_1$-$C_4$ alkoxy.

Embodiment 60. Compounds according to embodiment 57, wherein
$R_5$ is of the formula:

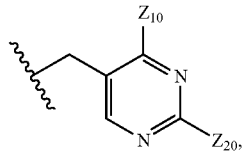

wherein
$Z_{10}$ is H or methyl; and
$Z_{20}$ is —($C_1$-$C_4$ alkyl)-C(O)$NR_6R_7$, hydroxy($C_1$-$C_4$)alkyl, $C_1$-$C_4$ dihydroxyalkyl, OH, halogen, $CF_3$, ($C_1$-$C_4$)alkyl, $OCF_3$, —$NR_6R_7$, $R_6R_7N$—($C_1$-$C_6$ alkyl)-, or —C(O)$NR_6R_7$, wherein
$R_6$ and $R_7$ at each occurrence are independently H, $C_1$-$C_6$ alkyl optionally substituted with 1, 2, or 3 groups that are independently $C_1$-$C_4$ alkoxycarbonyl, halogen, $C_3$-$C_6$ cycloalkyl, OH, SH, or $C_1$-$C_4$ alkoxy.

Embodiment 61. Compounds according to embodiment 57, wherein
$R_5$ is of the formula:

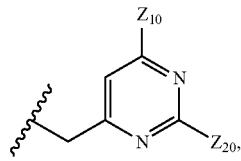

wherein
$Z_{10}$ is H or methyl; and
$Z_{20}$ is —($C_1$-$C_4$ alkyl)-C(O)$NR_6R_7$, hydroxy($C_1$-$C_4$)alkyl, $C_1$-$C_4$ dihydroxyalkyl, OH, halogen, $CF_3$, ($C_1$-$C_4$)alkyl, $OCF_3$, —$NR_6R_7$, $R_6R_7N$—($C_1$-$C_6$ alkyl)-, or —C(O)$NR_6R_7$, wherein
$R_6$ and $R_7$ at each occurrence are independently H, $C_1$-$C_6$ alkyl optionally substituted with 1, 2, or 3 groups that are independently $C_1$-$C_4$ alkoxycarbonyl, halogen, $C_3$-$C_6$ cycloalkyl, OH, SH, or $C_1$-$C_4$ alkoxy.

Embodiment 62. Compounds according to embodiment 57, wherein
$R_5$ is of the formula:

wherein
$Z_{10}$ is H or methyl; and
$Z_{20}$ is —($C_1$-$C_4$ alkyl)-C(O)$NR_6R_7$, hydroxy($C_1$-$C_4$)alkyl, $C_1$-$C_4$ dihydroxyalkyl, OH, halogen, $CF_3$, ($C_1$-$C_4$)alkyl, $OCF_3$, —$NR_6R_7$, $R_6R_7N$—($C_1$-$C_6$ alkyl)-, or —C(O)$NR_6R_7$, wherein
$R_6$ and $R_7$ at each occurrence are independently H, $C_1$-$C_6$ alkyl optionally substituted with 1, 2, or 3 groups that are independently $C_1$-$C_4$ alkoxycarbonyl, halogen, $C_3$-$C_6$ cycloalkyl, OH, SH, or $C_1$-$C_4$ alkoxy.

Embodiment 63. Compounds according to embodiment 57, wherein
$R_5$ is of the formula:

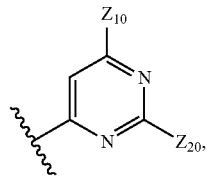

wherein
$Z_{10}$ is H or methyl; and
$Z_{20}$ is —($C_1$-$C_4$ alkyl)-C(O)$NR_6R_7$, hydroxy($C_1$-$C_4$)alkyl, $C_1$-$C_4$ dihydroxyalkyl, OH, halogen, $CF_3$, ($C_1$-$C_4$)alkyl, $OCF_3$, —$NR_6R_7$, $R_6R_7N$—($C_1$-$C_6$ alkyl)-, or —C(O)$NR_6R_7$, wherein
$R_6$ and $R_7$ at each occurrence are independently H, $C_1$-$C_6$ alkyl optionally substituted with 1, 2, or 3 groups that are independently $C_1$-$C_4$ alkoxycarbonyl, halogen, $C_3$-$C_6$ cycloalkyl, OH, SH, or $C_1$-$C_4$ alkoxy.

Embodiment 64. Compounds according to embodiment 57, wherein
$R_5$ is of the formula:

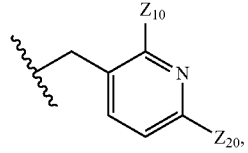

wherein
$Z_{10}$ is H or methyl; and
$Z_{20}$ is —($C_1$-$C_4$ alkyl)-C(O)$NR_6R_7$, hydroxy($C_1$-$C_4$)alkyl, $C_1$-$C_4$ dihydroxyalkyl, OH, halogen, $CF_3$, ($C_1$-$C_4$)alkyl, $OCF_3$, —$NR_6R_7$, $R_6R_7N$—($C_1$-$C_6$ alkyl)-, or —C(O)$NR_6R_7$, wherein
$R_6$ and $R_7$ at each occurrence are independently H, $C_1$-$C_6$ alkyl optionally substituted with 1, 2, or 3 groups that are independently $C_1$-$C_4$ alkoxycarbonyl, halogen, $C_3$-$C_6$ cycloalkyl, OH, SH, or $C_1$-$C_4$ alkoxy.

Embodiment 65. Compounds according to embodiment 57, wherein
$R_5$ is of the formula:

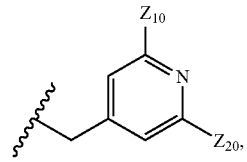

wherein
$Z_{10}$ is H or methyl; and
$Z_{20}$ is —($C_1$-$C_4$ alkyl)-C(O)$NR_6R_7$, hydroxy($C_1$-$C_4$)alkyl, $C_1$-$C_4$ dihydroxyalkyl, OH, halogen, $CF_3$, ($C_1$-$C_4$)alkyl, $OCF_3$, —$NR_6R_7$, $R_6R_7N$—($C_1$-$C_6$ alkyl)-, or —C(O)$NR_6R_7$, wherein
$R_6$ and $R_7$ at each occurrence are independently H, $C_1$-$C_6$ alkyl optionally substituted with 1, 2, or 3 groups that are independently $C_1$-$C_4$ alkoxycarbonyl, halogen, $C_3$-$C_6$ cycloalkyl, OH, SH, or $C_1$-$C_4$ alkoxy.

Embodiment 66. Compounds according to embodiment 57, wherein $R_5$ is of the formula:

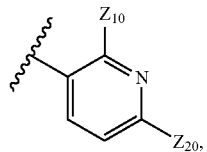

wherein $Z_{10}$ is H or methyl; and $Z_{20}$ is —($C_1$-$C_4$ alkyl)-C(O)$NR_6R_7$, hydroxy($C_1$-$C_4$)alkyl, $C_1$-$C_4$ dihydroxyalkyl, OH, halogen, $CF_3$, ($C_1$-$C_4$)alkyl, $OCF_3$, —$NR_6R_7$, $R_6R_7$N—($C_1$-$C_6$ alkyl)-, or —C(O)$NR_6R_7$, wherein $R_6$ and $R_7$ at each occurrence are independently H, $C_1$-$C_6$ alkyl optionally substituted with 1, 2, or 3 groups that are independently $C_1$-$C_4$ alkoxycarbonyl, halogen, $C_3$-$C_6$ cycloalkyl, OH, SH, or $C_1$-$C_4$ alkoxy.

Embodiment 67. Compounds according to embodiment 57, wherein $R_5$ is of the formula:

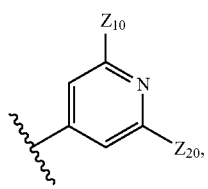

wherein $Z_{10}$ is H or methyl; and $Z_{20}$ is —($C_1$-$C_4$ alkyl)-C(O)$NR_6R_7$, hydroxy($C_1$-$C_4$)alkyl, $C_1$-$C_4$ dihydroxyalkyl, OH, halogen, $CF_3$, ($C_1$-$C_4$)alkyl, $OCF_3$, —$NR_6R_7$, $R_6R_7$N—($C_1$-$C_6$ alkyl)-, or —C(O)$NR_6R_7$, wherein $R_6$ and $R_7$ at each occurrence are independently H, $C_1$-$C_6$ alkyl optionally substituted with 1, 2, or 3 groups that are independently $C_1$-$C_4$ alkoxycarbonyl, halogen, $C_3$-$C_6$ cycloalkyl, OH, SH, or $C_1$-$C_4$ alkoxy.

Embodiment 68. Compounds according to embodiment 3, wherein $R_4$ is H, alkyl optionally substituted with one or two groups that are independently $CO_2R$, —$CO_2$alkyl, —C(O)$NR_6R_7$, —C(O)$R_6$, —N($R_{30}$) C(O)$NR_{16}R_{17}$, —N($R_{30}$)C(O)—($C_1$-$C_6$)alkoxy, or —$NR_6R_7$, —C(O)$NR_6R_7$, phenyl($C_1$-$C_6$)alkoxy, phenyl($C_1$-$C_6$)alkyl, hydroxyalkyl, dihydroxyalkyl, haloalkyl, alkoxy, hydroxyalkoxy-, ($R_6R_7$N)-alkoxy-, $R_6R_7$NC(O)-alkoxy-, $R_6$C(O)N($R_7$)alkoxy-, alkoxyalkyl, or alkoxyalkoxy, wherein the phenyl groups are unsubstituted or substituted with 1, 2, 3, 4, or 5 groups that are independently halogen, hydroxy, alkoxy, alkyl, nitro, $CF_3$, $OCF_3$.

Embodiment 69. Compounds according to embodiment 1 wherein $R_1$ is H, halogen, alkyl optionally substituted with $C_1$-$C_4$ alkoxycarbonyl, $C_2$-$C_6$ alkenyl optionally substituted with $C_1$-$C_4$ alkoxycarbonyl, $C_2$-$C_4$ alkynyl, $C_1$-$C_4$ haloalkyl, carboxaldehyde, $C_1$-$C_4$ hydroxyalkyl, phenyl($C_1$-$C_6$)alkoxy, benzyl, phenethyl, phenpropyl, CN, or phenyl($C_1$-$C_6$)alkanoyl, wherein the phenyl groups are unsubstituted or substituted with 1, 2, or 3 groups that are independently halogen, $C_1$-$C_4$ alkyl, $C_1$-$C_4$ alkoxy, nitro, CN, $CF_3$, $OCF_3$ or $CO_2H$;

$R_2$ is OH, benzyloxy, phenyloxy, phenyloxy($C_1$-$C_6$)alkyl, phenyl ($C_1$-$C_4$)thioalkoxy, —OC(O)NH($CH_2$)$_n$phenyl, —OC(O)N(alkyl)($CH_2$)$_n$phenyl, di($C_1$-$C_6$)alkylamino, $C_2$-$C_6$ alkynyl, pyridyl, pyrimidyl, pyridazyl, pyrazolyl, imidazolyl, pyrrolyl, tetrahydroquinolinyl, tetrahydroisoquinolinyl, tetrazolyl, pyrazinyl, benzimidazolyl, triazinyl, tetrahydrofuryl, piperidinyl, hexahydropyrimidinyl, thiazolyl, thienyl, or $CO_2H$, wherein n is 0, 1, 2, 3, 4, 5 or 6;

each of the above is unsubstituted or substituted with 1, 2, 3, 4, or 5 groups that are independently halogen, $NR_6R_7$, ($C_1$-$C_4$)haloalkyl, ($C_1$-$C_4$)haloalkoxy, ($C_1$-$C_6$) alkyl, pyridyl, —($C_1$-$C_6$)alkyl-N(R)—$CO_2R_{30}$, or $NR_6R_7$—($C_1$-$C_6$ alkyl)-, $R_4$ is H, alkyl optionally substituted with one or two groups that are independently $CO_2H$, —$CO_2$alkyl, —C(O)NRR, —N($R_{30}$)C(O)NRR, —N($R_{30}$)C(O)—($C_1$-$C_6$)alkoxy, or —$NR_6R_7$, phenyl($C_1$-$C_6$)alkoxy, phenyl($C_1$-$C_6$)alkyl, hydroxyalkyl, wherein the phenyl groups are unsubstituted or substituted with 1, 2, 3, 4, or 5 groups that are independently halogen, hydroxy, alkoxy, alkyl, nitro, $CF_3$, or $OCF_3$; and $R_5$ is phenyl($C_1$-$C_6$)alkyl, ($C_1$-$C_6$)alkyl, phenyl, piperidinyl ($C_1$-$C_6$)alkyl, thienyl($C_1$-$C_6$)alkyl, indolyl, quinolinyl, isoquinolinyl, isoindolyl, indol-2-onyl, indazolyl, indolyl($C_1$-$C_6$)alkyl, quinolinyl($C_1$-$C_6$)alkyl, isoquinolinyl($C_1$-$C_6$) alkyl, isoindolyl($C_1$-$C_6$)alkyl, indol-2-onyl($C_1$-$C_6$)alkyl, naphthyl($C_1$-$C_6$)alkyl, pyridyl($C_1$-$C_6$)alkyl, pyrimidyl ($C_1$-$C_6$)alkyl, pyrazinyl($C_1$-$C_6$)alkyl, or wherein each of the above is unsubstituted or substituted with 1, 2, 3, 4, or 5 groups that are independently alkyl, halogen, alkoxy, benzyloxy, thioalkoxy, —$CO_2$($C_1$-$C_5$ alkyl), $CO_2H$, CN, amidinooxime, $NR_8R_9$, $NR_6R_7$—($C_1$-$C_6$ alkyl)-, —C(O)$NR_6R_7$, amidino, $CF_3$, or $OCF_3$;

$R_8$ is hydrogen, $C_1$-$C_6$ alkyl, $C_1$-$C_6$ alkanoyl, phenyl $C_1$-$C_6$ alkyl and phenyl —$C_1$-$C_6$ alkanoyl; and $R_9$ is aminoalkyl, mono $C_1$-$C_6$ alkylamino $C_1$-$C_6$ alkyl, di $C_1$-$C_6$ alkylamino $C_1$-$C_6$ alkyl, $C_1$-$C_6$ alkyl, $C_1$-$C_6$ alkanoyl, phenyl $C_1$-$C_4$ alkyl, indazolyl, and phenyl $C_1$-$C_4$ alkanoyl.

In this embodiment, it is preferred that when $R_2$ is benzyloxy, $R_4$ is H, and $R_5$ is benzyl or methyl, $R_1$ is not hydrogen; and no more than two of $R_1$, $R_2$, $R_4$, and $R_5$ are simultaneously hydrogen.

Embodiment 70. Compounds according to embodiment 69 wherein $R_1$ is H, halogen, $C_1$-$C_4$ alkyl optionally substituted with $C_1$-$C_4$ alkoxycarbonyl, $C_2$-$C_4$ alkenyl optionally substituted with $C_1$-$C_4$ alkoxycarbonyl, $C_2$-$C_4$ alkynyl, or carboxaldehyde;

$R_2$ is benzyloxy, OH, phenyloxy, phenyloxy($C_1$-$C_6$)alkyl, phenyl ($C_1$-$C_4$)thioalkoxy, or pyridyl; wherein each of the above is optionally substituted with 1, 2, 3, 4, or 5 groups that are independently halogen, —($C_1$-$C_6$)alkyl-N(R)—$CO_2R_{30}$, $NR_6R_7$, ($C_1$-$C_4$)haloalkyl, ($C_1$-$C_4$)haloalkoxy, ($C_1$-$C_6$)alkyl, pyridyl, or $NR_6R_7$—($C_1$-$C_6$ alkyl)-.

Embodiment 71. Compounds according to embodiment 69 wherein $R_4$ is H, $(C_1-C_6)$alkyl optionally substituted with one or two groups that are independently $CO_2H$, —$CO_2$alkyl, —C(O)NRR, —N($R_{30}$)C(O)NRR, —N($R_{30}$)C(O)—$(C_1-C_6)$alkoxy, or —$NR_6R_7$, phenyl$(C_1-C_6)$alkoxy, or hydroxy$(C_1-C_6)$alkyl, wherein the phenyl groups are unsubstituted or substituted with 1, 2, or 3 groups that are independently halogen, hydroxy, $C_1-C_4$ alkoxy, $C_1-C_4$ alkyl, nitro, $CF_3$, $OCF_3$; and $R_5$ is benzyl, phenethyl, phenpropyl, phenbutyl, $(C_1-C_6)$alkyl, phenyl, pyridyl, pyrimidyl, indolyl, indazolyl, indolyl $(C_1-C_6)$alkyl, naphthyl$(C_1-C_6)$alkyl, thienyl$(C_1-C_6)$alkyl, pyridyl$(C_1-C_6)$alkyl, pyrimidyl$(C_1-C_6)$alkyl, or pyrazinyl$(C_1-C_6)$alkyl, and wherein each of the above is unsubstituted or substituted with 1, 2, or 3 groups that are independently alkyl, halogen, alkoxy, benzyloxy, thioalkoxy, —$CO_2(C_1-C_5$ alkyl), $CF_3$, $OCF_3$, $CO_2H$, CN, amidinooxime.

In this embodiment, it is preferred that when $R_2$ is benzyloxy, $R_4$ is H, and $R_5$ is benzyl or methyl, $R_1$ is not hydrogen; and no more than two of $R_1$, $R_2$, $R_4$, and $R_5$ are simultaneously hydrogen.

Embodiment 72. Compounds according to embodiment 69, wherein $R_4$ is H, $(C_1-C_4)$alkyl optionally substituted with one or two groups that are independently $CO_2H$, —$CO_2$alkyl, —C(O)NRR, —N($R_{30}$)C(O)NRR, —N($R_{30}$)C(O)—$(C_1-C_6)$alkoxy, or —$NR_6R_7$, phenyl$(C_1-C_6)$alkoxy, benzyl, phenethyl, phenpropyl, or hydroxy$(C_1-C_6)$alkyl, wherein the phenyl groups are unsubstituted or substituted with 1, 2, or 3 groups that are independently halogen, hydroxy, $C_1-C_4$ alkoxy, $C_1-C_4$ alkyl, nitro, $CF_3$, $OCF_3$; and $R_5$ is indolyl, quinolinyl, isoquinolinyl, isoindolyl, indol-2-onyl, indolyl$(C_1-C_6)$alkyl, quinolinyl$(C_1-C_6)$alkyl, isoquinolinyl$(C_1-C_6)$alkyl, isoindolyl$(C_1-C_6)$alkyl, indol-2-onyl$(C_1-C_6)$alkyl, each of which is unsubstituted or substituted with 1, 2, or 3 groups that are independently $C_1-C_4$ alkyl, halogen, $CF_3$, $OCF_3$, —$CO_2CH_3$, $C_1-C_4$ hydroxyalkyl, $C_1-C_4$ alkoxy, —$CO_2(C_1-C_5$ alkyl), benzyloxy, —$NR_8R_9$, $NR_6R_7$—$(C_1-C_6$ alkyl)-, —$C(O)NR_6R_7$, or amidinooxime; wherein $R_6$ and $R_7$ are independently at each occurrence H, alkyl, hydroxyalkyl, alkoxy, alkoxyalkyl, alkanoyl, phenylalkyl, phenylalkoxy, or phenylalkanoyl, wherein each is unsubstituted or substituted with 1, 2, or 3 groups that are independently, halogen, hydroxy, $C_1-C_4$ alkoxy, OH, SH, $C_3-C_6$ cycloalkyl, $C_1-C_4$ alkyl, $CF_3$, or $OCF_3$; or $R_6$, $R_7$, and the nitrogen to which they are attached form a morpholinyl, thiomorpholinyl, or piperazinyl ring which is optionally substituted with 1 or 2 groups that are independently $C_1-C_4$ alkyl, hydroxy, hydroxy $C_1-C_4$ alkyl, or halogen.

Embodiment 73. Compounds according to embodiment 69 wherein $R_1$ is chloro, bromo, iodo, or H; and $R_5$ is benzyl, phenethyl, phenpropyl, phenyl, quinolinyl, indolyl, isoquinolinyl, isoindolyl, indol-2-onyl, indolyl$(C_1-C_6)$alkyl, quinolinyl$(C_1-C_6)$alkyl, isoquinolinyl$(C_1-C_6)$alkyl, isoindolyl$(C_1-C_6)$alkyl, indol-2-onyl$(C_1-C_6)$alkyl, piperidinyl $C_1-C_4$ alkyl, thienyl $C_1-C_4$ alkyl, —$CH_2$-pyridyl, or pyridyl, each of which is unsubstituted or substituted with 1, 2, or 3 groups that are independently $C_1-C_4$ alkyl, halogen, $CF_3$, $OCF_3$, $C_1-C_4$ hydroxyalkyl, $C_1-C_4$ alkoxy, —$CO_2(C_1-C_5$ alkyl), benzyloxy, $NR_8R_9$, $NR_6R_7$ $C_1-C_4$ alkyl, —$C(O)NR_6R_7$, and amidinooxime; wherein $R_6$ and $R_7$ are independently at each occurrence H, alkyl, hydroxyalkyl, alkoxy, alkoxyalkyl, alkanoyl, phenylalkyl, phenylalkoxy, or phenylalkanoyl, wherein each is unsubstituted or substituted with 1, 2, or 3 groups that are independently, halogen, hydroxy, $C_1-C_4$ alkoxy, OH, SH, $C_3-C_6$ cycloalkyl, $C_1-C_4$ alkyl, $CF_3$, or $OCF_3$; or $R_6$, $R_7$, and the nitrogen to which they are attached form a morpholinyl, thiomorpholinyl, or piperazinyl ring which is optionally substituted with 1 or 2 groups that are independently $C_1-C_4$ alkyl, hydroxy, hydroxy $C_1-C_4$ alkyl, or halogen.

Embodiment 74. Compounds according to embodiment 73, wherein $R_5$ is benzyl, phenethyl, phenpropyl, or phenyl, each of which is unsubstituted or substituted with 1, 2, or 3 groups that are independently $C_1-C_4$ alkyl, halogen, $CF_3$, $OCF_3$, —$CO_2CH_3$, $C_1-C_4$ hydroxyalkyl, $C_1-C_4$ alkoxy, —$CO_2(C_1-C_5$ alkyl), benzyloxy, $NR_8R_9$, $NR_6R_7$ $C_1-C_4$ alkyl, —$C(O)NR_6R_7$, and amidinooxime.

Embodiment 75. Compounds according to embodiment 73, wherein $R_5$ is quinolinyl, indolyl, isoquinolinyl, isoindolyl, indol-2-onyl, indolyl$(C_1-C_6)$alkyl, quinolinyl$(C_1-C_6)$alkyl, isoquinolinyl$(C_1-C_6)$alkyl, isoindolyl$(C_1-C_6)$alkyl, indol-2-onyl$(C_1-C_6)$alkyl, piperidinyl $C_1-C_4$ alkyl, thienyl $C_1-C_4$ alkyl, —$CH_2$-pyridyl, or pyridyl, each of which is unsubstituted or substituted with 1, 2, or 3 groups that are independently $C_1-C_4$ alkyl, halogen, $CF_3$, $OCF_3$, —$CO_2CH_3$, $C_1-C_4$ hydroxyalkyl, $C_1-C_4$ alkoxy, —$CO_2(C_1-C_5$ alkyl), benzyloxy, $NR_8R_9$, $NR_6R_7$ $C_1-C_4$ alkyl, —$C(O)NR_6R_7$, and amidinooxime.

Embodiment 76. Compounds according to any one of embodiments 73, 74, or 75 wherein $R_2$ is benzyloxy, or phenethyloxy;
each of the above is unsubstituted or substituted with 1, 2, or 3, groups that are independently —$(C_1-C_6)$alkyl-N(R)—$CO_2R_{30}$, fluoro, chloro, bromo, $CF_3$, or $(C_1-C_4)$alkyl.

Embodiment 77. Compounds according to any one of embodiments 73, 74 or 75 wherein $R_2$ is phenyloxy$(C_1-C_6)$alkyl, wherein the phenyl group is unsubstituted or substituted with 1, 2, or 3, groups that are independently —$(C_1-C_6)$alkyl-N(R)—$CO_2R_{30}$, fluoro, chloro, bromo, $CF_3$, or $(C_1-C_4)$alkyl.

Embodiment 78. Compounds according to embodiment 1 or 69, wherein $R_1$ is H, halogen, $C_1-C_4$ alkyl optionally substituted with $C_1-C_4$ alkoxycarbonyl, $C_2-C_4$ alkenyl optionally substituted with $C_1-C_4$ alkoxycarbonyl, $C_2-C_4$ alkynyl, or carboxaldehyde.

Embodiment 79. Compounds according to embodiment 78, wherein $R_2$ is benzyloxy, OH, phenyloxy, phenyloxy$(C_1-C_6)$alkyl, or phenyl$(C_1-C_4)$thioalkoxy, wherein each of the above is optionally substituted with 1, 2, 3, 4, or 5 groups that are independently halogen, —$(C_1-C_6)$alkyl-N(R)—$CO_2R_{30}$, $NR_6R_7$, $(C_1-C_4)$haloalkyl, $(C_1-C_4)$haloalkoxy, $(C_1-C_6)$alkyl, pyridyl, or $NR_6R_7$—$(C_1-C_6$ alkyl)-.

Embodiment 80. Compounds according to embodiment 79, wherein $R_4$ is H, or $(C_1-C_4)$alkyl optionally substituted with one or two groups that are independently $CO_2H$, —$CO_2$alkyl, —C(O)NRR, —N($R_{30}$)C(O)NRR, —N($R_{30}$)C(O)—$(C_1-C_6)$alkoxy, OH, or —$NR_6R_7$.

Embodiment 81. Compounds according to embodiment 80, wherein $R_5$ is phenyl, naphthyl, indolyl, pyridyl, quinolinyl, isoquinolinyl, isoindolyl, indol-2-onyl, indolyl($C_1$-$C_6$) alkyl, quinolinyl($C_1$-$C_6$)alkyl, isoquinolinyl($C_1$-$C_6$)alkyl, isoindolyl($C_1$-$C_6$)alkyl, indol-2-onyl($C_1$-$C_6$)alkyl, pyridazinyl, pyrimidinyl, or pyrazinyl, pyridazinyl($C_1$-$C_6$) alkyl, pyrimidinyl($C_1$-$C_6$)alkyl, or pyrazinyl($C_1$-$C_6$)alkyl, each of which is unsubstituted or substituted with 1, 2, 3, 4 or 5 groups that are independently $C_1$-$C_4$ alkyl, halogen, $CF_3$, $OCF_3$, —$CO_2CH_3$, $C_1$-$C_4$ hydroxyalkyl, $C_1$-$C_4$ alkoxy, —$CO_2(C_1$-$C_5$ alkyl), benzyloxy, —$NR_8R_9$, —C(O)$NR_6R_7$, $NR_6R_7$ $C_1$-$C_4$ alkyl, and amidinooxime; wherein $R_6$ and $R_7$ are independently at each occurrence H, $C_1$-$C_4$ alkyl, $C_1$-$C_4$ hydroxyalkyl, $C_1$-$C_4$ alkoxy, $C_1$-$C_4$ alkoxy $C_1$-$C_4$ alkyl, $C_1$-$C_4$ alkanoyl, phenyl $C_1$-$C_4$ alkyl, phenyl $C_1$-$C_4$ alkoxy, or phenyl $C_1$-$C_4$ alkanoyl, wherein each is unsubstituted or substituted with 1, 2, or 3 groups that are independently, halogen, hydroxy, $C_1$-$C_4$ alkoxy, $C_1$-$C_4$ alkyl, OH, SH, $C_3$-$C_6$ cycloalkyl, $CF_3$, or $OCF_3$; or $R_6$, $R_7$, and the nitrogen to which they are attached form a morpholinyl, thiomorpholinyl, or piperazinyl ring which is optionally substituted with 1 or 2 groups that are independently $C_1$-$C_4$ alkyl, hydroxy, hydroxy $C_1$-$C_4$ alkyl, or halogen.

Embodiment 82. Compounds according to embodiment 81, wherein $R_1$ is H, halogen, methyl, ethyl, $C_2$-$C_4$ alkenyl $C_2$-$C_4$ alkynyl, or carboxaldehyde;

$R_2$ is benzyloxy, OH, phenyloxy, phenyloxy($C_1$-$C_6$)alkyl, or phenyl($C_1$-$C_4$)thioalkoxy, wherein each of the above is optionally substituted with 1, 2, 3, or 4 groups that are independently halogen, —($C_1$-$C_6$)alkyl-N(R)—$CO_2R_{30}$, $NR_6R_7$, $NR_6R_7$ $C_1$-$C_4$ alkyl, ($C_1$-$C_4$)haloalkyl, ($C_1$-$C_4$)haloalkoxy, ($C_1$-$C_6$)alkyl, or pyridyl; and $R_4$ is H, ($C_1$-$C_4$)alkyl optionally substituted with one or two groups that are independently $CO_2H$, —$CO_2$alkyl, —C(O)NRR, —N($R_{30}$)C(O)NRR, —N($R_{30}$)C(O)—($C_1$-$C_6$) alkoxy, OH, or —$NR_6R_7$.

Embodiment 83. Compounds according to embodiment 82, wherein $R_5$ is phenyl optionally substituted with 1, 2, 3, 4, or 5 groups that are independently halogen, $C_1$-$C_6$ alkyl, —$NR_{10}R_{11}$, $C_1$-$C_4$ alkoxy, —C(O)$NR_{10}R_{11}$, —$CO_2H$, $NR_{10}R_{11}$ $C_1$-$C_4$ alkyl, $C_1$-$C_6$ alkyl, $C_1$-$C_6$ alkoxycarbonyl, $C_1$-$C_6$ alkoxy, CHO, —$SO_2NH_2$, $C_1$-$C_4$ haloalkyl, $C_1$-$C_6$ hydroxyalkyl, —$C_1$-$C_4$ alkyl-$NR_{12}$C(O)$NR_{13}R_{14}$, —$C_1$-$C_4$ alkyl-$NR_{12}$C(O)—($C_1$-$C_4$ alkyl)-$NR_{13}R_{14}$, —$C_1$-$C_4$ alkyl-$NR_{12}$C(O)$OR_{15}$, or —$C_1$-$C_4$ alkyl-$NR_{12}$C(O)—($C_1$-$C_4$ alkyl)-$R_{15}$, wherein $R_{10}$ and $R_{11}$ at each occurrence are independently H, $C_1$-$C_6$ alkyl, amino $C_1$-$C_4$ alkyl, NH($C_1$-$C_6$ alkyl)alkyl, N($C_1$-$C_6$ alkyl)($C_1$-$C_6$ alkyl)$C_1$-$C_6$ alkyl, $C_1$-$C_6$ hydroxyalkyl, $C_1$-$C_6$ alkoxy $C_1$-$C_6$ alkyl, OH, —$SO_2$ ($C_1$-$C_6$ alkyl), or $C_1$-$C_6$ alkanoyl, or $R_{10}$, $R_{11}$, and the nitrogen to which they are attached form a piperidinyl, pyrrolidinyl, piperazinyl, or a morpholinyl ring optionally substituted with 1 or 2 groups that are independently alkyl or halogen, $R_{12}$ is H or $C_1$-$C_6$ alkyl;

$R_{13}$ and $R_{14}$ are independently H or $C_1$-$C_6$ alkyl; or $R_{13}$ and $R_{14}$ and the nitrogen to which they are attached form a morpholinyl ring; and $R_{15}$ is $C_1$-$C_6$ alkoxy; —OC(O)$C_1$-$C_6$ alkyl, OH.

Embodiment 84. Compounds according to embodiment 83, wherein $R_5$ is phenyl optionally substituted with 1, 2, 3, 4, or 5 groups that are independently halogen, $C_1$-$C_6$ alkyl, —$NR_{10}R_{11}$, $NR_{10}R_{11}$ $C_1$-$C_6$ alkyl, $C_1$-$C_4$ alkoxy, or —C(O)$NR_{10}R_{11}$, —$CO_2H$, —$C_1$-$C_4$ alkyl-$NR_{10}R_{11}$, $C_1$-$C_6$ alkyl, $C_1$-$C_6$ alkoxycarbonyl, $C_1$-$C_6$ alkoxy, CHO, —$SO_2NH_2$, $C_1$-$C_4$ haloalkyl, $C_1$-$C_6$ hydroxyalkyl, —$C_1$-$C_4$ alkyl-$NR_{12}$C(O)$NR_{13}R_{14}$, —$C_1$-$C_4$ alkyl-$NR_{12}$C(O)—($C_1$-$C_4$ alkyl)-$NR_{13}R_{14}$, —$C_1$-$C_4$ alkyl-$NR_{12}$C(O)$OR_{15}$, or —$C_1$-$C_4$ alkyl-$NR_{12}$C(O)—($C_1$-$C_4$ alkyl)-$R_{15}$ wherein $R_{10}$ and $R_{11}$ at each occurrence are independently H, $C_1$-$C_6$ alkyl, amino $C_1$-$C_4$ alkyl, NH($C_1$-$C_6$ alkyl)alkyl, N($C_1$-$C_6$ alkyl)($C_1$-$C_6$ alkyl)$C_1$-$C_6$ alkyl, $C_1$-$C_6$ hydroxyalkyl, $C_1$-$C_6$ alkoxy $C_1$-$C_6$ alkyl, OH, —$SO_2$ ($C_1$-$C_6$ alkyl), or $C_1$-$C_6$ alkanoyl, $R_{12}$ is H or $C_1$-$C_6$ alkyl;

$R_{13}$ and $R_{14}$ are independently H or $C_1$-$C_6$ alkyl; or $R_{13}$ and $R_{14}$ and the nitrogen to which they are attached form a morpholinyl ring; and $R_{15}$ is $C_1$-$C_6$ alkoxy; —OC(O)$C_1$-$C_6$ alkyl, OH.

Embodiment 85. Compounds according to embodiment 84, wherein $R_5$ is phenyl optionally substituted with 1, 2, 3, 4, or 5 groups that are independently halogen, $C_1$-$C_6$ alkyl, —$NR_{10}R_{11}$, $NR_{10}R_{11}$ $C_1$-$C_4$ alkyl, $C_1$-$C_4$ alkoxy, —C(O)$NR_{10}R_{11}$, wherein $R_{10}$ and $R_{11}$ at each occurrence are independently H, $C_1$-$C_6$ alkyl, amino $C_1$-$C_4$ alkyl, NH($C_1$-$C_6$ alkyl)alkyl, N($C_1$-$C_6$ alkyl)($C_1$-$C_6$ alkyl)$C_1$-$C_6$ alkyl, $C_1$-$C_6$ hydroxyalkyl, $C_1$-$C_6$ alkoxy $C_1$-$C_6$ alkyl, OH, —$SO_2$ ($C_1$-$C_6$ alkyl), $C_1$-$C_6$ alkanoyl.

Embodiment 86. Compounds according to embodiment 85, wherein $R_5$ is phenyl optionally substituted with 1, 2, 3, 4, or 5 groups that are independently halogen, $C_1$-$C_6$ alkyl, —$NR_{10}R_{11}$, or $C_1$-$C_4$ alkoxy.

Embodiment 87. Compounds according to embodiment 85, wherein $R_5$ is substituted with at least one —C(O)$NR_{10}R_{11}$.

Embodiment 88. Compounds according to embodiment 87, wherein $R_{10}$ and $R_{11}$ at each occurrence are independently H, $C_1$-$C_6$ alkyl, amino $C_1$-$C_4$ alkyl, NH($C_1$-$C_6$ alkyl)alkyl, N($C_1$-$C_6$ alkyl)($C_1$-$C_6$ alkyl)$C_1$-$C_6$ alkyl, $C_1$-$C_6$ hydroxyalkyl, $C_1$-$C_6$ alkoxy $C_1$-$C_6$ alkyl.

Embodiment 89. Compounds according to embodiment 88, wherein $R_{10}$ is H.

Embodiment 90. Compounds according to embodiment 87, wherein $R_{10}$ and $R_{11}$ at each occurrence are independently H, $C_1$-$C_6$ alkyl, OH, —$SO_2$ ($C_1$-$C_6$ alkyl), $C_1$-$C_6$ alkanoyl.

Embodiment 91. Compounds according to embodiment 82, wherein $R_5$ is phenyl optionally substituted with 1, 2, 3, 4, or 5 groups that are independently halogen, $C_1$-$C_6$ alkyl, $NH_2$, NH($C_1$-$C_6$ alkyl), N($C_1$-$C_6$ alkyl)($C_1$-$C_6$ alkyl), $C_1$-$C_4$ alkoxy, —C(O)$NR_{10}R_{11}$, wherein each of the above alkyl groups is optionally substituted with 1 or 2 groups that are independently OH, or methoxy; wherein $R_{10}$, $R_{11}$, and the nitrogen to which they are attached form a piperidinyl, pyrrolidinyl, piperazinyl, or a morpholinyl ring optionally substituted with 1 or 2 groups that are independently alkyl or halogen.

Embodiment 92. Compounds according to embodiment 82, wherein $R_5$ is phenyl optionally substituted with 1, 2, 3, 4, or 5 groups that are independently halogen, $C_1$-$C_6$ alkyl, $C_1$-$C_4$ alkoxy, —$CO_2H$, —$C_1$-$C_4$ alkyl-$NR_{10}R_{11}$, $C_1$-$C_6$ alkoxycarbonyl, $C_1$-$C_6$ alkoxy, CHO, —$SO_2NH_2$, $C_1$-$C_4$ haloalkyl, $C_1$-$C_6$ hydroxyalkyl, —$C_1$-$C_4$ alkyl-$NR_{12}C(O)NR_{13}R_{14}$, —$C_1$-$C_4$ alkyl-$NR_{12}C(O)$—($C_1$-$C_4$ alkyl)-$NR_{13}R_{14}$, —$C_1$-$C_4$ alkyl-$NR_{12}C(O)OR_{15}$, or —$C_1$-$C_4$ alkyl-$NR_{12}C(O)$—($C_1$-$C_4$ alkyl)-$R_{15}$, —$OC(O)C_1$-$C_6$ alkyl, or OH wherein $R_{12}$ is H or $C_1$-$C_6$ alkyl;

$R_{13}$ and $R_{14}$ are independently H or $C_1$-$C_6$ alkyl; or $R_{13}$ and $R_{14}$ and the nitrogen to which they are attached form a morpholinyl ring;

$R_{15}$ is $C_1$-$C_6$ alkoxy.

Embodiment 93. Compounds according to embodiment 92, wherein $R_5$ is phenyl optionally substituted with 1, 2, 3, 4, or 5 groups that are independently halogen, $C_1$-$C_4$ alkyl, $C_1$-$C_4$ alkoxy, —$CO_2H$, $C_1$-$C_4$ alkoxycarbonyl, $C_1$-$C_4$ alkoxy, CHO, $SO_2NH_2$, $C_1$-$C_4$ haloalkyl, $C_1$-$C_4$ hydroxyalkyl.

Embodiment 94. Compounds according to embodiment 92, wherein $R_5$ is phenyl optionally substituted with 1, 2, 3, 4, or 5 groups that are independently halogen, $C_1$-$C_4$ alkyl, $C_1$-$C_4$ alkoxy, —$CO_2H$, —$C_1$-$C_4$ alkyl-$NR_{10}R_{11}$, —$C_1$-$C_4$ alkyl-$NR_{12}C(O)NR_{13}R_{14}$, —$C_1$-$C_4$ alkyl-$NR_{12}C(O)$—($C_1$-$C_4$ alkyl)-$NR_{13}R_{14}$, —$C_1$-$C_4$ alkyl-$NR_{12}C(O)OR_{15}$, or —$C_1$-$C_4$ alkyl-$NR_{12}C(O)$—($C_1$-$C_4$ alkyl)-$R_{15}$, or —$OC(O)C_1$-$C_6$ alkyl, wherein $R_{12}$ is H or $C_1$-$C_6$ alkyl;

$R_{13}$ and $R_{14}$ are independently H or $C_1$-$C_6$ alkyl; or $R_{13}$ and $R_{14}$ and the nitrogen to which they are attached form a morpholinyl ring;

$R_{15}$ is $C_1$-$C_6$ alkoxy.

Embodiment 95. Compounds according to embodiment 94, wherein $R_5$ is phenyl optionally substituted with 1, 2, 3, 4, or 5 groups that are independently halogen, $C_1$-$C_4$ alkyl, $C_1$-$C_4$ alkoxy, —$CO_2H$, —$C_1$-$C_4$ alkyl-$NR_{10}R_{11}$, —$C_1$-$C_4$ alkyl-$NR_{12}C(O)NR_{13}R_{14}$, —$C_1$-$C_4$ alkyl-$NR_{12}C(O)$—($C_1$-$C_4$ alkyl)-$NR_{13}R_{14}$, wherein $R_{12}$ is H or $C_1$-$C_6$ alkyl;

$R_{13}$ and $R_{14}$ are independently H or $C_1$-$C_6$ alkyl; or $R_{13}$ and $R_{14}$ and the nitrogen to which they are attached form a morpholinyl ring.

Embodiment 96. Compounds according to any one of embodiments 92, 93, 94, or 95, wherein the phenyl group is substituted with two groups that are meta to each other.

Embodiment 97. Compounds according to any one of embodiments 92, 93, 94, or 95, wherein the phenyl group is substituted with two groups that are para to each other.

Embodiment 98. Compounds according to embodiment 82, wherein $R_5$ is indolyl, pyridyl, pyridazinyl, pyrimidinyl, indazolyl, quinolinyl, isoquinolinyl, isoindolyl, indol-2-onyl, pyridazinyl, pyrimidinyl, or pyrazinyl, each of which is unsubstituted or substituted with 1, 2, 3, 4 or 5 groups that are independently $C_1$-$C_4$ alkyl, halogen, $CF_3$, $OCF_3$, —$CO_2CH_3$, $C_1$-$C_4$ hydroxyalkyl, $C_1$-$C_4$ alkoxy, —$CO_2$ ($C_1$-$C_5$ alkyl), benzyloxy, $NR_8R_9$, $NR_6R_7$ $C_1$-$C_4$ alkyl, —$C(O)NR_6R_7$, or amidinooxime; wherein $R_6$ and $R_7$ are independently at each occurrence H, $C_1$-$C_4$ alkyl, $C_1$-$C_4$ hydroxyalkyl, $C_1$-$C_4$ alkoxy, $C_1$-$C_4$ alkoxy $C_1$-$C_4$ alkyl, $C_1$-$C_4$ alkanoyl, phenyl $C_1$-$C_4$ alkyl, phenyl $C_1$-$C_4$ alkoxy, or phenyl $C_1$-$C_4$ alkanoyl, wherein each is unsubstituted or substituted with 1, 2, or 3 groups that are independently, halogen, OH, SH, $C_3$-$C_6$ cycloalkyl, $C_1$-$C_4$ alkoxy, $C_1$-$C_4$ alkyl, OH, $CF_3$, or $OCF_3$; or $R_6$, $R_7$, and the nitrogen to which they are attached form a morpholinyl, thiomorpholinyl, or piperazinyl ring which is optionally substituted with 1 or 2 groups that are independently $C_1$-$C_4$ alkyl, hydroxy, hydroxy $C_1$-$C_4$ alkyl, or halogen.

Embodiment 99. Compounds according to embodiment 98, wherein $R_5$ is indolyl, pyridyl, pyrimidinyl, indazolyl, or pyrazinyl, each of which is unsubstituted or substituted with 1, 2, 3, or 4 groups that are independently $C_1$-$C_4$ alkyl, halogen, $CF_3$, $OCF_3$, —$CO_2CH_3$, $C_1$-$C_4$ hydroxyalkyl, $C_1$-$C_4$ alkoxy, —$CO_2(C_1$-$C_5$ alkyl), benzyloxy, —$C(O)NR_6R_7$, —$NR_8R_9$, $NR_6R_7$ $C_1$-$C_4$ alkyl, and amidinooxime; wherein $R_6$ and $R_7$ are independently at each occurrence H, $C_1$-$C_4$ alkyl, $C_1$-$C_4$ hydroxyalkyl, $C_1$-$C_4$ alkoxy, $C_1$-$C_4$ alkoxy $C_1$-$C_4$ alkyl, $C_1$-$C_4$ alkanoyl, phenyl $C_1$-$C_4$ alkyl, phenyl $C_1$-$C_4$ alkoxy, or phenyl $C_1$-$C_4$ alkanoyl, wherein each is unsubstituted or substituted with 1, 2, or 3 groups that are independently, halogen, OH, SH, $C_3$-$C_6$ cycloalkyl, $C_1$-$C_4$ alkoxy, $C_1$-$C_4$ alkyl, OH, $CF_3$, or $OCF_3$.

Embodiment 100. Compounds according to embodiment 99, wherein $R_5$ is indolyl, pyridyl, or pyrazinyl, each of which is unsubstituted or substituted with 1, 2, 3, or 4 groups that are independently $C_1$-$C_4$ alkyl, halogen, $CF_3$, $OCF_3$, —$CO_2CH_3$, $C_1$-$C_4$ hydroxyalkyl, $C_1$-$C_4$ alkoxy, —$CO_2$ ($C_1$-$C_5$ alkyl), benzyloxy, —$C(O)NR_6R_7$, $NR_8R_9$, $NR_6R_7$—$C_1$-$C_4$ alkyl-, and amidinooxime; wherein $R_6$ and $R_7$ are independently at each occurrence H, $C_1$-$C_4$ alkyl, $C_1$-$C_4$ hydroxyalkyl, $C_1$-$C_4$ alkoxy, $C_1$-$C_4$ alkoxy $C_1$-$C_4$ alkyl, each of which is optionally substituted with 1, 2, or 3 groups that are independently halogen, OH, SH, $C_3$-$C_6$ cycloalkyl, $C_1$-$C_4$ alkoxy, $C_1$-$C_4$ alkyl, OH, $CF_3$, or $OCF_3$.

Embodiment 101. Compounds according to embodiment 98, wherein $R_5$ is indolyl, pyridyl, pyridazinyl, pyrimidinyl, or pyrazinyl, each of which is unsubstituted or substituted with 1, 2, 3, 4 or 5 groups that are independently $C_1$-$C_4$ alkyl, halogen, $CF_3$, $OCF_3$, —$CO_2CH_3$, $C_1$-$C_4$ hydroxyalkyl, $C_1$-$C_4$ alkoxy, —$CO_2(C_1$-$C_5$ alkyl), benzyloxy, —$C(O)NH_2$, —$C(O)NH(C_1$-$C_6$ alkyl) wherein the alkyl group is optionally substituted with OH or methoxy, —$C(O)N(C_1$-$C_6$ alkyl)($C_1$-$C_6$ alkyl) wherein each alkyl group is independently and optionally substituted with OH or methoxy, —$C(O)NR_6R_7$, $NR_8R_9$, $NR_6R_7$ $C_1$-$C_4$ alkyl, —$C_1$-$C_4$ alkyl-$NH_2$, —$C_1$-$C_4$ alkyl-$NH(C_1$-$C_6$ alkyl) wherein each alkyl group is independently and optionally substituted with OH or methoxy, —$C_1$-$C_4$ alkyl-$N(C_1$-$C_6$ alkyl)($C_1$-$C_6$ alkyl) wherein each alkyl group is independently and optionally substituted with OH or methoxy, and amidinooxime; wherein $R_6$, $R_7$, and the nitrogen to which they are attached form a morpholinyl, thiomorpholinyl, or piperazinyl ring which is optionally substituted with 1 or 2 groups that are independently $C_1$-$C_4$ alkyl, hydroxy, hydroxy $C_1$-$C_4$ alkyl, or halogen.

Embodiment 102. Compounds according to any one of embodiments 98, 99, 100, or 101, wherein $R_1$ is H, halogen, methyl, or carboxaldehyde;

$R_2$ is benzyloxy, phenyloxy, phenyloxy($C_1$-$C_6$)alkyl, or phenyl ($C_1$-$C_4$)thioalkoxy, wherein each of the above is optionally substituted with 1, 2, 3, or 4 groups that are independently halogen, —($C_1$-$C_6$)alkyl-N(R)—$CO_2R_{30}$, $NR_6R_7$, $(C_1-C_4)$haloalkyl, $(C_1-C_4)$haloalkoxy, $(C_1-C_6)$ alkyl, $NR_6R_7(C_1-C_6)$alkyl, pyridyl, morpholinyl, thiomorpholinyl, piperazinyl pyridyl$(C_1-C_6)$alkyl, morpholinyl $(C_1-C_6)$alkyl, thiomorpholinyl$(C_1-C_6)$alkyl, or piperazinyl $(C_1-C_6)$alkyl wherein the pyridyl, morpholinyl, thiomorpholinyl, and piperazinyl rings are optionally substituted with 1 or 2 groups that are independently $C_1-C_4$ alkyl, or halogen; wherein $R_6$ and $R_7$ are independently at each occurrence H, $C_1-C_4$ alkyl optionally substituted with 1 or two groups that are independently OH, halogen or methoxy, $C_1-C_4$ hydroxyalkyl, $C_1-C_4$ alkoxy, $C_1-C_4$ alkoxy $C_1-C_4$ alkyl, $C_1-C_4$ alkanoyl, benzyl, benzyloxy, or phenyl $C_1-C_4$ alkanoyl, wherein each is unsubstituted or substituted with 1, 2, or 3 groups that are independently, halogen, OH, SH, $C_3-C_6$ cycloalkyl, $C_1-C_4$ alkoxy, $C_1-C_4$ alkyl, —$CF_3$, or $OCF_3$, and $R_4$ is H, $(C_1-C_3)$alkyl optionally substituted with one or two groups that are independently $CO_2H$, —$CO_2$alkyl, —C(O)NRR, —$N(R_{30})C(O)NRR$, —$N(R_{30})C(O)$—$(C_1-C_6)$alkoxy, —$NR_6R_7$, $NR_6R_7C_1-C_4$ alkyl, or hydroxy$(C_1-C_3)$alkyl.

Embodiment 103. Compounds according to embodiment 102, wherein $R_1$ is H or halogen.

Embodiment 104. Compounds according to embodiment 80, wherein $R_5$ is phenyl$(C_1-C_6)$alkyl, $(C_1-C_6)$alkyl, piperidinyl$(C_1-C_6)$alkyl, thienyl$(C_1-C_6)$alkyl, indolyl$(C_1-C_6)$alkyl, naphthyl $(C_1-C_6)$alkyl, pyridyl$(C_1-C_6)$alkyl, pyrimidyl$(C_1-C_6)$alkyl, quinolinyl$(C_1-C_6)$alkyl, isoquinolinyl$(C_1-C_6)$alkyl, isoindolyl$(C_1-C_6)$alkyl, indol-2-onyl$(C_1-C_6)$alkyl, pyridazinyl$(C_1-C_6)$alkyl, pyrazinyl$(C_1-C_6)$alkyl, or pyrazinyl$(C_1-C_6)$alkyl, wherein each of the above is unsubstituted or substituted with 1, 2, 3, 4, or 5 groups that are independently alkyl, halogen, alkoxy, benzyloxy, hydroxyalkyl, thioalkoxy, —$CO_2$ $(C_1-C_5$ alkyl), $CO_2H$, CN, amidinooxime, $NR_8R_9$, $NR_6R_7$—$(C_1-C_6$ alkyl)-, —$C(O)NR_6R_7$, amidino, $CF_3$, or $OCF_3$;

$R_8$ is hydrogen, $C_1-C_6$ alkyl, $C_1-C_6$ alkanoyl, phenyl $C_1-C_6$ alkyl and phenyl $C_1-C_6$ alkanoyl; and $R_9$ is aminoalkyl, mono $C_1-C_6$ alkylamino $C_1-C_6$ alkyl, di $C_1-C_6$ alkylamino $C_1-C_6$ alkyl, $C_1-C_6$ alkyl, $C_1-C_6$ alkanoyl, phenyl $C_1-C_4$ alkyl, indazolyl, and phenyl $C_1-C_4$ alkanoyl.

In this embodiment, it is preferred that when $R_2$ is benzyloxy, $R_4$ is H, and $R_5$ is benzyl or methyl, $R_1$ is not hydrogen; and no more than two of $R_1$, $R_2$, $R_4$, and $R_5$ are simultaneously hydrogen.

Embodiment 105. Compounds according to embodiment 104, wherein $R_5$ is phenyl$(C_1-C_6)$alkyl, which is unsubstituted or substituted with 1, 2, 3, 4, or 5 groups that are independently alkyl, halogen, alkoxy, benzyloxy, thioalkoxy, —$CO_2(C_1-C_5$ alkyl), $CO_2H$, CN, amidinooxime, $NR_8R_9$, $NR_6R_7$—$(C_1-C_6$ alkyl)-, —$C(O)NR_6R_7$, amidino, $CF_3$, or $OCF_3$; wherein $R_6$ and $R_7$ are independently at each occurrence H, $C_1-C_4$ alkyl, $C_1-C_4$ hydroxyalkyl, $C_1-C_4$ alkoxy, $C_1-C_4$ alkoxy $C_1-C_4$ alkyl, $C_1-C_4$ alkanoyl, phenyl $C_1-C_4$ alkyl, phenyl $C_1-C_4$ alkoxy, or phenyl $C_1-C_4$ alkanoyl, wherein each is unsubstituted or substituted with 1, 2, or 3 groups that are independently, halogen, OH, SH, $C_3-C_6$ cycloalkyl, $C_1-C_4$ alkoxy, $C_1-C_4$ alkyl, $CF_3$, or $OCF_3$; or $R_6$, $R_7$, and the nitrogen to which they are attached form a morpholinyl, thiomorpholinyl, or piperazinyl ring which is optionally substituted with 1 or 2 groups that are independently $C_1-C_4$ alkyl, hydroxy, hydroxy $C_1-C_4$ alkyl, or halogen;

$R_8$ is hydrogen, $C_1-C_6$ alkyl, $C_1-C_6$ alkanoyl, phenyl $C_1-C_6$ alkyl and phenyl $C_1-C_6$ alkanoyl; and $R_9$ is aminoalkyl, mono $C_1-C_6$ alkylamino $C_1-C_6$ alkyl, di $C_1-C_6$ alkylamino $C_1-C_6$ alkyl, $C_1-C_6$ alkyl, $C_1-C_6$ alkanoyl, phenyl $C_1-C_4$ alkyl, indazolyl, and phenyl $C_1-C_4$ alkanoyl.

Embodiment 106. Compounds according to embodiment 105, wherein $R_5$ is phenyl$(C_1-C_6)$alkyl, which is unsubstituted or substituted with 1, 2, 3, 4, or 5 groups that are independently CN, halogen, $C_1-C_4$ alkoxy, $C_1-C_4$ thioalkoxy, $C_1-C_4$ haloalkyl, $C_1-C_4$ alkyl, $C_1-C_4$ haloalkyl, $C_1-C_4$ haloalkoxy, —$C(O)NR_2OR_{21}$, wherein $R_{20}$ and $R_{21}$ are independently H, $C_1-C_6$ alkyl, $C_1-C_6$ hydroxyalkyl, $C_1-C_6$ alkoxy $C_1-C_6$ alkyl, or $R_{20}$, $R_{21}$, and the nitrogen to which they are attached form a piperazinyl, or morpholinyl ring, each of which is optionally substituted with 1 or 2 groups that are independently alkyl or halogen.

Embodiment 107. Compounds according to embodiment 106, wherein $R_5$ is phenyl$(C_1-C_4)$alkyl, which is unsubstituted or substituted with 1, 2, 3, 4, or 5 groups that are independently CN, halogen, $C_1-C_4$ alkoxy, $C_1-C_4$ haloalkyl, $C_1-C_4$ alkyl, $C_1-C_4$ haloalkoxy, —$C(O)NR_2OR_{21}$, wherein $R_{20}$ and $R_2$, are independently H, $C_1-C_6$ alkyl, $C_1-C_6$ hydroxyalkyl, $C_1-C_6$ alkoxy $C_1-C_6$ alkyl, or $R_{20}$, $R_{21}$, and the nitrogen to which they are attached form a piperazinyl, or morpholinyl ring, each of which is optionally substituted with 1 or 2 groups that are independently alkyl or halogen.

Embodiment 108. Compounds according to embodiment 107, wherein $R_5$ is benzyl or phenethyl, each of which is unsubstituted or substituted with 1, 2, 3, 4, or 5 groups that are independently CN, halogen, $C_1-C_4$ alkoxy, $CF_3$, $OCF_3$, $C_1-C_4$ alkyl, —$C(O)NR_2OR_{21}$, wherein $R_{20}$ and $R_2$, are independently H, $C_1-C_6$ alkyl, $C_1-C_6$ hydroxyalkyl, $C_1-C_6$ alkoxy $C_1-C_6$ alkyl, or $R_{20}$, $R_{21}$, and the nitrogen to which they are attached form a piperazinyl, or morpholinyl ring, each of which is optionally substituted with 1 or 2 groups that are independently alkyl or halogen.

Embodiment 109. Compounds according to embodiment 108, wherein $R_5$ is benzyl or phenethyl, each of which is unsubstituted or substituted with 1, 2, 3, 4, or 5 groups that are independently halogen, methoxy, ethoxy, $CF_3$, $OCF_3$, methyl, ethyl, or —$C(O)NR_2OR_{21}$, wherein $R_{20}$ and $R_{21}$ are independently H, $C_1-C_6$ alkyl, $C_1-C_6$ hydroxyalkyl, $C_1-C_6$ alkoxy $C_1-C_6$ alkyl, Embodiment 110. Compounds according to embodiment 108, wherein $R_5$ is benzyl or phenethyl, each of which is unsubstituted or substituted with 1, 2, 3, 4, or 5 groups that are independently halogen, methoxy, ethoxy, $CF_3$, $OCF_3$, methyl, ethyl, or —$C(O)NR_2OR_{21}$, wherein $R_{20}$, $R_{21}$, and the nitrogen to which they are attached form a piperazinyl, or morpholinyl ring, each of which is optionally substituted with 1 or 2 groups that are independently alkyl or halogen.

Embodiment 111. Compounds according to embodiment 109 or embodiment 110, wherein $R_5$ is substituted on the phenyl ring with 1, 2, 3, 4, or 5 groups and wherein there is a group at the para position of the phenyl.

Embodiment 112. Compounds according to embodiment 103, wherein $R_5$ is piperidinyl($C_1$-$C_6$)alkyl, thienyl($C_1$-$C_6$)alkyl, indolyl($C_1$-$C_6$)alkyl, pyridyl($C_1$-$C_6$)alkyl, pyrimidyl($C_1$-$C_6$)alkyl, quinolinyl($C_1$-$C_6$)alkyl, isoquinolinyl($C_1$-$C_6$)alkyl, isoindolyl($C_1$-$C_6$)alkyl, indol-2-onyl($C_1$-$C_6$)alkyl, pyridazinyl($C_1$-$C_6$)alkyl, or pyrazinyl($C_1$-$C_6$)alkyl, or pyrazinyl($C_1$-$C_6$)alkyl, or pyrazinyl($C_1$-$C_6$)alkyl, wherein
each of the above is unsubstituted or substituted with 1, 2, 3, 4, or 5 groups that are independently $C_1$-$C_6$ alkyl, halogen, $C_1$-$C_6$ alkoxy, $C_1$-$C_6$ hydroxyalkyl, benzyloxy, $C_1$-$C_6$ thioalkoxy, —$CO_2$($C_1$-$C_5$ alkyl), $CO_2H$, CN, amidinooxime, $NR_8R_9$, $NR_6R_7$—($C_1$-$C_6$ alkyl)-, —C(O)$NR_6R_7$, amidino, $CF_3$, or $OCF_3$;

$R_8$ is hydrogen, $C_1$-$C_6$ alkyl, $C_1$-$C_6$ alkanoyl, phenyl $C_1$-$C_6$ alkyl and phenyl $C_1$-$C_6$ alkanoyl; and $R_9$ is aminoalkyl, mono $C_1$-$C_6$ alkylamino $C_1$-$C_6$ alkyl, di $C_1$-$C_6$ alkylamino $C_1$-$C_6$ alkyl, $C_1$-$C_6$ alkyl, $C_1$-$C_6$ alkanoyl, phenyl $C_1$-$C_4$ alkyl, indazolyl, and phenyl $C_1$-$C_4$ alkanoyl.

In this embodiment, it is preferred that when $R_2$ is benzyloxy, $R_4$ is H, and $R_5$ is benzyl or methyl, $R_1$ is not hydrogen; and no more than two of $R_1$, $R_2$, $R_4$, and $R_5$ are simultaneously hydrogen.

Embodiment 113. Compounds according to embodiment 112, wherein $R_5$ is piperidinyl($C_1$-$C_4$)alkyl, thienyl($C_1$-$C_4$)alkyl, indolyl($C_1$-$C_4$)alkyl, pyridyl($C_1$-$C_4$)alkyl, pyrimidyl($C_1$-$C_4$)alkyl, or pyrazinyl($C_1$-$C_4$)alkyl, each of which is unsubstituted.

Embodiment 114. Compounds according to embodiment 112, wherein $R_5$ is indolyl($C_1$-$C_4$)alkyl, pyrimidyl($C_1$-$C_4$)alkyl, or pyrazinyl($C_1$-$C_4$)alkyl, wherein
each of the above is unsubstituted or substituted with 1, 2, 3, or 4 groups that are independently $C_1$-$C_6$ alkyl, halogen, $C_1$-$C_6$ alkoxy, $C_1$-$C_6$ hydroxyalkyl, benzyloxy, $C_1$-$C_6$ thioalkoxy, —$CO_2$($C_1$-$C_5$ alkyl), $CO_2H$, CN, amidinooxime, $NR_8R_9$, $NR_6R_7$—($C_1$-$C_6$ alkyl)-, amidino, —C(O)$NR_2OR_{21}$, $CF_3$, or $OCF_3$; wherein $R_6$ and $R_7$ are independently at each occurrence H, $C_1$-$C_4$ alkyl, $C_1$-$C_4$ hydroxyalkyl, $C_1$-$C_4$ alkoxy, $C_1$-$C_4$ alkoxy $C_1$-$C_4$ alkyl, $C_1$-$C_4$ alkanoyl, benzyl, benzyloxy, or phenyl $C_1$-$C_4$ alkanoyl, wherein each is unsubstituted or substituted with 1, 2, or 3 groups that are independently, halogen, OH, SH, $C_3$-$C_6$ cycloalkyl, $C_1$-$C_4$ alkoxy, $C_1$-$C_4$ alkyl, $CF_3$, or $OCF_3$; or $R_6$, $R_7$, and the nitrogen to which they are attached form a morpholinyl, thiomorpholinyl, or piperazinyl ring which is optionally substituted with 1 or 2 groups that are independently $C_1$-$C_4$ alkyl, hydroxy, hydroxy $C_1$-$C_4$ alkyl, or halogen;

$R_8$ is hydrogen, $C_1$-$C_6$ alkyl, $C_1$-$C_6$ alkanoyl, phenyl $C_1$-$C_4$ alkyl and phenyl $C_1$-$C_4$ alkanoyl; and $R_9$ is aminoalkyl, mono $C_1$-$C_6$ alkylamino $C_1$-$C_6$ alkyl, di $C_1$-$C_6$ alkylamino $C_1$-$C_6$ alkyl, $C_1$-$C_6$ alkyl, $C_1$-$C_6$ alkanoyl, phenyl $C_1$-$C_4$ alkyl, indazolyl, and phenyl $C_1$-$C_4$ alkanoyl;

$R_{20}$ and $R_{21}$ are independently H, $C_1$-$C_6$ alkyl, $C_1$-$C_6$ hydroxyalkyl, $C_1$-$C_6$ alkoxy $C_1$-$C_6$ alkyl, or $R_{20}$, $R_{21}$, and the nitrogen to which they are attached form a piperazinyl, or morpholinyl ring, each of which is optionally substituted with 1 or 2 groups that are independently alkyl or halogen Embodiment 115. Compounds according to embodiment 114, wherein $R_5$ is indolyl($C_1$-$C_4$)alkyl, or pyrazinyl($C_1$-$C_4$)alkyl, wherein
each of the above is unsubstituted or substituted with 1, 2, 3, or 4 groups that are independently $C_1$-$C_6$ alkyl, halogen, $C_1$-$C_6$ alkoxy, $C_1$-$C_6$ hydroxyalkyl, benzyloxy, $C_1$-$C_6$ thioalkoxy, —$CO_2$($C_1$-$C_5$ alkyl), $CO_2H$, CN, —C(O)$NR_2OR_{21}$, $CF_3$, or $OCF_3$; wherein $R_{20}$ and $R_{21}$ are independently H, $C_1$-$C_6$ alkyl, $C_1$-$C_6$ hydroxyalkyl, $C_1$-$C_6$ alkoxy $C_1$-$C_6$ alkyl, or $R_{20}$, $R_{21}$, and the nitrogen to which they are attached form a piperazinyl, or morpholinyl ring, each of which is optionally substituted with 1 or 2 groups that are independently alkyl or halogen.

Embodiment 116. Compounds according to embodiment 102 or embodiment 103, wherein $R_5$ is isoquinolinyl, isoindolyl, indol-2-onyl, quinolinyl($C_1$-$C_6$)alkyl, isoquinolinyl($C_1$-$C_6$)alkyl, isoindolyl($C_1$-$C_6$)alkyl, indol-2-onyl($C_1$-$C_6$)alkyl, wherein
each of the above is unsubstituted or substituted with 1, 2, 3, 4, or 5 groups that are independently $C_1$-$C_6$ alkyl, halogen, $C_1$-$C_6$ alkoxy, $C_1$-$C_6$ hydroxyalkyl, benzyloxy, $C_1$-$C_6$ thioalkoxy, —$CO_2$($C_1$-$C_5$ alkyl), $CO_2H$, CN, amidinooxime, $NR_8R_9$, $NR_6R_7$—($C_1$-$C_6$ alkyl)-, —C(O)$NR_6R_7$, amidino, $CF_3$, or $OCF_3$.

Embodiment 117. Compounds according to embodiment 1 or 2, wherein $R_1$ is H, halogen, methyl, ethyl, $C_2$-$C_4$ alkenyl, $C_2$-$C_4$ alkynyl, or carboxaldehyde;

$R_2$ is benzyloxy, OH, phenyloxy, phenyloxy($C_1$-$C_6$)alkyl, or phenyl($C_1$-$C_4$)thioalkoxy, wherein each of the above is optionally substituted with 1, 2, 3, or 4 groups that are independently halogen, —($C_1$-$C_6$)alkyl-N(R)—$CO_2R_{30}$, $NR_6R_7$, ($C_1$-$C_4$)haloalkyl, ($C_1$-$C_4$)haloalkoxy, ($C_1$-$C_6$) alkyl, pyridyl, or $NR_6R_7$—($C_1$-$C_6$ alkyl)-; and $R_4$ is H, ($C_1$-$C_4$)alkyl optionally substituted with one or two groups that are independently $CO_2H$, —$CO_2$alkyl, —C(O)NRR, —N($R_{30}$)C(O)NRR, —N($R_{30}$)C(O)—($C_1$-$C_6$) alkoxy, or —$NR_6R_7$, or hydroxy($C_1$-$C_4$)alkyl;

$R_5$ is $C_3$-$C_7$ cycloalkyl or $C_3$-$C_7$ cycloalkylalkyl, each of which is optionally substituted with 1 or 2 groups that are independently alkyl, alkoxy, halogen, —$NR_6R_7$, or $NR_6R_7$—($C_1$-$C_6$ alkyl)-, wherein each of the alkyl groups is optionally substituted with 1 or 2 groups that are independently OH, methoxy, $NH_2$, or halogen.

Embodiment 118. Compounds according to embodiment 117, wherein $R_5$ is $C_3$-$C_7$ cycloalkyl or $C_3$-$C_7$ cycloalkyl $C_1$-$C_4$ alkyl, each of which is optionally substituted with 1 or 2 groups that are independently $C_1$-$C_4$ alkyl, $C_1$-$C_4$ alkoxy, halogen, —$NR_6R_7$, or $NR_6R_7$—($C_1$-$C_6$ alkyl)- wherein each of the alkyl groups is optionally substituted with 1 or 2 groups that are independently OH, methoxy, or $NH_2$;

$R_6$ and $R_7$ are independently at each occurrence H, $C_1$-$C_4$ alkyl, $C_1$-$C_4$ hydroxyalkyl, $C_1$-$C_4$ alkoxy, $C_1$-$C_4$ alkoxy $C_1$-$C_4$ alkyl, $C_1$-$C_4$ alkanoyl, benzyl, benzyloxy, or phenyl $C_1$-$C_4$ alkanoyl, wherein each is unsubstituted or substituted with 1, 2, or 3 groups that are independently, halogen, OH, SH, $C_3$-$C_6$ cycloalkyl, $C_1$-$C_4$ alkoxy, $C_1$-$C_4$ alkyl, $CF_3$, or $OCF_3$; or $R_6$, $R_7$, and the nitrogen to which they are attached form a morpholinyl, thiomorpholinyl, or piperazinyl ring which is optionally substituted with 1 or 2 groups that are independently $C_1$-$C_4$ alkyl, hydroxy, hydroxy $C_1$-$C_4$ alkyl, or halogen.

Embodiment 119. Compounds according to embodiment 118, wherein $R_1$ is H, halogen, methyl, ethyl;

$R_2$ is benzyloxy, phenyloxy, phenyloxy($C_1$-$C_6$)alkyl, or phenyl ($C_1$-$C_4$)thioalkoxy, wherein each of the above is optionally substituted with 1, 2, 3, or 4 groups that are independently halogen, —($C_1$-$C_6$)alkyl-N(R)—$CO_2R_{30}$, amino, mono or dialkylamino, —$NR_6R_7$, ($C_1$-$C_4$)haloalkyl, ($C_1$-$C_4$) haloalkoxy, ($C_1$-$C_6$)alkyl, or $NR_6R_7$—($C_1$-$C_6$ alkyl)-; and $R_4$ is H, methyl, ($C_1$-$C_4$)alkyl optionally substituted with one or two groups that are independently $CO_2H$, —$CO_2$alkyl, —C(O)NRR, —N($R_{30}$)C(O)NRR, —N($R_{30}$)C(O)—($C_1$-$C_6$)alkoxy, or —$NR_6R_7$ or hydroxy($C_1$-$C_2$)alkyl.

Embodiment 120. Compounds according to embodiment 119, wherein $R_2$ is substituted with two halogens and is further optionally substituted with 1 or 2 groups that are independently halogen, —($C_1$-$C_6$)alkyl-N(R)—$CO_2R_{30}$, amino, mono or dialkylamino, —$NR_6R_7$, ($C_1$-$C_4$)haloalkyl, ($C_1$-$C_4$) haloalkoxy, ($C_1$-$C_6$)alkyl, or $NR_6R_7$—($C_1$-$C_6$ alkyl).

Embodiment 121. Compounds according to embodiment 1 or 2, wherein $R_5$ is H, alkyl optionally substituted with 1, 2, or 3 groups that are independently phenylalkoxycarbonyl, —$NR_8R_9$, halogen, —C(O)$NR_8R_9$, alkoxycarbonyl, or alkanoyl, alkoxyalkyl optionally substituted with one trimethylsilyl group, alkoxycarbonyl, amino, hydroxyalkyl, alkenyl optionally substituted with alkoxycarbonyl, alkynyl, —$SO_2$-alkyl, or alkoxy optionally substituted with one trimethylsilyl group, wherein each of the above is unsubstituted or substituted with 1, 2, 3, 4, or 5 groups that are independently alkyl, halogen, alkoxy, phenylalkoxy, thioalkoxy, —$SO_2$alkyl, alkoxycarbonyl, phenylalkoxycarbonyl, $CO_2H$, CN, OH, amidinooxime, $NR_8R_9$, $NR_6R_7$—($C_1$-$C_6$ alkyl)-, —C(O)$NR_6R_7$, amidino, hydroxyalkyl, carboxaldehyde, —$NR_6R_7$, haloalkyl, or haloalkoxy;

wherein $R_8$ is hydrogen, alkyl, alkanoyl, phenylalkyl and arylalkanoyl; and wherein $R_9$ is alkyl, alkanoyl, phenylalkyl, heteroaryl, aminoalkyl, monoalkylaminoalkyl, dialkylaminoalkyl, and arylalkanoyl.

In this embodiment, it is preferred that when $R_2$ is benzyloxy, $R_4$ is H, and $R_5$ is benzyl or methyl, $R_1$ is not hydrogen; and no more than two of $R_1$, $R_2$, $R_4$, and $R_5$ are simultaneously hydrogen.

Embodiment 122. Compounds according to embodiment 1 or 2, wherein $R_5$ is H, alkyl optionally substituted with 1, 2, or 3 groups that are independently phenylalkoxycarbonyl, —$NR_8R_9$, halogen, —C(O)$NR_8R_9$, alkoxycarbonyl, or alkanoyl, alkoxyalkyl optionally substituted with one trimethylsilyl group, alkoxycarbonyl, amino, hydroxyalkyl, alkenyl optionally substituted with alkoxycarbonyl, alkynyl, —$SO_2$-alkyl, alkoxy optionally substituted with one trimethylsilyl group, wherein each of the above is unsubstituted or substituted with 1, 2, 3, 4, or 5 groups that are independently alkyl, halogen, alkoxy, phenylalkoxy, thioalkoxy, —$SO_2$alkyl, alkoxycarbonyl, phenylalkoxycarbonyl, $CO_2H$, CN, OH, amidinooxime, $NR_8R_9$, $NR_6R_7$—($C_1$-$C_6$ alkyl)-, —C(O)$NR_6R_7$, amidino, hydroxyalkyl, carboxaldehyde, —$NR_6R_7$, haloalkyl, or haloalkoxy;

wherein $R_8$ is hydrogen, alkyl, alkanoyl, phenylalkyl and arylalkanoyl; and wherein $R_9$ is alkyl, alkanoyl, phenylalkyl, heteroaryl, aminoalkyl, monoalkylaminoalkyl, dialkylaminoalkyl, and arylalkanoyl.

In this embodiment, it is preferred that when $R_2$ is benzyloxy, $R_4$ is H, and $R_5$ is benzyl or methyl, $R_1$ is not hydrogen; and no more than two of $R_1$, $R_2$, $R_4$, and $R_5$ are simultaneously hydrogen.

Embodiment 123. Compounds according to any one of embodiments 117, 118, 119, 120, 121, or 122, wherein $R_1$ is H, halogen, methyl, ethyl, $C_2$-$C_4$ alkenyl, $C_2$-$C_4$ alkynyl, or carboxaldehyde;

$R_2$ is benzyloxy, OH, phenyloxy, phenyloxy($C_1$-$C_6$)alkyl, or phenyl($C_1$-$C_4$)thioalkoxy, wherein each of the above is optionally substituted with 1, 2, 3, or 4 groups that are independently halogen, —($C_1$-$C_6$)alkyl-N(R)—$CO_2R_{30}$, $NR_6R_7$, ($C_1$-$C_4$)haloalkyl, ($C_1$-$C_4$)haloalkoxy, ($C_1$-$C_6$) alkyl, pyridyl, or $NR_6R_7$—($C_1$-$C_6$ alkyl)-; and $R_4$ is H, ($C_1$-$C_4$)alkyl optionally substituted with one or two groups that are independently $CO_2H$, —$CO_2$alkyl, —C(O)NRR, —N($R_{30}$)C(O)NRR, —N($R_{30}$)C(O)—($C_1$-$C_6$) alkoxy, or —$NR_6R_7$, or hydroxy($C_1$-$C_4$)alkyl.

Embodiment 123A. Compounds according to embodiment 122, wherein $R_5$ is H, alkyl optionally substituted with 1, 2, or 3 groups that are independently phenylalkoxycarbonyl, —$NR_8R_9$, halogen, —C(O)$NR_8R_9$, alkoxycarbonyl, or alkanoyl, alkoxyalkyl optionally substituted with one trimethylsilyl group, alkoxycarbonyl, amino, hydroxyalkyl, alkenyl optionally substituted with alkoxycarbonyl, alkynyl, —$SO_2$-alkyl, alkoxy optionally substituted with one trimethylsilyl group, wherein wherein $R_8$ is hydrogen, $C_1$-$C_4$ alkyl, $C_1$-$C_4$ alkanoyl, phenyl $C_1$-$C_4$ alkyl and phenyl $C_1$-$C_4$ alkanoyl;

wherein $R_9$ is $C_1$-$C_4$ alkyl, $C_1$-$C_4$ alkanoyl, phenyl $C_1$-$C_4$ alkyl, pyridyl, aminoalkyl, monoalkylaminoalkyl, dialkylaminoalkyl, and phenyl $C_1$-$C_4$ alkanoyl.

Embodiment 124. Compounds according to embodiment 123A, wherein $R_5$ is $C_1$-$C_6$ alkyl optionally substituted with 1, 2, or 3 groups that are independently phenyl $C_1$-$C_4$ alkoxycarbonyl, $NH_2$, mono $C_1$-$C_4$ alkylamino, di $C_1$-$C_4$ alkylamino, halogen, —C(O)$NH_2$, —C(O)NH($C_1$-$C_6$ alkyl) wherein the alkyl is optionally substituted with OH, $NH_2$, or methoxy, —C(O)N ($C_1$-$C_6$ alkyl)($C_1$-$C_6$ alkyl) wherein each alkyl is optionally substituted with OH, $NH_2$, or methoxy, $C_1$-$C_4$ alkoxycarbonyl, and $C_1$-$C_4$ alkanoyl, or $R_5$ is $C_1$-$C_4$ alkoxy $C_1$-$C_4$ alkyl, $C_1$-$C_4$ alkoxycarbonyl, amino, $C_1$-$C_4$ hydroxyalkyl, $C_2$-$C_4$ alkenyl optionally substituted with $C_1$-$C_4$ alkoxycarbonyl, $C_2$-$C_4$ alkynyl, —$SO_2$—$C_1$-$C_4$ alkyl, or $C_1$-$C_4$ alkoxy.

Embodiment 125. A compound of the formula

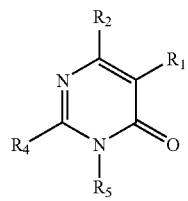

or a pharmaceutically acceptable salt thereof, wherein
$R_1$ is halogen, $NO_2$, alkyl, carboxaldehyde, hydroxyalkyl, arylalkoxy, arylalkyl, CN, aryl, alkanoyl, alkoxy, alkoxyalkyl, haloalkyl, or arylalkanoyl,
  wherein the aryl portion of arylalkoxy, arylalkyl, and arylalkanoyl is unsubstituted or substituted with 1, 2, 3, 4, or 5 groups that are independently halogen, ($C_1$-$C_4$)alkyl, ($C_1$-$C_4$)alkoxy, nitro, CN, haloalkyl, haloalkoxy or $CO_2H$;
  wherein the alkyl portion of the alkyl, hydroxyalkyl, arylalkoxy, arylalkyl, alkanoyl, alkoxy, alkoxyalkyl and arylalkanoyl groups is unsubstituted or substituted with 1, 2, or 3 groups that are independently halogen, $C_1$-$C_4$ alkoxy, $C_1$-$C_4$ alkoxycarbonyl, or spirocyclopropyl;
$R_2$ is aryl, heteroaryl, arylalkenyl, arylalkoxy, aryloxyalkyl, arylalkyl, OH, alkynyl, aryloxy, aryloxyalkyl, arylthioalkoxy, alkoxy, —OC(O)NH($CH_2$)$_n$aryl, —OC(O)N(alkyl)($CH_2$)$_n$aryl, —OSO$_2$($C_1$-$C_6$)alkyl, —OSO$_2$aryl, alkyl, alkoxyalkoxy, $NR_8R_9$, or $CO_2H$, wherein
n is 0, 1, 2, 3, 4, 5 or 6;
  each of the above is unsubstituted or substituted with 1, 2, 3, 4, or 5 groups that are independently halogen, —($C_1$-$C_6$)alkyl-N(R)—$CO_2R_{30}$, alkoxy, alkoxycarbonyl, CN, $NR_6R_7$ haloalkyl, haloalkoxy, alkyl, heteroaryl, heteroarylalkyl, $NR_6R_7$—($C_1$-$C_6$ alkyl)-, phenyl, —$SO_2$-phenyl wherein the phenyl groups are optionally substituted with 1, 2, or 3 groups that are independently halogen or $NO_2$; or —OC(O)$NR_6R_7$, wherein
    $R_6$ and $R_7$ are independently at each occurrence H, alkyl, alkoxy, alkoxyalkyl, alkoxycarbonyl, —$SO_2$-alkyl, OH, hydroxyalkyl, —($C_1$-$C_4$)alkyl-$CO_2$-alkyl, heteroarylalkyl, alkanoyl, arylalkyl, arylalkoxy, or arylalkanoyl, wherein each of the above is unsubstituted or substituted with 1, 2, or 3 groups that are independently, halogen, alkoxy, heterocycloalkyl, OH, SH, $C_3$-$C_6$ cycloalkyl, $NH_2$, NH(alkyl), N(alkyl)(alkyl), —O-alkanoyl, alkyl, haloalkyl, or haloalkoxy; or
    $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, $C_1$-$C_4$ alkoxy, hydroxy, hydroxy $C_1$-$C_4$ alkyl, or halogen;
    R at each occurrence is independently H or $C_1$-$C_6$ alkyl;
    $R_{30}$ is $C_1$-$C_6$ alkyl optionally substituted with 1 or 2 groups that are independently OH, SH, halogen, amino, monoalkylamino, dialkylamino or $C_3$-$C_6$ cycloalkyl;
$R_4$ is H, alkyl optionally substituted with one or two groups that are independently $CO_2H$, —$CO_2$alkyl, —C(O)NRR, —N($R_{30}$)C(O)NRR, —N($R_{30}$)C(O)—($C_1$-$C_6$)alkoxy, or —$NR_6R_7$, arylalkoxy, arylalkyl, hydroxyalkyl, haloalkyl, alkoxy, carboxaldehyde, $CO_2H$, alkoxyalkyl, or alkoxyalkoxy, wherein the aryl portion of arylalkoxy, arylalkyl is unsubstituted or substituted with 1, 2, 3, 4, or 5 groups that are independently halogen, hydroxy, alkoxy, alkyl, nitro, haloalkyl, or haloalkoxy; and
$R_5$ is H, arylalkyl, alkyl, aryl, alkoxy, heterocycloalkylalkyl, heteroarylalkyl, heterocycloalkyl, cycloalkyl, cycloalkylalkyl, -alkyl-5-aryl, -alkyl-$SO_2$-aryl, —($C_1$-$C_4$) alkyl-C(O)-heterocycloalkyl, —$SO_2$-aryl, or heteroaryl, wherein
  each of the above is unsubstituted or substituted with 1, 2, 3, 4, or 5 groups that are independently alkyl, halogen, alkoxy, aryl, arylalkoxy, thioalkoxy, alkoxycarbonyl, arylalkoxycarbonyl, OH, $CO_2H$, CN, amidinooxime, $NR_8R_9$, $NR_6R_7$—($C_1$-$C_6$ alkyl)-, —C(O)$NR_6R_7$, —($C_1$-$C_4$ alkyl)-C(O)$NR_6R_7$, amidino, hydroxyalkyl, —$SO_2$alkyl, —$SO_2H$, —$SO_2NR_6R_7$, —$NR_6R_7$, alkanoyl wherein the alkyl portion is optionally substituted with OH, halogen or alkoxy, haloalkyl, —($C_1$-$C_4$ alkyl)-$NR_{15}$C(O)$NR_{16}R_{17}$, —($C_1$-$C_4$ alkyl)-$NR_{15}$C(O)$R_{18}$, —O—$CH_2$—O—, —O—$CH_2CH_2$—O—, or haloalkoxy; wherein
    $R_8$ at each occurrence is independently hydrogen, alkyl, alkanoyl, arylalkyl and arylalkanoyl wherein each of the above is optionally substituted with 1, 2, 3, 4, or 5 groups that are independently alkyl, alkoxy, alkoxycarbonyl, halogen, or haloalkyl; and
    $R_9$ at each occurrence is independently alkyl, alkanoyl, arylalkyl cycloalkyl, alkenyl, heteroaryl, cycloalkylalkyl, arylalkanoyl, —$SO_2$-phenyl, and aryl wherein each of the above is optionally substituted with 1, 2, 3, 4, or 5 groups that are independently alkyl, alkoxy, alkoxycarbonyl, halogen, or haloalkyl;
    $R_{15}$ is H or $C_1$-$C_6$ alkyl;
    $R_{16}$ and $R_{17}$ are independently H or $C_1$-$C_6$ alkyl; or
    $R_{16}$, $R_{17}$, and the nitrogen to which they are attached form a morpholinyl ring; and
    $R_{18}$ is $C_1$-$C_6$ alkyl optionally substituted with —O—($C_2$-$C_6$ alkanoyl, $C_1$-$C_6$ hydroxyalkyl, $C_1$-$C_6$ alkoxy, $C_1$-$C_6$ alkoxy $C_1$-$C_6$ alkyl; amino $C_1$-$C_6$ alkyl, mono or dialkylamino $C_1$-$C_6$ alkyl.

In this embodiment, it is preferred that:
$R_6$ and $R_7$ are not simultaneously OH;
$R_6$ and $R_7$ are not simultaneously —$SO_2$($C_1$-$C_6$ alkyl);
when $R_2$ is OH, $R_4$ is methyl and $R_5$ is phenyl, $R_1$ is not acetyl; and
$R_4$ and $R_5$ are not simultaneously hydrogen.

Embodiment 126. Compounds according to embodiment 125 wherein
$R_1$ is halogen, $C_1$-$C_6$ alkyl, phenyl, carboxaldehyde, $C_1$-$C_6$ hydroxyalkyl, phenyl $C_1$-$C_6$ alkoxy, phenyl $C_1$-$C_6$ alkyl, CN, $C_1$-$C_6$ alkanoyl, $C_1$-$C_6$ alkoxy, $C_1$-$C_6$ alkoxy $C_1$-$C_6$ alkyl, $C_1$-$C_6$ haloalkyl, or phenyl $C_1$-$C_6$ alkanoyl,
  wherein the above phenyl groups are unsubstituted or substituted with 1, 2, or 3 groups that are independently halogen, ($C_1$-$C_4$)alkyl, ($C_1$-$C_4$)alkoxy, nitro, CN, $C_1$-$C_4$ haloalkyl, $C_1$-$C_4$ haloalkoxy or $CO_2H$;
  wherein the above alkyl groups are unsubstituted or substituted with 1, 2, or 3 groups that are independently halogen, methoxy, or ethoxy,
$R_2$ is phenylalkoxy, OH, phenyloxy, phenyloxy($C_1$-$C_6$)alkyl, phenylthio($C_1$-$C_4$)alkoxy, alkoxy, alkenyl, phenethyl, —OC(O)NH($CH_2$)$_n$phenyl, —OC(O)N (alkyl)($CH_2$)$_n$ phenyl, alkyl, alkoxyalkyl, $NR_8R_9$, pyridyl, pyrimidyl, pyridazyl, pyrazolyl, imidazolyl, pyrrolyl, tetrahydroquinolinyl, amino, tetrahydroisoquinolinyl, tetrazolyl, pyrazinyl, benzimidazolyl, triazinyl, tetrahydrofuryl, piperidinyl, hexahydropyrimidinyl, thiazolyl, thienyl, or $CO_2H$, wherein n is 0, 1, 2, or 3;

each of the above is unsubstituted or substituted with 1, 2, 3, 4, or 5 groups that are independently halogen, $—(C_1-C_6)$alkyl-$N(R)$—$CO_2R_{30}$, haloalkyl, haloalkoxy, alkyl, thienyl, pyridyl, or phenyl optionally substituted with 1, 2, or 3 halogens;

$R_6$ and $R_7$ are independently at each occurrence H, alkyl, alkoxy, alkoxyalkyl, hydroxyalkyl, alkoxycarbonyl, $—(C_1-C_4)$alkyl-$CO_2$-alkyl, alkanoyl, phenylalkyl, phenylalkoxy, or phenylalkanoyl, wherein each of the above is unsubstituted or substituted with 1, 2, or 3 groups that are independently, halogen, OH, SH, $C_3-C_6$ cycloalkyl, alkoxy, $NH_2$, $NH(C_1-C_6$ alkyl), $N(C_1-C_6$ alkyl)$(C_1-C_6$ alkyl), alkyl, $CF_3$ or $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1-C_4$ alkyl, hydroxy, hydroxy $C_1-C_4$ alkyl, or halogen;

$R_4$ is H, alkyl optionally substituted with one or two groups that are independently $CO_2H$, $—CO_2$alkyl, $—C(O)NRR$, $—N(R_{30})C(O)NRR$, $—N(R_{30})C(O)—(C_1-C_6)$alkoxy, or $—NR_6R_7$, phenylalkoxy, phenylalkyl, hydroxyalkyl, carboxaldehyde, haloalkyl, alkoxy, alkoxyalkyl, or alkoxyalkoxy, wherein the above phenyl groups are unsubstituted or substituted with 1, 2, or 3 groups that are independently halogen, hydroxy, alkoxy, alkyl, nitro, haloalkyl, or haloalkoxy; and $R_5$ is benzyl, phenethyl, $(C_1-C_6)$alkyl, phenyl, naphthyl, alkoxy, piperidinyl, pyrrolidinyl, imidazolidinyl, piperazinyl, isoquinolinyl, tetrahydroisoquinolinyl, indolyl, 1H-indazolyl, pyridyl, pyrimidyl, pyridazyl, pyrazinyl, piperidinyl$(C_1-C_6)$alkyl, pyrrolidinyl$(C_1-C_6)$alkyl, imidazolidinyl $(C_1-C_6)$alkyl, piperazinyl$(C_1-C_6)$alkyl, pyridyl$(C_1-C_6)$ alkyl, pyrimidyl$(C_1-C_6)$alkyl, pyridazyl$(C_1-C_6)$alkyl, pyrazinyl$(C_1-C_6)$alkyl, isoquinolinyl$(C_1-C_6)$alkyl, tetrahydroisoquinolinyl$(C_1-C_6)$alkyl, indolyl$(C_1-C_6)$alkyl, or 1H-indazolyl$(C_1-C_6)$alkyl, and wherein each of the above is unsubstituted or substituted with 1, 2, 3, 4, or 5 groups that are independently alkyl, halogen, alkoxy, hydroxyalkyl, phenylalkoxy, thioalkoxy, alkoxycarbonyl, phenylalkoxycarbonyl, OH, $CO_2H$, CN, amidinooxime, $NR_8R_9$, $NR_6R_7—(C_1-C_6$ alkyl), $—C(O)NR_6R_7$, amidino, piperazinyl, morpholinyl, $—SO_2$ $(C_1-C_6)$alkyl, $—SO_2NH_2$, $—SO_2NH(C_1-C_6)$ alkyl, $—SO_2N(C_1-C_6)$alkyl$(C_1-C_6)$alkyl, haloalkyl, or haloalkoxy.

In this embodiment, it is preferred that when $R_2$ is OH, $R_4$ is methyl and $R_5$ is phenyl, $R_1$ is not acetyl; and $R_4$ and $R_5$ are not simultaneously hydrogen.

Embodiment 127. Compounds according to embodiment 126 wherein $R_1$ is halogen, alkyl, carboxaldehyde, hydroxyalkyl, phenylalkoxy, phenyl, benzyl, phenethyl, phenpropyl, phenbutyl, CN, $(C_2-C_6)$alkanoyl, haloalkyl, or phenylCO—, phenyl$CH_2$CO—, phenyl$CH_2CH_2$CO—, wherein the above phenyl groups are unsubstituted or substituted with 1, 2, or 3 groups that are independently halogen, $(C_1-C_4)$alkyl, $(C_1-C_4)$alkoxy, nitro, CN, haloalkyl, haloalkoxy or $CO_2H$;

wherein the above alkyl groups are unsubstituted or substituted with 1, 2, or 3 groups that are independently halogen, methoxy, or ethoxy, $R_2$ is benzyloxy, phenethyloxy, phenpropyloxy, OH, phenyloxy, phenyloxy$(C_1-C_6)$alkyl, phenylthio$(C_1-C_4)$alkoxy, $NR_8R_9$, $(C_1-C_6)$alkyl, alkynyl, phenethyl, $—OC(O)N$ $(CH_3)CH_2$phenyl, alkoxyalkoxy, pyridyl, pyrimidyl, pyridazyl, pyrazolyl, imidazolyl, pyrrolyl, pyrazinyl, piperidinyl, hexahydropyrimidinyl, benzimidazolyl, or thienyl, wherein each of the above is unsubstituted or substituted with 1, 2, or 3 groups that are independently halogen, $—(C_1-C_6)$ alkyl-$N(R)$—$CO_2R_{30}$, $CF_3$, $OCF_3$, $(C_1-C_4)$alkyl, thienyl, pyridyl, or phenyl optionally substituted with 1, 2, or 3 halogens;

$R_6$ and $R_7$ are independently at each occurrence H, $(C_1-C_6)$ alkyl, $(C_1-C_6)$alkoxy, $(C_1-C_6)$alkoxy$(C_1-C_6)$alkyl, $(C_1-C_6)$alkoxycarbonyl, hydroxy$(C_1-C_6)$alkyl, $—(C_1-C_4)$ alkyl-$CO_2$-alkyl, $(C_1-C_6)$alkanoyl, phenyl$(C_1-C_6)$alkyl, phenyl$(C_1-C_6)$alkoxy, or phenyl$(C_1-C_6)$alkanoyl, wherein each of the above is unsubstituted or substituted with 1, 2, or 3 groups that are independently, halogen, $(C_1-C_6)$alkoxy, $NH_2$, OH, SH, $C_3-C_6$ cycloalkyl, $(C_1-C_6)$alkyl, $CF_3$ or $OCF_3$; or $R_6$, $R_7$, and the nitrogen to which they are attached form a morpholinyl, piperidinyl, pyrrolidinyl, or piperazinyl ring which is optionally substituted with 1 or 2 groups that are independently $C_1-C_4$ alkyl, hydroxy, hydroxy $C_1-C_4$ alkyl, or halogen;

$R_4$ is H, alkyl optionally substituted with one or two groups that are independently $CO_2H$, $—CO_2$alkyl, $—C(O)NRR$, $—N(R_{30})C(O)NRR$, $—N(R_{30})C(O)—(C_1-C_6)$alkoxy, or $—NR_6R_7$, benzyloxy, phenethyloxy, phenpropyloxy, benzyl, phenethyl, phenpropyl, hydroxyalkyl, halo$(C_1-C_4)$ alkyl, carboxaldehyde, alkoxy, alkoxyalkyl, or alkoxyalkoxy, wherein the above phenyl groups are unsubstituted or substituted with 1, 2, or 3 groups that are independently halogen, hydroxy, alkoxy, alkyl, nitro, $CF_3$ or $OCF_3$; and $R_5$ is benzyl, phenethyl, phenpropyl, phenbutyl, $(C_1-C_6)$ alkyl, phenyl, piperidinyl, pyrrolidinyl, imidazolidinyl, piperidinyl$(C_1-C_6)$alkyl, pyrrolidinyl$(C_1-C_6)$alkyl, imidazolidinyl$(C_1-C_6)$alkyl, pyridyl, pyrimidyl, pyridazyl, pyrazinyl, pyridyl$(C_1-C_6)$alkyl, pyrimidyl$(C_1-C_6)$alkyl, pyridazyl$(C_1-C_6)$alkyl, or pyrazinyl$(C_1-C_6)$alkyl wherein each of the above is unsubstituted or substituted with 1, 2, 3, 4, or 5 groups that are independently alkyl, halogen, haloalkyl, $NR_8R_9$, $NR_6R_7—(C_1-C_6$ alkyl)-, carboxaldehyde, morpholinyl, $SO_2NH_2$, $SO_2NH(alkyl)$, $SO_2N$ (alkyl)(alkyl), alkoxy, hydroxyalkyl, benzyloxy, thioalkoxy, OH, $CO_2H$, CN, $—CO_2(C_1-C_5$ alkyl), phenylalkoxycarbonyl, amidinooxime, amidino, $—C(O)NR_6R_7$, $CF_3$, $CF_2CF_3$, $ClCH_2$, or $OCF_3$.

In this embodiment, it is preferred that when $R_2$ is OH, $R_4$ is methyl and $R_5$ is phenyl, $R_1$ is not acetyl.

Embodiment 128. Compounds according to embodiment 127 wherein $R_1$ is halogen, alkyl, carboxaldehyde, hydroxy$(C_1-C_4)$alkyl, phenylalkoxy, benzyl, phenethyl, $—C(O)CH_3$, phenylCO—, or phenyl$CH_2$CO—, wherein the above phenyl groups are unsubstituted or substituted with 1, 2, or 3 groups that are independently halogen, $(C_1-C_4)$alkyl, $(C_1-C_4)$alkoxy, nitro, CN, $CF_3$, or $OCF_3$;

wherein the above alkyl groups are unsubstituted or substituted with 1, 2, or 3 groups that are independently halogen, methoxy, or ethoxy;

$R_2$ is benzyloxy, phenethyloxy, phenpropyloxy, OH, phenyloxy, phenyloxy$(C_1-C_6)$alkyl, phenethyl, $NR_8R_9$, $—S$-benzyl, or $(C_1-C_6)$alkyl, wherein each of the above is unsubstituted or substituted with 1, 2, or 3 groups that are independently halogen, —($C_1$-$C_6$)alkyl-N(R)—$CO_2R_{30}$, $CF_3$, $OCF_3$, alkyl, thienyl, or pyridyl;

$R_6$ and $R_7$ are independently at each occurrence H, ($C_1$-$C_6$)alkyl, ($C_1$-$C_6$)alkoxy, ($C_1$-$C_6$)alkoxy($C_1$-$C_6$)alkyl, ($C_1$-$C_6$)alkoxycarbonyl, hydroxy($C_1$-$C_6$)alkyl, ($C_1$-$C_4$)alkyl-$CO_2$-alkyl, ($C_1$-$C_6$)alkanoyl, phenyl($C_1$-$C_6$)alkyl, phenyl($C_1$-$C_6$)alkoxy, or phenyl($C_1$-$C_6$)alkanoyl, wherein each of the above is unsubstituted or substituted with 1, 2, or 3 groups that are independently, halogen, ($C_1$-$C_6$)alkoxy, $NH_2$, OH, SH, $C_3$-$C_6$ cycloalkyl, ($C_1$-$C_6$)alkyl, $CF_3$ or $OCF_3$; or $R_6$, $R_7$, and the nitrogen to which they are attached form a morpholinyl, piperidinyl, pyrrolidinyl, or piperazinyl ring which is optionally substituted with 1 or 2 groups that are independently $C_1$-$C_4$ alkyl, hydroxy, hydroxy $C_1$-$C_4$ alkyl, or halogen;

$R_4$ is H, alkyl optionally substituted with one or two groups that are independently $CO_2H$, —$CO_2$alkyl, —C(O)NRR, —N($R_{30}$) C(O)NRR, —N($R_{30}$)C(O)—($C_1$-$C_6$)alkoxy, or —$NR_6R_7$, benzyloxy, phenethyloxy, phenpropyloxy, benzyl, or hydroxyalkyl, wherein the above phenyl groups are unsubstituted or substituted with 1, 2, or 3 groups that are independently halogen, hydroxy, alkoxy, alkyl, nitro, $CF_3$ or $OCF_3$; and $R_5$ is benzyl, phenethyl, phenpropyl, phenbutyl, ($C_1$-$C_6$)alkyl, phenyl, pyridyl, pyrazinyl, pyrimidinyl, pyrazinyl ($C_1$-$C_6$)alkyl, pyrimidinyl($C_1$-$C_6$)alkyl, or pyridyl($C_1$-$C_4$)alkyl, wherein each of the above is unsubstituted or substituted with 1, 2, 3, 4, or 5 groups that are independently alkyl, halogen, haloalkyl, morpholinyl, —$SO_2$ ($C_1$-$C_6$)alkyl, —$SO_2NH_2$, —$SO_2NH(C_1$-$C_6$), —$SO_2N(C_1$-$C_6$)($C_1$-$C_6$), ($C_1$-$C_4$)alkoxy, phenyl($C_1$-$C_4$)alkoxy, thio($C_1$-$C_4$)alkoxy, ($C_1$-$C_4$)alkoxycarbonyl, OH, $CO_2H$, CN, amidinooxime, amidino, $NR_8R_9$, $NR_6R_7$—($C_1$-$C_6$ alkyl)-, hydroxyalkyl, $CONR_6R_7$, $CF_3$, or $OCF_3$.

Embodiment 129. Compounds according to embodiment 128 wherein $R_1$ is halogen, alkyl, carboxaldehyde, or hydroxyalkyl;

$R_2$ is benzyloxy, phenethyloxy, phenpropyloxy, OH, phenyloxy, phenyloxy($C_1$-$C_6$)alkyl, phenethyl, phenylthioalkoxy, or ($C_1$-$C_4$)alkyl, wherein each of the above is unsubstituted or substituted with 1, 2, or 3 groups that are independently halogen, —($C_1$-$C_6$)alkyl-N(R)—$CO_2R_{30}$, $CF_3$, $OCF_3$, alkyl, thienyl, or pyridyl;

$R_4$ is H, ($C_1$-$C_4$)alkyl optionally substituted with one or two groups that are independently $CO_2H$, —$CO_2$alkyl, —C(O)NRR, —N($R_{30}$) C(O)NRR, —N($R_{30}$)C(O)—($C_1$-$C_6$)alkoxy, or —$NR_6R_7$, benzyloxy, or phenethyloxy, wherein the above phenyl groups are unsubstituted or substituted with 1, 2, or 3 groups that are independently halogen, hydroxy, ($C_1$-$C_4$)alkoxy, ($C_1$-$C_4$)alkyl, nitro, $CF_3$ or $OCF_3$; and $R_5$ is benzyl, phenethyl, ($C_1$-$C_6$)alkyl, phenyl, indazolyl, or pyridyl, wherein each of the above is unsubstituted or substituted with 1, 2, 3, 4, or 5 groups that are independently ($C_1$-$C_4$)alkyl, halogen, OH, $CO_2H$, CN, ($C_1$-$C_4$)alkoxy, —C(O)pyrrolidine, —$SO_2$ ($C_1$-$C_6$)alkyl, benzyloxy, —$CO_2(C_1$-$C_5$ alkyl), amidino, thio($C_1$-$C_4$)alkoxy, amidinooxime, $CF_3$, $NR_8R_9$, $NR_6R_7$—($C_1$-$C_6$ alkyl)-, $CONR_6R_7$, or $OCF_3$.

Embodiment 130. Compounds according to embodiment 129 wherein $R_1$ is chloro, bromo, iodo, methyl, $C_2$-$C_3$ alkenyl, $C_2$-$C_3$ alkynyl; and $R_5$ is benzyl, phenethyl, phenpropyl, phenyl, or pyridyl, each of which is unsubstituted or substituted with 1, 2, or 3 groups that are independently alkyl, OH, halogen, alkoxy, $NH_2$, $NH(C_1$-$C_6$)alkyl, $N(C_1$-$C_6$)alkyl($C_1$-$C_6$)alkyl, $NR_8R_9$, $NR_6R_7$—($C_1$-$C_6$ alkyl)-, $CONR_6R_7$, and amidinooxime; wherein $R_6$ and $R_7$ are independently H, $C_1$-$C_4$ alkyl, $C_1$-$C_6$ alkanoyl, wherein the alkyl and alkanoyl groups are optionally substituted with 1, 2, or 3 groups that are independently OH, halogen, or $C_3$-$C_7$ cyclopropyl.

Embodiment 131. Compounds according to embodiment 130 wherein $R_2$ is benzyloxy, phenethyl, phenyloxy($C_1$-$C_6$)alkyl, or phenethyloxy, each of which is unsubstituted or substituted with 1, 2, or 3 groups that are independently halogen, —($C_1$-$C_6$)alkyl-N(R)—$CO_2R_{30}$, $CF_3$, $OCF_3$, or ($C_1$-$C_4$)alkyl.

Embodiment 132. Compounds according to embodiment 125, wherein $R_5$ is benzyl, phenethyl, thienyl($C_1$-$C_6$ alkyl), piperidinyl($C_1$-$C_6$)alkyl, pyrrolidinyl($C_1$-$C_6$)alkyl, imidazolidinyl($C_1$-$C_6$) alkyl, piperazinyl($C_1$-$C_6$)alkyl, pyridyl($C_1$-$C_6$)alkyl, pyrimidyl($C_1$-$C_6$)alkyl, pyridazyl($C_1$-$C_6$)alkyl, pyrazinyl ($C_1$-$C_6$)alkyl, isoquinolinyl($C_1$-$C_6$)alkyl, tetrahydroisoquinolinyl($C_1$-$C_6$)alkyl, indolyl($C_1$-$C_6$)alkyl, or 1H-indazolyl($C_1$-$C_6$)alkyl, wherein each of the above is unsubstituted or substituted with 1, 2, 3, 4, or 5 groups that are independently ($C_1$-$C_6$)alkyl, halogen, ($C_1$-$C_6$)alkoxy, ($C_1$-$C_6$)hydroxyalkyl, phenyl ($C_1$-$C_6$)alkoxy, ($C_1$-$C_6$)thioalkoxy, ($C_1$-$C_6$)alkoxycarbonyl, phenyl($C_1$-$C_6$)alkoxycarbonyl, OH, $CO_2H$, CN, amidinooxime, $NR_8R_9$, $NR_6R_7$—($C_1$-$C_6$ alkyl)-, C(O)$NR_6R_7$, amidino, piperazinyl, morpholinyl, —$SO_2$ ($C_1$-$C_6$)alkyl, —$SO_2NH_2$, —$SO_2NH(C_1$-$C_6$)alkyl, —$SO_2N$ ($C_1$-$C_6$)alkyl($C_1$-$C_6$)alkyl, ($C_1$-$C_4$)haloalkyl, —($C_1$-$C_4$ alkyl)-$NR_{15}C(O)NR_{16}R_{17}$, —($C_1$-$C_4$ alkyl)-$NR_{15}C(O)$ $R_{18}$, —O—$CH_2$—O, —O—$CH_2CH_2$—O—, or ($C_1$-$C_4$) haloalkoxy; wherein $R_6$ and $R_7$ are independently at each occurrence H, ($C_1$-$C_6$)alkyl, ($C_1$-$C_6$)alkoxy, ($C_1$-$C_6$)alkoxy($C_1$-$C_6$) alkyl, ($C_1$-$C_6$)alkoxycarbonyl, ($C_1$-$C_6$)hydroxyalkyl, —($C_1$-$C_4$)alkyl-$CO_2$—($C_1$-$C_6$)alkyl, ($C_1$-$C_6$)alkanoyl, phenyl($C_1$-$C_6$)alkyl, phenyl($C_1$-$C_6$)alkoxy, or phenyl($C_1$-$C_6$)alkanoyl, wherein each of the above is unsubstituted or substituted with 1, 2, or 3 groups that are independently, halogen, ($C_1$-$C_4$)alkoxy, $NH_2$, OH, SH, $C_3$-$C_6$ cycloalkyl, $NH(C_1$-$C_6$ alkyl), $N(C_1$-$C_6$ alkyl)($C_1$-$C_6$ alkyl), ($C_1$-$C_4$)alkyl, $CF_3$ or $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, hydroxy, hydroxy $C_1$-$C_4$ alkyl, or halogen; and $R_{18}$ is $C_1$-$C_6$ alkyl optionally substituted with —O— ($C_2$-$C_6$ alkanoyl, $C_1$-$C_6$ hydroxyalkyl, $C_1$-$C_6$ alkoxy, $C_1$-$C_6$ alkoxy $C_1$-$C_6$ alkyl; amino $C_1$-$C_6$ alkyl, mono or dialkylamino $C_1$-$C_6$ alkyl.

In this embodiment, it is preferred that $R_6$ and $R_7$ are not simultaneously OH; and $R_6$ and $R_7$ are not simultaneously —$SO_2(C_1$-$C_6$ alkyl).

Embodiment 133. Compounds according to embodiment 132, wherein $R_1$ is halogen, methyl, ethyl, $C_2$-$C_4$ alkenyl, $C_2$-$C_4$ alkynyl, or carboxaldehyde;

$R_2$ is benzyloxy, OH, phenyloxy, phenyloxy($C_1$-$C_6$)alkyl, or phenyl($C_1$-$C_4$)thioalkoxy, wherein each of the above is optionally substituted with 1, 2, 3, or 4 groups that are independently halogen, —($C_1$-$C_6$)alkyl-N(R)—$CO_2R_{30}$, $NR_6R_7$, ($C_1$-$C_4$)haloalkyl, ($C_1$-$C_4$)haloalkoxy, ($C_1$-$C_6$) alkyl, or pyridyl; and $R_4$ is H, ($C_1$-$C_4$)alkyl optionally substituted with one or two groups that are independently $CO_2H$, —$CO_2$alkyl, —C(O) NRR, —N($R_{30}$)C(O)NRR, —N($R_{30}$)C(O)—($C_1$-$C_6$) alkoxy, or —$NR_6R_7$, or hydroxy($C_1$-$C_4$)alkyl.

Embodiment 134. Compounds according to embodiment 133, wherein $R_5$ is benzyl, or phenethyl, wherein each is unsubstituted or substituted with 1, 2, 3, 4, or 5 groups that are independently ($C_1$-$C_6$)alkyl, halogen, ($C_1$-$C_6$)alkoxy, ($C_1$-$C_6$)hydroxyalkyl, phenyl($C_1$-$C_6$)alkoxy, ($C_1$-$C_6$)thioalkoxy, ($C_1$-$C_6$)alkoxycarbonyl, phenyl($C_1$-$C_6$)alkoxycarbonyl, OH, $CO_2H$, CN, amidinooxime, $NR_8R_9$, $NR_6R_7$—($C_1$-$C_6$ alkyl)-, —C(O)$NR_6R_7$, —($C_1$-$C_4$ alkyl)-C(O)$NR_6R_7$amidino, piperazinyl, morpholinyl, —$SO_2$ ($C_1$-$C_6$) alkyl, —$SO_2NH_2$, —$SO_2NH$($C_1$-$C_6$)alkyl, —$SO_2N$($C_1$-$C_6$)alkyl($C_1$-$C_6$)alkyl, ($C_1$-$C_4$)haloalkyl, —($C_1$-$C_4$ alkyl)-$NR_{15}C(O)R_{18}$, —O—$CH_2$—O—, —O—$CH_2CH_2$—O—, or ($C_1$-$C_4$)haloalkoxy; wherein $R_6$ and $R_7$ are independently at each occurrence H, ($C_1$-$C_6$) alkyl, ($C_1$-$C_6$)alkoxy, ($C_1$-$C_6$)alkoxy($C_1$-$C_6$)alkyl, ($C_1$-$C_6$)alkoxycarbonyl, ($C_1$-$C_6$)hydroxyalkyl, —($C_1$-$C_4$) alkyl-$CO_2$—($C_1$-$C_6$)alkyl, ($C_1$-$C_6$)alkanoyl, phenyl($C_1$-$C_6$)alkyl, phenyl($C_1$-$C_6$)alkoxy, or phenyl($C_1$-$C_6$) alkanoyl, wherein each of the above is unsubstituted or substituted with 1, 2, or 3 groups that are independently, halogen, ($C_1$-$C_4$)alkoxy, $NH_2$, OH, SH, $C_3$-$C_6$ cycloalkyl, NH($C_1$-$C_6$ alkyl), N($C_1$-$C_6$ alkyl)($C_1$-$C_6$ alkyl), ($C_1$-$C_4$)alkyl, $CF_3$ or $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, hydroxy, hydroxy $C_1$-$C_4$ alkyl, or halogen; and $R_{18}$ is $C_1$-$C_6$ alkyl optionally substituted with —O—($C_2$-$C_6$ alkanoyl, $C_1$-$C_6$ hydroxyalkyl, $C_1$-$C_6$ alkoxy, $C_1$-$C_6$ alkoxy $C_1$-$C_6$ alkyl, amino $C_1$-$C_6$ alkyl, or mono or dialkylamino $C_1$-$C_6$ alkyl.

In this embodiment, it is preferred that $R_6$ and $R_7$ are not simultaneously OH; and $R_6$ and $R_7$ are not simultaneously —$SO_2$($C_1$-$C_6$ alkyl).

Embodiment 135. Compounds according to embodiment 134, wherein $R_5$ is benzyl or phenethyl, wherein each is optionally substituted with 1, 2, 3, 4, or 5 groups that are independently $C_1$-$C_6$ alkyl, —C(O)$NR_6R_7$, —($C_1$-$C_4$ alkyl)-C(O)$NR_6R_7$, $NR_8R_9$, halogen, $C_1$-$C_6$ alkoxy, $CO_2H$, —($C_1$-$C_4$ alkyl)-$CO_2H$, $C_1$-$C_6$ thioalkoxy, amidinooxime, $C_1$-$C_6$ alkoxycarbonyl, —($C_1$-$C_4$ alkyl)-$C_1$-$C_6$ alkoxycarbonyl, $C_1$-$C_6$ hydroxyalkyl, —($C_1$-$C_4$ alkyl)-CN, CN, phenyl $C_1$-$C_6$ alkoxy, OH, $C_1$-$C_4$ haloalkyl, $C_1$-$C_4$ haloalkoxy, $NR_6R_7$—($C_1$-$C_6$ alkyl)-, —($C_1$-$C_4$ alkyl)-$NR_{15}C(O)R_{18}$, amidinooxime, —$SO_2$($C_1$-$C_6$ alkyl), —O—$CH_2$—O—, —O—$CH_2CH_2$—O—, phenyl $C_1$-$C_4$ alkoxy, or phenyl; wherein $R_6$ and $R_7$ at each occurrence are independently H, OH, $C_1$-$C_6$ alkyl, amino $C_1$-$C_4$ alkyl, NH($C_1$-$C_6$ alkyl)alkyl, N($C_1$-$C_6$ alkyl)($C_1$-$C_6$ alkyl)$C_1$-$C_6$ alkyl, $C_1$-$C_6$ hydroxyalkyl, $C_1$-$C_6$ alkoxy $C_1$-$C_6$ alkyl, —$SO_2$($C_1$-$C_6$ alkyl) each of which is optionally substituted with 1, 2, or 3 groups that are independently halogen, OH, SH, $C_3$-$C_6$ cycloalkyl, $C_1$-$C_4$ alkoxy, $C_1$-$C_4$ alkyl, OH, $CF_3$, or $OCF_3$;

or $R_6$, $R_7$, and the nitrogen to which they are attached form a piperidinyl, pyrrolidinyl, piperazinyl, or a morpholinyl, thiomorpholinyl, ring optionally substituted with 1 or 2 groups that are independently alkyl, hydroxy, hydroxy $C_1$-$C_4$ alkyl, or halogen, $R_{18}$ is $C_1$-$C_6$ alkyl optionally substituted with —O—($C_2$-$C_6$ alkanoyl, $C_1$-$C_6$ hydroxyalkyl, $C_1$-$C_6$ alkoxy, $C_1$-$C_6$ alkoxy $C_1$-$C_6$ alkyl; amino $C_1$-$C_6$ alkyl, mono or dialkylamino $C_1$-$C_6$ alkyl.

In this embodiment, it is preferred that $R_6$ and $R_7$ are not simultaneously OH; and $R_6$ and $R_7$ are not simultaneously —$SO_2$($C_1$-$C_6$ alkyl).

Embodiment 136. Compounds according to embodiment 135, wherein $R_5$ is benzyl or phenethyl, wherein each is optionally substituted with 1, 2, 3, 4, or 5 groups that are independently $C_1$-$C_6$ alkyl, —C(O)$NR_6R_7$, —($C_1$-$C_4$ alkyl)-C(O)$NR_6R_7$, halogen, $C_1$-$C_6$ alkoxy, $CO_2H$, —($C_1$-$C_4$ alkyl)-$CO_2H$, $C_1$-$C_6$ thioalkoxy, amidinooxime, $C_1$-$C_6$ alkoxycarbonyl, —($C_1$-$C_4$ alkyl)-$C_1$-$C_6$ alkoxycarbonyl, $C_1$-$C_6$ hydroxyalkyl, —($C_1$-$C_4$ alkyl)-CN, CN, phenyl $C_1$-$C_6$ alkoxy, OH, $C_1$-$C_4$ haloalkyl, $C_1$-$C_4$ haloalkoxy, $NR_6R_7$—($C_1$-$C_6$ alkyl)-, $NR_8R_9$, —($C_1$-$C_4$ alkyl)-$NR_{15}C(O)R_{18}$, amidinooxime, —$SO_2$($C_1$-$C_6$ alkyl), —O—$CH_2$—O—, —O—$CH_2CH_2$—O—, phenyl $C_1$-$C_4$ alkoxy, or phenyl; wherein $R_6$ and $R_7$ at each occurrence are independently H, OH, $C_1$-$C_6$ alkyl, amino $C_1$-$C_4$ alkyl, NH($C_1$-$C_6$ alkyl)alkyl, N($C_1$-$C_6$ alkyl)($C_1$-$C_6$ alkyl)$C_1$-$C_6$ alkyl, $C_1$-$C_6$ hydroxyalkyl, $C_1$-$C_6$ alkoxy $C_1$-$C_6$ alkyl, —$SO_2$($C_1$-$C_6$ alkyl) each of which is optionally substituted with 1, 2, or 3 groups that are independently halogen, OH, SH, $C_3$-$C_6$ cycloalkyl, $C_1$-$C_4$ alkoxy, $C_1$-$C_4$ alkyl, OH, $CF_3$, or $OCF_3$; and $R_{18}$ is $C_1$-$C_6$ alkyl optionally substituted with —O—($C_2$-$C_6$ alkanoyl, $C_1$-$C_6$ hydroxyalkyl, $C_1$-$C_6$ alkoxy, $C_1$-$C_6$ alkoxy $C_1$-$C_6$ alkyl; amino $C_1$-$C_6$ alkyl, mono or dialkylamino $C_1$-$C_6$ alkyl.

In this embodiment, it is preferred that $R_6$ and $R_7$ are not simultaneously OH; and $R_6$ and $R_7$ are not simultaneously —$SO_2$($C_1$-$C_6$ alkyl).

Embodiment 137. Compounds according to embodiment 136, wherein $R_5$ is benzyl which is optionally substituted with 1, 2, 3, 4, or 5 groups that are independently $C_1$-$C_4$ alkyl, —C(O) $NR_6R_7$, —($C_1$-$C_4$ alkyl)-C(O)$NR_6R_7$, halogen, $C_1$-$C_4$ alkoxy, $CO_2H$, $C_1$-$C_4$ thioalkoxy, $C_1$-$C_4$ alkoxycarbonyl, $C_1$-$C_6$ hydroxyalkyl, CN, OH, $NR_6R_7$—($C_1$-$C_6$ alkyl)-, $NR_8R_9$, —$SO_2$($C_1$-$C_6$ alkyl), or benzyloxy; wherein $R_6$ and $R_7$ at each occurrence are independently H, OH, $C_1$-$C_6$ alkyl, amino $C_1$-$C_4$ alkyl, NH($C_1$-$C_6$ alkyl)alkyl, N($C_1$-$C_6$ alkyl)($C_1$-$C_6$ alkyl)$C_1$-$C_6$ alkyl, $C_1$-$C_6$ hydroxyalkyl, $C_1$-$C_6$ alkoxy $C_1$-$C_6$ alkyl, —$SO_2$($C_1$-$C_6$ alkyl) each of which is optionally substituted with 1, 2, or 3 groups that are independently halogen, OH, SH, $C_3$-$C_6$ cycloalkyl, $C_1$-$C_4$ alkoxy, $C_1$-$C_4$ alkyl, OH, $CF_3$, or $OCF_3$.

In this embodiment, it is preferred that $R_6$ and $R_7$ are not simultaneously OH; and $R_6$ and $R_7$ are not simultaneously —$SO_2$($C_1$-$C_6$ alkyl).

Embodiment 138. Compounds according to embodiment 137, wherein $R_5$ is benzyl which is optionally substituted with 1, 2, 3, 4, or 5 groups that are independently $C_1$-$C_4$ alkyl, —C(O)NR$_6$R$_7$, —($C_1$-$C_4$ alkyl)-C(O)NR$_6$R$_7$, halogen, $C_1$-$C_4$ alkoxy, $C_1$-$C_4$ thioalkoxy, $C_1$-$C_4$ alkoxycarbonyl, $C_1$-$C_6$ hydroxyalkyl, CN, NR$_8$R$_9$, or NR$_6$R$_7$—($C_1$-$C_6$ alkyl)-; wherein $R_6$ and $R_7$ at each occurrence are independently H, OH, $C_1$-$C_6$ alkyl, amino $C_1$-$C_4$ alkyl, NH($C_1$-$C_6$ alkyl)alkyl, N($C_1$-$C_6$ alkyl)($C_1$-$C_6$ alkyl)$C_1$-$C_6$ alkyl, $C_1$-$C_6$ hydroxyalkyl, or $C_1$-$C_4$ alkoxy $C_1$-$C_4$ alkyl each of which is optionally substituted with 1, 2, or 3 groups that are independently halogen, OH, SH, $C_3$-$C_6$ cycloalkyl, $C_1$-$C_4$ alkoxy, $C_1$-$C_4$ alkyl, OH, CF$_3$, or OCF$_3$.

In this embodiment, it is preferred that $R_6$ and $R_7$ are not simultaneously OH.

Embodiment 139. Compounds according to embodiment 138, wherein the $R_5$ group is disubstituted with two groups that are meta to each other.

Embodiment 140. Compounds according to embodiment 135, wherein $R_5$ is benzyl which is optionally substituted with 1, 2, 3, 4, or 5 groups that are independently $C_1$-$C_4$ alkyl, —C(O)NR$_6$R$_7$, —($C_1$-$C_4$ alkyl)-C(O)NR$_6$R$_7$, NR$_8$R$_9$, NR$_6$R$_7$—($C_1$-$C_6$ alkyl)-, halogen, $C_1$-$C_4$ alkoxy, CO$_2$H, —($C_1$-$C_4$ alkyl)-CO$_2$H, —($C_1$-$C_4$ alkyl)-$C_1$-$C_6$ alkoxycarbonyl, —($C_1$-$C_4$ alkyl)-CN, CN, phenyl $C_1$-$C_6$ alkoxy, CF$_3$, OCF$_3$, —($C_1$-$C_4$ alkyl)-NR$_{15}$C(O)R$_{18}$, amidinooxime, —O—CH$_2$—O—, —O—CH$_2$CH$_2$—O—, or phenyl; wherein $R_6$ and $R_7$ at each occurrence are independently H, $C_1$-$C_4$ alkyl, amino $C_1$-$C_4$ alkyl, NH($C_1$-$C_4$ alkyl)alkyl, N($C_1$-$C_4$ alkyl)($C_1$-$C_4$ alkyl)$C_1$-$C_4$ alkyl, $C_1$-$C_6$ hydroxyalkyl, $C_1$-$C_4$ alkoxy $C_1$-$C_4$ alkyl, or OH, each of which is optionally substituted with 1, 2, or 3 groups that are independently halogen, OH, SH, $C_3$-$C_6$ cycloalkyl, $C_1$-$C_4$ alkoxy, $C_1$-$C_4$ alkyl, OH, CF$_3$, or OCF$_3$; and $R_{18}$ is $C_1$-$C_6$ alkyl, $C_1$-$C_6$ hydroxyalkyl, $C_1$-$C_6$ alkoxy, $C_1$-$C_4$ alkoxy $C_1$-$C_6$ alkyl; amino $C_1$-$C_6$ alkyl, mono or dialkylamino $C_1$-$C_6$ alkyl.

In this embodiment, it is preferred that $R_6$ and $R_7$ are not simultaneously OH.

Embodiment 141. Compounds according to embodiment 135, wherein $R_5$ is benzyl or phenethyl, wherein each is optionally substituted with 1, 2, 3, 4, or 5 groups that are independently $C_1$-$C_6$ alkyl, —C(O)NR$_6$R$_7$, —($C_1$-$C_4$ alkyl)-C(O)NR$_6$R$_7$, halogen, $C_1$-$C_6$ alkoxy, CO$_2$H, —($C_1$-$C_4$ alkyl)-CO$_2$H, $C_1$-$C_6$ thioalkoxy, amidinooxime, $C_1$-$C_6$ alkoxycarbonyl, —($C_1$-$C_4$ alkyl)-$C_1$-$C_6$ alkoxycarbonyl, $C_1$-$C_6$ hydroxyalkyl, —($C_1$-$C_4$ alkyl)-CN, CN, phenyl $C_1$-$C_6$ alkoxy, OH, $C_1$-$C_4$ haloalkyl, $C_1$-$C_4$ haloalkoxy, NR$_8$R$_9$, NR$_6$R$_7$—($C_1$-$C_6$ alkyl)-, —($C_1$-$C_4$ alkyl)-NR$_{15}$C(O)R$_{18}$, amidinooxime, —SO$_2$($C_1$-$C_6$ alkyl), —O—CH$_2$—O—, —O—CH$_2$CH$_2$—O—, phenyl $C_1$-$C_4$ alkoxy, or phenyl; wherein $R_6$, $R_7$, and the nitrogen to which they are attached form a piperidinyl, pyrrolidinyl, piperazinyl, or a morpholinyl, thiomorpholinyl, ring optionally substituted with 1 or 2 groups that are independently alkyl, hydroxy, hydroxy $C_1$-$C_4$ alkyl, or halogen, $R_{18}$ is $C_1$-$C_6$ alkyl optionally substituted with —O—($C_2$-$C_6$ alkanoyl, $C_1$-$C_6$ hydroxyalkyl, $C_1$-$C_6$ alkoxy, $C_1$-$C_6$ alkoxy $C_1$-$C_6$ alkyl; amino $C_1$-$C_6$ alkyl, mono or dialkylamino $C_1$-$C_6$ alkyl.

In this embodiment, it is preferred that $R_6$ and $R_7$ are not simultaneously OH; and $R_6$ and $R_7$ are not simultaneously —SO$_2$($C_1$-$C_6$ alkyl).

Embodiment 142. Compounds according to embodiment 141, wherein $R_5$ is benzyl which is optionally substituted with 1, 2, 3, 4, or 5 groups that are independently $C_1$-$C_4$ alkyl, —C(O)NR$_6$R$_7$, —($C_1$-$C_4$alkyl)-C(O)NR$_6$R$_7$, halogen, $C_1$-$C_4$ alkoxy, CO$_2$H, $C_1$-$C_4$ thioalkoxy, $C_1$-$C_4$ alkoxycarbonyl, $C_1$-$C_6$ hydroxyalkyl, CN, OH, NR$_8$R$_9$, NR$_6$R$_7$—($C_1$-$C_6$ alkyl)-, —SO$_2$($C_1$-$C_6$ alkyl), or benzyloxy; and wherein $R_6$ and $R_7$ at each occurrence are independently H, OH, $C_1$-$C_6$ alkyl, amino $C_1$-$C_4$ alkyl, NH($C_1$-$C_6$ alkyl)alkyl, N($C_1$-$C_6$ alkyl)($C_1$-$C_6$ alkyl)$C_1$-$C_6$ alkyl, $C_1$-$C_6$ hydroxyalkyl, $C_1$-$C_6$ alkoxy $C_1$-$C_6$ alkyl, or —SO$_2$($C_1$-$C_6$ alkyl), each of which is optionally substituted with 1, 2, or 3 groups that are independently halogen, OH, SH, $C_3$-$C_6$ cycloalkyl, $C_1$-$C_4$ alkoxy, $C_1$-$C_4$ alkyl, OH, CF$_3$, or OCF$_3$.

In this embodiment, it is preferred that $R_6$ and $R_7$ are not simultaneously OH; and $R_6$ and $R_7$ are not simultaneously —SO$_2$($C_1$-$C_6$ alkyl).

Embodiment 143. Compounds according to embodiment 135, wherein $R_5$ is benzyl which is optionally substituted with 1, 2, 3, 4, or 5 groups that are independently $C_1$-$C_4$ alkyl, —C(O)NR$_6$R$_7$, —($C_1$-$C_4$alkyl)-C(O)NR$_6$R$_7$, NR$_6$R$_7$—($C_1$-$C_6$ alkyl)-, NR$_8$R$_9$, halogen, $C_1$-$C_4$ alkoxy, $C_1$-$C_4$ thioalkoxy, $C_1$-$C_4$ alkoxycarbonyl, $C_1$-$C_6$ hydroxyalkyl, or CN; wherein $R_6$ and $R_7$ at each occurrence are independently H, OH, $C_1$-$C_6$ alkyl, amino $C_1$-$C_4$ alkyl, NH($C_1$-$C_6$ alkyl)alkyl, N($C_1$-$C_6$ alkyl)($C_1$-$C_6$ alkyl)$C_1$-$C_6$ alkyl, $C_1$-$C_6$ hydroxyalkyl, or $C_1$-$C_4$ alkoxy $C_1$-$C_4$ alkyl, each of which is optionally substituted with 1, 2, or 3 groups that are independently halogen, OH, SH, $C_3$-$C_6$ cycloalkyl, $C_1$-$C_4$ alkoxy, $C_1$-$C_4$ alkyl, OH, CF$_3$, or OCF$_3$.

In this embodiment, it is preferred that $R_6$ and $R_7$ are not simultaneously OH.

Embodiment 144. Compounds according to embodiment 143, wherein the $R_5$ group is disubstituted with two groups that are meta to each other.

Embodiment 145. Compounds according to embodiment 125, wherein $R_5$ is phenyl, which is optionally substituted with 1, 2, 3, 4, or 5 groups that are independently $C_1$-$C_4$ alkyl, —C(O)NR$_6$R$_7$, —NR$_6$R$_7$, NR$_6$R$_7$($C_1$-$C_6$ alkyl), NR$_8$R$_9$, $C_1$-$C_6$ hydroxyalkyl, halogen, $C_1$-$C_4$ alkoxy, CO$_2$H, OH, $C_1$-$C_6$ alkoxycarbonyl, carboxaldehyde, $C_1$-$C_4$ haloalkyl, —($C_1$-$C_4$ alkyl)-NR$_{15}$C(O)NR$_{16}$R$_{17}$, —($C_1$-$C_4$ alkyl)-NR$_{15}$C(O)R$_{18}$; wherein $R_6$ and $R_7$ at each occurrence are independently H, OH, $C_1$-$C_6$ alkyl, amino $C_1$-$C_4$ alkyl, NH($C_1$-$C_6$ alkyl)alkyl, N($C_1$-$C_6$ alkyl)($C_1$-$C_6$ alkyl)$C_1$-$C_6$ alkyl, $C_1$-$C_6$ hydroxyalkyl, $C_1$-$C_6$ alkoxy $C_1$-$C_6$ alkyl, —SO$_2$($C_1$-$C_6$ alkyl), —SO$_2$NH$_2$, —SO$_2$NH($C_1$-$C_6$ alkyl), —SO$_2$N($C_1$-$C_6$ alkyl)($C_1$-$C_6$ alkyl), or $C_1$-$C_6$ alkanoyl, each of which is optionally substituted with 1, 2, or 3 groups that are independently halogen, OH, SH, $C_3$-$C_6$ cycloalkyl, $C_1$-$C_4$ alkoxy, $C_1$-$C_4$ alkyl, OH, CF$_3$, or OCF$_3$; or $R_6$, $R_7$, and the nitrogen to which they are attached form a piperidinyl, pyrrolidinyl, piperazinyl, or a morpholinyl ring optionally substituted with 1 or 2 groups that are independently alkyl, hydroxy, hydroxy $C_1$-$C_4$ alkyl, or halogen, $R_{15}$ is H or $C_1$-$C_6$ alkyl;

$R_{16}$ and $R_{17}$ are independently H or $C_1$-$C_6$ alkyl; or $R_{16}$, $R_{17}$, and the nitrogen to which they are attached form a morpholinyl ring;

$R_{18}$ is $C_1$-$C_6$ alkyl optionally substituted with —O—($C_2$-$C_6$ alkanoyl, $C_1$-$C_6$ hydroxyalkyl, $C_1$-$C_6$ alkoxy, $C_1$-$C_6$ alkoxy $C_1$-$C_6$ alkyl; amino $C_1$-$C_6$ alkyl, mono or dialkylamino $C_1$-$C_6$ alkyl.

In this embodiment, it is preferred that $R_6$ and $R_7$ are not simultaneously OH.

Embodiment 146. Compounds according to embodiment 145, wherein $R_5$ is phenyl, which is optionally substituted with 1, 2, 3, 4, or 5 groups that are independently $C_1$-$C_4$ alkyl, —($C_1$-$C_4$ alkyl)-C(O)$NR_6R_7$, —C(O)$NR_6R_7$, —$NR_6R_7$, $NR_6R_7$ ($C_1$-$C_6$ alkyl), $NR_8R_9$, $C_1$-$C_6$ hydroxyalkyl, halogen, $C_1$-$C_4$ alkoxy, $CO_2H$, OH, $C_1$-$C_6$ alkoxycarbonyl, carboxaldehyde, $C_1$-$C_4$ haloalkyl, —($C_1$-$C_4$ alkyl)-$NR_{15}$C(O)$NR_{16}R_{17}$, —($C_1$-$C_4$ alkyl)-$NR_{15}$C(O)$R_{18}$; wherein $R_6$ and $R_7$ at each occurrence are independently H, OH, $C_1$-$C_6$ alkyl, amino $C_1$-$C_4$ alkyl, NH($C_1$-$C_6$ alkyl)alkyl, N($C_1$-$C_6$ alkyl)($C_1$-$C_6$ alkyl)$C_1$-$C_6$ alkyl, $C_1$-$C_6$ hydroxyalkyl, $C_1$-$C_6$ alkoxy $C_1$-$C_6$ alkyl, —$SO_2$($C_1$-$C_6$ alkyl), —$SO_2NH_2$, —$SO_2$NH($C_1$-$C_6$ alkyl), —$SO_2$N($C_1$-$C_6$ alkyl)($C_1$-$C_6$ alkyl), or $C_1$-$C_6$ alkanoyl each of which is optionally substituted with 1, 2, or 3 groups that are independently halogen, OH, SH, $C_3$-$C_6$ cycloalkyl, $C_1$-$C_4$ alkoxy, $C_1$-$C_4$ alkyl, OH, $CF_3$, or $OCF_3$;

$R_{15}$ is H or $C_1$-$C_6$ alkyl;

$R_{16}$ and $R_{17}$ are independently H or $C_1$-$C_6$ alkyl; or $R_{16}$, $R_{17}$, and the nitrogen to which they are attached form a morpholinyl ring;

$R_{18}$ is $C_1$-$C_6$ alkyl optionally substituted with —O—($C_2$-$C_6$ alkanoyl, $C_1$-$C_6$ hydroxyalkyl, $C_1$-$C_6$ alkoxy, $C_1$-$C_6$ alkoxy $C_1$-$C_6$ alkyl; amino $C_1$-$C_6$ alkyl, mono or dialkylamino $C_1$-$C_6$ alkyl.

Embodiment 147. Compounds according to embodiment 146, wherein $R_1$ is halogen, methyl, ethyl, $C_2$-$C_4$ alkenyl, $C_2$-$C_4$ alkynyl, or carboxaldehyde;

$R_2$ is benzyloxy, OH, phenyloxy, phenyloxy($C_1$-$C_6$)alkyl, or phenyl($C_1$-$C_4$)thioalkoxy, wherein each of the above is optionally substituted with 1, 2, 3, or 4 groups that are independently halogen, —($C_1$-$C_6$)alkyl-N(R)—$CO_2R_{30}$, $NR_6R_7$, ($C_1$-$C_4$)haloalkyl, ($C_1$-$C_4$)haloalkoxy, ($C_1$-$C_6$) alkyl, pyridyl, or $NR_6R_7$—($C_1$-$C_6$ alkyl)-; and $R_4$ is H, ($C_1$-$C_4$)alkyl optionally substituted with one or two groups that are independently $CO_2H$, —$CO_2$alkyl, —C(O)NRR, —N($R_{30}$)C(O)NRR, —N($R_{30}$)C(O)—($C_1$-$C_6$) alkoxy, or —$NR_6R_7$, or hydroxy($C_1$-$C_4$)alkyl.

Embodiment 148. Compounds according to embodiment 147, wherein $R_5$ is phenyl, which is optionally substituted with 1, 2, 3, 4, or 5 groups that are independently $C_1$-$C_4$ alkyl, —C(O)$NR_6R_7$, —($C_1$-$C_4$ alkyl)-C(O)$NR_6R_7$, —$NR_6R_7$, $NR_6R_7$ ($C_1$-$C_6$ alkyl), $C_1$-$C_6$ hydroxyalkyl, halogen, $C_1$-$C_4$ alkoxy, $CO_2H$, OH, $C_1$-$C_6$ alkoxycarbonyl, carboxaldehyde, $C_1$-$C_4$ haloalkyl, wherein $R_6$ and $R_7$ at each occurrence are independently H, OH, $C_1$-$C_6$ alkyl, amino $C_1$-$C_4$ alkyl, NH($C_1$-$C_6$ alkyl)alkyl, N($C_1$-$C_6$ alkyl)($C_1$-$C_6$ alkyl)$C_1$-$C_6$ alkyl, $C_1$-$C_6$ hydroxyalkyl, $C_1$-$C_6$ alkoxy $C_1$-$C_6$ alkyl, —$SO_2$($C_1$-$C_6$ alkyl), —$SO_2NH_2$, —$SO_2$NH($C_1$-$C_6$ alkyl), —$SO_2$N($C_1$-$C_6$ alkyl)($C_1$-$C_6$ alkyl), or $C_1$-$C_6$ alkanoyl, each of which is optionally substituted with 1, 2, or 3 groups that are independently halogen, OH, SH, $C_3$-$C_6$ cycloalkyl, $C_1$-$C_4$ alkoxy, $C_1$-$C_4$ alkyl, OH, $CF_3$, or $OCF_3$.

Embodiment 149. Compounds according to embodiment 125, wherein $R_5$ is thienyl($C_1$-$C_6$ alkyl), piperidinyl($C_1$-$C_6$)alkyl, pyrrolidinyl($C_1$-$C_6$)alkyl, imidazolidinyl($C_1$-$C_6$)alkyl, piperazinyl($C_1$-$C_6$)alkyl, pyridyl($C_1$-$C_6$)alkyl, pyrimidyl($C_1$-$C_6$) alkyl, pyridazyl($C_1$-$C_6$)alkyl, pyrazinyl($C_1$-$C_6$)alkyl, isoquinolinyl($C_1$-$C_6$)alkyl, tetrahydroisoquinolinyl($C_1$-$C_6$)alkyl, indolyl($C_1$-$C_6$)alkyl, 1H-indazolyl($C_1$-$C_6$)alkyl, dihydroindolonyl($C_1$-$C_6$ alkyl), indolinyl($C_1$-$C_6$ alkyl), dihydroisoindolyl($C_1$-$C_6$ alkyl), dihydrobenzimdazolyl ($C_1$-$C_6$ alkyl), or dihydrobenzoimidazolonyl($C_1$-$C_6$ alkyl), wherein each of the above is unsubstituted or substituted with 1, 2, 3, 4, or 5 groups that are independently ($C_1$-$C_6$)alkyl, halogen, ($C_1$-$C_6$)alkoxy, ($C_1$-$C_6$)hydroxyalkyl, phenyl ($C_1$-$C_6$)alkoxy, ($C_1$-$C_6$)thioalkoxy, ($C_1$-$C_6$)alkoxycarbonyl, phenyl($C_1$-$C_6$)alkoxycarbonyl, OH, $CO_2H$, CN, amidinooxime, $NR_8R_9$, $NR_6R_7$—($C_1$-$C_6$ alkyl)-, —C(O)$NR_6R_7$, —($C_1$-$C_4$ alkyl)-C(O)$NR_6R_7$, amidino, piperazinyl, morpholinyl, —$SO_2$ ($C_1$-$C_6$)alkyl, —$SO_2NH_2$, —$SO_2$NH($C_1$-$C_6$)alkyl, —$SO_2$N($C_1$-$C_6$) alkyl($C_1$-$C_6$)alkyl, ($C_1$-$C_4$)haloalkyl, —($C_1$-$C_4$ alkyl)-$NR_{15}$C(O)$NR_{16}R_{17}$, —($C_1$-$C_4$ alkyl)-$NR_{15}$C(O)$R_{18}$, —O—$CH_2$—O, —O—$CH_2CH_2$—O—, or ($C_1$-$C_4$)haloalkoxy; wherein $R_6$ and $R_7$ are independently at each occurrence H, ($C_1$-$C_6$)alkyl, ($C_1$-$C_6$)alkoxy, ($C_1$-$C_6$)alkoxy($C_1$-$C_6$) alkyl, ($C_1$-$C_6$)alkoxycarbonyl, ($C_1$-$C_6$)hydroxyalkyl, —($C_1$-$C_4$)alkyl-$CO_2$—($C_1$-$C_6$)alkyl, ($C_1$-$C_6$)alkanoyl, phenyl($C_1$-$C_6$)alkyl, phenyl($C_1$-$C_6$)alkoxy, or phenyl($C_1$-$C_6$)alkanoyl, wherein each of the above is unsubstituted or substituted with 1, 2, or 3 groups that are independently, halogen, ($C_1$-$C_4$)alkoxy, OH, SH, $C_3$-$C_6$ cycloalkyl, $NH_2$, NH($C_1$-$C_6$ alkyl), N($C_1$-$C_6$ alkyl)($C_1$-$C_6$ alkyl), ($C_1$-$C_4$)alkyl, $CF_3$ or $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, hydroxy, hydroxy $C_1$-$C_4$ alkyl, or halogen; and $R_{18}$ is $C_1$-$C_6$ alkyl optionally substituted with —O— ($C_2$-$C_6$ alkanoyl, $C_1$-$C_6$ hydroxyalkyl, $C_1$-$C_6$ alkoxy, $C_1$-$C_6$ alkoxy $C_1$-$C_6$ alkyl; amino $C_1$-$C_6$ alkyl, mono or dialkylamino $C_1$-$C_6$ alkyl.

In this embodiment, it is preferred that $R_6$ and $R_7$ are not simultaneously OH; and $R_6$ and $R_7$ are not simultaneously —$SO_2$($C_1$-$C_6$ alkyl).

Embodiment 150. Compounds according to embodiment 149, wherein $R_1$ is halogen, methyl, ethyl, $C_2$-$C_4$ alkenyl, $C_2$-$C_4$ alkynyl, or carboxaldehyde;

$R_2$ is benzyloxy, OH, phenyloxy, phenyloxy($C_1$-$C_6$)alkyl, or phenyl($C_1$-$C_4$) thioalkoxy, wherein each of the above is optionally substituted with 1, 2, 3, or 4 groups that are independently halogen, —($C_1$-$C_6$)alkyl-N(R)—$CO_2R_{30}$, $NR_6R_7$, ($C_1$-$C_4$)haloalkyl, ($C_1$-$C_4$)haloalkoxy, ($C_1$-$C_6$) alkyl, pyridyl, or $NR_6R_7$—($C_1$-$C_6$ alkyl)-; and $R_4$ is H, ($C_1$-$C_4$)alkyl optionally substituted with one or two groups that are independently $CO_2H$, —$CO_2$alkyl, —C(O)NRR, —N($R_{30}$)C(O)NRR, —N($R_{30}$)C(O)—($C_1$-$C_6$) alkoxy, or —$NR_6R_7$, or hydroxy($C_1$-$C_4$)alkyl.

Embodiment 151. Compounds according to embodiment 150, wherein $R_5$ is thienyl($C_1$-$C_6$ alkyl), indolyl($C_1$-$C_6$ alkyl), pyridinyl ($C_1$-$C_6$ alkyl), piperazinyl($C_1$-$C_6$ alkyl), or pyrazinyl($C_1$-$C_6$ alkyl) each of which is optionally substituted with 1, 2, or 3 groups that are independently $C_1$-$C_4$ alkyl, $C_1$-$C_4$ hydroxyalkyl, halogen, —C(O)NR$_6$R$_7$, —(C$_1$-C$_4$ alkyl)-C(O)NR$_6$R$_7$, C$_1$-C$_6$ alkoxycarbonyl, —NR$_6$R$_7$, NR$_6$R$_7$—(C$_1$-C$_6$ alkyl)-, haloalkyl, C$_1$-C$_6$ alkanoyl, R$_6$ and R$_7$ at each occurrence are independently H, C$_1$-C$_6$ alkyl optionally substituted with 1, 2, or 3 groups that are independently C$_1$-C$_4$ alkoxycarbonyl, halogen, C$_3$-C$_6$ cycloalkyl, OH, SH, or C$_1$-C$_4$ alkoxy;

or

R$_6$, R$_7$, and the nitrogen to which they are attached form a piperidinyl, pyrrolidinyl, piperazinyl, or a morpholinyl ring optionally substituted with 1 or 2 groups that are independently alkyl, hydroxy, hydroxy C$_1$-C$_4$ alkyl, or halogen.

Embodiment 152. Compounds according to embodiment 151, wherein

R$_5$ is thienyl(C$_1$-C$_6$ alkyl), indolyl(C$_1$-C$_6$ alkyl), pyridinyl (C$_1$-C$_6$ alkyl), piperazinyl(C$_1$-C$_6$ alkyl), or pyrazinyl(C$_1$-C$_6$ alkyl).

Embodiment 153. Compounds according to embodiment 151, wherein

R$_4$ is H, methyl, ethyl, or —CH$_2$OH;

R$_5$ is pyridinyl(C$_1$-C$_6$ alkyl), or pyrazinyl(C$_1$-C$_6$ alkyl) each of which is optionally substituted with 1, 2, or 3 groups that are independently C$_1$-C$_4$ alkyl, C$_1$-C$_4$ hydroxyalkyl, halogen, —C(O)NR$_6$R$_7$, —(C$_1$-C$_4$ alkyl)-C(O)NR$_6$R$_7$, C$_1$-C$_6$ alkoxycarbonyl, —NR$_6$R$_7$, NR$_6$R$_7$—(C$_1$-C$_6$ alkyl)-, CF$_3$, C$_1$-C$_6$ alkanoyl, wherein R$_6$ and R$_7$ at each occurrence are independently H, C$_1$-C$_6$ alkyl optionally substituted with 1, 2, or 3 groups that are independently C$_1$-C$_4$ alkoxycarbonyl, halogen, C$_3$-C$_6$ cycloalkyl, OH, SH, or C$_1$-C$_4$ alkoxy;

or

R$_6$, R$_7$, and the nitrogen to which they are attached form a piperidinyl, pyrrolidinyl, piperazinyl, or a morpholinyl ring optionally substituted with 1 or 2 groups that are independently alkyl, hydroxy, hydroxy C$_1$-C$_4$ alkyl, or halogen.

Embodiment 154. Compounds according to embodiment 153, wherein

R$_4$ is H, alkyl substituted with one or two groups that are independently CO$_2$H, —CO$_2$—(C$_1$-C$_6$)alkyl, —C(O)NRR, —N(R$_{30}$)C(O)NRR, —N(R$_{30}$)C(O)—(C$_1$-C$_6$) alkoxy, or —NR$_6$R$_7$.

Embodiment 155. Compounds according to embodiment 16, wherein

R$_1$ is halogen, or methyl;

R$_2$ is benzyloxy, which is optionally substituted with 1, 2, 3, or 4 groups that are independently halogen, —(C$_1$-C$_6$) alkyl-N(R)—CO$_2$R$_{30}$, CF$_3$, OCF$_3$, or (C$_1$-C$_4$)alkyl; and R$_4$ is H, methyl, ethyl, —CH$_2$OH, —CH$_2$CO$_2$—(C$_1$-C$_4$ alkyl), or C$_2$ hydroxyalkyl.

Embodiment 156. Compounds according to any one of embodiments 16, 17, 138, 143, 148, 149, 151 or 153, wherein R$_1$ is halogen, or methyl;

R$_2$ is benzyloxy, which is optionally substituted with 1, 2, 3, or 4 groups that are independently halogen, —(C$_1$-C$_6$) alkyl-N(R)—CO$_2$R$_{30}$, CF$_3$, OCF$_3$, or (C$_1$-C$_4$)alkyl; and R$_4$ is alkyl substituted with one group that is CO$_2$H, —CO$_2$—(C$_1$-C$_6$)alkyl, —C(O)NRR, —N(R$_{30}$)C(O)NRR, —N(R$_{30}$)C(O)—(C$_1$-C$_6$)alkoxy, or —NR$_6$R$_7$.

Embodiment 157. Compounds according to embodiment 125, wherein

R$_5$ is isoquinolinyl(C$_1$-C$_6$ alkyl), tetrahydroisoquinolinyl(C$_1$-C$_6$ alkyl), 1H-indazolyl(C$_1$-C$_6$ alkyl), dihydroindolonyl (C$_1$-C$_6$ alkyl), indolinyl(C$_1$-C$_6$ alkyl), dihydroisoindolyl (C$_1$-C$_6$ alkyl), dihydrobenzimdazolyl(C$_1$-C$_6$ alkyl), dihydrobenzoimidazolonyl(C$_1$-C$_6$ alkyl), each of which is unsubstituted or substituted with 1, 2, or 3 groups that are independently alkyl, alkoxy, halogen, C$_1$-C$_6$ alkoxycarbonyl, alkanoyl optionally substituted with 1 or 2 groups that are independently selected from the group consisting of OH, NH$_2$, NH(C$_1$-C$_6$ alkyl), and N(C$_1$-C$_6$ alkyl) (C$_1$-C$_6$ alkyl), —C(O)NR$_6$R$_7$, —(C$_1$-C$_4$ alkyl)-C(O)NR$_6$R$_7$, NR$_6$R$_7$—(C$_1$-C$_6$ alkyl)-, —NR$_6$R$_7$, or SO$_2$H; or piperidinyl C$_1$-C$_4$ alkyl optionally substituted with 1, 2, or 3 groups that are independently C$_1$-C$_4$ alkyl, C$_1$-C$_4$ alkoxy, halogen, —C(O)NR$_6$R$_7$, —(C$_1$-C$_4$ alkyl)-C(O)NR$_6$R$_7$, NR$_6$R$_7$—(C$_1$-C$_6$ alkyl)-, or —NR$_6$R$_7$, or C$_1$-C$_6$ alkoxycarbonyl.

Embodiment 158. Compounds according to embodiment 157, wherein

R$_5$ is isoquinolinyl(C$_1$-C$_4$ alkyl), piperidinyl C$_1$-C$_4$ alkyl, tetrahydroisoquinolinyl(C$_1$-C$_4$ alkyl), 1H-indazolyl(C$_1$-C$_4$ alkyl), dihydroindolonyl(C$_1$-C$_4$ alkyl), indolinyl(C$_1$-C$_4$ alkyl), dihydroisoindolyl(C$_1$-C$_4$ alkyl), dihydrobenzimdazolyl(C$_1$-C$_4$ alkyl), or dihydrobenzoimidazolonyl(C$_1$-C$_4$ alkyl).

Embodiment 159. Compounds according to embodiment 157, wherein

R$_5$ is piperidinyl C$_1$-C$_4$ alkyl optionally substituted with 1, 2, or 3 groups that are independently C$_1$-C$_4$ alkyl, C$_1$-C$_4$ alkoxy, halogen, or C$_1$-C$_6$ alkoxycarbonyl.

Embodiment 160. Compounds according to embodiment 125, wherein

R$_5$ is pyrimidyl, indolinyl, indolyl, 1H-isoindolyl, isoquinolinyl, tetrahydroisoquinolinyl, benzimidazolyl, dihydro-1H-benzimidazolyl, pyrrolyl, imidazolyl, or each of which is optionally substituted with 1, 2, or 3 groups independently selected from the group consisting of C$_1$-C$_6$ alkoxycarbonyl, C$_1$-C$_4$ thioalkoxy, each of which is unsubstituted or substituted with 1, 2, or 3 groups that are independently —C(O)NR$_6$R$_7$, —(C$_1$-C$_4$ alkyl)-C(O)NR$_6$R$_7$, NR$_6$R$_7$—(C$_1$-C$_6$ alkyl)-, —NR$_6$R$_7$, alkyl, alkoxy, halogen, C$_1$-C$_6$ alkoxycarbonyl, or alkanoyl optionally substituted with 1 or 2 groups that are independently selected from the group consisting of OH, NH$_2$, NH(C$_1$-C$_6$ alkyl), and N(C$_1$-C$_6$ alkyl)(C$_1$-C$_6$ alkyl), and SO$_2$H; or pyridyl, pyrazolyl, optionally substituted with 1, 2, or 3 groups that are independently —C(O)NR$_6$R$_7$, —(C$_1$-C$_4$ alkyl)-C(O)NR$_6$R$_7$, NR$_6$R$_7$—(C$_1$-C$_6$ alkyl)-, —NR$_6$R$_7$, C$_1$-C$_4$ alkyl, C$_1$-C$_4$ hydroxyalkyl, halogen, C$_1$-C$_6$ alkoxycarbonyl, —NR$_6$R$_7$, NR$_6$R$_7$—(C$_1$-C$_6$ alkyl)-, CF$_3$, C$_1$-C$_6$ alkanoyl, wherein R$_6$ and R$_7$ at each occurrence are independently H, C$_1$-C$_6$ alkyl optionally substituted with 1, 2, or 3 groups that are independently C$_1$-C$_4$ alkoxycarbonyl, halogen, C$_3$-C$_6$ cycloalkyl, OH, SH, or C$_1$-C$_4$ alkoxy;

or

R$_6$, R$_7$, and the nitrogen to which they are attached form a piperidinyl, pyrrolidinyl, piperazinyl, or a morpholinyl ring optionally substituted with 1 or 2 groups that are independently alkyl, hydroxy, hydroxy C$_1$-C$_4$ alkyl, or halogen.

Embodiment 161. Compounds according to embodiment 160, wherein

R$_5$ is pyrimidyl, pyrrolyl, imidazolyl, or pyrazolyl, each of which is optionally substituted with 1, 2, or 3 groups independently selected from C$_1$-C$_6$ alkoxycarbonyl, C$_1$-C$_4$ thioalkoxy, each of which is unsubstituted or substituted with 1, 2, or 3 groups that are independently alkyl, alkoxy, halogen, C$_1$-C$_6$ alkoxycarbonyl, —C(O)NR$_6$R$_7$, —(C$_1$-C$_4$ alkyl)-C(O)NR$_6$R$_7$, NR$_6$R$_7$—(C$_1$-C$_6$ alkyl)-, or —NR$_6$R$_7$, or C$_1$-C$_4$ alkanoyl optionally substituted with 1 or 2 groups that are independently selected from the group consisting of OH, $NH_2$, —NH($C_1$-$C_6$ alkyl), and N($C_2$-$C_6$ alkyl)($C_1$-$C_6$ alkyl), or $SO_2H$.

Embodiment 162. Compounds according to embodiment 160, wherein $R_5$ is pyridyl or pyrazolyl, optionally substituted with 1, 2, or 3 groups that are independently $C_1$-$C_4$ alkyl, $C_1$-$C_4$ hydroxyalkyl, halogen, —C(O)$NR_6R_7$, —($C_1$-$C_4$ alkyl)-C(O)$NR_6R_7$, $NR_6R_7$—($C_1$-$C_6$ alkyl)-, or —$NR_6R_7$, $C_1$-$C_6$ alkoxycarbonyl, —$NR_6R_7$, $NR_6R_7$—($C_1$-$C_6$ alkyl)-, $CF_3$, $C_1$-$C_6$ alkanoyl, wherein $R_6$ and $R_7$ at each occurrence are independently H, $C_1$-$C_6$ alkyl optionally substituted with 1, 2, or 3 groups that are independently $C_1$-$C_4$ alkoxycarbonyl, halogen, $C_3$-$C_6$ cycloalkyl, OH, SH, or $C_1$-$C_4$ alkoxy; or $R_6$, $R_7$, and the nitrogen to which they are attached form a piperidinyl, pyrrolidinyl, piperazinyl, or a morpholinyl ring optionally substituted with 1 or 2 groups that are independently alkyl, hydroxy, hydroxy $C_1$-$C_4$ alkyl, or halogen.

Embodiment 163. Compounds according to embodiment 162, wherein $R_5$ is pyridyl or pyrazolyl, optionally substituted with 1, 2, or 3 groups that are independently $C_1$-$C_4$ alkyl, $C_1$-$C_4$ hydroxyalkyl, halogen, —C(O)$NR_6R_7$, —($C_1$-$C_4$ alkyl)-C(O)$NR_6R_7$, $NR_6R_7$—($C_1$-$C_6$ alkyl)-, —$NR_6R_7$, $C_1$-$C_6$ alkoxycarbonyl, $CF_3$, $C_1$-$C_6$ alkanoyl, wherein $R_6$ and $R_7$ at each occurrence are independently H, $C_1$-$C_6$ alkyl optionally substituted with 1, 2, or 3 groups that are independently $C_1$-$C_4$ alkoxycarbonyl, halogen, $C_3$-$C_6$ cycloalkyl, OH, SH, or $C_1$-$C_4$ alkoxy.

Embodiment 164. Compounds according to embodiment 162, wherein $R_5$ is pyridyl or pyrazolyl, optionally substituted with 1, 2, or 3 groups that are independently $C_1$-$C_4$ alkyl, $C_1$-$C_4$ hydroxyalkyl, halogen, —C(O)$NR_6R_7$, —($C_1$-$C_4$ alkyl)-C(O)$NR_6R_7$, $NR_6R_7$—($C_1$-$C_6$ alkyl)-, —$NR_6R_7$, $C_1$-$C_6$ alkoxycarbonyl, $CF_3$, $C_1$-$C_6$ alkanoyl, wherein $R_6$, $R_7$, and the nitrogen to which they are attached form a piperidinyl, pyrrolidinyl, piperazinyl, or a morpholinyl ring optionally substituted with 1 or 2 groups that are independently alkyl-, hydroxy, hydroxy $C_1$-$C_4$ alkyl, or halogen.

Embodiment 165. Compounds according to any one of embodiments 157, 158, 159, 160, 161, 162, 163, or 164 wherein $R_1$ is halogen, methyl, ethyl, $C_2$-$C_4$ alkenyl, $C_2$-$C_4$ alkynyl, or carboxaldehyde;

$R_2$ is benzyloxy, OH, phenyloxy, phenyloxy($C_1$-$C_6$)alkyl, or phenyl($C_1$-$C_4$)thioalkoxy, wherein each of the above is optionally substituted with 1, 2, 3, or 4 groups that are independently halogen, —($C_1$-$C_6$)alkyl-N(R)—$CO_2R_{30}$, $NR_6R_7$, ($C_1$-$C_4$)haloalkyl, ($C_1$-$C_4$)haloalkoxy, ($C_1$-$C_6$) alkyl, pyridyl, or $NR_6R_7$—($C_1$-$C_6$ alkyl)-; and $R_4$ is H, ($C_1$-$C_4$)alkyl substituted with one group that is $CO_2H$, —$CO_2$—($C_1$-$C_6$)alkyl, —C(O)NRR, —N($R_{30}$)C(O)NRR, —N($R_{30}$)C(O)—($C_1$-$C_6$)alkoxy, or —$NR_6R_7$, hydroxy($C_1$-$C_4$)alkyl.

Embodiment 166. Compounds according to embodiment 125, wherein.

$R_5$ is $C_1$-$C_6$ alkyl optionally substituted with 1 or 2, groups that are independently $C_1$-$C_4$ alkoxycarbonyl, or halogen, or $R_5$ is $C_1$-$C_4$ alkoxy, ethyl, methyl, cyclopropylmethyl, cycloalkyl, or alkynyl, or $R_5$ is $C_2$-$C_6$ alkenyl optionally substituted with $C_1$-$C_4$ alkoxycarbonyl or cyclohexyl.

Embodiment 167. Compounds according to embodiment 166, wherein $R_1$ is halogen, methyl, ethyl, $C_2$-$C_4$ alkenyl, $C_2$-$C_4$ alkynyl, or carboxaldehyde;

$R_2$ is benzyloxy, OH, phenyloxy, phenyloxy($C_1$-$C_6$)alkyl, or phenyl($C_1$-$C_4$)thioalkoxy, wherein each of the above is optionally substituted with 1, 2, 3, or 4 groups that are independently halogen, —($C_1$-$C_6$)alkyl-N(R)—$CO_2R_{30}$, $NR_6R_7$, ($C_1$-$C_4$)haloalkyl, ($C_1$-$C_4$)haloalkoxy, ($C_1$-$C_6$) alkyl, pyridyl, or $NR_6R_7$—($C_1$-$C_6$ alkyl)-; and $R_4$ is H, ($C_1$-$C_4$)alkyl substituted with one group that is $CO_2H$, —$CO_2$—($C_1$-$C_6$)alkyl, —C(O)NRR, —N($R_{30}$)C(O)NRR, —N($R_{30}$)C(O)—($C_1$-$C_6$)alkoxy, or —$NR_6R_7$, hydroxy($C_1$-$C_4$)alkyl; wherein $R_6$ and $R_7$ at each occurrence are independently H, $C_1$-$C_6$ alkyl optionally substituted with 1, 2, or 3 groups that are independently $C_1$-$C_4$ alkoxycarbonyl, halogen, $C_3$-$C_6$ cycloalkyl, OH, SH, or $C_1$-$C_4$ alkoxy; or $R_6$, $R_7$, and the nitrogen to which they are attached form a piperidinyl, pyrrolidinyl, piperazinyl, or a morpholinyl ring optionally substituted with 1 or 2 groups that are independently alkyl, hydroxy, hydroxy $C_1$-$C_4$ alkyl, or halogen.

Embodiment 168. Compounds according to embodiment 167, wherein $R_5$ is $C_1$-$C_6$ alkyl optionally substituted with 1 or 2, groups that are independently $C_1$-$C_4$ alkoxycarbonyl, or halogen, or $R_5$ is $C_1$-$C_4$ alkoxy, ethyl, methyl, cyclopropylmethyl, cyclohexyl, cyclopentyl, $C_2$-$C_6$ alkynyl, or $R_5$ is $C_2$-$C_6$ alkenyl optionally substituted with $C_1$-$C_4$ alkoxycarbonyl or cyclohexyl.

Embodiment 169. Compounds according to embodiment 125, wherein $R_2$ is phenylalkynyl, —OC(O)NH($CH_2$)$_n$aryl, —OC(O)N(alkyl)($CH_2$)$_n$aryl, —$OSO_2$($C_1$-$C_6$)alkyl, —$OSO_2$aryl, $NR_8R_9$, or $NR_8R_9$—($C_1$-$C_4$ alkyl); wherein n is 0, 1, 2, 3, 4, 5 or 6;

each of the above is unsubstituted or substituted with 1, 2, 3, 4, or 5 groups that are independently halogen, —($C_1$-$C_6$)alkyl-N(R)—$CO_2R_{30}$, alkoxy, alkoxycarbonyl, CN, $NR_6R_7$, haloalkyl, haloalkoxy, alkyl, heteroaryl, heteroarylalkyl, $NR_6R_7$—($C_1$-$C_6$ alkyl)-, phenyl, —$SO_2$-phenyl wherein the phenyl groups are optionally substituted with 1, 2, or 3 groups that are independently halogen or $NO_2$; or —OC(O)$NR_6R_7$, wherein $R_6$ and $R_7$ are independently at each occurrence H, alkyl, alkoxy, alkoxyalkyl, alkoxycarbonyl, —$SO_2$-alkyl, OH, hydroxyalkyl, —($C_1$-$C_4$)alkyl-$CO_2$-alkyl, heteroarylalkyl, alkanoyl, arylalkyl, arylalkoxy, or arylalkanoyl, wherein each of the above is unsubstituted or substituted with 1, 2, or 3 groups that are independently, halogen, alkoxy, heterocycloalkyl, OH, $NH_2$, $C_3$-$C_6$ cycloalkyl, NH(alkyl), N(alkyl)(alkyl), —O-alkanoyl, alkyl, $C_1$-$C_4$ haloalkyl, or $C_1$-$C_4$ haloalkoxy; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, $C_1$-$C_4$ alkoxy, hydroxy, hydroxy $C_1$-$C_4$ alkyl, or halogen.

Embodiment 170. Compounds according to embodiment 169, wherein
$R_1$ is halogen, methyl, ethyl, $C_2$-$C_4$ alkenyl, $C_2$-$C_4$ alkynyl, or carboxaldehyde; and
$R_4$ is H, $(C_1$-$C_4)$alkyl substituted with one group that is $CO_2H$, —$CO_2$—$(C_1$-$C_6)$alkyl, —C(O)NRR, —N($R_{30}$)C(O)NRR, —N($R_{30}$)C(O)—$(C_1$-$C_6)$alkoxy, —$NR_6R_7$, $NR_6R_7$—$(C_1$-$C_6$ alkyl)-, or hydroxy$(C_1$-$C_4)$alkyl.

Embodiment 171. Compounds according to embodiment 170, wherein
$R_5$ is phenyl, optionally substituted with 1, 2, 3, 4, or 5 groups that are independently halogen, $C_1$-$C_4$ alkyl, $C_1$-$C_4$ alkoxy, $CF_3$, $OCF_3$, —$(C_1$-$C_4$ alkyl)-C(O)$NR_6R_7$, $NR_6R_7$—$(C_1$-$C_6$ alkyl)-, —$NR_6R_7$, or C(O)$NR_6R_7$, wherein
$R_6$ and $R_7$ are independently at each occurrence H, $C_1$-$C_6$ alkyl, $C_1$-$C_6$ alkoxy, $C_1$-$C_6$ alkoxy $C_1$-$C_6$ alkyl, $C_1$-$C_6$ alkoxycarbonyl, OH, $C_1$-$C_6$ hydroxyalkyl, —$(C_1$-$C_4)$alkyl-$CO_2$-alkyl, pyridyl $C_1$-$C_6$ alkyl, $C_1$-$C_6$ alkanoyl, benzyl, phenyl $C_1$-$C_6$ alkoxy, or phenyl $C_1$-$C_6$ alkanoyl, wherein each of the above is unsubstituted or substituted with 1, 2, or 3 groups that are independently, halogen, $C_1$-$C_6$ alkoxy, piperidinyl $C_1$-$C_6$ alkyl, morpholinyl $C_1$-$C_6$ alkyl, piperazinyl $C_1$-$C_6$ alkyl, OH, SH, $C_3$-$C_6$ cycloalkyl, $NH_2$, NH(alkyl), N(alkyl)(alkyl), —O—$C_1$-$C_4$ alkanoyl, $C_1$-$C_4$ alkyl, $CF_3$, or $OCF_3$; or
$R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, $C_1$-$C_4$ alkoxy, hydroxy, hydroxy $C_1$-$C_4$ alkyl, or halogen; or
$R_5$ is benzyl optionally substituted with 1, 2, 3, 4, or 5 groups that are independently halogen, $C_1$-$C_6$ alkyl, $C_1$-$C_6$ alkoxy, CN, $CF_3$, $OCF_3$, —$(C_1$-$C_4$ alkyl)-C(O)$NR_6R_7$, $NR_6R_7$—$(C_1$-$C_6$ alkyl)-, —$NR_6R_7$, or C(O)$NR_6R_7$.

Embodiment 172. Compounds according to embodiment 171, wherein
$R_2$ is $NR_8R_9$, or $NR_8R_9$—$(C_1$-$C_4$ alkyl)-; wherein
$R_8$ at each occurrence is independently hydrogen, $C_1$-$C_6$ alkyl, $C_1$-$C_6$ alkanoyl, phenyl$(C_1$-$C_6)$alkyl or phenyl $(C_1$-$C_6)$alkanoyl wherein each of the above is optionally substituted with 1, 2, 3, 4, or 5 groups that are independently $C_1$-$C_6$ alkyl, $C_1$-$C_6$ alkoxy, $C_1$-$C_6$ alkoxycarbonyl, halogen, or $C_1$-$C_4$ haloalkyl; and
$R_9$ at each occurrence is independently $C_1$-$C_6$ alkyl, $C_1$-$C_6$ alkanoyl, phenyl$(C_1$-$C_6)$alkyl, $C_3$-$C_7$ cycloalkyl, $C_2$-$C_6$ alkenyl, pyridyl, pyridazinyl, pyrimidinyl, pyrazinyl, imidazolyl, $C_3$-$C_7$ cycloalkyl$(C_1$-$C_6)$alkyl, phenyl$(C_1$-$C_6)$alkanoyl, —$SO_2$-phenyl, and phenyl wherein each of the above is optionally substituted with 1, 2, 3, 4, or 5 groups that are independently $C_1$-$C_6$ alkyl, $C_1$-$C_6$ alkoxy, $C_1$-$C_6$ alkoxycarbonyl, halogen, or $C_1$-$C_4$ haloalkyl.

Embodiment 173. Compounds according to embodiment 172, wherein
$R_8$ is H.

Embodiment 174. Compounds according to embodiment 173, wherein
$R_2$ is —NH-benzyl option substituted with 1, 2, or 3 groups that are independently halogen, $C_1$-$C_4$ alkyl, $C_1$-$C_4$ alkoxy, $CF_3$, $OCF_3$,
or
$R_2$ is —NH—C(O)phenyl, wherein the phenyl group is optionally substituted with 1, 2, or 3 groups that are independently halogen, $C_1$-$C_4$ alkyl, or $C_1$-$C_4$ alkoxy; or
$R_2$ is —NH-allyl.

Embodiment 175. Compounds according to embodiment 174, wherein
$R_1$ is chloro, bromo, iodo, or methyl; and
$R_5$ is benzyl optionally substituted with 1, 2, 3, 4, or 5 groups that are independently halogen, —$(C_1$-$C_4$ alkyl)-C(O)$NR_6R_7$, $NR_6R_7$—$(C_1$-$C_6$ alkyl)-, —$NR_6R_7$, $C_1$-$C_6$ alkyl, $C_1$-$C_6$ alkoxy, CN, $CF_3$, $OCF_3$, or C(O)$NR_6R_7$.

Embodiment 176. Compounds according to embodiment 174, wherein
$R_1$ is chloro, bromo, iodo, or methyl; and
$R_5$ is phenyl, optionally substituted with 1, 2, 3, 4, or 5 groups that are independently halogen, —$(C_1$-$C_4$ alkyl)-C(O)$NR_6R_7$, $NR_6R_7$—$(C_1$-$C_6$ alkyl)-, —$NR_6R_7$, $C_1$-$C_4$ alkyl, $C_1$-$C_4$ alkoxy, $CF_3$, $OCF_3$, or C(O)$NR_6R_7$.

Embodiment 177. A compound of the formula

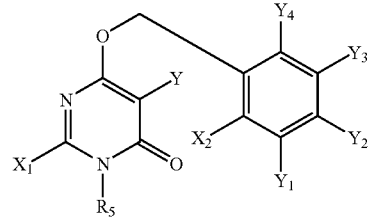

or pharmaceutically acceptable salts thereof, wherein
$R_5$ is

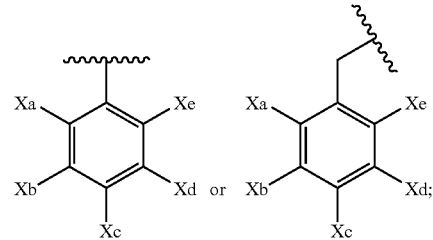

wherein
$X_1$, $X_2$, $X_a$, $X_b$, $X_c$, $X_d$, and $X_e$ at are independently selected from —C(O)$NR_6R_7$, —$NR_6R_7$, hydroxy$(C_1$-$C_4)$alkyl, H, OH, halogen, haloalkyl, alkyl, haloalkoxy, heteroaryl, heterocycloalkyl, $C_3$-$C_7$ cycloalkyl, $NR_6R_7$—$(C_1$-$C_6$ alkyl)-, —$CO_2$—$(C_1$-$C_6)$alkyl, —N(R)C(O)$NR_6R_7$, —N(R)C(O)—$(C_1$-$C_6)$alkoxy, $CO_2H$—$(C_1$-$C_6$ alkyl)-, or —$SO_2NR_6R_7$; wherein
the heteroaryl and heterocycloalkyl groups are optionally substituted with —$NR_6R_7$, —C(O)$NR_6R_7$, $NR_6R_7$—$(C_1$-$C_6$ alkyl)-, $C_1$-$C_6$ alkyl, $C_1$-$C_6$ alkoxy, or halogen;
$R_6$ and $R_7$ are independently at each occurrence H, $C_1$-$C_6$ alkyl, $C_1$-$C_6$ alkoxy, $C_1$-$C_6$ alkoxy $C_1$-$C_6$ alkyl, $C_1$-$C_6$ alkoxycarbonyl, OH, $C_1$-$C_6$ hydroxyalkyl, $C_1$-$C_6$ thiohydroxyalkyl, —$(C_1$-$C_4)$alkyl-$CO_2$-alkyl, pyridyl $C_1$-$C_6$ alkyl, $C_1$-$C_6$ alkanoyl, benzyl, phenyl $C_1$-$C_6$ alkoxy, or phenyl $C_1$-$C_6$ alkanoyl, wherein each of the above is unsubstituted or substituted with 1, 2, or 3 groups that are independently, halogen, $C_3$-$C_6$ cycloalkyl, $C_1$-$C_6$ alkoxy, piperidinyl $C_1$-$C_6$ alkyl, morpholinyl $C_1$-$C_6$ alkyl, piperazinyl $C_1$-$C_6$ alkyl, OH, SH, $NH_2$, NH(alkyl), N(alkyl)(alkyl), —O—$C_1$-$C_4$ alkanoyl, $C_1$-$C_4$ alkyl, $CF_3$, or $OCF_3$; or
$R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, $C_1$-$C_4$ alkoxy, hydroxy, hydroxy $C_1$-$C_4$ alkyl, or halogen;

R at each occurrence is independently H or $C_1$-$C_6$ alkyl; and

Y, $Y_1$, $Y_2$, $Y_3$, and $Y_4$ are independently selected from H, halogen, alkyl, carboxaldehyde, hydroxyalkyl, alkenyl, alkynyl, CN, alkanoyl, alkoxy, alkoxyalkyl, haloalkyl, and carboxyl.

Embodiment 178. Compounds according to embodiment 177, wherein $Y_2$, $Y_4$, and Y are independently halogen; and
$Y_1$ and $Y_3$ are both hydrogen.

Embodiment 179. Compounds according to embodiment 178, wherein $X_1$ is H, methyl, —$NR_6R_7$, $NR_6R_7$—($C_1$-$C_6$ alkyl)-, —C(O)$NR_6R_7$, $C_1$-$C_6$ hydroxyalkyl, or —($C_1$-$C_4$ alkyl)-morpholinyl.

Embodiment 180. Compounds according to embodiment 179, wherein $X_a$ and $X_e$ are independently halogen, is $NH_2$, NH($C_1$-$C_6$ alkyl), N($C_1$-$C_6$ alkyl)($C_1$-$C_6$ alkyl) or methyl.

Embodiment 181. Compounds according to embodiment 180, wherein $X_b$ or $X_c$ is —$NR_6R_7$, $NR_6R_7$—($C_1$-$C_6$ alkyl)-, —C(O)$NR_6R_7$, —$SO_2NR_6R_7$, or halogen; wherein $R_6$ and $R_7$ are independently at each occurrence H, $C_1$-$C_6$ alkyl, $C_1$-$C_6$ alkoxy, $C_1$-$C_6$ alkoxy $C_1$-$C_6$ alkyl, $C_1$-$C_6$ alkoxycarbonyl, OH, $C_1$-$C_6$ hydroxyalkyl, —($C_1$-$C_4$) alkyl-$CO_2$-alkyl, pyridyl $C_1$-$C_6$ alkyl, $C_1$-$C_6$ alkanoyl, benzyl, phenyl $C_1$-$C_6$ alkoxy, or phenyl $C_1$-$C_6$ alkanoyl, wherein each of the above is unsubstituted or substituted with 1, 2, or 3 groups that are independently, halogen, $C_3$-$C_6$ cycloalkyl, $C_1$-$C_6$ alkoxy, piperidinyl $C_1$-$C_6$ alkyl, morpholinyl $C_1$-$C_6$ alkyl, piperazinyl $C_1$-$C_6$ alkyl, OH, SH, $NH_2$, NH(alkyl), N(alkyl)(alkyl), —O—$C_1$-$C_4$ alkanoyl, $C_1$-$C_4$ alkyl, $CF_3$, or $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, $C_1$-$C_4$ alkoxy, hydroxy, hydroxy $C_1$-$C_4$ alkyl, or halogen.

Embodiment 182. Compounds according to embodiment 181, wherein $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, $C_1$-$C_4$ alkoxy, hydroxy, hydroxy $C_1$-$C_4$ alkyl, or halogen.

Embodiment 183. Compounds according to embodiment 181, wherein $R_6$, $R_7$, and the nitrogen to which they are attached form a piperazinyl ring which is optionally substituted with 1 or 2 groups that are independently $C_1$-$C_4$ alkyl, $C_1$-$C_4$ alkoxy, hydroxy, hydroxy $C_1$-$C_4$ alkyl, or halogen.

Embodiment 184. Compounds according to embodiment 181, wherein $R_6$ and $R_7$ are independently at each occurrence H, $C_1$-$C_6$ alkyl, $C_1$-$C_6$ alkoxy, $C_1$-$C_6$ alkoxy $C_1$-$C_6$ alkyl, $C_1$-$C_6$ alkoxycarbonyl, OH, $C_1$-$C_6$ hydroxyalkyl, —($C_1$-$C_4$) alkyl-$CO_2$-alkyl, pyridyl $C_1$-$C_6$ alkyl, $C_1$-$C_6$ alkanoyl, benzyl, phenyl $C_1$-$C_6$ alkoxy, or phenyl $C_1$-$C_6$ alkanoyl, wherein each of the above is unsubstituted or substituted with 1, 2, or 3 groups that are independently, halogen, $C_3$-$C_6$ cycloalkyl, $C_1$-$C_6$ alkoxy, piperidinyl $C_1$-$C_6$ alkyl, morpholinyl $C_1$-$C_6$ alkyl, piperazinyl $C_1$-$C_6$ alkyl, OH, $NH_2$, NH(alkyl), N(alkyl)(alkyl), —O—$C_1$-$C_4$ alkanoyl, $C_1$-$C_4$ alkyl, $CF_3$, or $OCF_3$.

Embodiment 185. Compounds according to embodiment 181, wherein $R_6$ and $R_7$ are independently at each occurrence H, $C_1$-$C_6$ alkyl, $C_1$-$C_6$ hydroxyalkyl, $C_1$-$C_6$ alkoxy, $C_1$-$C_6$ alkoxy $C_1$-$C_6$ alkyl, or $C_1$-$C_6$ alkanoyl, wherein each of the above is optionally substituted with 1, 2, or 3 groups that are independently OH, SH, halogen, or $C_3$-$C_6$ cycloalkyl.

Embodiment 186. Compounds according to embodiment 180, wherein $X_a$ and $X_e$ are independently fluoro, chloro, or methyl; and
$X_c$ is hydrogen or halogen.

Embodiment 187. Compounds according to embodiment 180, wherein $X_a$ is halogen;
$X_e$ is $NH_2$, NH($C_1$-$C_6$ alkyl) or N($C_1$-$C_6$ alkyl)($C_1$-$C_6$ alkyl);
$X_b$ and $X_d$ are both hydrogen.

Embodiment 188. Compounds according to embodiment 187, wherein $X_c$ is —$NR_6R_7$, $NR_6R_7$ $C_1$-$C_6$ alkyl, —$SO_2NR_6R_7$, or halogen; wherein $R_6$ and $R_7$ are independently at each occurrence H, $C_1$-$C_6$ alkyl, $C_1$-$C_6$ alkoxy, $C_1$-$C_6$ alkoxy $C_1$-$C_6$ alkyl, $C_1$-$C_6$ alkoxycarbonyl, OH, $C_1$-$C_6$ hydroxyalkyl, —($C_1$-$C_4$) alkyl-$CO_2$-alkyl, pyridyl $C_1$-$C_6$ alkyl, $C_1$-$C_6$ alkanoyl, benzyl, phenyl $C_1$-$C_6$ alkoxy, or phenyl $C_1$-$C_6$ alkanoyl, wherein each of the above is unsubstituted or substituted with 1, 2, or 3 groups that are independently, halogen, $C_3$-$C_6$ cycloalkyl, $C_1$-$C_6$ alkoxy, piperidinyl $C_1$-$C_6$ alkyl, morpholinyl $C_1$-$C_6$ alkyl, piperazinyl $C_1$-$C_6$ alkyl, OH, SH, $NH_2$, NH(alkyl), N(alkyl)(alkyl), —O—$C_1$-$C_4$ alkanoyl, $C_1$-$C_4$ alkyl, $CF_3$, or $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, $C_1$-$C_4$ alkoxy, hydroxy, hydroxy $C_1$-$C_4$ alkyl, or halogen.

Embodiment 189. Compounds according to embodiment 188, wherein $X_c$ is fluoro, chloro, $NH_2$, NH($C_1$-$C_6$ alkyl), N($C_1$-$C_6$ alkyl)($C_1$-$C_6$ alkyl), —$SO_2NH_2$, —$SO_2NH(C_1$-$C_6$ alkyl), —$SO_2N(C_1$-$C_6$ alkyl)($C_1$-$C_6$ alkyl), or piperazinyl, wherein the piperazinyl group is optionally substituted with 1 or 2 groups that are independently $C_1$-$C_4$ alkyl, $C_1$-$C_4$ alkoxy, hydroxy, hydroxy $C_1$-$C_4$ alkyl, or halogen.

Embodiment 190. Compounds according to either embodiment 180 or 187, wherein $X_c$ is —C(O)$NR_6R_7$, —($C_1$-$C_6$ alkyl)-C(O)$NR_6R_7$, $NR_6R_7$, or $NR_6R_7$—($C_1$-$C_6$ alkyl)-; wherein $R_6$ and $R_7$ are independently at each occurrence H, $C_1$-$C_6$ alkyl, $C_1$-$C_6$ alkoxy, $C_1$-$C_6$ alkoxy $C_1$-$C_6$ alkyl, $C_1$-$C_6$ alkoxycarbonyl, OH, $C_1$-$C_6$ hydroxyalkyl, —($C_1$-$C_4$) alkyl-$CO_2$-alkyl, pyridyl $C_1$-$C_6$ alkyl, $C_1$-$C_6$ alkanoyl, benzyl, phenyl $C_1$-$C_6$ alkoxy, or phenyl $C_1$-$C_6$ alkanoyl, wherein each of the above is unsubstituted or substituted with 1, 2, or 3 groups that are independently, halogen, $C_3$-$C_6$ cycloalkyl, $C_1$-$C_6$ alkoxy, piperidinyl $C_1$-$C_6$ alkyl, morpholinyl $C_1$-$C_6$ alkyl, piperazinyl $C_1$-$C_6$ alkyl, OH, $NH_2$, NH(alkyl), N(alkyl)(alkyl), —O—$C_1$-$C_4$ alkanoyl, $C_1$-$C_4$ alkyl, $CF_3$, or $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, $C_1$-$C_4$ alkoxy, hydroxy, hydroxy $C_1$-$C_4$ alkyl, or halogen.

Embodiment 191. Compounds according to embodiment 190, wherein $R_6$ is hydrogen; and $R_7$ is $C_1$-$C_6$ alkyl or $C_1$-$C_6$ alkanoyl, each of which is optionally substituted with 1, 2, or 3 groups that are independently $NH_2$, $NH(C_1$-$C_6$ alkyl), $N(C_1$-$C_6$ alkyl)($C_1$-$C_6$ alkyl), OH, SH, cyclopropyl, or $C_1$-$C_4$ alkoxy.

Embodiment 192. Compounds according to embodiment 191, wherein $R_7$ is $C_1$-$C_6$ alkanoyl optionally substituted with 1, 2, or 3 groups that are independently OH, cyclopropyl, or $NH_2$.

Embodiment 193. Compounds according to embodiment 178, wherein $X_a$ is hydrogen;

$X_b$, $X_c$, or $X_d$ is —C(O)$NR_6R_7$, —($C_1$-$C_6$ alkyl)-C(O)$NR_6R_7$, $NR_6R_7$, $NR_6R_7$—($C_1$-$C_6$ alkyl)- or —$CO_2$—($C_1$-$C_6$)alkyl; wherein $R_6$ and $R_7$ are independently at each occurrence H, $C_1$-$C_6$ alkyl, $C_1$-$C_6$ alkoxy, $C_1$-$C_6$ alkoxy $C_1$-$C_6$ alkyl, $C_1$-$C_6$ alkoxycarbonyl, OH, $C_1$-$C_6$ hydroxyalkyl, —($C_1$-$C_4$) alkyl-$CO_2$-alkyl, pyridyl $C_1$-$C_6$ alkyl, $C_1$-$C_6$ alkanoyl, benzyl, phenyl $C_1$-$C_6$ alkoxy, or phenyl $C_1$-$C_6$ alkanoyl, wherein each of the above is unsubstituted or substituted with 1, 2, or 3 groups that are independently, halogen, $C_3$-$C_6$ cycloalkyl, $C_1$-$C_6$ alkoxy, piperidinyl $C_1$-$C_6$ alkyl, morpholinyl $C_1$-$C_6$ alkyl, piperazinyl $C_1$-$C_6$ alkyl, OH, $NH_2$, NH(alkyl), N(alkyl)(alkyl), —O—$C_1$-$C_4$ alkanoyl, $C_1$-$C_4$ alkyl, $CF_3$, or $OCF_3$; or $R_6$, $R_7$, and the nitrogen to which they are attached form a morpholinyl, piperidinyl, pyrrolidinyl, or piperazinyl ring which is optionally substituted with 1 or 2 groups that are independently $C_1$-$C_4$ alkyl, $C_1$-$C_4$ alkoxy, hydroxy, hydroxy $C_1$-$C_4$ alkyl, or halogen; and $X_e$ is hydrogen, methyl, $C_1$-$C_2$ alkoxy, or halogen.

Embodiment 194. Compounds according to embodiment 193, wherein $X_b$ is $NR_6R_7$, or $NR_6R_7$—($C_1$-$C_6$ alkyl)-, —C(O)$NR_6R_7$ or —$CO_2$—($C_1$-$C_6$)alkyl; wherein $R_6$ is hydrogen or $C_1$-$C_4$ alkyl;

$R_7$ is OH, $C_1$-$C_6$ alkyl or $C_1$-$C_6$ alkanoyl, wherein the alkyl and alkanoyl groups substituted with 1, 2, or 3 groups that are independently $NH_2$, $NH(C_1$-$C_6$ alkyl), $N(C_1$-$C_6$ alkyl)($C_1$-$C_6$ alkyl), $C_3$-$C_6$ cycloalkyl, OH, or $C_1$-$C_4$ alkoxy.

Embodiment 195. Compounds according to embodiment 180, wherein $X_a$ is halogen;

$X_b$ is $NR_6R_7$, $NR_6R_7$—($C_1$-$C_6$ alkyl)-, —C(O)$NR_6R_7$, or —$CO_2$—($C_1$-$C_6$)alkyl;

$X_c$ is $NR_6R_7$, $NR_6R_7$—($C_1$-$C_6$ alkyl)-, —C(O)$NR_6R_7$, halogen, —$CO_2$—($C_1$-$C_6$)alkyl, $NH_2$, $NH(C_1$-$C_6$ alkyl), $N(C_1$-$C_6$ alkyl)($C_1$-$C_6$ alkyl), —$SO_2NH_2$, —$SO_2NH(C_1$-$C_6$ alkyl), —$SO_2N(C_1$-$C_6$ alkyl)($C_1$-$C_6$ alkyl), or piperazinyl, wherein the piperazinyl group is optionally substituted with 1 or 2 groups that are independently $C_1$-$C_4$ alkyl, $C_1$-$C_4$ alkoxy, hydroxy, hydroxy $C_1$-$C_4$ alkyl, or halogen;

$X_d$ is hydrogen;

$X_e$ is H, methyl, $NH_2$, $NH(C_1$-$C_6$ alkyl) or $N(C_1$-$C_6$ alkyl)($C_1$-$C_6$ alkyl).

Embodiment 196. Compounds according to embodiment 178, wherein $X_1$, $X_2$, $X_a$, $X_b$, $X_c$, $X_d$, and $X_e$ are independently selected from H, OH, halogen, $CF_3$, alkyl, $OCF_3$, pyridyl, pyridazinyl, pyrimidyl, pyrazinyl, thienyl, furyl, pyrrolyl, piperidinyl, piperazinyl, or $C_3$-$C_7$ cycloalkyl, wherein each of the above is optionally substituted with —$NR_6R_7$, —C(O)$NR_6R_7$, $NR_6R_7$—($C_1$-$C_6$ alkyl)-, $C_1$-$C_6$ alkyl, $C_1$-$C_6$ alkoxy, or halogen.

Embodiment 197. Compounds according to embodiment 196, wherein at least three of $X_1$, $X_2$, $X_a$, $X_b$, $X_c$, $X_d$, and $X_e$ are hydrogen.

In another aspect, the invention provides pharmaceutical compositions comprising at least one pharmaceutically acceptable carrier, solvent, adjuvant or excipient and a compound or salt of formula I, embodiment 118, or embodiment 181.

The invention further provides pharmaceutical compositions comprising at least one pharmaceutically acceptable carrier, solvent, adjuvant or excipient and compounds according to any of the preceding embodiments.

As noted above, the invention encompasses methods of treating a TNF mediated disorder, a p38 kinase mediated disorder, inflammation and/or arthritis in a subject, the method comprising treating a subject having or susceptible to such disorder or condition with a therapeutically-effective amount of a compound of formula I.

More specifically, the invention provides methods for treating or preventing inflammation; arthritis, rheumatoid arthritis, spondylarthropathies, gouty arthritis, osteoarthritis, systemic lupus erthematosus, juvenile arthritis, and other arthritic conditions; neuroinflammation; allergy, Th2 mediated diseases; pain, neuropathic pain; fever; pulmonary disorders, lung inflammation, adult respiratory distress syndrome, pulmonary sarcoisosis, asthma, silicosis, chronic pulmonary inflammatory disease, and chronic obstructive pulmonary disease (COPD); cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis; cardiomyopathy; stroke including ischemic and hemorrhagic stroke; reperfusion injury; renal reperfusion injury; ischemia including stroke and brain ischemia, and ischemia resulting from cardiac/coronary bypass; neurotrauma and brain trauma including closed head injury; brain edema; neurodegenerative disorders; liver disease and nephritis; gastrointestinal conditions, inflammatory bowel disease, Crohn's disease, gastritis, irritable bowel syndrome, ulcerative colitis; ulcerative diseases, gastric ulcers; ophthalmic diseases, retinitis, retinopathies, uveitis, ocular photophobia, acute injury to the eye tissue and ocular traumas such as post-traumatic glaucoma, traumatic optic neuropathy, and central retinal artery occlusion (CRAO); periodontal disease; opthalmological conditions, retinitis, retinopathies (including diabetic retinopathy), uveitis, ocular photophobia, nonglaucomatous optic nerve atrophy, and age related macular degeneration (ARMD) (including ARMD-atrophic form), corneal graft rejection, ocular neovascularization, retinal neovascularization, neovascularization following injury or infection, retrolental fibroplasias, neovascular glaucoma; glaucoma including primary open angle glaucoma (POAG), juvenile onset primary open-angle glaucoma, angle-closure glaucoma, pseudoexfoliative glaucoma, anterior ischemic optic neuropathy (AION), ocular hypertension, Reiger's syndrome, normal tension glaucoma, neovascular glaucoma, ocular inflammation and corticosteroid-induced glaucoma; diabetes; diabetic nephropathy; skin-related conditions, psoriasis, eczema, burns, dermatitis, keloid formation, scar tissue formation, angiogenic disorders; viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus; myalgias due to infection; influenza; endotoxic shock; toxic shock syndrome; autoimmune disease, graft vs. host reaction and allograft rejections; treatment of bone resorption diseases, osteoporosis; multiple sclerosis; disorders of the female reproductive system, endometriosis; hemaginomas, infantile hemagionmas, angiofibroma of the nasopharynx, avascular necrosis of bone; benign and malignant tumors/neoplasia, cancer, colorectal cancer, brain cancer, bone cancer, epithelial call-derived neoplasia (epithelial carcinoma), basal cell carcinoma, adenocarcinoma, gastrointestinal cancer, lip cancer, mouth cancer, esophageal cancer, small bowel cancer, stomach cancer, colon cancer, liver cancer, bladder cancer, pancreas cancer, ovarian cancer, cervical cancer, lung cancer, breast cancer, skin cancer, squamous cell and/or basal cell cancers, prostate cancer, renal cell carcinoma, and other known cancers that affect epithelial cells throughout the body; leukemia; lymphoma; systemic lupus erthrematosis (SLE); angiogenesis including neoplasia; metastasis; central nervous system disorders, central nervous system disorders having an inflammatory or apoptotic component, Alzheimer's disease, Parkinson's disease, Huntington's disease, amyotrophic lateral sclerosis, spinal cord injury, and peripheral neuropathy; Canine B-Cell Lymphoma. Compounds of the invention are also useful for preventing the production or expression of cyclooxygenase-2, or cyclooxygenase-2 activity.

In this aspect, the invention encompasses methods of treating a p38 kinase or TNF-alpha mediated disorder comprising administering to a patient in need thereof a therapeutically effective amount of compounds or salts according to embodiment 1, 118, or 181 and at least one pharmaceutically acceptable carrier, adjuvant, solvent or excipient.

Representative compounds of the invention are:

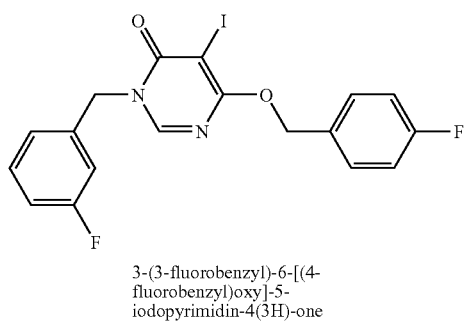

3-(3-fluorobenzyl)-6-[(4-fluorobenzyl)oxy]-5-iodopyrimidin-4(3H)-one

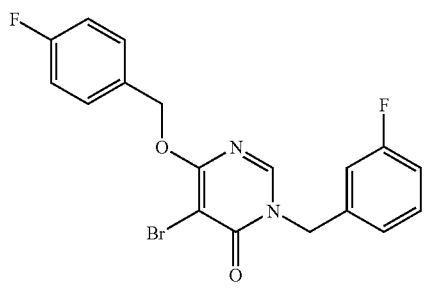

5-bromo-3-(3-fluorobenzyl)-6-[(4-fluorobenzyl)oxy]pyrimidin-4(3H)-one

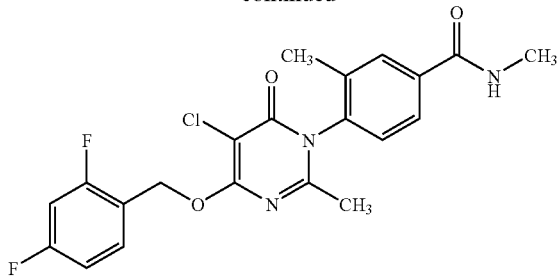

4-[5-chloro-4-[(2,4-difluorobenzyl)oxy]-2-methyl-6-oxopyrimidin-1(6H)-yl]-N,3-dimethylbenzamide

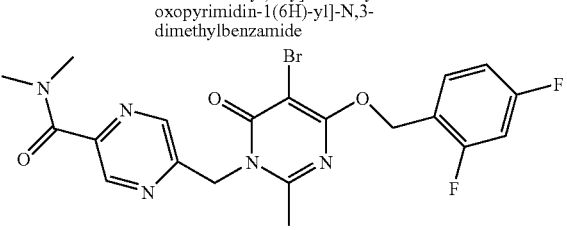

5-{[5-bromo-4-[(2,4-difluorobenzyl)oxy]-2-methyl-6-oxopyrimidin-1(6H)-yl]methyl}-N,N-dimethylpyrazine-2-carboxamide

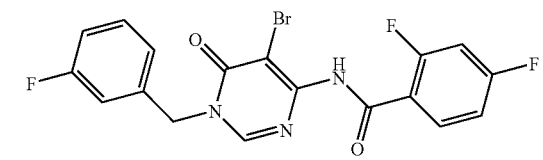

N-[5-bromo-1-(3-fluorobenzyl)-6-oxo-1,6-dihydropyrimidin-4-yl]-2,4-difluorobenzamide.

Other representative compounds of the invention are
3-(2-bromobenzyl)-5-[(2-bromobenzyl)oxy]pyrimidin-4 (3H)-one;
3-benzyl-5-bromo-6-(2-phenylethyl)pyrimidin-4(3H)-one;
3-benzyl-5-bromo-6-(3-phenylpropyl)pyrimidin-4(3H)-one;
3-benzyl-5-bromo-6-[(2,6-dichlorobenzyl)oxy]pyrimidin-4 (3H)-one;
3-benzyl-5-bromo-6-[(2-chlorobenzyl)oxy]pyrimidin-4 (3H)-one;
3-benzyl-5-bromo-6-[(s-chlorobenzyl)oxy]-2-methylpyrimidin-4(3H)-one;
3-benzyl-5-bromo-6-[(4-chlorobenzyl)oxy]pyrimidin-4 (3H)-one;
3-benzyl-5-bromo-6-{[2-(trifluoromethyl)benzyl] oxy}pyrimidin-4(3H)-one;
3-benzyl-5-methyl-6-(2-phenylethyl)pyrimidin-4(3H)-one;
3-benzyl-5-methyl-6-(3-phenylpropyl)pyrimidin-4(3H)-one;
3-benzyl-6-(benzyloxy)-5-(hydroxymethyl)pyrimidin-4 (3H)-one;
3-benzyl-6-(benzyloxy)-1,5-dibromo-2-methylpyrimidin-4 (3H)-one;
3-benzyl-6-(benzyloxy)-1,5-dibromopyrimidin-4(3H)-one;
3-benzyl-6-(benzyloxy)-5-bromopyrimidin-4(3H)-one;
3-benzyl-6-(benzyloxy)-5-chloropyrimidin-4(3H)-one;
3-benzyl-6-(benzyloxy)-5-methylpyrimidin-4(3H)-one;
3-benzyl-6-(benzyloxy)-2-methylpyrimidin-4(3H)-one;
3-benzyl-6-(benzyloxy)pyrimidin-4(3H)-one;
3-benzyl-6-(benzylthio)-5-bromopyrimidin-4(3H)-one;
3-benzyl-6-(benzylthio)-5-methylpyrimidin-4(3H)-one;

3-benzyl-6-(benzylthio)pyrimidin-4(3H)-one;
3-benzyl-6-[(2,6-dichlorobenzyl)oxy]pyrimidin-4(3H)-one;
3-benzyl-6-[(2-chlorobenzyl)oxy]pyrimidin-4(3H)-one;
3-benzyl-6-[(3-chlorobenzyl)oxy]-2-methylpyrimidin-4(3H)-one;
3-benzyl-6-[(3-chlorobenzyl)oxy]pyrimidin-4(3H)-one;
3-benzyl-6-hydroxypyrimidin-4(3H)-one;
5-acetyl-6-hydroxy-2-methyl-1-[choro]phenylpyrimidin-4(3H)-one;
5-benzoyl-2-(benzyloxy)-3-methylpyrimidin-4(3H)-one;
5-benzyl-2-(benzyloxy)-3-methylpyrimidin-4(3H)-one;
5-bromo-3-(5-chlorobenzyl)-6-[(4-chlorobenzyl)oxy]pyrimidin-4(3H)-one;
5-bromo-3-(4-chlorobenzyl)-6-[(4-chlorobenzyl)oxy]pyrimidin-4(3H)-one;
5-bromo-3-(4-fluorobenzyl)-6-[(4-fluorobenzyl)oxy]pyrimidin-4(3H)-one;
5-bromo-3-(4-methoxybenzyl)-6-phenoxypyrimidin-4(3H)-one;
5-bromo-3-(4-methylbenzyl)-6-[(4-methylbenzyl)oxy]pyrimidin-4(3H)-one;
5-bromo-6-[(4-chlorobenzyl)oxy]-3-(2-phenylethyl)pyrimidin-4(3H)-one;
5-bromo-6-[(4-chlorobenzyl)oxy]-3-(4-fluorobenzyl)pyrimidin-4(3H)-one;
5-bromo-6-[(4-chlorobenzyl)oxy]-3-(4-methoxybenzyl)pyrimidin-4(3H)-one;
5-bromo-6-[(4-chlorobenzyl)oxy]-3-[2-(phenylthio)ethyl]pyrimidin-4(3H)-one;
5-bromo-6-[(4-fluorobenzyl)oxy]-3-(3-phenylpropyl)pyrimidin-4(3H)-one;
5-bromo-6-hydroxy-3-(4-hydroxybenzyl)pyrimidin-4(3H)-one;
6-(benzyloxy)-3-(2-fluorobenzyl)pyrimidin-4(3H)-one;
6-(benzyloxy)-3-(3-fluorobenzyl)pyrimidin-4(3H)-one;
6-(benzyloxy)-3-(4-bromobenzyl)pyrimidin-4(3H)-one;
6-(benzyloxy)-3-(4-chlorobenzyl)pyrimidin-4(3H)-one;
6-(benzyloxy)-3-(4-fluorobenzyl)pyrimidin-4(3H)-one;
6-(benzyloxy)-3-[6-(benzyloxy)benzyl]-5-bromopyrimidin-4(3H)-one;
6-(benzyloxy)-5-bromo-3-(2-thien-2-ylethyl)pyrimidin-4(3H)-one;
6-(benzyloxy)-5-bromo-3-(4-fluorobenzyl)pyrimidin-4(3H)-one;
6-(benzyloxy)-5-bromo-3-(4-tert-butylbenzyl)pyrimidin-4(3H)-one;
6-(benzyloxy)-5-bromo-3-(piperidin-3-ylmethyl)pyrimidin-4(3H)-one hydrochloride;
6-(benzyloxy)-5-bromo-3-(piperidin-4-ylmethyl)pyrimidin-4(3H)-one hydrochloride;
6-(benzyloxy)-5-bromo-3-[4-(methylthio)benzyl]pyrimidin-4(3H)-one;
6-(benzyloxy)-5-bromo-3-[4-(trifluoromethoxy)benzyl]pyrimidin-4(3H)-one;
6-(benzyloxy)-5-bromo-3-ethylpyrimidin-4(3H)-one;
6-(benzyloxy)-5-bromo-3-methylpyrimidin-4(3H)-one;
6-(benzyloxy)-5-bromo-3-methylpyrimidin-4(3H)-one hydrobromide;
6-amino-3-benzylpyrimidin-4(3H)-one;
1-bromo-3-(2-chloro-6-fluorobenzyl)-5-methylpyrimidin-4(3H)-one;
1-benzyl-4-(benzyloxy)-6-oxo-1,6-dihydropyrimidine-5-carbaldehyde;
1-benzyl-4-chloro-6-oxo-1,6-dihydropyrimidine-5-carbaldehyde;
1-benzyl-4-hydroxy-6-oxo-1,6-dihydropyrimidine-5-carbaldehyde;
1-benzyl-6-oxo-1,6-dihydropyrimidin-4-yl methanesulfonate;
1-benzyl-6-oxo-1,6-dihydropyrimidin-4-yl methyl(phenyl)carbamate;
1-benzyl-6-oxo-4-phenoxy-1,6-dihydropyrimidine-5-carbaldehyde;
1-benzyl-5-bromo-6-oxo-1,6-dihydropyrimidin-4-yl methyl(phenyl)carbamate; or
2-(benzyloxy)-1-methyl-6-oxo-1,6-dihydropyrimidine-5-carbonitrile.

Embodiment 203. Compounds according to embodiment 1 embodiment 118, or embodiment 181, which is
3-(2,6-dichlorophenyl)-6-hydroxy-2-methylpyrimidin-4(1H)-one;
3-(3-fluorobenzyl)-6-hydroxy-2-methylpyrimidin-4(3H)-one;
3-(3-fluorobenzyl)-6-hydroxypyrimidin-4(3H)-one;
3-benzyl-5-bromo-6-(phenylethynyl)pyrimidin-4(3H)-one;
3-benzyl-5-bromo-6-[(4-methylbenzyl)oxy]pyrimidin-4(3H)-one;
3-Benzyl-5-bromo-6-[2,6-(dichlorobenzyl)oxy]pyrimidin-4(3H)-one;
3-benzyl-5-bromo-6-hydroxypyrimidin-4(3H)-one;
3-benzyl-6-(benzyloxy)-3-ethylpyrimidin-4(3H)-one;
3-benzyl-6-(benzyloxy)-5-iodopyrimidin-4(3H)-one;
3-benzyl-6-(benzyloxy)-3-vinylpyrimidin-4(3H)-one;
3-Benzyl-6-[2,6-(dichlorobenzyl)oxy]pyrimidin-4(3H)-one;
3-Benzyl-6-[benzylthio]-5-bromopyrimidin-4(3H)-one;
3-benzyl-6-hydroxy-2-methylpyrimidin-4(3H)-one;
5-acetyl-3-(2,6-dichlorophenyl)-6-hydroxy-6-methylpyrimidin-4(3H)-one;
5-acetyl-3-(2-chlorophenyl)-4-hydroxy-2-methylpyrimidin-4(3H)-one;
5-acetyl-6-(benzyloxy)-3-(2-chlorophenyl)-2-methylpyrimidin-4(3H)-one;
5-bromo-3-(3-fluorobenzyl)-6-(2-phenylethyl)pyrimidin-4(3H)-one;
5-bromo-3-(3-fluorobenzyl)-6-(phenylethynyl)pyrimidin-4(3H)-one;
5-bromo-3-(3-fluorobenzyl)-6-hydroxy-2-methylpyrimidin-4(3H)-one;
5-bromo-3-(3-fluorobenzyl)-6-hydroxypyrimidin-4(3H)-one;
5-bromo-3-(3-fluorobenzyl)-2-methyl-6-(2-phenylethyl)pyrimidin-4(3H)-one;
5-bromo-3-(3-fluorobenzyl)-6-methyl-6-(phenylethynyl)pyrimidin-4(3H)-one;
6-(benzylamino)-3-(3-fluorobenzyl)pyrimidin-4(3H)-one;
6-(benzylamino)-5-bromo-3-(3-fluorobenzyl)pyrimidin-4(3H)-one;
6-(benzyloxy)-3-(2,6-dichlorophenyl)-2-methylpyrimidin-4(3H)-one;
6-(benzyloxy)-3-(3-fluorobenzyl)-5-[(trimethylsilyl)ethynyl]pyrimidin-4(3H)-one;
6-(benzyloxy)-3-(3-fluorobenzyl)-5-iodopyrimidin-4(3H)-one;
6-(benzyloxy)-3-(4-methylbenzyl)pyrimidin-4(3H)-one;
6-(benzyloxy)-3-(4-tert-butylbenzyl)pyrimidin-4(3H)-one;
6-(benzyloxy)-3-[4-(trifluoromethoxy)benzyl]pyrimidin-4(3H)-one;
6-(benzyloxy)-3-[4-(trifluoromethyl)benzyl]pyrimidin-4(3H)-one;
6-(benzyloxy)-5-bromo-3-[2-(trifluoromethyl)benzyl]pyrimidin-4(3H)-one;
6-(benzyloxy)-5-bromo-3-[3-(trifluoromethyl)benzyl]pyrimidin-4(3H)-one;

6-(benzyloxy)-5-bromo-3-[4-(trifluoromethyl)benzyl]pyrimidin-4(3H)-one;
6-(benzyloxy)-5-bromopyrimidin-4(3H)-one;
6-(benzyloxy)-3-ethynyl-3-(3-fluorobenzyl)pyrimidin-4(3H)-one;
6-[(2,6-dichlorobenzyl)oxy]pyrimidine-4-one;
1-benzyl-2-methyl-6-oxo-1,6-dihydropyrimidin-4-yl 4-bromobenzenesulfonate;
1-benzyl-5-bromo-6-oxo-1,6-dihydropyrimidin-4-yl trifluoromethanesulfonate;
4-{[4-(benzyloxy)-6-oxopyrimidin-1(6H)-yl]methyl}benzonitrile;
5-bromo-1-(3-fluorobenzyl)-6-oxo-1,6-dihydropyrimidin-4-yl trifluoromethanesulfonate;
5-bromo-1-(3-fluorobenzyl)-2-methyl-6-oxo-1,6-dihydropyrimidin-4-yl trifluoromethanesulfonate;
4-{[4-(benzyloxy)-5-bromo-6-oxopyrimidin-1(6H)-yl]methyl}-2-methylbenzoate; or
4-{[4-(benzyloxy)-6-oxopyrimidin-1(6H)-yl]methyl}-2-methylbenzoate.

Still other representative compounds of the invention are
3-[5-bromo-4-[(2,4-difluorobenzyl)oxy]-2-methyl-6-oxopyrimidin-1(6H)-yl]-4-methylbenzamide;
5-bromo-3-(2,4-difluorobenzyl)-6-[(2,4-difluorobenzyl)oxy]pyrimidin-4(3H)-one;
5-bromo-3-(2,6-dichlorophenyl)-6-[(2,4-difluorobenzyl)oxy]-2-methylpyrimidin-4(3H)-one;
5-bromo-3-(2,6-dichlorophenyl)-6-[(4-fluorobenzyl)oxy]-2-methylpyrimidin-4(3H)-one;
5-bromo-3-(2,6-dimethylphenyl)-6-[(4-fluorobenzyl)oxy]-2-methylpyrimidin-4(3H)-one;
5-bromo-3-(3-fluorobenzyl)-6-[(3-methylbenzyl)oxy]pyrimidin-4-one;
5-bromo-6-[(2,4-difluorobenzyl)oxy]-3-(2-fluorobenzyl)pyrimidin-4(3H)-one;
5-bromo-6-[(2,4-difluorobenzyl)oxy]-3-(2-methoxy-2-methylphenyl)-2-methylpyrimidin-4(3H)-one;
5-bromo-6-[(2,4-difluorobenzyl)oxy]-3-(3-fluorobenzyl)pyrimidin-4(3H)-one;
5-bromo-6-[(2,4-difluorobenzyl)oxy]-3-(3-methoxybenzyl)pyrimidin-4(3H)-one;
5-bromo-6-[(2,4-difluorobenzyl)oxy]-2-methyl-3-(pyridin-3-ylmethyl)pyrimidin-4(3H)-one;
5-bromo-6-[(5-chlorobenzyl)oxy]-3-(3-fluorobenzyl)pyrimidin-4(3H)-one;
5-bromo-6-[(4-fluorobenzyl)oxy]-3-(pyridin-3-ylmethyl)pyrimidin-4(3H)-one;
5-bromo-6-[(4-fluorobenzyl)oxy]-3-(pyridin-4-ylmethyl)pyrimidin-4(3H)-one;
5-bromo-6-[(4-fluorobenzyl)oxy]-2-methyl-3-(pyrimidin-4-ylmethyl)pyrimidin-4(3H)-one;
5-bromo-6-[(4-fluorobenzyl)oxy]-2-methyl-3-(pyridin-3-ylmethyl)pyrimidin-4(3H)-one;
5-bromo-6-[(4-fluorobenzyl)oxy]-2-methyl-3-(pyridin-4-ylmethyl)pyrimidin-4(3H)-one; or
4-{[5-bromo-4-[(4-fluorobenzyl)oxy]-6-oxopyrimidin-1(6H)-yl]methyl}benzonitrile.

Other representative compounds of the invention are
3-(1-acetyl-1H-benzimidazol-5-yl)-5-chloro-6-[(2,4-difluorobenzyl)oxy]-2-methylpyrimidin-4(3H)-one;
3-(1-acetyl-1H-imidazol-4-yl)-5-chloro-6-[(2,4-difluorobenzyl)oxy]-2-methylpyrimidin-4(3H)-one;
3-(1-acetyl-1H-indol-5-yl)-5-chloro-6-[(2,4-difluorobenzyl)oxy]-2-methylpyrimidin-4(3H)-one;
3-(1-acetyl-1H-pyrazol-4-yl)-5-chloro-6-[(2,4-difluorobenzyl)oxy]-2-methylpyrimidin-4(3H)-one;
3-(1-acetyl-1H-pyrrol-3-yl)-5-chloro-6-[(2,4-difluorobenzyl)oxy]-2-methylpyrimidin-4(3H)-one;
3-(1-acetyl-2,3-dihydro-1H-indol-5-yl)-5-chloro-6-[(2,4-difluorobenzyl)oxy]-2-methylpyrimidin-4(3H)-one;
3-(1-acetyl-3-glycoloyl-2,3-dihydro-1H-benzimidazol-5-yl)-5-chloro-6-[(2,4-difluorobenzyl)oxy]-2-methylpyrimidin-4(3H)-one;
3-(1H-indazol-5-yl)-6-(1H-indazol-5-ylamino)-2-methylpyrimidin-4(3H)-one;
3-(2,6-difluoro-phenyl)-6-methoxy-2-methyl-1-phenethyl-1H-pyrimidin-4-one;
3-(2-acetyl-1,2,3,4-tetrahydroisoquinolin-6-yl)-5-chloro-6-[(2,4-difluorobenzyl)oxy]-2-methylpyrimidin-4(3H)-one;
3-(2-acetyl-1,2,3,4-tetrahydroisoquinolin-7-yl)-5-chloro-6-[(2,4-difluorobenzyl)oxy]-2-methylpyrimidin-4(3H)-one;
3-(2-acetyl-2,3-dihydro-1H-isoindol-5-yl)-5-chloro-6-[(2,4-difluorobenzyl)oxy]-2-methylpyrimidin-4(3H)-one;
3-(2-Chloro-4-hydroxy-phenyl)-6-(2,4-difluoro-benzyloxy)-2-methyl-1H-pyrimidin-4-one;
3-(3-{[Bis-(2-hydroxy-ethyl)-amino]-methyl}-benzyl)-5-bromo-6-(2,4-difluoro-benzyloxy)-2-methyl-1H-pyrimidin-4-one;
3-(3-acetyl-1-glycoloyl-2,3-dihydro-1H-benzimidazol-5-yl)-5-chloro-6-[(2,4-difluorobenzyl)oxy]-2-methylpyrimidin-4(3H)-one;
3-(3-Aminomethyl-2-fluoro-benzyl)-5-bromo-6-(2,4-difluoro-benzyloxy)-3H-pyrimidin-4-one;
3-(3-Aminomethyl-benzyl)-5-bromo-6-(2,4-difluoro-benzyloxy)-2-methyl-3H-pyrimidin-4-one;
3-(3-Aminomethyl-benzyl)-6-benzyloxy-5-bromo-3H-pyrimidin-4-one;
3-(3-Fluoro-benzyl)-6-(4-fluoro-benzyloxy)-5-iodo-1H-pyrimidin-4-one;
3-(3-fluorobenzyl)-6-(phenylethynyl)pyrimidin-4(3H)-one;
3-(3-fluorobenzyl)-6-[(4-fluorobenzyl)oxy]-5-methylpyrimidin-4(3H)-one;
3-(4-{[Bis-(2-hydroxy-ethyl)-amino]-methyl}-benzyl)-5-bromo-6-(2,4-difluoro-benzyloxy)-2-methyl-3H-pyrimidin-4-one;
3-(4-Aminomethyl-benzyl)-5-bromo-6-(2,4-difluoro-benzyloxy)-2-methyl-3H-pyrimidin-4-one;
3-(4-Aminomethyl-benzyl)-6-benzyloxy-5-bromo-3H-pyrimidin-4-one;
3-(4-Bromo-2,6-difluoro-phenyl)-6-(2,4-difluoro-benzyloxy)-2-methyl-1H-pyrimidin-4-one;
3-(4-bromo-2-methylphenyl)-6-[(2,4-difluorobenzyl)oxy]-2-methylpyrimidin-4(3H)-one;
3-(4-Chloro-benzyl)-3-[3-(4-chloro-phenyl)-[1,2,4]oxadiazol-5-yl]-3H-pyrimidin-4-one;
3-(4-fluorobenzyl)-6-[(4-fluorobenzyl)oxy]pyrimidin-4(3H)-one;
3-(4-methoxybenzyl)-6-phenoxypyrimidin-4(3H)-one;
3-(biphenyl-4-ylmethyl)-5-bromo-6-[(4-fluorobenzyl)oxy]pyrimidin-4(3H)-one;
1,3-diacetyl-5-{[5-chloro-6-[(2,4-difluorobenzyl)oxy]-4-oxopyrimidin-3(3H)-yl]methyl}-1,3-dihydro-2H-benzimidazol-2-one;
3,5-dibenzyl-6-hydroxy-2-methylpyrimidin-4(3H)-one;
3-[(1-acetyl-1H-indol-5-yl)methyl]-5-chloro-6-[(2,4-difluorobenzyl)oxy]pyrimidin-4(3H)-one;
3-[(1-acetyl-2,3-dihydro-1H-benzimidazol-5-yl)methyl]-5-chloro-6-[(2,4-difluorobenzyl)oxy]pyrimidin-4(3H)-one;
3-[(1-acetyl-2,3-dihydro-1H-indol-5-yl)methyl]-5-chloro-6-[(2,4-difluorobenzyl)oxy]pyrimidin-4(3H)-one;
3-[(1-acetyl-3-glycoloyl-2,3-dihydro-1H-benzimidazol-5-yl)methyl]-5-chloro-6-[(2,4-difluorobenzyl)oxy]pyrimidin-4(3H)-one;

3-[(2-acetyl-1,2,3,4-tetrahydroisoquinolin-5-yl)methyl]-5-chloro-6-[(2,4-difluorobenzyl)oxy]pyrimidin-4(3H)-one;
3-[(2-acetyl-1,2,3,4-tetrahydroisoquinolin-6-yl)methyl]-5-chloro-6-[(2,4-difluorobenzyl)oxy]pyrimidin-4(3H)-one;
3-[(2-acetyl-2,3-dihydro-1H-isoindol-5-yl)methyl]-5-chloro-6-[(2,4-difluorobenzyl)oxy]pyrimidin-4(3H)-one;
3-[(3-acetyl-1-glycoloyl-2,3-dihydro-1H-benzimidazol-5-yl)methyl]-5-chloro-6-[(2,4-difluorobenzyl)oxy]pyrimidin-4(3H)-one;
3-[(3-acetyl-2,3-dihydro-1H-benzimidazol-5-yl)methyl]-5-chloro-6-[(2,4-difluorobenzyl)oxy]pyrimidin-4(3H)-one;
3-[1,3-bis(2-hydroxy-2-methylpropanoyl)-2,3-dihydro-1H-benzimidazol-5-yl]-5-chloro-6-[(2,4-difluorobenzyl)oxy]-2-methylpyrimidin-4(3H)-one;
3-[1,3-bis(3-hydroxy-5-methylbutanoyl)-2,3-dihydro-1H-benzimidazol-5-yl]-5-chloro-6-[(2,4-difluorobenzyl)oxy]-2-methylpyrimidin-4(3H)-one;
3-[1,3-bis(3-hydroxypropanoyl)-2,3-dihydro-1H-benzimidazol-5-yl]-5-chloro-6-[(2,4-difluorobenzyl)oxy]-2-methylpyrimidin-4(3H)-one;
3-[1,3-bis(methylsulfonyl)-2,3-dihydro-1H-benzimidazol-5-yl]-5-chloro-6-[(2,4-difluorobenzyl)oxy]-2-methylpyrimidin-4(3H)-one;
3-[1,3-bis(N-methylglycyl)-2,3-dihydro-1H-benzimidazol-5-yl]-5-chloro-6-[(2,4-difluorobenzyl)oxy]-2-methylpyrimidin-4(3H)-one;
3-[1-acetyl-3-(2-hydroxy-2-methylpropanoyl)-2,3-dihydro-1H-benzimidazol-5-yl]-5-chloro-6-[(2,4-difluorobenzyl)oxy]-2-methylpyrimidin-4(3H)-one;
3-[1-acetyl-3-(3-hydroxy-5-methylbutanoyl)-2,3-dihydro-1H-benzimidazol-5-yl]-5-chloro-6-[(2,4-difluorobenzyl)oxy]-2-methylpyrimidin-4(3H)-one;
3-[1-acetyl-3-(3-hydroxypropanoyl)-2,3-dihydro-1H-benzimidazol-5-yl]-5-chloro-6-[(2,4-difluorobenzyl)oxy]-2-methylpyrimidin-4(3H)-one;
3-[1-acetyl-3-(methylsulfonyl)-2,3-dihydro-1H-benzimidazol-5-yl]-5-chloro-6-[(2,4-difluorobenzyl)oxy]-2-methylpyrimidin-4(3H)-one;
3-[1-acetyl-3-(N-methylglycyl)-2,3-dihydro-1H-benzimidazol-5-yl]-5-chloro-6-[(2,4-difluorobenzyl)oxy]-2-methylpyrimidin-4(3H)-one;
3-[2-(aminomethyl)benzyl]-5-bromo-6-[(2,4-difluorobenzyl)oxy]-2-methylpyrimidin-4(3H)-one;
3-[2-(aminomethyl)benzyl]-5-bromo-6-[(2,4-difluorobenzyl)oxy]pyrimidin-4(3H)-one;
3-[2-(aminomethyl)benzyl]-6-(benzyloxy)-5-bromopyrimidin-4(3H)-one;
3-[2-chloro-5-(hydroxymethyl)phenyl]-6-[(2,4-difluorobenzyl)oxy]-2-methylpyrimidin-4(3H)-one;
3-[3-(2-aminoethyl)benzyl]-5-bromo-6-[(2,4-difluorobenzyl)oxy]pyrimidin-4(3H)-one trifluoroacetate;
3-[3-(aminomethyl)benzyl]-5-bromo-6-[(2,4-difluorobenzyl)oxy]pyrimidin-4(3H)-one trifluoroacetate;
3-[3-(aminomethyl)benzyl]-5-bromo-6-[(4-fluorobenzyl)oxy]pyrimidin-4(3H)-one trifluoroacetate;
3-[3-(aminomethyl)benzyl]-5-bromo-6-[(4-fluorobenzyl)oxy]pyrimidin-4(3H)-one;
3-[3-(aminomethyl)phenyl]-5-bromo-6-[(2,4-difluorobenzyl)oxy]-2-methylpyrimidin-4(3H)-one;
3-[3-acetyl-3-(2-hydroxy-2-methylpropanoyl)-2,3-dihydro-1H-benzimidazol-5-yl]-5-chloro-6-[(2,4-difluorobenzyl)oxy]-2-methylpyrimidin-4(3H)-one;
3-[3-acetyl-3-(3-hydroxy-5-methylbutanoyl)-2,3-dihydro-1H-benzimidazol-5-yl]-5-chloro-6-[(2,4-difluorobenzyl)oxy]-2-methylpyrimidin-4(3H)-one;
3-[3-acetyl-3-(3-hydroxypropanoyl)-2,3-dihydro-1H-benzimidazol-5-yl]-5-chloro-6-[(2,4-difluorobenzyl)oxy]-2-methylpyrimidin-4(3H)-one;
3-[3-acetyl-3-(methylsulfonyl)-2,3-dihydro-1H-benzimidazol-5-yl]-5-chloro-6-[(2,4-difluorobenzyl)oxy]-2-methylpyrimidin-4(3H)-one;
3-[3-acetyl-3-(N-methylglycyl)-2,3-dihydro-1H-benzimidazol-5-yl]-5-chloro-6-[(2,4-difluorobenzyl)oxy]-2-methylpyrimidin-4(3H)-one;
3-{[1,3-bis(2-hydroxy-2-methylpropanoyl)-2,3-dihydro-1H-benzimidazol-5-yl]methyl}-5-chloro-6-[(2,4-difluorobenzyl)oxy]pyrimidin-4(3H)-one;
3-{[1,3-bis(3-hydroxy-3-methylbutanoyl)-2,3-dihydro-1H-benzimidazol-5-yl]methyl}-5-chloro-6-[(2,4-difluorobenzyl)oxy]pyrimidin-4(3H)-one;
3-{[1,3-bis(3-hydroxypropanoyl)-2,3-dihydro-1H-benzimidazol-5-yl]methyl}-5-chloro-6-[(2,4-difluorobenzyl)oxy]pyrimidin-4(3H)-one;
3-{[1,3-bis(methylsulfonyl)-2,3-dihydro-1H-benzimidazol-5-yl]methyl}-5-chloro-6-[(2,4-difluorobenzyl)oxy]pyrimidin-4(3H)-one;
3-{[1,3-bis(N-methylglycyl)-2,3-dihydro-1H-benzimidazol-5-yl]methyl}-5-chloro-6-[(2,4-difluorobenzyl)oxy]pyrimidin-4(3H)-one;
3-{[1-acetyl-3-(2-hydroxy-2-methylpropanoyl)-2,3-dihydro-1H-benzimidazol-5-yl]methyl}-5-chloro-6-[(2,4-difluorobenzyl)oxy]pyrimidin-4(3H)-one;
3-{[1-acetyl-3-(3-hydroxy-3-methylbutanoyl)-2,3-dihydro-1H-benzimidazol-5-yl]methyl}-5-chloro-6-[(2,4-difluorobenzyl)oxy]pyrimidin-4(3H)-one;
3-{[1-acetyl-3-(3-hydroxypropanoyl)-2,3-dihydro-1H-benzimidazol-5-yl]methyl}-5-chloro-6-[(2,4-difluorobenzyl)oxy]pyrimidin-4(3H)-one;
3-{[1-acetyl-3-(methylsulfonyl)-2,3-dihydro-1H-benzimidazol-5-yl]methyl}-5-chloro-6-[(2,4-difluorobenzyl)oxy]pyrimidin-4(3H)-one;
3-{[1-acetyl-3-(N-methylglycyl)-2,3-dihydro-1H-benzimidazol-5-yl]methyl}-5-chloro-6-[(2,4-difluorobenzyl)oxy]pyrimidin-4(3H)-one;
3-{[3-acetyl-1-(2-hydroxy-2-methylpropanoyl)-2,3-dihydro-1H-benzimidazol-5-yl]methyl}-5-chloro-6-[(2,4-difluorobenzyl)oxy]pyrimidin-4(3H)-one;
3-{[3-acetyl-1-(3-hydroxy-3-methylbutanoyl)-2,3-dihydro-1H-benzimidazol-5-yl]methyl}-5-chloro-6-[(2,4-difluorobenzyl)oxy]pyrimidin-4(3H)-one;
3-{[3-acetyl-1-(3-hydroxypropanoyl)-2,3-dihydro-1H-benzimidazol-5-yl]methyl}-5-chloro-6-[(2,4-difluorobenzyl)oxy]pyrimidin-4(3H)-one;
3-{[3-acetyl-1-(methylsulfonyl)-2,3-dihydro-1H-benzimidazol-5-yl]methyl}-5-chloro-6-[(2,4-difluorobenzyl)oxy]pyrimidin-4(3H)-one;
3-{[3-acetyl-1-(N-methylglycyl)-2,3-dihydro-1H-benzimidazol-5-yl]methyl}-5-chloro-6-[(2,4-difluorobenzyl)oxy]pyrimidin-4(3H)-one;
1-acetyl-5-{[5-chloro-6-[(2,4-difluorobenzyl)oxy]-2-oxopyrimidin-3(3H)-yl]methyl}-1,3-dihydro-2H-benzimidazol-2-one;
1-acetyl-5-{[5-chloro-6-[(2,4-difluorobenzyl)oxy]-2-oxopyrimidin-3(3H)-yl]methyl}-3-glycoloyl-1,3-dihydro-2H-benzimidazol-2-one;
1-acetyl-5-{[5-chloro-6-[(2,4-difluorobenzyl)oxy]-2-oxopyrimidin-3(3H)-yl]methyl}-3-(2-hydroxy-2-methylpropanoyl)-1,3-dihydro-2H-benzimidazol-2-one;
1-acetyl-5-{[5-chloro-6-[(2,4-difluorobenzyl)oxy]-2-oxopyrimidin-3(3H)-yl]methyl}-3-(N-methylglycyl)-1,3-dihydro-2H-benzimidazol-2-one;

1-acetyl-5-{[5-chloro-6-[(2,4-difluorobenzyl)oxy]-2-oxopyrimidin-3(3H)-yl]methyl}-3-(3-hydroxypropanoyl)-1,3-dihydro-2H-benzimidazol-2-one;
1-acetyl-5-{[5-chloro-6-[(2,4-difluorobenzyl)oxy]-2-oxopyrimidin-3(3H)-yl]methyl}-3-(3-hydroxy-3-methylbutanoyl)-1,3-dihydro-2H-benzimidazol-2-one;
1-acetyl-5-{[5-chloro-6-[(2,4-difluorobenzyl)oxy]-2-oxopyrimidin-3(3H)-yl]methyl}-3-(methylsulfonyl)-1,3-dihydro-2H-benzimidazol-2-one;
1-acetyl-6-{[5-chloro-6-[(2,4-difluorobenzyl)oxy]-2-oxopyrimidin-3(3H)-yl]methyl}-1,3-dihydro-2H-benzimidazol-2-one;
3-allyl-5-(2,4-difluorobenzyl)-6-[(2,4-difluorobenzyl)oxy]-2-methylpyrimidin-4(3H)-one;
3-allyl-5-bromo-6-[(2,4-difluorobenzyl)oxy]-2-methylpyrimidin-4(3H)-one;
3-Allyl-5-chloro-6-(2,4-difluoro-benzyloxy)-2-methyl-3H-pyrimidin-4-one;
3-Benzenesulfonyl-6-benzyloxy-5-bromo-3H-pyrimidin-4-one;
3-Benzo[1,3]dioxol-5-ylmethyl-5-bromo-6-(2,4-difluorobenzyloxy)-3H-pyrimidin-4-one;
3-benzyl-5-[(benzylamino)methyl]-6-(benzyloxy)pyrimidin-4(3H)-one;
3-Benzyl-5-bromo-6-(2,4-difluoro-benzyloxy)-2-methyl-1H-pyrimidin-4-one;
3-benzyl-5-bromo-2-methyl-6-{[2-(trifluoromethyl)benzyl]oxy}pyrimidin-4(3H)-one;
3-benzyl-6-(1-naphthylmethoxy)pyrimidin-4(3H)-one;
3-benzyl-6-(benzyloxy)-5-{[(2-cyclohexylethyl)amino]methyl}pyrimidin-4(3H)-one;
3-benzyl-6-(benzyloxy)-5-bromo-2-methylpyrimidin-4(3H)-one;
3-benzyl-6-(benzylthio)-3,5-dibromopyrimidin-4(3H)-one;
3-benzyl-6-[(4-methylbenzyl)oxy]pyrimidin-4(3H)-one;
3-benzyl-6-benzyloxy-5-bromo-1H-pyrimidin-4-one;
3-benzyl-6-benzyloxy-5-bromo-2-methyl-1H-pyrimidin-4-one;
3-benzyl-6-benzyloxy-5-chloro-1H-pyrimidin-4-one;
3-benzyl-6-phenoxypyrimidin-4(3H)-one;
3-Benzyl-1-[5-(3,4-dichloro-benzylsulfanyl)-[1,3,4]oxadiazol-2-yl]-3H-pyrimidin-4-one;
3-cyclohexyl-6-[(2,4-difluorobenzyl)oxy]-3,6-dimethylpyrimidin-4(3H)-one;
5-benzyl-6-hydroxy-3-(2-phenylethyl)pyrimidin-4(3H)-one;
5-bromo-3-(2,6-dichlorophenyl)-6-[(4-fluorophenyl)ethynyl]-2-methylpyrimidin-4(3H)-one;
5-bromo-3-(2,6-dichlorophenyl)-6-[2-(4-fluorophenyl)ethyl]-2-methylpyrimidin-4(3H)-one;
5-bromo-3-(2,6-difluoro-phenyl)-6-methoxy-2-methyl-1-(4-methyl-benzyl)-3H-pyrimidin-4-one;
5-bromo-3-(2,6-difluoro-phenyl)-6-methoxy-2-methyl-1-phenethyl-1H-pyrimidin-4-one;
5-bromo-3-(2,6-difluoro-phenyl)-6-methoxy-2-methyl-1-styryl-1H-pyrimidin-4-one;
5-bromo-3-(2,6-difluoro-phenyl)-6-methoxy-2-methyl-1-vinyl-3H-pyrimidin-4-one;
5-bromo-3-(2,6-dimethylphenyl)-2-methyl-6-[(2,4,6-trifluorobenzyl)oxy]pyrimidin-4(3H)-one;
5-bromo-3-(3,5-dibromo-2,6-difluoro-4-hydroxyphenyl)-6-[(2,4-difluorobenzyl)oxy]-2-methylpyrimidin-4(3H)-one;
5-bromo-3-(3-fluorobenzyl)-6-(1-phenylethoxy)pyrimidin-4(3H)-one;
5-bromo-3-(3-fluoro-benzyl)-6-(2,3,4-trifluoro-benzyloxy)-3H-pyrimidin-4-one;
5-bromo-3-(3-fluoro-benzyl)-6-(2-hydroxymethyl-benzyloxy)-3H-pyrimidin-4-one;
5-Bromo-3-(3-fluoro-benzyl)-6-(3-isopropyl-phenyl)-3H-pyrimidin-4-one;
5-bromo-3-(3-fluoro-benzyl)-6-(3-methoxy-phenyl)-3H-pyrimidin-4-one;
5-bromo-3-(3-fluoro-benzyl)-6-(5-methyl-benzyloxy)-3H-pyrimidin-4-one;
5-Bromo-3-(3-fluoro-benzyl)-6-(3-trifluoromethyl-phenyl)-3H-pyrimidin-4-one;
5-bromo-3-(3-fluoro-benzyl)-6-(4-fluoro-benzyloxy)-3H-pyrimidin-4-one;
5-bromo-3-(3-fluoro-benzyl)-6-(4-fluoro-phenyl)-3H-pyrimidin-4-one;
5-bromo-3-(3-fluorobenzyl)-6-[(2-methylbenzyl)oxy]pyrimidin-4(3H)-one;
5-bromo-3-(3-fluorobenzyl)-6-[(3,4,5-trimethoxyphenyl)amino]pyrimidin-4(3H)-one;
5-bromo-3-(3-fluorobenzyl)-6-[(3-fluorobenzyl)amino]pyrimidin-4(3H)-one;
5-bromo-3-(3-fluorobenzyl)-6-[(3-fluorobenzyl)oxy]pyrimidin-4(3H)-one;
5-bromo-3-(3-fluorobenzyl)-6-[(3-methoxybenzyl)oxy]pyrimidin-4(3H)-one;
5-bromo-3-(3-fluorobenzyl)-6-[(5-methylbenzyl)oxy]pyrimidin-4(3H)-one;
5-bromo-3-(3-fluorobenzyl)-6-[(4-methoxybenzyl)oxy]pyrimidin-4(3H)-one;
5-bromo-3-(3-fluorobenzyl)-6-[(E)-2-(4-fluorophenyl)vinyl]pyrimidin-4(3H)-one;
5-bromo-3-(3-fluorobenzyl)-6-[4-(4-fluorophenyl)piperazin-1-yl]pyrimidin-4(3H)-one;
5-bromo-3-(3-fluorobenzyl)-6-{[2-(hydroxymethyl)benzyl]oxy}pyrimidin-4(3H)-one;
5-bromo-3-(3-fluorobenzyl)-6-{[3-(trifluoromethyl)benzyl]amino}pyrimidin-4(3H)-one;
5-bromo-3-(3-fluorobenzyl)-6-{[4-(trifluoromethyl)benzyl]oxy}pyrimidin-4(3H)-one;
5-bromo-3-(3-fluorobenzyl)-6-{[4-fluoro-2-(trifluoromethyl)benzyl]amino}pyrimidin-4(3H)-one;
5-bromo-3-(3-fluoro-benzyl)-6-naphthalen-2-yl-3H-pyrimidin-4-one;
5-bromo-3-(3-fluoro-benzyl)-6-thiophen-3-yl-3H-pyrimidin-4-one;
5'-bromo-3'-(3-fluoro-benzyl)-6-methoxy-3H-[3,6']bipyrimidinyl-4'-one;
5-bromo-3-(4-bromo-2,6-difluorophenyl)-6-[(2,4-difluorobenzyl)oxy]-2-methylpyrimidin-4(3H)-one;
5-bromo-3-(4-fluoro-benzyl)-6-(4-fluoro-benzyloxy)-3H-pyrimidin-4-one;
5-bromo-3-(4-fluorobenzyl)-6-[(4-fluorobenzyl)amino]-2-methylpyrimidin-4(3H)-one;
5-bromo-3-(4-tert-butylbenzyl)-6-[(2,4-difluorobenzyl)oxy]pyrimidin-4(3H)-one;
5-bromo-3-(4-tert-butylbenzyl)-6-[(4-fluorobenzyl)oxy]pyrimidin-4(3H)-one;
5-bromo-3-(cyclohexylmethyl)-6-[(4-fluorobenzyl)oxy]pyrimidin-4(3H)-one;
5-bromo-3-(cyclopropylmethyl)-6-[(2,4-difluorobenzyl)oxy]-2-methylpyrimidin-4(3H)-one;
5-bromo-3-(cyclopropylmethyl)-6-[(4-fluorobenzyl)oxy]pyrimidin-4(3H)-one;
5-bromo-3-[2-chloro-5-(hydroxymethyl)phenyl]-6-[(2,4-difluorobenzyl)oxy]-2-methylpyrimidin-4(3H)-one;
5-bromo-3-{[5-(chloromethyl)pyrazin-2-yl]methyl}-6-[(2,4-difluorobenzyl)oxy]-2-methylpyrimidin-4(3H)-one;

5-Bromo-6-(2,4-difluoro-benzyloxy)-3-(2,3-dihydro-1H-indol-5-ylmethyl)-3H-pyrimidin-4-one;
5-bromo-6-(2,4-difluoro-benzyloxy)-3-(2-methyl-4-methylamino-pyrimidin-5-ylmethyl)-3H-pyrimidin-4-one;
5-bromo-6-(2,4-difluoro-benzyloxy)-3-(3-dimethylaminomethyl-benzyl)-3H-pyrimidin-4-one;
5-bromo-6-(2,4-difluoro-benzyloxy)-3-(3-dimethylaminomethyl-benzyl)-2-methyl-3H-pyrimidin-4-one;
5-bromo-6-(2,4-difluoro-benzyloxy)-3-(3-fluoro-benzyl)-3H-pyrimidin-4-one;
5-bromo-6-(2,4-difluoro-benzyloxy)-3-(3-hydroxymethyl-benzyl)-2-methyl-3H-pyrimidin-4-one;
5-bromo-6-(2,4-difluoro-benzyloxy)-3-(3-methoxy-benzyl)-3H-pyrimidin-4-one;
5-bromo-6-(2,4-difluoro-benzyloxy)-3-(5-methylaminomethyl-benzyl)-3H-pyrimidin-4-one;
5-bromo-6-(2,4-difluoro-benzyloxy)-3-(4-dimethylaminomethyl-benzyl)-2-methyl-3H-pyrimidin-4-one;
5-bromo-6-(2,4-difluoro-benzyloxy)-3-(4-dimethylaminomethyl-benzyl)-3H-pyrimidin-4-one;
5-bromo-6-(2,4-difluoro-benzyloxy)-3-(4-hydroxy-benzyl)-2-methyl-3H-pyrimidin-4-one;
5-bromo-6-(2,4-difluoro-benzyloxy)-3-(4-hydroxymethyl-benzyl)-2-methyl-3H-pyrimidin-4-one;
5-bromo-6-(2,4-difluoro-benzyloxy)-3-(4-methoxy-benzyl)-2-methyl-3H-pyrimidin-4-one;
5-bromo-6-(2,4-difluoro-benzyloxy)-3-[1-(2-hydroxyacetyl)-2,3-dihydro-1H-indol-5-ylmethyl]-2-methyl-3H-pyrimidin-4-one;
5-bromo-6-(2,4-difluoro-benzyloxy)-3-[3-(isopropylaminomethyl)-benzyl]-1H-pyrimidin-4-one;
5-bromo-6-(2,4-difluoro-benzyloxy)-3-[3-(isopropylaminomethyl)-benzyl]-2-methyl-3H-pyrimidin-4-one;
5-bromo-6-(2,4-difluoro-benzyloxy)-3-[4-(1-hydroxy-1-methyl-ethyl)-benzyl]-2-methyl-3H-pyrimidin-4-one;
5-bromo-6-(2,4-difluoro-benzyloxy)-3-[4-(isopropylaminomethyl)-benzyl]-2-methyl-3H-pyrimidin-4-one;
5-bromo-6-(2,4-difluoro-benzyloxy)-3-{3-[(2-hydroxy-ethylamino)-methyl]-benzyl}-2-methyl-3H-pyrimidin-4-one;
5-Bromo-6-(2,4-difluoro-benzyloxy)-2-methyl-3-(1H-pyrazol-3-ylmethyl)-3H-pyrimidin-4-one;
5-bromo-6-(2,4-difluoro-benzyloxy)-2-methyl-3-(3-morpholin-4-ylmethyl-benzyl)-3H-pyrimidin-4-one;
5-bromo-6-(2,4-difluoro-benzyloxy)-2-methyl-3-(3-piperazin-1-ylmethyl-benzyl)-3H-pyrimidin-4-one;
5-bromo-6-(2,4-difluoro-benzyloxy)-2-methyl-3-(3-piperidin-1-ylmethyl-benzyl)-3H-pyrimidin-4-one;
5-bromo-6-(2,4-difluoro-benzyloxy)-2-methyl-3-(4-methylaminomethyl-benzyl)-3H-pyrimidin-4-one;
5-bromo-6-(2,4-difluoro-benzyloxy)-2-methyl-3-(4-morpholin-4-ylmethyl-benzyl)-3H-pyrimidin-4-one;
5-bromo-6-(2,4-difluoro-benzyloxy)-2-methyl-3-(4-piperazin-1-ylmethyl-benzyl)-3H-pyrimidin-4-one;
5-bromo-6-(2,4-difluoro-benzyloxy)-2-methyl-3-(4-piperidin-1-ylmethyl-benzyl)-3H-pyrimidin-4-one;
5-bromo-6-(2,4-difluoro-benzyloxy)-2-methyl-3-[3-(morpholine-4-carbonyl)-benzyl]-3H-pyrimidin-4-one;
5-bromo-6-(2,4-difluoro-benzyloxy)-2-methyl-3-[3-(piperidine-1-carbonyl)-benzyl]-3H-pyrimidin-4-one;
5-bromo-6-(2,4-difluoro-benzyloxy)-2-methyl-3-[3-(pyrrolidine-1-carbonyl)-benzyl]-3H-pyrimidin-4-one;
5-bromo-6-(2,4-difluoro-benzyloxy)-2-methyl-3-[4-(4-methyl-piperazine-1-carbonyl)-benzyl]-3H-pyrimidin-4-one;
5-bromo-6-(2,4-difluoro-benzyloxy)-2-methyl-3-[4-(morpholine-4-carbonyl)-benzyl]-3H-pyrimidin-4-one;
5-bromo-6-(2,4-difluoro-benzyloxy)-2-methyl-3-[4-(piperidine-1-carbonyl)-benzyl]-3H-pyrimidin-4-one;
5-bromo-6-(2,4-difluoro-benzyloxy)-2-methyl-3-[4-(pyrrolidine-1-carbonyl)-benzyl]-3H-pyrimidin-4-one;
5-bromo-6-(5-chloro-benzyloxy)-3-(3-fluoro-benzyl)-3H-pyrimidin-4-one;
5-bromo-6-(4-chloro-benzyloxy)-3-(2-phenylsulfanyl-ethyl)-3H-pyrimidin-4-one;
5-bromo-6-[(2,4-difluorobenzyl)amino]-3-(2,6-difluorophenyl)-2-methylpyrimidin-4(3H)-one trifluoroacetate;
5-bromo-6-[(2,4-difluorobenzyl)amino]-3-(3-fluorobenzyl)pyrimidin-4(3H)-one;
5-bromo-6-[(2,4-difluorobenzyl)oxy]-3-({5-[(dimethylamino)methyl]pyrazin-2-yl}methyl)-2-methylpyrimidin-4(3H)-one trifluoroacetate;
5-bromo-6-[(2,4-difluorobenzyl)oxy]-3-(1H-indazol-5-ylmethyl)pyrimidin-4(3H)-one;
5-bromo-6-[(2,4-difluorobenzyl)oxy]-3-(2,6-difluoro-4-morpholin-4-ylphenyl)-2-methylpyrimidin-4(3H)-one;
5-bromo-6-[(2,4-difluorobenzyl)oxy]-3-(2,6-difluorophenyl)-5-(1,2-dihydroxyethyl)-2-methylpyrimidin-4(3H)-one;
5-bromo-6-[(2,4-difluorobenzyl)oxy]-3-(2,6-difluorophenyl)-5-(1,2-dihydroxy-2-phenylethyl)-2-methylpyrimidin-4(3H)-one;
5-bromo-6-[(2,4-difluorobenzyl)oxy]-3-(2,6-difluorophenyl)-5-(hydroxymethyl)-2-methylpyrimidin-4(3H)-one;
5-bromo-6-[(2,4-difluorobenzyl)oxy]-3-(2,6-difluorophenyl)-1-iodo-2-methylpyrimidin-4(1H)-one;
5-bromo-6-[(2,4-difluorobenzyl)oxy]-3-(2,6-difluorophenyl)-2-(hydroxymethyl)pyrimidin-4(3H)-one;
5-bromo-6-[(2,4-difluorobenzyl)oxy]-3-(2,6-difluorophenyl)-2-(morpholin-4-ylmethyl)pyrimidin-4(3H)-one;
5-bromo-6-[(2,4-difluorobenzyl)oxy]-3-(2,6-difluorophenyl)-2-[(dimethylamino)methyl]pyrimidin-4(3H)-one;
5-bromo-6-[(2,4-difluorobenzyl)oxy]-3-(2,6-difluorophenyl)-2-[(ethoxyamino)methyl]pyrimidin-4(3H)-one;
5-bromo-6-[(2,4-difluorobenzyl)oxy]-3-(2,6-difluorophenyl)-2-{([(2-methoxyethyl)amino]methyl)pyrimidin-4(3H)-one;
5-bromo-6-[(2,4-difluorobenzyl)oxy]-3-(2,6-difluorophenyl)-2-methylpyrimidin-4(3H)-one;
5-bromo-6-[(2,4-difluorobenzyl)oxy]-3-(2,6-difluorophenyl)-2-methyl-5-vinylpyrimidin-4(3H)-one;
5-bromo-6-[(2,4-difluorobenzyl)oxy]-3-(2,6-difluorophenyl)-2-methyl-5-oxiran-2-ylpyrimidin-4(3H)-one;
5-bromo-6-[(2,4-difluorobenzyl)oxy]-3-(2,6-difluorophenyl)-2-methyl-1-[(E)-2-phenylvinyl]pyrimidin-4(1H)-one;
5-bromo-6-[(2,4-difluorobenzyl)oxy]-3-(2,6-dimethylphenyl)-2-methylpyrimidin-4(3H)-one;
5-bromo-6-[(2,4-difluorobenzyl)oxy]-3-(pyridin-3-ylmethyl)pyrimidin-4(3H)-one;
5-bromo-6-[(2,4-difluorobenzyl)oxy]-3-[(5-{[(2-hydroxyethyl)(methyl)amino]methyl}pyrazin-2-yl)methyl]-2-methylpyrimidin-4(3H)-one trifluoroacetate (salt);
5-bromo-6-[(2,4-difluorobenzyl)oxy]-3-[2-(dimethylamino)-4,6-difluorophenyl]-2-methylpyrimidin-4(3H)-one;
5-bromo-6-[(2,4-difluorobenzyl)oxy]-3-[2-(dimethylamino)-4,6-difluorophenyl]-2-methylpyrimidin-4(3H)-one hydrochloride;
5-bromo-6-[(2,4-difluorobenzyl)oxy]-3-[2,6-difluoro-4-(4-methylpiperazin-1-yl)phenyl]-2-methylpyrimidin-4(3H)-one;
5-bromo-6-[(2,4-difluorobenzyl)oxy]-3-[2-fluoro-5-(hydroxymethyl)phenyl]-2-methylpyrimidin-4(3H)-one;

5-bromo-6-[(2,4-difluorobenzyl)oxy]-3-[2-fluoro-6-(4-methylpiperazin-1-yl)phenyl]-2-methylpyrimidin-4(3H)-one trifluoroacetate;
5-bromo-6-[(2,4-difluorobenzyl)oxy]-3-[3-(hydroxymethyl)phenyl]-2-methylpyrimidin-4(3H)-one
5-bromo-6-[(2,4-difluorobenzyl)oxy]-3-[4-(dimethylamino)-2,6-difluorophenyl]-2-methylpyrimidin-4(3H)-one;
5-bromo-6-[(2,4-difluorobenzyl)oxy]-3-[4-(hydroxymethyl)-2-methoxyphenyl]-2-methylpyrimidin-4(3H)-one;
5-bromo-6-[(2,4-difluorobenzyl)oxy]-3-[5-(1-hydroxy-1-methylethyl)-2-methylphenyl]-2-methylpyrimidin-4(3H)-one;
5-bromo-6-[(2,4-difluorobenzyl)oxy]-3-[5-(hydroxymethyl)-2-methylphenyl]-2-methylpyrimidin-4(3H)-one;
5-bromo-6-[(2,4-difluorobenzyl)oxy]-3-{[5-(1-hydroxy-1-methylethyl)pyrazin-2-yl]methyl}-2-methylpyrimidin-4(3H)-one;
5-bromo-6-[(2,4-difluorobenzyl)oxy]-3-([5-(hydroxymethyl)pyrazin-2-yl]methyl)-2-methylpyrimidin-4(3H)-one;
5-bromo-6-[(2,4-difluorobenzyl)oxy]-3-{2,4-difluoro-6-[(2-hydroxyethyl)(methyl)amino]phenyl}-2-methylpyrimidin-4(3H)-one;
5-bromo-6-[(2,4-difluorobenzyl)oxy]-3-{2,6-difluoro-4-[(2-hydroxyethyl)(methyl)amino]phenyl}-2-methylpyrimidin-4(3H)-one;
5-bromo-6-[(2,4-difluorobenzyl)oxy]-3-{3-[(dimethylamino)methyl]phenyl}-2-methylpyrimidin-4(3H)-one;
5-bromo-6-[(2,4-difluorobenzyl)oxy]-3-{5-[(dimethylamino)methyl]-2-methylphenyl}-2-methylpyrimidin-4(3H)-one hydrochloride;
5-bromo-6-[(2,4-difluorobenzyl)oxy]-3-{5-[(isopropylamino)methyl]-2-methylphenyl}-2-methylpyrimidin-4(3H)-one hydrochloride;
5-bromo-6-[(2,4-difluorobenzyl)oxy]-5'-(1-hydroxy-1-methylethyl)-2-methyl-6H-1,2'-bipyrimidin-6-one;
5-bromo-6-[(2,4-difluorobenzyl)oxy]-2-(hydroxymethyl)-3-(2,4,6-trifluorophenyl)pyrimidin-4(3H)-one;
5-bromo-6-[(2,4-difluorobenzyl)oxy]-2-methyl-3-({5-[(4-methylpiperazin-1-yl)carbonyl]pyrazin-2-yl}methyl)pyrimidin-4(3H)-one trifluoroacetate;
5-bromo-6-[(2,4-difluorobenzyl)oxy]-2-methyl-3-({5-[(methylamino)methyl]pyrazin-2-yl}methyl)pyrimidin-4(3H)-one trifluoroacetate;
5-bromo-6-[(2,4-difluorobenzyl)oxy]-2-methyl-3-(2,4,6-trifluorophenyl)pyrimidin-4(3H)-one;
5-bromo-6-[(2,4-difluorobenzyl)oxy]-2-methyl-3-(2-morpholin-4-ylethyl)pyrimidin-4(3H)-one;
5-bromo-6-[(2,4-difluorobenzyl)oxy]-2-methyl-3-(tetrahydrofuran-2-ylmethyl)pyrimidin-4(3H)-one;
5-bromo-6-[(2,4-difluorobenzyl)oxy]-2-methyl-3-[(5-methylpyrazin-2-yl)methyl]pyrimidin-4(3H)-one;
5-bromo-6-[(2,4-difluorobenzyl)oxy]-2-methyl-3-[2-(methylthio)pyrimidin-4-yl]pyrimidin-4(3H)-one;
5-bromo-6-[(2,4-difluorobenzyl)oxy]-2-methyl-3-[2-(trifluoromethyl)phenyl]pyrimidin-4(3H)-one;
5-bromo-6-[(2,4-difluorobenzyl)oxy]-2-methyl-3-[2-methyl-5-(morpholin-4-ylcarbonyl)phenyl]pyrimidin-4(3H)-one;
5-bromo-6-[(2,4-difluorobenzyl)oxy]-2-methyl-3-[3-(morpholin-4-ylcarbonyl)phenyl]pyrimidin-4(3H)-one;
5-bromo-6-[(2,4-difluorobenzyl)oxy]-2-methyl-3-[3-(piperazin-1-ylcarbonyl)benzyl]pyrimidin-4(3H)-one hydrochloride;
5-bromo-6-[(2,4-difluorobenzyl)oxy]-2-methyl-3-[3-(piperidin-1-ylcarbonyl)phenyl]pyrimidin-4(3H)-one;
5-bromo-6-[(2,4-difluorobenzyl)oxy]-2-methyl-3-[3-(pyrrolidin-1-ylcarbonyl)phenyl]pyrimidin-4(3H)-one;
5-bromo-6-[(2,4-difluorobenzyl)oxy]-2-methyl-3-[4-(morpholin-4-ylcarbonyl)phenyl]pyrimidin-4(3H)-one;
5-bromo-6-[(2,4-difluorobenzyl)oxy]-2-methyl-3-[4-(piperazin-1-ylcarbonyl)benzyl]pyrimidin-4(3H)-one hydrochloride;
5-bromo-6-[(2,4-difluorobenzyl)oxy]-2-methyl-3-[4-(piperazin-1-ylcarbonyl)phenyl]pyrimidin-4(3H)-one hydrochloride;
5-bromo-6-[(2,4-difluorobenzyl)oxy]-2-methyl-3-[4-(piperidin-1-ylcarbonyl)phenyl]pyrimidin-4(3H)-one;
5-bromo-6-[(2,4-difluorobenzyl)oxy]-2-methyl-3-[4-(pyrrolidin-1-ylcarbonyl)phenyl]pyrimidin-4(3H)-one;
5-bromo-6-[(2,4-difluorobenzyl)oxy]-2-methyl-3-{3-[(4-methylpiperazin-1-yl)carbonyl]phenyl}pyrimidin-4(3H)-one;
5-bromo-6-[(2,4-difluorobenzyl)oxy]-2-methyl-3-{4-[(4-methylpiperazin-1-yl)carbonyl]benzyl}pyrimidin-4(3H)-one;
5-bromo-6-[(2,4-difluorobenzyl)oxy]-2-methylpyrimidin-4(3H)-one;
5-bromo-6-[(2,4-difluorophenyl)amino]-3-(3-fluorobenzyl)pyrimidin-4(3H)-one;
5-bromo-6-[(2,6-difluorobenzyl)oxy]-3-(2,6-dimethylphenyl)-2-methylpyrimidin-4(3H)-one;
5-bromo-6-[(2,6-difluorobenzyl)oxy]-2-methyl-3-(pyridin-4-ylmethyl)pyrimidin-4(3H)-one;
5-bromo-6-[(3,4-difluorobenzyl)oxy]-3-(3-fluorobenzyl)pyrimidin-4(3H)-one;
5-bromo-6-[(4-chloro-2-fluorobenzyl)amino]-3-(3-fluorobenzyl)pyrimidin-4(3H)-one;
5-bromo-6-[(4-fluorobenzyl)oxy]-3-(4-methoxybenzyl)pyrimidin-4(3H)-one;
5-bromo-6-[(4-fluorobenzyl)oxy]-3-[2-(hydroxymethyl)benzyl]pyrimidin-4(3H)-one;
5-bromo-6-[(4-fluorobenzyl)oxy]-3-[3-(trifluoromethyl)benzyl]pyrimidin-4(3H)-one;
5-bromo-6-[(4-fluorobenzyl)oxy]-3-[4-(trifluoromethyl)benzyl]pyrimidin-4(3H)-one;
5-bromo-6-[(4-tert-butylbenzyl)oxy]-3-(3-fluorobenzyl)pyrimidin-4(3H)-one;
5-bromo-6-hydroxy-3-(4-hydroxybenzyl)pyrimidin-4(3H)-one hydrochloride;
5-bromo-2-methyl-3-(pyridin-4-ylmethyl)-6-[(2,4,6-trifluorobenzyl)oxy]pyrimidin-4(3H)-one;
5-bromo-2-methyl-3-pyridin-3-ylmethyl-6-[(pyridin-3-ylmethyl)-amino]-1H-pyrimidin-4-one;
5-chloro-3-(1,3-diacetyl-2,3-dihydro-1H-benzimidazol-5-yl)-6-[(2,4-difluorobenzyl)oxy]-2-methylpyrimidin-4(3H)-one;
5-chloro-3-(4-fluorobenzyl)-6-[(4-fluorobenzyl)oxy]pyrimidin-4(3H)-one;
5-chloro-3-[(1,3-diacetyl-2,3-dihydro-1H-benzimidazol-5-yl)methyl]-6-[(2,4-difluorobenzyl)oxy]pyrimidin-4(3H)-one;
5-chloro-3-[2-chloro-5-(hydroxymethyl)phenyl]-6-[(2,4-difluorobenzyl)oxy]-2-methylpyrimidin-4(3H)-one;
5-chloro-6-(2,4-difluoro-benzyloxy)-3-(3-fluoro-benzyl)-1H-pyrimidin-4-one;
5-chloro-6-(2,4-difluoro-benzyloxy)-3-(3-methanesulfonyl-benzyl)-3H-pyrimidin-4-one;
5-Chloro-6-(2,4-difluoro-benzyloxy)-3-(5-hydroxymethyl-pyrazin-2-ylmethyl)-2-methyl-3H-pyrimidin-4-one;
5-Chloro-6-(2,4-difluoro-benzyloxy)-3-[4-(1,2-dihydroxy-ethyl)-2-methyl-phenyl]-2-methyl-3H-pyrimidin-4-one;

5-chloro-6-(2,4-difluoro-benzyloxy)-3-[4-(isopropylamino-methyl)-benzyl]-3H-pyrimidin-4-one;
5-Chloro-6-(2,4-difluoro-benzyloxy)-2-methyl-3-(5-methyl-pyrazin-2-ylmethyl)-3H-pyrimidin-4-one;
5-chloro-6-[(2,4-difluorobenzyl)amino]-3-(2,6-difluorophenyl)-2-methylpyrimidin-4(3H)-one;
5-chloro-6-[(2,4-difluorobenzyl)oxy]-3-(1,2,3,4-tetrahydroisoquinolin-5-ylmethyl)pyrimidin-4(3H)-one;
5-chloro-6-[(2,4-difluorobenzyl)oxy]-3-(1,2,3,4-tetrahydroisoquinolin-6-ylmethyl)pyrimidin-4(3H)-one;
5-chloro-6-[(2,4-difluorobenzyl)oxy]-3-(1,3-diglycoloyl-2,3-dihydro-1H-benzimidazol-5-yl)-2-methylpyrimidin-4(3H)-one;
5-chloro-6-[(2,4-difluorobenzyl)oxy]-3-(1-glycoloyl-1H-benzimidazol-5-yl)-2-methylpyrimidin-4(3H)-one;
5-chloro-6-[(2,4-difluorobenzyl)oxy]-3-(1-glycoloyl-1H-imidazol-4-yl)-2-methylpyrimidin-4(3H)-one;
5-chloro-6-[(2,4-difluorobenzyl)oxy]-3-(1-glycoloyl-1H-indol-5-yl)-2-methylpyrimidin-4(3H)-one;
5-chloro-6-[(2,4-difluorobenzyl)oxy]-3-(1-glycoloyl-1H-pyrazol-4-yl)-2-methylpyrimidin-4(3H)-one;
5-chloro-6-[(2,4-difluorobenzyl)oxy]-3-(1-glycoloyl-1H-pyrrol-3-yl)-2-methylpyrimidin-4(3H)-one;
5-chloro-6-[(2,4-difluorobenzyl)oxy]-3-(1-glycoloyl-2,3-dihydro-1H-indol-5-yl)-2-methylpyrimidin-4(3H)-one;
5-chloro-6-[(2,4-difluorobenzyl)oxy]-3-(1H-indol-5-ylmethyl)pyrimidin-4(3H)-one;
5-chloro-6-[(2,4-difluorobenzyl)oxy]-3-(2,3-dihydro-1H-benzimidazol-5-ylmethyl)pyrimidin-4(3H)-one;
5-chloro-6-[(2,4-difluorobenzyl)oxy]-3-(2,3-dihydro-1H-indol-5-ylmethyl)pyrimidin-4(3H)-one;
5-chloro-6-[(2,4-difluorobenzyl)oxy]-3-(2,3-dihydro-1H-isoindol-5-ylmethyl)pyrimidin-4(3H)-one;
5-chloro-6-[(2,4-difluorobenzyl)oxy]-3-(2,6-difluorophenyl)-6-(hydroxymethyl)pyrimidin-4(3H)-one;
5-chloro-6-[(2,4-difluorobenzyl)oxy]-3-(2,6-difluorophenyl)-6-[(dimethylamino)methyl]pyrimidin-4(3H)-one;
5-chloro-6-[(2,4-difluorobenzyl)oxy]-3-(2,6-difluorophenyl)-2-methylpyrimidin-4(3H)-one;
5-chloro-6-[(2,4-difluorobenzyl)oxy]-3-(2-glycoloyl-1,2,3,4-tetrahydroisoquinolin-6-yl)-2-methylpyrimidin-4(3H)-one;
5-chloro-6-[(2,4-difluorobenzyl)oxy]-3-(2-glycoloyl-1,2,3,4-tetrahydroisoquinolin-7-yl)-2-methylpyrimidin-4(3H)-one;
5-chloro-6-[(2,4-difluorobenzyl)oxy]-3-(2-glycoloyl-2,3-dihydro-1H-isoindol-5-yl)-2-methylpyrimidin-4(3H)-one;
5-chloro-6-[(2,4-difluorobenzyl)oxy]-3-(isoquinolin-5-ylmethyl)pyrimidin-4(3H)-one trifluoroacetate;
5-chloro-6-[(2,4-difluorobenzyl)oxy]-3-(isoquinolin-6-ylmethyl)pyrimidin-4(3H)-one;
5-chloro-6-[(2,4-difluorobenzyl)oxy]-3-[(1,3-diglycoloyl-2,3-dihydro-1H-benzimidazol-5-yl)methyl]pyrimidin-4(3H)-one;
5-chloro-6-[(2,4-difluorobenzyl)oxy]-3-[(1-glycoloyl-2,3-dihydro-1H-indol-5-yl)methyl]pyrimidin-4(3H)-one;
5-chloro-6-[(2,4-difluorobenzyl)oxy]-3-[(1-glycoloyl-2,3-dihydro-1H-benzimidazol-5-yl)methyl]pyrimidin-4(3H)-one;
5-chloro-6-[(2,4-difluorobenzyl)oxy]-3-[(2-glycoloyl-1,2,3,4-tetrahydroisoquinolin-6-yl)methyl]pyrimidin-4(3H)-one;
5-chloro-6-[(2,4-difluorobenzyl)oxy]-3-[(2-glycoloyl-1,2,3,4-tetrahydroisoquinolin-5-yl)methyl]pyrimidin-4(3H)-one;
5-chloro-6-[(2,4-difluorobenzyl)oxy]-3-[(2-glycoloyl-2,3-dihydro-1H-isoindol-5-yl)methyl]pyrimidin-4(3H)-one;
5-chloro-6-[(2,4-difluorobenzyl)oxy]-3-[(3-glycoloyl-2,3-dihydro-1H-benzimidazol-5-yl)methyl]pyrimidin-4(3H)-one;
5-chloro-6-[(2,4-difluorobenzyl)oxy]-3-[1-(2-hydroxy-2-methylpropanoyl)-2,3-dihydro-1H-indol-5-yl]-2-methylpyrimidin-4(3H)-one;
5-chloro-6-[(2,4-difluorobenzyl)oxy]-3-[1-(2-hydroxy-2-methylpropanoyl)-1H-indol-5-yl]-2-methylpyrimidin-4(3H)-one;
5-chloro-6-[(2,4-difluorobenzyl)oxy]-3-[1-(2-hydroxy-2-methylpropanoyl)-1H-benzimidazol-5-yl]-2-methylpyrimidin-4(3H)-one;
5-chloro-6-[(2,4-difluorobenzyl)oxy]-3-[1-(2-hydroxy-2-methylpropanoyl)-3-(N-methylglycyl)-2,3-dihydro-1H-benzimidazol-5-yl]-2-methylpyrimidin-4(3H)-one;
5-chloro-6-[(2,4-difluorobenzyl)oxy]-3-[1-(2-hydroxy-2-methylpropanoyl)-3-(3-hydroxypropanoyl)-2,3-dihydro-1H-benzimidazol-5-yl]-2-methylpyrimidin-4(3H)-one;
5-chloro-6-[(2,4-difluorobenzyl)oxy]-3-[1-(2-hydroxy-2-methylpropanoyl)-3-(methylsulfonyl)-2,3-dihydro-1H-benzimidazol-5-yl]-2-methylpyrimidin-4(3H)-one;
5-chloro-6-[(2,4-difluorobenzyl)oxy]-3-[1-(2-hydroxy-2-methylpropanoyl)-1H-pyrrol-3-yl]-2-methylpyrimidin-4(3H)-one;
5-chloro-6-[(2,4-difluorobenzyl)oxy]-3-[1-(2-hydroxy-2-methylpropanoyl)-1H-imidazol-4-yl]-2-methylpyrimidin-4(3H)-one;
5-chloro-6-[(2,4-difluorobenzyl)oxy]-3-[1-(2-hydroxy-2-methylpropanoyl)-1H-pyrazol-4-yl]-2-methylpyrimidin-4(3H)-one;
5-chloro-6-[(2,4-difluorobenzyl)oxy]-3-[1-(3-hydroxy-3-methylbutanoyl)-2,3-dihydro-1H-indol-5-yl]-2-methylpyrimidin-4(3H)-one;
5-chloro-6-[(2,4-difluorobenzyl)oxy]-3-[1-(3-hydroxy-3-methylbutanoyl)-1H-indol-5-yl]-2-methylpyrimidin-4(3H)-one;
5-chloro-6-[(2,4-difluorobenzyl)oxy]-3-[1-(3-hydroxy-3-methylbutanoyl)-1H-benzimidazol-5-yl]-2-methylpyrimidin-4(3H)-one;
5-chloro-6-[(2,4-difluorobenzyl)oxy]-3-[1-(3-hydroxy-3-methylbutanoyl)-3-(2-hydroxy-2-methylpropanoyl)-2,3-dihydro-1H-benzimidazol-5-yl]-2-methylpyrimidin-4(3H)-one;
5-chloro-6-[(2,4-difluorobenzyl)oxy]-3-[1-(3-hydroxy-3-methylbutanoyl)-3-(N-methylglycyl)-2,3-dihydro-1H-benzimidazol-5-yl]-2-methylpyrimidin-4(3H)-one;
5-chloro-6-[(2,4-difluorobenzyl)oxy]-3-[1-(3-hydroxy-3-methylbutanoyl)-3-(3-hydroxypropanoyl)-2,3-dihydro-1H-benzimidazol-5-yl]-2-methylpyrimidin-4(3H)-one;
5-chloro-6-[(2,4-difluorobenzyl)oxy]-3-[1-(3-hydroxy-3-methylbutanoyl)-3-(methylsulfonyl)-2,3-dihydro-1H-benzimidazol-5-yl]-2-methylpyrimidin-4(3H)-one;
5-chloro-6-[(2,4-difluorobenzyl)oxy]-3-[1-(3-hydroxy-3-methylbutanoyl)-1H-pyrrol-3-yl]-2-methylpyrimidin-4(3H)-one;
5-chloro-6-[(2,4-difluorobenzyl)oxy]-3-[1-(3-hydroxy-3-methylbutanoyl)-1H-imidazol-4-yl]-2-methylpyrimidin-4(3H)-one;
5-chloro-6-[(2,4-difluorobenzyl)oxy]-3-[1-(3-hydroxy-3-methylbutanoyl)-1H-pyrazol-4-yl]-2-methylpyrimidin-4(3H)-one;
5-chloro-6-[(2,4-difluorobenzyl)oxy]-3-[1-(3-hydroxypropanoyl)-1H-indol-5-yl]-2-methylpyrimidin-4(3H)-one;
5-chloro-6-[(2,4-difluorobenzyl)oxy]-3-[1-(3-hydroxypropanoyl)-1H-benzimidazol-5-yl]-2-methylpyrimidin-4(3H)-one;

5-chloro-6-[(2,4-difluorobenzyl)oxy]-3-[1-(3-hydroxypropanoyl)-1H-pyrrol-3-yl]-2-methylpyrimidin-4(3H)-one;

5-chloro-6-[(2,4-difluorobenzyl)oxy]-3-[1-(3-hydroxypropanoyl)-1H-imidazol-4-yl]-2-methylpyrimidin-4(3H)-one;

5-chloro-6-[(2,4-difluorobenzyl)oxy]-3-[1-(3-hydroxypropanoyl)-1H-pyrazol-4-yl]-2-methylpyrimidin-4(3H)-one;

5-chloro-6-[(2,4-difluorobenzyl)oxy]-3-[1-(3-hydroxypropanoyl)-2,3-dihydro-1H-indol-5-yl]-2-methylpyrimidin-4(3H)-one;

5-chloro-6-[(2,4-difluorobenzyl)oxy]-3-[1-(3-hydroxypropanoyl)-3-(N-methylglycyl)-2,3-dihydro-1H-benzimidazol-5-yl]-2-methylpyrimidin-4(3H)-one;

5-chloro-6-[(2,4-difluorobenzyl)oxy]-3-[1-(3-hydroxypropanoyl)-3-(methylsulfonyl)-2,3-dihydro-1H-benzimidazol-5-yl]-2-methylpyrimidin-4(3H)-one;

5-chloro-6-[(2,4-difluorobenzyl)oxy]-3-[1-glycoloyl-3-(2-hydroxy-2-methylpropanoyl)-2,3-dihydro-1H-benzimidazol-5-yl]-2-methylpyrimidin-4(3H)-one;

5-chloro-6-[(2,4-difluorobenzyl)oxy]-3-[1-glycoloyl-3-(3-hydroxy-3-methylbutanoyl)-2,3-dihydro-1H-benzimidazol-5-yl]-2-methylpyrimidin-4(3H)-one;

5-chloro-6-[(2,4-difluorobenzyl)oxy]-3-[1-glycoloyl-3-(3-hydroxypropanoyl)-2,3-dihydro-1H-benzimidazol-5-yl]-2-methylpyrimidin-4(3H)-one;

5-chloro-6-[(2,4-difluorobenzyl)oxy]-3-[1-glycoloyl-3-(methylsulfonyl)-2,3-dihydro-1H-benzimidazol-5-yl]-2-methylpyrimidin-4(3H)-one;

5-chloro-6-[(2,4-difluorobenzyl)oxy]-3-[1-glycoloyl-3-(N-methylglycyl)-2,3-dihydro-1H-benzimidazol-5-yl]-2-methylpyrimidin-4(3H)-one;

5-chloro-6-[(2,4-difluorobenzyl)oxy]-3-[2-(2-hydroxy-2-methylpropanoyl)-2,3-dihydro-1H-isoindol-5-yl]-2-methylpyrimidin-4(3H)-one;

5-chloro-6-[(2,4-difluorobenzyl)oxy]-3-[2-(2-hydroxy-2-methylpropanoyl)-1,2,3,4-tetrahydroisoquinolin-6-yl]-2-methylpyrimidin-4(3H)-one;

5-chloro-6-[(2,4-difluorobenzyl)oxy]-3-[2-(2-hydroxy-2-methylpropanoyl)-1,2,3,4-tetrahydroisoquinolin-7-yl]-2-methylpyrimidin-4(3H)-one;

5-chloro-6-[(2,4-difluorobenzyl)oxy]-3-[2-(3-hydroxy-3-methylbutanoyl)-2,3-dihydro-1H-isoindol-5-yl]-2-methylpyrimidin-4(3H)-one;

5-chloro-6-[(2,4-difluorobenzyl)oxy]-3-[2-(3-hydroxy-3-methylbutanoyl)-1,2,3,4-tetrahydroisoquinolin-6-yl]-2-methylpyrimidin-4(3H)-one;

5-chloro-6-[(2,4-difluorobenzyl)oxy]-3-[2-(3-hydroxy-3-methylbutanoyl)-1,2,3,4-tetrahydroisoquinolin-7-yl]-2-methylpyrimidin-4(3H)-one;

5-chloro-6-[(2,4-difluorobenzyl)oxy]-3-[2-(3-hydroxypropanoyl)-1,2,3,4-tetrahydroisoquinolin-6-yl]-2-methylpyrimidin-4(3H)-one;

5-chloro-6-[(2,4-difluorobenzyl)oxy]-3-[2-(3-hydroxypropanoyl)-1,2,3,4-tetrahydroisoquinolin-7-yl]-2-methylpyrimidin-4(3H)-one;

5-chloro-6-[(2,4-difluorobenzyl)oxy]-3-[2-(3-hydroxypropanoyl)-2,3-dihydro-1H-isoindol-5-yl]-2-methylpyrimidin-4(3H)-one;

5-chloro-6-[(2,4-difluorobenzyl)oxy]-3-[2,6-difluoro-4-(4-methylpiperazin-1-yl)phenyl]-2-methylpyrimidin-4(3H)-one;

5-chloro-6-[(2,4-difluorobenzyl)oxy]-3-[3-(2-hydroxy-2-methylpropanoyl)-1-(N-methylglycyl)-2,3-dihydro-1H-benzimidazol-5-yl]-2-methylpyrimidin-4(3H)-one;

5-chloro-6-[(2,4-difluorobenzyl)oxy]-3-[3-(2-hydroxy-2-methylpropanoyl)-1-(3-hydroxypropanoyl)-2,3-dihydro-1H-benzimidazol-5-yl]-2-methylpyrimidin-4(3H)-one;

5-chloro-6-[(2,4-difluorobenzyl)oxy]-3-[3-(2-hydroxy-2-methylpropanoyl)-1-(methylsulfonyl)-2,3-dihydro-1H-benzimidazol-5-yl]-2-methylpyrimidin-4(3H)-one;

5-chloro-6-[(2,4-difluorobenzyl)oxy]-3-[3-(3-hydroxy-5-methylbutanoyl)-1-(2-hydroxy-2-methylpropanoyl)-2,3-dihydro-1H-benzimidazol-5-yl]-2-methylpyrimidin-4(3H)-one;

5-chloro-6-[(2,4-difluorobenzyl)oxy]-3-[3-(3-hydroxy-5-methylbutanoyl)-1-(N-methylglycyl)-2,3-dihydro-1H-benzimidazol-5-yl]-2-methylpyrimidin-4(3H)-one;

5-chloro-6-[(2,4-difluorobenzyl)oxy]-3-[3-(3-hydroxy-5-methylbutanoyl)-1-(3-hydroxypropanoyl)-2,3-dihydro-1H-benzimidazol-5-yl]-2-methylpyrimidin-4(3H)-one;

5-chloro-6-[(2,4-difluorobenzyl)oxy]-3-[3-(3-hydroxy-3-methylbutanoyl)-1-(methylsulfonyl)-2,3-dihydro-1H-benzimidazol-5-yl]-2-methylpyrimidin-4(3H)-one;

5-chloro-6-[(2,4-difluorobenzyl)oxy]-3-[3-(3-hydroxypropanoyl)-1-(N-methylglycyl)-2,3-dihydro-1H-benzimidazol-5-yl]-2-methylpyrimidin-4(3H)-one;

5-chloro-6-[(2,4-difluorobenzyl)oxy]-3-[3-(3-hydroxypropanoyl)-1-(methylsulfonyl)-2,3-dihydro-1H-benzimidazol-5-yl]-2-methylpyrimidin-4(3H)-one;

5-chloro-6-[(2,4-difluorobenzyl)oxy]-3-[3-(hydroxymethyl)phenyl]-2-methylpyrimidin-4(3H)-one;

5-chloro-6-[(2,4-difluorobenzyl)oxy]-3-[3-glycoloyl-1-(2-hydroxy-2-methylpropanoyl)-2,3-dihydro-1H-benzimidazol-5-yl]-2-methylpyrimidin-4(3H)-one;

5-chloro-6-[(2,4-difluorobenzyl)oxy]-3-[3-glycoloyl-1-(3-hydroxy-3-methylbutanoyl)-2,3-dihydro-1H-benzimidazol-5-yl]-2-methylpyrimidin-4(3H)-one;

5-chloro-6-[(2,4-difluorobenzyl)oxy]-3-[3-glycoloyl-1-(3-hydroxypropanoyl)-2,3-dihydro-1H-benzimidazol-5-yl]-2-methylpyrimidin-4(3H)-one;

5-chloro-6-[(2,4-difluorobenzyl)oxy]-3-[3-glycoloyl-1-(methylsulfonyl)-2,3-dihydro-1H-benzimidazol-5-yl]-2-methylpyrimidin-4(3H)-one;

5-chloro-6-[(2,4-difluorobenzyl)oxy]-3-[3-glycoloyl-1-(N-methylglycyl)-2,3-dihydro-1H-benzimidazol-5-yl]-2-methylpyrimidin-4(3H)-one;

5-chloro-6-[(2,4-difluorobenzyl)oxy]-3-[5-(hydroxymethyl)-2-methylphenyl]-2-methylpyrimidin-4(3H)-one;

5-chloro-6-[(2,4-difluorobenzyl)oxy]-3-{[1-(2-hydroxy-2-methylpropanoyl)-2,3-dihydro-1H-indol-5-yl]methyl}pyrimidin-4(3H)-one;

5-chloro-6-[(2,4-difluorobenzyl)oxy]-3-{[1-(2-hydroxy-2-methylpropanoyl)-2,3-dihydro-1H-benzimidazol-5-yl]methyl}pyrimidin-4(3H)-one;

5-chloro-6-[(2,4-difluorobenzyl)oxy]-3-{[1-(2-hydroxy-2-methylpropanoyl)-3-(N-methylglycyl)-2,3-dihydro-1H-benzimidazol-5-yl]methyl}pyrimidin-4(3H)-one;

5-chloro-6-[(2,4-difluorobenzyl)oxy]-3-{[1-(2-hydroxy-2-methylpropanoyl)-3-(3-hydroxypropanoyl)-2,3-dihydro-1H-benzimidazol-5-yl]methyl}pyrimidin-4(3H)-one;

5-chloro-6-[(2,4-difluorobenzyl)oxy]-3-{[1-(2-hydroxy-2-methylpropanoyl)-3-(methylsulfonyl)-2,3-dihydro-1H-benzimidazol-5-yl]methyl}pyrimidin-4(3H)-one;

5-chloro-6-[(2,4-difluorobenzyl)oxy]-3-{[1-(3-hydroxy-3-methylbutanoyl)-2,3-dihydro-1H-indol-5-yl]methyl}pyrimidin-4(3H)-one;

5-chloro-6-[(2,4-difluorobenzyl)oxy]-3-{[1-(3-hydroxy-3-methylbutanoyl)-2,3-dihydro-1H-benzimidazol-5-yl]methyl}pyrimidin-4(3H)-one;

5-chloro-6-[(2,4-difluorobenzyl)oxy]-3-{[1-(3-hydroxy-3-methylbutanoyl)-3-(2-hydroxy-2-methylpropanoyl)-2,3-dihydro-1H-benzimidazol-5-yl]methyl}pyrimidin-4(3H)-one;

5-chloro-6-[(2,4-difluorobenzyl)oxy]-3-{[1-(3-hydroxy-3-methylbutanoyl)-3-(N-methylglycyl)-2,3-dihydro-1H-benzimidazol-5-yl]methyl}pyrimidin-4(3H)-one;

5-chloro-6-[(2,4-difluorobenzyl)oxy]-3-{[1-(3-hydroxy-3-methylbutanoyl)-3-(3-hydroxypropanoyl)-2,3-dihydro-1H-benzimidazol-5-yl]methyl}pyrimidin-4(3H)-one;

5-chloro-6-[(2,4-difluorobenzyl)oxy]-3-{[1-(3-hydroxy-3-methylbutanoyl)-3-(methylsulfonyl)-2,3-dihydro-1H-benzimidazol-5-yl]methyl}pyrimidin-4(3H)-one;

5-chloro-6-[(2,4-difluorobenzyl)oxy]-3-{[1-(3-hydroxypropanoyl)-2,3-dihydro-1H-indol-5-yl]methyl}pyrimidin-4(3H)-one;

5-chloro-6-[(2,4-difluorobenzyl)oxy]-3-{[1-(3-hydroxypropanoyl)-2,3-dihydro-1H-benzimidazol-5-yl]methyl}pyrimidin-4(3H)-one;

5-chloro-6-[(2,4-difluorobenzyl)oxy]-3-{[1-(3-hydroxypropanoyl)-3-(N-methylglycyl)-2,3-dihydro-1H-benzimidazol-5-yl]methyl}pyrimidin-4(3H)-one;

5-chloro-6-[(2,4-difluorobenzyl)oxy]-3-{[1-(3-hydroxypropanoyl)-3-(methylsulfonyl)-2,3-dihydro-1H-benzimidazol-5-yl]methyl}pyrimidin-4(3H)-one;

5-chloro-6-[(2,4-difluorobenzyl)oxy]-3-{[1-(methylsulfonyl)-2,3-dihydro-1H-indol-5-yl]methyl}pyrimidin-4(3H)-one;

5-chloro-6-[(2,4-difluorobenzyl)oxy]-3-{[1-(methylsulfonyl)-2,3-dihydro-1H-benzimidazol-5-yl]methyl}pyrimidin-4(3H)-one;

5-chloro-6-[(2,4-difluorobenzyl)oxy]-3-{[1-(N-methylglycyl)-2,3-dihydro-1H-indol-5-yl]methyl}pyrimidin-4(3H)-one;

5-chloro-6-[(2,4-difluorobenzyl)oxy]-3-{[1-(N-methylglycyl)-2,3-dihydro-1H-benzimidazol-5-yl]methyl}pyrimidin-4(3H)-one;

5-chloro-6-[(2,4-difluorobenzyl)oxy]-3-{[1-(N-methylglycyl)-3-(methylsulfonyl)-2,3-dihydro-1H-benzimidazol-5-yl]methyl}pyrimidin-4(3H)-one;

5-chloro-6-[(2,4-difluorobenzyl)oxy]-3-{[1-glycoloyl-3-(2-hydroxy-2-methylpropanoyl)-2,3-dihydro-1H-benzimidazol-5-yl]methyl}pyrimidin-4(3H)-one;

5-chloro-6-[(2,4-difluorobenzyl)oxy]-3-{[1-glycoloyl-3-(3-hydroxypropanoyl)-2,3-dihydro-1H-benzimidazol-5-yl]methyl}pyrimidin-4(3H)-one;

5-chloro-6-[(2,4-difluorobenzyl)oxy]-3-{[1-glycoloyl-3-(3-hydroxy-3-methylbutanoyl)-2,3-dihydro-1H-benzimidazol-5-yl]methyl}pyrimidin-4(3H)-one;

5-chloro-6-[(2,4-difluorobenzyl)oxy]-3-{[1-glycoloyl-3-(methylsulfonyl)-2,3-dihydro-1H-benzimidazol-5-yl]methyl}pyrimidin-4(3H)-one;

5-chloro-6-[(2,4-difluorobenzyl)oxy]-3-{[1-glycoloyl-3-(N-methylglycyl)-2,3-dihydro-1H-benzimidazol-5-yl]methyl}pyrimidin-4(3H)-one;

5-chloro-6-[(2,4-difluorobenzyl)oxy]-3-{[2-(2-hydroxy-2-methylpropanoyl)-2,3-dihydro-1H-isoindol-5-yl]methyl}pyrimidin-4(3H)-one;

5-chloro-6-[(2,4-difluorobenzyl)oxy]-3-{[2-(2-hydroxy-2-methylpropanoyl)-1,2,3,4-tetrahydroisoquinolin-6-yl]methyl}pyrimidin-4(3H)-one;

5-chloro-6-[(2,4-difluorobenzyl)oxy]-3-{[2-(2-hydroxy-2-methylpropanoyl)-1,2,3,4-tetrahydroisoquinolin-5-yl]methyl}pyrimidin-4(3H)-one;

5-chloro-6-[(2,4-difluorobenzyl)oxy]-3-{[2-(3-hydroxy-3-methylbutanoyl)-2,3-dihydro-1H-isoindol-5-yl]methyl}pyrimidin-4(3H)-one;

5-chloro-6-[(2,4-difluorobenzyl)oxy]-3-{[2-(3-hydroxy-3-methylbutanoyl)-1,2,3,4-tetrahydroisoquinolin-6-yl]methyl}pyrimidin-4(3H)-one;

5-chloro-6-[(2,4-difluorobenzyl)oxy]-3-{[2-(3-hydroxy-3-methylbutanoyl)-1,2,3,4-tetrahydroisoquinolin-5-yl]methyl}pyrimidin-4(3H)-one;

5-chloro-6-[(2,4-difluorobenzyl)oxy]-3-{[2-(3-hydroxypropanoyl)-1,2,3,4-tetrahydroisoquinolin-6-yl]methyl}pyrimidin-4(3H)-one;

5-chloro-6-[(2,4-difluorobenzyl)oxy]-3-{[2-(3-hydroxypropanoyl)-1,2,3,4-tetrahydroisoquinolin-5-yl]methyl}pyrimidin-4(3H)-one;

5-chloro-6-[(2,4-difluorobenzyl)oxy]-3-{[2-(3-hydroxypropanoyl)-2,3-dihydro-1H-isoindol-5-yl]methyl}pyrimidin-4(3H)-one;

5-chloro-6-[(2,4-difluorobenzyl)oxy]-3-{[2-(methylsulfonyl)-1,2,3,4-tetrahydroisoquinolin-6-yl]methyl}pyrimidin-4(3H)-one;

5-chloro-6-[(2,4-difluorobenzyl)oxy]-3-{[2-(methylsulfonyl)-1,2,3,4-tetrahydroisoquinolin-5-yl]methyl}pyrimidin-4(3H)-one;

5-chloro-6-[(2,4-difluorobenzyl)oxy]-3-{[2-(methylsulfonyl)-2,3-dihydro-1H-isoindol-5-yl]methyl}pyrimidin-4(3H)-one;

5-chloro-6-[(2,4-difluorobenzyl)oxy]-3-{[2-(N-methylglycyl)-1,2,3,4-tetrahydroisoquinolin-6-yl]methyl}pyrimidin-4(3H)-one;

5-chloro-6-[(2,4-difluorobenzyl)oxy]-3-{[2-(N-methylglycyl)-1,2,3,4-tetrahydroisoquinolin-5-yl]methyl}pyrimidin-4(3H)-one;

5-chloro-6-[(2,4-difluorobenzyl)oxy]-3-{[2-(N-methylglycyl)-2,3-dihydro-1H-isoindol-5-yl]methyl}pyrimidin-4(3H)-one;

5-chloro-6-[(2,4-difluorobenzyl)oxy]-3-{[3-(2-hydroxy-2-methylpropanoyl)-2,3-dihydro-1H-benzimidazol-5-yl]methyl}pyrimidin-4(3H)-one;

5-chloro-6-[(2,4-difluorobenzyl)oxy]-3-{[3-(2-hydroxy-2-methylpropanoyl)-1-(N-methylglycyl)-2,3-dihydro-1H-benzimidazol-5-yl]methyl}pyrimidin-4(3H)-one;

5-chloro-6-[(2,4-difluorobenzyl)oxy]-3-{[3-(2-hydroxy-2-methylpropanoyl)-1-(3-hydroxypropanoyl)-2,3-dihydro-1H-benzimidazol-5-yl]methyl}pyrimidin-4(3H)-one;

5-chloro-6-[(2,4-difluorobenzyl)oxy]-3-{[3-(2-hydroxy-2-methylpropanoyl)-1-(methylsulfonyl)-2,3-dihydro-1H-benzimidazol-5-yl]methyl}pyrimidin-4(3H)-one;

5-chloro-6-[(2,4-difluorobenzyl)oxy]-3-{[3-(3-hydroxy-3-methylbutanoyl)-2,3-dihydro-1H-benzimidazol-5-yl]methyl}pyrimidin-4(3H)-one;

5-chloro-6-[(2,4-difluorobenzyl)oxy]-3-{[3-(3-hydroxy-3-methylbutanoyl)-1-(2-hydroxy-2-methylpropanoyl)-2,3-dihydro-1H-benzimidazol-5-yl]methyl}pyrimidin-4(3H)-one;

5-chloro-6-[(2,4-difluorobenzyl)oxy]-3-{[3-(3-hydroxy-3-methylbutanoyl)-1-(N-methylglycyl)-2,3-dihydro-1H-benzimidazol-5-yl]methyl}pyrimidin-4(3H)-one;

5-chloro-6-[(2,4-difluorobenzyl)oxy]-3-{[3-(3-hydroxy-3-methylbutanoyl)-1-(methylsulfonyl)-2,3-dihydro-1H-benzimidazol-5-yl]methyl}pyrimidin-4(3H)-one;

5-chloro-6-[(2,4-difluorobenzyl)oxy]-3-{[3-(3-hydroxy-3-methylbutanoyl)-1-(3-hydroxypropanoyl)-2,3-dihydro-1H-benzimidazol-5-yl]methyl}pyrimidin-4(3H)-one;

5-chloro-6-[(2,4-difluorobenzyl)oxy]-3-{[3-(3-hydroxypropanoyl)-1-(N-methylglycyl)-2,3-dihydro-1H-benzimidazol-5-yl]methyl}pyrimidin-4(3H)-one;

5-chloro-6-[(2,4-difluorobenzyl)oxy]-3-{[3-(3-hydroxypropanoyl)-1-(methylsulfonyl)-2,3-dihydro-1H-benzimidazol-5-yl]methyl}pyrimidin-4(3H)-one;

5-chloro-6-[(2,4-difluorobenzyl)oxy]-3-{[3-(3-hydroxypropanoyl)-2,3-dihydro-1H-benzimidazol-5-yl]methyl}pyrimidin-4(3H)-one;

5-chloro-6-[(2,4-difluorobenzyl)oxy]-3-{[3-(methylsulfonyl)-2,3-dihydro-1H-benzimidazol-5-yl]methyl}pyrimidin-4(3H)-one;
5-chloro-6-[(2,4-difluorobenzyl)oxy]-3-{[3-(N-methylglycyl)-1-(methylsulfonyl)-2,3-dihydro-1H-benzimidazol-5-yl]methyl}pyrimidin-4(3H)-one;
5-chloro-6-[(2,4-difluorobenzyl)oxy]-3-{[3-(N-methylglycyl)-2,3-dihydro-1H-benzimidazol-5-yl]methyl}pyrimidin-4(3H)-one;
5-chloro-6-[(2,4-difluorobenzyl)oxy]-3-{[3-glycoloyl-1-(2-hydroxy-2-methylpropanoyl)-2,3-dihydro-1H-benzimidazol-5-yl]methyl}pyrimidin-4(3H)-one;
5-chloro-6-[(2,4-difluorobenzyl)oxy]-3-{[3-glycoloyl-1-(3-hydroxypropanoyl)-2,3-dihydro-1H-benzimidazol-5-yl]methyl}pyrimidin-4(3H)-one;
5-chloro-6-[(2,4-difluorobenzyl)oxy]-3-{[3-glycoloyl-1-(3-hydroxy-3-methylbutanoyl)-2,3-dihydro-1H-benzimidazol-5-yl]methyl}pyrimidin-4(3H)-one;
5-chloro-6-[(2,4-difluorobenzyl)oxy]-3-{[3-glycoloyl-1-(methylsulfonyl)-2,3-dihydro-1H-benzimidazol-5-yl]methyl}pyrimidin-4(3H)-one;
5-chloro-6-[(2,4-difluorobenzyl)oxy]-3-{[3-glycoloyl-1-(N-methylglycyl)-2,3-dihydro-1H-benzimidazol-5-yl]methyl}pyrimidin-4(3H)-one;
5-chloro-6-[(2,4-difluorobenzyl)oxy]-3-{[5-(hydroxymethyl)pyrazin-2-yl]methyl}-2-methylpyrimidin-4(3H)-one;
5-chloro-6-[(2,4-difluorobenzyl)oxy]-1-isoquinolin-7-yl-2-methylpyrimidin-4(3H)-one;
5-chloro-6-[(2,4-difluorobenzyl)oxy]-6-(hydroxymethyl)-3-(2,4,6-trifluorophenyl)pyrimidin-4(3H)-one;
5-chloro-6-[(2,4-difluorobenzyl)oxy]-2-methyl-3-(2,4,6-trifluorophenyl)pyrimidin-4(3H)-one;
5-chloro-6-[(2,4-difluorobenzyl)oxy]-2-methyl-3-[(5-methylpyrazin-2-yl)methyl]pyrimidin-4(3H)-one;
5-chloro-6-[(2,4-difluorobenzyl)oxy]-2-methyl-3-[3-(methylsulfonyl)-2,3-dihydro-1H-indol-5-yl]pyrimidin-4(3H)-one;
5-chloro-6-[(2,4-difluorobenzyl)oxy]-2-methyl-3-[3-(methylsulfonyl)-1H-indol-5-yl]pyrimidin-4(3H)-one;
5-chloro-6-[(2,4-difluorobenzyl)oxy]-2-methyl-3-[3-(methylsulfonyl)-1H-benzimidazol-5-yl]pyrimidin-4(3H)-one;
5-chloro-6-[(2,4-difluorobenzyl)oxy]-2-methyl-3-[1-(methylsulfonyl)-1H-pyrrol-3-yl]pyrimidin-4(3H)-one;
5-chloro-6-[(2,4-difluorobenzyl)oxy]-2-methyl-3-[1-(methylsulfonyl)-1H-imidazol-4-yl]pyrimidin-4(3H)-one;
5-chloro-6-[(2,4-difluorobenzyl)oxy]-2-methyl-3-[1-(methylsulfonyl)-1H-pyrazol-4-yl]pyrimidin-4(3H)-one;
5-chloro-6-[(2,4-difluorobenzyl)oxy]-2-methyl-3-[1-(N-methylglycyl)-2,3-dihydro-1H-indol-5-yl]pyrimidin-4(3H)-one;
5-chloro-6-[(2,4-difluorobenzyl)oxy]-2-methyl-3-[1-(N-methylglycyl)-1H-indol-5-yl]pyrimidin-4(3H)-one;
5-chloro-6-[(2,4-difluorobenzyl)oxy]-2-methyl-3-[1-(N-methylglycyl)-1H-benzimidazol-5-yl]pyrimidin-4(3H)-one;
5-chloro-6-[(2,4-difluorobenzyl)oxy]-2-methyl-3-[1-(N-methylglycyl)-3-(methylsulfonyl)-2,3-dihydro-1H-benzimidazol-5-yl]pyrimidin-4(3H)-one;
5-chloro-6-[(2,4-difluorobenzyl)oxy]-2-methyl-3-[1-(N-methylglycyl)-1H-pyrrol-3-yl]pyrimidin-4(3H)-one;
5-chloro-6-[(2,4-difluorobenzyl)oxy]-2-methyl-3-[1-(N-methylglycyl)-1H-imidazol-4-yl]pyrimidin-4(3H)-one;
5-chloro-6-[(2,4-difluorobenzyl)oxy]-2-methyl-3-[1-(N-methylglycyl)-1H-pyrazol-4-yl]pyrimidin-4(3H)-one;
5-chloro-6-[(2,4-difluorobenzyl)oxy]-2-methyl-3-[2-(methylsulfonyl)-2,3-dihydro-1H-isoindol-5-yl]pyrimidin-4(3H)-one;
5-chloro-6-[(2,4-difluorobenzyl)oxy]-2-methyl-3-[2-(methylsulfonyl)-1,2,3,4-tetrahydroisoquinolin-6-yl]pyrimidin-4(3H)-one;
5-chloro-6-[(2,4-difluorobenzyl)oxy]-2-methyl-3-[2-(methylsulfonyl)-1,2,3,4-tetrahydroisoquinolin-7-yl]pyrimidin-4(3H)-one;
5-chloro-6-[(2,4-difluorobenzyl)oxy]-2-methyl-3-[2-(N-methylglycyl)-2,3-dihydro-1H-isoindol-5-yl]pyrimidin-4(3H)-one;
5-chloro-6-[(2,4-difluorobenzyl)oxy]-2-methyl-3-[2-(N-methylglycyl)-1,2,3,4-tetrahydroisoquinolin-6-yl]pyrimidin-4(3H)-one;
5-chloro-6-[(2,4-difluorobenzyl)oxy]-2-methyl-3-[2-(N-methylglycyl)-1,2,3,4-tetrahydroisoquinolin-7-yl]pyrimidin-4(3H)-one;
5-chloro-6-[(2,4-difluorobenzyl)oxy]-2-methyl-3-[3-(N-methylglycyl)-1-(methylsulfonyl)-2,3-dihydro-1H-benzimidazol-5-yl]pyrimidin-4(3H)-one;
4-({[5-bromo-3-(3-fluorobenzyl)-4-oxo-3,4-dihydropyrimidin-6-yl]oxy}methyl)benzonitrile;
6-(2,4-difluoro-benzyloxy)-3-(3-fluoro-benzyl)-5-iodo-1H-pyrimidin-4-one;
6-(2,4-difluoro-benzyloxy)-2-methyl-3-(2,4,6-trifluoro-phenyl)-1H-pyrimidin-4-one;
6-(allylamino)-3-(2,6-difluorophenyl)-1-iodo-2-methylpyrimidin-4(3H)-one;
6-(allylamino)-5-bromo-3-(2,6-difluorophenyl)-1-iodo-2-methylpyrimidin-4(3H)-one;
6-(allylamino)-5-bromo-3-(2,6-difluorophenyl)-2-methylpyrimidin-4(3H)-one;
6-(benzylamino)-3-(3-fluorobenzyl)-2-methyl-5-nitropyrimidin-4(3H)-one;
6-(benzylamino)-5-bromo-3-(2,6-difluorophenyl)-1-iodo-2-methylpyrimidin-4(3H)-one;
6-(benzyloxy)-3-(2,2-diethoxyethyl)pyrimidin-4(3H)-one;
6-(benzyloxy)-3-(2-oxopropyl)pyrimidin-4(3H)-one;
6-(benzyloxy)-3-(3-fluorobenzyl)-5-(trifluoromethyl)pyrimidin-4(3H)-one;
6-(benzyloxy)-3-(3-fluorobenzyl)-5-methylpyrimidin-4(3H)-one;
6-(benzyloxy)-3-(piperidin-3-ylmethyl)pyrimidin-4(3H)-one trifluoroacetate;
6-(benzyloxy)-3-[4-(methylsulfonyl)benzyl]pyrimidin-4(3H)-one
6-(benzyloxy)-3-[4-(methylthio)benzyl]pyrimidin-4(3H)-one
6-(benzyloxy)-3-ethylpyrimidin-4(3H)-one
6-(benzyloxy)-5-bromo-3-(2,6-dichlorophenyl)-2-methylpyrimidin-4(3H)-one;
6-(benzyloxy)-5-bromo-3-(2-fluorobenzyl)pyrimidin-4(3H)-one;
6-(benzyloxy)-5-bromo-3-(2-morpholin-4-ylethyl)pyrimidin-4(3H)-one;
6-(benzyloxy)-5-bromo-3-(3-fluorobenzyl)pyrimidin-4(3H)-one;
6-(benzyloxy)-5-bromo-3-(3-morpholin-4-yl-3-oxopropyl)pyrimidin-4(3H)-one;
6-(benzyloxy)-5-bromo-3-(3-oxo-3-piperazin-1-ylpropyl)pyrimidin-4(3H)-one hydrochloride;
6-(benzyloxy)-5-bromo-3-(4-bromobenzyl)pyrimidin-4(3H)-one;
6-(benzyloxy)-5-bromo-3-(4-chlorobenzyl)pyrimidin-4(3H)-one;

6-(benzyloxy)-5-bromo-3-(4-methylbenzyl)pyrimidin-4(3H)-one;
6-(benzyloxy)-5-bromo-3-(piperidin-3-ylmethyl)pyrimidin-4(3H)-one;
6-(benzyloxy)-5-bromo-3-[(6-fluoropyridin-3-yl)methyl]pyrimidin-4(3H)-one;
6-(benzyloxy)-5-bromo-3-[2-(2-thienyl)ethyl]pyrimidin-4(3H)-one;
6-(benzyloxy)-5-bromo-3-[2-(3-thienyl)ethyl]pyrimidin-4(3H)-one;
6-(benzyloxy)-5-bromo-3-[4-(morpholin-4-ylcarbonyl)phenyl]pyrimidin-4(3H)-one;
6-(benzyloxy)-5-bromo-3-piperidin-4-ylpyrimidin-4(3H)-one hydrochloride;
4-(biphenyl-2-ylmethoxy)-5-bromo-3-(3-fluorobenzyl)pyrimidin-4(3H)-one;
6-[(2,4-difluorobenzyl)oxy]-3-(2,6-difluoro-4-hydroxyphenyl)-2-methylpyrimidin-4(3H)-one;
6-[(2,4-difluorobenzyl)oxy]-3-(2,6-difluoro-4-morpholin-4-ylphenyl)-2-methylpyrimidin-4(3H)-one;
6-[(2,4-difluorobenzyl)oxy]-3-(2,6-difluorophenyl)-6-(hydroxymethyl)pyrimidin-4(3H)-one;
6-[(2,4-difluorobenzyl)oxy]-3-(2,6-difluorophenyl)-2-methylpyrimidin-4(3H)-one;
6-[(2,4-difluorobenzyl)oxy]-3-(3-fluorobenzyl)-4-oxo-3,4-dihydropyrimidine-5-carbonitrile;
6-[(2,4-difluorobenzyl)oxy]-3-(3-fluorobenzyl)-5-methylpyrimidin-4(3H)-one;
6-[(2,4-difluorobenzyl)oxy]-3-(4-methoxybenzyl)-2-methylpyrimidin-4(3H)-one;
6-[(2,4-difluorobenzyl)oxy]-3-[2,6-difluoro-4-(4-methylpiperazin-1-yl)phenyl]-2-methylpyrimidin-4(3H)-one;
6-[(2,4-difluorobenzyl)oxy]-3-[4-(dimethylamino)-2,6-difluorophenyl]-2-methylpyrimidin-4(3H)-one;
6-[(2,4-difluorobenzyl)oxy]-3-[5-(hydroxymethyl)-2-methylphenyl]-2-methylpyrimidin-4(3H)-one;
6-[(2,4-difluorobenzyl)oxy]-3-{2,6-difluoro-4-[(2-hydroxyethyl)(methyl)amino]phenyl}-2-methylpyrimidin-4(3H)-one;
6-[(2,4-difluorobenzyl)oxy]-2-(hydroxymethyl)-3-(2,4,6-trifluorophenyl)pyrimidin-4(3H)-one;
6-[(2,4-difluorobenzyl)oxy]-2-(hydroxymethyl)-3-(pyridin-3-ylmethyl)pyrimidin-4(3H)-one;
6-[(2,4-difluorobenzyl)oxy]-2-methyl-3-(tetrahydrofuran-2-ylmethyl)pyrimidin-4(3H)-one;
6-[(2,4-difluorobenzyl)oxy]-2-methyl-3-[2-(trifluoromethyl)phenyl]pyrimidin-4(3H)-one;
6-[(2,4-difluorobenzyl)oxy]-2-methyl-3-prop-2-yn-1-ylpyrimidin-4(3H)-one;
6-[3-amino-1-(2,4-difluoro-phenyl)-propoxy]-5-bromo-2-methyl-3-pyridin-3-ylmethyl-3H-pyrimidin-4-one;
6-([2-(aminomethyl)-4-fluorobenzyl]oxy)-5-bromo-3-(2,6-difluorophenyl)-2-methylpyrimidin-4(3H)-one trifluoroacetate;
6-anilino-5-bromo-3-(3-fluorobenzyl)pyrimidin-4(3H)-one;
6-benzo[1,3]dioxol-5-yl-5-bromo-3-(3-fluoro-benzyl)-3H-pyrimidin-4-one;
6-benzyloxy-3-difluoromethyl-3H-pyrimidin-4-one;
6-benzyloxy-3H-pyrimidin-4-one;
6-benzyloxy-5-bromo-3-(2-chloro-phenyl)-2-methyl-3H-pyrimidin-4-one;
6-benzyloxy-5-bromo-3-(3-fluoro-benzyl)-3H-pyrimidin-4-one;
6-benzyloxy-5-bromo-3-(4-bromo-benzyl)-3H-pyrimidin-4-one;
6-benzyloxy-5-bromo-3-(4-chloro-benzyl)-3H-pyrimidin-4-one;
6-benzyloxy-5-bromo-3-(4-fluoro-benzyl)-3H-pyrimidin-4-one;
6-benzyloxy-5-bromo-3-(4-methylsulfanyl-benzyl)-3H-pyrimidin-4-one;
6-benzyloxy-5-bromo-3-methanesulfonyl-3H-pyrimidin-4-one;
6-benzyloxy-5-methyl-3H-pyrimidin-4-one;
6-phenoxy-3-{[2-(trimethylsilyl)ethoxy]methyl}pyrimidin-4(3H)-one;
6-phenoxy-3H-pyrimidin-4-one;
1-[4-(5-chloro-phenyl)-piperazine-1-carbonyl]-3-(3,4-dichloro-benzyl)-3H-pyrimidin-4-one;
1-methyl-3-phenyl-3H-pyrimidin-4-one;
5-bromo-3-(3-fluorobenzyl)-6-(4-methylpiperazin-1-yl)pyrimidin-4(3H)-one trifluoroacetate;
3-([5-bromo-4-[(2,4-difluorobenzyl)oxy]-2-methyl-6-oxopyrimidin-1(6H)-yl]methyl)-N,N-dimethylbenzamide;
3-{[5-bromo-4-[(2,4-difluorobenzyl)oxy]-2-methyl-6-oxopyrimidin-1(6H)-yl]methyl}-N-methylbenzamide;
3-([5-bromo-4-[(2,4-difluorobenzyl)oxy]-2-methyl-6-oxopyrimidin-1(6H)-yl]methyl)-N-(2-hydroxyethyl)benzamide;
3-{[5-bromo-4-[(2,4-difluorobenzyl)oxy]-2-methyl-6-oxopyrimidin-1(6H)-yl]methyl}-N,N-bis(2-hydroxyethyl)benzamide;
3-{[5-bromo-4-[(2,4-difluorobenzyl)oxy]-2-methyl-6-oxopyrimidin-1(6H)-yl]methyl}-N-isopropylbenzamide;
3-[5-bromo-4-[(2,4-difluorobenzyl)oxy]-2-methyl-6-oxopyrimidin-1(6H)-yl]-4-methylbenzaldehyde;
3-[5-bromo-4-[(2,4-difluorobenzyl)oxy]-2-methyl-6-oxopyrimidin-1(6H)-yl]-N-(2-hydroxyethyl)-4-methylbenzamide;
3-[5-bromo-4-[(2,4-difluorobenzyl)oxy]-2-methyl-6-oxopyrimidin-1(6H)-yl]-N-hydroxybenzamide;
3-[5-bromo-4-[(2,4-difluorobenzyl)oxy]-2-methyl-6-oxopyrimidin-1(6H)-yl]-N,N-dimethylbenzamide;
3-[5-bromo-4-[(2,4-difluorobenzyl)oxy]-2-methyl-6-oxopyrimidin-1(6H)-yl]-N-(2-hydroxyethyl)benzamide;
3-[5-bromo-4-[(2,4-difluorobenzyl)oxy]-2-methyl-6-oxopyrimidin-1(6H)-yl]-N-isopropylbenzamide;
3-[5-bromo-4-[(2,4-difluorobenzyl)oxy]-2-methyl-6-oxopyrimidin-1(6H)-yl]-N,4-dimethylbenzamide;
3-[5-bromo-4-[(2,4-difluorobenzyl)oxy]-2-methyl-6-oxopyrimidin-1(6H)-yl]-4-methylbenzoic acid;
3-[5-bromo-4-[(2,4-difluorobenzyl)oxy]-2-methyl-6-oxopyrimidin-1(6H)-yl]benzoic acid;
3-[5-bromo-4-[(2,4-difluorobenzyl)oxy]-2-methyl-6-oxopyrimidin-1(6H)-yl]-N-[2-(dimethylamino)ethyl]benzamide;
3-[5-bromo-4-[(2,4-difluorobenzyl)oxy]-2-methyl-6-oxopyrimidin-1(6H)-yl]-N-(2-methoxyethyl)benzamide;
3-[5-bromo-4-[(2,4-difluorobenzyl)oxy]-2-methyl-6-oxopyrimidin-1(6H)-yl]-N-[2-(dimethylamino)ethyl]-N-methylbenzamide;
3-[5-bromo-4-[(2,4-difluorobenzyl)oxy]-2-methyl-6-oxopyrimidin-1(6H)-yl]-N-(2-hydroxyethyl)-N-methylbenzamide;
3-[5-bromo-4-[(2,4-difluorobenzyl)oxy]-2-methyl-6-oxopyrimidin-1(6H)-yl]-N-(2-methoxyethyl)-N-methylbenzamide;
4-[5-bromo-4-[(2,4-difluorobenzyl)oxy]-2-methyl-6-oxopyrimidin-1(6H)-yl]-N-(2-hydroxyethyl)benzamide;
4-[5-bromo-4-[(2,4-difluorobenzyl)oxy]-2-methyl-6-oxopyrimidin-1(6H)-yl]benzoic acid;
2-{[4-(benzyloxy)-5-bromo-6-oxopyrimidin-1(6H)-yl]methyl}benzonitrile;

2-(3-{[5-bromo-4-[(2,4-difluorobenzyl)oxy]-6-oxopyrimidin-1(6H)-yl]methyl}phenyl)acetamide;
2-chloro-N-[3-(2,6-dichlorobenzyl)-4-oxo-5-(trifluoromethyl)-3,4-dihydropyrimidin-1(2H)-yl]-4-fluorobenzamide;
6-oxo-2-(2-phenylethyl)-1,6-dihydropyrimidine-5-carbonitrile;
6-oxo-2-phenyl-1,6-dihydropyrimidine-5-carbonitrile;
methyl 3-{[4-(benzyloxy)-5-bromo-6-oxopyrimidin-1(6H)-yl]methyl}benzoate;
3-([4-(benzyloxy)-5-bromo-6-oxopyrimidin-1(6H)-yl]methyl)benzonitrile;
3-{[5-bromo-4-[(2,4-difluorobenzyl)oxy]-6-oxopyrimidin-1(6H)-yl]methyl}benzamide;
3-{[5-bromo-4-[(2,4-difluorobenzyl)oxy]-2-methyl-6-oxopyrimidin-1(6H)-yl]methyl}benzonitrile;
methyl 3-{[5-bromo-4-[(2,4-difluorobenzyl)oxy]-2-methyl-6-oxopyrimidin-1(6H)-yl]methyl}benzoate;
3-{[5-bromo-4-[(2,4-difluorobenzyl)oxy]-2-methyl-6-oxopyrimidin-1(6H)-yl]methyl}benzamide;
3-{[5-bromo-4-[(2,4-difluorobenzyl)oxy]-2-methyl-6-oxopyrimidin-1(6H)-yl]methyl}-N-hydroxybenzamide;
1-benzyl-5-bromo-2-methyl-6-oxo-1,6-dihydropyrimidin-4-yl methanesulfonate;
1-benzyl-2-methyl-6-oxo-1,6-dihydropyrimidin-4-yl methanesulfonate;
3-benzyl-N-(2-morpholin-4-ylethyl)-4-oxo-3,4-dihydropyrimidine-1(2H)-carboxamide;
N-(4-{[5-chloro-4-[(2,4-difluorobenzyl)oxy]-2-methyl-6-oxopyrimidin-1(6H)-yl]methyl}benzyl)-1-hydroxycyclopropanecarboxamide;
2-({[5-bromo-6-oxo-1-(pyridin-3-ylmethyl)-1,6-dihydropyrimidin-4-yl]oxy}methyl)-5-fluorobenzonitrile;
2-({3-[5-bromo-4-[(2,4-difluorobenzyl)oxy]-2-methyl-6-oxopyrimidin-1(6H)-yl]benzyl}amino)-2-oxoethyl acetate;
2-(2-([5-bromo-4-[(2,4-difluorobenzyl)oxy]-6-oxopyrimidin-1(6H)-yl]methyl)phenyl)acetamide;
2-[({1-[(4-amino-2-methylpyrimidin-5-yl)methyl]-5-bromo-2-methyl-6-oxo-1,6-dihydropyrimidin-4-yl}oxy)methyl]-5-fluorobenzonitrile;
2-[4-(benzyloxy)-6-oxopyrimidin-1(6H)-yl]acetamide;
2-{[5-bromo-4-[(2,4-difluorobenzyl)oxy]-6-oxopyrimidin-1(6H)-yl]methyl}benzonitrile;
2-{[5-bromo-4-[(2,4-difluorobenzyl)oxy]-2-methyl-6-oxopyrimidin-1(6H)-yl]methyl}benzonitrile;
2-{[5-bromo-4-[(2,4-difluorobenzyl)oxy]-2-methyl-6-oxopyrimidin-1(6H)-yl]methyl}benzamide;
2-{[4-(benzyloxy)-5-bromo-6-oxopyrimidin-1(6H)-yl]methyl}benzamide;
(4-{[4-(benzyloxy)-5-bromo-6-oxopyrimidin-1(6H)-yl]methyl}phenyl)acetic acid;
[5-bromo-4-[(2,4-difluorobenzyl)oxy]-2-methyl-6-oxopyrimidin-1(6H)-yl]acetic acid;
[5-bromo-6-[(2,4-difluorobenzyl)oxy]-3-(2,6-difluorophenyl)-2-methyl-4-oxo-3,4-dihydropyrimidin-1(2H)-yl]methyl carbamate;
ethyl [2-({[5-bromo-1-(2,6-difluorophenyl)-2-methyl-6-oxo-1,6-dihydropyrimidin-4-yl]oxy}methyl)-5-fluorobenzyl]carbamate;
tert-butyl (3-{[5-bromo-4-[(2,4-difluorobenzyl)oxy]-6-oxopyrimidin-1(6H)-yl]methyl}benzyl)carbamate;
ethyl (3-{[5-bromo-4-[(2,4-difluorobenzyl)oxy]-6-oxopyrimidin-1(6H)-yl]methyl}phenyl)acetate;
(3-{[5-bromo-4-[(2,4-difluorobenzyl)oxy]-6-oxopyrimidin-1(6H)-yl]methyl}phenyl)acetonitrile;
methyl (3-{[5-bromo-4-[(2,4-difluorobenzyl)oxy]-2-methyl-6-oxopyrimidin-1(6H)-yl]methyl}benzyl)carbamate;
tert-butyl (3-{[5-bromo-4-[(4-fluorobenzyl)oxy]-6-oxopyrimidin-1(6H)-yl]methyl}benzyl)carbamate;
N'-[3-chloro-5-(trifluoromethyl)pyridin-2-yl]-3-(2,6-dichlorobenzyl)-4-oxo-3,4-dihydropyrimidine-1(2H)-carbohydrazide;
3-(2,6-dichlorobenzyl)-4-oxo-N-[3-(trifluoromethyl)benzyl]-3,4-dihydropyrimidine-1(2H)-carboxamide;
3-(2,6-dichlorobenzyl)-4-oxo-N-[4-(trifluoromethoxy)phenyl]-3,4-dihydropyrimidine-1(2H)-carboxamide;
3-(2,6-dichlorobenzyl)-4-oxo-N-[3-(trifluoromethyl)phenyl]-3,4-dihydropyrimidine-1(2H)-carboxamide;
N-(4-chlorophenyl)-3-(2,6-dichlorobenzyl)-4-oxo-3,4-dihydropyrimidine-1(2H)-carboxamide;
3-(2,6-dichlorobenzyl)-N-[2-(dimethylamino)ethyl]-4-oxo-3,4-dihydropyrimidine-1(2H)-carboxamide;
3-(3,4-dichlorobenzyl)-N-(2,4-difluorophenyl)-4-oxo-3,4-dihydropyrimidine-1(2H)-carboxamide;
1-benzyl-5-bromo-2-methyl-6-oxo-1,6-dihydropyrimidin-4-yl 4-bromobenzenesulfonate;
{4-[({6-(benzyloxy)-5-bromo-3-[4-(carboxymethyl)benzyl]-3,4-dihydropyrimidin-4-yl}oxy)methyl]phenyl}acetic acid;
3-(2,6-dichlorobenzyl)-N-(2,4-difluorophenyl)-4-oxo-3,4-dihydropyrimidine-1(2H)-carboxamide;
3-(2,6-dichlorobenzyl)-N-(2-morpholin-4-ylethyl)-4-oxo-3,4-dihydropyrimidine-1(2H)-carboxamide;
N-benzyl-3-(2,6-dichlorobenzyl)-4-oxo-3,4-dihydropyrimidine-1(2H)-carboxamide;
3-(2,6-dichlorobenzyl)-N-[3-(dimethylamino)propyl]-4-oxo-3,4-dihydropyrimidine-1(2H)-carboxamide;
4-[5-bromo-4-[(2,4-difluorobenzyl)oxy]-2-methyl-6-oxopyrimidin-1(6H)-yl]-N-hydroxybenzamide;
4-[5-bromo-4-[(2,4-difluorobenzyl)oxy]-2-methyl-6-oxopyrimidin-1(6H)-yl]-N-methylbenzamide;
4-[5-bromo-4-[(2,4-difluorobenzyl)oxy]-2-methyl-6-oxopyrimidin-1(6H)-yl]-N,N-dimethylbenzamide;
4-[5-bromo-4-[(2,4-difluorobenzyl)oxy]-2-methyl-6-oxopyrimidin-1(6H)-yl]-N,N-bis(2-hydroxyethyl)benzamide;
4-[5-bromo-4-[(2,4-difluorobenzyl)oxy]-2-methyl-6-oxopyrimidin-1(6H)-yl]-N-isopropylbenzamide;
4-[5-bromo-4-[(2,4-difluorobenzyl)oxy]-2-methyl-6-oxopyrimidin-1(6H)-yl]benzamide;
4-{[5-chloro-4-[(2,4-difluorobenzyl)oxy]-6-oxopyrimidin-1(6H)-yl]methyl}benzamide;
4-[5-chloro-4-[(2,4-difluorobenzyl)oxy]-2-methyl-6-oxopyrimidin-1(6H)-yl]-N,3-dimethylbenzamide;
4-[5-chloro-4-[(2,4-difluorobenzyl)oxy]-2-methyl-6-oxopyrimidin-1(6H)-yl]-1H-imidazole-1-carboxamide;
4-[5-chloro-4-[(2,4-difluorobenzyl)oxy]-2-methyl-6-oxopyrimidin-1(6H)-yl]-1H-pyrazole-1-carboxamide;
4-[4-(benzyloxy)-5-bromo-6-oxopyrimidin-1(6H)-yl]benzoic acid;
4-[4-[(2,4-difluorobenzyl)oxy]-2-methyl-6-oxopyrimidin-1(6H)-yl]-3-methylbenzoic acid;
4-([5-bromo-4-[(2,4-difluorobenzyl)oxy]-2-methyl-6-oxopyrimidin-1(6H)-yl]methyl)-N,N-dimethylbenzamide
4-{[5-chloro-4-[(2,4-difluorobenzyl)amino]-2-methyl-6-oxopyrimidin-1(6H)-yl]methyl}benzonitrile trifluoroacetate;
4-{[4-(benzyloxy)-5-bromo-6-oxopyrimidin-1(6H)-yl]methyl}benzoic acid;
4-{[4-(benzyloxy)-5-bromo-6-oxopyrimidin-1(6H)-yl]methyl}benzonitrile;
4-{[4-(benzyloxy)-5-bromo-6-oxopyrimidin-1(6H)-yl]methyl}-N'-hydroxybenzenecarboximidamide;

3-[5-bromo-4-[(2,4-difluorobenzyl)oxy]-2-methyl-6-oxopyrimidin-1(6H)-yl]-N-methylbenzamide;
3-[5-bromo-4-[(2,4-difluorobenzyl)oxy]-2-methyl-6-oxopyrimidin-1(6H)-yl]benzamide;
3-[5-bromo-4-[(2,4-difluorobenzyl)oxy]-2-methyl-6-oxopyrimidin-1(6H)-yl]-N-(2-methoxyethyl)-4-methylbenzamide;
3-[5-bromo-4-[(2,4-difluorobenzyl)oxy]-2-methyl-6-oxopyrimidin-1(6H)-yl]-N,N,4-trimethylbenzamide;
methyl 3-{[5-chloro-4-[(2,4-difluorobenzyl)oxy]-6-oxopyrimidin-1(6H)-yl]methyl}-2-fluorobenzoate;
3-{[5-chloro-4-[(2,4-difluorobenzyl)oxy]-6-oxopyrimidin-1(6H)-yl]methyl}-2-fluorobenzamide;
3-[5-chloro-4-[(2,4-difluorobenzyl)oxy]-2-methyl-6-oxopyrimidin-1(6H)-yl]-N,4-dimethylbenzamide;
3-[5-chloro-4-[(2,4-difluorobenzyl)oxy]-2-methyl-6-oxopyrimidin-1(6H)-yl]-4-methylbenzamide;
3-[5-chloro-4-[(2,4-difluorobenzyl)oxy]-2-methyl-6-oxopyrimidin-1(6H)-yl]-4-fluoro-N-methylbenzamide;
3-[5-chloro-4-[(2,4-difluorobenzyl)oxy]-2-methyl-6-oxopyrimidin-1(6H)-yl]-4-fluorobenzamide;
3-[5-chloro-4-[(2,4-difluorobenzyl)oxy]-2-methyl-6-oxopyrimidin-1(6H)-yl]benzoic acid;
3-[5-chloro-4-[(2,4-difluorobenzyl)oxy]-2-methyl-6-oxopyrimidin-1(6H)-yl]-2-methylbenzoic acid;
3-[5-chloro-4-[(2,4-difluorobenzyl)oxy]-2-methyl-6-oxopyrimidin-1(6H)-yl]-1H-pyrrole-1-carboxamide;
methyl 3-[4-[(2,4-difluorobenzyl)oxy]-2-methyl-6-oxopyrimidin-1(6H)-yl]benzoate;
3-acetyl-5-{[5-chloro-4-[(2,4-difluorobenzyl)oxy]-6-oxopyrimidin-1(6H)-yl]methyl}-1-(3-hydroxy-3-methylbutanoyl)-1,3-dihydro-2H-benzimidazol-2-one;
3-acetyl-5-{[5-chloro-4-[(2,4-difluorobenzyl)oxy]-6-oxopyrimidin-1(6H)-yl]methyl}-2-oxo-2,3-dihydro-1H-benzimidazole-1-carboxamide;
3-acetyl-5-{[5-chloro-4-[(2,4-difluorobenzyl)oxy]-6-oxopyrimidin-1(6H)-yl]methyl}-1-(methylsulfonyl)-1,3-dihydro-2H-benzimidazol-2-one;
3-acetyl-6-[5-chloro-4-[(2,4-difluorobenzyl)oxy]-2-methyl-6-oxopyrimidin-1(6H)-yl]-2,3-dihydro-1H-benzimidazole-1-carboxamide;
3-acetyl-6-{[5-chloro-4-[(2,4-difluorobenzyl)oxy]-6-oxopyrimidin-1(6H)-yl]methyl}-2,3-dihydro-1H-benzimidazole-1-carboxamide;
3-acetyl-6-{[5-chloro-4-[(2,4-difluorobenzyl)oxy]-6-oxopyrimidin-1(6H)-yl]methyl}-2-oxo-2,3-dihydro-1H-benzimidazole-1-carboxamide;
2-[5-bromo-4-[(2,4-difluorobenzyl)oxy]-2-methyl-6-oxopyrimidin-1(6H)-yl]-6-methylnicotinonitrile;
6-[5-bromo-4-[(2,4-difluorobenzyl)oxy]-2-methyl-6-oxopyrimidin-1(6H)-yl]nicotinic acid;
6-[5-bromo-4-[(2,4-difluorobenzyl)oxy]-2-methyl-6-oxopyrimidin-1(6H)-yl]-N-methylnicotinamide;
6-[5-bromo-4-[(2,4-difluorobenzyl)oxy]-2-methyl-6-oxopyrimidin-1(6H)-yl]-N-(2-hydroxyethyl)nicotinamide;
6-[5-bromo-4-[(2,4-difluorobenzyl)oxy]-2-methyl-6-oxopyrimidin-1(6H)-yl]-N-(2-methoxyethyl)nicotinamide;
6-{[5-bromo-1-(5-carboxypyridin-2-yl)-2-methyl-6-oxo-1,6-dihydropyrimidin-4-yl]oxy}nicotinic acid;
4-{[4-(benzyloxy)-5-bromo-6-oxopyrimidin-1(6H)-yl]methyl}benzamide;
methyl 4-{[4-(benzyloxy)-5-bromo-6-oxopyrimidin-1(6H)-yl]methyl}benzoate;
4-{[4-(benzyloxy)-5-bromo-6-oxopyrimidin-1(6H)-yl]methyl}benzoic acid;
4-{[4-(benzyloxy)-5-bromo-6-oxopyrimidin-1(6H)-yl]methyl}benzonitrile;
4-{[4-(benzyloxy)-5-bromo-6-oxopyrimidin-1(6H)-yl]methyl}-N'-hydroxybenzenecarboximidamide;
4-{[5-bromo-4-[(2,4-difluorobenzyl)oxy]-6-oxopyrimidin-1(6H)-yl]methyl}benzamide;
methyl 4-{[5-bromo-4-[(2,4-difluorobenzyl)oxy]-6-oxopyrimidin-1(6H)-yl]methyl}benzoate;
4-{[5-bromo-4-[(2,4-difluorobenzyl)oxy]-2-methyl-6-oxopyrimidin-1(6H)-yl]methyl}benzonitrile;
methyl 4-{[5-bromo-4-[(2,4-difluorobenzyl)oxy]-2-methyl-6-oxopyrimidin-1(6H)-yl]methyl}benzoate;
4-{[5-bromo-4-[(2,4-difluorobenzyl)oxy]-2-methyl-6-oxopyrimidin-1(6H)-yl]methyl}benzamide;
4-{[5-bromo-4-[(2,4-difluorobenzyl)oxy]-2-methyl-6-oxopyrimidin-1(6H)-yl]methyl}benzoic acid;
4-{[5-bromo-4-[(2,4-difluorobenzyl)oxy]-2-methyl-6-oxopyrimidin-1(6H)-yl]methyl}-N-hydroxybenzamide;
4-{[5-bromo-4-[(2,4-difluorobenzyl)oxy]-2-methyl-6-oxopyrimidin-1(6H)-yl]methyl}-N-methylbenzamide;
4-{[5-bromo-4-[(2,4-difluorobenzyl)oxy]-2-methyl-6-oxopyrimidin-1(6H)-yl]methyl}-N,N-dimethylbenzamide;
4-{[5-bromo-4-[(2,4-difluorobenzyl)oxy]-2-methyl-6-oxopyrimidin-1(6H)-yl]methyl}-N-(2-hydroxyethyl)benzamide;
4-{[5-bromo-4-[(2,4-difluorobenzyl)oxy]-2-methyl-6-oxopyrimidin-1(6H)-yl]methyl}-N,N-bis(2-hydroxyethyl)benzamide;
4-{[5-bromo-4-[(2,4-difluorobenzyl)oxy]-2-methyl-6-oxopyrimidin-1(6H)-yl]methyl}-N-isopropylbenzamide;
4-{[5-bromo-4-[(2,4-difluorobenzyl)oxy]-2-methyl-6-oxopyrimidin-1(6H)-yl]methyl}-N-[2-(dimethylamino)ethyl]benzamide;
4-{[5-bromo-4-[(2,4-difluorobenzyl)oxy]-2-methyl-6-oxopyrimidin-1(6H)-yl]methyl}-N-(2-methoxyethyl)benzamide;
4-{[5-bromo-4-[(2,4-difluorobenzyl)oxy]-2-methyl-6-oxopyrimidin-1(6H)-yl]methyl}-N-(2-hydroxyethyl)-N-methylbenzamide;
4-{[5-bromo-4-[(2,4-difluorobenzyl)oxy]-2-methyl-6-oxopyrimidin-1(6H)-yl]methyl}-N-(2-methoxyethyl)-N-methylbenzamide;
5-bromo-4-[(2,4-difluorobenzyl)oxy]-2-methyl-6-oxo-6H-1,4'-bipyrimidine-2'-carbonitrile;
4-{[5-bromo-4-[(4-fluorobenzyl)oxy]-6-oxopyrimidin-1(6H)-yl]methyl}benzonitrile;
4-[5-bromo-4-[(2,4-difluorobenzyl)oxy]-2-methyl-6-oxopyrimidin-1(6H)-yl]-3,5-dichlorobenzenesulfonamide;
3-acetyl-5-{[5-chloro-4-[(2,4-difluorobenzyl)oxy]-6-oxopyrimidin-1(6H)-yl]methyl}-1-glycoloyl-1,3-dihydro-2H-benzimidazol-2-one;
3-acetyl-5-{[5-chloro-4-[(2,4-difluorobenzyl)oxy]-6-oxopyrimidin-1(6H)-yl]methyl}-1-(2-hydroxy-2-methylpropanoyl)-1,3-dihydro-2H-benzimidazol-2-one;
3-acetyl-5-{[5-chloro-4-[(2,4-difluorobenzyl)oxy]-6-oxopyrimidin-1(6H)-yl]methyl}-1-(N-methylglycyl)-1,3-dihydro-2H-benzimidazol-2-one;
3-acetyl-5-{[5-chloro-4-[(2,4-difluorobenzyl)oxy]-6-oxopyrimidin-1(6H)-yl]methyl}-1-(3-hydroxypropanoyl)-1,3-dihydro-2H-benzimidazol-2-one;
3-[4-(benzyloxy)-5-bromo-6-oxopyrimidin-1(6H)-yl]propanamide;
3-[4-(benzyloxy)-5-bromo-6-oxopyrimidin-1(6H)-yl]propanoic acid;
3-[4-[(2,4-difluorobenzyl)oxy]-2-methyl-6-oxopyrimidin-1(6H)-yl]-4-methylbenzoic acid;
3-[4-[(2,4-difluorobenzyl)oxy]-2-methyl-6-oxopyrimidin-1(6H)-yl]benzaldehyde;

3-acetyl-5-[5-chloro-4-[(2,4-difluorobenzyl)oxy]-2-methyl-6-oxopyrimidin-1(6H)-yl]-2,3-dihydro-1H-benzimidazole-1-carboxamide;

3-acetyl-5-{[5-chloro-4-[(2,4-difluorobenzyl)oxy]-6-oxopyrimidin-1(6H)-yl]methyl}-2,3-dihydro-1H-benzimidazole-1-carboxamide;

3-{[5-bromo-4-[(2,4-difluorobenzyl)oxy]-2-methyl-6-oxopyrimidin-1(6H)-yl]methyl}benzoic acid;

3-{[4-(benzyloxy)-5-bromo-6-oxopyrimidin-1(6H)-yl]methyl}benzamide;

3-{[5-chloro-4-[(2,4-difluorobenzyl)amino]-2-methyl-6-oxopyrimidin-1(6H)-yl]methyl}benzonitrile;

5-{[5-bromo-4-[(2,4-difluorobenzyl)oxy]-2-methyl-6-oxopyrimidin-1(6H)-yl]methyl}-N,N-dimethylpyrazine-2-carboxamide;

5-{[5-bromo-4-[(2,4-difluorobenzyl)oxy]-2-methyl-6-oxopyrimidin-1(6H)-yl]methyl}-N-(2-hydroxyethyl)-N-methylpyrazine-2-carboxamide;

5-{[5-bromo-4-[(2,4-difluorobenzyl)oxy]-2-methyl-6-oxopyrimidin-1(6H)-yl]methyl}-N-(2,3-dihydroxypropyl)pyrazine-2-carboxamide;

5-{[5-bromo-4-[(2,4-difluorobenzyl)oxy]-2-methyl-6-oxopyrimidin-1(6H)-yl]methyl}-N-methylpyrazine-2-carboxamide;

5-{[5-chloro-4-[(2,4-difluorobenzyl)oxy]-6-oxopyrimidin-1(6H)-yl]methyl}-1,3-dihydro-2H-indol-2-one;

5-{[5-chloro-4-[(2,4-difluorobenzyl)oxy]-6-oxopyrimidin-1(6H)-yl]methyl}indoline-1-carboxamide;

5-{[5-chloro-4-[(2,4-difluorobenzyl)oxy]-6-oxopyrimidin-1(6H)-yl]methyl}-1,3-dihydro-2H-isoindole-2-carboxamide;

5-{[5-chloro-4-[(2,4-difluorobenzyl)oxy]-6-oxopyrimidin-1(6H)-yl]methyl}-3,4-dihydroisoquinoline-2(1H)-carboxamide;

5-{[5-chloro-4-[(2,4-difluorobenzyl)oxy]-6-oxopyrimidin-1(6H)-yl]methyl}-2,3-dihydro-1H-benzimidazole-1-carboxamide;

5-{[5-chloro-4-[(2,4-difluorobenzyl)oxy]-6-oxopyrimidin-1(6H)-yl]methyl}-3-glycoloyl-2,3-dihydro-1H-benzimidazole-1-carboxamide;

5-{[5-chloro-4-[(2,4-difluorobenzyl)oxy]-6-oxopyrimidin-1(6H)-yl]methyl}-3-(2-hydroxy-2-methylpropanoyl)-2,3-dihydro-1H-benzimidazole-1-carboxamide;

5-{[5-chloro-4-[(2,4-difluorobenzyl)oxy]-6-oxopyrimidin-1(6H)-yl]methyl}-3-(N-methylglycyl)-2,3-dihydro-1H-benzimidazole-1-carboxamide;

5-{[3-chloro-4-[(2,4-difluorobenzyl)oxy]-2-oxopyrimidin-1(2H)-yl]methyl}-3-(3-hydroxypropanoyl)-2,3-dihydro-1H-benzimidazole-1-carboxamide;

5-{[5-chloro-4-[(2,4-difluorobenzyl)oxy]-6-oxopyrimidin-1(6H)-yl]methyl}-3-(3-hydroxy-3-methylbutanoyl)-2,3-dihydro-1H-benzimidazole-1-carboxamide;

5-{[5-chloro-4-[(2,4-difluorobenzyl)oxy]-6-oxopyrimidin-1(6H)-yl]methyl}-1H-benzimidazole-1,3(2H)-dicarboxamide;

5-{[5-chloro-4-[(2,4-difluorobenzyl)oxy]-6-oxopyrimidin-1(6H)-yl]methyl}-3-(methylsulfonyl)-2,3-dihydro-1H-benzimidazole-1-carboxamide;

5-{[5-chloro-4-[(2,4-difluorobenzyl)oxy]-6-oxopyrimidin-1(6H)-yl]methyl}-1,3-dihydro-2H-benzimidazol-2-one;

5-{[5-chloro-4-[(2,4-difluorobenzyl)oxy]-6-oxopyrimidin-1(6H)-yl]methyl}-1-glycoloyl-1,3-dihydro-2H-benzimidazol-2-one;

5-{[5-chloro-4-[(2,4-difluorobenzyl)oxy]-6-oxopyrimidin-1(6H)-yl]methyl}-1-(2-hydroxy-2-methylpropanoyl)-1,3-dihydro-2H-benzimidazol-2-one;

5-{[5-chloro-4-[(2,4-difluorobenzyl)oxy]-6-oxopyrimidin-1(6H)-yl]methyl}-1-(N-methylglycyl)-1,3-dihydro-2H-benzimidazol-2-one;

5-{[5-chloro-4-[(2,4-difluorobenzyl)oxy]-6-oxopyrimidin-1(6H)-yl]methyl}-1-(3-hydroxypropanoyl)-1,3-dihydro-2H-benzimidazol-2-one;

5-{[5-chloro-4-[(2,4-difluorobenzyl)oxy]-6-oxopyrimidin-1(6H)-yl]methyl}-1-(3-hydroxy-3-methylbutanoyl)-1,3-dihydro-2H-benzimidazol-2-one;

5-{[5-chloro-4-[(2,4-difluorobenzyl)oxy]-6-oxopyrimidin-1(6H)-yl]methyl}-2-oxo-2,3-dihydro-1H-benzimidazole-1-carboxamide;

5-{[5-chloro-4-[(2,4-difluorobenzyl)oxy]-6-oxopyrimidin-1(6H)-yl]methyl}-1-(methylsulfonyl)-1,3-dihydro-2H-benzimidazol-2-one;

5-{[5-chloro-4-[(2,4-difluorobenzyl)oxy]-6-oxopyrimidin-1(6H)-yl]methyl}-1,3-diglycoloyl-1,3-dihydro-2H-benzimidazol-2-one;

5-{[5-chloro-4-[(2,4-difluorobenzyl)oxy]-6-oxopyrimidin-1(6H)-yl]methyl}-3-glycoloyl-1-(2-hydroxy-2-methylpropanoyl)-1,3-dihydro-2H-benzimidazol-2-one;

5-{[5-chloro-4-[(2,4-difluorobenzyl)oxy]-6-oxopyrimidin-1(6H)-yl]methyl}-3-glycoloyl-1-(N-methylglycyl)-1,3-dihydro-2H-benzimidazol-2-one;

5-{[5-chloro-4-[(2,4-difluorobenzyl)oxy]-6-oxopyrimidin-1(6H)-yl]methyl}-3-glycoloyl-1-(3-hydroxypropanoyl)-1,3-dihydro-2H-benzimidazol-2-one;

5-{[5-chloro-4-[(2,4-difluorobenzyl)oxy]-6-oxopyrimidin-1(6H)-yl]methyl}-3-glycoloyl-1-(3-hydroxy-3-methylbutanoyl)-1,3-dihydro-2H-benzimidazol-2-one;

5-{[5-chloro-4-[(2,4-difluorobenzyl)oxy]-6-oxopyrimidin-1(6H)-yl]methyl}-3-glycoloyl-2-oxo-2,3-dihydro-1H-benzimidazole-1-carboxamide;

5-{[5-chloro-4-[(2,4-difluorobenzyl)oxy]-6-oxopyrimidin-1(6H)-yl]methyl}-3-glycoloyl-1-(methylsulfonyl)-1,3-dihydro-2H-benzimidazol-2-one;

5-{[5-chloro-4-[(2,4-difluorobenzyl)oxy]-6-oxopyrimidin-1(6H)-yl]methyl}-1-glycoloyl-3-(2-hydroxy-2-methylpropanoyl)-1,3-dihydro-2H-benzimidazol-2-one;

5-{[5-chloro-4-[(2,4-difluorobenzyl)oxy]-6-oxopyrimidin-1(6H)-yl]methyl}-1,3-bis(2-hydroxy-2-methylpropanoyl)-1,3-dihydro-2H-benzimidazol-2-one;

5-{[5-chloro-4-[(2,4-difluorobenzyl)oxy]-6-oxopyrimidin-1(6H)-yl]methyl}-3-(2-hydroxy-2-methylpropanoyl)-1-(N-methylglycyl)-1,3-dihydro-2H-benzimidazol-2-one;

5-{[5-chloro-4-[(2,4-difluorobenzyl)oxy]-6-oxopyrimidin-1(6H)-yl]methyl}-3-(2-hydroxy-2-methylpropanoyl)-1-(3-hydroxypropanoyl)-1,3-dihydro-2H-benzimidazol-2-one;

5-{[5-chloro-4-[(2,4-difluorobenzyl)oxy]-6-oxopyrimidin-1(6H)-yl]methyl}-1-(3-hydroxy-3-methylbutanoyl)-3-(2-hydroxy-2-methylpropanoyl)-1,3-dihydro-2H-benzimidazol-2-one;

5-{[5-chloro-4-[(2,4-difluorobenzyl)oxy]-6-oxopyrimidin-1(6H)-yl]methyl}-3-(2-hydroxy-2-methylpropanoyl)-2-oxo-2,3-dihydro-1H-benzimidazole-1-carboxamide;

5-{[5-chloro-4-[(2,4-difluorobenzyl)oxy]-6-oxopyrimidin-1(6H)-yl]methyl}-3-(2-hydroxy-2-methylpropanoyl)-1-(methylsulfonyl)-1,3-dihydro-2H-benzimidazol-2-one;

5-{[5-chloro-4-[(2,4-difluorobenzyl)oxy]-6-oxopyrimidin-1(6H)-yl]methyl}-1-glycoloyl-3-(N-methylglycyl)-1,3-dihydro-2H-benzimidazol-2-one;

5-{[5-chloro-4-[(2,4-difluorobenzyl)oxy]-6-oxopyrimidin-1(6H)-yl]methyl}-1-(2-hydroxy-2-methylpropanoyl)-3-(N-methylglycyl)-1,3-dihydro-2H-benzimidazol-2-one;

5-{[5-chloro-4-[(2,4-difluorobenzyl)oxy]-6-oxopyrimidin-1(6H)-yl]methyl}-1,3-bis(N-methylglycyl)-1,3-dihydro-2H-benzimidazol-2-one;

5-{[5-chloro-4-[(2,4-difluorobenzyl)oxy]-6-oxopyrimidin-1 (6H)-yl]methyl}-1-(3-hydroxypropanoyl)-3-(N-methylglycyl)-1,3-dihydro-2H-benzimidazol-2-one;

5-{[5-chloro-4-[(2,4-difluorobenzyl)oxy]-6-oxopyrimidin-1 (6H)-yl]methyl}-1-(3-hydroxy-3-methylbutanoyl)-3-(N-methylglycyl)-1,3-dihydro-2H-benzimidazol-2-one;

5-{[5-chloro-4-[(2,4-difluorobenzyl)oxy]-6-oxopyrimidin-1 (6H)-yl]methyl}-3-(N-methylglycyl)-2-oxo-2,3-dihydro-1H-benzimidazole-1-carboxamide;

5-{[5-chloro-4-[(2,4-difluorobenzyl)oxy]-6-oxopyrimidin-1 (6H)-yl]methyl}-3-(N-methylglycyl)-1-(methylsulfonyl)-1,3-dihydro-2H-benzimidazol-2-one;

5-{[5-chloro-4-[(2,4-difluorobenzyl)oxy]-6-oxopyrimidin-1 (6H)-yl]methyl}-1-glycoloyl-3-(3-hydroxypropanoyl)-1,3-dihydro-2H-benzimidazol-2-one;

5-{[5-chloro-4-[(2,4-difluorobenzyl)oxy]-6-oxopyrimidin-1 (6H)-yl]methyl}-1-(2-hydroxy-2-methylpropanoyl)-3-(3-hydroxypropanoyl)-1,3-dihydro-2H-benzimidazol-2-one;

5-{[5-chloro-4-[(2,4-difluorobenzyl)oxy]-6-oxopyrimidin-1 (6H)-yl]methyl}-3-(3-hydroxypropanoyl)-1-(N-methylglycyl)-1,3-dihydro-2H-benzimidazol-2-one;

5-{[5-chloro-4-[(2,4-difluorobenzyl)oxy]-6-oxopyrimidin-1 (6H)-yl]methyl}-1,3-bis(3-hydroxypropanoyl)-1,3-dihydro-2H-benzimidazol-2-one;

5-{[5-chloro-4-[(2,4-difluorobenzyl)oxy]-6-oxopyrimidin-1 (6H)-yl]methyl}-1-(3-hydroxy-3-methylbutanoyl)-3-(3-hydroxypropanoyl)-1,3-dihydro-2H-benzimidazol-2-one;

5-{[5-chloro-4-[(2,4-difluorobenzyl)oxy]-6-oxopyrimidin-1 (6H)-yl]methyl}-3-(3-hydroxypropanoyl)-2-oxo-2,3-dihydro-1H-benzimidazole-1-carboxamide;

5-{[5-chloro-4-[(2,4-difluorobenzyl)oxy]-6-oxopyrimidin-1 (6H)-yl]methyl}-3-(3-hydroxypropanoyl)-1-(methylsulfonyl)-1,3-dihydro-2H-benzimidazol-2-one;

5-{[5-chloro-4-[(2,4-difluorobenzyl)oxy]-6-oxopyrimidin-1 (6H)-yl]methyl}-1-glycoloyl-3-(3-hydroxy-3-methylbutanoyl)-1,3-dihydro-2H-benzimidazol-2-one;

5-{[5-chloro-4-[(2,4-difluorobenzyl)oxy]-6-oxopyrimidin-1 (6H)-yl]methyl}-3-(3-hydroxy-3-methylbutanoyl)-1-(2-hydroxy-2-methylpropanoyl)-1,3-dihydro-2H-benzimidazol-2-one;

5-{[5-chloro-4-[(2,4-difluorobenzyl)oxy]-6-oxopyrimidin-1 (6H)-yl]methyl}-3-(3-hydroxy-3-methylbutanoyl)-1-(N-methylglycyl)-1,3-dihydro-2H-benzimidazol-2-one;

5-{[5-chloro-4-[(2,4-difluorobenzyl)oxy]-6-oxopyrimidin-1 (6H)-yl]methyl}-3-(3-hydroxy-3-methylbutanoyl)-1-(3-hydroxypropanoyl)-1,3-dihydro-2H-benzimidazol-2-one;

5-{[5-chloro-4-[(2,4-difluorobenzyl)oxy]-6-oxopyrimidin-1 (6H)-yl]methyl}-1,3-bis(3-hydroxy-3-methylbutanoyl)-1,3-dihydro-2H-benzimidazol-2-one;

5-{[5-chloro-4-[(2,4-difluorobenzyl)oxy]-6-oxopyrimidin-1 (6H)-yl]methyl}-3-(3-hydroxy-3-methylbutanoyl)-2-oxo-2,3-dihydro-1H-benzimidazole-1-carboxamide;

5-{[5-chloro-4-[(2,4-difluorobenzyl)oxy]-6-oxopyrimidin-1 (6H)-yl]methyl}-3-(3-hydroxy-3-methylbutanoyl)-1-(methylsulfonyl)-1,3-dihydro-2H-benzimidazol-2-one;

5-{[5-chloro-4-[(2,4-difluorobenzyl)oxy]-6-oxopyrimidin-1 (6H)-yl]methyl}-2-oxo-1H-benzimidazole-1,3(2H)-dicarboxamide;

5-{[5-chloro-4-[(2,4-difluorobenzyl)oxy]-6-oxopyrimidin-1 (6H)-yl]methyl}-1-glycoloyl-3-(methylsulfonyl)-1,3-dihydro-2H-benzimidazol-2-one;

5-{[5-chloro-4-[(2,4-difluorobenzyl)oxy]-6-oxopyrimidin-1 (6H)-yl]methyl}-1-(2-hydroxy-2-methylpropanoyl)-3-(methylsulfonyl)-1,3-dihydro-2H-benzimidazol-2-one;

5-{[5-chloro-4-[(2,4-difluorobenzyl)oxy]-6-oxopyrimidin-1 (6H)-yl]methyl}-1-(N-methylglycyl)-3-(methylsulfonyl)-1,3-dihydro-2H-benzimidazol-2-one;

5-{[5-chloro-4-[(2,4-difluorobenzyl)oxy]-6-oxopyrimidin-1 (6H)-yl]methyl}-1-(3-hydroxypropanoyl)-3-(methylsulfonyl)-1,3-dihydro-2H-benzimidazol-2-one;

5-{[5-chloro-4-[(2,4-difluorobenzyl)oxy]-6-oxopyrimidin-1 (6H)-yl]methyl}-1-(3-hydroxy-3-methylbutanoyl)-3-(methylsulfonyl)-1,3-dihydro-2H-benzimidazol-2-one;

5-{[5-chloro-4-[(2,4-difluorobenzyl)oxy]-6-oxopyrimidin-1 (6H)-yl]methyl}-3-(methylsulfonyl)-2-oxo-2,3-dihydro-1H-benzimidazole-1-carboxamide;

5-{[5-chloro-4-[(2,4-difluorobenzyl)oxy]-6-oxopyrimidin-1 (6H)-yl]methyl}-1,3-bis(methylsulfonyl)-1,3-dihydro-2H-benzimidazol-2-one;

4-chloro-3-[5-chloro-4-[(2,4-difluorobenzyl)oxy]-2-methyl-6-oxopyrimidin-1(6H)-yl]-N-methylbenzamide;

5-[5-chloro-4-[(2,4-difluorobenzyl)oxy]-2-methyl-6-oxopyrimidin-1(6H)-yl]indoline-1-carboxamide;

5-[5-chloro-4-[(2,4-difluorobenzyl)oxy]-2-methyl-6-oxopyrimidin-1(6H)-yl]-1H-indole-1-carboxamide;

5-[5-chloro-4-[(2,4-difluorobenzyl)oxy]-2-methyl-6-oxopyrimidin-1(6H)-yl]-1,3-dihydro-2H-isoindole-2-carboxamide;

5-[5-chloro-4-[(2,4-difluorobenzyl)oxy]-2-methyl-6-oxopyrimidin-1(6H)-yl]-1H-benzimidazole-1-carboxamide;

5-[5-chloro-4-[(2,4-difluorobenzyl)oxy]-2-methyl-6-oxopyrimidin-1(6H)-yl]-3-glycoloyl-2,3-dihydro-1H-benzimidazole-1-carboxamide;

5-[5-chloro-4-[(2,4-difluorobenzyl)oxy]-2-methyl-6-oxopyrimidin-1(6H)-yl]-3-(2-hydroxy-2-methylpropanoyl)-2,3-dihydro-1H-benzimidazole-1-carboxamide;

5-[5-chloro-4-[(2,4-difluorobenzyl)oxy]-2-methyl-6-oxopyrimidin-1(6H)-yl]-3-(N-methylglycyl)-2,3-dihydro-1H-benzimidazole-1-carboxamide;

5-[5-chloro-4-[(2,4-difluorobenzyl)oxy]-2-methyl-6-oxopyrimidin-1(6H)-yl]-3-(3-hydroxypropanoyl)-2,3-dihydro-1H-benzimidazole-1-carboxamide;

5-[5-chloro-4-[(2,4-difluorobenzyl)oxy]-2-methyl-6-oxopyrimidin-1(6H)-yl]-3-(3-hydroxy-3-methylbutanoyl)-2,3-dihydro-1H-benzimidazole-1-carboxamide;

5-[5-chloro-4-[(2,4-difluorobenzyl)oxy]-2-methyl-6-oxopyrimidin-1(6H)-yl]-1H-benzimidazole-1,3(2H)-dicarboxamide;

5-[5-chloro-4-[(2,4-difluorobenzyl)oxy]-2-methyl-6-oxopyrimidin-1(6H)-yl]-3-(methylsulfonyl)-2,3-dihydro-1H-benzimidazole-1-carboxamide;

5-{[4-(benzyloxy)-6-oxopyrimidin-1(6H)-yl]methyl}-5-methylimidazolidine-2,4-dione;

5-bromo-6-[(2,4-difluorobenzyl)oxy]-3-(2,6-difluorophenyl)-2-[2-(2,4-difluorophenyl)ethyl]-4-oxo-3,4-dihydropyrimidine-1(2H)-carbaldehyde;

5-bromo-6-[(2,4-difluorobenzyl)oxy]-3-(2,6-difluorophenyl)-2-methyl-4-oxo-3,4-dihydropyrimidine-1(2H)-carbaldehyde;

5-bromo-6-[(2,4-difluorobenzyl)oxy]-3-(2,6-difluorophenyl)-2-methyl-4-oxo-3,4-dihydropyrimidine-1(2H)-carbaldehyde oxime;

5-bromo-6-[(2,4-difluorobenzyl)oxy]-3-(2,6-difluorophenyl)-2-methyl-4-oxo-3,4-dihydropyrimidine-1(2H)-carbonitrile;

5-bromo-4-[(2,4-difluorobenzyl)oxy]-1-(2,6-difluorophenyl)-6-oxo-1,6-dihydropyrimidine-2-carbaldehyde;

5-bromo-4-[(2,4-difluorobenzyl)oxy]-1-(2,6-difluorophenyl)-6-oxo-1,6-dihydropyrimidine-2-carboxylic acid;

5-chloro-3-(2,6-dichlorobenzyl)-N-(2,4-difluorophenyl)-4-oxo-3,4-dihydropyrimidine-1(2H)-carboxamide;

5-chloro-3-(2,6-dichlorobenzyl)-N-methyl-4-oxo-N-phenyl-3,4-dihydropyrimidine-1(2H)-carboxamide;

N-benzyl-5-chloro-3-(2,6-dichlorobenzyl)-4-oxo-3,4-dihydropyrimidine-1(2H)-carboxamide;

6-{[5-chloro-4-[(2,4-difluorobenzyl)oxy]-6-oxopyrimidin-1(6H)-yl]methyl}-3-glycoloyl-2-oxo-2,3-dihydro-1H-benzimidazole-1-carboxamide;

6-{[5-chloro-4-[(2,4-difluorobenzyl)oxy]-6-oxopyrimidin-1(6H)-yl]methyl}-3-(2-hydroxy-2-methylpropanoyl)-2-oxo-2,3-dihydro-1H-benzimidazole-1-carboxamide;

6-{[5-chloro-4-[(2,4-difluorobenzyl)oxy]-6-oxopyrimidin-1(6H)-yl]methyl}-3-(N-methylglycyl)-2-oxo-2,3-dihydro-1H-benzimidazole-1-carboxamide;

6-{[5-chloro-4-[(2,4-difluorobenzyl)oxy]-6-oxopyrimidin-1(6H)-yl]methyl}-3-(3-hydroxypropanoyl)-2-oxo-2,3-dihydro-1H-benzimidazole-1-carboxamide;

6-{[5-chloro-4-[(2,4-difluorobenzyl)oxy]-6-oxopyrimidin-1(6H)-yl]methyl}-3-(3-hydroxy-3-methylbutanoyl)-2-oxo-2,3-dihydro-1H-benzimidazole-1-carboxamide;

6-{[5-chloro-4-[(2,4-difluorobenzyl)oxy]-6-oxopyrimidin-1(6H)-yl]methyl}-3-(methylsulfonyl)-2-oxo-2,3-dihydro-1H-benzimidazole-1-carboxamide;

6-{[5-chloro-4-[(2,4-difluorobenzyl)oxy]-6-oxopyrimidin-1(6H)-yl]methyl}-1-(methylsulfonyl)-1,3-dihydro-2H-benzimidazol-2-one;

6-oxo-2-pyridin-3-yl-1,6-dihydropyrimidine-5-carbonitrile;

6-oxo-2-pyridin-3-yl-1,6-dihydropyrimidine-5-carboxylic acid;

7-[5-chloro-4-[(2,4-difluorobenzyl)oxy]-2-methyl-6-oxopyrimidin-1(6H)-yl]-3,4-dihydroisoquinoline-2(1H)-carboxamide;

benzyl (5-nitro-2,6-dioxo-3,6-dihydropyrimidin-1(2H)-yl)acetate;

benzyl N-[(benzyloxy)carbonyl]-3-[4-(benzyloxy)-6-oxopyrimidin-1(6H)-yl]alaninate;

benzyl N-acetyl-3-[4-(benzyloxy)-6-oxopyrimidin-1(6H)-yl]alaninate;

ethyl [4-(benzyloxy)-6-oxopyrimidin-1(6H)-yl]acetate;

ethyl [4-(benzyloxy)-5-bromo-6-oxopyrimidin-1(6H)-yl]acetate;

ethyl 3-[5-bromo-4-[(2,4-difluorobenzyl)oxy]-2-methyl-6-oxopyrimidin-1(6H)-yl]benzoate;

ethyl 3-[4-(benzyloxy)-5-bromo-6-oxopyrimidin-1(6H)yl]propanoate;

ethyl 6-[5-bromo-4-[(2,4-difluorobenzyl)oxy]-2-methyl-6-oxopyrimidin-1(6H)-yl]nicotinate;

N-(3-aminopropyl)-4-{[5-bromo-4-[(2,4-difluorobenzyl)oxy]-2-methyl-6-oxopyrimidin-1(6H)-yl]methyl}benzamide hydrochloride;

N-[3-(2,6-dichlorobenzyl)-4-oxo-5-(trifluoromethyl)-3,4-dihydropyrimidin-1(2H)-yl]-4-isopropoxybenzamide;

N-[5-bromo-1-(3-fluorobenzyl)-6-oxo-1,6-dihydropyrimidin-4-yl]-1-phenylmethanesulfonamide;

N-[5-bromo-1-(3-fluorobenzyl)-6-oxo-1,6-dihydropyrimidin-4-yl]-2,4-difluorobenzamide;

N-[5-bromo-1-(3-fluorobenzyl)-6-oxo-1,6-dihydropyrimidin-4-yl]-2,5-difluorobenzamide;

N-[5-bromo-1-(3-fluorobenzyl)-6-oxo-1,6-dihydropyrimidin-4-yl]-2,6-difluorobenzamide;

N-[5-bromo-1-(3-fluorobenzyl)-6-oxo-1,6-dihydropyrimidin-4-yl]-4-fluorobenzamide;

N-[5-bromo-1-(3-fluorobenzyl)-6-oxo-1,6-dihydropyrimidin-4-yl]benzenesulfonamide;

N-[5-bromo-1-(3-fluorobenzyl)-6-oxo-1,6-dihydropyrimidin-4-yl]-N'-(2,4-difluorophenyl)urea;

N-[1-acetyl-3-(4-chlorobenzyl)-2-methyl-4-oxo-1,2,3,4-tetrahydropyrimidin-5-yl]-4-chlorobenzamide;

N'-{[(3-benzyl-4-oxo-3,4-dihydropyrimidin-1(2H)-yl)carbonyl]oxy}pyridine-4-carboximidamide;

N-(3-{[5-bromo-4-[(2,4-difluorobenzyl)oxy]-2-methyl-6-oxopyrimidin-1(6H)-yl]methyl}benzyl)acetamide;

5-chloro-3-(2,6-dichlorobenzyl)-4-oxo-N-[3-(trifluoromethyl)phenyl]-3,4-dihydropyrimidine-1(2H)-carboxamide;

6-[5-chloro-4-[(2,4-difluorobenzyl)oxy]-2-methyl-6-oxopyrimidin-1(6H)-yl]-3,4-dihydroisoquinoline-2(1H)-carboxamide;

6-[5-chloro-4-[(2,4-difluorobenzyl)oxy]-2-methyl-6-oxopyrimidin-1(6H)-yl]-3-glycoloyl-2,3-dihydro-1H-benzimidazole-1-carboxamide;

6-[5-chloro-4-[(2,4-difluorobenzyl)oxy]-2-methyl-6-oxopyrimidin-1(6H)-yl]-3-(2-hydroxy-2-methylpropanoyl)-2,3-dihydro-1H-benzimidazole-1-carboxamide;

6-[5-chloro-4-[(2,4-difluorobenzyl)oxy]-2-methyl-6-oxopyrimidin-1(6H)-yl]-3-(N-methylglycyl)-2,3-dihydro-1H-benzimidazole-1-carboxamide;

6-[5-chloro-4-[(2,4-difluorobenzyl)oxy]-2-methyl-6-oxopyrimidin-1(6H)-yl]-3-(3-hydroxypropanoyl)-2,3-dihydro-1H-benzimidazole-1-carboxamide;

6-[5-chloro-4-[(2,4-difluorobenzyl)oxy]-2-methyl-6-oxopyrimidin-1(6H)-yl]-3-(3-hydroxy-3-methylbutanoyl)-2,3-dihydro-1H-benzimidazole-1-carboxamide;

6-[5-chloro-4-[(2,4-difluorobenzyl)oxy]-2-methyl-6-oxopyrimidin-1(6H)-yl]-3-(methylsulfonyl)-2,3-dihydro-1H-benzimidazole-1-carboxamide;

6-{[5-chloro-4-[(2,4-difluorobenzyl)oxy]-6-oxopyrimidin-1(6H)-yl]methyl}-3,4-dihydroisoquinoline-2(1H)-carboxamide;

6-{[5-chloro-4-[(2,4-difluorobenzyl)oxy]-6-oxopyrimidin-1(6H)-yl]methyl}-2,3-dihydro-1H-benzimidazole-1-carboxamide;

6-{[5-chloro-4-[(2,4-difluorobenzyl)oxy]-6-oxopyrimidin-1(6H)-yl]methyl}-3-glycoloyl-2,3-dihydro-1H-benzimidazole-1-carboxamide;

6-{[5-chloro-4-[(2,4-difluorobenzyl)oxy]-6-oxopyrimidin-1(6H)-yl]methyl}-3-(2-hydroxy-2-methylpropanoyl)-2,3-dihydro-1H-benzimidazole-1-carboxamide;

6-{[5-chloro-4-[(2,4-difluorobenzyl)oxy]-6-oxopyrimidin-1(6H)-yl]methyl}-3-(N-methylglycyl)-2,3-dihydro-1H-benzimidazole-1-carboxamide;

6-{[5-chloro-4-[(2,4-difluorobenzyl)oxy]-6-oxopyrimidin-1(6H)-yl]methyl}-3-(3-hydroxypropanoyl)-2,3-dihydro-1H-benzimidazole-1-carboxamide;

6-{[5-chloro-4-[(2,4-difluorobenzyl)oxy]-6-oxopyrimidin-1(6H)-yl]methyl}-3-(3-hydroxy-3-methylbutanoyl)-2,3-dihydro-1H-benzimidazole-1-carboxamide;

6-{[5-chloro-4-[(2,4-difluorobenzyl)oxy]-6-oxopyrimidin-1(6H)-yl]methyl}-3-(methylsulfonyl)-2,3-dihydro-1H-benzimidazole-1-carboxamide;

6-{[5-chloro-4-[(2,4-difluorobenzyl)oxy]-6-oxopyrimidin-1(6H)-yl]methyl}-1-glycoloyl-1,3-dihydro-2H-benzimidazol-2-one;

6-{[5-chloro-4-[(2,4-difluorobenzyl)oxy]-6-oxopyrimidin-1(6H)-yl]methyl}-1-(2-hydroxy-2-methylpropanoyl)-1,3-dihydro-2H-benzimidazol-2-one;

6-{[5-chloro-4-[(2,4-difluorobenzyl)oxy]-6-oxopyrimidin-1(6H)-yl]methyl}-1-(N-methylglycyl)-1,3-dihydro-2H-benzimidazol-2-one;

6-{[5-chloro-4-[(2,4-difluorobenzyl)oxy]-6-oxopyrimidin-1(6H)-yl]methyl}-1-(3-hydroxypropanoyl)-1,3-dihydro-2H-benzimidazol-2-one;

6-{[5-chloro-4-[(2,4-difluorobenzyl)oxy]-6-oxopyrimidin-1(6H)-yl]methyl}-1-(3-hydroxy-3-methylbutanoyl)-1,3-dihydro-2H-benzimidazol-2-one;

6-{[5-chloro-4-[(2,4-difluorobenzyl)oxy]-6-oxopyrimidin-1(6H)-yl]methyl}-2-oxo-2,3-dihydro-1H-benzimidazole-1-carboxamide;

N-(3-{[5-bromo-4-[(2,4-difluorobenzyl)oxy]-2-methyl-6-oxopyrimidin-1(6H)-yl]methyl}benzyl)methanesulfonamide;

N-(3-{[5-bromo-4-[(2,4-difluorobenzyl)oxy]-2-methyl-6-oxopyrimidin-1(6H)-yl]methyl}benzyl)-2-hydroxyacetamide;

N'-{3-[5-bromo-4-[(2,4-difluorobenzyl)oxy]-2-methyl-6-oxopyrimidin-1(6H)-yl]benzyl}-N,N-dimethylurea;

N-{3-[5-bromo-4-[(2,4-difluorobenzyl)oxy]-2-methyl-6-oxopyrimidin-1(6H)-yl]benzyl}methanesulfonamide;

N-{3-[5-bromo-4-[(2,4-difluorobenzyl)oxy]-2-methyl-6-oxopyrimidin-1(6H)-yl]benzyl}acetamide;

N-{3-[5-bromo-4-[(2,4-difluorobenzyl)oxy]-2-methyl-6-oxopyrimidin-1(6H)-yl]benzyl}urea;

N-(2-aminoethyl)-4-{[5-bromo-4-[(2,4-difluorobenzyl)oxy]-2-methyl-6-oxopyrimidin-1(6H)-yl]methyl}benzamide hydrochloride;

N-(3-aminopropyl)-3-[5-bromo-4-[(2,4-difluorobenzyl)oxy]-2-methyl-6-oxopyrimidin-1(6H)-yl]benzamide hydrochloride;

N-(3-aminopropyl)-3-[4-(benzyloxy)-5-bromo-6-oxopyrimidin-1(6H)-yl]propanamide hydrochloride;

N-(3-aminopropyl)-3-{[5-bromo-4-[(2,4-difluorobenzyl)oxy]-2-methyl-6-oxopyrimidin-1(6H)-yl]methyl}benzamide hydrochloride;

N-(3-aminopropyl)-4-[5-bromo-4-[(2,4-difluorobenzyl)oxy]-2-methyl-6-oxopyrimidin-1(6H)-yl]benzamide hydrochloride;

N-{3-[5-bromo-4-[(2,4-difluorobenzyl)oxy]-2-methyl-6-oxopyrimidin-1(6H)-yl]benzyl}-2-methoxyacetamide;

N-{3-[5-bromo-4-[(2,4-difluorobenzyl)oxy]-2-methyl-6-oxopyrimidin-1(6H)-yl]benzyl}-2-hydroxyacetamide;

N-{3-[5-bromo-4-[(2,4-difluorobenzyl)oxy]-2-methyl-6-oxopyrimidin-1(6H)-yl]benzyl}-N'-methylurea;

N-{3-[5-bromo-4-[(2,4-difluorobenzyl)oxy]-2-methyl-6-oxopyrimidin-1(6H)-yl]benzyl}morpholine-4-carboxamide;

N-(4-{[5-chloro-4-[(2,4-difluorobenzyl)oxy]-2-methyl-6-oxopyrimidin-1(6H)-yl]methyl}phenyl)-2-hydroxyacetamide;

N-(4-{[5-chloro-4-[(2,4-difluorobenzyl)oxy]-2-methyl-6-oxopyrimidin-1(6H)-yl]methyl}phenyl)acetamide;

N$^1$-{3-[5-bromo-4-[(2,4-difluorobenzyl)oxy]-2-methyl-6-oxopyrimidin-1(6H)-yl]benzyl}glycinamide hydrochloride;

N-allyl-2-[(3-benzyl-4-oxo-3,4-dihydropyrimidin-1(2H)-yl)carbonyl]hydrazinecarbothioamide;

tert-butyl 3-{[4-(benzyloxy)-6-oxopyrimidin-1(6H)-yl]methyl}piperidine-1-carboxylate;

tert-butyl 3-{[4-(benzyloxy)-5-bromo-6-oxopyrimidin-1(6H)-yl]methyl}piperidine-1-carboxylate;

tert-butyl 4-[5-bromo-1-(3-fluorobenzyl)-6-oxo-1,6-dihydropyrimidin-4-yl]piperazine-1-carboxylate;

tert-butyl 4-[(benzyloxy)-5-bromo-6-oxopyrimidin-1(6H)-yl]piperidine-1-carboxylate;

tert-butyl 4-{[4-(benzyloxy)-5-bromo-6-oxopyrimidin-1(6H)-yl]methyl}piperidine-1-carboxylate;

ethyl 5-{[5-bromo-4-[(2,4-difluorobenzyl)oxy]-2-methyl-6-oxopyrimidin-1(6H)-yl]methyl}pyrazine-2-carboxylate;

ethyl 5-{[5-chloro-4-[(2,4-difluorobenzyl)oxy]-2-methyl-6-oxopyrimidin-1(6H)-yl]methyl}pyrazine-2-carboxylate;

ethyl N-(5-{[5-bromo-4-[(2,4-difluorobenzyl)oxy]-2-methyl-6-oxopyrimidin-1(6H)-yl]methyl}-2-methylpyrimidin-4-yl)glycinate trifluoroacetate;

methyl N-acetyl-3-[4-(benzyloxy)-6-oxopyrimidin-1(6H)-yl]alaninate;

N-(2-aminoethyl)-3-[5-bromo-4-[(2,4-difluorobenzyl)oxy]-2-methyl-6-oxopyrimidin-1(6H)-yl]benzamide hydrochloride;

N-(2-aminoethyl)-3-[4-(benzyloxy)-5-bromo-6-oxopyrimidin-1(6H)-yl]propanamide hydrochloride;

N-(2-aminoethyl)-3-{[5-bromo-4-[(2,4-difluorobenzyl)oxy]-2-methyl-6-oxopyrimidin-1(6H)-yl]methyl}benzamide hydrochloride;

N-(2-aminoethyl)-4-[5-bromo-4-[(2,4-difluorobenzyl)oxy]-2-methyl-6-oxopyrimidin-1(6H)-yl]benzamide hydrochloride;

methyl 4-{[5-bromo-1-(3-fluorobenzyl)-6-oxo-1,6-dihydropyrimidin-4-yl]amino}benzoate;

methyl 4-{[4-(benzyloxy)-6-oxopyrimidin-1(6H)-yl]methyl}benzoate;

methyl 3-[5-chloro-4-[(2,4-difluorobenzyl)oxy]-2-methyl-6-oxopyrimidin-1(6H)-yl]-4-methylbenzoate;

methyl 3-[5-chloro-4-[(2,4-difluorobenzyl)oxy]-2-methyl-6-oxopyrimidin-1(6H)-yl]-4-fluorobenzoate;

methyl 3-[4-(benzyloxy)-5-bromo-6-oxopyrimidin-1(6H)-yl]propanoate;

methyl 3-{[5-bromo-4-[(2,4-difluorobenzyl)oxy]-6-oxopyrimidin-1(6H)-yl]methyl}benzoate;

methyl 5-bromo-4-[(2,4-difluorobenzyl)oxy]-2-methyl-6-oxopyrimidine-1(6H)-carboxylate;

methyl 3-chloro-4-[(2,4-difluorobenzyl)oxy]-2-methyl-6-oxopyrimidin-1(6H)-yl]benzoate;

methyl 4-[5-bromo-4-[(2,4-difluorobenzyl)oxy]-2-methyl-6-oxopyrimidin-1(6H)-yl]-3-chlorobenzoate;

methyl 4-[5-bromo-4-[(2,4-difluorobenzyl)oxy]-2-methyl-6-oxopyrimidin-1(6H)-yl]benzoate;

methyl {3-[5-bromo-4-[(2,4-difluorobenzyl)oxy]-2-methyl-6-oxopyrimidin-1(6H)-yl]benzyl}carbamate;

methyl 3-[5-bromo-4-[(2,4-difluorobenzyl)oxy]-2-methyl-6-oxopyrimidin-1(6H)-yl]benzoate;

methyl 3-[5-bromo-4-[(2,4-difluorobenzyl)oxy]-2-methyl-6-oxopyrimidin-1(6H)-yl]-4-methylbenzoate;

methyl 4-[5-chloro-4-[(2,4-difluorobenzyl)oxy]-6-oxopyrimidin-1(6H)-yl]benzoate;

methyl (2E)-4-[4-[(2,4-difluorobenzyl)oxy]-2-methyl-6-oxopyrimidin-1(6H)-yl]but-2-enoate;

methyl [2-({[5-bromo-1-(2,6-difluorophenyl)-2-methyl-6-oxo-1,6-dihydropyrimidin-4-yl]oxy}methyl)-3,5-difluorobenzyl]carbamate; or methyl 2-{[5-bromo-4-[(4-fluorobenzyl)oxy]-6-oxopyrimidin-1(6H)-yl]methyl}benzoate.

Further representative compounds of the invention are

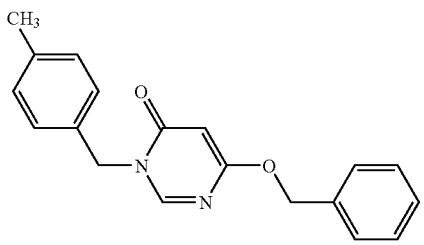

Example 1

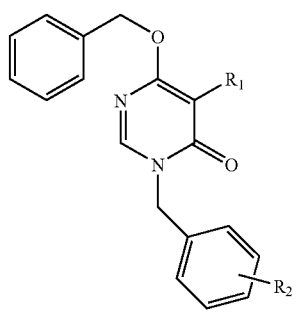

Examples 3-10

| Example No. | R₁ | R₂ |
|---|---|---|
| Ex. 3 | —H | 4-Br |
| Ex. 4 | —Br | 4-Br |
| Ex. 5 | —H | 4-Cl |
| Ex. 6 | —Br | 4-Cl |
| Ex. 7 | —H | 3-F |
| Ex. 8 | —Br | 3-F |
| Ex. 9 | —H | 2-F |
| Ex. 10 | —Br | 2-F |

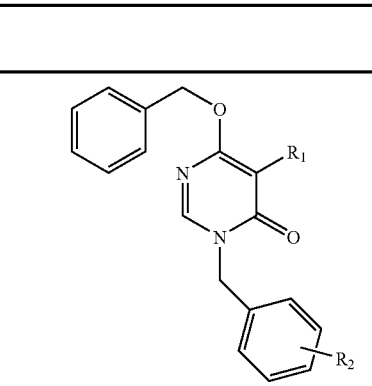

Examples 12-19

| Example No. | R₁ | R₂ |
|---|---|---|
| Ex. 12 | —Br | 4-benzyloxy |
| Ex. 13 | —H | 4-CO₂Me |
| Ex. 14 | —Br | 4-CO₂Me |
| Ex. 15 | —Br | 4-CO₂H |
| Ex. 16 | —H | 4-CN |
| Ex. 17 | —Br | 4-CN |
| Ex. 18 | —H | 4-tButyl |
| Ex. 19 | —Br | 4-tButyl |

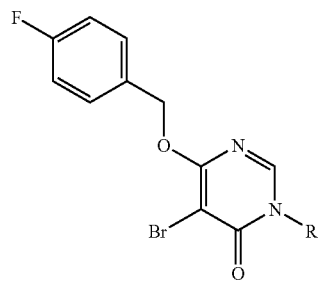

Examples 60-69

| Example No. | R |
|---|---|
| Ex. 60 | pyridin-4-ylmethyl |
| Ex. 61 | pyridin-3-ylmethyl |
| Ex. 62 | 4-tert-butylbenzyl |
| Ex. 63 | 3-trifluoromethylbenzyl |
| Ex. 64 | Biphenyl-2-ylmethyl |
| Ex. 65 | 4-methoxybenzyl |
| Ex. 66 | 4-cyanobenzyl |
| Ex. 67 | 4-trifluoromethylbenzyl |
| Ex. 68 | Biphenyl-4-ylmethyl |
| Ex. 69 | cyclohexylmethyl |

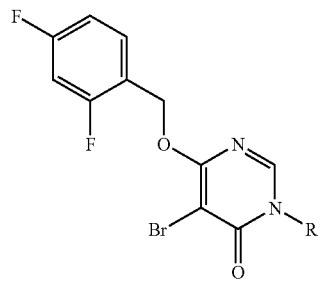

Examples 89-101.

| Example No. | R |
|---|---|
| Ex. 89 | pyridin-3-ylmethyl |
| Ex. 90 | pyridin-4-ylmethyl |
| Ex. 91 | pyridin-2-ylmethyl |
| Ex. 92 | 4-tert-butyl)benzyl |
| Ex. 93 | 3-methoxybenzyl |
| Ex. 94 | Benzo[1,3]dioxol-5-ylmethyl |
| Ex. 95 | 2-fluorobenzyl |

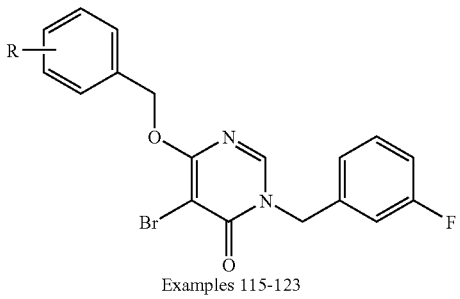

Examples 115-123

| Example No. | R |
|---|---|
| Ex. 115 | 3-methoxy |
| Ex. 116 | 4-tert-butyl |
| Ex. 117 | 3-methyl |
| Ex. 118 | 4-trifluoromethyl |
| Ex. 119 | 4-cyano |
| Ex. 120 | 2-methyl |
| Ex. 121 | 2-phenyl |
| Ex. 122 | 4-methoxy |
| Ex. 123 | 2-CO$_2$CH$_3$ |

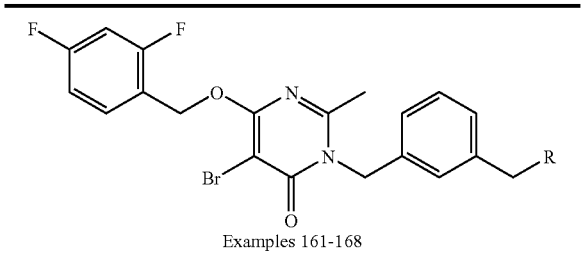

Examples 161-168

| Example No. | R |
|---|---|
| Ex. 161 | —NH$_2$ |
| Ex. 162 | morpholin-4-yl |
| Ex. 163 | dimethylamino |
| Ex. 164 | isopropylamino |
| Ex. 165 | piperidin-1-yl |
| Ex. 166 | (2-hydroxyethyl)amino |
| Ex. 167 | bis(2-hydroxyethyl)amino |
| Ex. 168 | piperazin-1-yl |

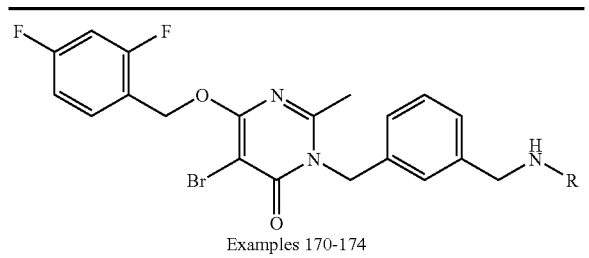

Examples 170-174

| Example No. | R |
|---|---|
| Ex. 170 | —C(O)CH$_3$ |
| Ex. 171 | —C(O)OCH$_3$ |
| Ex. 172 | —SO$_2$CH$_3$ |
| Ex. 173 | —C(O)CH$_2$OH |
| Ex. 174 | —C(O)NH$_2$ |

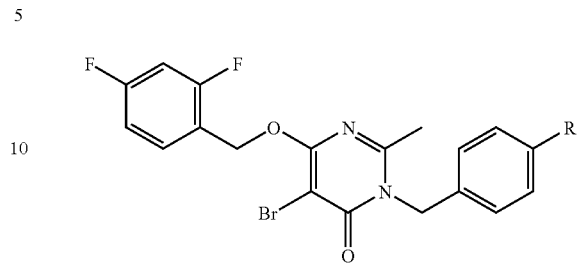

Examples 175-185

| Example No. | R |
|---|---|
| Ex. 175 | —CH$_2$NHCH(CH$_3$)$_2$ |
| Ex. 176 | morpholin-4-ylmethyl |
| Ex. 177 | —CH$_2$N(CH$_3$)$_2$ |
| Ex. 178 | piperidin-1-ylmethyl |
| Ex. 179 | [bis(2-hydroxyethyl)amino]methyl |
| Ex. 180 | —CH$_2$NHCH$_2$CH$_2$OH |
| Ex. 181 | piperazin-1-ylmethyl |
| Ex. 182 | —CH$_2$NHC(O)OCH$_3$ |
| Ex. 183 | —CH$_2$NHC(O)CH$_3$ |
| Ex. 184 | —CH$_2$NHSO$_2$CH$_3$ |
| Ex. 185 | —CH$_2$NHC(O)NH$_2$ |

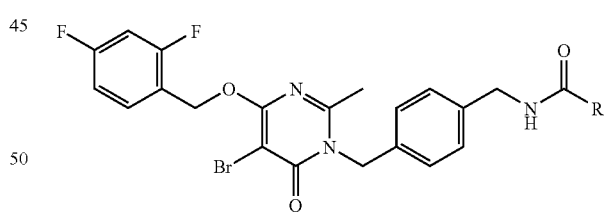

Examples 188-193

| Compound No. | R |
|---|---|
| Ex. 188 | CH$_2$OCOCH$_3$ |
| Ex. 189 | C(CH$_3$)$_2$OH |
| Ex. 190 | C(—CH$_2$CH$_2$—)OH |
| Ex. 191 | CH$_2$NH$_2$ |
| Ex. 192 | CH$_2$OH |
| Ex. 193 | CH$_2$NHCOCH$_3$ |

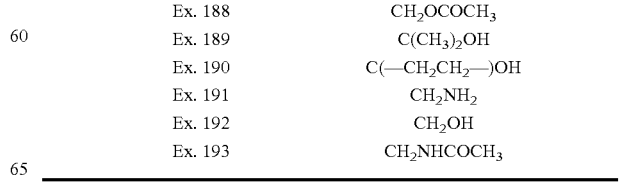

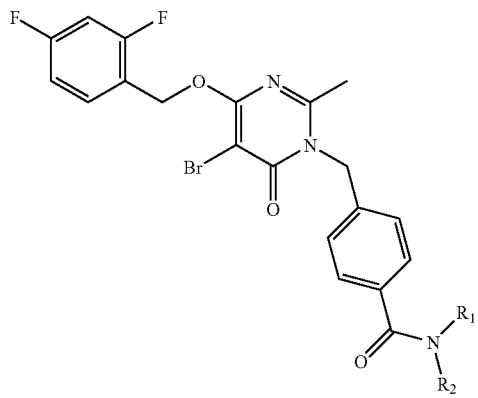

Example 216-231
5-bromo-6-(2,4-difluorobenzyloxy)-2-methyl-3-[4-(aminocarbonyl)-benzyl]pyrimidin-4(3H)-ones

| Compound No. | $R_1$ | $R_2$ |
| --- | --- | --- |
| Ex. 216 | CH$_2$CH$_2$NH— | CH$_2$CH$_2$NH— |
| Ex. 217 | H | CH$_2$CH$_2$NH$_2$ |
| Ex. 218 | H | CH$_2$CH$_2$CH$_2$NH$_2$ |
| Ex. 219 | H | OH |
| Ex. 220 | H | CH$_3$ |
| Ex. 221 | CH$_3$ | CH$_3$ |
| Ex. 222 | CH$_2$CH$_2$O— | CH$_2$CH$_2$O— |
| Ex. 223 | CH$_2$CH$_2$OH | CH$_2$CH$_2$OH |
| Ex. 224 | CH$_2$CH$_2$CH$_2$— | CH$_2$CH$_2$CH$_2$— |
| Ex. 225 | H | CH(CH$_3$)$_2$ |
| Ex. 226 | CH$_2$CH$_2$— | CH$_2$CH$_2$— |
| Ex. 227 | CH$_2$CH$_2$N(CH$_3$)— | CH$_2$CH$_2$N(CH$_3$)— |
| Ex. 228 | H | CH$_2$CH$_2$N(CH$_3$)$_2$ |
| Ex. 229 | H | CH$_2$CH$_2$OCH$_3$ |
| Ex. 230 | CH$_3$ | CH$_2$CH$_2$OH |
| Ex. 231 | CH$_3$ | CH$_2$CH$_2$OCH$_3$ |

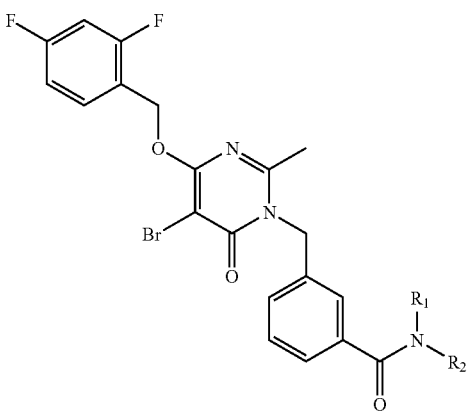

Examples 250-261

| Compound No. | $R_1$ | $R_2$ |
| --- | --- | --- |
| Ex. 250 | CH$_2$CH$_2$NH— | CH$_2$CH$_2$NH— |
| Ex. 251 | H | CH$_2$CH$_2$NH$_2$ |
| Ex. 252 | H | CH$_2$CH$_2$CH$_2$NH$_2$ |
| Ex. 253 | H | OH |
| Ex. 254 | CH$_3$ | CH$_3$ |
| Ex. 255 | H | CH$_3$ |
| Ex. 256 | CH$_2$CH$_2$O— | CH$_2$CH$_2$O— |
| Ex. 257 | H | CH$_2$CH$_2$OH |
| Ex. 258 | CH$_2$CH$_2$OH | CH$_2$CH$_2$OH |
| Ex. 259 | CH$_2$CH$_2$CH$_2$— | CH$_2$CH$_2$CH$_2$— |
| Ex. 260 | H | CH(CH$_3$)$_2$ |
| Ex. 261 | CH$_2$CH$_2$— | CH$_2$CH$_2$— |

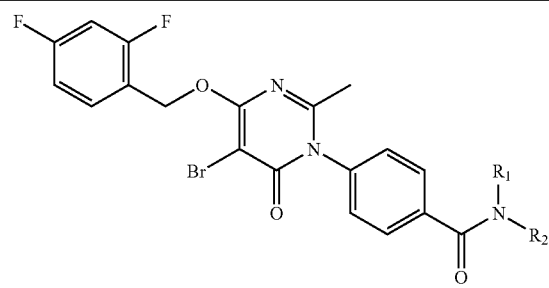

Examples 233-243

| Compound No. | $R_1$ | $R_2$ |
| --- | --- | --- |
| Ex. 233 | CH$_2$CH$_2$NH— | CH$_2$CH$_2$NH— |
| Ex. 234 | H | CH$_2$CH$_2$NH$_2$ |
| Ex. 235 | H | CH$_2$CH$_2$CH$_2$NH$_2$ |
| Ex. 236 | H | OH |
| Ex. 237 | H | CH$_3$ |
| Ex. 238 | CH$_3$ | CH$_3$ |
| Ex. 239 | CH$_2$CH$_2$O— | CH$_2$CH$_2$O— |
| Ex. 240 | CH$_2$CH$_2$OH | CH$_2$CH$_2$OH |
| Ex. 241 | CH$_2$CH$_2$CH$_2$— | CH$_2$CH$_2$CH$_2$— |
| Ex. 242 | H | CH(CH$_3$)$_2$ |
| Ex. 243 | CH$_2$CH$_2$— | CH$_2$CH$_2$— |

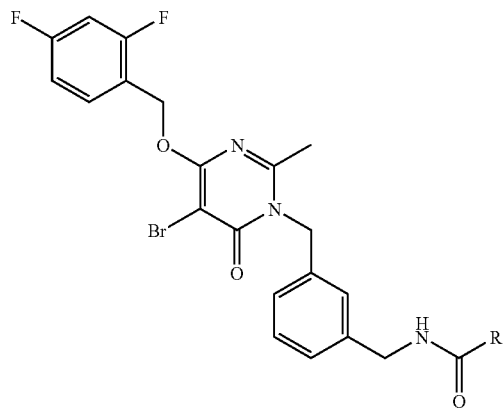

Example 263-265
HCl in dioxane to afford the compounds as hydrochloride salts.

| Compound No. | R |
| --- | --- |
| Ex. 263 | CH$_2$NH$_2$ |
| Ex. 264 | CH$_2$NHCOCH$_3$ |
| Ex. 265 | CH$_2$OCOCH$_3$ |

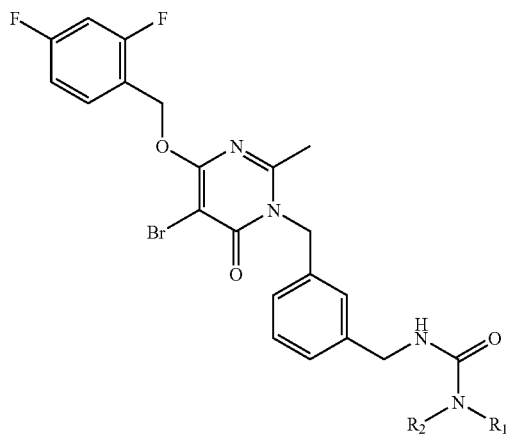

Example 268-270

| Compound No. | R₁ | R₂ |
|---|---|---|
| Ex. 268 | CH₂CH₂N— | CH₂CH₂N— |
| Ex. 269 | H | CH₃ |
| Ex. 270 | CH₂CH₂O— | CH₂CH₂O— |

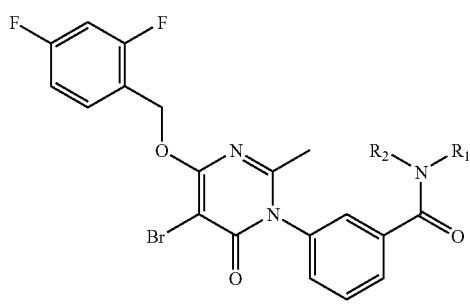

Example 274-289

| Compound No. | R1 | R2 |
|---|---|---|
| Ex. 274 | CH2CH2NH— | CH2CH2NH— |
| Ex. 275 | H | CH2CH2NH2 |
| Ex. 276 | H | CH2CH2CH2NH2 |
| Ex. 277 | H | OH |
| Ex. 278 | CH3 | CH3 |
| Ex. 279 | CH2CH2O— | CH2CH2O— |
| Ex. 280 | H | CH2CH2OH |
| Ex. 281 | CH2CH2CH2— | CH2CH2CH2— |
| Ex. 282 | H | CH(CH3)2 |
| Ex. 283 | CH2CH2— | CH2CH2— |
| Ex. 284 | CH2CH2N(CH3)— | CH2CH2N(CH3)— |
| Ex. 285 | H | CH2CH2N(CH3)2 |
| Ex. 286 | H | CH2CH2OCH3 |
| Ex. 287 | CH3 | CH2CH2N(CH3)2 |
| Ex. 288 | CH3 | CH2CH2OH |
| Ex. 289 | CH3 | CH2CH2OCH3 |

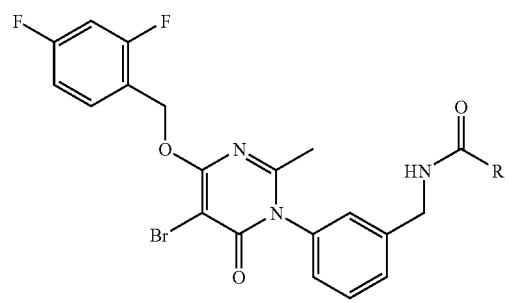

Example 295-296

| Compound No. | R |
|---|---|
| Ex. 295 | CH₃ |
| Ex. 296 | OCH₃ |

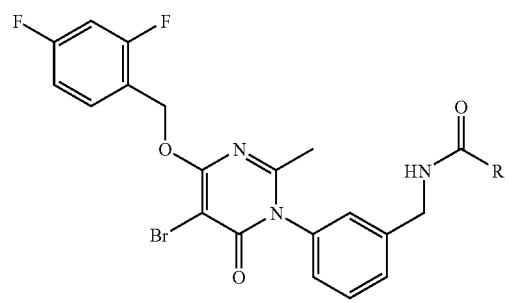

Examples 298-300

| Compound No. | R |
|---|---|
| Ex. 298 | CH₂OCOCH₃ |
| Ex. 299 | CH₂NH₂ |
| Ex. 300 | CH₂OH |

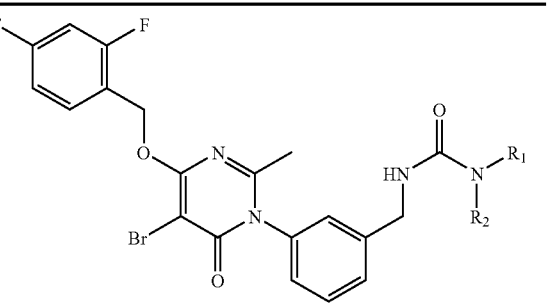

Examples 302-303

| Compound No. | R₁ | R₂ |
|---|---|---|
| Ex. 302 | H | CH₃ |
| Ex. 303 | CH₂CH₂O— | CH₂CH₂O— |

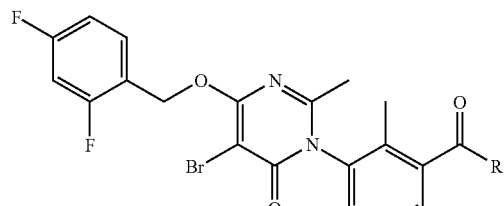

Examples 329-337

| Example No. | R |
|---|---|
| Ex. 329 | —NHCH$_2$CH$_2$OCH$_3$ |
| Ex. 330 | —N(CH$_3$)$_2$ |
| Ex. 331 | —NHCH$_2$CH$_2$OH |
| Ex. 332 | —NHCH$_3$ |
| Ex. 333 | —N(CH$_3$)CH$_2$CH$_2$OH |
| Ex. 334 | 4-methylpiperazin-1-yl |
| Ex. 335 | morpholin-4-yl |
| Ex. 336 | —N(CH$_3$)CH$_2$CH$_2$OCH$_3$ |
| Ex. 337 | —NH$_2$ |

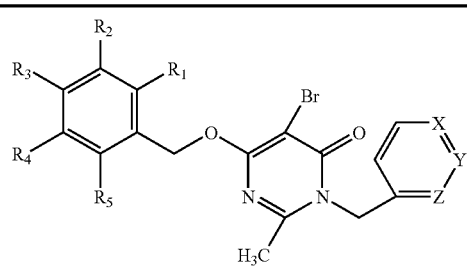

Examples 425-427, 429-435, 436-437

| Ex. No. | R$_1$ | R$_2$ | R$_3$ | R$_4$ | R$_5$ | X | Y | Z |
|---|---|---|---|---|---|---|---|---|
| 425 | H | H | F | H | H | N | CH | CH |
| 426 | F | H | F | H | F | N | CH | CH |
| 427 | F | H | H | H | F | N | CH | CH |
| 429 | H | H | F | H | H | CH | N | CH |
| 430 | F | H | F | H | F | CH | N | CH |
| 431 | F | H | H | H | H | CH | N | CH |
| 432 | F | H | F | F | H | CH | N | CH |
| 433 | F | H | Cl | H | H | CH | N | CH |
| 434 | Cl | H | F | H | H | CH | N | CH |
| 435 | F | H | H | H | F | CH | N | CH |
| 436 | H | H | F | H | H | CH | CH | N |
| 437 | F | H | F | H | F | CH | CH | N |
| 438 | F | H | F | H | H | CH | CH | N |

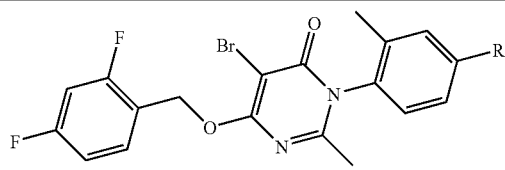

Examples 473-476

| Compound No. | R |
|---|---|
| Ex. 473 | —CO$_2$H |
| Ex. 474 | —CH$_2$OH |
| Ex. 475 | C(O)NH(CH$_2$)$_2$OCH$_3$ |
| Ex. 476 | C(O)NHCH$_3$ |

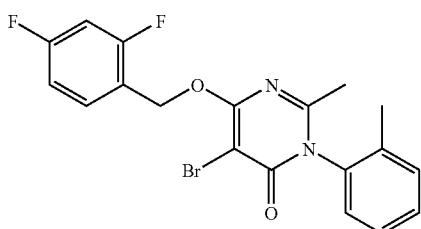

Examples 488-491

| Compound No. | R |
|---|---|
| Ex. 488 | —NH(CH$_2$)$_2$OCH$_3$ |
| Ex. 489 | —NHCH$_3$ |
| Ex. 490 | —N(CH$_3$)$_2$ |
| Ex. 491 | -morpholine |

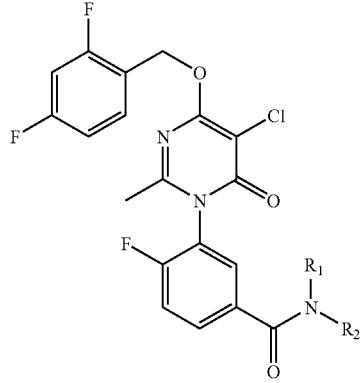

Examples 509-518

| Example No. | R$_1$ | R$_2$ |
|---|---|---|
| Ex. 509 | CH$_3$ | CH$_3$ |
| Ex. 510 | H | CH$_2$CH$_2$OH |
| Ex. 511 | CH$_2$CH$_2$N(CH$_3$)— | CH$_2$CH$_2$N(CH$_3$)— |
| Ex. 512 | CH$_2$CH$_2$O— | CH$_2$CH$_2$O— |
| Ex. 513 | H | CH$_2$CH$_2$OCH$_3$ |
| Ex. 514 | CH$_3$ | CH$_2$CH$_2$OH |
| Ex. 515 | H | CH$_2$CH$_2$CH$_2$OH |
| Ex. 516 | H | CH$_2$CH(OH)CH$_2$OH |
| Ex. 517 | H | C(CH$_3$)$_2$CH$_2$OH— |
| Ex. 518 | CH$_2$CH$_2$NH— | CH$_2$CH$_2$NH— |

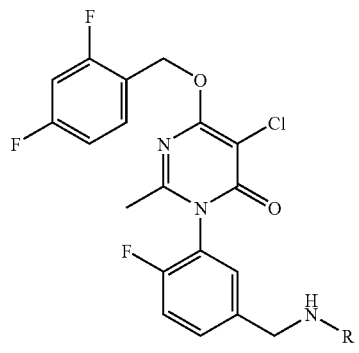

Examples 525-528

| Ex. No. | R |
|---|---|
| Ex. 525 | —C(O)CH₃ |
| Ex. 526 | —C(O)CH₂OCH₃ |
| Ex. 527 | —SO₂CH₃ |
| Ex. 528 | —C(O)NH₂ |

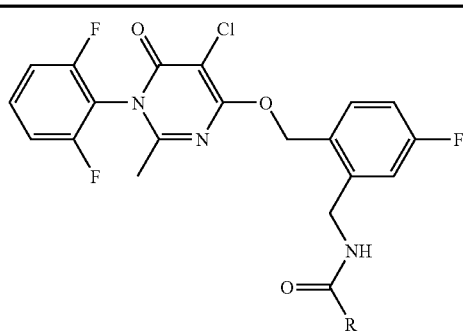

Examples 531-551

| Compound No. | R |
|---|---|
| Ex. 531 | —OCH₃ |
| Ex. 532 | —CF₃ |
| Ex. 533 | —O-isopropyl |
| Ex. 534 | —NH—CH₂CH₃ |
| Ex. 535 | —O-tetrahydrofuran-3-yl |
| Ex. 536 | —O-propyl |
| Ex. 537 | —O—CH₂CH=CH₂ |
| Ex. 538 | —O—CH₂C≡CH |
| Ex. 539 | —O-tButyl |
| Ex. 540 | —NH-tButyl |
| Ex. 541 | —SO₂CH₂CH₂CH₃ |
| Ex. 542 | —SO₂CH₂CH₃ |
| Ex. 543 | —NH-isopropyl |
| Ex. 544 | —CH₂OCH₃ |
| Ex. 545 | —NHCH₃ |
| Ex. 546 | —N(CH₃)(tButyl) |
| Ex. 547 | —NH(cyclopropyl) |
| Ex. 548 | —NHCH₂CF₃ |
| Ex. 549 | —NHCH₂(cyclopropyl) |
| Ex. 550 | —NHCH₂(tButyl) |
| Ex. 551 | —N(CH₃)₂ |

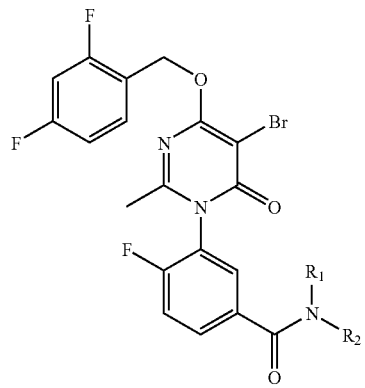

Example 601-603

| Compound No. | R₁ | R₂ |
|---|---|---|
| Ex. 601 | CH₂CH₂O— | CH₂CH₂— |
| Ex. 602 | CH₃ | CH₂CH₂OH |
| Ex. 603 | H | CH₂C(CH₃)₂OH |

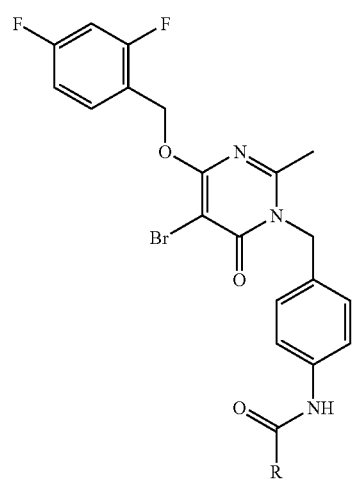

Examples 614-616

| Compound No. | R |
|---|---|
| Ex. 614 | CH₂OH |
| Ex. 615 | CH₂OCOCH₃ |
| Ex. 616 | SO₂N(CH₃)₂ |

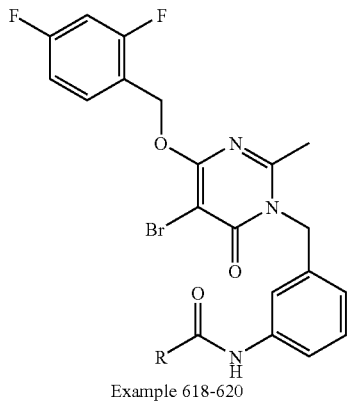

Example 618-620

| Compound No. | R |
|---|---|
| Ex. 618 | CH$_2$OH |
| Ex. 619 | CH$_2$OCOCH$_3$ |
| Ex. 620 | SO$_2$N(CH$_3$)$_2$ |

Other representative compounds of the invention are
methyl 3-{[5-bromo-4-[(2,4-difluorobenzyl)oxy]-6-oxopyrimidin-1(6H)-yl]methyl}benzoate;
methyl 4-{[5-bromo-4-[(2,4-difluorobenzyl)oxy]-6-oxopyrimidin-1(6H)-yl]methyl}benzoate;
3-{[5-bromo-4-[(2,4-difluorobenzyl)oxy]-6-oxopyrimidin-1(6H)-yl]methyl}benzamide;
4-{[5-bromo-4-[(2,4-difluorobenzyl)oxy]-6-oxopyrimidin-1(6H)-yl]methyl}benzamide;
3-(3-Aminomethyl-2-fluorobenzyl)-5-bromo-6-(2,4-difluorobenzyloxy)-3H-pyrimidin-4-one;
methyl 3-{[5-chloro-4-[(2,4-difluorobenzyl)oxy]-6-oxopyrimidin-1(6H)-yl]methyl}-2-fluorobenzoate;
3-{[5-chloro-4-[(2,4-difluorobenzyl)oxy]-6-oxopyrimidin-1(6H)-yl]methyl}-2-fluorobenzamide;
5-bromo-6-(2,4-difluorobenzyloxy)-3-(3-fluorobenzyl)-3H-pyrimidin-4-one;
5-bromo-3-(3-fluorobenzyl)-6-(2,3,4-trifluorobenzyloxy)-3H-pyrimidin-4-one;
3-[3-(2-aminoethyl)benzyl]-5-bromo-6-(2,4-difluorobenzyloxy)-3H-pyrimidin-4-one;
6-(benzyloxy)-5-bromopyrimidin-4(3H)-one;
5-chloro-6-(2,4-difluorobenzyloxy)-3-(3-fluorobenzyl)-3H-pyrimidin-4-one;
5-bromo-6-(3-chlorobenzyloxy)-3-(3-fluorobenzyl)-3H-pyrimidin-4-one;
5-bromo-6-(3,4-difluorobenzyloxy)-3-(3-fluorobenzyl)-3H-pyrimidin-4-one;
5-bromo-3-(3-fluorobenzyl)-6-(4-fluorobenzyloxy)-3H-pyrimidin-4-one;
5-bromo-3-(3-fluorobenzyl)-6-(3-fluorobenzyloxy)-3H-pyrimidin-4-one;
5-bromo-3-(3-fluorobenzyl)-6-(2-hydroxymethylbenzyloxy)-3H-pyrimidin-4-one;
2-(2-{[5-bromo-4-[(2,4-difluorobenzyl)oxy]-6-oxopyrimidin-1(6H)-yl]methyl}phenyl)acetamide;
ethyl (3-{[5-bromo-4-[(2,4-difluorobenzyl)oxy]-6-oxopyrimidin-1(6H)-yl]methyl}phenyl)acetate;
2-(3-{[5-bromo-4-[(2,4-difluorobenzyl)oxy]-6-oxopyrimidin-1(6H)-yl]methyl}phenyl)acetamide;
6-(2,4-difluorobenzyloxy)-3-(3-fluorobenzyl)-5-methyl-3H-pyrimidin-4-one;
6-(2,4-difluorobenzyloxy)-3-(3-fluorobenzyl)-5-iodo-3H-pyrimidin-4-one;
4-[(2,4-difluorobenzyl)oxy]-1-(3-fluorobenzyl)-6-oxo-1,6-dihydropyrimidine-5-carbonitrile;
3-cyclohexyl-6-(2,4-difluorobenzyloxy)-2,5-dimethyl-3H-pyrimidin-4-one;
5-chloro-6-(2,4-difluorobenzyloxy)-2-methyl-3-(1H-pyrazol-4-ylmethyl)-3H-pyrimidin-4-one;
4-{[4-(benzyloxy)-5-bromo-6-oxopyrimidin-1(6H)-yl]methyl}benzonitrile;
3-{[4-(benzyloxy)-5-bromo-6-oxopyrimidin-1(6H)-yl]methyl}benzonitrile;
3-[4-(aminomethyl)benzyl]-6-(benzyloxy)-5-bromopyrimidin-4(3H)-one;
3-[3-(aminomethyl)benzyl]-6-(benzyloxy)-5-bromopyrimidin-4(3H)-one;
3-[2-(aminomethyl)benzyl]-6-(benzyloxy)-5-bromopyrimidin-4(3H)-one;
4-{[4-(benzyloxy)-5-bromo-6-oxopyrimidin-1(6H)-yl]methyl}benzamide;
3-{[4-(benzyloxy)-5-bromo-6-oxopyrimidin-1(6H)-yl]methyl}benzamide;
2-{[4-(benzyloxy)-5-bromo-6-oxopyrimidin-1(6H)-yl]methyl}benzamide;
methyl 3-{[4-(benzyloxy)-5-bromo-6-oxopyrimidin-1(6H)-yl]methyl}benzoate;
methyl 4-{[4-(benzyloxy)-5-bromo-6-oxopyrimidin-1(6H)-yl]methyl}benzoate;
4-[4-(benzyloxy)-5-bromo-6-oxopyrimidin-1(6H)-yl]benzonitrile;
2-[4-(benzyloxy)-5-bromo-6-oxopyrimidin-1(6H)-yl]benzonitrile;
(4-{[4-(benzyloxy)-5-bromo-6-oxopyrimidin-1(6H)-yl]methyl}phenyl)acetic acid
2-{[5-bromo-4-[(2,4-difluorobenzyl)oxy]-2-methyl-6-oxopyrimidin-1(6H)-yl]methyl}benzonitrile;
3-([5-bromo-4-[(2,4-difluorobenzyl)oxy]-2-methyl-6-oxopyrimidin-1(6H)-yl]methyl)benzonitrile;
4-{[5-bromo-4-[(2,4-difluorobenzyl)oxy]-2-methyl-6-oxopyrimidin-1(6H)-yl]methyl}benzonitrile;
4-{[5-bromo-4-[(2,4-difluorobenzyl)oxy]-2-methyl-6-oxopyrimidin-1(6H)-yl]methyl}benzamide;
methyl 4-{[5-bromo-4-[(2,4-difluorobenzyl)oxy]-2-methyl-6-oxopyrimidin-1(6H)-yl]methyl}benzoate;
methyl 3-{[5-bromo-4-[(2,4-difluorobenzyl)oxy]-2-methyl-6-oxopyrimidin-1(6H)-yl]methyl}benzoate;
3-{[5-bromo-4-[(2,4-difluorobenzyl)oxy]-2-methyl-6-oxopyrimidin-1(6H)-yl]methyl}benzamide;
2-{[5-bromo-4-[(2,4-difluorobenzyl)oxy]-2-methyl-6-oxopyrimidin-1(6H)-yl]methyl}benzamide
3-[2-(aminomethyl)benzyl]-5-bromo-6-[(2,4-difluorobenzyl)oxy]-2-methylpyrimidin-4(3H)-one;
5-bromo-3-[3-(bromomethyl)benzyl]-6-[(2,4-difluorobenzyl)oxy]-2-methylpyrimidin-4(3H)-one;
5-bromo-3-[4-(bromomethyl)benzyl]-6-[(2,4-difluorobenzyl)oxy]-2-methylpyrimidin-4(3H)-one;
3-[4-(aminomethyl)benzyl]-5-bromo-6-[(2,4-difluorobenzyl)oxy]-2-methylpyrimidin-4(3H)-one;
3-{[5-bromo-4-[(2,4-difluorobenzyl)oxy]-2-methyl-6-oxopyrimidin-1(6H)-yl]methyl}benzoic acid;
4-(4-{[5-bromo-4-[(2,4-difluorobenzyl)oxy]-2-methyl-6-oxopyrimidin-1(6H)-yl]methyl}benzoyl)piperazine-1-carboxamide;
N-(4-{[5-bromo-4-[(2,4-difluorobenzyl)oxy]-2-methyl-6-oxopyrimidin-1(6H)-yl]methyl}benzyl)-2-methoxyacetamide;

3-{4-[(4-acetylpiperazin-1-yl)carbonyl]benzyl}-5-bromo-6-[(2,4-difluorobenzyl)oxy]-2-methylpyrimidin-4(3H)-one;

5-bromo-6-[(2,4-difluorobenzyl)oxy]-2-methyl-3-(4-{[4-(methylsulfonyl)piperazin-1-yl]carbonyl}benzyl)pyrimidin-4(3H)-one;

methyl 4-[4-(benzyloxy)-5-bromo-6-oxopyrimidin-1(6H)-yl]benzoate;

4-[4-(benzyloxy)-5-bromo-6-oxopyrimidin-1(6H)-yl]benzoic acid;

4-[4-(benzyloxy)-5-bromo-6-oxopyrimidin-1(6H)-yl]benzamide;

3-[4-(aminomethyl)phenyl]-6-(benzyloxy)-5-bromopyrimidin-4(3H)-one;

6-(benzyloxy)-5-bromo-3-(4-methylbenzyl)pyrimidin-4(3H)-one;

6-(benzyloxy)-5-bromo-3-ethylpyrimidin-4(3H)-one;

methyl 4-[5-chloro-4-[(2,4-difluorobenzyl)oxy]-6-oxopyrimidin-1(6H)-yl]benzoate;

5-bromo-6-[(2,4-difluorobenzyl)oxy]-3-[3-(hydroxymethyl)phenyl]-2-methylpyrimidin-4(3H)-one;

methyl 4-[5-bromo-4-[(2,4-difluorobenzyl)oxy]-2-methyl-6-oxopyrimidin-1(6H)-yl]benzoate;

4-[5-bromo-4-[(2,4-difluorobenzyl)oxy]-2-methyl-6-oxopyrimidin-1(6H)-yl]benzoic acid;

6-(benzyloxy)-3-(3-fluorobenzyl)-5-(trifluoromethyl)pyrimidin-4(3H)-one;

4-{[5-bromo-4-[(2,4-difluorobenzyl)oxy]-2-methyl-6-oxopyrimidin-1(6H)-yl]methyl}benzoic acid;

5-bromo-6-[(2,4-difluorobenzyl)oxy]-3-[4-(hydroxymethyl)benzyl]-2-methylpyrimidin-4(3H)-one;

5-bromo-6-[(2,4-difluorobenzyl)oxy]-3-[4-(1-hydroxy-1-methylethyl)benzyl]-2-methylpyrimidin-4(3H)-one;

5-bromo-6-[(2,4-difluorobenzyl)oxy]-2-methyl-3-{4-[(methylamino)methyl]benzyl}pyrimidin-4(3H)-one;

6-[(2,4-difluorobenzyl)oxy]-3-(4-methoxybenzyl)-2-methylpyrimidin-4-(3H)-one;

5-bromo-6-hydroxy-3-(4-hydroxybenzyl)pyrimidin-4(3H)-one;

5-bromo-6-[(2,4-difluorobenzyl)oxy]-3-(4-methoxybenzyl)-2-methylpyrimidin-4(3H)-one;

5-bromo-6-[(2,4-difluorobenzyl)oxy]-3-(4-hydroxybenzyl)-2-methylpyrimidin-4(3H)-one;

5-bromo-6-[(2,4-difluorobenzyl)oxy]-3-{4-[(4-hydroxy-4-methylpiperidin-1-yl)carbonyl]benzyl}-2-methylpyrimidin-4(3H)-one;

4-{[5-bromo-4-[(2,4-difluorobenzyl)oxy]-2-methyl-6-oxopyrimidin-1(6H)-yl]methyl}-N-(2-hydroxy-2-methylpropyl)benzamide;

5-bromo-6-[(2,4-difluorobenzyl)oxy]-3-{4-[(4-hydroxypiperidin-1-yl)carbonyl]benzyl}-2-methylpyrimidin-4(3H)-one;

4-{[5-bromo-4-[(2,4-difluorobenzyl)oxy]-2-methyl-6-oxopyrimidin-1(6H)-yl]methyl}-N-(2-hydroxyethyl)benzamide;

6-(benzyloxy)-5-bromo-3-methylpyrimidin-4(3H)-one hydrobromide;

6-(benzyloxy)-5-bromo-3-methylpyrimidin-4(3H)-one;

4-[5-bromo-4-[(2,4-difluorobenzyl)oxy]-2-methyl-6-oxopyrimidin-1(6H)-yl]-N-(2-hydroxyethyl)benzamide;

4-{[4-(benzyloxy)-5-bromo-6-oxopyrimidin-1(6H)-yl]methyl}-N'-hydroxybenzenecarboximidamide;

4-[S-bromo-4-[(2,4-difluorobenzyl)oxy]-2-methyl-6-oxopyrimidin-1(6H)-yl]benzamide;

6-(benzyloxy)-5-bromo-3-[4-(morpholin-4-ylcarbonyl)phenyl]pyrimidin-4(3H)-one;

6-(Benzyloxy)-5-bromo-3-[4-(piperazin-1-ylcarbonyl)phenyl]pyrimidin-4(3H)-one hydrochloride;

4-[4-(benzyloxy)-5-bromo-6-oxopyrimidin-1(6H)-yl]-N-hydroxybenzamide;

methyl 4-{[5-chloro-4-[(2,4-difluorobenzyl)oxy]-2-methyl-6-oxopyrimidin-1(6H)-yl]methyl}benzoate;

3-{[5-bromo-4-[(2,4-difluorobenzyl)oxy]-2-methyl-6-oxopyrimidin-1(6H)-yl]methyl}-N-methylbenzamide;

6-(benzyloxy)-5-bromo-3-(piperidin-4-ylmethyl)pyrimidin-4(3H)-one hydrochloride;

6-(benzyloxy)-3-[4-(trifluoromethyl)benzyl]pyrimidin-4(3H)-one;

N-(3-{[5-bromo-4-[(2,4-difluorobenzyl)oxy]-2-methyl-6-oxopyrimidin-1(6H)-yl]methyl}benzyl)-2-methoxyacetamide;

N-(3-{[5-bromo-4-[(2,4-difluorobenzyl)oxy]-2-methyl-6-oxopyrimidin-1(6H)-yl]methyl}benzyl)-2-hydroxy-2-methylpropanamide;

N'-(3-{[5-bromo-4-[(2,4-difluorobenzyl)oxy]-2-methyl-6-oxopyrimidin-1(6H)-yl]methyl}benzyl)-N,N-dimethylurea;

N-(3-{[5-bromo-4-[(2,4-difluorobenzyl)oxy]-2-methyl-6-oxopyrimidin-1(6H)-yl]methyl}benzyl)-1-hydroxycyclopropanecarboxamide;

6-(benzyloxy)-5-bromo-3-[4-(trifluoromethyl)benzyl]pyrimidin-4(3H)-one;

3-[5-bromo-4-[(2,4-difluorobenzyl)oxy]-2-methyl-6-oxopyrimidin-1(6H)-yl]benzoic acid;

ethyl 3-[5-bromo-4-[(2,4-difluorobenzyl)oxy]-2-methyl-6-oxopyrimidin-1(6H)-yl]benzoate;

3-[5-bromo-4-[(2,4-difluorobenzyl)oxy]-2-methyl-6-oxopyrimidin-1(6H)-yl]-N-methylbenzamide;

6-(benzyloxy)-5-bromo-3-(piperidin-3-ylmethyl)pyrimidin-4(3H)-one hydrochloride;

6-(benzyloxy)-5-bromo-3-(2-thien-3-ylethyl)pyrimidin-4(3H)-one;

3-[5-bromo-4-[(2,4-difluorobenzyl)oxy]-2-methyl-6-oxopyrimidin-1(6H)-yl]benzamide;

3-[5-chloro-4-[(2,4-difluorobenzyl)oxy]-2-methyl-6-oxopyrimidin-1(6H)-yl]benzoic acid;

5-chloro-6-[(2,4-difluorobenzyl)oxy]-3-[3-(hydroxymethyl)phenyl]-2-methylpyrimidin-4(3H)-one;

3-[3-(aminomethyl)phenyl]-5-bromo-6-[(2,4-difluorobenzyl)oxy]-2-methylpyrimidin-4(3H)-one;

N-{3-[5-bromo-4-[(2,4-difluorobenzyl)oxy]-2-methyl-6-oxopyrimidin-1(6H)-yl]benzyl}methanesulfonamide;

N-(3-[5-bromo-4-[(2,4-difluorobenzyl)oxy]-2-methyl-6-oxopyrimidin-1(6H)-yl]benzyl)-2-methoxyacetamide;

6-(benzyloxy)-5-bromo-3-(2-thien-2-ylethyl)pyrimidin-4(3H)-one;

N'-(3-[5-bromo-4-[(2,4-difluorobenzyl)oxy]-2-methyl-6-oxopyrimidin-1(6H)-yl]benzyl)-N,N-dimethylurea;

N-(3-[5-bromo-4-[(2,4-difluorobenzyl)oxy]-2-methyl-6-oxopyrimidin-1(6H)-yl]benzyl)urea;

5-bromo-6-[(2,4-difluorobenzyl)oxy]-3-{3-[(dimethylamino)methyl]phenyl}-2-methylpyrimidin-4(3H)-one;

N-{4-[4-(benzyloxy)-5-bromo-6-oxopyrimidin-1(6H)-yl]benzyl}acetamide;

N-{4-[4-(benzyloxy)-5-bromo-6-oxopyrimidin-1(6H)-yl]benzyl}-2-hydroxyacetamide;

5-bromo-6-[(2,4-difluorobenzyl)oxy]-2-methyl-3-(2-morpholin-4-ylethyl)pyrimidin-4(3H)-one;

ethyl 3-[4-(benzyloxy)-5-bromo-6-oxopyrimidin-1(6H)-yl]propanoate;

6-(benzyloxy)-5-bromo-3-[3-(trifluoromethyl)benzyl]pyrimidin-4(3H)-one;

methyl 3-[4-(benzyloxy)-5-bromo-6-oxopyrimidin-1(6H)-yl]propanoate;

N-[5-bromo-1-(3-fluorobenzyl)-6-oxo-1,6-dihydropyrimidin-4-yl]-2,6-difluorobenzamide;
5-bromo-3-(4-bromo-2,6-difluorophenyl)-6-[(2,4-difluorobenzyl)oxy]-2-methylpyrimidin-4(3H)-one;
5-bromo-6-[(2,4-difluorobenzyl)oxy]-2-methyl-3-(2,4,6-trifluorophenyl)pyrimidin-4(3H)-one;
5-chloro-6-[(2,4-difluorobenzyl)oxy]-2-methyl-3-(2,4,6-trifluorophenyl)pyrimidin-4(3H)-one;
5-bromo-6-[(2,4-difluorobenzyl)oxy]-2-(hydroxymethyl)-3-(2,4,6-trifluorophenyl)pyrimidin-4(3H)-one;
5-chloro-6-[(2,4-difluorobenzyl)oxy]-2-(hydroxymethyl)-3-(2,4,6-trifluorophenyl)pyrimidin-4(3H)-one;
5-bromo-6-[(2,4-difluorobenzyl)oxy]-3-(2,6-difluoro-4-morpholin-4-ylphenyl)-2-methylpyrimidin-4(3H)-one;
5-bromo-6-[(2,4-difluorobenzyl)oxy]-3-[2,6-difluoro-4-(4-methylpiperazin-1-yl)phenyl]-2-methylpyrimidin-4(3H)-one;
6-(benzyloxy)-5-bromo-3-[2-(trifluoromethyl)benzyl]pyrimidin-4(3H)-one;
5-chloro-6-[(2,4-difluorobenzyl)oxy]-3-[2,6-difluoro-4-(4-methylpiperazin-1-yl)phenyl]-2-methylpyrimidin-4(3H)-one;
5-bromo-6-[(2,4-difluorobenzyl)oxy]-3-[4-(dimethylamino)-2,6-difluorophenyl]-2-methylpyrimidin-4(3H)-one;
5-bromo-6-[(2,4-difluorobenzyl)oxy]-3-{2,6-difluoro-4-[(2-hydroxyethyl)(methyl)amino]phenyl}-2-methylpyrimidin-4(3H)-one;
5-bromo-3-(3,5-dibromo-2,6-difluoro-4-hydroxyphenyl)-6-[(2,4-difluorobenzyl)oxy]-2-methylpyrimidin-4(3H)-one;
2-{4-[5-bromo-4-[(2,4-difluorobenzyl)oxy]-2-methyl-6-oxopyrimidin-1(6H)-yl]-3,5-difluorophenoxy}acetamide;
5-bromo-6-[(2,4-difluorobenzyl)oxy]-3-[2,6-difluoro-4-(2-hydroxyethoxy)phenyl]-2-methylpyrimidin-4(3H)-one;
5-bromo-3-(2,6-difluorophenyl)-6-{[4-fluoro-2-(hydroxymethyl)benzyl]oxy}-2-methylpyrimidin-4(3H)-one;
5-chloro-3-(2,6-difluorophenyl)-6-{[4-fluoro-2-(hydroxymethyl)benzyl]oxy}-2-methylpyrimidin-4(3H)-one;
3-[5-bromo-4-[(2,4-difluorobenzyl)oxy]-2-methyl-6'-oxopyrimidin-1(6H)-yl]-2-methyl-N-(2-morpholin-4-ylethyl)benzamide;
6-(benzyloxy)-3-[4-(trifluoromethoxy)benzyl]pyrimidin-4(3H)-one;
5-bromo-6-[(2,4-difluorobenzyl)oxy]-3-[3-(hydroxymethyl)-2-methylphenyl]-2-methylpyrimidin-4(3H)-one;
3-[5-chloro-4-[(2,4-difluorobenzyl)oxy]-2-methyl-6-oxopyrimidin-1(6H)-yl]-N-(2-methoxyethyl)-2-methylbenzamide;
6-(benzyloxy)-5-bromo-3-[4-(trifluoromethoxy)benzyl]pyrimidin-4(3H)-one;
3-[5-chloro-4-[(2,4-difluorobenzyl)oxy]-2-methyl-6-oxopyrimidin-1(6H)-yl]-N,2-dimethylbenzamide;
3-[5-chloro-4-[(2,4-difluorobenzyl)oxy]-2-methyl-6-oxopyrimidin-1(6H)-yl]-N-(2-hydroxyethyl)-2-methylbenzamide;
3-[5-chloro-4-[(2,4-difluorobenzyl)oxy]-2-methyl-6-oxopyrimidin-1(6H)-yl]-2-methylbenzamide;
4-[5-chloro-4-[(2,4-difluorobenzyl)oxy]-6-oxopyrimidin-1(6H)-yl]-3,5-difluorobenzonitrile;
3-[4-(aminomethyl)-2,6-difluorophenyl]-5-chloro-6-[(2,4-difluorobenzyl)oxy]pyrimidin-4(3H)-one hydrochloride;
5-chloro-6-[(2,4-difluorobenzyl)oxy]-3-{2,6-difluoro-4-[(methylamino)methyl]phenyl}pyrimidin-4(3H)-one hydrochloride;
5-chloro-3-(4-{[(cyclopropylmethyl)amino]methyl}-2,6-difluorophenyl)-6-[(2,4-difluorobenzyl)oxy]pyrimidin-4(3H)-one hydrochloride;

4-[5-chloro-4-[(2,4-difluorobenzyl)oxy]-6-oxopyrimidin-1(6H)-yl]-3,5-difluoro-N,N-dimethylbenzamide;
4-[5-chloro-4-[(2,4-difluorobenzyl)oxy]-6-oxopyrimidin-1(6H)-yl]-3-fluoro-5-methoxybenzonitrile;
N-{4-[5-chloro-4-[(2,4-difluorobenzyl)oxy]-6-oxopyrimidin-1(6H)-yl]-3,5-difluorobenzyl}urea;
3-benzyl-6-(benzyloxy)-2-methylpyrimidin-4(3H)-one;
2-({4-[5-chloro-4-[(2,4-difluorobenzyl)oxy]-6-oxopyrimidin-1(6H)-yl]-3,5-difluorobenzyl}amino)-1,1-dimethyl-2-oxoethyl acetate;
N-{4-[5-chloro-4-[(2,4-difluorobenzyl)oxy]-6-oxopyrimidin-1(6H)-yl]-3,5-difluorobenzyl}acetamide;
N-{4-[5-chloro-4-[(2,4-difluorobenzyl)oxy]-6-oxopyrimidin-1(6H)-yl]-3,5-difluorobenzyl}-2-methoxyacetamide;
N-{4-[5-chloro-4-[(2,4-difluorobenzyl)oxy]-6-oxopyrimidin-1(6H)-yl]-3,5-difluorobenzyl}-2-furamide;
N-{4-[5-chloro-4-[(2,4-difluorobenzyl)oxy]-6-oxopyrimidin-1(6H)-yl]-3,5-difluorobenzyl}-1H-imidazole-4-carboxamide;
N-{4-[5-chloro-4-[(2,4-difluorobenzyl)oxy]-6-oxopyrimidin-1(6H)-yl]-3,5-difluorobenzyl}prolinamide;
N-{4-[5-chloro-4-[(2,4-difluorobenzyl)oxy]-6-oxopyrimidin-1(6H)-yl]-3,5-difluorobenzyl}-3-hydroxy-3-methylbutanamide;
N-{4-[5-chloro-4-[(2,4-difluorobenzyl)oxy]-6-oxopyrimidin-1(6H)-yl]-3,5-difluorobenzyl}-1-hydroxycyclopropanecarboxamide;
N-{4-[5-chloro-4-[(2,4-difluorobenzyl)oxy]-6-oxopyrimidin-1(6H)-yl]-3,5-difluorobenzyl}-2-hydroxy-2-methylpropanamide;
4-[5-bromo-4-[(2,4-difluorobenzyl)oxy]-6-oxopyrimidin-1(6H)-yl]-3,5-difluorobenzonitrile;
3-benzyl-6-(benzyloxy)-5-bromo-2-methylpyrimidin-4(3H)-one;
5-bromo-3-(3-fluorobenzyl)-2-methyl-6-(2-phenylethyl)pyrimidin-4(3H)-one;
5-bromo-3-(3-fluorobenzyl)-6-(1-phenylethoxy)pyrimidin-4(3H)-one;
5-bromo-3-(3-fluorobenzyl)-6-[(E)-2-(4-fluorophenyl)ethenyl]pyrimidin-4(3H)-one;
6-(benzyloxy)-5-bromo-3-[(6-fluoropyridin-3-yl)methyl]pyrimidin-4(3H)-one;
5-bromo-6-[(2,4-difluorobenzyl)oxy]-3-(2,6-dimethylphenyl)-2-methylpyrimidin-4(3H)-one;
5-bromo-3-(2,6-dimethylphenyl)-6-[(4-fluorobenzyl)oxy]-2-methylpyrimidin-4(3H)-one;
5-bromo-3-(2,6-dimethylphenyl)-2-methyl-6-[(2,4,6-trifluorobenzyl)oxy]pyrimidin-4(3H)-one;
5-bromo-6-[(2,6-difluorobenzyl)oxy]-3-(2,6-dimethylphenyl)-2-methylpyrimidin-4(3H)-one;
5-bromo-3-(2,6-dichlorophenyl)-6-[(4-fluorobenzyl)oxy]-2-methylpyrimidin-4(3H)-one;
5-bromo-3-(2,6-dichlorophenyl)-6-[(2,4-difluorobenzyl)oxy]-2-methylpyrimidin-4(3H)-one;
3-benzyl-6-(benzyloxy)-1,5-dibromo-2-methylpyrimidin-4(3H)-one;
5-bromo-3-(2,6-dichlorophenyl)-6-[(2,6-difluorobenzyl)oxy]-2-methylpyrimidin-4(3H)-one;
5-bromo-6-[(2,4-difluorobenzyl)oxy]-3-(2-methoxy-2-methylphenyl)-2-methylpyrimidin-4(3H)-one;
4-[5-bromo-4-[(2,4-difluorobenzyl)oxy]-2-methyl-6-oxopyrimidin-1(6H)-yl]-3,5-dichlorobenzenesulfonamide;
5-bromo-6-[(2,4-difluorobenzyl)oxy]-3-(2,6-difluorophenyl)-2-methylpyrimidin-4(3H)-one;
5-bromo-6-[(2,4-difluorobenzyl)oxy]-3-(2,6-difluorophenyl)-1-iodo-2-methylpyrimidin-4(1H)-one;

5-bromo-6-[(2,4-difluorobenzyl)oxy]-3-[2-(dimethylamino)-4,6-difluorophenyl]-2-methylpyrimidin-4(3H)-one;
5-bromo-6-[(2,4-difluorobenzyl)oxy]-3-{2,4-difluoro-6-[(2-hydroxyethyl)(methyl)amino]phenyl}-2-methylpyrimidin-4(3H)-one;
2-({[5-bromo-1-(2,6-difluorophenyl)-2-methyl-6-oxo-1,6-dihydropyrimidin-4-yl]oxy}methyl)-5-fluorobenzonitrile;
6-{[2-(aminomethyl)-4-fluorobenzyl]oxy}-5-bromo-3-(2,6-difluorophenyl)-2-methylpyrimidin-4(3H)-one trifluoroacetate;
N-[2-({[5-bromo-1-(2,6-difluorophenyl)-2-methyl-6-oxo-1,6-dihydropyrimidin-4-yl]oxy}methyl)-5-fluorobenzyl]urea;
3-benzyl-6-[(3-chlorobenzyl)oxy]-2-methylpyrimidin-4(3H)-one;
methyl [2-({[5-bromo-1-(2,6-difluorophenyl)-2-methyl-6-oxo-1,6-dihydropyrimidin-4-yl]oxy}methyl)-5-fluorobenzyl]carbamate;
N-[2-({[5-bromo-1-(2,6-difluorophenyl)-2-methyl-6-oxo-1,6-dihydropyrimidin-4-yl]oxy}methyl)-5-fluorobenzyl]-2-hydroxyacetamide;
ethyl [2-({[5-chloro-1-(2,6-difluorophenyl)-2-methyl-6-oxo-1,6-dihydropyrimidin-4-yl]oxy}methyl)-5-fluorobenzyl]carbamate;
isobutyl [2-({[5-chloro-1-(2,6-difluorophenyl)-2-methyl-6-oxo-1,6-dihydropyrimidin-4-yl]oxy}methyl)-5-fluorobenzyl]carbamate;
cyclopropylmethyl [2-({[5-chloro-1-(2,6-difluorophenyl)-2-methyl-6-oxo-1,6-dihydropyrimidin-4-yl]oxy}methyl)-5-fluorobenzyl]carbamate;
3-[(4-amino-2-methylpyrimidin-5-yl)methyl]-5-bromo-6-[(2,4-difluorobenzyl)oxy]-2-methylpyrimidin-4(3H)-one trifluoroacetate;
3-[(4-amino-2-methylpyrimidin-5-yl)methyl]-5-bromo-6-[(2,4-difluorobenzyl)oxy]-2-methylpyrimidin-4(3H)-one hydrochloride;
3-[(4-amino-2-methylpyrimidin-5-yl)methyl]-5-chloro-6-[(2,4-difluorobenzyl)oxy]-2-methylpyrimidin-4(3H)-one trifluoroacetate;
3-[(4-amino-2-methylpyrimidin-5-yl)methyl]-5-chloro-6-[(2,4-difluorobenzyl)oxy]-2-methylpyrimidin-4(3H)-one hydrochloride;
5-bromo-6-[(2,4-difluorobenzyl)oxy]-3-(1H-indazol-5-ylmethyl)-2-methylpyrimidin-4(3H)-one trifluoroacetate;
3-benzyl-5-bromo-6-[(3-chlorobenzyl)oxy]-2-methylpyrimidin-4(3H)-one;
$N^1$-(5-{[5-bromo-4-[(2,4-difluorobenzyl)oxy]-2-methyl-6-oxopyrimidin-1(6H)-yl]methyl}-2-methylpyrimidin-4-yl)glycinamide trifluoroacetate;
5-bromo-6-[(2,4-difluorobenzyl)oxy]-2-methyl-3-{[2-(methylthio)pyrimidin-4-yl]methyl}pyrimidin-4(3H)-one;
5-bromo-6-[(2,4-difluorobenzyl)oxy]-2-methyl-3-{[2-(methylsulfonyl)pyrimidin-4-yl]methyl}pyrimidin-4(3H)-one;
4-{[5-bromo-4-[(2,4-difluorobenzyl)oxy]-2-methyl-6-oxopyrimidin-1(6H)-yl]methyl}pyrimidine-2-carbonitrile trifluoroacetate;
6-{[2-(aminomethyl)-4-fluorobenzyl]oxy}-5-bromo-3-(2,6-difluorophenyl)-2-methylpyrimidin-4(3H)-one trifluoroacetate;
5-bromo-6-[(2,4-difluorobenzyl)oxy]-3-[(2-methoxypyrimidin-4-yl)methyl]-2-methylpyrimidin-4(3H)-one trifluoroacetate;
methyl 4-([5-bromo-4-[(2,4-difluorobenzyl)oxy]-2-methyl-6-oxopyrimidin-1(6H)-yl]methyl)pyrimidine-2-carboxylate trifluoroacetate;
5-bromo-6-[(2,4-difluorobenzyl)oxy]-3-[(2-hydroxypyrimidin-4-yl)methyl]-2-methylpyrimidin-4(3H)-one trifluoroacetate;
4-{[5-bromo-4-[(2,4-difluorobenzyl)oxy]-2-methyl-6-oxopyrimidin-1(6H)-yl]methyl}pyrimidine-2-carboxamide trifluoroacetate;
methyl [(4-{[5-bromo-4-[(2,4-difluorobenzyl)oxy]-2-methyl-6-oxopyrimidin-1(6H)-yl]methyl}pyrimidin-2-yl)methyl]carbamate;
3-benzyl-6-[2,6-(dichlorobenzyl)oxy]pyrimidin-4(3H)-one;
5-bromo-6-[(2,4-difluorobenzyl)oxy]-2-methyl-3-[(5-methylpyrazin-2-yl)methyl]pyrimidin-4(3H)-one;
5-bromo-6-[(2,4-difluorobenzyl)oxy]-2-methyl-3-(pyrazin-2-ylmethyl)pyrimidin-4(3H)-one;
5-bromo-6-[(2,4-difluorobenzyl)oxy]-3-{[5-(hydroxymethyl)pyrazin-2-yl]methyl}-2-methylpyrimidin-4(3H)-one;
5-bromo-6-[(2,4-difluorobenzyl)oxy]-3-{(5-[(dimethylamino)methyl]pyrazin-2-yl}methyl)-2-methylpyrimidin-4(3H)-one trifluoroacetate;
5-bromo-6-[(2,4-difluorobenzyl)oxy]-3-[(5-{[(2-hydroxyethyl)(methyl)amino]-methyl}pyrazin-2-yl)methyl]-2-methylpyrimidin-4(3H)-one trifluoroacetate;
5-bromo-6-[(2,4-difluorobenzyl)oxy]-2-methyl-3-({5-[(4-methylpiperazin-1-yl)carbonyl]pyrazin-2-yl}methyl)pyrimidin-4(3H)-one trifluoroacetate;
5-bromo-6-[(2,4-difluorobenzyl)oxy]-2-methyl-3-({5-[(4-methylpiperazin-1-yl)carbonyl]pyrazin-2-yl}methyl)pyrimidin-4(3H)-one;
5-{[5-bromo-4-[(2,4-difluorobenzyl)oxy]-2-methyl-6-oxopyrimidin-1(6H)-yl]methyl}-N-(2-hydroxyethyl)-N-methylpyrazine-2-carboxamide;
5-{[5-bromo-4-[(2,4-difluorobenzyl)oxy]-2-methyl-6-oxopyrimidin-1(6H)-yl]methyl}-N-(2,3-dihydroxypropyl)pyrazine-2-carboxamide;
5-{[5-bromo-4-[(2,4-difluorobenzyl)oxy]-2-methyl-6-oxopyrimidin-1(6H)-yl]methyl}-N-(2-hydroxyethyl)pyrazine-2-carboxamide;
3-Benzyl-5-bromo-6-[2,6-(dichlorobenzyl)oxy]pyrimidin-4(3H)-one;
5-bromo-6-[(2,4-difluorobenzyl)oxy]-3-{[5-(methoxymethyl)pyrazin-2-yl]methyl}-2-methylpyrimidin-4(3H)-one;
5-bromo-6-[(2,4-difluorobenzyl)oxy]-3-({5-[(2-methoxyethoxy)methyl]pyrazin-2-yl}methyl)-2-methylpyrimidin-4(3H)-one;
(5-{[5-bromo-4-[(2,4-difluorobenzyl)oxy]-2-methyl-6-oxopyrimidin-1(6H)-yl]methyl}pyrazin-2-yl)methyl carbamate;
3-benzyl-5-bromo-4-oxo-3,4-dihydropyrimidin-6-yl methyl (phenyl)carbamate;
6-(benzyloxy)-5-ethynyl-3-(3-fluorobenzyl)pyrimidin-4(3H)-one;
6-(benzylamino)-5-bromo-3-(3-fluorobenzyl)pyrimidin-4(3H)-one;
6-(benzyloxy)-3-(3-fluorobenzyl)-5-methylpyrimidin-4(3H)-one;
3-(3-fluorobenzyl)-6-[(4-fluorobenzyl)oxy]-5-iodopyrimidin-4(3H)-one;
3-(3-fluorobenzyl)-6-[(4-fluorobenzyl)oxy]-5-methylpyrimidin-4(3H)-one;
3-benzyl-5-bromo-6-[(2,4-difluorobenzyl)oxy]-2-methylpyrimidin-4(3H)-one;
3-benzyl-6-[(2-chlorobenzyl)oxy]pyrimidin-4(3H)-one;

N-[5-bromo-1-(3-fluorobenzyl)-6-oxo-1,6-dihydropyrimidin-4-yl]-4-fluorobenzamide;
5-chloro-6-[(2,4-difluorobenzyl)oxy]-3-(2,6-difluorophenyl)-2-methylpyrimidin-4(3H)-one;
5-bromo-3-(4-fluorobenzyl)-6-[(4-fluorobenzyl)amino]-2-methylpyrimidin-4(3H)-one;
5-bromo-3-(cyclopropylmethyl)-6-[(2,4-difluorobenzyl)oxy]-2-methylpyrimidin-4(3H)-one;
5-bromo-6-[(2,4-difluorobenzyl)oxy]-2-methyl-3-(pyridin-4-ylmethyl)pyrimidin-4(3H)-one;
5-bromo-6-[(2,4-difluorobenzyl)oxy]-2-methyl-3-(pyridin-3-ylmethyl)pyrimidin-4(3H)-one;
3-Benzyl-5-bromo-6-[(2-chlorobenzyl)oxy]pyrimidin-4(3H)-one;
5-bromo-6-[(2,4-difluorobenzyl)oxy]-2-methyl-3-(pyridin-2-ylmethyl)pyrimidin-4(3H)-one;
5-bromo-6-[2-(4-fluorophenyl)ethyl]-2-methyl-3-(pyridin-3-ylmethyl)pyrimidin-4(3H)-one;
3-benzyl-5-bromo-6-[(4-methylbenzyl)oxy]pyrimidin-4(3H)-one;
5-bromo-6-[2-(4-fluorophenyl)ethyl]-2-methyl-3-(pyridin-4-ylmethyl)pyrimidin-4(3H)-one;
5-chloro-6-[(2,4-difluorobenzyl)oxy]-2-methyl-3-(pyridin-3-ylmethyl)pyrimidin-4(3H)-one;
3-[(4-amino-2-methylpyrimidin-5-yl)methyl]-5-bromo-2-methyl-6-[(2,4,6-trifluorobenzyl)oxy]pyrimidin-4(3H)-one trifluoroacetate;
5-bromo-6-[(2,4-difluorobenzyl)oxy]-2-methyl-3-{[2-methyl-4-(methylamino)pyrimidin-5-yl]methyl}pyrimidin-4(3H)-one trifluoroacetate;
ethyl N-(5-{[5-bromo-4-[(2,4-difluorobenzyl)oxy]-2-methyl-6-oxopyrimidin-1(6H)-yl]methyl}-2-methylpyrimidin-4-yl)glycinate-trifluoroacetaldehyde (1:1);
N-(5-([5-chloro-4-[(2,4-difluorobenzyl)oxy]-2-methyl-6-oxopyrimidin-1(6H)-yl]methyl)-2-methylpyrimidin-4-yl)-2-hydroxyacetamide trifluoroacetate;
5-chloro-6-[(2,4-difluorobenzyl)oxy]-2-methyl-3-[(5-methylpyrazin-2-yl)methyl]pyrimidin-4(3H)-one;
5-bromo-6-[(2,4-difluorobenzyl)oxy]-2-methyl-3-({5-[(methylamino)methyl]pyrazin-2-yl}methyl)pyrimidin-4(3H)-one trifluoroacetate;
ethyl 5-{[5-chloro-4-[(2,4-difluorobenzyl)oxy]-2-methyl-6-oxopyrimidin-1(6H)-yl]methyl}pyrazine-2-carboxylate;
5-chloro-6-[(2,4-difluorobenzyl)oxy]-3-{[5-(hydroxymethyl)pyrazin-2-yl]methyl}-2-methylpyrimidin-4(3H)-one;
3-Benzyl-6-[(3-chlorobenzyl)oxy]pyrimidin-4(3H)-one;
5-{[5-bromo-4-[(2,4-difluorobenzyl)oxy]-2-methyl-6-oxopyrimidin-1(6H)-yl]methyl}-N,N-dimethylpyrazine-2-carboxamide;
5-{[5-bromo-4-[(2,4-difluorobenzyl)oxy]-2-methyl-6-oxopyrimidin-1(6H)-yl]methyl}-N-methylpyrazine-2-carboxamide;
5-bromo-6-[(2,4-difluorobenzyl)oxy]-3{[5-(1-hydroxy-1-methylethyl)pyrazin-2-yl]methyl}-2-methylpyrimidin-4(3H)-one;
5-{[5-bromo-4-[(2,4-difluorobenzyl)oxy]-2-methyl-6-oxopyrimidin-1(6H)-yl]methyl}-N-(2-methoxyethyl)pyrazine-2-carboxamide;
5-bromo-6-[(2,4-difluorobenzyl)oxy]-2-methyl-3-{[5-(morpholin-4-ylcarbonyl)pyrazin-2-yl]methyl}pyrimidin-4(3H)-one;
5-chloro-6-[(2,4-difluorobenzyl)oxy]-3-({5-[(4-hydroxypiperidin-1-yl)carbonyl]pyrazin-2-yl}methyl)-2-methylpyrimidin-4(3H)-one;
5-{[5-chloro-4-[(2,4-difluorobenzyl)oxy]-2-methyl-6-oxopyrimidin-1(6H)-yl]methyl}-N-(3-hydroxy-2,2-dimethylpropyl)pyrazine-2-carboxamide;
5-{[5-chloro-4-[(2,4-difluorobenzyl)oxy]-2-methyl-6-oxopyrimidin-1(6H)-yl]methyl}-N-(2,2,2-trifluoroethyl)pyrazine-2-carboxamide;
3-allyl-5-bromo-6-[(2,4-difluorobenzyl)oxy]-2-methylpyrimidin-4(3H)-one;
3-allyl-5-chloro-6-[(2,4-difluorobenzyl)oxy]-2-methylpyrimidin-4(3H)-one;
3-benzyl-6-[benzylthio]-5-bromopyrimidin-4(3H)-one;
methyl (2E)-4-[5-bromo-4-[(2,4-difluorobenzyl)oxy]-2-methyl-6-oxopyrimidin-1(6H)-yl]but-2-enoate;
5-bromo-6-[(2,4-difluorobenzyl)oxy]-2-methyl-3-prop-2-ynylpyrimidin-4(3H)-one;
6-[(2,4-difluorobenzyl)oxy]-2-(hydroxymethyl)-3-(pyridin-3-ylmethyl)pyrimidin-4(3H)-one;
5-bromo-6-[(2,4-difluorobenzyl)oxy]-2-(hydroxymethyl)-3-(pyridin-3-ylmethyl)pyrimidin-4(3H)-one;
5-bromo-6-[(2,4-difluorobenzyl)oxy]-2-[(dimethylamino)methyl]-3-(pyridin-3-ylmethyl)pyrimidin-4(3H)-one;
5-bromo-6-[(2,4-difluorobenzyl)oxy]-3-(2,6-difluorophenyl)-2-(hydroxymethyl)pyrimidin-4(3H)-one;
5-chloro-6-[(2,4-difluorobenzyl)oxy]-3-(2,6-difluorophenyl)-2-(hydroxymethyl)pyrimidin-4(3H)-one;
5-bromo-4-[(2,4-difluorobenzyl)oxy]-1-(2,6-difluorophenyl)-6-oxo-1,6-dihydropyrimidine-2-carbaldehyde;
5-bromo-6-[(2,4-difluorobenzyl)oxy]-3-(2,6-difluorophenyl)-2-[(dimethylamino)methyl]pyrimidin-4(3H)-one;
5-bromo-6-[(2,4-difluorobenzyl)oxy]-3-(2,6-difluorophenyl)-2-(morpholin-4-ylmethyl)pyrimidin-4(3H)-one;
3-Benzyl-5-bromo-6-{[2-(trifluoromethyl)benzyl]oxy}pyrimidin-4(3H)-one;
5-bromo-6-[(2,4-difluorobenzyl)oxy]-3-(2,6-difluorophenyl)-2-{[(2-methoxyethyl)amino]methyl}pyrimidin-4(3H)-one;
5-bromo-4-[(2,4-difluorobenzyl)oxy]-1-(2,6-difluorophenyl)-6-oxo-1,6-dihydropyrimidine-2-carboxylic acid;
methyl 4-[5-bromo-4-[(2,4-difluorobenzyl)oxy]-2-methyl-6-oxopyrimidin-1(6H)-yl)]-3-methylbenzoate;
5-bromo-6-[(2,4-difluorobenzyl)oxy]-2-methyl-3-(2-methyl-4-vinylphenyl)pyrimidin-4(3H)-one;
5-bromo-6-[(2,4-difluorobenzyl)oxy]-3-[4-(1,2-dihydroxyethyl)-2-methylphenyl]-2-methylpyrimidin-4(3H)-one;
methyl 3-[5-bromo-4-[(2,4-difluorobenzyl)oxy]-2-methyl-6-oxopyrimidin-1(6H)-yl]-4-chlorobenzoate;
3-benzyl-6-(benzyloxy)-5-iodopyrimidin-4(3H)-one;
3-[5-bromo-4-[(2,4-difluorobenzyl)oxy]-2-methyl-6-oxopyrimidin-1(6H)-yl]-4-chlorobenzoic acid;
5-bromo-6-[(2,4-difluorobenzyl)oxy]-3-[5-(hydroxymethyl)-2-methylphenyl]-2-methylpyrimidin-4(3H)-one;
5-chloro-6-[(2,4-difluorobenzyl)oxy]-3-[5-(hydroxymethyl)-2-methylphenyl]-2-methylpyrimidin-4(3H)-one;
5-bromo-6-[(2,4-difluorobenzyl)oxy]-3-[5-(hydroxymethyl)-2-methylphenyl]-2-methylpyrimidin-4(3H)-one;
5-bromo-6-[(2,4-difluorobenzyl)oxy]-3-{5-[(dimethylamino)methyl]-2-methylphenyl}-2-methylpyrimidin-4(3H)-one hydrochloride;
5-bromo-6-[(2,4-difluorobenzyl)oxy]-3-(5-[(isopropylamino)methyl]-2-methylphenyl)-2-methylpyrimidin-4(3H)-one hydrochloride;
3-[5-bromo-4-[(2,4-difluorobenzyl)oxy]-2-methyl-6-oxopyrimidin-1(6H)-yl]-N-(2-hydroxyethyl)-4-methylbenzamide;
3-benzyl-6-(benzyloxy)-5-vinylpyrimidin-4(3H)-one;

5-bromo-6-[(2,4-difluorobenzyl)oxy]-3-[5-(1-hydroxy-1-methylethyl)-2-methylphenyl]-2-methylpyrimidin-4(3H)-one;

methyl 3-[5-chloro-4-[(2,4-difluorobenzyl)oxy]-2-methyl-6-oxopyrimidin-1(6H)-yl]-4-methylbenzoate;

methyl 4-[5-bromo-4-[(2,4-difluorobenzyl)oxy]-2-methyl-6-oxopyrimidin-1(6H)-yl]-3-chlorobenzoate;

5-bromo-6-[(2,4-difluorobenzyl)amino]-3-(3-fluorobenzyl)pyrimidin-4(3H)-one;

5-bromo-3-(3-fluorobenzyl)-6-{[3-(trifluoromethyl)benzyl]amino}pyrimidin-4(3H)-one;

5-bromo-3-(3-fluorobenzyl)-6-{[4-fluoro-2-(trifluoromethyl)benzyl]amino}pyrimidin-4(3H)-one;

5-bromo-6-[(4-chloro-2-fluorobenzyl)amino]-3-(3-fluorobenzyl)pyrimidin-4(3H)-one;

5-bromo-3-(3-fluorobenzyl)-6-[(3-fluorobenzyl)amino]pyrimidin-4(3H)-one;

3-benzyl-6-(benzyloxy)-5-ethylpyrimidin-4(3H)-one;

5-bromo-6-[(2,4-difluorobenzyl)amino]-2-methyl-3-(pyridin-4-ylmethyl)pyrimidin-4(3H)-one;

5-bromo-6-[(2,4-difluorobenzyl)amino]-2-methyl-3-(pyridin-3-ylmethyl)pyrimidin-4(3H)-one;

5-bromo-6-[(2,4-difluorobenzyl)amino]-3-(2,6-difluorophenyl)-2-methylpyrimidin-4(3H)-one;

5-chloro-6-[(2,4-difluorobenzyl)amino]-3-(2,6-difluorophenyl)-2-methylpyrimidin-4(3H)-one;

3-{[5-chloro-4-[(2,4-difluorobenzyl)amino]-2-methyl-6-oxopyrimidin-1(6H)-yl]methyl}benzonitrile;

4-{[5-chloro-4-[(2,4-difluorobenzyl)amino]-2-methyl-6-oxopyrimidin-1(6H)-yl]methyl}benzonitrile;

5-bromo-6-[(2,4-difluorobenzyl)oxy]-3-[2-fluoro-5-(hydroxymethyl)phenyl]-2-methylpyrimidin-4(3H)-one;

3-[5-chloro-4-[(2,4-difluorobenzyl)oxy]-2-methyl-6-oxopyrimidin-1(6H)-yl]-4-fluorobenzoic acid;

3-[5-chloro-4-[(2,4-difluorobenzyl)oxy]-2-methyl-6-oxopyrimidin-1(6H)-yl]-4-fluoro-N-methylbenzamide;

5-acetyl-6-(benzyloxy)-3-(2-chlorophenyl)-2-methylpyrimidin-4(3H)-one;

3-[5-bromo-4-[(2,4-difluorobenzyl)oxy]-2-methyl-6-oxopyrimidin-1(6H)-yl]-4-fluorobenzoic acid;

3-benzyl-5-bromo-6-(2-phenylethyl)pyrimidin-4(3H)-one;

3-[5-bromo-4-[(2,4-difluorobenzyl)oxy]-2-methyl-6-oxopyrimidin-1(6H)-yl]-4-methoxybenzoic acid;

3-[5-bromo-4-[(2,4-difluorobenzyl)oxy]-2-methyl-6-oxopyrimidin-1(6H)-yl]-4-methoxy-N-methylbenzamide;

3-[5-bromo-4-[(2,4-difluorobenzyl)oxy]-2-methyl-6-oxopyrimidin-1(6H)-yl]-4-methoxy-N,N-dimethylbenzamide;

3-[5-(aminomethyl)-2-fluorophenyl]-5-chloro-6-[(2,4-difluorobenzyl)oxy]-2-methylpyrimidin-4(3H)-one hydrochloride;

3-[5-chloro-4-[(2,4-difluorobenzyl)oxy]-2-methyl-6-oxopyrimidin-1(6H)-yl]-4-fluoro-N-[2-hydroxy-1-(hydroxymethyl)ethyl]benzamide;

2-({[5-chloro-1-(2,6-difluorophenyl)-2-methyl-6-oxo-1,6-dihydropyrimidin-4-yl]oxy}methyl)-5-fluorobenzonitrile;

6-{[2-(aminomethyl)-4-fluorobenzyl]oxy}-5-chloro-3-(2,6-difluorophenyl)-2-methylpyrimidin-4(3H)-one trifluoroacetate;

5-bromo-3-(3-fluorobenzyl)-6-(2-phenylethyl)pyrimidin-4(3H)-one;

5-bromo-6-[(2,4-difluorobenzyl)oxy]-3-([5-(1-hydroxy-1-methylethyl)pyridin-2-yl]methyl)-2-methylpyrimidin-4(3H)-one;

5-bromo-6-[(2,4-difluorobenzyl)oxy]-3-([5-(hydroxymethyl)pyridin-2-yl]methyl)-2-methylpyrimidin-4(3H)-one;

6-{[5-bromo-4-[(2,4-difluorobenzyl)oxy]-2-methyl-6-oxopyrimidin-1(6H)-yl]methyl}-N-(2-hydroxyethyl)-N-methylnicotinamide;

6-{[5-bromo-4-[(2,4-difluorobenzyl)oxy]-2-methyl-6-oxopyrimidin-1(6H)-yl]methyl}-N-(2-hydroxyethyl)nicotinamide;

6-([5-bromo-4-[(2,4-difluorobenzyl)oxy]-2-methyl-6-oxopyrimidin-1(6H)-yl]methyl)-N,N-dimethylnicotinamide;

5-bromo-6-[(2,4-difluorobenzyl)oxy]-2-methyl-3-[2-(trifluoromethyl)phenyl]pyrimidin-4(3H)-one;

5-bromo-6-[(2,4-difluorobenzyl)oxy]-3-(2,6-difluorophenyl)-2-methyl-1-vinylpyrimidin-4(1H)-one;

5-bromo-6-[(2,4-difluorobenzyl)oxy]-3-(2,6-difluorophenyl)-1-(1,2-dihydroxyethyl)-2-methylpyrimidin-4(1H)-one;

5-bromo-6-[(2,4-difluorobenzyl)oxy]-3-(2,6-difluorophenyl)-1-(hydroxymethyl)-2-methylpyrimidin-4(1H)-one;

6-(benzyloxy)-5-bromo-3-(2,6-difluorophenyl)-2-methylpyrimidin-4(3H)-one;

[5-bromo-6-[(2,4-difluorobenzyl)oxy]-3-(2,6-difluorophenyl)-2-methyl-4-oxo-3,4-dihydropyrimidin-1(2H)-yl]methyl carbamate;

5-bromo-6-[(2,4-difluorobenzyl)oxy]-3-(2,6-difluorophenyl)-2-methyl-4-oxo-3,4-dihydropyrimidine-1(2H)-carbaldehyde;

5-bromo-6-[(2,4-difluorobenzyl)oxy]-3-(2,6-difluorophenyl)-2-methyl-4-oxo-3,4-dihydropyrimidine-1(2H)-carbaldehyde oxime;

5-bromo-6-[(2,4-difluorobenzyl)oxy]-3-(2,6-difluorophenyl)-2-methyl-4-oxo-3,4-dihydropyrimidine-1(2H)-carbonitrile;

6-(benzyloxy)-5-bromo-3-(2,6-difluorophenyl)-1-iodo-2-methylpyrimidin-4(1H)-one;

5-bromo-6-[(2,4-difluorobenzyl)oxy]-3-(2,6-difluorophenyl)-2-methyl-1-oxiran-2-ylpyrimidin-4(1H)-one;

6-(benzylamino)-5-bromo-3-(2,6-difluorophenyl)-1-iodo-2-methylpyrimidin-4(1H)-one;

6-(benzyloxy)-5-ethynyl-3-(3-fluorobenzyl)pyrimidin-4(3H)-one;

5-bromo-6-[(2,4-difluorobenzyl)oxy]-3-(2,6-difluorophenyl)-2-methyl-1-[(E)-2-phenylethenyl]pyrimidin-4(1H)-one;

6-(allylamino)-5-bromo-3-(2,6-difluorophenyl)-1-iodo-2-methylpyrimidin-4(1H)-one;

6-(allylamino)-3-(2,6-difluorophenyl)-1-iodo-2-methylpyrimidin-4(1H)-one;

6-(allylamino)-3-(2,6-difluorophenyl)-1-iodo-2-methylpyrimidin-4(1H)-one;

ethyl 6-[5-bromo-4-[(2,4-difluorobenzyl)oxy]-2-methyl-6-oxopyrimidin-1(6H)-yl]nicotinate;

5-bromo-6-[(2,4-difluorobenzyl)oxy]-5'-(1-hydroxy-1-methylethyl)-2-methyl-4H-3,2'-bipyrimidin-4-one;

5-bromo-6-[(2,4-difluorobenzyl)oxy]-3-(2-furylmethyl)-2-methylpyrimidin-4(3H)-one;

6-(benzylamino)-5-bromo-3-(3-fluorobenzyl)pyrimidin-4(3H)-one;

5-bromo-6-[(2,4-difluorobenzyl)oxy]-2-methyl-3-(thien-2-ylmethyl)pyrimidin-4(3H)-one;

5-bromo-3-(2,6-difluorophenyl)-6-(2-furylmethoxy)-2-methylpyrimidin-4(3H)-one;

5-bromo-3-[2-fluoro-6-(3-furylmethoxy)phenyl]-6-(3-furylmethoxy)-2-methylpyrimidin-4(3H)-one;

5-bromo-3-[2-fluoro-6-(thien-3-ylmethoxy)phenyl]-2-methyl-6-(thien-3-ylmethoxy)pyrimidin-4(3H)-one;

methyl 2-[5-bromo-4-[(2,4-difluorobenzyl)oxy]-2-methyl-6-oxopyrimidin-1(6H)-yl]-4-[(methylamino)carbonyl]benzoate;

3-[5-bromo-4-[(2,4-difluorobenzyl)oxy]-2-methyl-6-oxopyrimidin-1(6H)-yl]-4-(1-hydroxy-1-methylethyl)-N-methylbenzamide;

4{[5-bromo-6-(2-furylmethoxy)-2-methyl-4-oxopyrimidin-3(3H)-yl]methyl}benzamide;

(−)-3-[5-bromo-4-[(2,4-difluorobenzyl)oxy]-2-methyl-6-oxopyrimidin-1(6H)-yl]-N,4-dimethylbenzamide;

(+)-3-[5-bromo-4-[(2,4-difluorobenzyl)oxy]-2-methyl-6-oxopyrimidin-1(6H)-yl]-N,4-dimethylbenzamide;

4-[5-bromo-4-[(2,4-difluorobenzyl)oxy]-2-methyl-6-oxopyrimidin-1(6H)-yl]-3-chlorobenzamide;

5-bromo-3-cyclopropylmethyl-6-(4-fluorobenzyloxy)-3H-pyrimidin-4-one;

3-[5-chloro-4-[(2,4-difluorobenzyl)oxy]-2-methyl-6-oxopyrimidin-1(6H)-yl]-4-methylbenzamide;

3-[5-chloro-4-[(2,4-difluorobenzyl)oxy]-2-methyl-6-oxopyrimidin-1(6H)-yl]-N,4-dimethylbenzamide;

N-{3-[5-chloro-4-[(2,4-difluorobenzyl)oxy]-2-methyl-6-oxopyrimidin-1(6H)-yl]-4-fluorobenzyl}propanamide;

N'-{3-[5-chloro-4-[(2,4-difluorobenzyl)oxy]-2-methyl-6-oxopyrimidin-1(6H)-yl]-4-fluorobenzyl}-N,N-dimethylurea;

N-{3-[5-chloro-4-[(2,4-difluorobenzyl)oxy]-2-methyl-6-oxopyrimidin-1(6H)-yl]-4-fluorobenzyl}-2-hydroxyacetamide;

N-{3-[5-chloro-4-[(2,4-difluorobenzyl)oxy]-2-methyl-6-oxopyrimidin-1(6H)-yl]-4-fluorobenzyl}-2-hydroxy-2-methylpropanamide;

$N^1$-{3-[5-chloro-4-[(2,4-difluorobenzyl)oxy]-2-methyl-6-oxopyrimidin-1(6H)-yl]-4-fluorobenzyl}glycinamide hydrochloride;

3-[5-bromo-4-[(2,4-difluorobenzyl)oxy]-2-methyl-6-oxopyrimidin-1(6H)-yl]-4-fluorobenzamide;

3-[5-bromo-4-[(2,4-difluorobenzyl)oxy]-2-methyl-6-oxopyrimidin-1(6H)-yl]-4-fluoro-N-methylbenzamide;

3-[5-bromo-4-[(2,4-difluorobenzyl)oxy]-2-methyl-6-oxopyrimidin-1(6H)-yl]-4-fluoro-N,N-dimethylbenzamide;

5-bromo-6-[(2,4-difluorobenzyl)oxy]-3-{2-fluoro-5-[(4-methylpiperazin-1-yl)carbonyl]phenyl}-2-methylpyrimidin-4(3H)-one;

methyl 4-[5-bromo-4-[(2,4-difluorobenzyl)oxy]-2-methyl-6-oxopyrimidin-1(6H)-yl]-3-fluorobenzoate;

4-([5-chloro-4-[(2,4-difluorobenzyl)oxy]-2-methyl-6-oxopyrimidin-1(6H)-yl]methyl)benzoic acid;

3-([5-chloro-4-[(2,4-difluorobenzyl)oxy]-2-methyl-6-oxopyrimidin-1(6H)-yl]methyl)benzamide;

3-([5-chloro-4-[(2,4-difluorobenzyl)oxy]-2-methyl-6-oxopyrimidin-1(6H)-yl]methyl)-N,N-dimethylbenzamide;

3-([5-chloro-4-[(2,4-difluorobenzyl)oxy]-2-methyl-6-oxopyrimidin-1(6H)-yl]methyl)-N-(2-hydroxy-2-methylpropyl)benzamide;

N-(4-[5-bromo-4-[(2,4-difluorobenzyl)oxy]-2-methyl-6-oxopyrimidin-1(6H)-yl]benzyl)-2-hydroxyacetamide;

3-[5-chloro-4-[(2,4-difluorobenzyl)oxy]-2-methyl-6-oxopyrimidin-1(6H)-yl]benzamide;

3-(4-aminobenzyl)-5-bromo-6-[(2,4-difluorobenzyl)oxy]-2-methylpyrimidin-4(3H)-one;

3-(3-aminobenzyl)-5-bromo-6-[(2,4-difluorobenzyl)oxy]-2-methylpyrimidin-4(3H)-one;

N-(4-{[5-bromo-4-[(2,4-difluorobenzyl)oxy]-2-methyl-6-oxopyrimidin-1(6H)-yl]methyl}phenyl)acetamide;

N-(3-{[5-bromo-4-[(2,4-difluorobenzyl)oxy]-2-methyl-6-oxopyrimidin-1(6H)-yl]methyl}phenyl)acetamide;

N-(4-{[5-bromo-4-[(2,4-difluorobenzyl)oxy]-2-methyl-6-oxopyrimidin-1(6H)-yl]methyl}benzyl)-N'-methylurea;

N-(4-{[5-bromo-4-[(2,4-difluorobenzyl)oxy]-2-methyl-6-oxopyrimidin-1(6H)-yl]methyl}benzyl)-N'-(2-hydroxy-2-methylpropyl)urea;

N-(4-{[5-bromo-4-[(2,4-difluorobenzyl)oxy]-2-methyl-6-oxopyrimidin-1(6H)-yl]methyl}benzyl)piperidine-1-carboxamide;

N-(4-{[5-bromo-4-[(2,4-difluorobenzyl)oxy]-2-methyl-6-oxopyrimidin-1(6H)-yl]methyl}benzyl)morpholine-4-carboxamide;

N-(4-{[5-bromo-4-[(2,4-difluorobenzyl)oxy]-2-methyl-6-oxopyrimidin-1(6H)-yl]methyl}benzyl)piperazine-1-carboxamide;

N-(4-{[5-bromo-4-[(2,4-difluorobenzyl)oxy]-2-methyl-6-oxopyrimidin-1(6H)-yl]methyl}benzyl)-N'-(2-hydroxyethyl)urea;

N'-(4-{[5-bromo-4-[(2,4-difluorobenzyl)oxy]-2-methyl-6-oxopyrimidin-1(6H)-yl]methyl}benzyl)-N,N-dimethylurea;

N-(4-{[5-bromo-4-[(2,4-difluorobenzyl)oxy]-2-methyl-6-oxopyrimidin-1(6H)-yl]methyl}benzyl)-4-hydroxypiperidine-1-carboxamide;

4-{[5-bromo-4-[(2,4-difluorobenzyl)oxy]-2-methyl-6-oxopyrimidin-1(6H)-yl]methyl}-N,N-dimethylbenzenesulfonamide;

4-{[5-bromo-4-[(2,4-difluorobenzyl)oxy]-2-methyl-6-oxopyrimidin-1(6H)-yl]methyl}-N-(2-hydroxyethyl)benzenesulfonamide;

4-{[S-bromo-4-[(2,4-difluorobenzyl)oxy]-2-methyl-6-oxopyrimidin-1(6H)-yl]methyl}-N-(2-hydroxy-2-methylpropyl)benzenesulfonamide;

5-chloro-6-(2,4-difluorobenzyloxy)-2-methyl-3-(1H-pyrazol-3-ylmethyl)-3H-pyrimidin-4-one;

5-chloro-6-(2,4-difluorobenzyloxy)-2-methyl-3-(2,3-dihydro-1H-indol-5-ylmethyl)-3H-pyrimidin-4-one;

5-{[5-chloro-4-[(2,4-difluorobenzyl)oxy]-2-methyl-6-oxopyrimidin-1(6H)-yl]methyl}-1,3-dihydro-2H-indol-2-one;

N-[(5-{[5-bromo-4-[(2,4-difluorobenzyl)oxy]-2-methyl-6-oxopyrimidin-1(6H)-yl]methyl}pyrazin-2-yl)methyl]-N-methylmethanesulfonamide;

methyl [(5-{[5-bromo-4-[(2,4-difluorobenzyl)oxy]-2-methyl-6-oxopyrimidin-1(6H)-yl]methyl}pyrazin-2-yl)methyl]methylcarbamate;

N-[(5-{[5-bromo-4-[(2,4-difluorobenzyl)oxy]-2-methyl-6-oxopyrimidin-1(6H)-yl]methyl}pyrazin-2-yl)methyl]-2-hydroxy-N,2-dimethylpropanamide;

5-{[5-bromo-4-[(2,4-difluorobenzyl)oxy]-2-methyl-6-oxopyrimidin-1(6H)-yl]methyl}-N-(2-hydroxy-2-methylpropyl)pyrazine-2-carboxamide;

3-[(5-Aminopyrazin-2-yl)methyl]-5-bromo-6-[(2,4-difluorobenzyl)oxy]-2-methylpyrimidin-4(3H)-one trifluoroacetate;

5-bromo-6-[(2,4-difluorobenzyl)oxy]-2-methyl-3-[(3-methyl-1,2,4-triazin-6-yl)methyl]pyrimidin-4(3H)-one trifluoroacetate;

5-bromo-6-[(2,4-difluorobenzyl)oxy]-3-(1H-indazol-5-yl)-2-methylpyrimidin-4(3H)-one;

5-bromo-6-[(2,4-difluorobenzyl)oxy]-3-(1H-indazol-6-yl)-2-methylpyrimidin-4(3H)-one;

methyl (2-{[(5-bromo-2-methyl-1-{2-methyl-5-[(methylamino)carbonyl]phenyl}-6-oxo-1,6-dihydropyrimidin-4-yl)oxy]methyl}-5-fluorobenzyl)carbamate;

methyl [2-({[5-bromo-1-(5-{[(2-hydroxyethyl)amino]carbonyl}-2-methylphenyl)-2-methyl-6-oxo-1,6-dihydropyrimidin-4-yl]oxy}methyl)-5-fluorobenzyl]carbamate;

methyl [2-({[5-bromo-1-(5-{[(2-hydroxy-2-methylpropyl)amino]carbonyl}-2-methylphenyl)-2-methyl-6-oxo-1,6-dihydropyrimidin-4-yl]oxy}methyl)-5-fluorobenzyl]carbamate;
methyl [2-({[5-bromo-1-(5-{[(2-methoxyethyl)amino]carbonyl}-2-methylphenyl)-2-methyl-6-oxo-1,6-dihydropyrimidin-4-yl]oxy}methyl)-5-fluorobenzyl]carbamate;
methyl {2-[({1-[5-(aminocarbonyl)-2-methylphenyl]-5-bromo-2-methyl-6-oxo-1,6-dihydropyrimidin-4-yl}oxy)methyl]-5-fluorobenzyl}carbamate;
N-[2-({[5-chloro-1-(2,6-difluorophenyl)-2-methyl-6-oxo-1,6-dihydropyrimidin-4-yl]oxy}methyl)-5-fluorobenzyl]-N'-phenylurea;
3-thienylmethyl [2-({[5-chloro-1-(2,6-difluorophenyl)-2-methyl-6-oxo-1,6-dihydropyrimidin-4-yl]oxy}methyl)-5-fluorobenzyl]carbamate;
ethyl (2-{[(5-bromo-2-methyl-1-{2-methyl-5-[(methylamino)carbonyl]phenyl}-6-oxo-1,6-dihydropyrimidin-4-yl)oxy]methyl}-5-fluorobenzyl)carbamate;
3-[5-bromo-4-{[2-({[(cyclopropylamino)carbonyl]amino}methyl)-4-fluorobenzyl]oxy}-2-methyl-6-oxopyrimidin-1(6H)-yl]-N,4-dimethylbenzamide;
2-[2-({[5-bromo-1-(2,6-difluorophenyl)-2-methyl-6-oxo-1,6-dihydropyrimidin-4-yl]oxy}methyl)-5-fluorophenoxy]-N-ethylacetamide;
methyl 3-[2-[(acetyloxy)methyl]-5-bromo-4-[(2,4-difluorobenzyl)oxy]-6-oxopyrimidin-1(6H)-yl]-4-methylbenzoate;
3-[5-bromo-4-[(2,4-difluorobenzyl)oxy]-2-(hydroxymethyl)-6-oxopyrimidin-1(6H)-yl]-4-methylbenzoic acid;
3-[5-bromo-4-[(2,4-difluorobenzyl)oxy]-2-(hydroxymethyl)-6-oxopyrimidin-1(6H)-yl]-N-(2-hydroxyethyl)-4-methylbenzamide;
3-[5-bromo-4-[(2,4-difluorobenzyl)oxy]-2-(hydroxymethyl)-6-oxopyrimidin-1(6H)-yl]-N,4-dimethylbenzamide;
3-[5-bromo-4-[(2,4-difluorobenzyl)oxy]-2-(hydroxymethyl)-6-oxopyrimidin-1(6H)-yl]-4-methylbenzamide;
(5-bromo-4-[(2,4-difluorobenzyl)oxy]-1-{2-methyl-5-[(methylamino)carbonyl]phenyl}-6-oxo-1,6-dihydropyrimidin-2-yl)methyl acetate;
(2E)-4-[5-bromo-4-[(2,4-difluorobenzyl)oxy]-2-methyl-6-oxopyrimidin-1(6H)-yl]-N-methylbut-2-enamide;
methyl 5-{[5-bromo-4-[(2,4-difluorobenzyl)oxy]-2-methyl-6-oxopyrimidin-1(6H)-yl]methyl}-2-furoate;
3-[5-bromo-4-[(2,4-difluorobenzyl)oxy]-2-methyl-6-oxopyrimidin-1(6H)-yl]-4-(hydroxymethyl)-N-methylbenzamide;
2-[5-bromo-4-[(2,4-difluorobenzyl)oxy]-2-methyl-6-oxopyrimidin-1(6H)-yl]-N,N'-dimethylterephthalamide;
2-[5-bromo-4-[(2,4-difluorobenzyl)oxy]-2-methyl-6-oxopyrimidin-1(6H)-yl]-N'-methylterephthalamide;
methyl 4-(aminocarbonyl)-2-[5-bromo-4-[(2,4-difluorobenzyl)oxy]-2-methyl-6-oxopyrimidin-1(6H)-yl]benzoate;
2-[5-bromo-4-[(2,4-difluorobenzyl)oxy]-2-methyl-6-oxopyrimidin-1(6H)-yl]-$N_1,N_1,N^4$-trimethylterephthalamide;
2-[5-bromo-4-[(2,4-difluorobenzyl)oxy]-2-methyl-6-oxopyrimidin-1(6H)-yl]-4-[(methylamino)carbonyl]benzyl carbamate;
5-bromo-6-[(2,4-difluorobenzyl)oxy]-3-(2,6-difluoro-4-vinylphenyl)-2-methylpyrimidin-4(3H)-one;
5-bromo-6-[(2,4-difluorobenzyl)oxy]-3-[4-(1,2-dihydroxyethyl)-2,6-difluorophenyl]-2-methylpyrimidin-4(3H)-one;
4-[5-bromo-4-[(2,4-difluorobenzyl)oxy]-2-methyl-6-oxopyrimidin-1(6H)-yl]-3,5-difluorobenzaldehyde;
4-[5-bromo-4-[(2,4-difluorobenzyl)oxy]-2-methyl-6-oxopyrimidin-1(6H)-yl]-3,5-difluorobenzyl carbamate;
5-chloro-6-[(2,4-difluorobenzyl)oxy]-2-methyl-3-[(5-methylpyrazin-2-yl)methyl]pyrimidin-4(3H)-one;
5-chloro-6-[(2,4-difluorobenzyl)oxy]-3-{[5-(hydroxymethyl)pyrazin-2-yl]methyl}-2-methylpyrimidin-4(3H)-one;
5-bromo-6-[(2,4-difluorobenzyl)oxy]-3-(2,3-dihydro-1H-indol-5-ylmethyl)pyrimidin-4(3H)-one;
5-bromo-6-[(2,4-difluorobenzyl)oxy]-3-[(1-glycoloyl-2,3-dihydro-1H-indol-5-yl)methyl]-2-methylpyrimidin-4(3H)-one;
5-bromo-6-[(2,4-difluorobenzyl)oxy]-2-methyl-3-(1H-pyrazol-3-ylmethyl)pyrimidin-4(3H)-one;
3-[5-chloro-4-[(2,4-difluorobenzyl)oxy]-2-methyl-6-oxopyrimidin-1(6H)-yl]-N,4-dimethylbenzamide;
3-[5-chloro-4-[(2,4-difluorobenzyl)oxy]-2-methyl-6-oxopyrimidin-1(6H)-yl]-4-fluoro-N-methylbenzamide;
4-chloro-3-[5-chloro-4-[(2,4-difluorobenzyl)oxy]-2-methyl-6-oxopyrimidin-1(6H)-yl]-N-methylbenzamide;
3-[5-chloro-4-[(2,4-difluorobenzyl)oxy]-2-methyl-6-oxopyrimidin-1(6H)-yl]-4-fluorobenzamide;
4-[5-chloro-4-[(2,4-difluorobenzyl)oxy]-2-methyl-6-oxopyrimidin-1(6H)-yl]-N,3-dimethylbenzamide;
5-chloro-6-[(2,4-difluorobenzyl)oxy]-3-[4-(1,2-dihydroxyethyl)-2-methylphenyl]-2-methylpyrimidin-4(3H)-one;
N-(4-{[5-chloro-4-[(2,4-difluorobenzyl)oxy]-2-methyl-6-oxopyrimidin-1(6H)-yl]methyl}phenyl)-2-hydroxyacetamide;
N-(4-{[5-chloro-4-[(2,4-difluorobenzyl)oxy]-2-methyl-6-oxopyrimidin-1(6H)-yl]methyl}benzyl)-1-hydroxycyclopropanecarboxamide;
N-(4-{[5-chloro-4-[(2,4-difluorobenzyl)oxy]-2-methyl-6-oxopyrimidin-1(6H)-yl]methyl}benzyl)-2-hydroxyacetamide;
N-(4-{[5-chloro-4-[(2,4-difluorobenzyl)oxy]-2-methyl-6-oxopyrimidin-1(6H)-yl]methyl}phenyl)acetamide;
ethyl [2-({[5-bromo-1-(2,6-difluorophenyl)-2-methyl-6-oxo-1,6-dihydropyrimidin-4-yl]oxy}methyl)-5-fluorobenzyl]carbamate;
3-[5-bromo-4-[(2,4-difluorobenzyl)oxy]-2-(2-hydroxyethyl)-6-oxopyrimidin-1(6H)-yl]-N,4-dimethylbenzamide;
5-bromo-6-[(2,4-difluorobenzyl)oxy]-3-[5-(2-hydroxyethyl)-2-methylphenyl]-2-methylpyrimidin-4(3H)-one;
5-[5-bromo-4-[(2,4-difluorobenzyl)oxy]-2-methyl-6-oxopyrimidin-1(6H)-yl]-2-(2-hydroxyethyl)-N,4-dimethylbenzamide;
3-[2-[(acetylamino)methyl]-5-bromo-4-[(2,4-difluorobenzyl)oxy]-6-oxopyrimidin-1(6H)-yl]-N,4-dimethylbenzamide;
3-allyl-5-bromo-6-[(2,4-difluorobenzyl)oxy]-2-(1-methylpiperidin-4-yl)pyrimidin-4(3H)-one;
5-bromo-4-[(2,4-difluorobenzyl)oxy]-2,4'-dimethyl-2'-(methylsulfonyl)-6H-1,5'-bipyrimidin-6-one;
5-bromo-4-[(2,4-difluorobenzyl)oxy]-2,4'-dimethyl-6-oxo-6H-1,5'-bipyrimidine-2'-carbonitrile;
2'-(aminomethyl)-5-bromo-4-[(2,4-difluorobenzyl)oxy]-2,4'-dimethyl-6H-1,5'-bipyrimidin-6-one;
5-bromo-4-[(2,4-difluorobenzyl)oxy]-2'-[(dimethylamino)methyl]-2,4'-dimethyl-6H-1,5'-bipyrimidin-6-one;
N-({5-bromo-4-[(2,4-difluorobenzyl)oxy]-2,4'-dimethyl-6-oxo-6H-1,5'-bipyrimidin-2'-yl}methyl)-2-hydroxyacetamide;
5-bromo-4-[(2,4-difluorobenzyl)oxy]-2,4'-dimethyl-6-oxo-6H-1,5'-bipyrimidine-2'-carboxylic acid;

5-bromo-4-[(2,4-difluorobenzyl)oxy]-2,4'-dimethyl-6-oxo-6H-1,5'-bipyrimidine-2'-carboxamide;

tert-butyl (3-{[5-bromo-4-[(4-fluorobenzyl)oxy]-6-oxopyrimidin-1(6H)-yl]methyl}benzyl)carbamate;

5-bromo-4-[(2,4-difluorobenzyl)oxy]-N,2,4'-trimethyl-6-oxo-6H-1,5'-bipyrimidine-2'-carboxamide;

N-(3-{[5-chloro-4-[(2,4-difluorobenzyl)oxy]-2-methyl-6-oxopyrimidin-1(6H)-yl]methyl}benzyl)-2-hydroxyacetamide;

N-(3-{[5-chloro-4-[(2,4-difluorobenzyl)oxy]-2-methyl-6-oxopyrimidin-1(6H)-yl]methyl}benzyl)-1-hydroxycyclopropanecarboxamide;

4-{[5-bromo-4-[(2,4-difluorobenzyl)oxy]-2-methyl-6-oxopyrimidin-1(6H)-yl]methyl}benzyl carbamate;

2-[(4-{[5-bromo-4-[(2,4-difluorobenzyl)oxy]-2-methyl-6-oxopyrimidin-1(6H)-yl]methyl}phenyl)amino]-1-methyl-2-oxoethyl acetate;

2-[(4-{[5-bromo-4-[(2,4-difluorobenzyl)oxy]-2-methyl-6-oxopyrimidin-1(6H)-yl]methyl}phenyl)amino]-1,1-dimethyl-2-oxoethyl acetate;

{1-[3-(aminocarbonyl)phenyl]-5-chloro-4-[(2,4-difluorobenzyl)oxy]-6-oxo-1,6-dihydropyrimidin-2-yl}methyl acetate 5-bromo-6-[(2,4-difluorobenzyl)oxy]-2-methyl-3-{[2-(methylthio)pyrimidin-5-yl]methyl}pyrimidin-4(3H)-one;

5-bromo-6-[(2,4-difluorobenzyl)oxy]-2-methyl-3-{[2-(methylsulfonyl)pyrimidin-5-yl]methyl}pyrimidin-4(3H)-one;

ethyl [2-({[5-bromo-1-(5-{[(2-hydroxyethyl)amino]carbonyl}-2-methylphenyl)-2-methyl-6-oxo-1,6-dihydropyrimidin-4-yl]oxy}methyl)-5-fluorobenzyl]carbamate;

3-(3-Aminomethylbenzyl)-5-bromo-6-(4-fluorobenzyloxy)-3H-pyrimidin-4-one;

5-bromo-6-[(2,4-difluorobenzyl)oxy]-3-[5-(1H-imidazol-2-yl)-2-methylphenyl]-2-methylpyrimidin-4(3H)-one trifluoroacetate;

5-bromo-6-[(2,4-difluorobenzyl)oxy]-3-[5-(5-hydroxy-1H-pyrazol-3-yl)-2-methylphenyl]-2-methylpyrimidin-4(3H)-one;

5-bromo-6-[(2,4-difluorobenzyl)oxy]-3-[5-(5-hydroxyisoxazol-3-yl)-2-methylphenyl]-2-methylpyrimidin-4(3H)-one;

3-[4-{[2-({[(cyclopropylamino)carbonyl]amino}methyl)-4-fluorobenzyl]oxy}-2-methyl-6-oxopyrimidin-1(6H)-yl]-N,4-dimethylbenzamide;

methyl 4-{[4-[(2,4-difluorobenzyl)oxy]-2-oxo-2H-pyrido[1,2-a]pyrimidin-1(9aH)-yl]methyl}benzoate;

5-{[5-bromo-4-[(2,4-difluorobenzyl)oxy]-2-methyl-6-oxopyrimidin-1(6H)-yl]methyl}-2-furamide;

5-[5-bromo-4-[(2,4-difluorobenzyl)oxy]-2-methyl-6-oxopyrimidin-1(6H)-yl]-2-furamide;

3-[3,5-bis(hydroxymethyl)phenyl]-5-bromo-6-[(2,4-difluorobenzyl)oxy]-2-methylpyrimidin-4(3H)-one;

5-[5-bromo-4-[(2,4-difluorobenzyl)oxy]-2-methyl-6-oxopyrimidin-1(6H)-yl]isophthalamide;

3-[3,5-bis(1-hydroxy-1-methylethyl)phenyl]-5-bromo-6-[(2,4-difluorobenzyl)oxy]-2-methylpyrimidin-4(3H)-one;

methyl 2-{[5-bromo-4-[(4-fluorobenzyl)oxy]-6-oxopyrimidin-1(6H)-yl]methyl}benzoate;

5-bromo-6-[(2,4-difluorobenzyl)oxy]-3-[4-(hydroxymethyl)phenyl]-2-methylpyrimidin-4(3H)-one;

5-bromo-6-[(2,4-difluorobenzyl)oxy]-3-[4-(1-hydroxy-1-methylethyl)phenyl]-2-methylpyrimidin-4(3H)-one 3-(5-amino-2-fluorophenyl)-5-bromo-6-[(2,4-difluorobenzyl)oxy]-2-methylpyrimidin-4(3H)-one hydrochloride;

N-{3-[5-bromo-4-[(2,4-difluorobenzyl)oxy]-2-methyl-6-oxopyrimidin-1(6H)-yl]-4-fluorophenyl}-2-hydroxyacetamide;

N-{3-[5-bromo-4-[(2,4-difluorobenzyl)oxy]-2-methyl-6-oxopyrimidin-1(6H)-yl]-4-fluorophenyl}-2-hydroxy-2-methylpropanamide;

4-[5-bromo-4-[(2,4-difluorobenzyl)oxy]-2-methyl-6-oxopyrimidin-1(6H)-yl]-3-fluoro-N,N-dimethylbenzamide;

5-chloro-6-[(2,4-difluorobenzyl)oxy]-3-[(1-glycoloyl-2,3-dihydro-1H-indol-5-yl)methyl]-2-methylpyrimidin-4(3H)-one;

5-chloro-6-[(2,4-difluorobenzyl)oxy]-3-{[1-(2-hydroxy-2-methylpropanoyl)-2,3-dihydro-1H-indol-5-yl]methyl}-2-methylpyrimidin-4(3H)-one;

5-chloro-6-[(2,4-difluorobenzyl)oxy]-3-{[1-(methoxyacetyl)-2,3-dihydro-1H-indol-5-yl]methyl}-2-methylpyrimidin-4(3H)-one;

5-{[5-chloro-4-[(2,4-difluorobenzyl)oxy]-2-methyl-6-oxopyrimidin-1(6H)-yl]methyl}-N,N-dimethylindoline-1-carboxamide;

5-bromo-6-(4-fluorobenzyloxy)-3-(2-hydroxymethylbenzyl)-3H-pyrimidin-4-one;

5-chloro-6-[(2,4-difluorobenzyl)oxy]-3-[(1-glycoloyl-2,3-dihydro-1H-indol-5-yl)methyl]pyrimidin-4(3H)-one;

5-chloro-6-[(2,4-difluorobenzyl)oxy]-3-[(1-glycoloyl-2,3-dihydro-1H-indol-5-yl)methyl]pyrimidin-4(3H)-one;

5-chloro-6-[(2,4-difluorobenzyl)oxy]-3-{[1-(methoxyacetyl)-2,3-dihydro-1H-indol-5-yl]methyl}pyrimidin-4(3H)-one;

5-{[5-chloro-4-[(2,4-difluorobenzyl)oxy]-6-oxopyrimidin-1(6H)-yl]methyl}-N,N-dimethylindoline-1-carboxamide;

5-bromo-6-(2,4-difluorobenzyloxy)-3-[(4-dimethylaminomethyl)benzyl]-3H-pyrimidin-4-one;

5-bromo-6-(2,4-difluorobenzyloxy)-3-[3-(isopropylaminomethyl)benzyl]-3H-pyrimidin-4-one;

5-bromo-6-(2,4-difluorobenzyloxy)-3-[(3-dimethylaminomethyl)benzyl]-3H-pyrimidin-4-one;

5-bromo-6-(2,4-difluorobenzyloxy)-3-[(3-methylaminomethyl)benzyl]-3H-pyrimidin-4-one;

tert-butyl (3-{[5-bromo-4-[(2,4-difluorobenzyl)oxy]-6-oxopyrimidin-1(6H)-yl]methyl}benzyl)carbamate;

3-[(3-aminomethyl)benzyl]-5-bromo-6-(2,4-difluorobenzyloxy)-3H-pyrimidin-4-one;

5-chloro-6-(2,4-difluorobenzyloxy)-3-[4-(isopropylaminomethyl)benzyl]-3H-pyrimidin-4-one;

5-chloro-6-(2,4-difluorobenzyloxy)-3-[(3-methanesulfonyl)benzyl]-3H-pyrimidin-4-one;

5-chloro-6-(2,4-difluorobenzyloxy)-3-[(4-methanesulfonyl)benzyl]-3H-pyrimidin-4-one;

4-{[5-chloro-4-[(2,4-difluorobenzyl)oxy]-6-oxopyrimidin-1(6H)-yl]methyl}benzamide;

5-chloro-6-(2,4-difluorobenzyloxy)-3-isoquinolin-5-ylmethyl-3H-pyrimidin-4-one;

5-chloro-6-(2,4-difluorobenzyloxy)-3-(1,2,3,4-tetrahydroisoquinolin-5-ylmethyl)-3H-pyrimidin-4-one;

5-chloro-6-(2,4-difluorobenzyloxy)-3-(1H-indol-5-ylmethyl)-3H-pyrimidin-4-one;

3-(1-acetyl-1H-indol-5-ylmethyl)-5-chloro-6-(2,4-difluorobenzyloxy)-3H-pyrimidin-4-one;

5-chloro-6-(2,4-difluorobenzyloxy)-3-(2,3-dihydro-1H-indol-5-ylmethyl)-3H-pyrimidin-4-one;

5-bromo-6-(2,4-difluorobenzyloxy)-3-(2,4-difluorobenzyl)-3H-pyrimidin-4-one;

(3-{[5-bromo-4-[(2,4-difluorobenzyl)oxy]-6-oxopyrimidin-1(6H)-yl]methyl}phenyl)acetonitrile;

2-{[5-bromo-4-[(2,4-difluorobenzyl)oxy]-6-oxopyrimidin-1(6H)-yl]methyl}benzonitrile; or 3-[(2-aminomethyl)benzyl)]-5-bromo-6-(2,4-difluorobenzyloxy)-3H-pyrimidin-4-one.

The above names were generated using ChemDraw Ultra version 6.0.2, which is commercially available from CambridgeSoft.com, Cambridge, Mass.; or ACD Namepro version 5.09, which is commercially available from ACDlabs.com.

Definitions

As used herein, the term "alkenyl" refers to straight and branched hydrocarbon groups having a designated number of carbon atoms and containing at least one carbon-carbon double bond. Examples of "alkenyl" include vinyl, allyl, and 2-methyl-3-heptene.

The term "alkoxy" represents an alkyl attached to the parent molecular moiety through an oxygen bridge. Examples of alkoxy groups include, for example, methoxy, ethoxy, propoxy and isopropoxy.

The term "thioalkoxy" represents an alkyl attached to the parent molecular moiety through a sulfur atom. Examples of thioalkoxy groups include, for example, thiomethoxy, thioethoxy, thiopropoxy and thioisopropoxy.

As used herein, the term "alkyl" refers to straight and branched chain hydrocarbon chains having the designated number of carbon atoms. Examples of "alkyl" include methyl, ethyl, propyl, isopropyl, butyl, iso-, sec- and tert-butyl, pentyl, hexyl, heptyl, 3-ethylbutyl, and the like. "Cx-Cy alkyl" represents an alkyl group of the specified number of carbons. For example, $C_1$-$C_4$ alkyl includes all alkyl groups that include at least one and no more than four carbon atoms. It also contains subgroups, such as, for example, $C_2$-$C_3$ alkyl or $C_1$-$C_3$ alkyl.

The term "aryl" refers to an aromatic hydrocarbon ring system containing at least one aromatic ring where the aromatic ring is optionally fused or otherwise attached to other aromatic hydrocarbon rings or non-aromatic hydrocarbon rings. Examples of aryl groups include, for example, phenyl, naphthyl, 1,2,3,4-tetrahydronaphthalene, indanyl, and biphenyl. Preferred examples of aryl groups include phenyl and naphthyl. The most preferred aryl group is phenyl. The aryl groups herein are unsubstituted or, as specified, substituted in one or more substitutable positions with various groups. Thus, such aryl groups can be optionally substituted with groups such as, for example, $C_1$-$C_6$ alkyl, $C_1$-$C_6$ alkoxy, halogen, hydroxy, cyano, nitro, amino, mono- or di-($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono- or di($C_1$-$C_6$)alkylamino($C_1$-$C_6$)alkyl.

The term "arylalkyl" refers to an aryl group, as defined above, attached to the parent molecular moiety through an alkyl group, as defined above. Preferred arylalkyl groups include, benzyl, phenethyl, phenpropyl, and phenbutyl. More preferred arylalkyl groups include benzyl and phenethyl. The most preferred arylalkyl group is benzyl. The aryl portions of these groups are unsubstituted or, as specified, substituted in one or more substitutable positions with various groups. Thus, such aryl groups can be optionally substituted with groups such as, for example, $C_1$-$C_6$ alkyl, $C_1$-$C_6$ alkoxy, halogen, hydroxy, cyano, nitro, amino, mono- or di-($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono- or di($C_1$-$C_6$)alkylamino($C_1$-$C_6$)alkyl.

The term "arylalkoxy" refers to an aryl group, as defined above, attached to the parent molecular moiety through an alkoxy group, as defined above. Preferred arylaloxy groups include, benzyloxy, phenethyloxy, phenpropyloxy, and phenbutyloxy. The most preferred arylalkoxy group is benzyloxy.

The term "cycloalkyl" refers to a $C_3$-$C_8$ cyclic hydrocarbon. Examples of cycloalkyl include cyclopropyl, cyclobutyl, cyclopentyl, cyclohexyl, cycloheptyl and cyclooctyl. More preferred cycloalkyl groups include cyclopropyl.

The term "cycloalkylalkyl," as used herein, refers to a $C_3$-$C_8$ cycloalkyl group attached to the parent molecular moiety through an alkyl group, as defined above. Examples of cycloalkylalkyl groups include cyclopropylmethyl and cyclopentylethyl.

The terms "halogen" or "halo" indicate fluorine, chlorine, bromine, or iodine.

The term "heterocycloalkyl," refers to a non-aromatic ring system containing at least one heteroatom selected from nitrogen, oxygen, and sulfur, wherein the non-aromatic heterocycle is attached to the core. The heterocycloalkyl ring may be optionally fused to or otherwise attached to other heterocycloalkyl rings, aromatic heterocycles, aromatic hydrocarbons and/or non-aromatic hydrocarbon rings. Preferred heterocycloalkyl groups have from 3 to 7 members. Examples of heterocycloalkyl groups include, for example, piperazine, 1,2,3,4-tetrahydroisoquinoline, morpholine, piperidine, tetrahydrofuran, pyrrolidine, and pyrazole. Preferred heterocycloalkyl groups include piperidinyl, piperazinyl, morpholinyl, and pyrrolidinyl. The heterocycloalkyl groups herein are unsubstituted or, as specified, substituted in one or more substitutable positions with various groups. Thus, such heterocycloalkyl groups can be optionally substituted with groups such as, for example, $C_1$-$C_6$ alkyl, $C_1$-$C_6$ alkoxy, halogen, hydroxy, cyano, nitro, amino, mono- or di-($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono- or di($C_1$-$C_6$)alkylamino($C_1$-$C_6$)alkyl.

The term "heteroaryl" refers to an aromatic ring system containing at least one heteroatom selected from nitrogen, oxygen, and sulfur where the heteroaryl ring is optionally fused or otherwise attached to one or more heteroaryl rings, aromatic or non-aromatic hydrocarbon rings, or heterocycloalkyl rings. Examples of heteroaryl groups include, for example, pyridine, furan, thiophene, 5,6,7,8-tetrahydroisoquinoline and pyrimidine. Preferred examples of heteroaryl groups include thienyl, benzothienyl, pyridyl, quinolyl, pyrazinyl, pyrimidyl, imidazolyl, benzimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl, and benzopyrazolyl. Preferred heteroaryl groups include pyridyl. The heteroaryl groups herein are unsubstituted or, as specified, substituted in one or more substitutable positions with various groups. Thus, such heteroaryl groups can be optionally substituted with groups such as, for example, $C_1$-$C_6$ alkyl, $C_1$-$C_6$ alkoxy, halogen, hydroxy, cyano, nitro, amino, mono- or di-($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono- or di($C_1$-$C_6$)alkylamino($C_1$-$C_6$)alkyl.

The term "heteroarylalkyl" refers to a heteroaryl group, as defined above, attached to the parent molecular moiety through an alkyl group, as defined above. Preferred heteroarylalkyl groups include, pyrazolemethyl, pyrazoleethyl, pyridylmethyl, pyridylethyl, thiazolemethyl, thiazoleethyl, imidazolemethyl, imidazoleethyl, thienylmethyl, thienylethyl, furanylmethyl, furanylethyl, isoxazolemethyl, isoxazoleethyl, pyrazinemethyl and pyrazineethyl. More preferred heteroarylalkyl groups include pyridylmethyl and pyridylethyl. The heteroaryl portions of these groups are unsubstituted or, as specified, substituted in one or more substitutable positions with various groups. Thus, such heteroaryl groups can be optionally substituted with groups such as, for example, $C_1$-$C_6$ alkyl, $C_1$-$C_6$ alkoxy, halogen, hydroxy, cyano, nitro, amino, mono- or di-($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono- or di($C_1$-$C_6$)alkylamino($C_1$-$C_6$)alkyl.

If two or more of the same substituents are on a common atom, e.g., di($C_1$-$C_6$)alkylamino, it is understood that the nature of each group is independent of the other.

As used herein, the term "p38 mediated disorder" refers to any and all disorders and disease states in which p38 plays a role, either by control of p38 itself, or by p38 causing another factor to be released, such as but not limited to IL-1, IL-6 or IL-8. A disease state in which, for instance, IL-1 is a major component, and whose production or action, is exacerbated or secreted in response to p38, would therefore be considered a disorder mediated by p38.

As TNF-beta has close structural homology with TNF-alpha (also known as cachectin), and since each induces similar biologic responses and binds to the same cellular receptor, the synthesis of both TNF-alpha and TNF-beta are inhibited by the compounds of the invention and thus are herein referred to collectively as "TNF" unless specifically delineated otherwise.

Compounds of invention include the compounds of Formula I and their corresponding pharmaceutically acceptable acid and base addition salts. If the compound of the invention is obtained as an acid addition salt, the free base can be obtained by basifying a solution of the acid salt. Conversely, if the product is a free base, an addition salt, particularly a pharmaceutically acceptable acid addition salt, may be produced by dissolving the free base in a suitable organic solvent and treating the solution with an acid, in accordance with conventional procedures for preparing such addition salts from base compounds.

Non-toxic pharmaceutically acceptable salts include, but are not limited to salts of inorganic acids such as hydrochloric, sulfuric, phosphoric, diphosphoric, hydrobromic, and nitric or salts of organic acids such as formic, citric, malic, maleic, fumaric, tartaric, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts.

The compounds of this invention may contain one or more asymmetric carbon atoms, so that the compounds can exist in different stereoisomeric forms. These compounds can be, for example, racemates, chiral non-racemic mixtures or mixtures of diastereomers. In these situations, the single enantiomers, i.e., optically active forms, can be obtained by asymmetric synthesis or by resolution of the racemates or mixtures. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography or selective crystallization, and removing the resolving agent to generate the original compound in enantiomerically enriched form. Any of the above procedures can be repeated to increase the enantiomeric purity of a compound.

The compounds of the invention may exist as atropisomers, i.e., chiral rotational isomers. The invention encompasses the racemic and the resolved atropisomers. The following illustration generically shows a compound (Z) that can exist as atropisomers as well as its two possible atropisomers (A) and (B). This illustration also shows each of atropisomers (A) and (B) in a Fischer projection. In this illustration, $R_1$, $R_2$, and $R_4$ carry the same definitions as set forth for Formula I, $R_{p'}$ is a substituent within the definition of $R_5$, and $R_p$ is a non-hydrogen substituent within the definition of $R_5$.

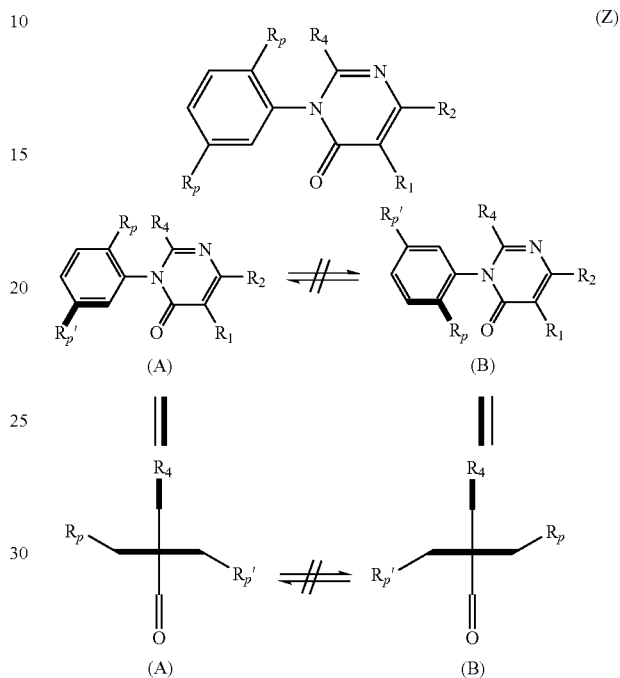

When the compounds described herein contain olefinic double bonds or other centers of geometric asymmetry, and unless otherwise specified, it is intended that the compounds include the cis, trans, Z- and E-configurations. Likewise, all tautomeric forms are also intended to be included.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants, and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

For oral administration, the pharmaceutical composition may be in the form of, for example, a tablet, hard or soft capsule, lozenges, dispensable powders, suspension, or liquid. The pharmaceutical composition is preferably made in the form of a dosage unit containing a particular amount of the active ingredient. Examples of such dosage units are tablets or capsules.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules, wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin or olive oil.

Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring, and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative, and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives, and buffering agents can be dissolved in the vehicle.

The active ingredient may also be administered by injection (IV, IM, subcutaneous or jet) as a composition wherein, for example, saline, dextrose, or water may be used as a suitable carrier. The pH of the composition may be adjusted, if necessary, with suitable acid, base, or buffer. Suitable bulking, dispersing, wetting or suspending agents, including mannitol and PEG 400, may also be included in the composition. A suitable parenteral composition can also include a compound formulated as a sterile solid substance, including lyophilized powder, in injection vials. Aqueous solution can be added to dissolve the compound prior to injection.

For disorders of the eye or other external tissues, e.g., mouth and skin, the formulations are preferably applied as a topical gel, spray, ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this invention may be constituted from known ingredients in a known manner. While the phase may comprise merely an emulsifier, it may comprise a mixture of at least one emulsifier with a fat or oil or with both a fat and an oil. Preferably, a hydrophilic emulsifier is included together with a lipophilic emulsifier, which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily, dispersed phase of the cream formulations. Emulsifiers and emulsion stabilizers suitable for use in the formulation of the invention include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The anti-inflammatory active ingredients are preferably present in such formulations in a concentration of 0.5 to 20%, advantageously 0.5 to 10% and particularly about 1.5% w/w. For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The amount of therapeutically active compounds that are administered and the dosage regimen for treating a disease condition with the compounds and/or compositions of this invention depends on a variety of factors, including the age, weight, sex and medical condition of the subject, the severity of the inflammation or inflammation related disorder, the route and frequency of administration, and the particular compound employed, and thus may vary widely. The pharmaceutical compositions may contain active ingredients in the range of about 0.1 to 1000 mg, preferably in the range of about 7.0 to 350 mg. A daily dose of about 0.01 to 100 mg/kg body weight, preferably between about 0.1 and about 50 mg/kg body weight and most preferably between about 0.5 to 30 mg/kg body weight, may be appropriate. The daily dose can be administered in one to four doses per day. In the case of skin conditions, it may be preferable to apply a topical preparation of compounds of this invention to the affected area two to four times a day.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It may be convenient to formulate the animal feed and drinking water compositions so that the animal takes in a therapeutically appropriate quantity of the composition along with its diet. It may also be convenient to present the composition as a premix for addition to the feed or drinking water.

The disclosures in this application of all articles and references, including patents, are incorporated herein by reference.

The invention is illustrated further by the following examples, which are not to be construed as limiting the invention in scope or spirit to the specific procedures described in them.

The starting materials and various intermediates may be obtained from commercial sources, prepared from commercially available compounds, or prepared using well-known synthetic methods.

General Synthetic Procedures

Representative procedures for the preparation of compounds of the invention are outlined below in the Schemes. The starting materials can be purchased or prepared using methods known to those skilled in the art. Similarly, the preparation of the various intermediates can be achieved using methods known in the art. The starting materials may be varied and additional steps employed to produce compounds encompassed by the invention, as demonstrated by the examples below. In addition, different solvents and reagents can typically be used to achieve the above transformations. Furthermore, in certain situations, it may be advantageous to alter the order in which the reactions are performed. Protection of reactive groups may also be necessary to achieve the above transformations. In general, the need for protecting groups, as well as the conditions necessary to attach and remove such groups, will be apparent to those skilled in the art of organic synthesis. When a protecting group is employed, deprotection will generally be required. Suitable protecting groups and methodology for protection and deprotection such as those described in *Protecting Groups in Organic Synthesis* by Greene and Wuts are known and appreciated in the art.

Schemes

The following schemes are representative of the methods that can be used to prepare these compounds.

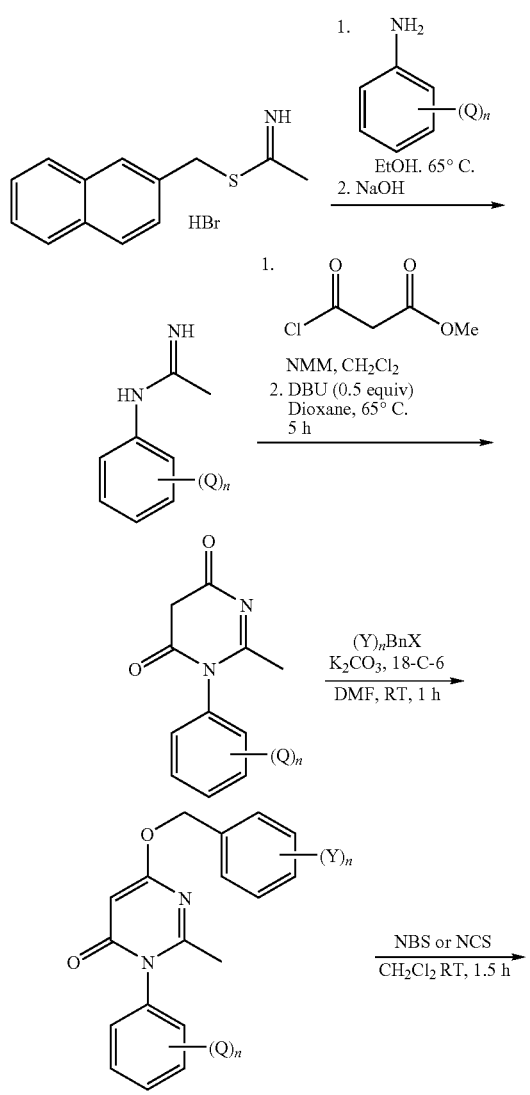

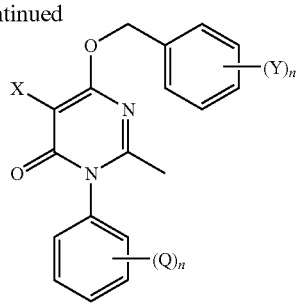

X is a bromo or chloro

In Scheme 1:

Each Q is independently alkyl, halogen, alkoxy, hydroxyalkyl, dihydroxyalkyl, arylalkoxy, thioalkoxy, alkoxycarbonyl, arylalkoxycarbonyl, $CO_2R$, CN, OH, hydroxyalkyl, dihydroxyalkyl, amidinooxime, $—NR_6R_7$, $—NR_8R_9$, $R_6R_7N—(C_1-C_6$ alkyl)-, carboxaldehyde, $SO_2$alkyl, $—SO_2H$, $—SO_2NR_6R_7$, alkanoyl wherein the alkyl portion is optionally substituted with OH, halogen or alkoxy, $—C(O)NR_6R_7$, $—(C_1-C_4$ alkyl)-$C(O)NR_6R_7$, amidino, haloalkyl, $—(C_1-C_4$ alkyl)-$NR_{15}C(O)NR_{16}R_{17}$, $—(C_1-C_4$ alkyl)-$NR_{15}C(O)R_{18}$, $—O—CH_2—O$, $—O—CH_2CH_2—O—$, or haloalkoxy; wherein $R_{15}$ is H or $C_1-C_6$ alkyl; and $R_{18}$ is $C_1-C_6$ alkyl optionally substituted with $—O—(C_2-C_6$ alkanoyl, $C_1-C_6$ hydroxyalkyl, $C_1-C_6$ dihydroxyalkyl, $C_1-C_6$ alkoxy, $C_1-C_6$ alkoxy $C_1-C_6$ alkyl; amino $C_1-C_6$ alkyl, mono or dialkylamino $C_1-C_6$ alkyl; and each Y is independently halogen, $—(C_1-C_6)$alkyl-$N(R)$—$CO_2R_{30}$, haloalkyl, heteroaryl, heteroarylalkyl, $—NR_6R_7$, $R_6R_7N—(C_1-C_6$ alkyl)-, $—C(O)NR_6R_7$, $—(C_1-C_4)$alkyl-$C(O)NR_6R_7$, $(C_1-C_4$ alkyl)-$NRC(O)NR_{16}R_{17}$, haloalkoxy, alkyl, CN, hydroxyalkyl, dihydroxyalkyl, alkoxy, alkoxycarbonyl, phenyl, $—SO_2$-phenyl wherein the phenyl and $—SO_2$-phenyl groups are optionally substituted with 1, 2, or 3 groups that are independently halogen or $NO_2$, or $—OC(O)NR_6R_7$, wherein $R_{16}$ and $R_{17}$ are independently H or $C_1-C_6$ alkyl; or $R_{16}$, $R_{17}$ and the nitrogen to which they are attached form a morpholinyl ring, wherein n is 0, 1, 2, 3, 4, or 5.

More preferably, n is 0-4, and even more preferably, n is 0-3.

In a preferred embodiment of Scheme 1, Q and Y carry the following definitions:

Q at each occurrence is independently alkyl, halogen, alkoxy, arylalkoxy, thioalkoxy, alkoxycarbonyl, arylalkoxycarbonyl, $CO_2H$, CN, amidinooxime, $NR_6R_7$, $R_6R_7N(C_1-C_6)$ alkyl, $—C(O)NR_6R_7$, $(C_1-C_4)$ alkyl-$C(O)NR_6R_7$, amidino, haloalkyl, or haloalkoxy; and n is 0, 1, 2, 3, 4, or 5;

Y at each occurrence is independently alkyl, halogen, alkoxy, arylalkoxy, thioalkoxy, alkoxycarbonyl, arylalkoxycarbonyl, $CO_2H$, CN, amidinooxime, $NR_6R_7$, $R_6R_7N(C_1-C_6)$ alkyl, $—C(O)NR_6R_7$, $(C_1-C_4)$alkyl-$C(O)NR_6R_7$, amidino, haloalkyl, or haloalkoxy; and n is 0, 1, 2, 3, 4, or 5;

X is a halide, preferably Br or Cl.

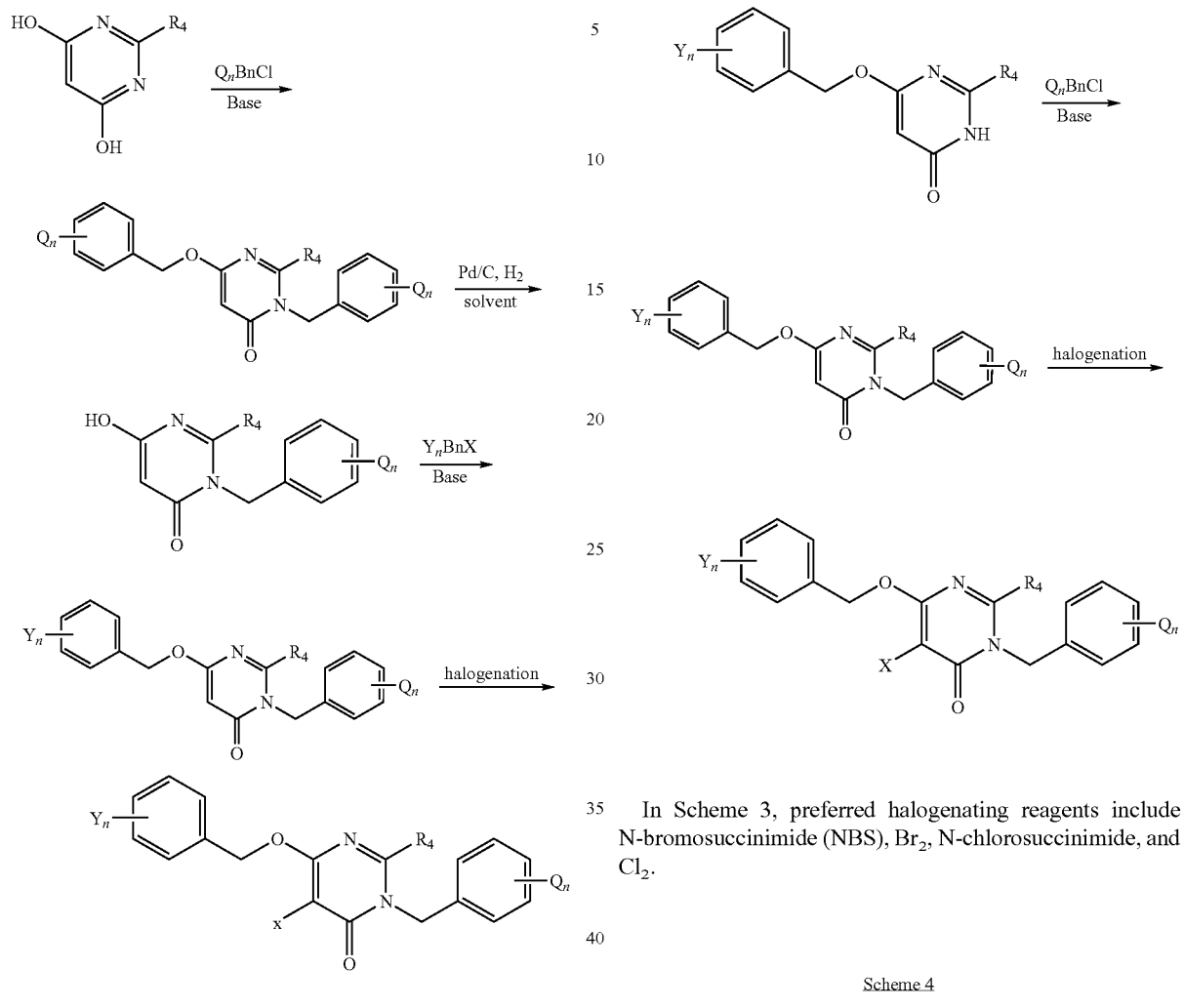
In Scheme 2:
R$_4$ is as defined for formula I, and in a preferred embodiment, R$_4$ is H, halogen, CH$_3$ or SCH$_3$. Preferred halogenating reagents include N-bromosuccinimide (NBS), Br$_2$, N-chlorosuccinimide, and Cl$_2$.
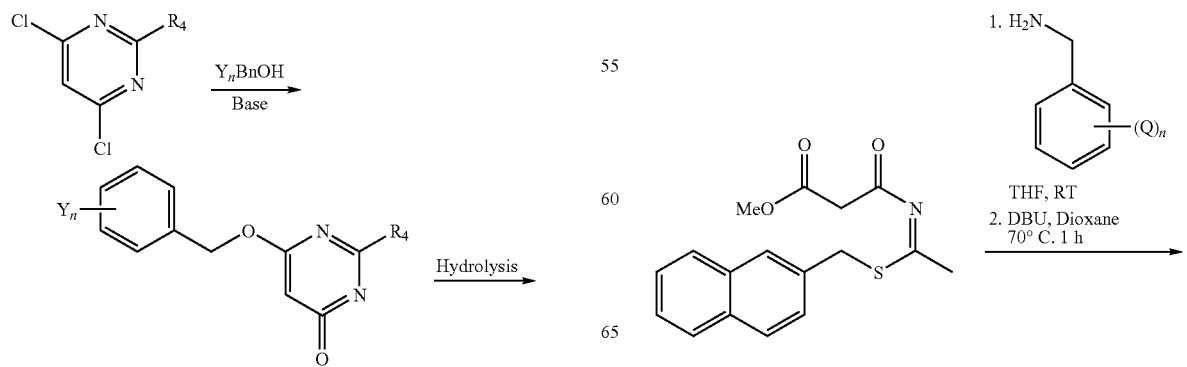
In Scheme 3, preferred halogenating reagents include N-bromosuccinimide (NBS), Br$_2$, N-chlorosuccinimide, and Cl$_2$.
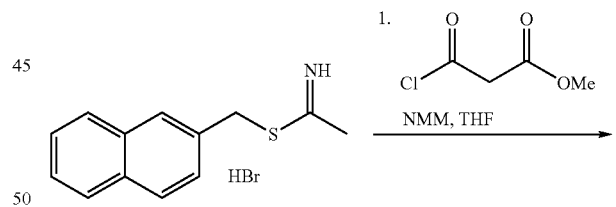

Scheme 5
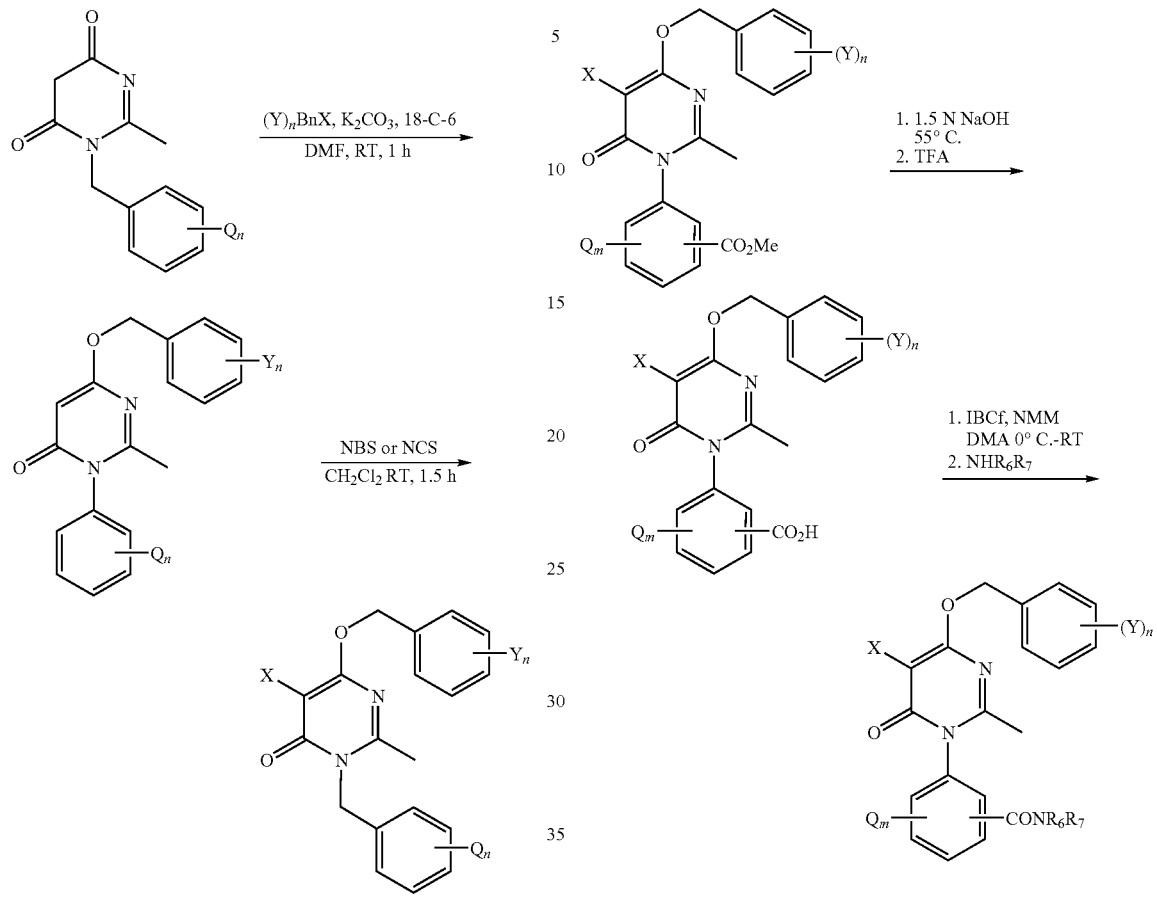
where m is 0, 1, 2, 3 or 4 and
n is 0, 1, 2, 3, 4, or 5.
Scheme 6
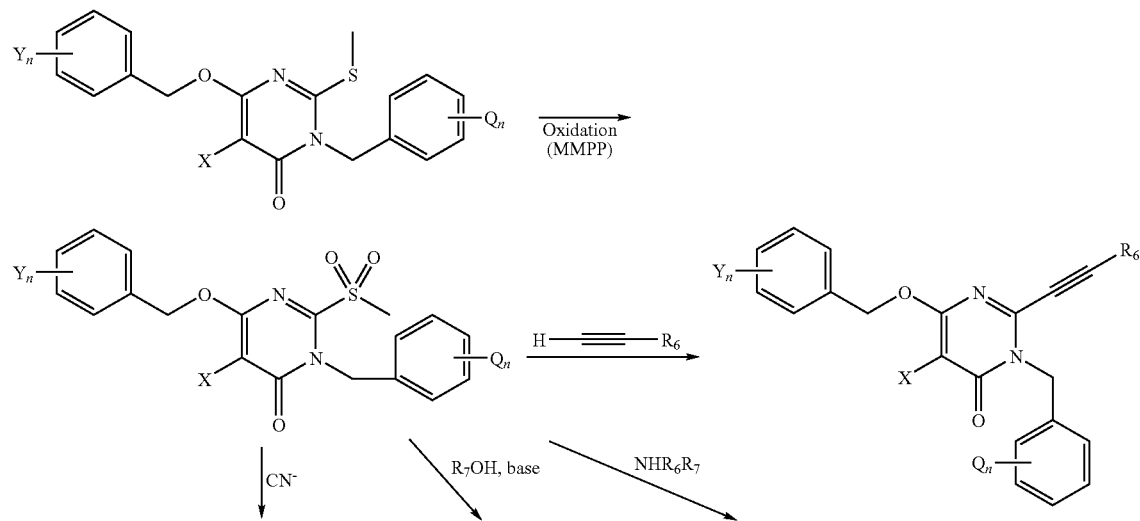

-continued
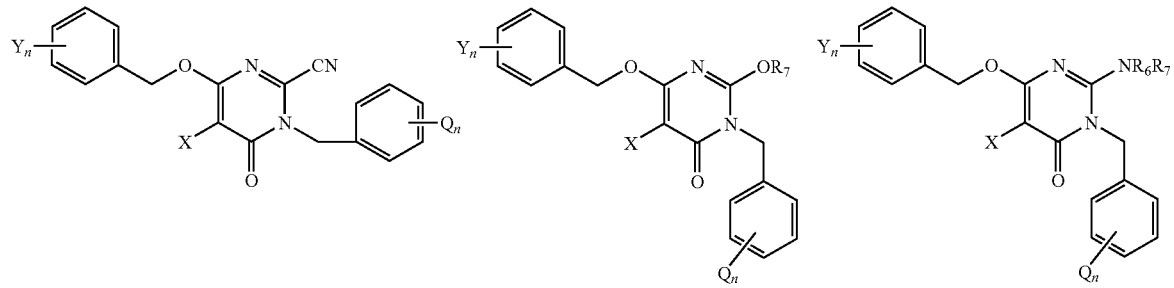
Scheme 7
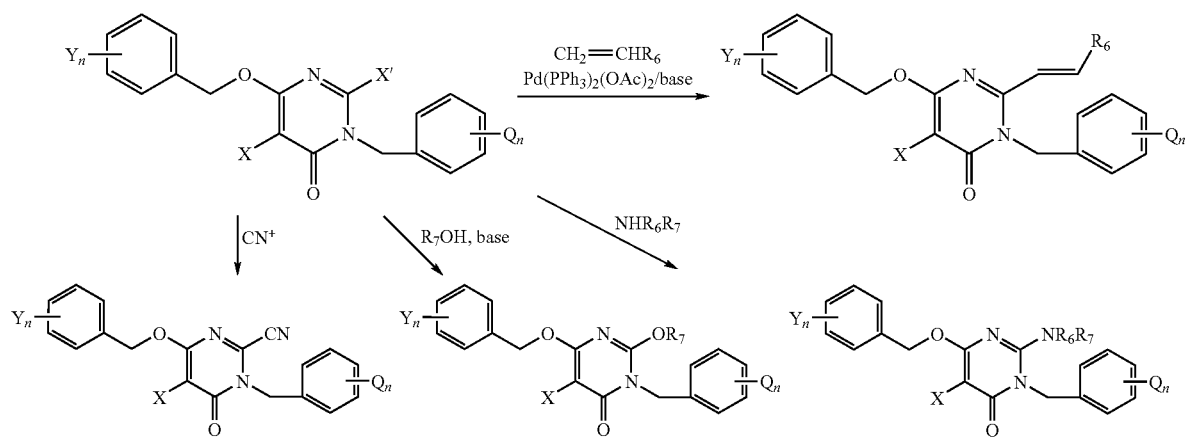
where X' is Cl, Br, I or SR.
Scheme 8
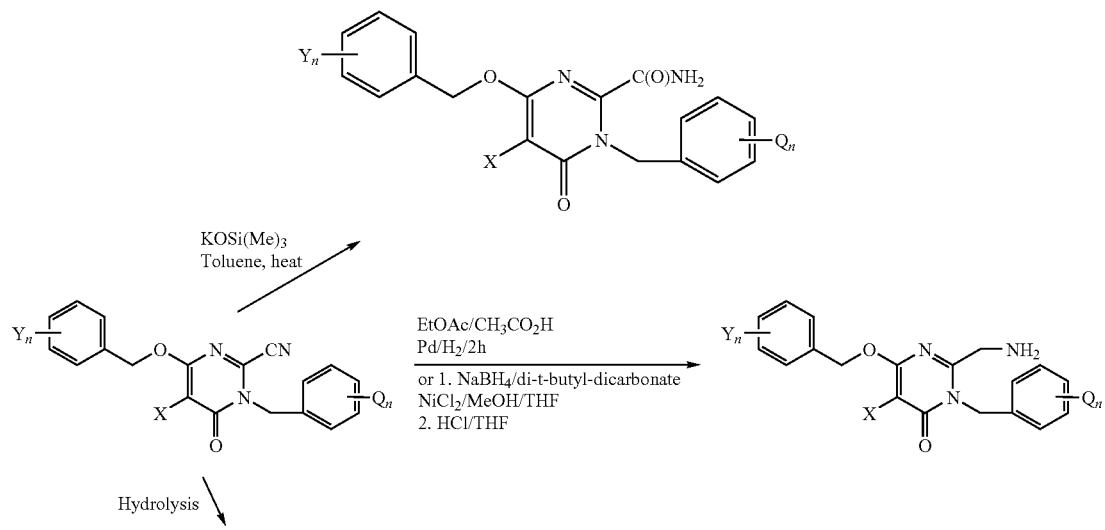

-continued
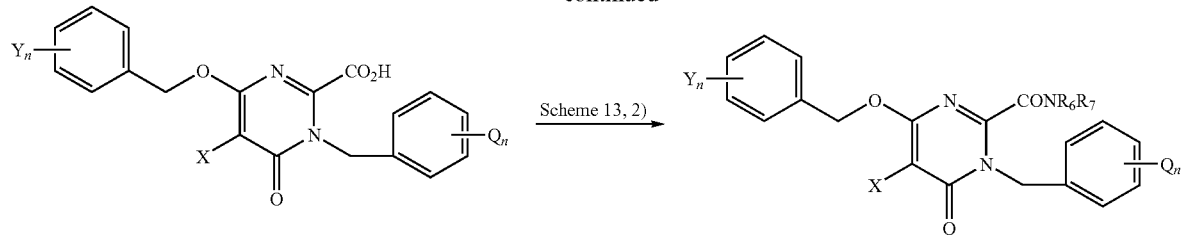
Scheme 9
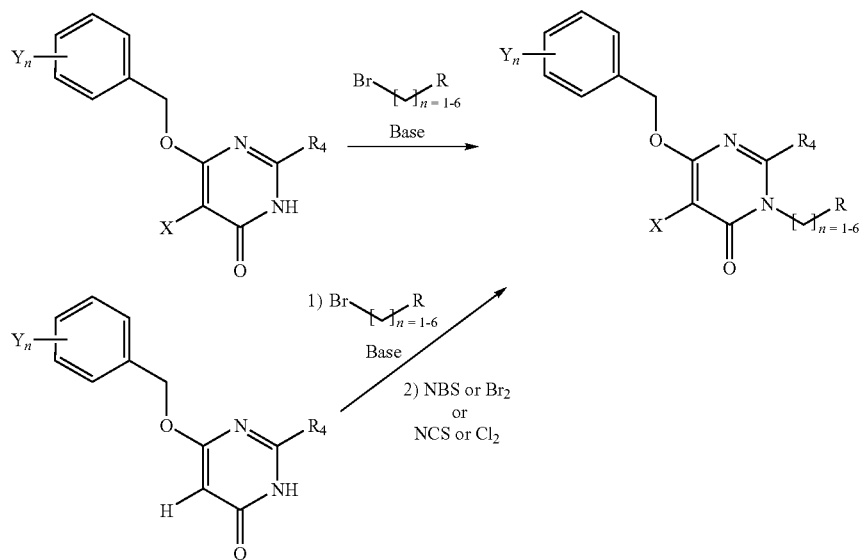
Scheme 10
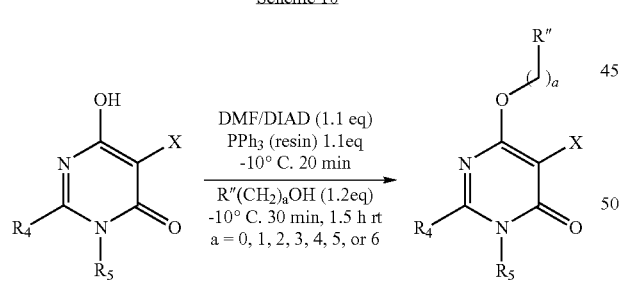
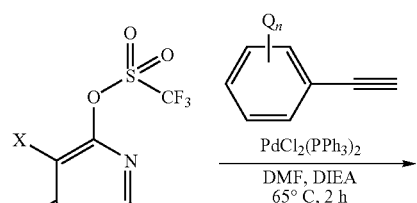
Scheme 11
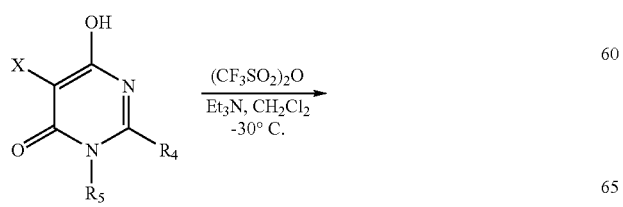
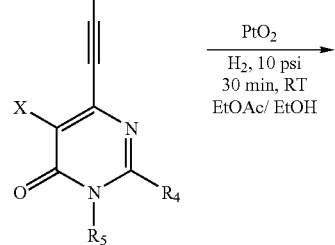

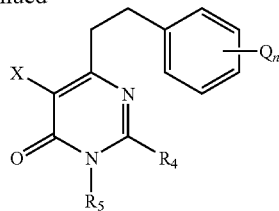
One of skill in the art will appreciate that other halides, such as chloro will work, and that all three halogens are not required. Further, the CN group can be replace with other activating groups, such as $NO_2$, $CO_2Me$, $CONH_2$, and —CH=$CH_2$ will also work.
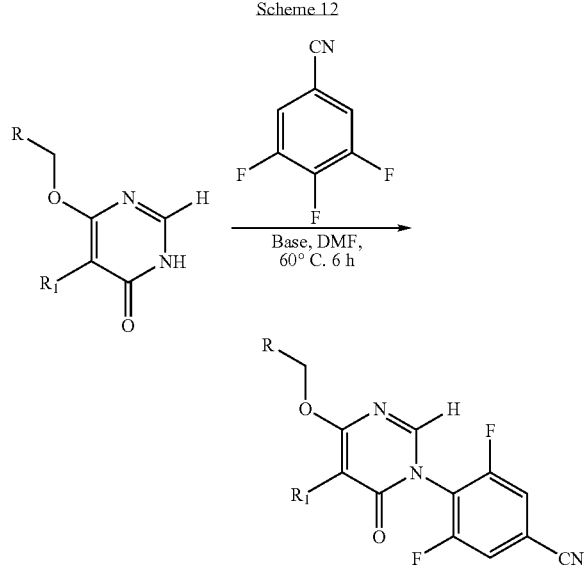
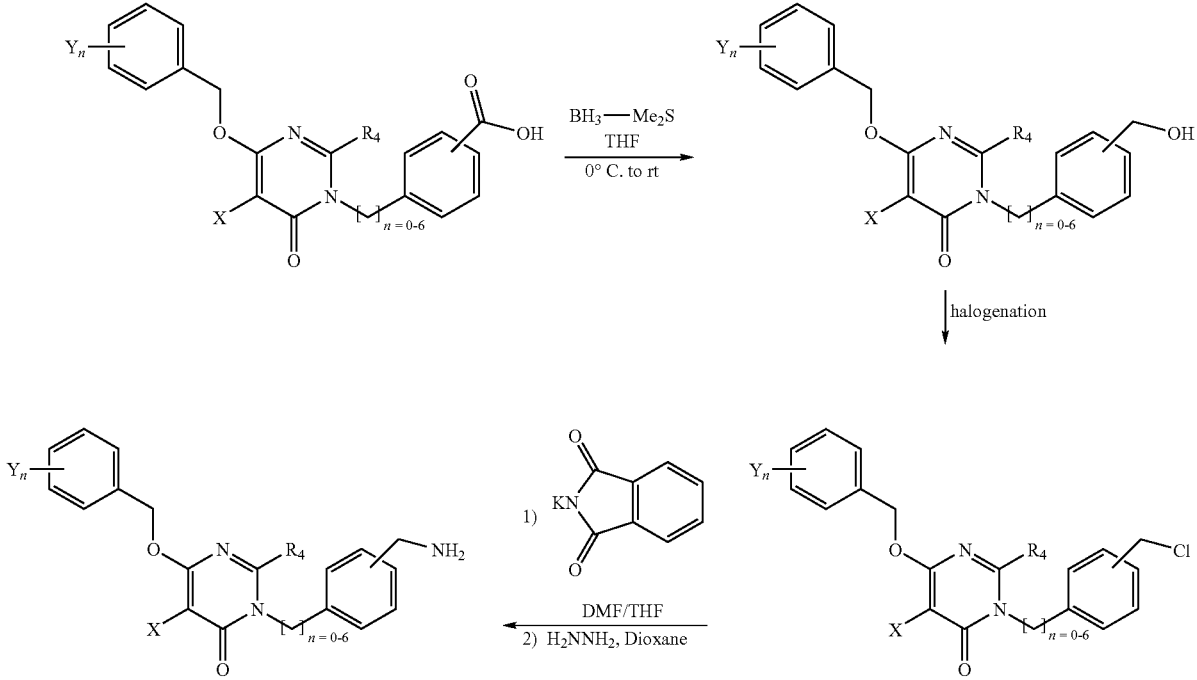

While the halogenation in Scheme 14 can be carried out using a variety of different halogenation reagents, or protocols, a preferred halogenation method includes using 2, 4, 6-trichloro-1, 3, 5-triazine (which is also known as cyanuric chloride) in DMF/CH$_2$Cl$_2$.
Scheme 15
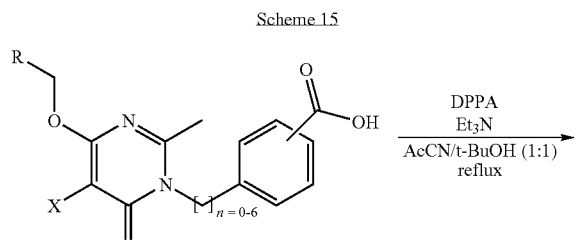
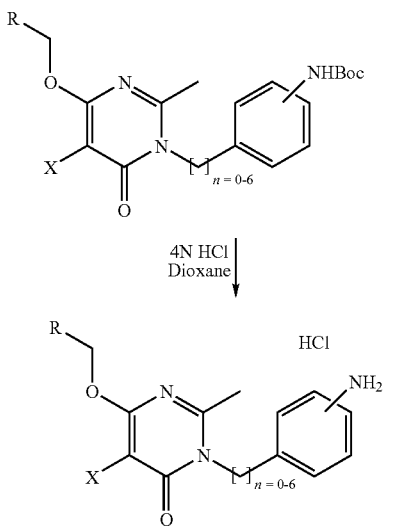
Scheme 16
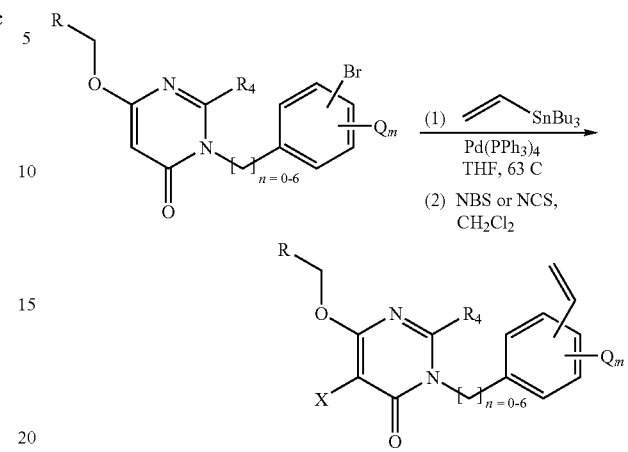
where m is 0, 1, 2, 3, or 4.
Scheme 17
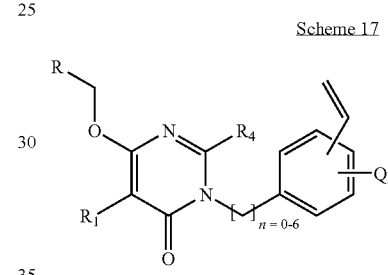
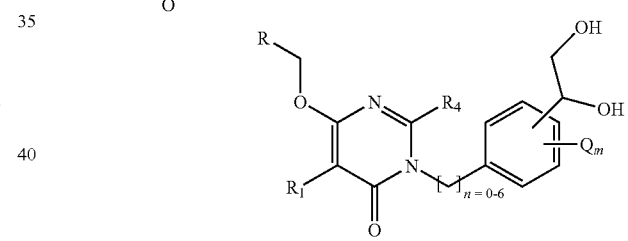
Scheme 18
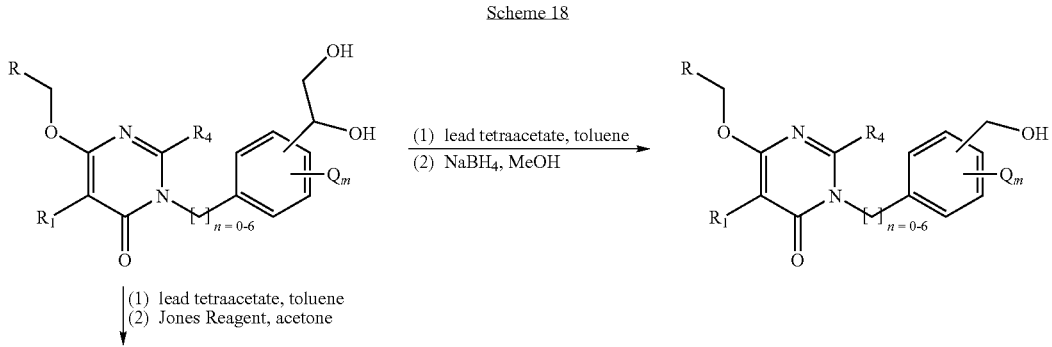

-continued

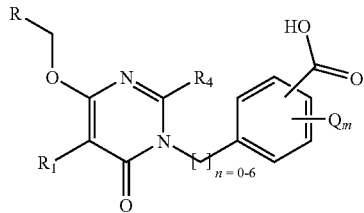

One of skill in the art will appreciate that periodic acid may also be used to affect the desired cleavage of the diol shown in Scheme 18. Further, one of skill in the art will recognize that after cleavage of the diol, the resulting aldehyde may be further elaborated using methods well known in the art, including for example, reductive amination.

Scheme 19

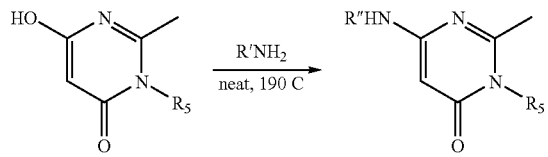

Scheme 20

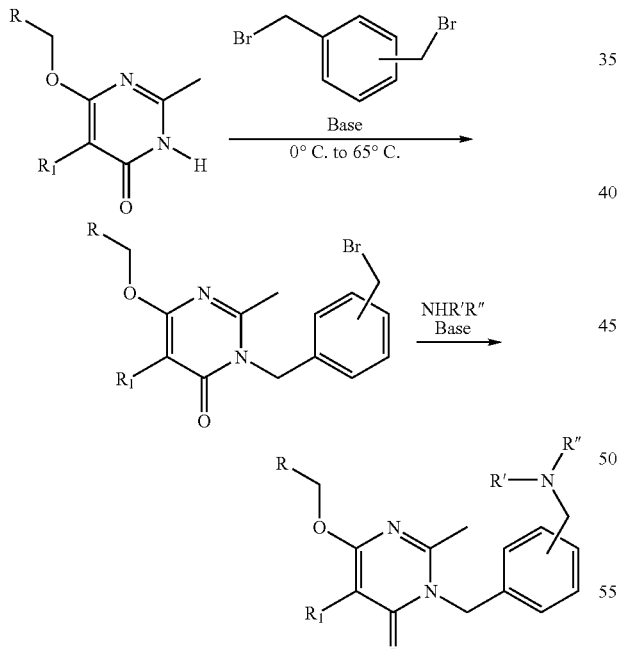

Scheme 21

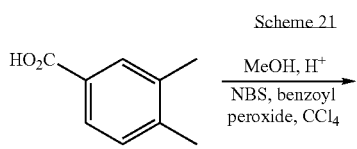

-continued

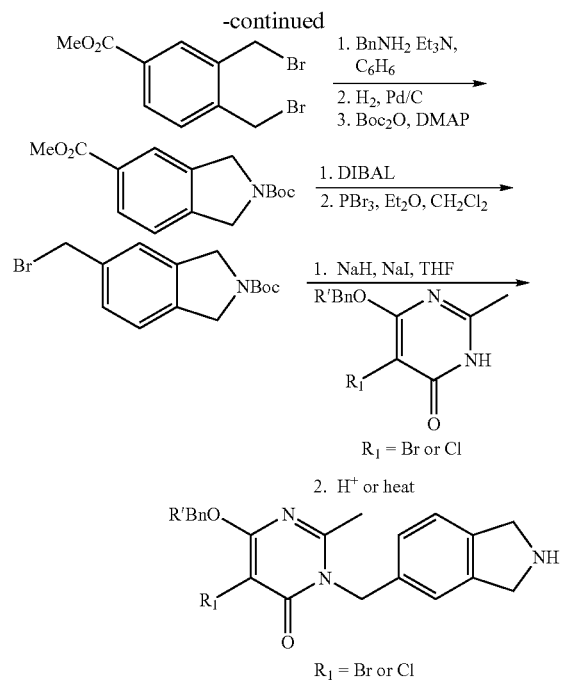

Scheme 22

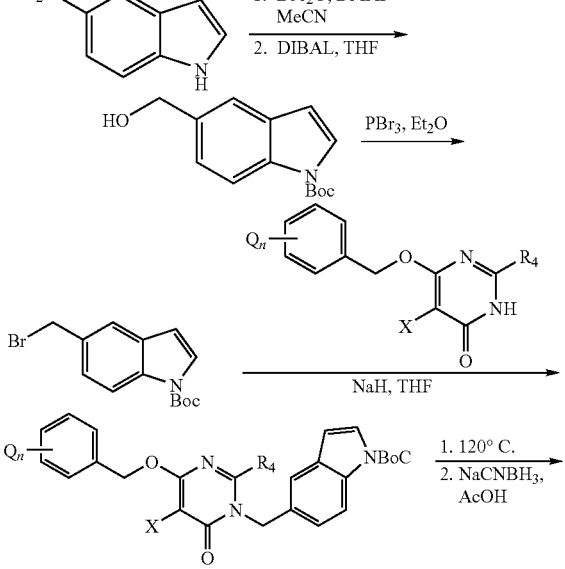

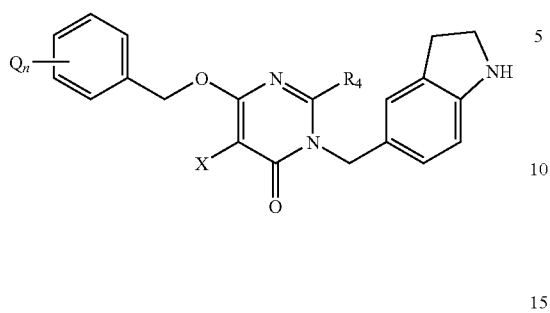
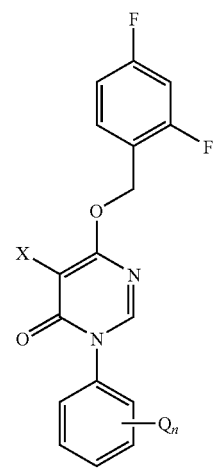
Scheme 23
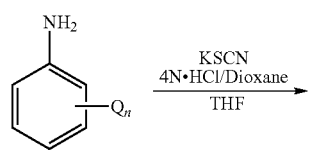
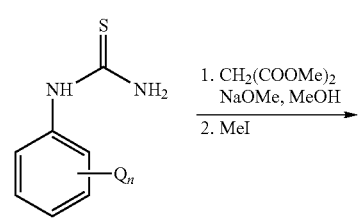
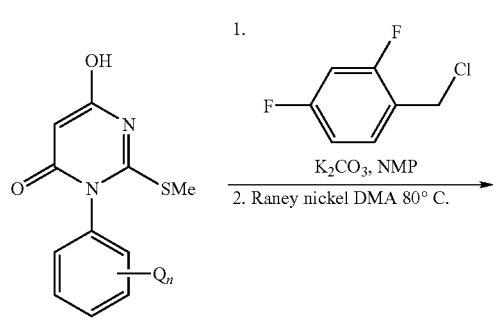
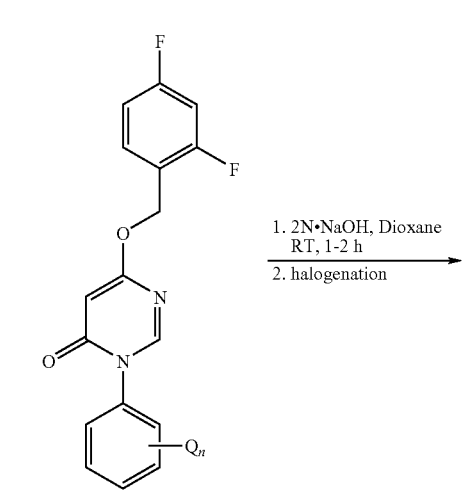
Scheme 24
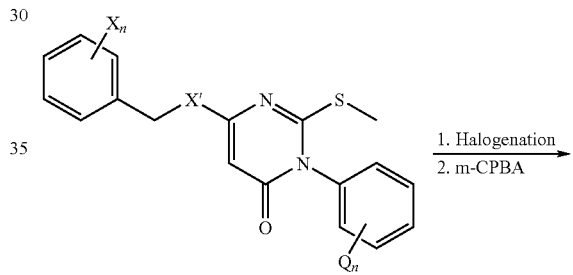
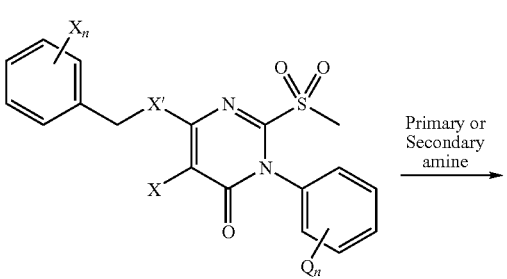
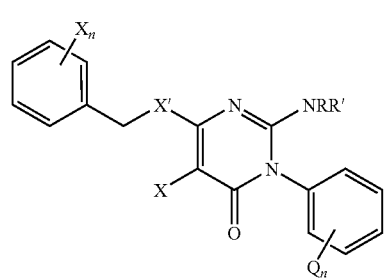

Scheme 25

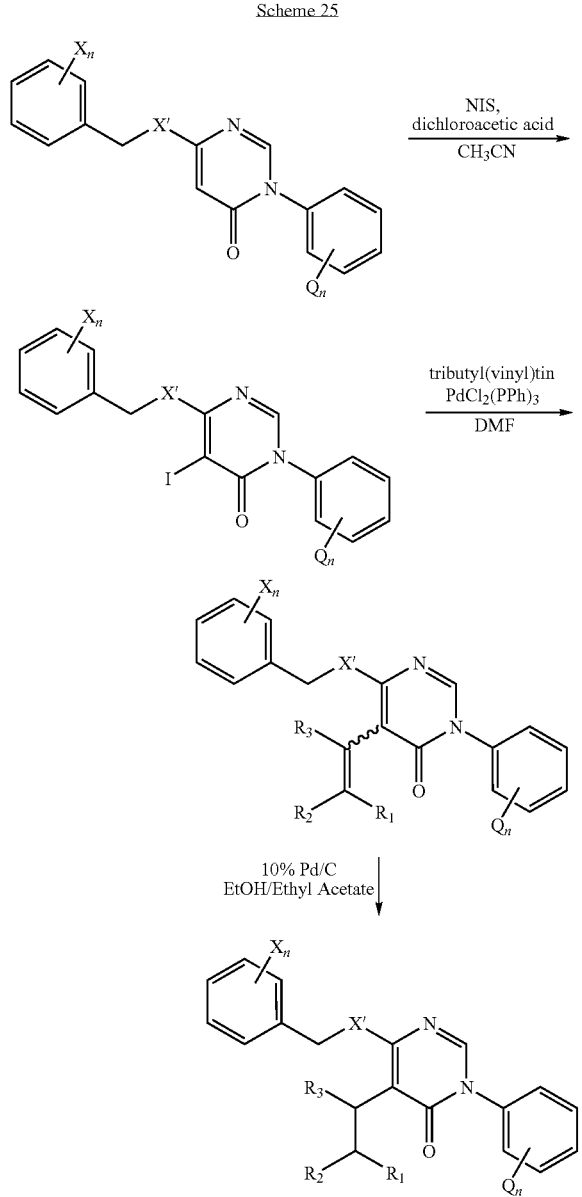

Experimental Procedures

Preparation of 3-benzyl-6-(benzyloxy)-5-bromopyrimidin-4(3H)-one

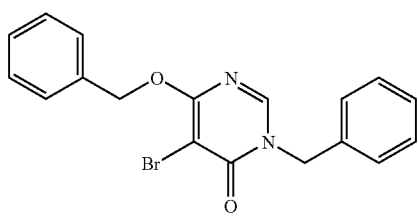

Step 1: Preparation of 3-benzyl-6-(benzyloxy)-pyrimidin-4(3H)-one

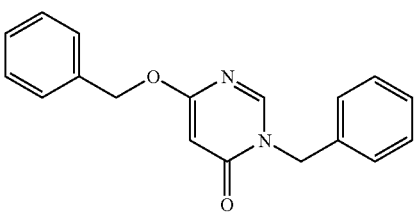

4,6-dihydroxypyrimidine (25.0 g, 0.223 mol) and potassium carbonate (65.1 g, 0.471 mol) are combined in 0.5 L anhydrous dimethylformamide. Benzyl chloride (55.7 g, 0.439 mol) is added dropwise over 30 minutes with stirring. After 4 h the solution is filtered, and the filtrate concentrated in vacuo. The residue is washed with acetonitrile, and the product is collected as a white solid by filtration (44.6 g, 68%). $^1$H-NMR (400 MHz, DMSO-$d_6$) δ 8.06 (m, 2 H), 7.61 (quartet, J=8.45 Hz, 1H), 7.30 (t, J=10.37 Hz, 1H), 7.12, (t, J=8.45 Hz, 1H), 7.09 (d, J=5.06 Hz, 2H), 5.14 (s, 2H). LC/MS $t_r$=5.29 minutes (0-95% acetonitrile/water, 0.05% trifluoroacetic acid, over 6 minutes at 1 ml/min with detection at 215 nm, at 50° C.) ES-MS m/z 293 (M+H).

Step 2: Preparation of the title compound 3-benzyl-6-(benzyloxy)-pyrimidin-4(3H)-one (from Step 1) (5.00 g, 17.1 mmol) and N-bromosuccinimide (3.15 g, 17.7 mmol) are stirred in 100 ml anhydrous dimethylformamide for 20 hours. The solution is poured onto 1 L of ice with stirring and allowed to come to room temperature, when the product is collected by filtration. (5.97 g). The product is recrystallized from 60 mL hot acetonitrile (4.75 g, 75%) $^1$H-NMR (400 MHz, DMSO-$d_6$) δ 7.92 (s, 1H), 7.28-7.44 (overlapping m, 9H), 7.24 (s, 1H), 5.43 (s, 2H), 5.12 (s, 2H). LC/MS $t_r$=5.89 minutes (0-95% acetonitrile/water, 0.05% trifluoroacetic acid, over 6 minutes at 1 ml/min with detection at 254 nm, at 50° C.) ES-MS m/z 371 (M+H). HRMS m/z 371 (M+H) 371.0399, calc. 371.0395.

Preparation of 3-[5-Bromo-4-[(2,4-difluorobenzyl)oxy]-2-methyl-6-oxopyrimidin-1(6H)-yl]-N,4-dimethylbenzamide

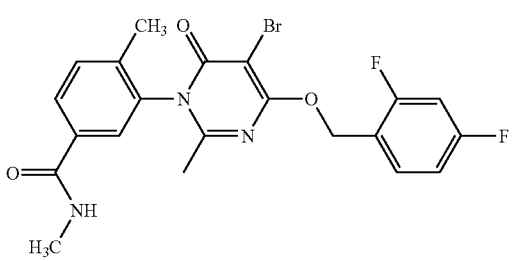

Step 1: Preparation of methyl 3-(Ethanimidoylamino)-4-methylbenzoate

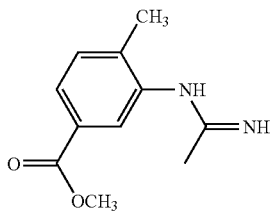

A mixture of 2-naphthylmethyl ethanimidothioate hydrobromide (20.0 g, 0.068 mol, (Tetrahedron Letters 38, 179-182, 1997) and methyl 3-amino-4-methylbenzoate (11.3 g, 0.068 mol) in ethanol (125 mL) is stirred at room temperature for 1 h and then heated at 65° C. for 2 h under argon atmosphere. The resulting clear solution is concentrated under reduced pressure and the residue is partitioned between water (100 ml) and ether (50 mL). The aqueous portion is washed with ether (2×50 mL) and lyophilized to give a white powder (12.0 g). This is suspended in water (25 mL), cold 0.5 N NaOH (90.0 mL) is added, and the mixture is extracted with EtOAc (3×50 mL). The combined EtOAc extracts are washed with brine, dried (anhy. $Na_2SO_4$), filtered, and concentrated to dryness to afford methyl 3-(ethanimidoylamino)-4-methylbenzoate (5.9 g, 42%) as a white powder. $^1$H NMR ($CD_3OD$/400 MHz) δ 7.61 (m, 1H), 7.40 (s, 1H), 7.26 (m, 1H), 3.85 (s, 3H), and 2.17 (s, 3H); ES-HRMS m/z 207.1128 (M+H calcd for $C_{11}H_{15}N_2O_2$ requires 207.1104).

Step 2: Preparation of methyl 4-methyl-3-(2-methyl-4,6-dioxo-5,6-dihydropyrimidin-1(4H)-yl)benzoate

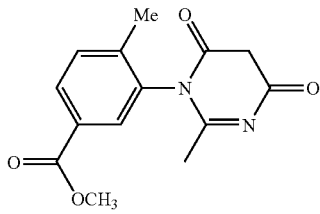

To a solution of methyl 3-(ethanimidoylamino)-4-methylbenzoate (2.5 g, 0.012 mol) in dichloromethane (25 mL) at −10° C., is added N-methylmorpholine (1.84 g, 0.018 mol) followed by the dropwise addition of a solution of methylmalonylchloride (2.54 g, 0.18 mol) in dichloromethane (8.0 mL). The resulting mixture is allowed to warm to room temperature over a period of 16 h. The reaction mixture is then cooled to −10° C. and additional N-methylmorpholine (0.37 g, 0.0036 mol) is added, followed by a solution of methylmalonylchloride (0.51 g, 0.0037 mol) in dichloromethane (5.0 mL). After stirring the reaction mixture at room temperature for 1 h, it is cooled to 0° C. and cold 5% $NaHCO_3$ (25 mL) is added. The organic phase is washed with water (2×15 mL), dried ($Na_2SO_4$), filtered, and concentrated to dryness to give a yellow syrup which is purified by silica gel flash chromatography using 35% EtOAc in hexanes. The appropriate fractions (MH$^+$, m/z=307) are pooled and concentrated to give a pale yellow syrup (1.8 g). The syrup (0.2 g, 0.00065 mol) is dissolved in dioxane (3.0 mL), DBU is added (0.05 g, 0.00033 mol) and the mixture is heated at 65° C. under argon atmosphere for 5 h. The reaction mixture is concentrated and the residue is purified by reverse-phase HPLC using 10-90% $CH_3CN$/Water gradient (40 min) at a flow rate of 80 mL/min. The appropriate fractions (MH$^+$, m/z=275) are combined and freeze-dried to afford the title compound (0.11 g, 61%) as a white powder: $^1$H NMR ($CD_3OD$/400 MHz) δ 8.04 (d, 1H, J=1.6 Hz), 7.87 (d, 1H, J=1.6 Hz), 7.56 (m, 1H), 5.46 (s, 1H) 3.89 (s, 3H), and 2.16 (s, 3H), 2.1 (s, 3H); ES-HRMS m/z 275.1045 (M+H calcd for $C_{14}H_{15}N_2O_4$ requires 275.1026).

Step 3: Preparation of Methyl 3-[4-[(2,4-difluorobenzyl)oxy]-2-methyl-6-oxopyrimidin-1(6H)-yl]-4-methylbenzoate

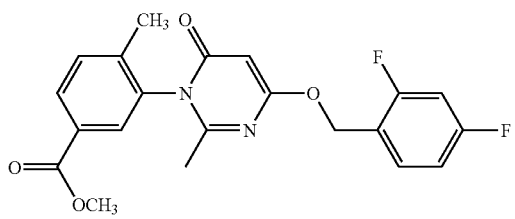

A mixture of methyl 4-methyl-3-(2-methyl-4,6-dioxo-5,6-dihydropyrimidin-1(4H)-yl)benzoate (0.1 g, 0.00036 mol, from Step 2), $K_2CO_3$ (0.075 g, 0.00054 mol) and 2,4 difluorobenzylbromide (0.075 g, 0.00036 mol) in DMF (2.0 mL) containing 18-crown-6 (0.005 g) is stirred at room temperature for 1 h under argon atmosphere. DMF is distilled in vacuo and the residue is purified by reverse-phase HPLC using 10-90% $CH_3CN$/Water gradient (40 min) at a flow rate of 80 mL/min. The appropriate fractions (MH$^+$, m/z=401) are combined and concentrated to a small volume (~20 mL). After cooling, 5% $NaHCO_3$ solution (10 mL) is added and the solution is extracted with dichloromethane (3×20 mL). The combined organic extracts are dried ($Na_2SO_4$), filtered, and concentrated to dryness to afford the title compound (0.12 g, 82%) as a white amorphous substance: $^1$H NMR ($CD_3OD$/400 MHz) δ 8.04 (d, 1H, J=1.6 Hz), 7.87 (d, 1H, J=1.16 Hz), 7.55 (m, 2H), 7.00 (m, 2H), 5.79 (s, 1H), 5.38 (s, 2H), 3.89 (s, 3H), 2.14 (s, 3H), and 2.12 (s, 3H); ES-HRMS m/z 401.1346 (M+H calcd for $C_{21}H_{19}N_2O_4F_2$ requires 401.1307).

Step 4: Preparation of Methyl 3-[5-bromo-4-[(2,4-difluorobenzyl)oxy]-2-methyl-6-oxopyrimidin-1(6H)-yl]-4-methylbenzoate

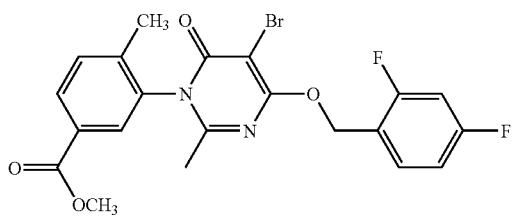

A mixture of methyl 3-[4-[(2,4-difluorobenzyl)oxy]-2-methyl-6-oxopyrimidin-1(6H)-yl]-4-methylbenzoate (0.41 g, 0.001 mol, from Step 3) and NBS (0.2 g, 0.0011 mol) in dichloromethane (5.0 mL) is stirred at room temperature for 1.5 h under argon atmosphere. The reaction mixture is purified by flash chromatography using 30% EtOAc in hexanes to furnish the title compound (0.37 g, 75%) as a white amorphous powder: $^1$H NMR (CD$_3$OD/400 MHz) δ 8.04 (d, 1H, J=1.6 Hz), 7.89 (d, 1H, J=1.6 Hz), 7.62 (m, 2H), 7.01 (m, 2H), 5.56 (s, 2H), 3.89 (s, 3H), 2.15 (s, 3H), and 2.133 (s, 3H); ES-HRMS m/z 479.0412 (M+H calcd for C$_{21}$H$_{18}$N$_2$O$_4$F$_2$Br requires 479.0413). $^{19}$F NMR (CD$_3$OD/400 MHz) −111.870 (m) and −115.95 (m).

Step 5: Preparation of 3-[5-Bromo-4-[(2,4-difluorobenzyl)oxy]-2-methyl-6-oxopyrimidin-1(6H)-yl]-4-methylbenzoic acid

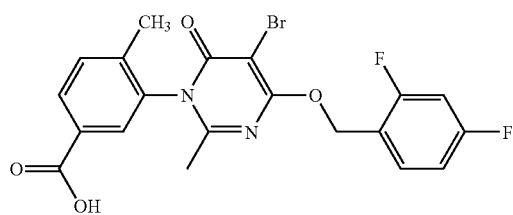

A mixture of methyl 3-[5-bromo-4-[(2,4-difluorobenzyl)oxy]-2-methyl-6-oxopyrimidin-1(6H)-yl]-4-methylbenzoate (0.40 g, 0.00084 mol, from Step 4), and 1.5 N NaOH (0.7 mL, 0.042 g, 0.001 mol) containing dioxane (0.5 mL) is stirred at 55° C. for 30 min. The resulting clear brown solution is cooled in an ice bath, diluted with water (3 mL), acidified with trifluoroacetic acid, and the product is purified by reverse-phase HPLC using 10-90% CH$_3$CN/Water gradient (40 min) at a flow rate of 80 mL/min. The appropriate fractions (MH$^+$, m/z=465) are combined and freeze-dried to afford the title compound (0.17 g, 44%) as a white powder: $^1$H NMR (CD$_3$OD/400 MHz) δ 8.04 (d, 1H, J=1.6 Hz), 7.87 (d, 1H, J=1.6 Hz), 7.54 (m, 2H), 6.99 (m 2H), 5.56 (s, 2H), 2.15 (s, 3H), and 2.13 (s, 3H); ES-HRMS m/z 465.0256 (M+H calcd for C$_{20}$H$_{16}$N$_2$O$_4$F$_2$Br requires 465.0256); $^{19}$F NMR (CD$_3$OD/400 MHz) −111.89 (m) and −115.95 (m).

Step 6: Preparation of Title Compound

To a solution of 3-[5-bromo-4-[(2,4-difluorobenzyl)oxy]-2-methyl-6-oxopyrimidin-1(6H)-yl]-4-methylbenzoic acid (0.16 g, 0.00034 mol, obtained from Step 5) at 0° C. is added isobutylchloroformate (0.063 g, 0.00046 mol) followed by the addition of N-methylmorpholine (0.064 g, 0.00064 mol). The resulting reaction mixture is stirred for 5 minutes under an argon atmosphere. The ice bath is then removed, the reaction mixture is stirred at room temperature for 20 minutes, then the reaction mixture is recooled to 0° C., and N-methylamine (0.5 mL of 2.0 M soln in THF) is added. The resulting mixture is stirred at room temperature for 10 min, concentrated in vacuo, and the residue is purified by reverse-phase HPLC using 10-90% CH$_3$CN/Water gradient (40 min) at a flow rate of 80 mL/min. The appropriate fractions (MH$^+$, m/z=478) are combined, concentrated to a small volume (~20 mL), cooled, 5% NaHCO$_3$ solution (10 mL) is added and then the combined fractions are extracted with dichloromethane (3×20 mL). The combined organic extracts are dried (Na$_2$SO$_4$), filtered, and concentrated to dryness to afford the title compound (0.16 g, 96%) as a white amorphous substance: $^1$H NMR (CD$_3$OD/400 MHz) δ 7.87 (dd 1H, J=8.0 Hz), 7.64 (d, 1H, J=1.6 Hz), 7.61 (m, 1H), 7.53 (d, 1H, J=8.0 Hz), 7.01 (m, 2H), 5.55 (m, 2H), 2.89 (s, 3H), 2.16 (s, 3H), and 2.12 (s, 3H); ES-HRMS m/z 478.0586 (M+H calcd for C$_{21}$H$_{19}$N$_2$O$_4$F$_2$ requires 478.0572). $^{19}$F NMR (CD$_3$OD/400 MHz) −111.84 (m) and −115.91 (m).

Preparation of 3-[5-Bromo-4-[(2,4-difluorobenzyl)oxy]-2-methyl-6-oxopyrimidin-1(6H)-yl]-4-methylbenzamide

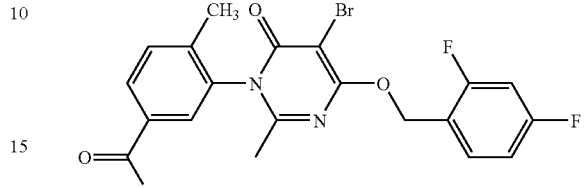

Step 1: Preparation of 3-[5-Bromo-4-[(2,4-difluorobenzyl)oxy]-2-methyl-6-oxopyrimidin-1(6H)-yl]-4-methylbenzoic acid

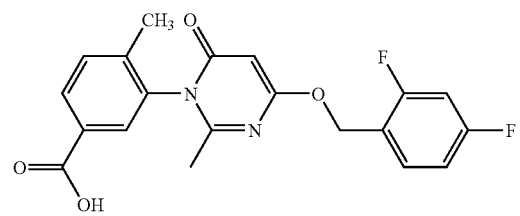

A mixture of methyl 3-[4-[(2,4-difluorobenzyl)oxy]-2-methyl-6-oxopyrimidin-1(6H)-yl]-4-methylbenzoate (0.20 g, 0.0005 mol) and 2N NaOH (0.4 mL, 0.0008 mol) in dioxane (0.25 mL) is stirred at room temperature for 45 min. The resulting clear solution is diluted with water (5.0 mL), acidified with acetic acid and extracted with dichloromethane (2×10 mL). The combined organic extracts are washed with water (2×10 mL), dried (Na$_2$SO$_4$), filtered, and concentrated to dryness to afford the title compound (0.15 g, 78%) as a white powder: $^1$H NMR (CD$_3$OD/400 MHz) δ 8.08 (m,1H), 7.85 (d, 1H, J=1.6 Hz), 7.55 (m, 2H), 7.00 (m, 2H), 5.80 (s, 1H), 5.38 (s, 2H), 2.14 (s, 3H), and 2.13 (s, 3H); ES-HRMS m/z 387.1166 (M+H calcd for C$_{20}$H$_{17}$N$_2$O$_4$F$_2$ requires 387.1151). $^{19}$F NMR (CD$_3$OD/400 MHz) −107.75 (m) and −112.08 (m).

Step 2. Preparation of Title Compound

To a suspension of 3-[5-Bromo-4-[(2,4-difluorobenzyl)oxy]-2-methyl-6-oxopyrimidin-1(6H)-yl]-4-methylbenzoic acid (0.15 g, 0.00039 mol, obtained from step 1) in dichloromethane (5.0 mL) and dioxane (1.0 mL) is added NBS (0.075 g, 0.00042 mol). The resulting reaction mixture is stirred at room temperature for 1 hour and then concentrated to dryness. The residue is dried in a desiccator for 1 hour, dissolved in dimethylacetamide (2.5 mL), isobutylchloroformate (0.075 mL, 0.00058 mol) is added, N-methylmorpholine (0.14 mL, 0.0013 mol) is then added, and the reaction mixture is stirred at 0° C. for 5 min under argon. After stirring the reaction mixture at room temperature for 30 min, it is cooled to 0° C., a solution of ammonia in isopropanol (1.2 mL of 2M ammonia in isopropanol) is added and the resulting reaction mixture is stirred at 0° C. for 30 min. The resulting mixture is concentrated to dryness under reduced pressure and the residue is purified by reverse-phase HPLC using 10-90% CH$_3$CN/Water gradient (40 min) at a flow rate of 80 mL/min. The appropriate fractions (MH$^+$, m/z=464) are combined and concentrated to a small volume (~25 mL), cooled, 5% NaHCO$_3$ solution (5.0 mL) is added and then the mixture is extracted with dichloromethane (2×20 mL). The combined organic extracts are dried (Na$_2$SO$_4$), filtered, and concentrated to dryness to afford the desired product (0.115 g, 77%) as a white powder: $^1$H NMR (CD$_3$OD/400 MHz) δ 7.95 (m 1H), 7.12 (d, 1H J=1.6 Hz), 7.62 (m 1H), 7.61 (m, 1H), 7.01 (m, 2H), 5.58 (m, 2H), 2.16 (s, 3H), and 2.12 (s, 3H); ES-HRMS m/z 464.0436 (M+H calcd for C$_{20}$H$_{17}$N$_3$O$_3$F$_2$Br requires 464.0416). $^{19}$F NMR (CD$_3$OD/400 MHz) −111.85 (m) and −115.92 (m).

Preparation of 4-{[5-bromo-4-[(2,4-difluorobenzyl)oxy]-2-methyl-6-oxopyrimidin-1(6H)-yl]methyl}-N-methylbenzamide

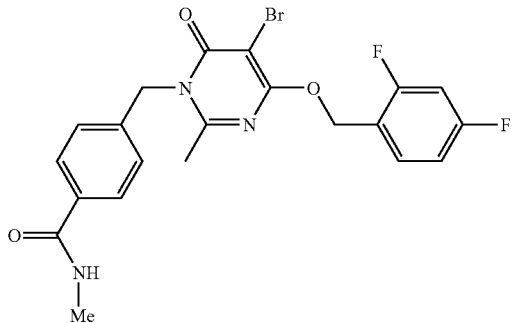

Step 1: Preparation of Methyl 3-({(1Z)-1-[(2-naphthylmethyl)thio]ethylidene}amino)-3-oxopropanoate

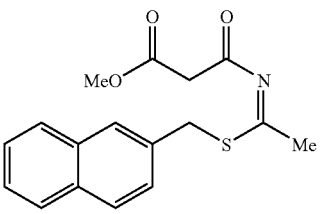

To a suspension of 2-naphthylmethyl ethanimidothioate hydrobromide (3.0 g, 0.01 mol) in THF (20.0 mL) at 0° C., is added N-methylmorpholine (2.4 mL. 0.022 mol), followed by the dropwise addition of a solution of methyl malonyl chloride (1.2 mL, 0.011 mol) in THF (5.0 mL). The resulting mixture is stirred at 0° C. for 30 min, and at room temperature for an additional 30 min. The mixture is diluted with cold water, (25 mL) and extracted with dichloromethane (2×20 mL). The combined organic extracts are washed with water, dried (Na$_2$SO$_4$), filtered and concentrated to dryness under reduced pressure to give a yellow syrup, which is purified by flash chromatography using 25% EtOAc in hexanes to give the title compound (1.9 g, 59%) as colorless syrup: ES-HRMS m/z 316.0993 (M+H calcd for C$_{17}$H$_{18}$NO$_3$SN requires 316.1002).

Step 2: Preparation of methyl 4-[(4-hydroxy-2-methyl-6-oxopyrimidin-1(6H)-yl)methyl]benzoate

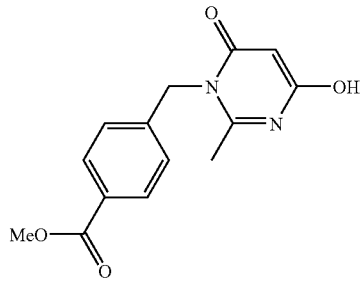

To a solution of methyl 3-({(1Z)-1-[(2-naphthylmethyl)thio]ethylidene}amino)-3-oxopropanoate (1.9 g, 0.006 mol, from step 1) in THF (25.0 mL), at 0° C., is added methyl-4-aminomethylbenzoate (1.1 g, 0.0067 mol). The reaction mixture is stirred at room temperature for 1 hour, and then concentrated to dryness. The resulting residue is dissolved in dioxane (20.0 mL), DBU (0.1 mL) is added, and the resulting reaction mixture is heated at 70° C. for 1 h under an argon atmosphere. After removing the solvent under reduced pressure, the residue is purified by reverse-phase HPLC using 10-90% CH$_3$CN/Water gradient (40 min) at a flow rate of 80 mL/min. The appropriate fractions (MH$^+$, m/z=275) are combined and freeze-dried to afford the title compound (0.33 g) as a white powder: $^1$H NMR (CD$_3$OD/400 MHz) δ 7.99 (d 2H, J=8.4 Hz), 7.29 (d, 2H, J=8.4 Hz), 5.42 (s, 1H), 5.36 (s, 2H), 3.88 (s, 3H), and 2.42 (s, 3H); ES-HRMS m/z 275.1021 (M+H calcd for C$_{14}$H$_{15}$N$_2$O$_4$ requires 275.1026).

Step 3. Preparation of methyl 4-{[4-[(2,4-difluorobenzyl)oxy]-2-methyl-6-oxopyrimidin-1(6H)-yl]methyl}benzoate

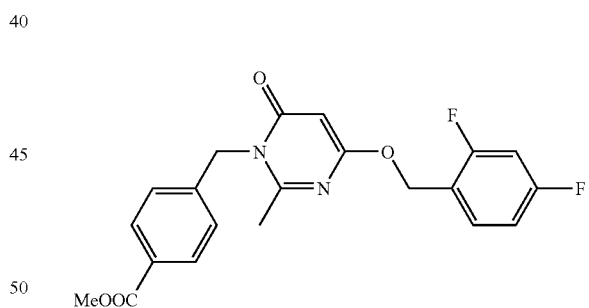

A mixture of methyl 4-[(4-hydroxy-2-methyl-6-oxopyrimidin-1(6H)-yl)methyl]benzoate (0.2 g, 0.00073 mol, from step 2), potassium carbonate (0.15 g, 0.001 mol), 2,4 difluorobenzylbromide (0.15 g, 0.00073 mol), and 18-crown-6 (0.011 g) in DMF is stirred at room temperature for 1 h under argon atmosphere. The DMF was distilled in vacuo and the residue is partitioned between dichloromethane (20 mL) and water (20 mL). The organic phase is washed with water, dried (Na$_2$SO$_4$), filtered and concentrated under reduced pressure. The resulting residue is purified by silica gel flash chromatography using 35% EtOAc in hexanes to afford the title compound (0.20 g, 69%) as a white powder: $^1$H NMR (CD$_3$OD/400 MHz) δ 7.98 (d 2H, J=8.4 Hz), 7.54 (m, 1H), 7.27 (d, 2H, J=8.4 Hz), 6.98 (m, 2H), 5.78 (s, 1H), 5.38 (s, 2H), 5.32 (s, 2H), 3.88 (s, 3H), and 2.44 (s, 3H); ES-HRMS m/z 401.1308 (M+H calcd for $C_{21}H_{19}N_2O_4F_2$ requires 401.1307). $^{19}F$ NMR ($CD_3OD$/400 MHz) −111.77 (m), 116.06 (m).

Step 4: Preparation of 4-{[4-[(2,4-difluorobenzyl) oxy]-2-methyl-6-oxopyrimidin-1(6H)-yl] methyl}benzoic acid

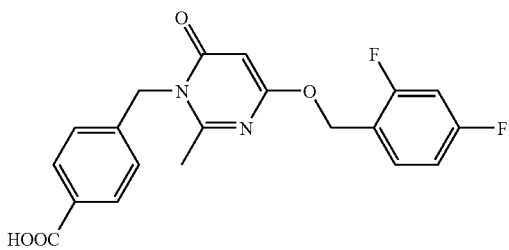

A mixture of methyl 4-{[4-[(2,4-difluorobenzyl)oxy]-2-methyl-6-oxopyrimidin-1(6H)-yl]methyl}benzoate (0.20 g, 0.0005 mol, from step 3) and 2N NaOH (0.4 mL, 0.0008 mol) in dioxane (0.25 mL) is stirred at room temperature for 45 min. The resulting clear solution is diluted with water (5.0 mL), acidified with acetic acid and extracted with dichloromethane (2×10 mL). The combined organic extracts are washed with water (2×10 mL), dried ($Na_2SO_4$), filtered and concentrated to dryness to afford the title compound (0.15 g, 78%) as a white powder: $^1H$ NMR ($CD_3OD$/400 MHz) δ 7.99 (d, 2H, J=8.0 Hz), 7.54 (m, 1H,), 7.27 (d, 2H, J=8.0 Hz), 6.00 (m, 2H), 5.78 (s, 1H), 5.39 (s, 2H), 5.32 (s, 2H), 2.45 (s, 3H), and 2.13 (s, 3H); ES-HRMS m/z 387.1134 (M+H calcd for $C_{20}H_{17}N_2O_4F_2$ requires 387.1151). $^{19}F$ NMR ($CD_3OD$/400 MHz) −111.79 (m) and −116.08 (m).

Step 5: Preparation of the title compound

To a suspension of 4-{[4-[(2,4-difluorobenzyl)oxy]-2-methyl-6-oxopyrimidin-1(6H)-yl]methyl}benzoic acid (0.18 g, 0.00047 mol, from step 4) in dichloromethane (3.0 mL) and dioxane (1.0 mL) is added NBS (0.09 g, 0.0005 mol). The resulting reaction mixture is stirred at room temperature for 3 hours, concentrated to dryness, and the residue is then dried in a desiccator for 2 h. This residue is dissolved in dimethylacetamide (2.5 mL), isobutylchloroformate (0.08 mL, 0.00062 mol) is added, N-methylmorpholine (0.0.08 mL, 0.00073 mol) is then added, and the reaction mixture is stirred at 0° C. for 5 min under argon. The reaction mixture is then stirred at room temperature for 30 min, it is recooled to 0° C., a solution of N-methylamine in THF (1.1 mL of 2M in THF) is then added, and the resulting reaction mixture is stirred at 0° C. for 30 min. The resulting mixture is concentrated to dryness under reduced pressure and the residue is purified by reverse-phase HPLC using 10-90% $CH_3CN$/Water gradient (40 min) at a flow rate of 80 mL/min. The appropriate fractions (MH+, m/z=478) are combined and concentrated to a small volume (~25 mL), cooled added 5% $NaHCO_3$ solution (5.0 mL) and extracted with dichloromethane (2×20 mL). The combined organic extracts are dried ($Na_2SO_4$), filtered and concentrated to dryness to afford the title compound (0.14 g, 64%) as a white powder: $^1H$ NMR ($CD_3OD$/400 MHz) δ 7.77 (d 2H, J=8.4 Hz), 7.58 (m, 1H), 7.26 (d, 2H, J=8.4 Hz), 7.01 (m, 2H), 5.49 (s, 2H), 5.42 (s, 2H), 2.89 (s, 3H), and 2.48 (s, 3H); ES-HRMS m/z 478.0596 (M+H calcd for $C_{21}H_{19}N_3O_3F_2Br$ requires 478.0572). $^{19}F$ NMR ($CD_3OD$/400 MHz) −111.99 (m) and −115.99 (m).

Preparation of 3-[5-chloro-4-[(2,4-difluorobenzyl)oxy]-2-(methylthio)-6-oxopyrimidin-1(6H)-yl]-4-methylbenzamide

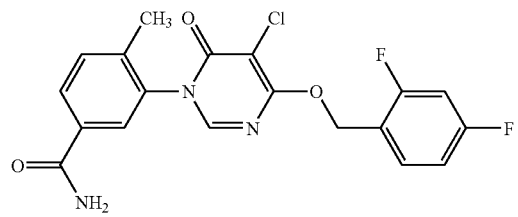

Step 1: Preparation of methyl 3-[(aminocarbonothioyl)amino]-4-methylbenzoate

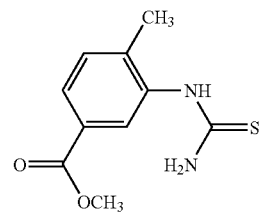

To a mixture of methyl-3-aminomethyl benzoate (5.7 g, 0.035 mol) and potassiumthiocyanate (5.0 g, 0.05 mol) in THF at 0° C., was added 4N HCl in dioxane (9.0 mL) and the resulting mixture was heated at 80° C. under argon for 20 h. After the removal of the solvents under educed pressure, the residue was triturated with water and filtered the precipitate. It was washed thoroughly washed with water and air dried to give a pale yellow substance. This material was further washed with hot ethylacetate (200 mL) and dried to give the title compound (3.85 g) as a white powder: $^1H$ NMR ($CD_3OD$/400 MHz) δ7.85 (m, 2H), 7.38 (m, (1H), 3.89 (s, 3H), and 2.33 (s, 3H); ES-HRMS m/z 225.0672 (M+H calcd for $C_{10}H_{13}N_2O_2S$ requires 225.0692).

Step 2: Preparation of methyl 3-[4-hydroxy-2-(methylthio)-6-oxopyrimidin-1(6H)-yl]-4-methylbenzoate

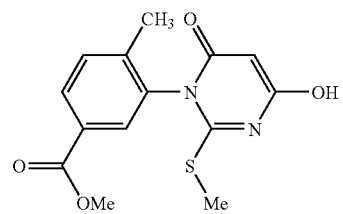

To a suspension of 3-[(aminocarbonothioyl)amino]-4-methylbenzoate (1.5 g, 0.067 mol) in methanol (15.0 mL) at 0° C., was added iodomethane (0.5 mL. 0.0077 mol) and stirred at room temperature for 30 min. The reaction mixture was then heated to reflux for 15 min, when a clear solution was obtained. It was concentrated under reduced pressure, the residue was dried in vacuo for 1 h and dissolved in dichloromethane (25.0 mL). This solution was cooled to −5° C., added N-methylmorpholine (1.38 g, 0.0136 mol) followed by the dropwise addition of a solution of methylmalonyl chloride (1.36 g, 0.01 mol) in dichloromethane (5.0 mL) and the resulting mixture was stirred at room temperature overnight under argon atmosphere. The mixture was cooled to −5° C. and added an additional amount of N-methylmorpholine (0.46 g, 0.0046 mol) followed by the addition of methylmalonyl chloride (0.62 g, 0.0045 mol) and stirred at room temperature for 2 h. The reaction mixture was then cooled to 10° C., added water (25 mL) and dichloromethane (25 mL) and the mixture was stirred for 30 min. The interfacial solid was filtered, washed with water and dried in a desiccator to give 1.1 g (55%) of the title compound as a white powder: $^1$H NMR (CD$_3$OD/400 MHz) δ 8.05 (d, 1H, J=8.4 Hz), 7.80 (s, 1H), 7.52 (d, 1H, J=8.4 Hz), 5.44 (s, 1H), 3.89 (s, 3H), 2.46 (s, 3H), and 2.15 (s, 3H); ES-HRMS m/z 307.0769 (M+H calcd for C$_{14}$H$_{15}$N$_2$O$_4$S requires 307.0747).

Step 3: Preparation of methyl 3-[4-[(2,4-difluorobenzyl)oxy]-2-(methylthio)-6-oxopyrimidin-1(6H)-yl]-4-methylbenzoate

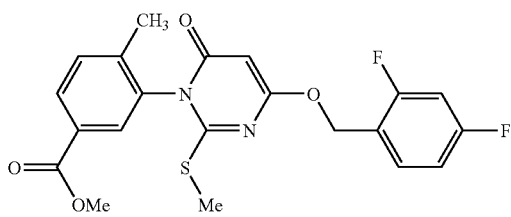

To a solution of methyl 3-[4-hydroxy-2-(methylthio)-6-oxopyrimidin-1(6H)-yl]-4-methylbenzoate (1.0 g, 0.0033 mol) in DMF (10.0 mL) obtained from step 2, was added potassium carbonate (0.7 g, 0.005 mol) followed by the addition of 2,4 difluorobenzyl bromide (0.8 g, 0.0039 mol) and stirred at 0° C. for 15 min. After stirring at room temperature for 30 min, DMF was distilled in vacuo and the residue was portioned between EtOAc (25 mL) and water (25 mL). The organic phase was washed with water, (2×20 mL), dried (Na$_2$SO$_4$) and concentrated. The resulting material was purified by flash chromatography using EtOAc/hexane (1:1 v/v) to afford the title compound (0.9 g, 64%) as a white powder: $^1$H NMR (CD$_3$OD/400 MHz) δ 8.08 (dd, 1H, J=8.4 Hz, & 1.6 Hz), 7.83 (d, 1H, J=1.6 Hz), 7.55 (m, 2H), 6.99 (m 2H), 5.64 (s, 1H), 5.48 (s, 2H), 3.89 (s, 3H), 2.50 (s, 3H), and 2.15 (s, 3H); ES-HRMS m/z 433.1016 (M+H calcd for C$_{21}$H$_{19}$N$_2$O$_4$SF$_2$ requires 433.1028).

Step 4: Preparation of 3-[4-[(2,4-difluorobenzyl)oxy]-2-(methylthio)-6-oxopyrimidin-1(6H)-yl]-4-methylbenzoic acid

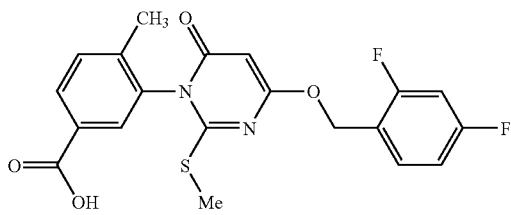

A mixture of the ester (0.4 g, 0.0009 mol) obtained from step 3, in 2N NaOH (0.9 mL) and dioxane (0.5 mL) was stirred at room temperature for 1.5 h. The resulting clear solution was diluted with water (5.0 mL), acidified with 5% citric acid and extracted with EtOAc (2×20 mL). The combined organic extracts were washed with water (2×15 mL), dried (Na$_2$SO$_4$), and concentrated to afford the title compound (0.38 g) as a white powder: $^1$H NMR (CD$_3$OD/400 MHz) δ 8.06 (d, 1H, J=8.0 Hz), 7.81 (s, 1H), 7.51 (m, 2H), 6.99 (m 2H), 5.64 (s, 1H), 5.48 (s, 2H), 2.50 (s, 3H), and 2.15 (s, 3H); ES-HRMS m/z 419.0892 (M+H calcd for C$_{20}$H$_{17}$N$_2$O$_4$SF$_2$ requires 419.0872).

Step 5: Preparation of 3-[5-chloro-4-[(2,4-difluorobenzyl)oxy]-2-(methylthio)-6-oxopyrimidin-1(6H)-yl]-4-methylbenzamide

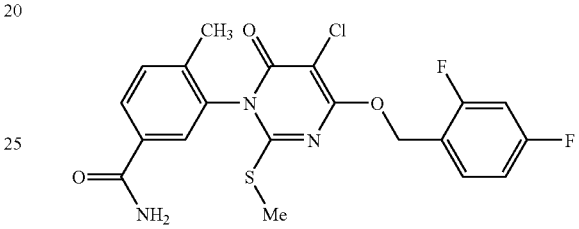

A mixture of 3-[4-[(2,4-difluorobenzyl)oxy]-2-(methylthio)-6-oxopyrimidin-1(6H)-yl]-4-methylbenzoic acid (0.5 g, 0.001 mol, from step 4), N-chlorosuccinimide (0.14 g, 0.001 mol) in dichloroethane containing dichloroacetic acid (0.2 mL) was heated at 65° C. for 3 h under argon atmosphere. An additional amount of N-chlorosuccinimide (0.05 g) was added and heating was continued for an additional 16 h. The reaction mixture was concentrated under reduced pressure and the residue was partitioned between EtOAc (25 mL) and water (30 mL). The organic phase was washed with water (2×10 mL), dried (Na$_2$SO$_4$), and concentrated to dryness under reduced pressure.

The resulting material was dried in vacuo for 3 h, dissolved in DMF (3.0 mL), added N-methylmorpholine (0.22 g, 0.0022 mol) followed by the addition of isobutylchloroformate (0.23 g, 0.0017 mol) and stirred at 0° C. under argon atmosphere. After 5 min, the mixture was stirred at room temperature for 30 min, cooled to 0° C. and added a solution of ammonia (1.8 mL of 2M soln in isopropanol) and the mixture was stirred at room temperature. After 30 min, an additional 1.0 mL of ammonia solution I isopropanol was added and continued stirring for another 30 min. After the removal of the solvents under reduced pressure the residue was purified by reverse-phase HPLC using 10-90% CH$_3$CN/Water gradient (40 min) at a flow rate of 80 mL/min. The appropriate fractions (MH$^+$, m/z=452) were combined and concentrated to a small volume (~20 mL), cooled added 5% sod. bicarbonate (10 mL) and extracted with dichloromethane (3×20 mL). The combined organic extracts were dried (Na$_2$SO$_4$) and concentrated to dryness to afford the title compound (0.15 g,) as a white powder: $^1$H NMR (CD$_3$OD/400 MHz) δ 7.87 (dd 1H, J=2.0 Hz & 8.0 Hz), 7.74 (d, 1H, J=2.0 Hz) 7.58 (m, 2H), 7.03 (m, 2H), 5.63 (m 2H), 2.53 (s, 3H), and 2.14 (s, 3H); ES-HRMS m/z 452.0633 (M+H calcd for C$_{20}$H$_{17}$N$_3$O$_3$F$_2$ClS requires 452.0642); $^{19}$F NMR (CD$_3$OD/400 MHz) −111.75 (m) and −115.99 (m).

Step 6: Preparation of the title compound 3-[5-chloro-4-[(2,4-difluorobenzyl)oxy]-6-oxopyrimidin-1(6H)-yl]-4-methylbenzamide

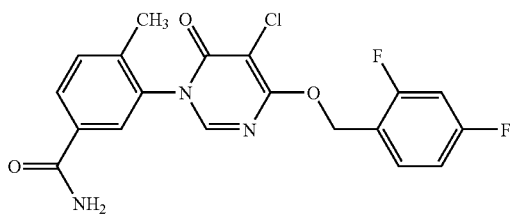

A mixture of 3-[5-chloro-4-[(2,4-difluorobenzyl)oxy]-2-(methylthio)-6-oxopyrimidin-1(6H)-yl]-4-methylbenzamide (0.15 g, 0.00033 mol from step 5), and Raney nickel (0.8 mL, 50% slurry in water) in ethanol (15.0 mL) was refluxed under argon atmosphere. After 12 h, added an additional 0.4 mL of Raney nickel and continued refluxing for another 4 h. The reaction mixture was cooled and the supernatant was decanted off. The catalyst was washed with ethanol, the combined ethanol washings and the supernatant were concentrated under reduced pressure and the resulting residue was purified by reverse-phase HPLC using 10-90% $CH_3CN$/Water gradient (40 min) at a flow rate of 80 mL/min. The appropriate fractions ($MH^+$, m/z=406 were combined and concentrated to a small volume (~20 mL), cooled added 5% sod. bicarbonate (10 mL) and extracted with dichloromethane (3×20 mL). The combined organic extracts were dried ($Na_2SO_4$) and concentrated to dryness to afford the title compound (0.075 g,) as a white powder: $^1$H NMR ($CD_3OD$/400 MHz) δ 8.31 (s, 1H ), 7.94 (dd, 1H. J=2.0 Hz & 8.0 Hz), 7.79 (d, 1H, J=2.0 Hz), 7.62 (m, 1H), 7.53 (m, 1H), 7.02 (m, 2H), 5.59 (m, 2H), and 2.19 (s, 3H); ES-HRMS m/z 406.0774 (M+H calcd for $C_{19}H_{15}N_3O_3F_2Cl$ requires 406.0765); $^{19}$F NMR ($CD_3OD$/400 MHz) −111.62 (m) and −115.94 (m).

Preparation of (±) 3-[5-bromo-4-[(2,4-difluorobenzyl)oxy]-2-methyl-6-oxopyrimidin-1(6H)-yl]-4-methyl-N-{1-[(methylamino)carbonyl]methyl}benzamide

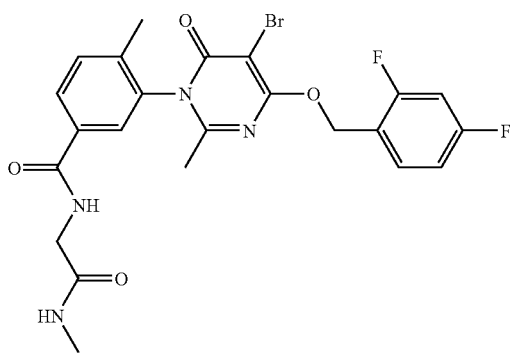

To a solution of 3-[5-bromo-4-[(2,4-difluorobenzyl)oxy]-2-methyl-6-oxopyrimidin-1(6H)-yl]-4-methylbenzoic acid (1.0 g, 0.022 mol) in dimethylacetamide (10.0 mL) at −20° C. was added isobutylchloroformate (0.36 g, 0.0028 mol), followed by dropwise addition of N-methylmorpholine (0.30 g, 0.003 mol) and stirred for 10 min under nitrogen atmosphere. The reaction mixture was then stirred at room temperature for 20 min, cooled to 0° C., and added N-methylmorpholine (0.30 g, 0.003 mol) followed by the addition of N-methylglycine amide hydrochloride (0.35 g, 0.0028 mol) and DMAP (0.025 g). The reaction mixture was stirred at room temperature for 4 h, and concentrated in vacuo. The resulting the residue was purified by reverse-phase HPLC using 10-90% $CH_3CN$/Water gradient (40 min) at a flow rate of 80 mL/min. The appropriate fractions ($MH^+$, m/z=535) were combined, and freeze-dried to give a white solid. This was dissolved in dichloromethane (25 mL), washed successively with 5% sodium bicarbonate (2×20 mL), water (2×20 mL), dried ($Na_2SO_4$), and concentrated to dryness to afford the racemic title compound (0.75 g, 65%) as a white amorphous substance: $^1$H NMR ($CD_3OD$/400 MHz) δ 7.96 (dd 1H, J=1.6 Hz, 8.0 Hz), 7.72 (d, 1H, J=1.6 Hz), 7.62 (m, 1H), 7.56 (d, 1H, J=8.0 Hz), 7.01 (m, 2H), 5.55 (abq, 2H), 3.99 (s, 2H), 2.74 (s, 3H), 2.18 (s, 3H), and 2.14 (s, 3H); ES-HRMS m/z 535.0792 (M+H calcd for $C_{23}H_{22}N_4O_4F_2$ Br requires 535.0787). $^{19}$F NMR ($CD_3OD$/400 MHz) −111.85 (m) and −115.91 (m).

Preparation of (−) 3-[5-bromo-4-[(2,4-difluorobenzyl)oxy]-2-methyl-6-oxopyrimidin-1(6H)-yl]-4-methyl-N-{1-[(methylamino)carbonyl]methyl}benzamide

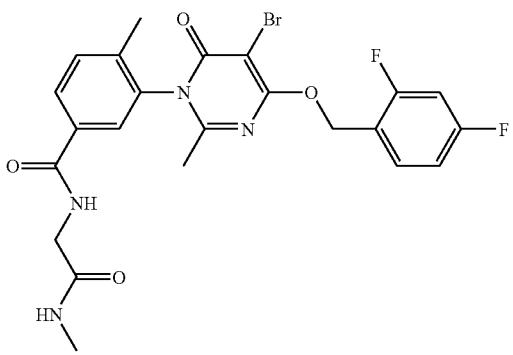

The racemic compound (1.9 g) was resolved using a Chiralpak AD-H column, 21×250 mm. The sample was dissolved in EtOH/MeOH (50/50 v/v, 25 mg/mL) and 2.7 mL of the solution was injected into the column and eluted with EtOH/MeOH (80/20 v/v) at a flow rate of 12 mL/min. Fractions with negative optical rotation were pooled together and concentrated under reduced pressure to give 0.69 g of the (−) isomer as a white solid:

$^1$H NMR ($CD_3OD$/400 MHz) δ 7.96 (dd 1H, J=2.0 Hz, 8.0 Hz), 7.72 (d, 1H, J=2.0 Hz), 7.62 (m, 1H), 7.55 (d, 1H, J=8.0 Hz), 7.01 (m, 2H), 5.55 (abq, 2H), 3.99 (s, 2H), 2.74 (s, 3H), 2.18 (s, 3H), and 2.14 (s, 3H); ES-HRMS m/z 535.0824 (M+H calcd for $C_{23}H_{22}N_4O_4F_2$ Br requires 535.0787). $^{19}$F NMR ($CD_3OD$/400 MHz) −111.85 (m) and −115.90 (m).

Preparation of (+) 3-[5-bromo-4-[(2,4-difluorobenzyl)oxy]-2-methyl-6-oxopyrimidin-1(6H)-yl]-4-methyl-N-{1-[(methylamino)carbonyl]methyl}benzamide

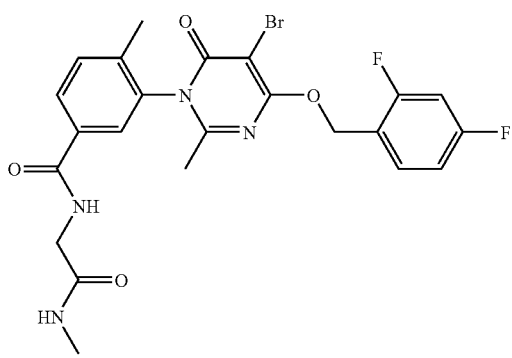

The title compound was isolated from the racemic material (1.9 g) according to the resolution procedure described for (−) 3-[5-bromo-4-[(2,4-difluorobenzyl)oxy]-2-methyl-6-oxopyrimidin-1(6H)-yl]-4-methyl-N-{1-[(methylamino)carbonyl]methyl}benzamide. Fractions with positive optical rotation were pooled together and concentrated under reduced pressure to give 0.82 g of the (+) isomer as an amorphous white solid: $^1$H NMR (CD$_3$OD/400 MHz) δ 7.95 (dd 1H, J=1.6 Hz, 8.0 Hz), 7.72 (d, 1H, J=2.0 Hz), 7.62 (m, 1H), 7.55 (d, 1H, J=8.4 Hz), 7.01 (m, 2H), 5.55 (abq, 2H), 3.98 (s, 2H), 2.74 (s, 3H), 2.18 (s, 3H), and 2.14 (s, 3H); ES-HRMS m/z 535.0770 (M+H calcd for C$_{23}$H$_{22}$N$_4$O$_4$F$_2$ Br requires 535.0787). $^{19}$F NMR (CD$_3$OD/400 MHz) −111.84 (m) and −115.89 (m).

Preparation of (−) 3-[5-bromo-4-[(2,4-difluorobenzyl)oxy]-2-methyl-6-oxopyrimidin-1(6H)-yl]-4-methylbenzamide

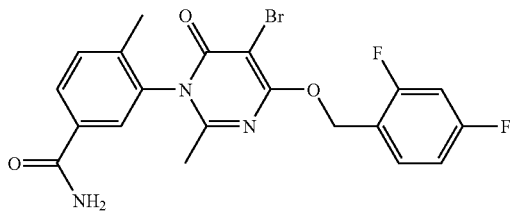

The racemic compound 3-[5-bromo-4-[(2,4-difluorobenzyl)oxy]-2-methyl-6-oxopyrimidin-1(6H)-yl]-4-methylbenzamide (90.0 mg) was resolved using a Chiralpak AD column, 4.5×250 mm. The sample was dissolved in 30% EtOH in hexane and 30 □L of the solution was injected into the column and eluted with 30% EtOH in hexane at a flow rate of 1.5 mL/min. Fractions with negative optical rotation were pooled together and concentrated under reduced pressure to give 39 mg of the (−) isomer as a white solid:

$^1$H NMR (CD$_3$OD/400 MHz) δ 7.94 (dd 1H, J=1.6 Hz, 8.0 Hz), 7.72 (d, 1H, J=1.6 Hz), 7.63 (m, 1H), 7.55 (d, 1H, J=8.0 Hz), 7.01 (m, 2H), 5.55 (abq, 2H), 2.17 (s, 3H), and 2.13 (s, 3H); ES-HRMS m/z 464.0439 (M+H calcd for C$_{20}$H$_{17}$N$_3$O$_3$F$_2$ Br requires 464.0416). $^{19}$F NMR (CD$_3$OD/400 MHz) −111.86 (m) and −115.92 (m).

Preparation of (+) 3-[5-bromo-4-[(2,4-difluorobenzyl)oxy]-2-methyl-6-oxopyrimidin-1(6H)-yl]-4-methylbenzamide

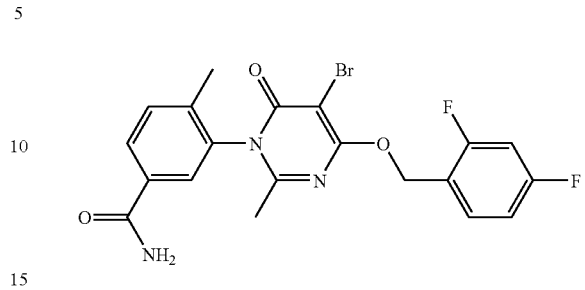

The title compound was isolated from the racemic material (90.0 mg) according to the resolution procedure described for (−) 3-[5-bromo-4-[(2,4-difluorobenzyl)oxy]-2-methyl-6-oxopyrimidin-1(6H)-yl]-4-methylbenzamide. Fractions with positive optical rotation were pooled together and concentrated under reduced pressure to give 38.5 mg of the (+) isomer as a white solid: $^1$H NMR (CD$_3$OD/400 MHz) δ 7.95 (dd 1H, J=2.0 Hz, 8.0 Hz), 7.72 (d, 1H, J=2.0 Hz), 7.63 (m, 1H), 7.55 (d, 1H, J=8.0 Hz), 7.01 (m, 2H), 5.55 (abq, 2H), 2.17 (s, 3H), and 2.13 (s, 3H); ES-HRMS m/z 535. (M+H); $^{19}$F NMR (CD$_3$OD/400 MHz) −111.84 (m) and −115.90 (m); ES-HRMS m/z 464.0410 (M+H calcd for C$_{20}$H$_{17}$N$_3$O$_3$F$_2$ Br requires 464.0416). $^{19}$F NMR (CD$_3$OD/400 MHz) −111.86 (m) and −115.92 (m).

Preparation of (−) 3-[5-Bromo-4-[(2,4-difluorobenzyl)oxy]-2-methyl-6-oxopyrimidin-1(6H)-yl]-N,4-dimethylbenzamide

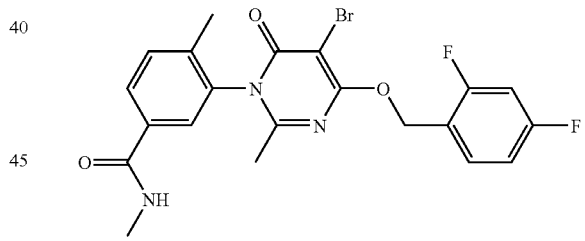

The racemic compound 3-[5-bromo-4-[(2,4-difluorobenzyl)oxy]-2-methyl-6-oxopyrimidin-1(6H)-yl]-N,4-dimethylbenzamide (82.0 mg) was resolved using a Chiralpak AD column, 4.5×250 mm. The sample was dissolved in 30% EtOH in hexane and 30 □L of the solution was injected into the column and eluted with 30% EtOH in hexane at a flow rate of 1.5 mL/min. Fractions with negative optical rotation were pooled together and concentrated under reduced pressure to give 37.6 mg of (−) isomer as a white solid:

$^1$H NMR (CDCl$_3$/400 MHz) δ 7.81 (dd 1H, J=1.6 Hz, 8.0 Hz), 7.54 (m, 1H), 7.48 (d, 1H J=1.6 Hz), 7.40 (d, 1H, J=8.0 Hz), 6.86 (m, 2H), 6.31 (br, 1H), 5.48 (abq, 2H), 2.78 (d, 3H, J=4.8 Hz), 2.14 (s, 3H), and 2.09 (s, 3H); ES-HRMS m/z 478.0580 (M+H calcd for C$_{21}$H$_{19}$N$_3$O$_3$F$_2$ Br requires 478.0572). $^{19}$F NMR (CD$_3$OD/400 MHz) −109.96 (m) and −114.02 (m).

Preparation of (+) 3-[5-Bromo-4-[(2,4-difluorobenzyl)oxy]-2-methyl-6-oxopyrimidin-1(6H)-yl]-N,4-dimethylbenzamide

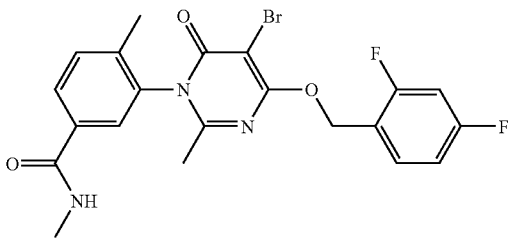

The title compound was isolated from the racemic material (82.0 mg) according to the resolution procedure described for (−) 3-[5-Bromo-4-[(2,4-difluorobenzyl)oxy]-2-methyl-6-oxopyrimidin-1(6H)-yl]-N,4-dimethylbenzamide. Fractions with positive optical rotation were pooled together and concentrated under reduced pressure to give 39.8 mg of (+) isomer as a white solid: $^1$H NMR (CDCl$_3$/400 MHz) δ 7.81 (dd 1H, J=1.6 Hz, 8.0 Hz), 7.52 (m, 1H), 7.48 (d, 1H, J=1.6 Hz), 7.41 (dd, 1H, J=8.0 Hz), 6.85 (m, 2H), 6.28 (br, 1H), 5.50 (abq, 2H), 2.81 (d, 3H, J=4.4 Hz), and 2.14 (s, 3H), and 2.09 (s, 3H); ES-HRMS m/z 478.0577 (M+H calcd for C$_{21}$H$_{19}$N$_3$O$_3$F$_2$ Br requires 478.0572). $^{19}$F NMR (CD$_3$OD/400 MHz) −109.97 (m) −114.03.

Preparation of (−) 3-[5-bromo-4-[(2,4-difluorobenzyl)oxy]-2-methyl-6-oxopyrimidin-1(6H)-yl]-4-methyl-N-{1-[aminocarbonyl]methyl}benzamide

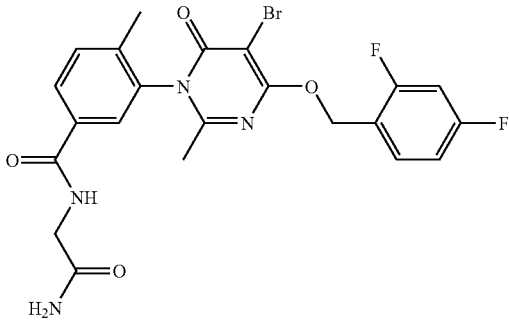

The racemic compound 3-(4-(2,4-difluorobenzyloxy)-5-bromo-2-methyl-6-oxopyrimidin-1(6H)-yl)-N-(carbamoylmethyl)-4-methylbenzamide (3.0 g) was resolved using a Chiralcel OJ-H column, 21×250 mm. The compound was dissolved in methanol (15 mg/mL), and injected 5 mL of the solution and eluted with methanol at a flow rate of 20.0 mL/min. Fractions with negative optical rotation were pooled together and concentrated under reduced pressure to give 1.42 g of the (−) isomer as a white solid: $^1$H NMR (CD$_3$OD/400 MHz) δ 7.96 (dd 1H, J=2.4 Hz, 10.4 Hz), 7.74 (d, 1H, J=2.4 Hz), 7.64 (m, 1H), 7.56 (d, 1H, J=11.2 Hz), 7.012 (m, 2H), 5.58 (abq, 2H), 4.02 (s, 2H), 2.19 (s, 3H), 2.15 (s, 3H); ES-HRMS m/z 521.0615 (M+H calcd for C$_{22}$H$_{20}$N$_4$O$_4$F$_2$ Br requires 521.0630). $^{19}$F NMR (CD$_3$OD/400 MHz) −111.85 (m) and −115.90 (m).

Preparation of (+) 3-[5-bromo-4-[(2,4-difluorobenzyl)oxy]-2-methyl-6-oxopyrimidin-1(6H)-yl]-4-methyl-N-{1-[aminocarbonyl]methyl}benzamide

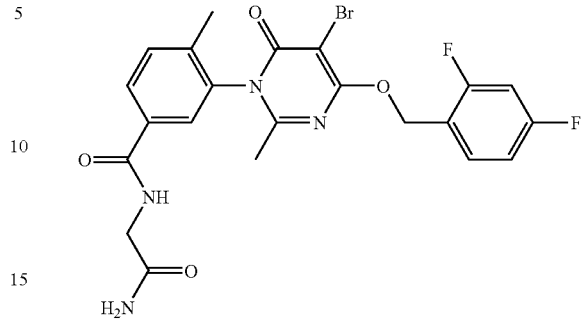

The title compound was isolated from the racemic material (3.0 g) according to the resolution procedure described for (−) 3-[5-bromo-4-[(2,4-difluorobenzyl)oxy]-2-methyl-6-oxopyrimidin-1(6H)-yl]-4-methyl-N-{1-[aminocarbonyl]methyl}benzamide. Fractions with positive optical rotation were pooled together and concentrated under reduced pressure to give 1.52 g of the (+) isomer as a white solid: $^1$H NMR (CD$_3$OD/400 MHz) δ 7.96 (dd 1H, J=2.4 Hz, 10.4 Hz), 7.74 (d, 1H, J=2.4 Hz), 7.62 (m, 1H), 7.56 (d, 1H, J=10.4 Hz), 7.02 (m, 2H), 5.58 (abq, 2H), 4.03 (s, 2H), 2.19 (s, 3H), 2.15 (s, 3H); ES-HRMS m/z 521.0670. (M+H calcd for C$_{22}$H$_{20}$N$_4$O$_4$F$_2$ Br requires 521.0630). $^{19}$F NMR (CD$_3$OD/400 MHz) −111.84 (m) and −115.90 (m).

Preparation of (±) 3-[5-bromo-4-[(2,4-difluorobenzyl)oxy]-2-methyl-6-oxopyrimidin-1(6H)-yl]-N-[(2S)-2,3-dihydroxypropyl]-4-methylbenzamide

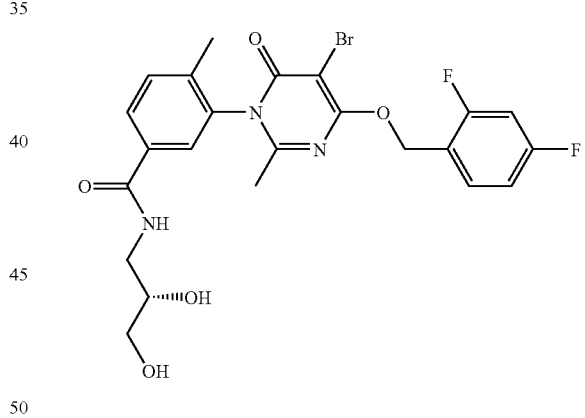

To a solution of 3-[5-bromo-4-[(2,4-difluorobenzyl)oxy]-2-methyl-6-oxopyrimidin-1(6H)-yl]-4-methylbenzoic acid (0.3 g, 0.65 mmol) in dimethylformamide (3.0 mL) at −10° C. was added isobutylchloroformate (0.13 g, 0.92 mmol) followed by the addition of N-methylmorpholine (0.130 g, 1.28 mmol). The mixture was stirred for 10 min. under argon atmosphere. The reaction mixture was then stirred at room temperature for 30 min, cooled to 0° C., and added S-3-amino-1,2 propanediol (0.118 g, 1.3 mmol). The resulting mixture was stirred at room temperature for 1.5 h, concentrated in vacuo, and the residue was purified by reverse-phase HPLC using 10-90% CH$_3$CN/Water gradient (40 min) at a flow rate of 80 mL/min. The appropriate fractions (MH$^+$, m/z=538) were combined, and freeze-dried to give a white solid. This was dissolved in dichloromethane (20 mL), washed successively with 5% sodium bicarbonate (2×15 mL), water (2×20 mL), dried (Na$_2$SO$_4$), and concentrated to dryness to afford the racemic title compound (0.15 g, 43%) as a white amorphous substance: ¹H NMR (CD₃OD/400 MHz) δ 7.89 (dd 1H, J=1.6 Hz, 8.0 Hz), 7.66 (d, 1H, J=1.6 Hz), 7.60 (m, 1H), 7.52 (d, 1H, J=8.0 Hz), 7.01 (m, 2H), 5.54 (abq, 2H), 3.77 (m, 1H), 3.51 (m, 3H), 3.38 (m, 1H), 2.74 (s, 3H), and 2.11 (s, 3H); ES-HRMS m/z 538.0782 (M+H calcd for C₂₃H₂₃N₃O₅F₂ Br requires 538.0784). ¹⁹F NMR (CD₃OD/400 MHz) −111.85 (m) and −115.91 (m).

Preparation of (−) 3-[5-bromo-4-[(2,4-difluorobenzyl)oxy]-2-methyl-6-oxopyrimidin-1(6H)-yl]-N-[(2S)-2,3-dihydroxypropyl]-4-methylbenzamide

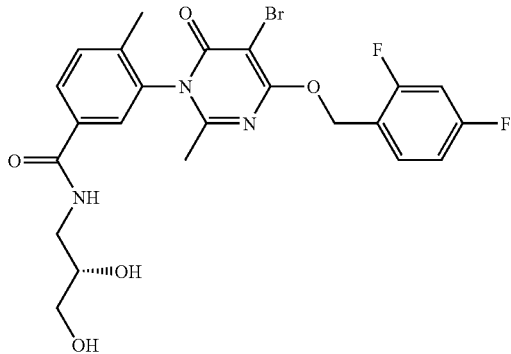

The diastereomeric mixture (±) 3-[5-bromo-4-[(2,4-difluorobenzyl)oxy]-2-methyl-6-oxopyrimidin-1(6H)-yl]-N-[(2S)-2,3-dihydroxypropyl]-4-methylbenzamide (0.15 g) was resolved using a ChiralPak AD column, 21×250 mm. The compound was dissolved in ethanol and eluted with ethanol containing 20% hexane at a flow rate of 8.0 mL/min. Fractions with negative optical rotation were pooled together and concentrated under reduced pressure to give 70 mg of the (−) isomer as a white solid: ¹H NMR (CD₃OD/400 MHz) δ 7.90 (dd 1H, J=2.0 Hz, 8.0 Hz), 7.68 (d, 1H, J=2.0 Hz), 7.60 (m, 1H), 7.56 (d, 1H, J=8.0 Hz), 7.012 (m, 2H), 5.56 (abq, 2H), 3.80 (m, 1H), 3.52 (m, 3H), 3.38 (m, 1H), 2.16 (s, 3H), and 2.12 (s, 3H); ES-HRMS m/z 538.0793 (M+H calcd for C₂₃H₂₃N₃O₅F₂ Br requires 538.0784). ¹⁹F NMR (CD₃OD/400 MHz) −111.87 (m) and −115.92 (m).

Preparation of (+) 3-[5-bromo-4-[(2,4-difluorobenzyl)oxy]-2-methyl-6-oxopyrimidin-1(6H)-yl]-N-[(2S)-2,3-dihydroxypropyl]-4-methylbenzamide

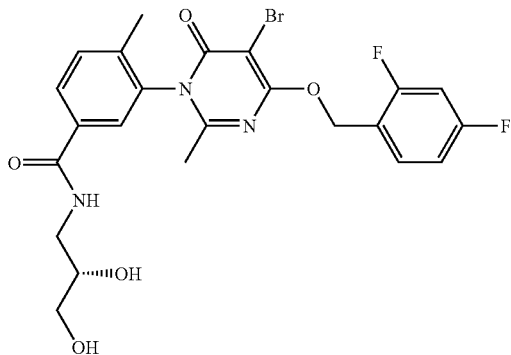

The title compound was isolated from the diastereomeric mixture (0.15 g) according to the resolution procedure described for (−) 3-[5-bromo-4-[(2,4-difluorobenzyl)oxy]-2-methyl-6-oxopyrimidin-1(6H)-yl]-N-[(2S)-2,3-dihydroxypropyl]-4-methylbenzamide. Fractions with positive optical rotation were pooled together and concentrated under reduced pressure to give 69.8 mg of the (+) isomer as a white solid: ¹H NMR (CD₃OD/400 MHz) δ 7.90 (dd 1H, J=2.0 Hz, 8.0 Hz), 7.67 (d, 1H, J=2.0 Hz), 7.60 (m, 1H), 7.56 (d, 1H, J=8.0 Hz), 7.012 (m, 2H), 5.55 (abq, 2H), 3.81 (m, 1H), 3.52 (m, 3H), 3.38 (m, 1H), 2.16 (s, 3H), and 2.12 (s, 3H); ES-HRMS m/z 538.0751 (M+H calcd for C₂₃H₂₃N₃O₅F₂ Br requires 538.0784). ¹⁹F NMR (CD₃OD/400 MHz) −111.87 (m) and −115.92 (m).

Preparation of (±) 3-[5-bromo-4-[(2,4-difluorobenzyl)oxy]-2-methyl-6-oxopyrimidin-1(6H)-yl]-N-[(2R)-2,3-dihydroxypropyl]-4-methylbenzamide

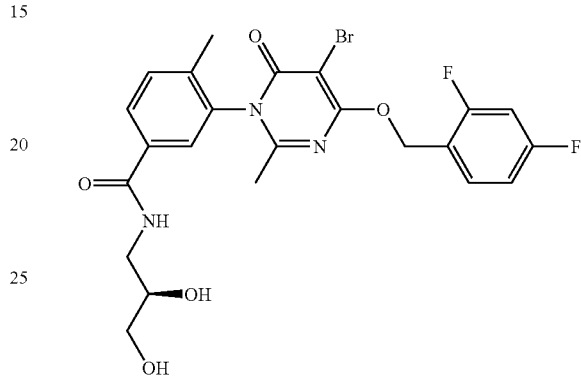

The title compound was prepared by employing a similar procedure as described for (±) 3-[5-bromo-4-[(2,4-difluorobenzyl)oxy]-2-methyl-6-oxopyrimidin-1(6H)-yl]-N-[(2S)-2,3-dihydroxypropyl]-4-methylbenzamide, substituting R-3-amino-1,2 propanediol for S-3-amino-1,2 propanediol.

Yield 46%: ¹H NMR (CD₃OD/400 MHz) δ 7.91 (dd 1H, J=1.6 Hz, 8.0 Hz), 7.67 (d, 1H, J=1.6 Hz), 7.60 (m, 1H), 7.56 (d, 1H, J=8.0 Hz), 6.97 (m, 2H), 5.54 (abq, 2H), 3.80 (m, 1H), 3.52 (m, 3H), 3.38 (m, 1H), 2.15 (s, 3H), and 2.11 (s, 3H); ES-HRMS m/z 538.0803 (M+H calcd for C₂₃H₂₃N₃O₅F₂ Br requires 538.0784). ¹⁹F NMR (CD₃OD/400 MHz) −111.86 (m) and −115.92 (m).

Preparation of (−) 3-[5-bromo-4-[(2,4-difluorobenzyl)oxy]-2-methyl-6-oxopyrimidin-1(6H)-yl]-N-[(2R)-2,3-dihydroxypropyl]-4-methylbenzamide

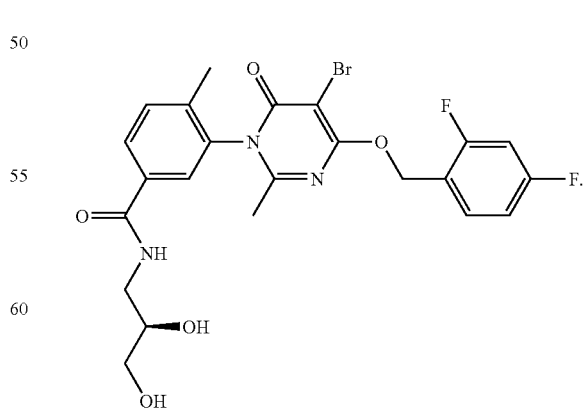

The diastereomeric compound (±) 3-[5-bromo-4-[(2,4-difluorobenzyl)oxy]-2-methyl-6-oxopyrimidin-1(6H)-yl]-N-

[(2R)-2,3-dihydroxypropyl]-4-methylbenzamide (0.24 g) was resolved using a ChiralPak AD column, 21×250 mm. The compound was dissolved in ethanol and eluted with ethanol containing 20% hexane at a flow rate of 8.0 mL/min. Fractions with negative optical rotation were pooled together and concentrated under reduced pressure to give 0.101 g of the (−) isomer as a white solid: $^1$H NMR (CD$_3$OD/400 MHz) δ 7.89 (dd 1H, J=2.0 Hz, 8.0 Hz), 7.67 (d, 1H, J=2.0 Hz), 7.60 (m, 1H), 7.53 (d, 1H, J=8.4 Hz), 6.98 (m, 2H), 5.56 (abq, 2H), 3.80 (m, 1H), 3.52 (m, 3H), 3.38 (m, 1H), 2.16 (s, 3H), and 2.12 (s, 3H); ES-HRMS m/z 538.0740 (M+H calcd for C$_{23}$H$_{23}$N$_3$O$_5$F$_2$ Br requires 538.0784). $^{19}$F NMR (CD$_3$OD/400 MHz) −111.87 (m) and −115.92 (m).

Preparation of (+) 3-[5-bromo-4-[(2,4-difluorobenzyl)oxy]-2-methyl-6-oxopyrimidin-1(6H)-yl]-N-[(2R)-2,3-dihydroxypropyl]-4-methylbenzamide

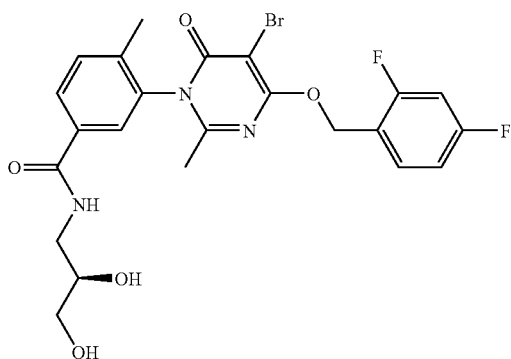

The title compound was isolated from the diastereomeric mixture (0.24 g) according to the resolution procedure described for (−) 3-[5-bromo-4-[(2,4-difluorobenzyl)oxy]-2-methyl-6-oxopyrimidin-1(6H)-yl]-N-[(2R)-2,3-dihydroxypropyl]-4-methylbenzamide. Fractions with positive optical rotation were pooled together and concentrated under reduced pressure to give 0.105 g of the (+) isomer as a white solid: $^1$H NMR (CD$_3$OD/400 MHz) δ 7.90 (dd 1H, J=2.0 Hz, 8.0 Hz), 7.68 (d, 1H, J=2.0 Hz), 7.60 (m, 1H), 7.54 (d, 1H, J=8.0 Hz), 6.99 (m, 2H), 5.56 (abq, 2H), 3.81 (m, 1H), 3.53 (m, 3H), 3.38 (m, 1H), 2.16 (s, 3H), and 2.12 (s, 3H); ES-HRMS m/z 538.0739 (M+H calcd for C$_{23}$H$_{23}$N$_3$O$_5$F$_2$ Br requires 538.0784). $^{19}$F NMR (CD$_3$OD/400 MHz) −111.87 (m) and −115.92 (m).

Preparation of (±) N-[(1S)-1-(aminocarbonyl)ethyl]-3-[5-bromo-4-[(2,4-difluorobenzyl)oxy]-2-methyl-6-oxopyrimidin-1(6H)-yl]-4-methylbenzamide

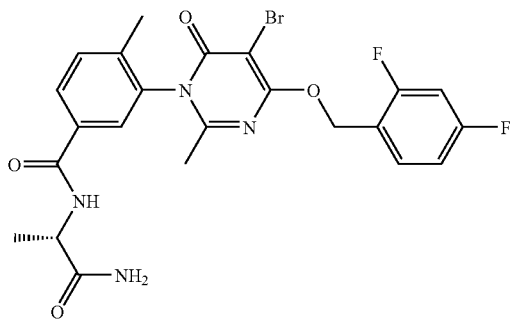

The title compound was prepared by employing a similar procedure as described for (±) 3-[5-bromo-4-[(2,4-difluorobenzyl)oxy]-2-methyl-6-oxopyrimidin-1(6H)-yl]-4-methyl-N-{1-[(methylamino)carbonyl]methyl}benzamide, substituting S-alanineamide hydrochloride for N-methylglycineamide hydrochloride. Yield 45%: $^1$H NMR (CD$_3$OD/400 MHz) δ 7.96 (m,1H), 7.73 (dd, 1H, J=2.0 Hz), 7.62 (m, 1H), 7.55 (d, 1H, J=8.0 Hz), 7.01 (m, 2H), 5.56 (abq, 2H), 4.55 (abq, 1H), 2.18 (s, 3H), 2.14 (s, 3H), and 1.45 (d, 3H, J=7.2 Hz); ES-HRMS m/z 535.0757 (M+H calcd for C$_{23}$H$_{22}$N$_4$O$_4$F$_2$ Br requires 535.0787). $^{19}$F NMR (CD$_3$OD/400 MHz) −111.86 (m) and −115.90 (m).

Preparation of (−) N-[(1S)-1-(aminocarbonyl)ethyl]-3-[5-bromo-4-[(2,4-difluorobenzyl)oxy]-2-methyl-6-oxopyrimidin-1(6H)-yl]-4-methylbenzamide

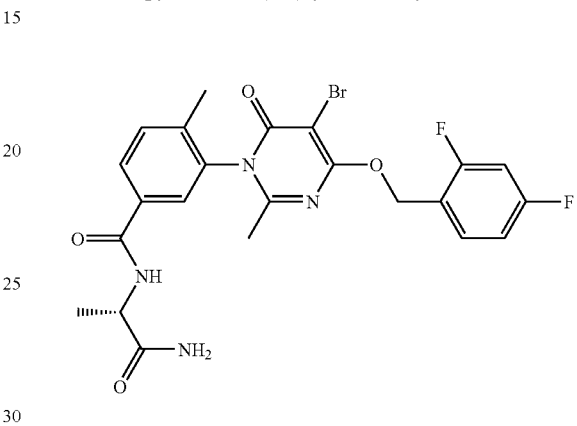

The diastereomeric mixture (±) N-[(1S)-1-(aminocarbonyl)ethyl]-3-[5-bromo-4-[(2,4-difluorobenzyl)oxy]-2-methyl-6-oxopyrimidin-1(6H)-yl]-4-methylbenzamide (2.0 g) was resolved using a Chiralcel AD-H column, 21×250 mm. The compound was dissolved in methanol (10 mg/mL), and injected 5 mL of the solution and eluted with methanol at a flow rate of 20.0 mL/min. Fractions with negative optical rotation were pooled together and concentrated under reduced pressure to give 1.01 g of the (−) isomer as an amorphous white solid: $^1$H NMR (CD$_3$OD/400 MHz) δ 7.96 (dd 1H, J=1.6 Hz, 8.0 Hz), 7.73 (d, 1H, J=2.0 Hz), 7.64 (m, 1H), 7.55 (d, 1H, J=8.0 Hz), 7.012 (m, 2H), 5.56 (abq, 2H), 4.53 (abq, 1H), 2.19 (s, 3H), 2.13 (s, 3H), and 1.44 (d, 3H, J=7.2 Hz); ES-HRMS m/z 535.0750 (M+H calcd for C$_{23}$H$_{22}$N$_4$O$_4$F$_2$ Br requires 535.0787). $^{19}$F NMR (CD$_3$OD/400 MHz) −111.88 (m) and −115.91 (m).

Preparation of (+) N-[(1S)-1-(aminocarbonyl)ethyl]-3-[5-bromo-4-[(2,4-difluorobenzyl)oxy]-2-methyl-6-oxopyrimidin-1(6H)-yl]-4-methylbenzamide

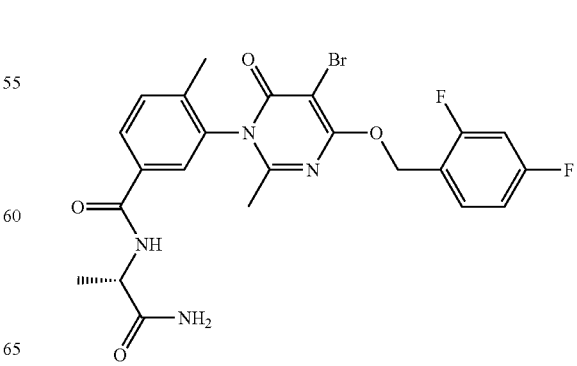

The title compound was isolated from the diastereomeric mixture (2.0 g) according to the resolution procedure described for (−) N-[(1S)-1-(aminocarbonyl)ethyl]-3-[5-bromo-4-[(2,4-difluorobenzyl)oxy]-2-methyl-6-oxopyrimidin-1(6H)-yl]-4-methylbenzamide. Fractions with positive optical rotation were pooled together and concentrated under reduced pressure to give 0.94 g of the (+) isomer as an amorphous white solid: $^1$H NMR (CD$_3$OD/400 MHz) δ 7.95 (dd 1H, J=2.0 Hz, 8.0 Hz), 7.75 (d, 1H, J=2.0 Hz), 7.64 (m, 1H), 7.54 (d, 1H, J=8.0 Hz), 7.01 (m, 2H), 5.56 (abq, 2H), 4.53 (abq, 1H), 2.19 (s, 3H), 2.13 (s, 3H), and 1.44 (d, 3H, J=7.2 Hz); ES-HRMS m/z 535.0742 (M+H calcd for C$_{23}$H$_{22}$N$_4$O$_4$F$_2$ Br requires 535.0787). $^{19}$F NMR (CD$_3$OD/400 MHz) −111.85 (m) and −115.90 (m).

Preparation of (±) 3-[5-bromo-4-[(2,4-difluorobenzyl)oxy]-2-methyl-6-oxopyrimidin-1(6H)-yl]-N-[(1R)-2-hydroxy-1-methylethyl]-4-methylbenzamide

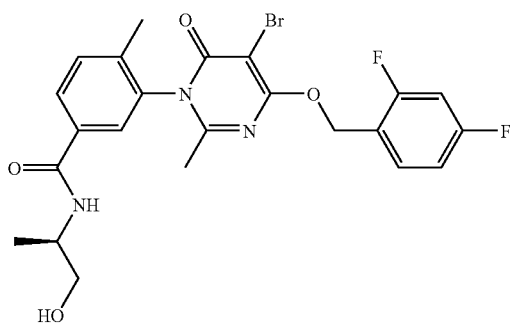

To a solution of 3-[5-bromo-4-[(2,4-difluorobenzyl)oxy]-2-methyl-6-oxopyrimidin-1(6H)-yl]-4-methylbenzoic acid (4.0 g, 0.0086 mol) in dimethylacetamide (10.0 mL) at −20° C. was added N-methylmorpholine (1.2 g, 0.012 mol), followed by the dropwise addition of a solution of isobutylchloroformate (1.58 g, 0.012 mmol) in dichloromethane (5.0 mL). The reaction mixture was stirred for 10 min. under argon atmosphere after which it was stirred at room temperature for 20 min. The reaction mixture was then cooled to 0° C., and added R-2-amino-1-propanol (0.97 g, 1.01 mol). The resulting mixture was stirred at room temperature for 1.5 h, concentrated in vacuo, and the residue was purified by reverse-phase HPLC using 10-90% CH$_3$CN/Water gradient (40 min) at a flow rate of 80 mL/min. The appropriate fractions (MH$^+$, m/z=522) were combined, and freeze-dried to give a white solid. This was dissolved in dichloromethane (20 mL), washed successively with 5% sodium bicarbonate (2×15 mL), water (2×20 mL), dried (Na$_2$SO$_4$), and concentrated to dryness to afford the racemic title compound (2.2 g, 49%) as a white amorphous substance: $^1$H NMR (CD$_3$OD/400 MHz) δ 7.91 (dd, 1H, J=1.6 Hz, & 6.4 Hz), 7.68 (d, 1H, J=1.6 Hz), 7.60 (m, 1H), 7.53 (d, 1H, J=8.4 Hz), 7.01 (m, 2H), 5.57 (abq, 2H), 4.18 (m, 1H), 3.56 (m, 2H), 2.17 (s, 3H), 2.13 (s, 3H), and 1.22 (d, 3H, J=6.8 Hz); ES-HRMS m/z 522.0860 (M+H calcd for C$_{23}$H$_{23}$N$_3$O$_4$F$_2$ Br requires 522.0835). $^{19}$F NMR (CD$_3$OD/400 MHz) −111.85 (m) and −115.90 (m).

Preparation of (±) 3-[5-bromo-4-[(2,4-difluorobenzyl)oxy]-2-methyl-6-oxopyrimidin-1(6H)-yl]-N-[(1S)-2-hydroxy-1-methylethyl]-4-methylbenzamide

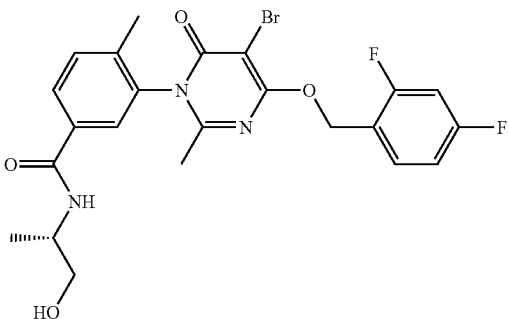

The title compound was prepared in a similar manner as described for (±) 3-[5-bromo-4-[(2,4-difluorobenzyl)oxy]-2-methyl-6-oxopyrimidin-1(6H)-yl]-N-[(1R)-2-hydroxy-1-methylethyl]-4-methylbenzamide substituting R-2-amino-1-propanol with S-2-amino-1-propanol. Yield 42%. $^1$H NMR (CD$_3$OD/400 MHz) δ 7.93 (d, 1H, J=1.6 Hz, & 6.4 Hz), 7.68 (s, 1H), 7.60 (m, 1H), 7.53 (d, 1H, J=8.0 Hz), 7.01 (m, 2H), 5.57 (abq, 2H), 4.18 (m, 1H), 3.56 (m, 2H), 2.17 (s, 3H), 2.13 (s, 3H), and 1.22 (d, 3H, J=6.8 Hz); ES-HRMS m/z 522.0821 (M+H calcd for C$_{23}$H$_{23}$N$_3$O$_4$F$_2$ Br requires 522.0835). $^{19}$F NMR (CD$_3$OD/400 MHz) 111.85 (m) and −115.90 (m).

Preparation of (±) 3-[5-bromo-4-[(2,4-difluorobenzyl)oxy]-2-methyl-6-oxopyrimidin-1(6H)-yl]-N-[(2S)-2-hydroxypropyl]-4-methylbenzamide

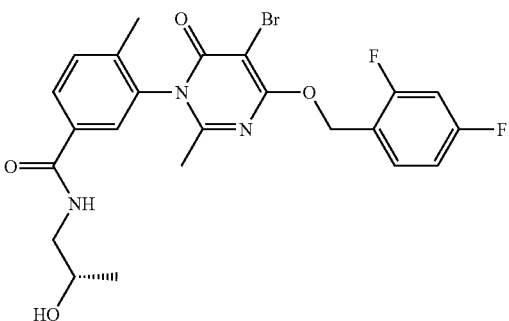

The title compound was prepared in a similar manner as described for (±) 3-[5-bromo-4-[(2,4-difluorobenzyl)oxy]-2-methyl-6-oxopyrimidin-1(6H)-yl]-N-[(1R)-2-hydroxy-1-methylethyl]-4-methylbenzamide substituting R-2-amino-1-propanol with S-1-amino-2-propanol. Yield 47%. $^1$H NMR (CD$_3$OD/400 MHz) δ 7.90 (d, 1H, J=1.6 Hz), 7.69 (d, 1H, J=2.0 Hz), 7.60 (m, 1H), 7.54 (d, 1H, J=8.0 Hz), 7.01 (m, 2H), 5.57 (abq, 2H), 4.18 (m, 1H), 3.39 (m, 1H), 3.31 (m, 1H), 2.17 (s, 3H), 2.13 (s, 3H), and 1.17 (d, 3H, J=6.4 Hz); ES-HRMS m/z 522.0863 (M+H calcd for C$_{23}$H$_{23}$N$_3$O$_4$F$_2$ Br requires 522.0835). $^{19}$F NMR (CD$_3$OD/400 MHz) −111.85 (m), and −115.9.

Preparation of (−) 3-[5-bromo-4-[(2,4-difluorobenzyl)oxy]-2-methyl-6-oxopyrimidin-1(6H)-yl]-N-[(2S)-2-hydroxypropyl]-4-methylbenzamide

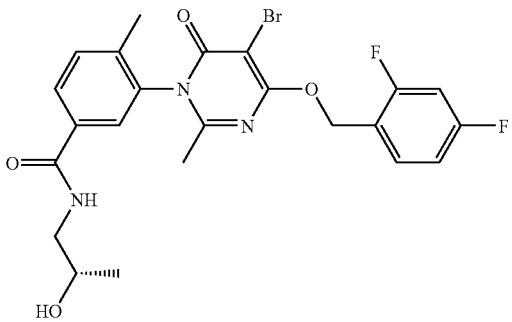

The diastereomeric mixture (2.0 g) was resolved using a Chiralpak AD-H column, 21×250 mm. The compound was dissolved in ethanol (15 mg/mL), and injected 4 mL of the solution and eluted with methanol at a flow rate of 10.0 mL/min. Fractions with negative optical rotation were pooled together and concentrated under reduced pressure to give 0.95 g of the (−) isomer as a white amorphous white solid: $^1$H NMR (CD$_3$OD/400 MHz) δ 7.93 (d, 1H, J=2.0 Hz, & 6.8 Hz), 7.70 (s, 1H), 7.60 (m, 1H), 7.55 (d, 1H, J=11.2 Hz, Hz), 7.01 (m, 2H), 5.57 (abq, 2H), 3.90 (abq, 1H), 3.38 (m,1H), 3.31 (m, 1H), 2.18 (s, 3H), 2.14 (s, 3H), and 1.18 (d, 3H, J=8.4 Hz); ES-HRMS m/z 522.0821 (M+H calcd for C$_{23}$H$_{23}$N$_3$O$_4$F$_2$ Br requires 522.0835). $^{19}$F NMR (CD$_3$OD/400 MHz) −111.85 (m) and −115.9.

Preparation of (+) 3-[5-bromo-4-[(2,4-difluorobenzyl)oxy]-2-methyl-6-oxopyrimidin-1(6H)-yl]-N-[(2S)-2-hydroxypropyl]-4-methylbenzamide

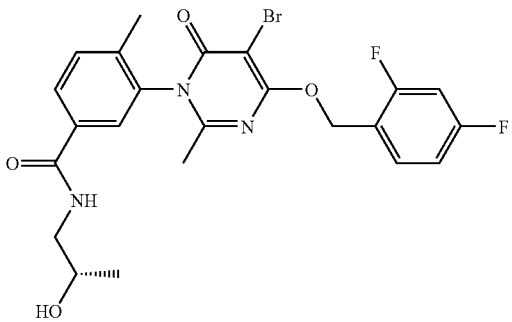

The title compound was isolated from the diastereomeric mixture (2.0 g) according to the resolution procedure described for (−) 3-[5-bromo-4-[(2,4-difluorobenzyl)oxy]-2-methyl-6-oxopyrimidin-1(6H)-yl]-N-[(2S)-2-hydroxypropyl]-4-methylbenzamide. Fractions with positive optical rotation were pooled together and concentrated under reduced pressure to give 0.9 g of the (+) isomer as a white amorphous white solid: $^1$H NMR (CD$_3$OD/400 MHz) δ 7.91 (d, 1H, J=1.6 Hz, & 8.0 Hz), 7.70 (s, 1H), 7.60 (m, 1H), 7.54 (d, 1H, J=8.0 Hz, Hz), 7.01 (m, 2H), 5.57 (abq, 2H), 3.93 (m, 1H), 3.40 (m, 1H), 3.28 (m, 1H), 2.17 (s, 3H), 2.14 (s, 3H), and 1.17 (d, 3H, J=6.8 Hz); ES-HRMS m/z 522.0820 (M+H calcd for C$_{23}$H$_{23}$N$_3$O$_4$F$_2$ Br requires 522.0835). $^{19}$F NMR (CD$_3$OD/400 MHz) −111.85 (m) and −115.9.

Preparation of (±) 3-[S-bromo-4-[(2,4-difluorobenzyl)oxy]-2-methyl-6-oxopyrimidin-1(6H)-yl]-N-[(2R)-2-hydroxypropyl]-4-methylbenzamide

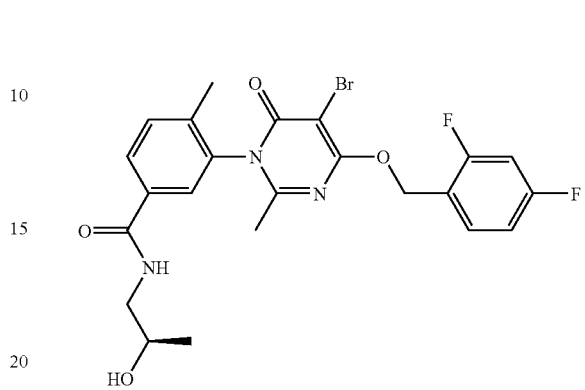

The title compound was prepared in a similar manner as described for (±) 3-[5-bromo-4-[(2,4-difluorobenzyl)oxy]-2-methyl-6-oxopyrimidin-1(6H)-yl]-N-[(1R)-2-hydroxy-1-methylethyl]-4-methylbenzamide substituting R-2-amino-1-propanol with R-1-amino-2-propanol. Yield 48%. $^1$H NMR (CD$_3$OD/400 MHz) δ 7.91 (d, 1H, J=1.6 Hz, & 8.0 Hz), 7.69 (d, 1H, J=1.6 Hz), 7.60 (m, 1H), 7.54 (d, 1H, J=8.0 Hz), 7.01 (m, 2H), 5.57 (abq, 2H), 3.90 (abq, 1H), 3.32 (m, 1H), 3.31 (m, 1H), 2.17 (s, 3H), 2.13 (s, 3H), and 1.17 (d, 3H, J=6.8 Hz); ES-HRMS m/z 522.0869 (M+H calcd for C$_{23}$H$_{23}$N$_3$O$_4$F$_2$ Br requires 522.0835). $^{19}$F NMR (CD$_3$OD/400 MHz) −111.85 (m), and −115.90.

Preparation of (−) 3-[5-bromo-4-[(2,4-difluorobenzyl)oxy]-2-methyl-6-oxopyrimidin-1(6H)-yl]-N-[(2R)-2-hydroxypropyl]-4-methylbenzamide

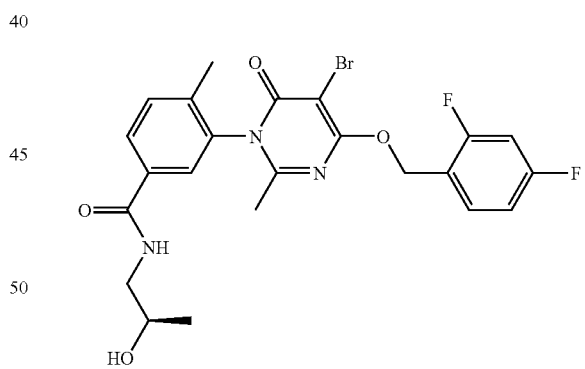

The diastereomeric compound (2.01 g) was resolved using a Chiralpak AD-H column, 21×250 mm. The compound was dissolved in ethanol (40 mg/mL), and injected 1.8 mL of the solution and eluted with ethanol at a flow rate of 10.0 mL/min. Fractions with negative optical rotation were pooled together and concentrated under reduced pressure to give 1.01 g of the (−) isomer as a white amorphous solid: $^1$H NMR (CD$_3$OD/400 Mz) 7.91 (d, 1H, J=1.6 Hz, 8.0 Hz), 7.69 (d, 1H, J=1.6 Hz), 7.60 (m, 1H), 7.01 (m, 2H), 5.57 (abq, 2H), 3.90 (abq, 1H), 3.40 (m,1H), 3.31 (m, 1H), 2.17 (s, 3H), 2.13 (s, 3H), and 1.18 (d, 3H, J=6.4 Hz); ES-HRMS m/z 522.0831 (M+H calcd for C$_{23}$H$_{23}$N$_3$O$_4$F$_2$ Br requires 522.0835). $^{19}$F NMR (CD$_3$OD/400 MHz) −111.86 (m), and −115.9.

Preparation of (+) 3-[5-bromo-4-[(2,4-difluorobenzyl)oxy]-2-methyl-6-oxopyrimidin-1(6H)-yl]-N-[(2R)-2-hydroxypropyl]-4-methylbenzamide

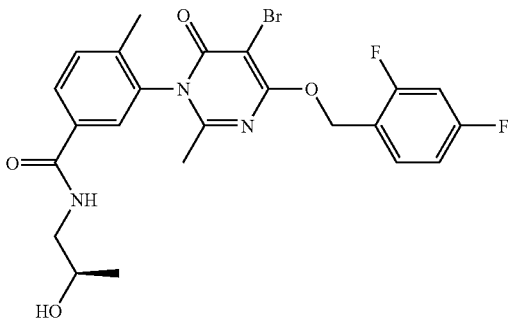

The title compound was isolated from the diastereomeric material (2.1 g) according to the resolution procedure described for 3-[3-bromo-6-methyl-2-oxo-4-[(2,4,6-trifluorobenzyl)oxy]pyridin-1(2H)-yl]-N-[(1S)-2-hydroxy-1-methylethyl]-4-methylbenzamide. Fractions with positive optical rotation were pooled together and concentrated under reduced pressure to give 1.0 g of the (+) isomer as a white amorphous white solid: $^1$H NMR (CD$_3$OD/400 MHz) δ 7.91 (d, 1H, J=1.6 Hz, & 8.0 Hz), 7.70 (s, 1H), 7.60 (m, 1H), 7.54 (d, 1H, J=8.0 Hz), 7.01 (m, 2H), 5.57 (abq, 2H), 3.93 (m, 1H), 3.40 (m, 1H), 3.28 (m, 1H), 2.17 (s, 3H), 2.14 (s, 3H), and 1.18 (d, 3H, J=6.4 Hz); ES-HRMS m/z 522.0830 (M+H calcd for C$_{23}$H$_{23}$N$_3$O$_4$F$_2$ Br requires 522.0835). $^{19}$F NMR (CD$_3$OD/400 MHz) −111.85 (m) and −115.9.

Preparation of (±) 3-[5-bromo-4-[(2,4-difluorobenzyl)oxy]-2-methyl-6-oxopyrimidin-1(6H)-yl]-N-(2-hydroxyethyl)-4-methylbenzamide

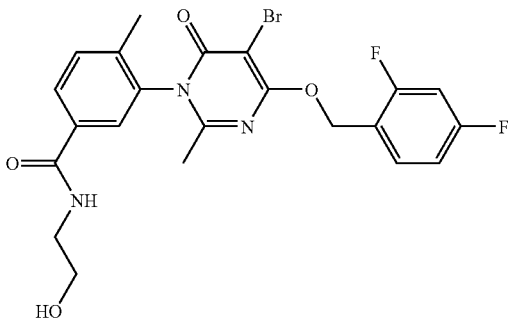

The title compound was prepared in a similar manner as described for (±) 3-[5-bromo-4-[(2,4-difluorobenzyl)oxy]-2-methyl-6-oxopyrimidin-1(6H)-yl]-N-[(1R)-2-hydroxy-1-methylethyl]-4-methylbenzamide substituting R-2-amino-1-propanol with 2-aminoethanol. Yield 70%. $^1$H NMR (CD$_3$OD/400 MHz) δ 7.91 (d, 1H, J=1.6 Hz, & 6.4 Hz), 7.68 (d, 1H, J=2.0 Hx), 7.60 (m, 1H), 7.54 (d, 1H, J=8.0 Hz), 7.01 (m, 2H), 5.57 (abq, 2H), 3.67 (t, 2H, J=6.0 Hz), 3.49 (t, 2H, J=6.0 Hz), 2.17 (s, 3H), and 2.13 (s, 3H); ES-HRMS m/z 508.0659 (M+H calcd for C$_{22}$H$_{21}$N$_3$O$_4$F$_2$ Br requires 508.0678). $^{19}$F NMR (CD$_3$OD/400 MHz) −111.85 (m) and −115.90 (m).

Preparation of (−) 3-[5-bromo-4-[(2,4-difluorobenzyl)oxy]-2-methyl-6-oxopyrimidin-1(6H)-yl]-N-(2-hydroxyethyl)-4-methylbenzamide

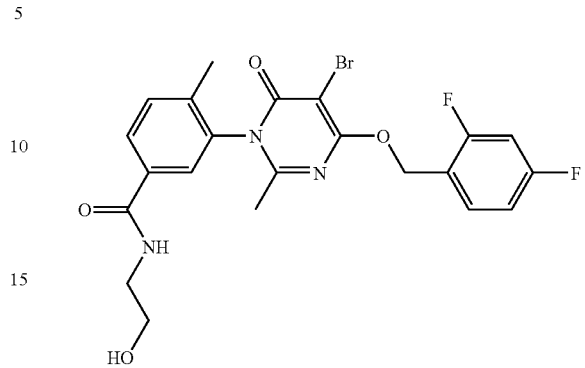

The racemic compound (3.0 g) was resolved using a Chiralpak AD-H column, 21×250 mm. The compound was dissolved in ethanol (15 mg/mL), and injected 4.0 mL of the solution and eluted with ethanol at a flow rate of 10.0 mL/min. Fractions with negative optical rotation were pooled together and concentrated under reduced pressure to give 1.18 g of the (−) isomer as a white amorphous solid: $^1$H NMR (CD$_3$OD/400 MHz) δ 7.91 (d, 1H, J=1.6 Hz, & 6.4 Hz), 7.68 (d, 1H, J=2.0 Hz), 7.60 (m, 1H), 7.54 (d, 1H, J=8.0 Hz), 7.01 (m, 2H), 5.57 (abq, 2H), 3.69 (t, 2H, J=5.6 Hz), 3.49 (t, 2H, J=5.6 Hz), 2.17 (s, 3H), and 2.13 (s, 3H); ES-HRMS m/z 508.0636 (M+H calcd for C$_{22}$H$_{21}$N$_3$O$_4$F$_2$ Br requires 508.0678). $^{19}$F NMR (CD$_3$OD/400 MHz) −111.86 (m), and −115.90

Preparation of (+) 3-[5-bromo-4-[(2,4-difluorobenzyl)oxy]-2-methyl-6-oxopyrimidin-1(6H)-yl]-N-(2-hydroxyethyl)-4-methylbenzamide

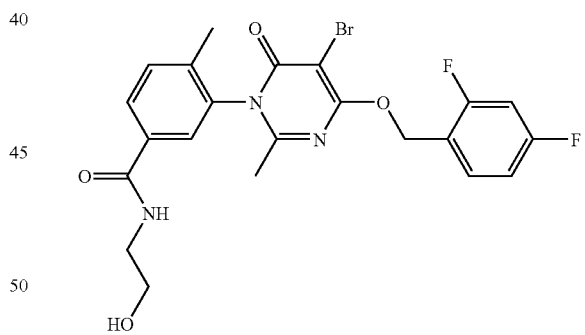

The title compound was isolated from the racemic material (3.0 g) according to the resolution procedure described for (−) 3-[5-bromo-4-[(2,4-difluorobenzyl)oxy]-2-methyl-6-oxopyrimidin-1(6H)-yl]-N-(2-hydroxyethyl)-4-methylbenzamide. Fractions with positive optical rotation were pooled together and concentrated under reduced pressure to give 1.35 g of the (+) isomer as a white amorphous white solid: $^1$H NMR (CD$_3$OD/400 MHz) δ 7.91 (d, 1H, J=2.0 Hz, & 8.0 Hz), 7.68 (d, 1H, J=2.0 Hz), 7.60 (m, 1H), 7.54 (d, 1H, J=8.0 Hz), 7.01 (m, 2H), 5.57 (abq, 2H), 3.69 (t, 2H, J=5.6 Hz), 3.49 (t, 2H, J=5.6 Hz), 2.17 (s, 3H), and 2.13 (s, 3H); ES-HRMS m/z 508.0664 (M+H calcd for C$_{22}$H$_{21}$N$_3$O$_4$F$_2$ Br requires 508.0678). $^{19}$F NMR (CD$_3$OD/400 MHz) −111.86 (m), and −115.90.

Preparation of (±) N-[(1S)-1-(aminocarbonyl)propyl]-3-[5-bromo-4-[(2,4-difluorobenzyl)oxy]-2-methyl-6-oxopyrimidin-1(6H)-yl]-4-methylbenzamide

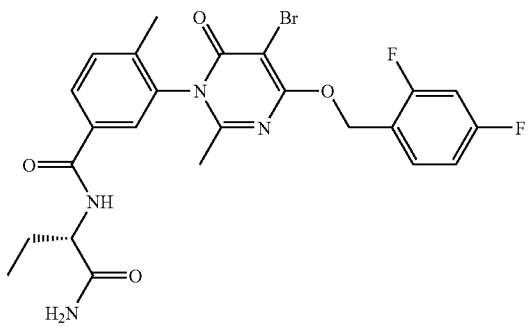

The title compound was prepared in a similar manner as described for (±) 3-[5-bromo-4-[(2,4-difluorobenzyl)oxy]-2-methyl-6-oxopyrimidin-1(6H)-yl]-N-[(1R)-2-hydroxy-1-methylethyl]-4-methylbenzamide substituting R-2-amino-1-propanol with S-alpha-aminobutyricacid amide. Yield 49%.
$^1$H NMR (CD$_3$OD/400 MHz) δ 8.38 (br, 1H), 7.95 (m, 1H), 7.73 (d, 1H, J=2.0 Hz), 7.60 (m, 1H), 7.55 (d, 1H, J=8.0 Hz), 7.02 (m, 2H), 5.57 (abq, 2H), 4.44 (m 1H), 2.18 (s, 3H), and 2.13 (s, 3H), 1.90 (m, 1H), 1.78 (m, 1H), and 1.01 (t, 3H, J=7.2 Hz); ES-HRMS m/z 549.0904 (M+H calcd for C$_{24}$H$_{24}$N$_4$O$_4$F$_2$ Br requires 549.0943). $^{19}$F NMR (CD$_3$OD/400 MHz) −111.86 (m) and −115.89 (m).

Preparation of (−) N-[(1S)-1-(aminocarbonyl)propyl]-3-[5-bromo-4-[(2,4-difluorobenzyl)oxy]-2-methyl-6-oxopyrimidin-1(6H)-yl]-4-methylbenzamide

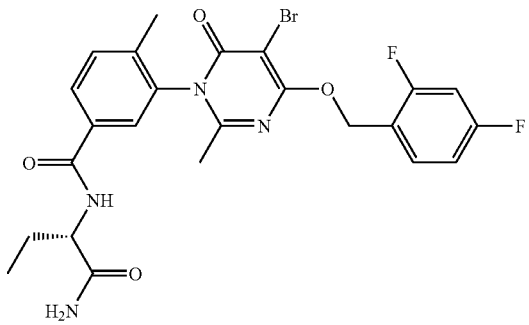

The diastereomeric mixture (0.9 g) was resolved using a Chiralpak AD-H column, 21×250 mm. The compound was dissolved in methanol (15 mg/mL), and injected 2.7 mL of the solution and eluted with ethanol at a flow rate of 20.0 mL/min. Fractions with negative optical rotation were pooled together and concentrated under reduced pressure to give 0.4 g of the (−) isomer as a white amorphous solid: $^1$H NMR (CD$_3$OD/400 MHz) δ 7.95 (dd, 1H, J=2.0 Hz, and 8.0 Hz), 7.73 (d, 1H, J=1.6 Hz), 7.60 (m, 1H), 7.55 (d, 1H, J=8.0 Hz), 7.01 (m, 2H), 5.57 (abq, 2H), 4.43 (m 1H), 2.18 (s, 3H), and 2.13 (s, 3H), 1.85 (m, 1H), 1.79 (m, 1H), and 1.01 (t, 3H, J=7.6 Hz); ES-HRMS m/z 549.0928 (M+H calcd for C$_{24}$H$_{24}$N$_4$O$_4$F$_2$ Br requires 549.0943). $^{19}$F NMR (CD$_3$OD/400 MHz) −111.86 (m) and −115.89 (m).

Preparation of (+) N-[(1S)-1-(aminocarbonyl)propyl]-3-[5-bromo-4-[(2,4-difluorobenzyl)oxy]-2-methyl-6-oxopyrimidin-1(6H)-yl]-4-methylbenzamide

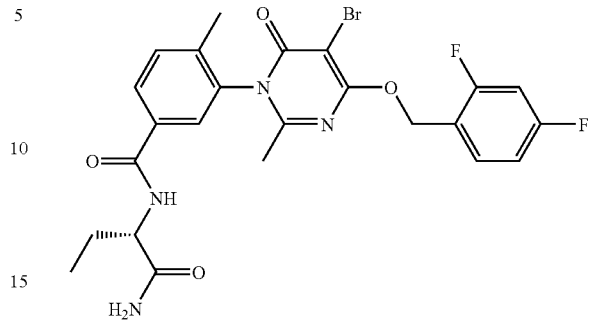

The title compound was isolated from the diastereomeric material (0.9 g) according to the resolution procedure described for (−) N-[(1S)-1-(aminocarbonyl)propyl]-3-[5-bromo-4-[(2,4-difluorobenzyl)oxy]-2-methyl-6-oxopyrimidin-1(6H)-yl]-4-methylbenzamide. Fractions with positive optical rotation were pooled together and concentrated under reduced pressure to give 0.52 g of the (+) isomer as an amorphous white solid: $^1$H NMR (CD$_3$OD/400 MHz) δ 7.93 (dd, 1H, J=2.0 Hz, and 8.0 Hz), 7.75 (d, 1H, J=2.0 Hz), 7.60 (m, 1H), 7.55 (d, 1H, J=8.0 Hz), 7.01 (m, 2H), 5.56 (abq, 2H), 4.44 (m 1H), 2.18 (s, 3H), 2.14 (s, 3H), 1.85 (m, 1H), 1.79 (m, 1H), and 1.01 (t, 3H, J=7.2 Hz); ES-HRMS m/z 549.0928 (M+H calcd for C$_{24}$H$_{24}$N$_4$O$_4$F$_2$ Br requires 549.0943). $^{19}$F NMR (CD$_3$OD/400 MHz) −111.86 (m), and −115.89 (m).

Preparation of 3-[5-chloro-4-[(2,4-difluorobenzyl)oxy]-6-oxopyrimidin-1(6H)-yl]-N-[1-(aminocarbonyl)methyl]-4-methylbenzamide

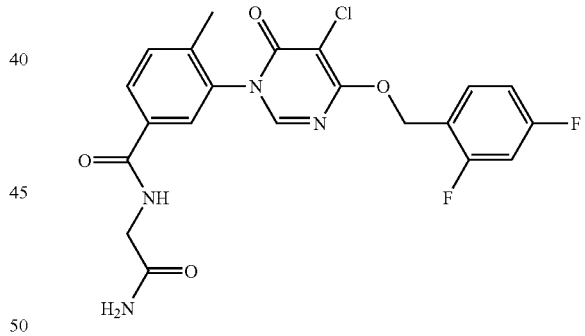

Step 1: Preparation of methyl 3-[4-[(2,4-difluorobenzyl)oxy]-6-oxopyrimidin-1(6H)-yl]-4-methylbenzoate

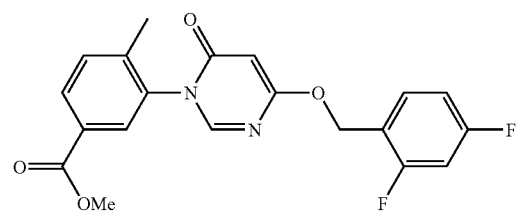

Methyl 3-[4-[(2,4-difluorobenzyl)oxy]-2-(methylthio)-6-oxopyrimidin-1(6H)-yl]-4-methylbenzoate (87 g, 0.20 mol) was dissolved in N,N-dimethylacetamide (870 mL) and heated to 80° C. Raney Ni was added and slight exotherm and off-gassing were observed. Reaction was complete. Heat and stirring were turned off. Since product had begun to precipitate from the cooled reaction mixture, heat was turned back on to 70° C. and stirring resumed. After redissolving the precipitate, the reaction mixture was allowed to cool for 15 min and then filtered through celite. Rinsed with 50° C. DMA and water, being careful not to let the celite pad go dry. The filtrate was added to 2 L of water and stirred. Product filtered, rinsed with water, and dried in the vacuum oven. When found to still be wet with DMA, slurried with water and stirred 1 h before filtering and redrying. Obtained the product as a white solid (63 g, 81%). $^1$H NMR (CD$_3$OD/400 MHz) δ8.28 (s, 1H), 8.04 (m, 1H), 7.90 (s, 1H), 7.55 (m, 2H), 6.99 (m, 2H), 5.87 (s, 1H), 5.39 (s, 2H), 3.88 (s, 3H), 2.19 (s, 3H). ESHRMS m/z 387.1195 (M+H calculated for C$_{20}$H$_{17}$F$_2$N$_2$O$_4$ requires 387.1151).

Step 2: Preparation of 3-[4-[(2,4-difluorobenzyl)oxy]-6-oxopyrimidin-1(6H)-yl]-4-methylbenzoic acid

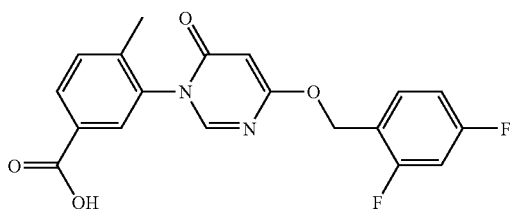

To a solution of methyl 3-[4-[(2,4-difluorobenzyl)oxy]-6-oxopyrimidin-1(6H)-yl]-4-methylbenzoate (from Step 1) (7.56 g, 19.6 mmol) in dioxane (30 mL) was added 2N NaOH (14.7 mL). Stirred at ambient temperature for 1 h. Concentrated to ~20 mL under reduced pressure. Cooled to 0° C. and added 5% citric acid to precipitate solid, filtered the precipitate, rinsed with water, and dried in vacuo overnight. Obtained product as an orange solid (6.62 g, 91%). Used without further purification. $^1$H NMR (CD$_3$OD/400 MHz) δ8.28 (s, 1H), 8.04 (m, 1H), 7.88 (s, 1H), 7.56 (q, 1H, J=8.4 Hz), 7.50 (d, 1H, J=8.0 Hz), 6.99 (m, 2H), 5.87 (s, 1H), 5.39 (s, 2H), 2.19 (s, 3H). ESHRMS m/z 373.1001 (M+H calculated for C$_{19}$H$_{15}$F$_2$N$_2$O$_4$ requires 373.0994).

Step 3: Preparation of 3-[5-chloro-4-[(2,4-difluorobenzyl)oxy]-6-oxopyrimidin-1(6H)-yl]-4-methylbenzoic acid

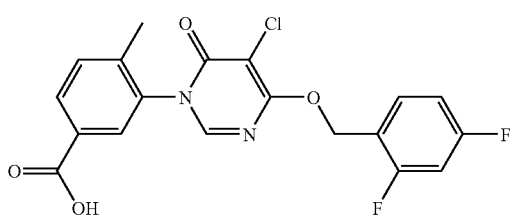

3-[4-[(2,4-difluorobenzyl)oxy]-6-oxopyrimidin-1(6H)-yl]-4-methylbenzoic acid (from Step 2) (6.62 g, 17.8 mmol), N-chlorosuccinimide (2.85 g, 21.3 mmol), and dichloroacetic acid (4 mL) are combined in dichloroethane (50 mL) and heated at 65° C. for 65 h. The reaction mixture is cooled to 0° C. and the precipitate is filtered, washed with cold dichloroethane, and dried in vacuo. Product obtained as a white solid (3.47 g, 48%). Used without further purification. $^1$H NMR (CD$_3$OD/300 MHz) δ8.32 (s, 1H), 8.09 (m, 1H), 7.94 (s, 1H), 7.62 (q, 1H, J=8.4 Hz), 7.54 (d, 1H, J=7.8 Hz), 7.03 (m, 2H), 5.61 (s, 2H), 2.21 (s, 3H).

Step 4: Preparation of the title compound (3-[5-chloro-4-[(2,4-difluorobenzyl)oxy]-6-oxopyrimidin-1(6H)-yl]-N-[1-(aminocarbonyl)methyl]-4-methylbenzamide)

To a cooled (0° C.) solution of 3-[5-chloro-4-[(2,4-difluorobenzyl)oxy]-6-oxopyrimidin-1(6H)-yl]-4-methylbenzoic acid (from Step 3) (0.25 g, 0.61 mmol) in DMA (2 mL) was added isobutyl chloroformate (0.96 mL stock solution prepared 0.1 mL in 0.9 mL DCM, 0.74 mmol) and 4-methylmorpholine (0.88 mL stock solution prepared 0.1 mL in 0.9 mL DMA, 0.80 mmol). Stirred at 0° C. for 5 min, ambient temperature for 30 min. Added NMM (0.1 mL, 0.92 mmol), glycineamide HCl (0.10 g, 0.92 mmol), and DMAP (0.01 g, 0.06 mmol) and stirred at ambient temperature for 1.5 h. Removed DMA under reduced pressure. Purified crude product by preparatory HPLC using a 10-90% CH$_3$CN/H$_2$O (30 min) gradient containing 0.5% TFA at a flow rate of 80 mL/min. Appropriate fractions (M+H m/z=463) were combined and concentrated to approximately 20 mL under reduced pressure. Added 5% NaHCO$_3$ (20 mL) and extracted with DCM (3×15 mL). The organic extracts were dried over Na$_2$SO$_4$, filtered, concentrated under reduced pressure, and dried in vacuo to give the desired product as an off-white solid (77 mg, 27%). $^1$H NMR (CD$_3$OD/400 MHz) δ8.32 (s, 1H), 7.96 (m, 1H), 7.80 (s, 1H), 7.61 (m, 1H), 7.54 (m, 1H), 7.01 (m, 2H), 5.60 (m, 2H), 4.01 (s, 2H), 2.20 (s, 3H). ESHRMS m/z 463.0990 (M+H calculated for C$_{21}$H$_{18}$ClF$_2$N$_4$O$_4$ requires 463.0979).

Preparation of 3-[5-chloro-4-[(2,4-difluorobenzyl)oxy]-6-oxopyrimidin-1(6H)-yl]-4-methyl-N-{1-[(methylamino)carbonyl]methyl}benzamide

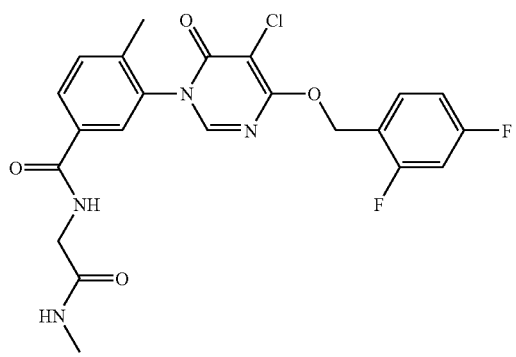

The title compound was prepared using a procedure similar to that used in Step 4 of the synthesis of 3-[5-chloro-4-[(2,4-difluorobenzyl)oxy]-6-oxopyrimidin-1(6H)-yl]-N-[1-(aminocarbonyl)methyl]-4-methylbenzamide by substituting glycine methyl amide HCl for glycineamide HCl. $^1$H NMR (CD$_3$OD/400 MHz) δ8.32 (s, 1H), 7.96 (m, 1H), 7.81 (s, 1H), 7.61 (q, 1H, J=8.4 Hz), 7.55 (d, 1H, J=8.0 Hz), 7.02 (m, 2H), 5.60 (m, 2H), 3.99 (s, 2H), 2.74 (s, 3H), 2.21 (s, 3H). ESHRMS m/z 477.1141 (M+H calculated for $C_{22}H_{20}ClF_2N_4O_4$ requires 477.1136).

Preparation of 3-[5-chloro-4-[(2,4-difluorobenzyl)oxy]-6-oxopyrimidin-1(6H)-yl]-N-[(2S)-2,3-dihydroxypropyl]-4-methylbenzamide

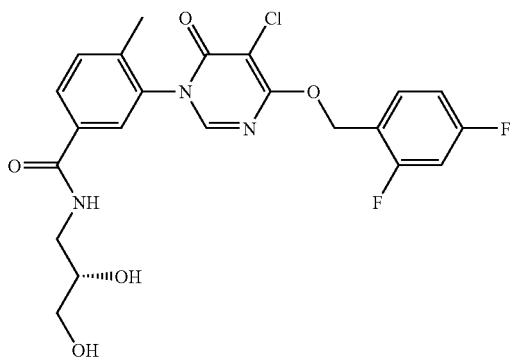

The title compound was prepared using a procedure similar to that used in Step 4 of the synthesis of 3-[5-chloro-4-[(2,4-difluorobenzyl)oxy]-6-oxopyrimidin-1(6H)-yl]-N-[1-(aminocarbonyl)methyl]-4-methylbenzamide by substituting (S)-(−)-3-amino-1,2-propanediol for glycineamide HCl. $^1$H NMR (CD$_3$OD/400 MHZ) δ8.32 (s, 1H), 7.92 (m, 1H), 7.77 (s, 1H), 7.61 (q, 1H, J=8.4 Hz), 7.53 (d, 1H, J=8.0 Hz), 7.02 (m, 2H), 5.60 (m, 2H), 3.81 (m, 1H), 3.55 (m, 3H), 3.39 (m, 1H), 2.20 (s, 3H). ESHRMS m/z 480.1131 (M+H calculated for $C_{22}H_{21}ClF_2N_3O_5$ requires 480.1132).

Preparation of N-[(1S)-1-(aminocarbonyl)ethyl]-3-[5-chloro-4-[(2,4-difluorobenzyl)oxy]-6-oxopyrimidin-1(6H)-yl]-4-methylbenzamide

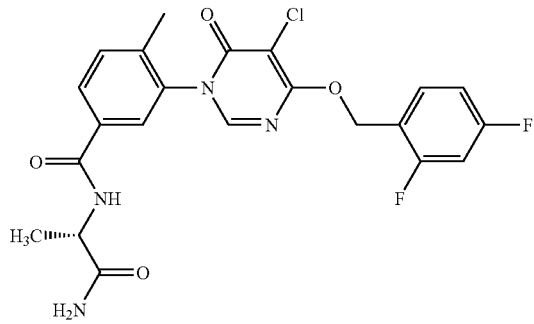

The title compound was prepared using a procedure similar to that used in Step 4 of the synthesis of 3-[5-chloro-4-[(2,4-difluorobenzyl)oxy]-6-oxopyrimidin-1(6H)-yl]-N-[1-(aminocarbonyl)methyl]-4-methylbenzamide by substituting L-alaninamide HCl for glycineamide HCl. $^1$H NMR (CD$_3$OD/400 MHz) δ8.32 (s, 1H), 7.96 (m, 1H), 7.82 (m, 1H), 7.61 (q, 1H, J=6.4 Hz), 7.53 (d, 1H, J=8.0 Hz), 7.02 (m, 2H), 5.60 (m, 2H), 4.55 (q, 1H, J=6.0 Hz), 2.20 (s, 3H), 1.45 (d, 3H, J=6.0 Hz). ESHRMS m/z 477.1141 (M+H calculated for $C_{22}H_{20}ClF_2N_4O_4$ requires 477.1136).

Preparation of 3-[5-chloro-4-[(2,4-difluorobenzyl)oxy]-6-oxopyrimidin-1(6H)-yl]-N-[(1S)-2-hydroxy-1-methylethyl]-4-methylbenzamide

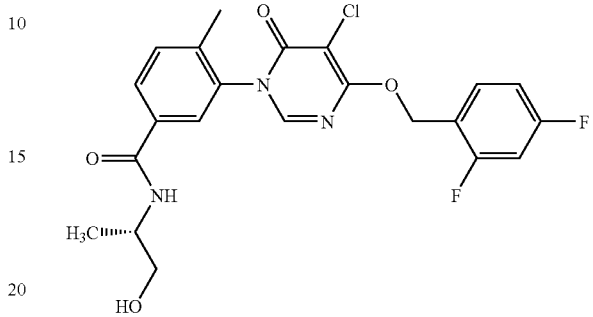

The title compound was prepared using a procedure similar to that used in Step 4 of the synthesis of 3-[5-chloro-4-[(2,4-difluorobenzyl)oxy]-6-oxopyrimidin-1(6H)-yl]-N-[1-(aminocarbonyl)methyl]-4-methylbenzamide by substituting (S)-(+)-2-amino-1-propanol for glycineamide HCl. $^1$H NMR (CD$_3$OD/400 MHz) δ8.32 (s, 1H), 7.92 (m, 1H), 7.77 (s, 1H), 7.61 (q, 1H, J=8.4 Hz), 7.52 (d, 1H, J=8.0 Hz), 7.02 (m, 2H), 5.60 (m, 2H), 4.16 (m, 1H), 3.58 (m, 2H), 2.20 (s, 3H), 1.22 (d, 3H, J=6.0 Hz). ESHRMS m/z 464.1198 (M+H calculated for $C_{22}H_{21}ClF_2N_3O_4$ requires 464.1183).

Preparation of 3-[5-chloro-4-[(2,4-difluorobenzyl)oxy]-6-oxopyrimidin-1(6H)-yl]-N-(2-hydroxyethyl)-4-methylbenzamide

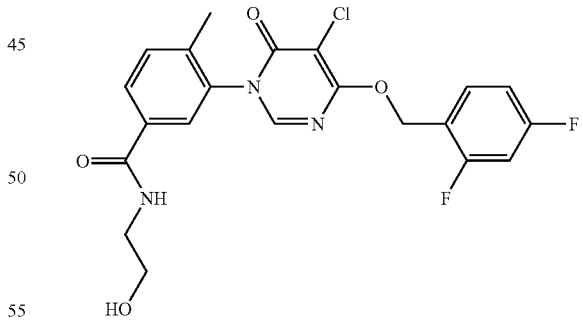

The title compound was prepared using a procedure similar to that used in Step 4 of the synthesis of 3-[5-chloro-4-[(2,4-difluorobenzyl)oxy]-6-oxopyrimidin-1(6H)-yl]-N-[1-(aminocarbonyl)methyl]-4-methylbenzamide by substituting ethanolamine for glycineamide HCl. $^1$H NMR (CD$_3$OD/400 MHz) δ8.32 (s, 1H), 7.92 (m, 1H), 7.77 (s, 1H), 7.61 (q, 1H, J=8.0 Hz), 7.53 (d, 1H, J=8.0 Hz), 7.02 (m, 2H), 5.60 (m, 2H), 3.69 (t, 2H, J=5.6 Hz), 3.49 (t, 2H, J=5.6 Hz), 2.20 (s, 3H). ESHRMS m/z 450.1029 (M+H calculated for $C_{21}H_{19}ClF_2N_3O_4$ requires 450.1027).

191

Preparation of 3-[5-chloro-4-[(2,4-difluorobenzyl)oxy]-6-oxopyrimidin-1(6H)-yl]-N-[(1R)-2-hydroxy-1-methylethyl]-4-methylbenzamide

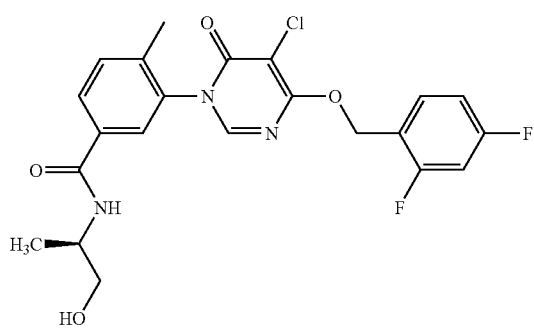

The title compound was prepared using a procedure similar to that used in Step 4 of the synthesis of 3-[5-chloro-4-[(2,4-difluorobenzyl)oxy]-6-oxopyrimidin-1(6H)-yl]-N-[1-(aminocarbonyl)methyl]-4-methylbenzamide by substituting (R)-(−)-2-amino-1-propanol for glycineamide HCl. $^1$H NMR (CD$_3$OD/400 MHz) δ8.32 (s, 1H), 7.92 (m, 1H), 7.77 (s, 1H), 7.61 (q, 1H, J=8.0 Hz), 7.52 (d, 1H, J=8.0 Hz), 7.02 (m, 2H), 5.60 (m, 2H), 4.16 (q, 1H, J=6.4 Hz), 3.56 (m, 2H), 2.20 (s, 3H), 1.22 (d, 3H, J=6.0 Hz). ESHRMS m/z 464.1186 (M+H calculated for C$_{22}$H$_{21}$ClF$_2$N$_3$O$_4$ requires 464.1183).

Preparation of 3-[5-bromo-4-[(2,4-difluorobenzyl)oxy]-6-oxopyrimidin-1(6H)-yl]-N-[1-(aminocarbonyl)methyl]-N,4-dimethylbenzamide

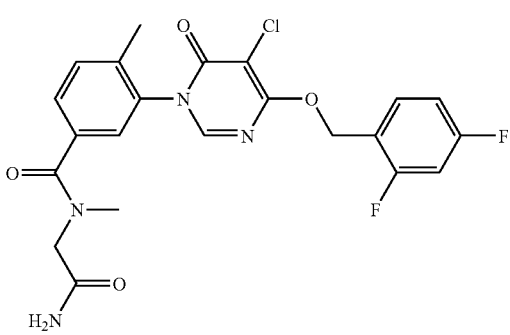

The title compound was prepared using a procedure similar to that used in Step 4 of the synthesis of 3-[5-chloro-4-[(2,4-difluorobenzyl)oxy]-6-oxopyrimidin-1(6H)-yl]-N-[1-(aminocarbonyl)methyl]-4-methylbenzamide by substituting sarcosinamide HCl for glycineamide HCl. $^1$H NMR (CD$_3$OD/400 MHz) δ8.31 (m, 1H), 7.61 (m, 2H), 7.52 (m, 2H), 7.02 (m, 2H), 5.59 (m, 2H), 4.19 (s, 1H), 4.01 (s, 1H), 3.07 (s, 3H), 2.18 (m, 3H). ESHRMS m/z 477.1158 (M+H calculated for C$_{22}$H$_{20}$ClF$_2$N$_4$O$_4$ requires 477.1136).

192

Preparation of 3-[5-chloro-4-[(2,4-difluorobenzyl)oxy]-6-oxopyrimidin-1(6H)-yl]-N-[(2R)-2,3-dihydroxypropyl]-4-methylbenzamide

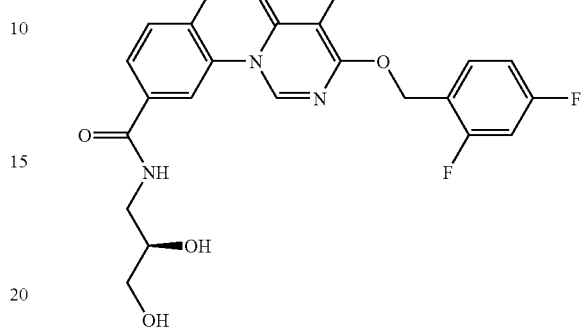

The title compound was prepared using a procedure similar to that used in Step 4 of the synthesis of 3-[5-chloro-4-[(2,4-difluorobenzyl)oxy]-6-oxopyrimidin-1(6H)-yl]-N-[1-(aminocarbonyl)methyl]-4-methylbenzamide by substituting (R)-(+)-3-amino-1,2-propanediol for glycineamide HCl. $^1$H NMR (CD$_3$OD/400 MHz) δ8.32 (s, 1H), 7.92 (m, 1H), 7.77 (s, 1H), 7.61 (q, 1H, J=8.0 Hz), 7.53 (d, 1H, J=8.0 Hz), 7.02 (m, 2H), 5.60 (m, 2H), 3.81 (m, 1H), 3.54 (m, 3H), 3.39 (m, 1H), 2.20 (s, 3H). ESHRMS m/z 480.1117 (M+H calculated for C$_{22}$H$_{21}$ClF$_2$N$_3$O$_5$ requires 480.1132).

Preparation of N-[(1R)-1-(aminocarbonyl)-2-hydroxyethyl]-3-[5-chloro-4-[(2,4-difluorobenzyl)oxy]-6-oxopyrimidin-1(6H)-yl]-4-methylbenzamide

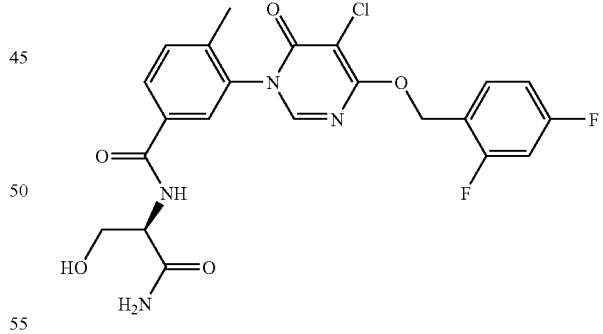

The title compound was prepared using a procedure similar to that used in Step 4 of the synthesis of 3-[5-chloro-4-[(2,4-difluorobenzyl)oxy]-6-oxopyrimidin-1(6H)-yl]-N-[1-(aminocarbonyl)methyl]-4-methylbenzamide by substituting L-serinamide HCl for glycineamide HCl. $^1$H NMR (CD$_3$OD/400 MHz) δ8.32 (s, 1H), 7.98 (m, 1H), 7.85 (m, 1H), 7.61 (q, 1H, J=8.4 Hz), 7.55 (d, 1H, J=8.0 Hz), 7.01 (m, 2H), 5.60 (m, 2H), 4.63 (m, 1H), 3.89 (d, 2H, J=5.6 Hz), 2.21 (s, 3H). ESHRMS m/z 493.1129 (M+H calculated for C$_{22}$H$_{20}$ClF$_2$N$_4$O$_5$ requires 493.1085).

Preparation of N-[(1R)-1-(aminocarbonyl)ethyl]-3-[5-chloro-4-[(2,4-difluorobenzyl)oxy]-6-oxopyrimidin-1(6H)-yl]-4-methylbenzamide

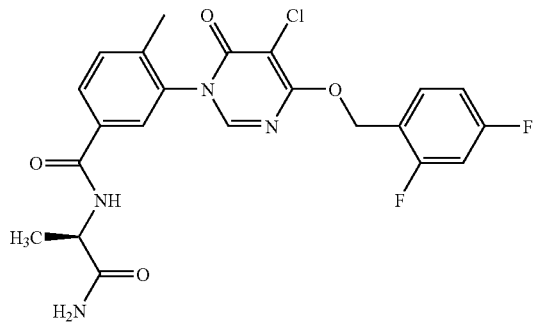

The title compound was prepared using a procedure similar to that used in Step 4 of the synthesis of 3-[5-chloro-4-[(2,4-difluorobenzyl)oxy]-6-oxopyrimidin-1(6H)-yl]-N-[1-(aminocarbonyl)methyl]-4-methylbenzamide by substituting D-alanine amide HCl for glycineamide HCl. $^1$H NMR (CD$_3$OD/400 MHz) δ 8.32 (s, 1H), 7.96 (m, 1H), 7.82 (m, 1H), 7.61 (q, 1H, J=8.4 Hz), 7.53 (d, 1H, J=8.0 Hz), 7.02 (m, 2H), 5.60 (m, 2H), 4.54 (q, 1H, J=6.0 Hz), 2.20 (s, 3H), 1.45 (d, 3H, J=6.0 Hz). ESHRMS m/1477.1104 (M+H calculated for C$_{22}$H$_{20}$ClF$_2$N$_4$O$_4$ requires 477.1136).

Preparation of 3-[5-bromo-4-[(2,4-difluorobenzyl)oxy]-6-oxopyrimidin-1(6H)-yl]-N-[(1S)-2-hydroxy-1-methylethyl]-4-methylbenzamide

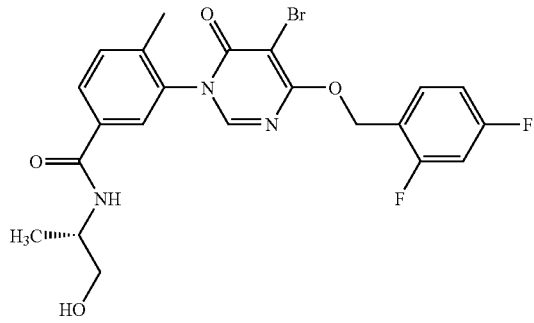

Step 1: Preparation of 3-[5-bromo-4-[(2,4-difluorobenzyl)oxy]-6-oxopyrimidin-1(6H)-yl]-4-methylbenzoic acid

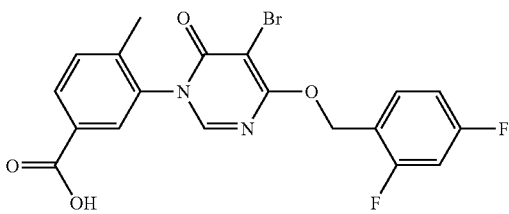

To a cooled (0° C.) solution of 3-[4-[(2,4-difluorobenzyl)oxy]-6-oxopyrimidin-1(6H)-yl]-4-methylbenzoic acid (5.76 g, 15.5 mmol) in DCM (35 mL) was added NBS (2.48 g, 13.9 mmol). Allowed reaction to warm to ambient temperature. After 5 h, cooled (0° C.) reaction mixture, filtered solid, washed with cold DCM and cold hexane, and dried in vacuo. Obtained product as orange solid (5.57 g, 80%). Used without further purification. $^1$H NMR (CD$_3$OD/400 MHz) δ8.29 (s, 1H), 8.05 (m, 1H), 7.91 (s, 1H), 7.60 (q, 1H, J=8.0 Hz), 7.51 (d, 1H, J=8.0 Hz), 6.99 (m, 2H), 5.57 (s, 2H), 2.17 (s, 3H). ESHRMS m/z 451.0095 (M+H calculated for C$_{19}$H$_{14}$BrF$_2$N$_2$O$_4$ requires 451.0100).

Step 2: Preparation of the title compound 3-[5-bromo-4-[(2,4-difluorobenzyl)oxy]-6-oxopyrimidin-1(6H)-yl]-N-[(1S)-2-hydroxy-1-methylethyl]-4-methylbenzamide To a cooled (0° C.) solution of 3-[5-bromo-4-[(2,4-difluorobenzyl)oxy]-6-oxopyrimidin-1(6H)-yl]-4-methylbenzoic acid (from Step 1) (0.80 g, 1.77 mmol) in DMA (3.2 mL) was added isobutyl chloroformate (0.28 mL, 2.13 mmol) and 4-methylmorpholine (0.25 mL, 2.30 mmol). Stirred at 0° C. for 5 min, ambient temperature for 30 min. Added (S)-(+)-2-amino-1-propanol (0.21 mL, 2.66 mmol) and DMAP (0.02 g, 0.18 mmol). Stirred at ambient temperature overnight. Purified crude product by preparatory HPLC using a 10-90% CH$_3$CN/H$_2$O (30 min) gradient containing 0.5% TFA at a flow rate of 80 mL/min. Appropriate fractions (M+H m/z=509) were combined and concentrated to approximately 20 mL under reduced pressure. Added 5% NaHCO$_3$ (20 mL) and extracted with DCM (3×15 mL). The organic extracts were dried over Na$_2$SO$_4$, filtered, concentrated under reduced pressure, and dried in vacuo to give the desired product as a pale yellow foam (0.61 g, 67%). $^1$H NMR (CD$_3$OD/400 MHz) δ8.32 (s, 1H), 7.92 (m, 1H), 7.76 (s, 1H), 7.61 (q, 1H, J=8.0 Hz), 7.52 (d, 1H, J=8.0 Hz), 7.01 (m, 2H), 5.60 (m, 2H), 4.16 (m, 1H), 3.57 (m, 2H), 2.19 (s, 3H), 1.22 (d, 3H, J=5.6 Hz). ESHRMS m/z 508.0666 (M+H calculated for C$_{22}$H$_{21}$BrF$_2$N$_3$O$_4$ requires 508.0678).

Preparation of 3-[5-bromo-4-[(2,4-difluorobenzyl)oxy]-6-oxopyrimidin-1(6H)-yl]-N-[(1R)-2-hydroxy-1-methylethyl]-4-methylbenzamide

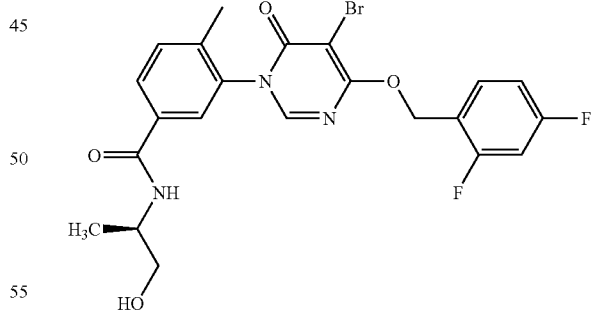

The title compound was prepared using a procedure similar to that used in Step 4 of the synthesis of 3-[5-bromo-4-[(2,4-difluorobenzyl)oxy]-6-oxopyrimidin-1(6H)-yl]-N-[(1S)-2-hydroxy-1-methylethyl]-4-methylbenzamide by substituting (R)-(−)-2-amino-1-propanol for (S)-(−)-2-amino-1-propanol HCl. $^1$H NMR (CD$_3$OD/400 MHz) δ8.32 (s, 1H), 7.92 (m, 1H), 7.76 (s, 1H), 7.61 (q, 1H, J=8.0 Hz), 7.52 (d, 1H, J=8.0 Hz), 7.01 (m, 2H), 5.59 (m, 2H), 4.16 (m, 1H), 3.57 (m, 2H), 2.19 (s, 3H), 1.22 (d, 3H, J=6.0 Hz). ESHRMS m/z 508.0684 (M+H calculated for C$_{22}$H$_{21}$BrF$_2$N$_3$O$_4$ requires 508.0678).

Preparation of 3-[5-bromo-4-[(2,4-difluorobenzyl) oxy]-6-oxopyrimidin-1(6H)-yl]-N,4-dimethylbenzamide

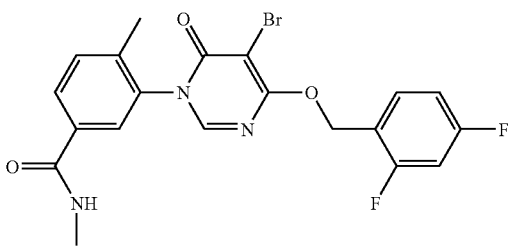

The title compound was prepared using a procedure similar to that used in Step 2 of the synthesis of 3-[5-bromo-4-[(2,4-difluorobenzyl)oxy]-6-oxopyrimidin-1(6H)-yl]-N-[(1S)-2-hydroxy-1-methylethyl]-4-methylbenzamide by substituting methylamine for (S)-(+)-2-amino-1-propanol. $^1$H NMR (CD$_3$OD/400 MHz) δ8.31 (s, 1H), 7.88 (m, 1H), 7.72 (s, 1H), 7.61 (q, 1H, J=8.0 Hz), 7.51 (d, 1H, J=8.0 Hz), 7.01 (m, 2H), 5.58 (m, 2H), 2.89 (s, 3H), 2.18 (s, 3H). ESHRMS m/z 481.0684 (M+H calculated for C$_{20}$H$_{16}$BrF$_2$N$_3$O$_3$ NH$_4$ requires 481.0681).

Preparation of N-[1-(aminocarbonyl)methyl]-3-[5-bromo-4-[(2,4-difluorobenzyl)oxy]-6-oxopyrimidin-1(6H)-yl]-4-methylbenzamide

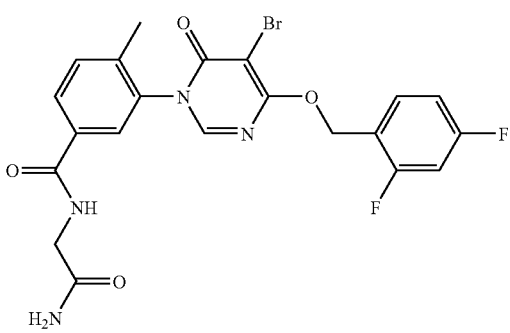

The title compound was prepared using a procedure similar to that used in Step 2 of the synthesis of 3-[5-bromo-4-[(2,4-difluorobenzyl)oxy]-6-oxopyrimidin-1(6H)-yl]-N-[(1S)-2-hydroxy-1-methylethyl]-4-methylbenzamide by substituting glycineamide HCl for (S)-(+)-2-amino-1-propanol. $^1$H NMR (CD$_3$OD/400 MHz) δ8.32 (s, 1H), 7.95 (m, 1H), 7.80 (s, 1H), 7.61 (q, 1H, J=8.4 Hz), 7.53 (d, 1H, J=8.0 Hz), 7.01 (m, 2H), 5.58 (m, 2H), 4.01 (s, 2H), 2.20 (s, 3H). ESHRMS m/z 507.0474 (M+H calculated for C$_{21}$H$_{18}$BrF$_2$N$_4$O$_4$ requires 507.0474).

Preparation of N-[(1R)-1-(aminocarbonyl)ethyl]-3-[5-bromo-4-[(2,4-difluorobenzyl)oxy]-6-oxopyrimidin-1(6H)-yl]-4-methylbenzamide

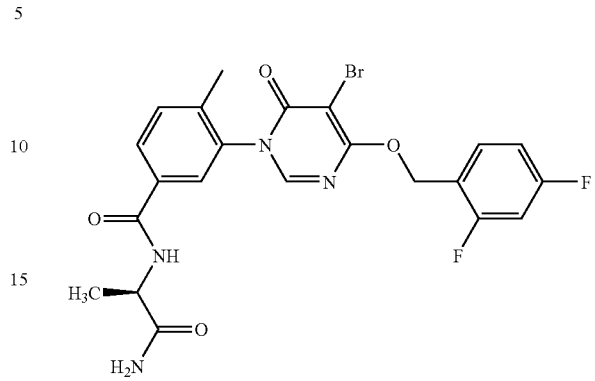

The title compound was prepared using a procedure similar to that used in Step 2 of the synthesis of 3-[5-bromo-4-[(2,4-difluorobenzyl)oxy]-6-oxopyrimidin-1(6H)-yl]-N-[(1S)-2-hydroxy-1-methylethyl]-4-methylbenzamide by substituting D-alanine amide HCl for (S)-(+)-2-amino-1-propanol. $^1$H NMR (CD$_3$OD/400 MHz) δ8.32 (s, 1H), 7.96 (m, 1H), 7.82 (m, 1H), 7.62 (q, 1H, J=8.0 Hz), 7.53 (d, 1H, J=8.0 Hz), 7.01 (m, 2H), 5.5.9 (m, 2H), 4.54 (q, 1H, J=6.0 Hz), 2.20 (s, 3H), 1.45 (d, 3H, J=6.0 Hz). ESHRMS m/z 521.0593 (M+H calculated for C$_{22}$H$_{20}$BrF$_2$N$_4$O$_4$ requires 521.0630).

Preparation of N-[(1S)-1-(aminocarbonyl)propyl]-3-[5-chloro-4-[(2,4-difluorobenzyl)oxy]-6-oxopyrimidin-1(6H)-yl]-4-methylbenzamide

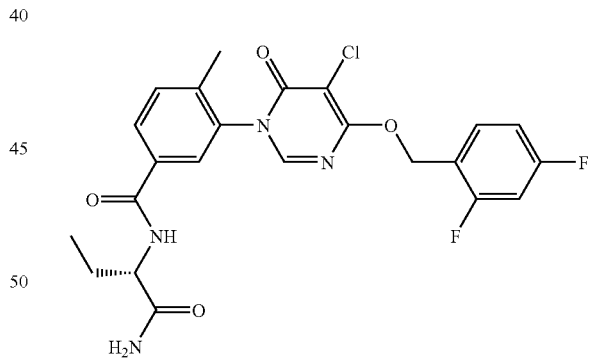

The title compound was prepared using a procedure similar to that used in Step 4 of the synthesis of 3-[5-chloro-4-[(2,4-difluorobenzyl)oxy]-6-oxopyrimidin-1(6H)-yl]-N-[1-(aminocarbonyl)methyl]-4-methylbenzamide by substituting L-alpha-aminobutyric acid amide for glycineamide HCl. $^1$H NMR (CD$_3$OD/400 MHz) δ8.32 (s, 1H), 7.95 (m, 1H), 7.83 (m, 1H), 7.61 (q, 1H, J=8.0 Hz), 7.54 (d, 1H, J=8.0 Hz), 7.01 (m, 2H), 5.60 (m, 2H), 4.45 (m, 1H), 2.20 (s, 3H), 1.93 (m, 1H), 1.79 (m, 1H), 1.01 (t, 3H, J=7.6 Hz). ESHRMS m/z 491.1303 (M+H calculated for C$_{23}$H$_{22}$ClF$_2$N$_4$O$_4$ requires 491.1292).

Preparation of 3-[5-chloro-4-[(2,4-difluorobenzyl)oxy]-6-oxopyrimidin-1(6H)-yl]-N-[(2S)-2-hydroxypropyl]-4-methylbenzamide

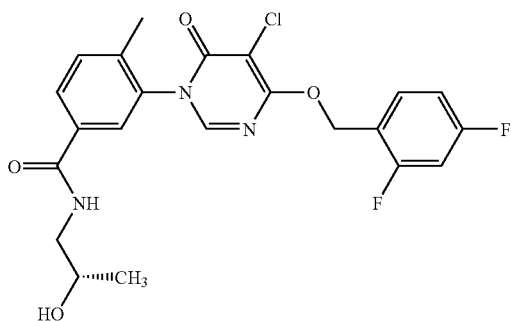

The title compound was prepared using a procedure similar to that used in Step 4 of the synthesis of 3-[5-chloro-4-[(2,4-difluorobenzyl)oxy]-6-oxopyrimidin-1(6H)-yl]-N-[1-(aminocarbonyl)methyl]-4-methylbenzamide by substituting (S)-(+)-1-amino-2-propanol for glycineamide HCl. $^1$H NMR (CD$_3$OD/400 MHz) δ8.32 (s, 1H), 7.92 (m, 1H), 7.77 (s, 1H), 7.61 (q, 1H, J=8.0 Hz), 7.53 (d, 1H, J=8.0 Hz), 7.02 (m, 2H), 5.60 (m, 2H), 3.93 (m, 1H), 3.39 (m, 2H), 2.20 (s, 3H), 1.18 (d, 3H, J=6.4 Hz). ESHRMS m/z 464.1154 (M+H calculated for C$_{22}$H$_{21}$ClF$_2$N$_3$O$_4$ requires 464.1183).

Preparation of 3-[5-chloro-4-[(2,4-difluorobenzyl)oxy]-6-oxopyrimidin-1(6H)-yl]-N-[(2R)-2-hydroxypropyl]-4-methylbenzamide

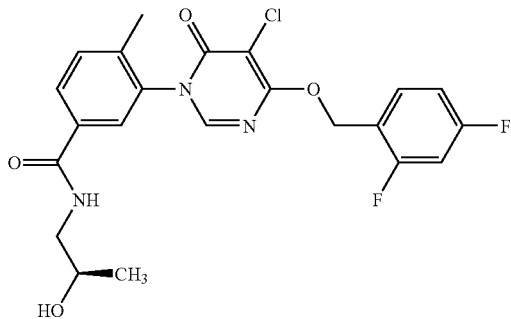

The title compound was prepared using a procedure similar to that used in Step 4 of the synthesis of 3-[5-chloro-4-[(2,4-difluorobenzyl)oxy]-6-oxopyrimidin-1(6H)-yl]-N-[1-(aminocarbonyl)methyl]-4-methylbenzamide by substituting (R)-(−)-1-amino-2-propanol for glycineamide HCl. $^1$H NMR (CD$_3$OD/400 MHz) δ8.32 (s, 1H), 7.92 (m, 1H), 7.77 (s, 1H), 7.61 (q, 1H, J=8.0 Hz), 7.53 (d, 1H, J=8.0 Hz), 7.02 (m, 2H), 5.60 (m, 2H), 3.94 (m, 1H), 3.30 (m, 2H), 2.20 (s, 3H), 1.18 (s, 3H). ESHRMS m/z 464.1167 (M+H calculated for C$_{22}$H$_{21}$ClF$_2$N$_3$O$_4$ requires 464.1183).

Preparation of 5-chloro-6-[(2,4-difluorobenzyl)oxy]-3-(5-{[(3S)-3-hydroxypyrrolidin-1-yl]carbonyl}-2-methylphenyl)pyrimidin-4(3H)-one

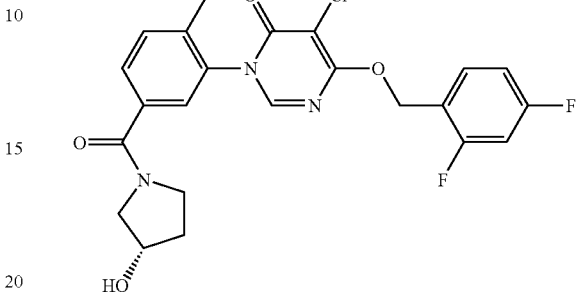

The title compound was prepared using a procedure similar to that used in Step 4 of the synthesis of 3-[5-chloro-4-[(2,4-difluorobenzyl)oxy]-6-oxopyrimidin-1(6H)-yl]-N-[1-(aminocarbonyl)methyl]-4-methylbenzamide by substituting (S)-3-hydroxypyrrolidine for glycineamide HCl. $^1$H NMR (CD$_3$OD/400 MHz) δ8.31 (d, 1H, J=7.6 Hz), 7.62 (m, 2H), 7.52 (m, 2H), 7.01 (m, 2H), 5.59 (m, 2H), 4.42 (m, 1H), 3.64 (m, 4H), 2.19 (s, 3H), 2.00 (m, 2H). ESHRMS m/z 476.1147 (M+H calculated for C$_{23}$H$_{21}$ClF$_2$N$_3$O$_4$ requires 476.1183).

Preparation of 3-[5-chloro-4-[(2,4-difluorobenzyl)oxy]-6-oxopyrimidin-1(6H)-yl]-4-methyl-N-1H-pyrazol-3-ylbenzamide

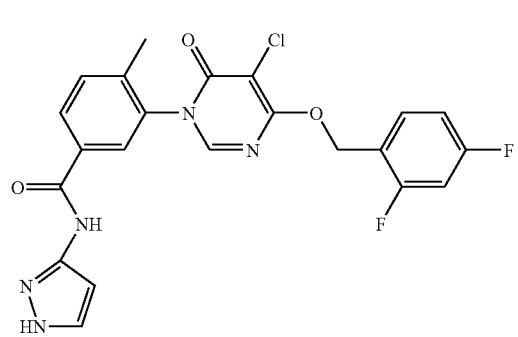

The title compound was prepared using a procedure similar to that used in Step 4 of the synthesis of 3-[5-chloro-4-[(2,4-difluorobenzyl)oxy]-6-oxopyrimidin-1(6H)-yl]-N-[1-(aminocarbonyl)methyl]-4-methylbenzamide by substituting 3-aminopyrazole for glycineamide HCl. $^1$H NMR (CD$_3$OD/400 MHz) δ8.37 (s, 1H), 8.14 (m, 2H), 8.08 (s, 1H), 7.60 (m, 2H), 7.01 (m, 2H), 6.06 (d, 1H, J=3.2 Hz), 5.60 (s, 2H), 2.23 (s, 3H).

Preparation of 3-[5-chloro-4-[(2,4-difluorobenzyl)oxy]-6-oxopyrimidin-1(6H)-yl]-N-(2-methoxyethyl)-4-methylbenzamide

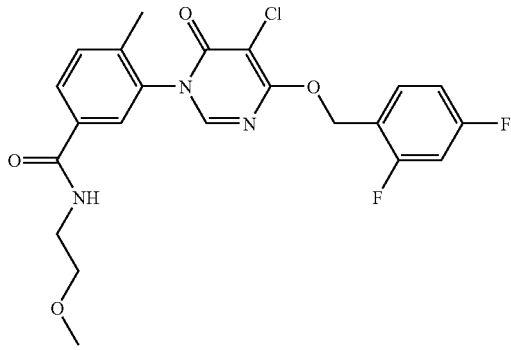

The title compound was prepared using a procedure similar to that used in Step 4 of the synthesis of 3-[5-chloro-4-[(2,4-difluorobenzyl)oxy]-6-oxopyrimidin-1(6H)-yl]-N-[1-(aminocarbonyl)methyl]-4-methylbenzamide by substituting 2-methoxyethylamine for glycineamide HCl. $^1$H NMR (CD$_3$OD/400 MHz) δ8.32 (s, 1H), 7.91 (m, 1H), 7.75 (s, 1H), 7.61 (q, 1H, J=8.4 Hz), 7.52 (d, 1H, J=8.0 Hz), 7.02 (m, 2H), 5.60 (m, 2H), 3.55 (s, 4H), 3.35 (s, 3H), 2.19 (s, 3H). ESHRMS m/z 464.1142 (M+H calculated for C$_{22}$H$_{21}$ClF$_2$N$_3$O$_4$ requires 464.1183).

Preparation of 3-[5-chloro-4-[(2,4-difluorobenzyl)oxy]-6-oxopyrimidin-1(6H)-yl]-4-methyl-N-[(2S)-tetrahydrofuran-2-ylmethyl]benzamide

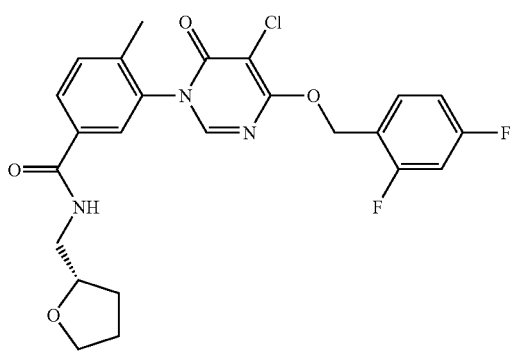

The title compound was prepared using a procedure similar to that used in Step 4 of the synthesis of 3-[5-chloro-4-[(2,4-difluorobenzyl)oxy]-6-oxopyrimidin-1(6H)-yl]-N-[1-(aminocarbonyl)methyl]-4-methylbenzamide by substituting (S)-(+)-tetrahydrofurfurylamine for glycineamide HCl. $^1$H NMR (CD$_3$OD/400 MHz) δ8.32 (s, 1H), 7.91 (m, 1H), 7.76 (s, 1H), 7.61 (q, 1H, J=8.0 Hz), 7.52 (d, 1H, J=8.4 Hz), 7.01 (m, 2H), 5.60 (m, 2H), 4.08 (m, 1H), 3.87 (q, 1H, J=6.8 Hz), 3.74 (q, 1H, J=7.6 Hz), 3.49 (m, 1H), 3.39 (m, 1H), 2.19 (s, 3H), 2.01 (m, 1H), 1.91 (m, 2H), 1.64 (m, 1H). ESHRMS m/z 490.1308 (M+H calculated for C$_{24}$H$_{23}$ClF$_2$N$_3$O$_4$ requires 490.1340).

Preparation of 3-[5-chloro-4-[(2,4-difluorobenzyl)oxy]-6-oxopyrimidin-1(6H)-yl]-4-methyl-N-[(2R)-tetrahydrofuran-2-ylmethyl]benzamide

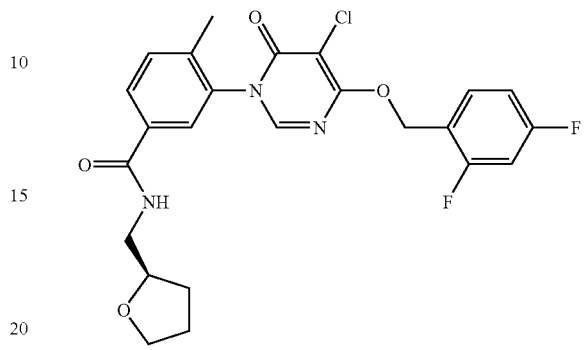

The title compound was prepared using a procedure similar to that used in Step 4 of the synthesis of 3-[5-chloro-4-[(2,4-difluorobenzyl)oxy]-6-oxopyrimidin-1(6H)-yl]-N-[1-(aminocarbonyl)methyl]-4-methylbenzamide by substituting (R)-(−)-tetrahydrofurfurylamine for glycineamide HCl. $^1$H NMR (CD$_3$OD/400 MHz) δ8.32 (s, 1H), 7.91 (m, 1H), 7.76 (s, 1H), 7.61 (q, 1H, J=8.4 Hz), 7.52 (d, 1H, J=8.0 Hz), 7.02 (m, 2H), 5.59 (m, 2H), 4.08 (m, 1H), 3.87 (q, 1H, J=6.8 Hz), 3.74 (q, 1H, J=7.6 Hz), 3.49 (m, 1H), 3.39 (m, 1H), 2.19 (s, 3H), 2.01 (m, 1H), 1.93 (m, 2H), 1.64 (m, 1H). ESHRMS m/z 490.1366 (M+H calculated for C$_{24}$H$_{23}$ClF$_2$N$_3$O$_4$ requires 490.1340).

Preparation of 5-chloro-6-[(2,4-difluorobenzyl)oxy]-3-(5-{[[(3R)-3-hydroxypyrrolidin-1-yl]carbonyl}-2-methylphenyl)pyrimidin-4(3H)-one

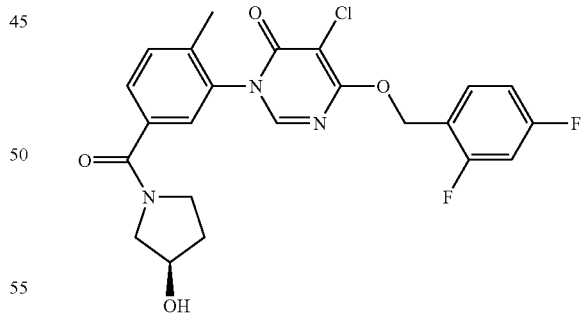

The title compound was prepared using a procedure similar to that used in Step 4 of the synthesis of 3-[5-chloro-4-[(2,4-difluorobenzyl)oxy]-6-oxopyrimidin-1(6H)-yl]-N-[1-(aminocarbonyl)methyl]-4-methylbenzamide by substituting (R)-(+)-3-pyrrolidinol for glycineamide HCl. $^1$H NMR (CD$_3$OD/400 MHz) δ8.31 (d, 1H, J=7.6 Hz), 7.62 (m, 2H), 7.52 (m, 2H), 7.01 (m, 2H), 5.51 (m, 2H), 4.42 (m, 1H), 3.65 (m, 4H), 2.19 (s, 3H), 2.00 (m, 2H). ESHRMS m/z 476.1175 (M+H calculated for C$_{23}$H$_{21}$ClF$_2$N$_3$O$_4$ requires 476.1183).

Preparation of 3-[4-[(2,4-difluorobenzyl)oxy]-5-ethyl-6-oxopyrimidin-1(6H)-yl]-N-[(1R)-2-hydroxy-1-methylethyl]-4-methylbenzamide

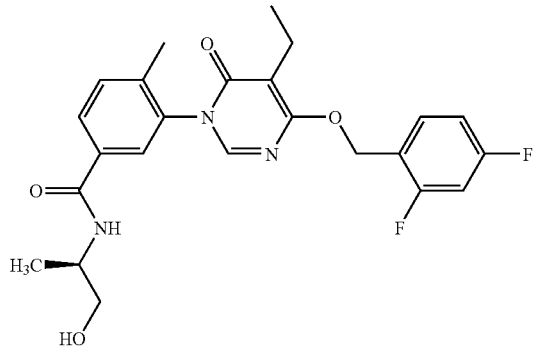

Step 1: Preparation of methyl 3-[4-[(2,4-difluorobenzyl)oxy]-5-iodo-6-oxopyrimidin-1(6H)-yl]-4-methylbenzoate

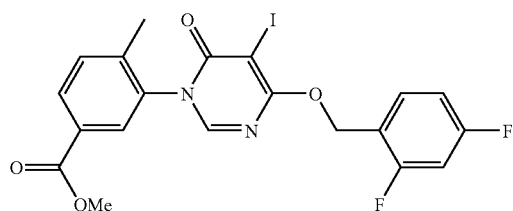

To a suspension of methyl 3-[4-[(2,4-difluorobenzyl)oxy]-6-oxopyrimidin-1(6H)-yl]-4-methylbenzoate (2.53 g, 6.55 mmol) and dichloroacetic acid (0.27 mL, 3.27 mmol) in acetonitrile (20 mL) was added N-iodosuccinimide (1.62 g, 7.20 mmol). Stirred at ambient temperature for 3.5 h. Cooled reaction mixture (0° C.), filtered solid, washed with cold acetonitrile, and dried in vacuo overnight. Obtained product as white solid (2.72 g, 81%). $^1$H NMR (CD$_3$OD/400 MHz) δ8.24 (s, 1H), 8.07 (m, 1H), 7.93 (s, 1H), 7.63 (q, 1H, J=8.4 Hz), 7.54 (d, 1H, J=8.0 Hz), 7.01 (t, 2H, J=8.4 Hz), 5.57 (s, 2H), 3.90 (s, 3H), 2.19 (s, 3H). ESHRMS m/z 513.0143 (M+H calculated for C$_{20}$H$_{16}$F$_2$IN$_2$O$_4$ requires 513.0117).

Step 2: Preparation of methyl 3-[4-[(2,4-difluorobenzyl)oxy]-6-oxo-5-vinylpyrimidin-1(6H)-yl]-4-methylbenzoate A round bottom flask containing methyl 3-[4-[(2,4-difluorobenzyl)oxy]-5-iodo-6-oxopyrimidin-1(6H)-yl]-4-methylbenzoate (2.50 g, 4.88 mmol) in N,N-dimethylformamide was evacuated and flushed with argon. Tributyl(vinyl)tin (2.3 g, 7.3 mmol) and dichlorobis(triphenylphosphine) palladium (II) (0.34 g, 0.49 mmol) were added in the nitrogen atmosphere of a glove box. Heated at 60° C. under argon overnight. Added additional tin (0.7 mL) and palladium (0.17 g) reagents and continued over weekend. No progress observed. Distilled DMF, washed crude product with ethyl acetate, and filtered through celite. The filtrate was concentrated and purified by flash column using 25% ethyl acetate in hexane as eluent. Used without further purification.

Step 3: Preparation of methyl 3-[4-[(2,4-difluorobenzyl)oxy]-5-ethyl-6-oxopyrimidin-1(6H)-yl]-4-methylbenzoate

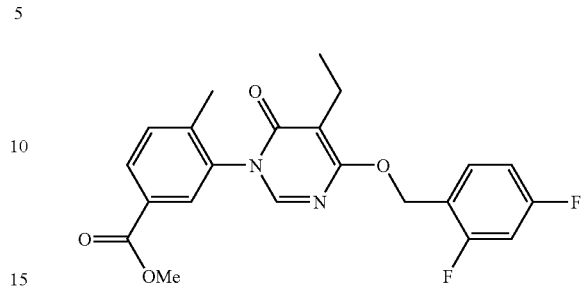

A solution of methyl 3-[4-[(2,4-difluorobenzyl)oxy]-6-oxo-5-vinylpyrimidin-1(6H)-yl]-4-methylbenzoate (from Step 2) (1.0 g) in EtOH (20 mL) was purged with N$_2$. 10% Pd/C (0.22 g) was added and the chamber was alternately evacuated and purged with H$_2$ (3×). Reaction at 25 psi was checked by mass spectrometry at 4 h but no product was detected. Added additional 10% Pd/C (0.36 g) and stirred at 32 psi overnight. Very little starting material remained. Crude product was filtered through celite, rinsed with ethyl acetate, and concentrated. This residue was dissolved in a small amount of ethyl acetate by heating; hexane was added and the mixture left in the fridge overnight. The precipitate was filtered and washed with cold ethyl acetate and hexane. The product was obtained as a yellow solid (0.58 g, 58%) and used without further purification. $^1$H NMR (CD$_3$OD/400 MHz) δ8.17 (s, 1H), 8.06 (m, 1H), 7.90 (s, 1H), 7.57 (q, 1H, J=8.4 Hz), 7.53 (d, 1H, J=8.0 Hz), 7.00 (m, 2H), 5.52 (s, 2H), 3.90 (s, 3H), 2.51 (q, 2H, J=7.6 Hz), 2.18 (s, 3H), 1.06 (t, 3H, J=7.6 Hz). ESHRMS m/z 415.1460 (M+H calculated for C$_{22}$H$_{21}$F$_2$N$_2$O$_4$ requires 415.1464).

Step 4: Preparation of 3-[4-[(2,4-difluorobenzyl)oxy]-5-ethyl-6-oxopyrimidin-1(6H)-yl]-4-methylbenzoic acid To a suspension of methyl 3-[4-[(2,4-difluorobenzyl)oxy]-5-ethyl-6-oxopyrimidin-1(6H)-yl]-4-methylbenzoate (from Step 3) (0.58 g, 1.40 mmol) in dioxane (2 mL) was added 2N NaOH (1.05 mL, 2.10 mmol). Stirred at ambient temperature for 2 h. Cooled reaction mixture (0° C.), added 5% citric acid to precipitate the product, filtered solid, washed with water, and dried in vacuo. Obtained the product as a pale yellow solid (0.53 g, 95%). Used without further purification.

Step 5: Preparation of the title compound

To a cooled solution (0° C.) of 3-[4-[(2,4-difluorobenzyl)oxy]-5-ethyl-6-oxopyrimidin-1(6H)-yl]-4-methylbenzoic acid (from Step 4) (0.25 g, 0.62 mmol) and 4-methylmorpholine (0.10 mL, 0.94 mmol) in DMA (2 mL) was added isobutyl chloroformate (0.12 mL, 0.94 mmol). Stirred 5 min at 0° C., 30 min at ambient temperature. Added (R)-(−)-2-amino-1-propanol (0.07 mL, 0.94 mmol) and DMAP (0.02 g, 0.12 mmol) to the cooled (0° C.) reaction mixture. Stirred at ambient temperature for 3 h. Purified crude product by preparatory HPLC using a 10-90% CH$_3$CN/H$_2$O (30 min) gradient containing 0.5% TFA at a flow rate of 80 mL/min. Appropriate fractions (M+H m/z=458) were combined and concentrated to approximately 20 mL under reduced pressure. Added 5% NaHCO$_3$ (20 mL) and extracted with DCM (3×15 mL). The organic extracts were dried over Na$_2$SO$_4$, filtered, concentrated under reduced pressure, and dried in vacuo to give the desired product as an off-white foam (0.20 g, 70%). $^1$H NMR (CD$_3$OD/400 MHz) δ8.18 (s, 1H), 7.90 (m, 1H), 7.73 (m, 1H), 7.57 (q, 1H, J=8.4 Hz), 7.50 (d, 1H, J=8.0 Hz), 7.01 (m, 2H), 5.52 (q, 2H, J=12.4 Hz), 4.16 (m, 1H), 3.57 (m, 2H), 2.21 (q, 2H, J=7.6 Hz), 2.17 (s, 3H), 1.22 (m, 3H), 1.05 (t, 3H, J=7.2 Hz). ESHRMS m/z 458.1855 (M+H calculated for C$_{24}$H$_{26}$F$_2$N$_3$O$_4$ requires 458.1886).

Preparation of 3-[4-[(2,4-difluorobenzyl)oxy]-5-ethyl-6-oxopyrimidin-1(6H)-yl]-N-(2-hydroxyethyl)-4-methylbenzamide

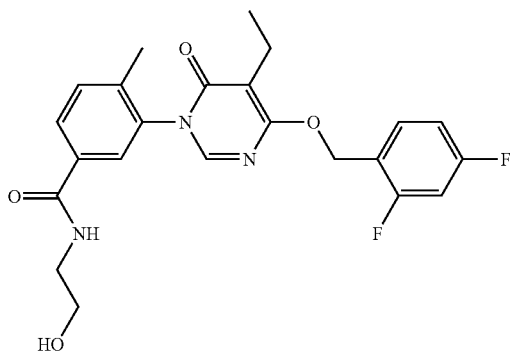

The title compound was prepared using a procedure similar to that used in Step 5 of the synthesis of 3-[4-[(2,4-difluorobenzyl)oxy]-5-ethyl-6-oxopyrimidin-1(6H)-yl]-N-[(1R)-2-hydroxy-1-methylethyl]-4-methylbenzamide by substituting ethanolamine for (R)-(−)-2-amino-1-propanol. $^1$H NMR (CD$_3$OD/400 MHz) δ8.19 (s, 1H), 7.90 (m, 1H), 7.73 (s, 1H), 7.57 (q, 1H, J=8.4 Hz), 7.51 (d, 1H, J=8.0 Hz), 7.00 (m, 2H), 5.51 (q, 2H, J=12.4 Hz), 3.69 (t, 2H, J=6.0 Hz), 3.48 (t, 2H, J=5.6 Hz), 2.51 (q, 2H, J=7.6 Hz), 2.17 (s, 3H), 1.05 (t, 3H, J=7.6 Hz). ESHRMS m/z 444.1704 (M+H calculated for C$_{23}$H$_{24}$F$_2$N$_3$O$_4$ requires 444.1729).

Preparation of 3-[5-bromo-4-[(2,4-difluorobenzyl)oxy]-2-(methylamino)-6-oxopyrimidin-1(6H)-yl]-N,4-dimethylbenzamide

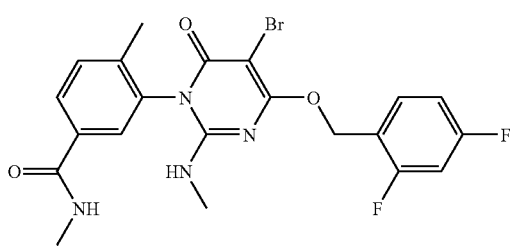

Step 1: Preparation of methyl 3-[5-bromo-4-[(2,4-difluorobenzyl)oxy]-2-(methylsulfonyl)-6-oxopyrimidin-1(6H)-yl]-4-methylbenzoate

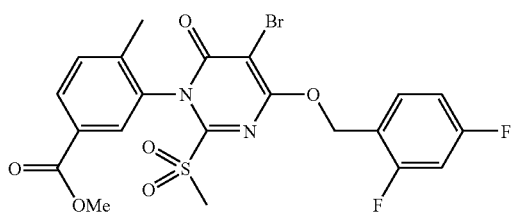

To a mixture of methyl 3-[4-[(2,4-difluorobenzyl)oxy]-2-(methylthio)-6-oxopyrimidin-1(6H)-yl]-4-methylbenzoate (0.99 g, 2.29 mmol) in DCM (5 mL) was added NBS (0.43 g, 2.40 mmol). After 2 h at ambient temperature, added mCPBA (0.40 g, 2.29 mmol). Added an additional aliquot of mCPBA (0.40 g, 2.29 mmol) after 30 min. After another 1.5 h, added additional mCPBA (0.20 g, 1.14 mmol) and stirred overnight at ambient temperature. Washed with water (~10 mL) and extracted in DCM. Crude extracts purified by flash column chromatography using 50% ethyl acetate/hexane as eluent. Appropriate fractions combined, concentrated under reduced pressure, and dried in vacuo to give the desired product as a yellow foam (0.89 g, 72%). $^1$H NMR (CD$_3$OD/400 MHz) δ8.04 (m, 1H), 7.94 (s, 1H), 7.60 (q, 1H, J=8.0 Hz), 7.46 (d, 1H, J=8.0 Hz), 7.02 (m, 2H), 5.59 (s, 2H), 3.87 (s, 3H), 3.13 (s, 3H), 2.16 (s, 3H). ESHRMS m/z 543.0030 (M+H calculated for C$_{21}$H$_{18}$BrF$_2$N$_2$O$_6$S requires 543.0032).

Step 2: Preparation of methyl 3-[5-bromo-4-[(2,4-difluorobenzyl)oxy]-2-(methylamino)-6-oxopyrimidin-1(6H)-yl]-4-methylbenzoate

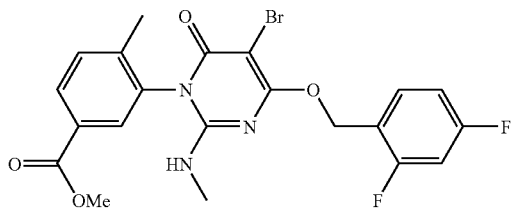

Methyl 3-[5-bromo-4-[(2,4-difluorobenzyl)oxy]-2-(methylsulfonyl)-6-oxopyrimidin-1(6H)-yl]-4-methylbenzoate (from Step 1) (0.35 g, 0.64 mmol), DMAP (0.01 g, 0.06 mmol), and methylamine (0.97 mL of a 2M solution in THF, 1.93 mmol) were combined and stirred at ambient temperature. Reaction complete after 4 h. Washed with 5% citric acid, extracted in DCM, dried over Na$_2$SO$_4$, filtered, concentrated, and dried in vacuo to give a brown film. Dissolved in a small amount of DCM, added hexane, and cooled. Filtered precipitate and washed with a solution of cold 50% DCM/hexane. Dried resulting white solid in vacuo (0.22 g, 69%). $^1$H NMR (CD$_3$OD/400 MHz) δ8.04 (m, 1H), 7.77 (s, 1H), 7.58 (q, 1H, J=8.8 Hz), 7.53 (d, 1H, J=8.4 Hz), 6.99 (m, 2H), 5.52 (s, 2H), 3.87 (s, 3H), 2.84 (s, 3H), 2.10 (s, 3H). ESHRMS m/z 494.0523 (M+H calculated for $C_2H_{19}BrF_2N_3O_4$ requires 494.0522).

Step 3: Preparation of methyl 3-[5-bromo-4-[(2,4-difluorobenzyl)oxy]-2-(methylamino)-6-oxopyrimidin-1(6H)-yl]-4-methylbenzoate

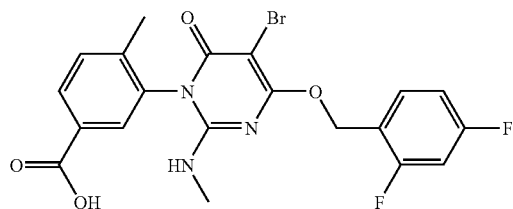

To a mixture of methyl 3-[5-bromo-4-[(2,4-difluorobenzyl)oxy]-2-(methylamino)-6-oxopyrimidin-1(6H)-yl]-4-methylbenzoate (from Step 2) (0.25 g, 0.51 mmol) in dioxane (2 mL) was added 2N NaOH (0.76 mmol). The reaction mixture was stirred at ambient temperature for 1.5 h, cooled (0° C.), and solid precipitated by the addition of 5% citric acid. The precipitate was filtered, washed with water, and dried in vacuo to give the desire product as a beige solid (0.21 g, 84%). $^1$H NMR (CD$_3$OD/400 MHz) δ8.05 (m, 1H), 7.76 (s, 1H), 7.58 (q, 1H, J=8.8 Hz), 7.51 (d, 1H, J=8.0 Hz), 6.99 (m, 2H), 5.52 (s, 2H), 2.84 (s, 3H), 2.10 (s, 3H). ESHRMS m/z 480.0403 (M+H calculated for $C_{20}H_{17}BrF_2N_3O_4$ requires 480.0365).

Step 4: Preparation of the Title Compound

To a cooled (0° C.) solution of methyl 3-[5-bromo-4-[(2,4-difluorobenzyl)oxy]-2-(methylamino)-6-oxopyrimidin-1(6H)-yl]-4-methylbenzoate (from Step 3) (0.18 g, 0.38 mmol) in N,N-dimethylacetamide (2 mL) was added isobutyl chloroformate (0.60 mL of a stock solution prepared 0.1 mL in 0.9 mL DCM, 0.46 mmol) and 4-methylmorpholine (0.55 mL of a stock solution prepared 0.1 mL in 0.9 mL DMA, 0.50 mmol). Stirred at 0° C. for 35 min. Added methylamine (0.29 mL of 2M solution in THF, 0.57 mmol). After 1 h, distilled DMA and purified the crude product by preparatory HPLC using a 10-90% CH$_3$CN/H$_2$O (30 min) gradient containing 0.5% TFA at a flow rate of 80 mL/min. Appropriate fractions (M+H m/z=494) were combined and concentrated to approximately 20 mL under reduced pressure. Added 5% NaHCO$_3$ (20 mL) and extracted with DCM (3×15 mL). The organic extracts were dried over Na$_2$SO$_4$, filtered, concentrated under reduced pressure, and dried in vacuo to give the desired product as a white solid (77 mg, 27%). $^1$H NMR (CD$_3$OD/400 MHz) δ7.86 (m, 1H), 7.58 (m, 2H), 7.51 (d, 1H, J=8.0 Hz), 6.98 (m, 2H), 5.52 (q, 2H, J=12.8 Hz), 2.87 (s, 3H), 2.84 (s, 3H), 2.09 (s, 3H). ESHRMS m/z 493.0659 (M+H calculated for $C_{21}H_{20}BrF_2N_4O_3$ requires 493.0681).

Preparation of N-[1-(aminocarbonyl)methyl]-3-[5-bromo-4-[(2,4-difluorobenzyl)oxy]-2-(methylamino)-6-oxopyrimidin-1(6H)-yl]-4-methylbenzamide

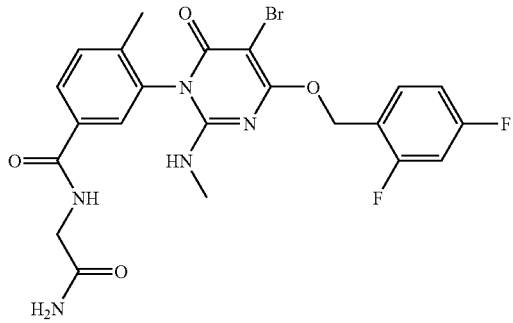

The title compound was prepared using a procedure similar to that used in Step 4 of the synthesis of 3-[5-bromo-4-[(2,4-difluorobenzyl)oxy]-2-(methylamino)-6-oxopyrimidin-1(6H)-yl]-N,4-dimethylbenzamide by substituting glycineamide HCl for methylamine. $^1$H NMR (CD$_3$OD/400 MHz) δ7.94 (m, 1H), 7.68 (s, 1H), 7.59 (q, 1H, J=8.4 Hz), 7.55 (d, 1H, J=8.0 Hz), 7.00 (m, 2H), 5.54 (q, 2H, J=11.6 Hz), 4.00 (s, 2H), 2.86 (s, 3H), 2.12 (s, 3H). ESHRMS m/z 536.0743 (M+H calculated for $C_{22}H_{21}BrF_2N_5O_4$ requires 536.0739).

Preparation of 3-[5-bromo-4-[(2,4-difluorobenzyl)oxy]-2-(methylamino)-6-oxopyrimidin-1(6H)-yl]-N-[(2S)-2,3-dihydroxypropyl]-4-methylbenzamide

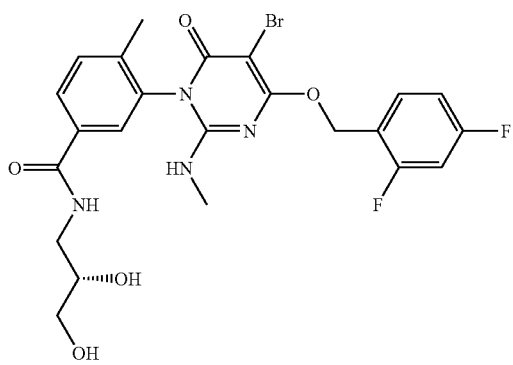

The title compound was prepared using a procedure similar to that used in Step 4 of the synthesis of 3-[5-bromo-4-[(2,4-difluorobenzyl)oxy]-2-(methylamino)-6-oxopyrimidin-1(6H)-yl]-N,4-dimethylbenzamide by substituting (S)-(−)-3-amino-1,2-propanediol for methylamine. $^1$H NMR (CD$_3$OD/400 MHz) δ7.89 (m, 1H), 7.56 (m, 3H), 6.98 (m, 2H), 5.52 (q, 2H, J=12.0 Hz), 3.77 (quintet, 1H, J=5.2 Hz), 3.50 (m, 3H), 3.36 (m, 1H), 2.83 (s, 3H), 2.10 (s, 3H). ESHRMS m/z 553.0875 (M+H calculated for $C_{23}H_{24}BrF_2N_4O_5$ requires 553.0893).

207

Preparation of N-allyl-3-[2-(allylamino)-5-chloro-4-[(2,4-difluorobenzyl)oxy]-6-oxopyrimidin-1(6H)-yl]-4-methylbenzamide

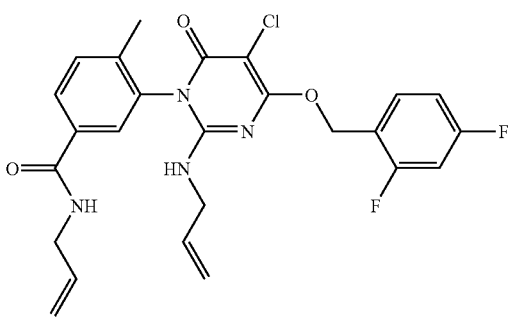

Step 1: Preparation of methyl 3-[5-chloro-4-[(2,4-difluorobenzyl)oxy]-2-(methylsulfonyl)-6-oxopyrimidin-1(6H)-yl]-4-methylbenzoate

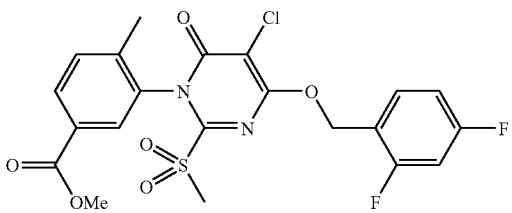

A mixture of methyl 3-[4-[(2,4-difluorobenzyl)oxy]-2-(methylthio)-6-oxopyrimidin-1(6H)-yl]-4-methylbenzoate (2.48 g, 5.73 mmol), NCS (0.84 g, 6.31 mmol), and dichloroacetic acid (~20 drops) in dichloroethane (20 mL) was heated at 60° C. overnight. Added mCPBA (0.99 g, 5.73 mmol) and stirred at ambient temperature for 1 h. Then, added second equivalent mCPBA (0.99 g, 5.73 mmol). Stirred overnight. Added additional mCPBA (0.49 g, 2.87 mmol) and stirred for ~65 h. Added additional mCPBA (0.49 g, 2.87 mmol) and stirred overnight at ambient temperature again. Reaction found to be complete. Washed with 5% NaHCO$_3$, extracted in DCM, dried over Na$_2$SO$_4$, filtered, concentrated, and dried in vacuo. Purified by flash column chromatography using 50% ethyl acetate/hexane as eluent. Obtained clean product as a white solid (1.56 g, 55%). $^1$H NMR (CD$_3$OD/400 MHz) δ8.07 (m, 1H), 7.96 (s, 1H), 7.62 (q, 1H, J=8.0 Hz), 7.48 (d, 1H, J=8.0 Hz), 7.05 (m, 2H), 5.62 (s, 2H), 3.89 (s, 3H), 3.45 (s, 3H), 2.18 (s, 3H). ESHRMS m/z 499.0514 (M+H calculated for C$_{21}$H$_{18}$ClF$_2$N$_2$O$_6$S requires 499.0537).

208

Step 2: Preparation of methyl 3-[2-(allylamino)-5-chloro-4-[(2,4-difluorobenzyl)oxy]-6-oxopyrimidin-1(6H)-yl]-4-methylbenzoate

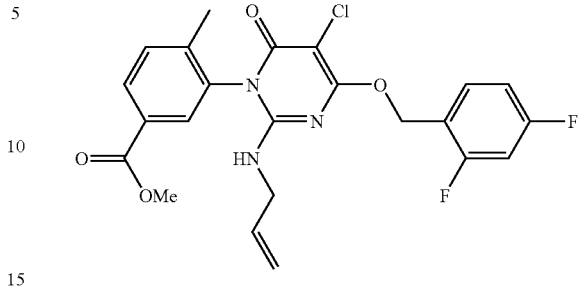

A mixture of methyl 3-[5-chloro-4-[(2,4-difluorobenzyl)oxy]-2-(methylsulfonyl)-6-oxopyrimidin-1(6H)-yl]-4-methylbenzoate (from Step 1) (3.02 g, 6.05 mmol), allyl amine (0.55 mL, 7.26 mmol), and DMAP (0.07 g, 0.61 mmol) in dioxane (8 mL) was stirred at ambient temperature overnight. Observed product and impurity (1:1 ratio). Added ethyl acetate (4 mL), cooled (0° C.) the reaction mixture, filtered the precipitate, and dried in vacuo to give the product as a white solid (1.17 g, 41%). $^1$H NMR (CD$_3$OD/400 MHz) δ8.08 (m, 1H), 7.82 (s, 1H), 7.57 (m, 2H), 7.00 (t, 2H, J=8.8 Hz), 5.80 (m, 1H), 5.51 (m, 2H), 5.07 (m, 2H), 4.56 (s, 1H), 3.93 (m, 1H), 3.89 (s, 3H), 3.65 (s, 3H). ESHRMS m/z 476.1184 (M+H calculated for C$_{23}$H$_{21}$ClF$_2$N$_3$O$_4$ requires 476.1183).

Step 3: Preparation of 3-[2-(allylamino)-5-chloro-4-[(2,4-difluorobenzyl)oxy]-6-oxopyrimidin-1(6H)-yl]-4-methylbenzoic acid

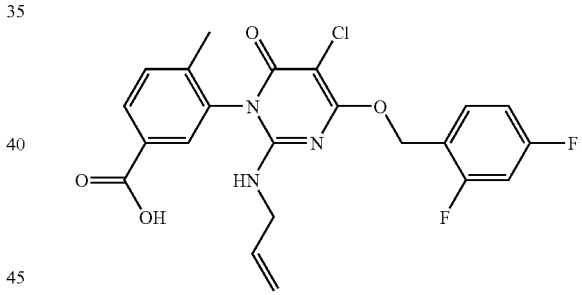

To a suspension of methyl 3-[2-(allylamino)-5-chloro-4-[(2,4-difluorobenzyl)oxy]-6-oxopyrimidin-1(6H)-yl]-4-methylbenzoate (from Step 2) (1.59 g, 3.34 mmol) in dioxane (7 mL) was added 2N NaOH (2.51 mL, 5.01 mmol). Stirred at ambient temperature for 1 h, cooled (0° C.), added 5% citric acid to precipitate the product, filtered precipitate, and dried in vacuo to give the desired compound as a white solid (1.30 g, 84%). $^1$H NMR (CD$_3$OD/400 MHz) δ8.08 (m, 1H), 7.81 (s, 1H), 7.56 (m, 2H), 7.00 (t, 2H, J=8.4 Hz), 5.80 (m, 1H), 5.51 (s, 2H), 5.07 (m, 2H), 3.93 (m, 2H), 2.14 (s, 3H). ESHRMS m/z 462.1006 (M+H calculated for C$_{22}$H$_{19}$ClF$_2$N$_3$O$_4$ requires 462.1027).

Step 4: Preparation of the Title Compound

To a cooled (0° C.) solution of 3-[2-(allylamino)-5-chloro-4-[(2,4-difluorobenzyl)oxy]-6-oxopyrimidin-1(6H)-yl]-4-methylbenzoic acid (from Step 3) (0.37 g, 0.80 mmol) in N,N-dimethylacetamide (2 mL) was added isobutyl chloroformate (0.12 mL, 0.96 mmol) and 4-methylmorpholine (0.11 mL, 1.04 mmol). Stirred at 0° C. for 5 min, ambient temperature for 30 min. Added allyl amine (0.09 mL, 1.20 mmol). Stirred at ambient temperature for 2 h. Purified by preparatory HPLC using a 10-90% CH$_3$CN/H$_2$O (30 min) gradient containing 0.5% TFA at a flow rate of 80 mL/min. Appropriate fractions (M+H m/z=494) were combined, freeze-dried, and lyophilized. Washed with 5% NaHCO$_3$ (20 mL) and extracted with DCM (3×15 mL). The organic extracts were dried over Na$_2$SO$_4$, filtered, concentrated under reduced pressure, and dried in vacuo to give the desired product as a white solid (0.24 g, 60%). $^1$H NMR (CD$_3$OD/400 MHz) δ7.93 (m, 1H), 7.67 (s, 1H), 7.55 (q, 2H, J=8.0 Hz), 7.00 (t, 2H, J=8.8 Hz), 5.90 (m, 1H), 5.80 (m, 1H), 5.51 (m, 2H), 5.21 (m, 1H), 5.09 (m, 3H), 3.95 (m, 4H), 2.14 (s, 3H). ESHRMS m/z 501.1520 (M+H calculated for C$_{25}$H$_{24}$ClF$_2$N$_4$O$_3$ requires 501.1500).

Preparation of 3-[5-bromo-4-[(2,4-difluorobenzyl)oxy]-6-oxopyrimidin-1(6H)-yl]-4-methyl-N-{1-[(methylamino)carbonyl]methyl}benzamide

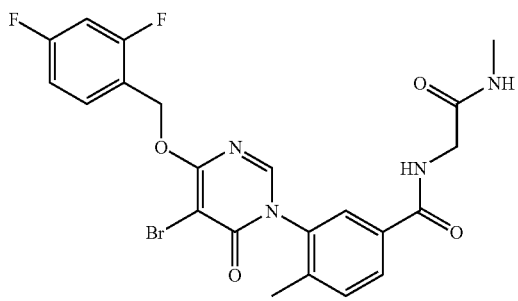

To a cold solution of 3-[5-bromo-4-[(2,4-difluorobenzyl)oxy]-6-oxopyrimidin-1(6H)-yl]-4-methylbenzoic acid (0.8 g, 1.7 mmol) in anhydrous dimethylacetamide (3.2 mL) was added isobutyl chloroformate (0.23 mL, 1.7 mmol) followed by N-methylmorpholine (0.25 mL, 2.2 mmol). The reaction mixture stirred under argon atmosphere at 0° C. for 10 min and then at room temperature for 30 min. At which time another equivalent of N-methylmorpholine (0.29 mL, 2.5 mmol) was added to reaction mixture, followed by the addition of glycine methyl amide HCl (0.33 g, 2.5 mmol) and DMAP (ca.). The reaction mixture stirred for 2 h at room temperature and then diluted with acetonitrile/water (2:1 v/v) to be purified by reverse phase HPLC using a 10-90% acetonitrile in water containing 0.5% TFA (30 min) gradient at a 80 mL/min flow rate. The appropriate fractions (M+H m/z=521) were collected and concentrated to a reduced volume. The resulting suspension was diluted with dichloromethane (30 mL) and washed with 5% NaHCO$_3$ (2×50 mL). The organic extracts were washed with water (2×25 mL) and dried over Na$_2$SO$_4$ (anhydrous). The organic extracts were concentrated under reduced pressure and dried in vacuo to afford the desired product (364.4 mg, 37%) as a white solid. $^1$H-NMR (CD$_3$OD, 400 MHz) δ 8.32 (s, 1H), 7.96 (dd, 1H, J=2 Hz), 7.80 (d, 1H, J=2 Hz), 7.62 (m, 1H), 7.55 (d, 1H, J=8.4 Hz), 7.01 (m, 2H), 5.60 (q, 2H, J=12.4 Hz), 3.98 (s, 2H), 2.74 (s, 3H), 2.20 (s, 3H); ES-HRMS m/z 521.0650 (M+H C$_{22}$H$_{20}$BrF$_2$N$_4$O$_4$ requires 521.0630).

Preparation of 3-[5-bromo-4-[(2,4-difluorobenzyl)oxy]-6-oxopyrimidin-1(6H)-yl]-N-[(2S)-2,3-dihydroxypropyl]-4-methylbenzamide

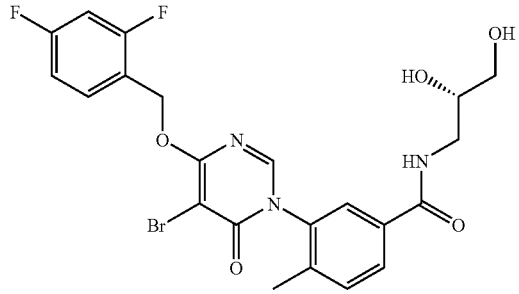

The title compound was prepared by a procedure similar to the one described for 3-[5-bromo-4-[(2,4-difluorobenzyl)oxy]-6-oxopyrimidin-1(6H)-yl]-4-methyl-N-{1-[(methylamino)carbonyl]methyl}benzamide using (S)-(−)-3-amino-1,2-propanediol (0.162 g 2.5 mmol) as the amine and without the addition of a second equivalent of N-methylmorpholine. After reverse phase HPLC purification, the organic extracts were concentrated under reduced pressure and dried in vacuo to afford the desired product (404.3 mg, 43%) as beige solid. $^1$H-NMR (CD$_3$OD, 400 MHz) δ 8.31 (s, 1H), 7.92 (dd, 1H, J=2 Hz), 7.76 (d, 1H, J=1.6 Hz), 7.62 (m, 1H), 7.55 (d, 1H, J=8 Hz), 7.01 (m, 2H), 5.59 (q, 2H, J=12.4 Hz), 3.80 (m, 1H), 3.53 (m, 3H), 3.39 (m, 1H), 2.19 (s, 3H); ES-HRMS m/z 524.0630 (M+H C$_{22}$H$_{21}$BrF$_2$N$_3$O$_5$ requires 524.0627).

Preparation of 3-[5-bromo-4-[(2,4-difluorobenzyl)oxy]-6-oxopyrimidin-1(6H)-yl]-N-[(2R)-2,3-dihydroxypropyl]-4-methylbenzamide

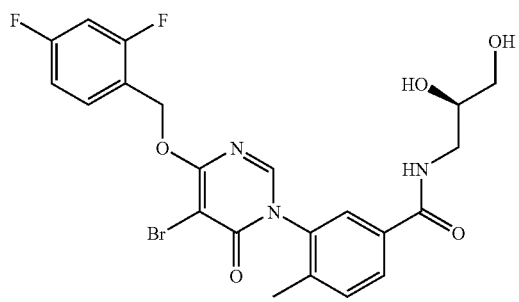

The title compound was prepared by a procedure similar to the one described for 3-[5-bromo-4-[(2,4-difluorobenzyl)oxy]-6-oxopyrimidin-1(6H)-yl]-4-methyl-N-{1-[(methylamino)carbonyl]methyl}benzamide using (R)-(+)-3-amino-1,2-propanediol (0.162 g 2.5 mmol) as the amine and without the addition of a second equivalent of N-methylmorpholine. After reverse phase HPLC purification, the organic extracts were concentrated under reduced pressure and dried in vacuo to afford the desired product (374.5 mg, 40%) as beige solid. $^1$H-NMR (CD$_3$OD, 400 MHz) δ 8.32 (s, 1H), 7.92 (dd, 1H, J=2 Hz), 7.77 (d, 1H, J=2 Hz), 7.62 (m, 1H), 7.55 (d, 1H, J=8.4 Hz), 7.04 (m, 2H), 5.60 (q, 2H, J=12.4 Hz), 3.80 (m, 1H), 3.53 (m, 3H), 3.39 (m, 1H), 2.19 (s, 3H); ES-HRMS m/z 524.0649 (M+H C$_{22}$H$_{21}$BrF$_2$N$_3$O$_5$ requires 524.0627).

Preparation of 3-[5-bromo-4-[(2,4-difluorobenzyl)oxy]-6-oxopyrimidin-1(6H)-yl]-N-(2-hydroxyethyl)-4-methylbenzamide

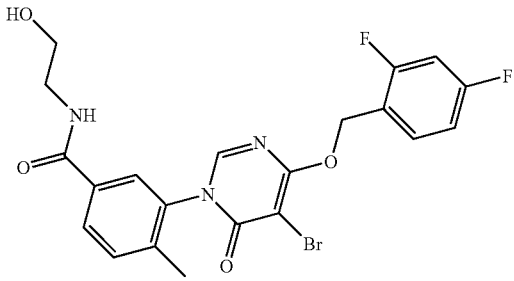

The title compound was prepared by a procedure similar to the one described for 3-[5-bromo-4-[(2,4-difluorobenzyl)oxy]-6-oxopyrimidin-1(6H)-yl]-4-methyl-N-(1-[(methylamino)carbonyl]methyl)benzamide using ethanolamine (0.16 mL 2.5 mmol) as the amine and without the addition of a second equivalent of N-methylmorpholine. After reverse phase HPLC purification, the organic extracts were concentrated under reduced pressure and dried in vacuo to afford the desired product (551.7 mg, 63%) as white solid. $^1$H-NMR (CD$_3$OD, 400 MHz) δ 8.32 (s, 1H), 7.92 (dd, 1H, J=2 Hz), 7.77 (d, 1H, J=2 Hz), 7.62 (m, 1H), 7.53 (d, 1H, J=8 Hz), 7.01 (m, 2H), 5.60 (q, 2H, J=12.4 Hz), 3.68 (t, 2H), 3.48 (t, 2H), 2.19 (s, 3H); ES-HRMS m/z 494.0518 (M+H C$_{21}$H$_{19}$BrF$_2$N$_3$O$_4$ requires 494.0522).

Preparation of N-[(1S)-1-(aminocarbonyl)ethyl]-3-[5-bromo-4-[(2,4-difluorobenzyl)oxy]-6-oxopyrimidin-1(6H)-yl]-4-methylbenzamide

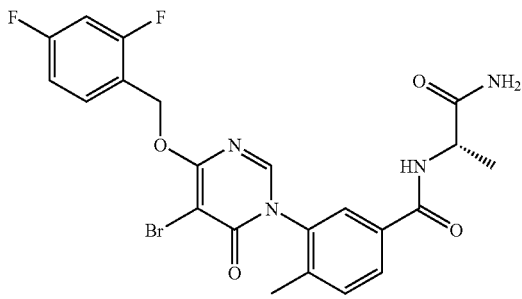

The title compound was prepared by a procedure similar to the one described for 3-[5-bromo-4-[(2,4-difluorobenzyl)oxy]-6-oxopyrimidin-1(6H)-yl]-4-methyl-N-{1-[(methylamino)carbonyl]methyl}benzamide using L-alaninamide HCl (0.33 g 2.5 mmol) as the amine. After reverse phase HPLC purification, the organic extracts were concentrated under reduced pressure and dried in vacuo to afford the desired product (370 mg, 40%) as beige solid. $^1$H-NMR (CD$_3$OD, 400 MHz) δ 8.32 (s, 1H), 7.95 (m, 1H), 7.83 (dd, 1H, J=2 Hz), 7.62 (m, 1H), 7.54 (d, 1H, J=8.4 Hz), 7.01 (m, 2H), 5.60 (q, 2H, J=12.4 Hz), 4.55 (m, 1H), 2.19 (s, 3H), 1.46 (dd, 3H J=1.2) ES-HRMS m/z 521.0598 (M+H C$_{22}$H$_{20}$BrF$_2$N$_4$O$_4$ requires 521.0630).

Preparation of 3-[5-bromo-4-[(2,4-difluorobenzyl)oxy]-6-oxopyrimidin-1(6H)-yl]-N-[(2S)-2-hydroxypropyl]-4-methylbenzamide

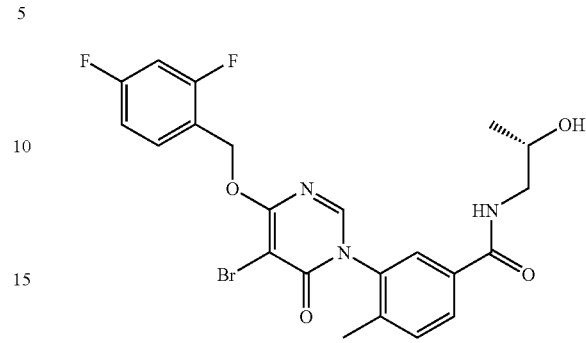

The title compound was prepared by a procedure similar to the one described for 3-[5-bromo-4-[(2,4-difluorobenzyl)oxy]-6-oxopyrimidin-1(6H)-yl]-4-methyl-N-{1-[(methylamino)carbonyl]methyl}benzamide using (S)-(+)-1-amino-2-propanol (0.16 mL 2.5 mmol) as the amine and without the addition of a second equivalent of N-methylmorpholine. After reverse phase HPLC purification, the organic extracts were concentrated under reduced pressure and dried in vacuo to afford the desired product (387.8 mg, 57%) as beige solid. $^1$H-NMR (CD$_3$OD, 400 MHz) δ 8.32 (s, 1H), 7.92 (dd, 1H, J=1.6 Hz), 7.77 (d, 1H, J=2 Hz), 7.62 (m, 1H), 7.53 (d, 1H, J=8.4 Hz), 7.01 (m, 2H), 5.59 (q, 2H, J=12.4 Hz), 3.92 (m, 1H), 3.32 (m, 2H), 2.19 (s, 3H), 1.18 (d, 3H, J=6.4 Hz); ES-HRMS m/z 508.0661 (M+H C$_{22}$H$_{21}$BrF$_2$N$_3$O$_4$ requires 508.0678).

Preparation of 3-[5-bromo-4-[(2,4-difluorobenzyl)oxy]-6-oxopyrimidin-1(6H)-yl]-N-[(2R)-2-hydroxypropyl]-4-methylbenzamide

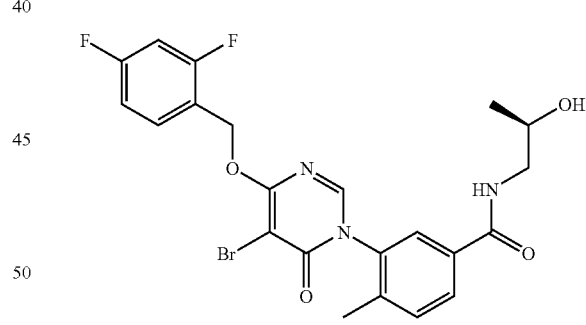

The title compound was prepared by a procedure similar to the one described for 3-[5-bromo-4-[(2,4-difluorobenzyl)oxy]-6-oxopyrimidin-1(6H)-yl]-4-methyl-N-{1-[(methylamino)carbonyl]methyl}benzamide using (R)-(−)-1-amino-2-propanol (0.16 mL 2.5 mmol) as the amine and without the addition of a second equivalent of N-methylmorpholine. After reverse phase HPLC purification, the organic extracts were concentrated under reduced pressure and dried in vacuo to afford the desired product (377.8 mg, 55%) as beige solid. $^1$H-NMR (CD$_3$OD, 400 MHz) δ 8.32 (s, 1H), 7.93 (dd, 1H, J=1.6 Hz), 7.77 (d, 1H, J=1.6 Hz), 7.62 (m, 1H), 7.53 (d, 1H, J=8 Hz), 7.01 (m, 2H), 5.60 (q, 2H, J=12.4 Hz), 3.93 (m, 1H), 3.32 (m, 2H), 2.19 (s, 3H), 1.18 (d, 3H, J=6.4 Hz); ES-HRMS m/z 508.0687 (M+H C$_{22}$H$_{21}$BrF$_2$N$_3$O$_4$ requires 508.0678).

Preparation of 3-[5-chloro-4-[(2,4-difluorobenzyl)oxy]-2-methyl-6-oxopyrimidin-1(6H)-yl]-4-methylbenzoic acid

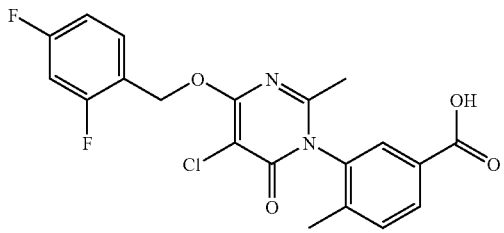

To a suspension of 3-[4-[(2,4-difluorobenzyl)oxy]-2-methyl-6-oxopyrimidin-1(6H)-yl]-4-methylbenzoic acid (1.0 g, 2.6 mmol) in anhydrous acetonitrile (15 mL) was added N-chlorosuccinimide (0.38 g, 2.9 mmol) and dichloroacetic acid (0.2 mL, 2.6 mmol). The reaction was heated in oil bath (70° C.) overnight under nitrogen. The reaction mixture was concentrated under reduced pressure to remove acetonitrile. The resulting residue was washed with water for 30 min, filtered, and rinsed with water. The white solid (830 mg, 82%) was dried in vacuo. $^1$H-NMR (CD$_3$OD, 400 MHz) δ 8.09 (dd, 1H, J=1.6 Hz), 7.88 (d, 1H, J=2 Hz), 7.56 (m, 2H), 7.01 (m, 2H), 5.57 (s, 2H), 2.16 (s, 3H), 2.13 (s, 3H); ES-HRMS m/z 421.0753 (M+H C$_{20}$H$_{16}$ClF$_2$N$_2$O$_4$ requires 421.0761).

Preparation of (±) 3-[5-chloro-4-[(2,4-difluorobenzyl)oxy]-2-methyl-6-oxopyrimidin-1(6H)-yl]-N-(2-hydroxyethyl)-4-methylbenzamide

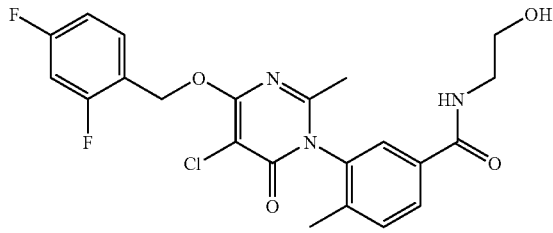

To a cold solution of 3-[5-chloro-4-[(2,4-difluorobenzyl)oxy]-2-methyl-6-oxopyrimidin-1(6H)-yl]-4-methylbenzoic acid (4.0 g, 9.5 mmol) in anhydrous dimethylacetamide (20 mL, −20° C.) and N-methylmorpholine (1.56 mL, 14.25 mmol) was added a solution of isobutyl chloroformate (1.84 mL, 14.25 mmol) in anhydrous dichloromethane (0.5 mL). The reaction mixture stirred under nitrogen atmosphere at −20° C. for 10 min and then at room temperature for 30 min. At which time it was cooled back down to 0° C. and ethanolamine (0.86 mL, 14.25 mmol) and DMAP (ca.) were added. The reaction mixture stirred for 30 min at 0° C., then at room temperature overnight. The solvent was removed by vacuum distillation and the residue was diluted with acetonitrile/water (1:1 v/v) to be purified by reverse phase HPLC using a 10-90% acetonitrile in water containing 0.5% TFA (30 min) gradient at a 80 mL/min flow rate. The appropriate fractions (M+H m/z=464) were collected, concentrated to a reduced volume, freeze-dried and lyophilized. The resulting white solid was diluted with dichloromethane (30 mL) and washed with 5% NaHCO$_3$ (2×50 mL). The organic extracts were washed with water (2×25 mL) and dried over Na$_2$SO$_4$ (anhydrous). The organic extracts were concentrated under reduced pressure and dried in vacuo to afford the desired product (2.625 g, 59%) as a white solid. $^1$H-NMR (CD$_3$OD, 400 MHz) δ 7.9 (dd, 1H, J=2 Hz), 7.69 (d, 1H, J=2 Hz), 7.62 (m, 1H), 7.5.5 (d, 1H, J=8.4 Hz), 7.01 (m, 2H), 5.58 (q, 2H, J=12.4 Hz), 3.68 (t, 2H, J=5.6 Hz), 3.46 (t, 2H, J=5.6 Hz), 2.17 (s, 3H), 2.12 (s, 3H); ES-HRMS m/z 464.1153 (M+H C$_{22}$H$_{21}$ClF$_2$N$_3$O$_4$ requires 464.1183).

Preparation of (−) 3-[5-chloro-4-[(2,4-difluorobenzyl)oxy]-2-methyl-6-oxopyrimidin-1(6H)-yl]-N-(2-hydroxyethyl)-4-methylbenzamide

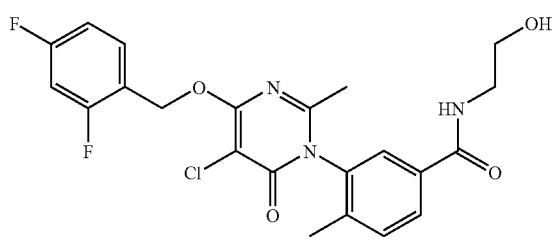

Racemic compound, (±) 3-[5-chloro-4-[(2,4-difluorobenzyl)oxy]-2-methyl-6-oxopyrimidin-1(6H)-yl]-N-(2-hydroxyethyl)-4-methylbenzamide (2.5 g), was resolved using a Chiralpak AD-H column, 21×250 mm. The sample was dissolved in EtOH (15 mg/mL). The injection volume was 4 mL and the material was eluted using EtOH with a flow rate of 10 mL/min. The fractions with (−) rotation were combined and reduced in vacuo to obtain the desired product (1.12 g) as a white solid. $^1$H-NMR (CD$_3$OD, 400 MHz) δ 7.92 (dd, 1H, J=2 Hz), 7.69 (d, 1H, J=2 Hz), 7.62 (m, 1H), 7.56 (d, 1H, J=8.4 Hz), 7.01 (m, 2H), 5.59 (q, 2H, J=12.4 Hz), 3.70 (t, 2H, J=5.6 Hz), 3.48 (t, 2H, J=5.6 Hz), 2.17 (s, 3H), 2.13 (s, 3H); ES-HRMS m/z 464.1166 (M+H C$_{22}$H$_{21}$ClF$_2$N$_3$O$_4$ requires 464.1183).

Preparation of (+) 3-[5-chloro-4-[(2,4-difluorobenzyl)oxy]-2-methyl-6-oxopyrimidin-1(6H)-yl]-N-(2-hydroxyethyl)-4-methylbenzamide

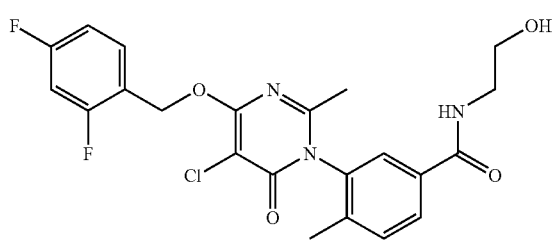

The title compound was isolated from racemic material, (±) 3-[5-chloro-4-[(2,4-difluorobenzyl)oxy]-2-methyl-6-oxopyrimidin-1(6H)-yl]-N-(2-hydroxyethyl)-4-methylbenzamide (2.5 g) according to resolution procedure for (−) 3-[5-chloro-4-[(2,4-difluorobenzyl)oxy]-2-methyl-6-oxopyrimidin-1(6H)-yl]-N-(2-hydroxyethyl)-4-methylbenzamide. The fractions with (+) rotation were combined and reduced in vacuo to obtain the desired product (1.32 g) as beige solid. $^1$H-NMR (CD$_3$OD, 400 MHz) δ 7.92 (dd, 1H, J=2 Hz), 7.69 (d, 1H, J=2 Hz), 7.62 (m, 1H), 7.56 (d, 1H, J=8.4 Hz), 7.01 (m, 2H), 5.59 (q, 2H, J=12.4 Hz), 3.70 (t, 2H, J=5.6 Hz), 3.48 (t, 2H, J=5.6 Hz), 2.17 (s, 3H), 2.13 (s, 3H); ES-HRMS m/z 464.1166 (M+H C$_{22}$H$_{21}$ClF$_2$N$_3$O$_4$ requires 464.1183).

Preparation of (±) 3-[5-chloro-4-[(2,4-difluorobenzyl)oxy]-2-methyl-6-oxopyrimidin-1(6H)-yl]-4-methyl-N-{1-[aminocarbonyl]methyl}benzamide

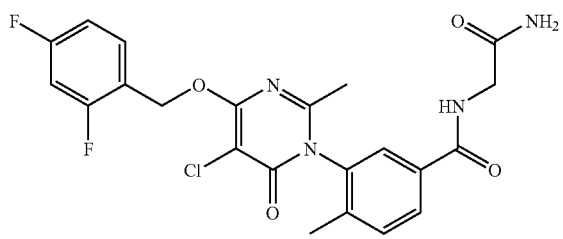

The title compound was prepared by a procedure similar to the one described for (±) 3-[5-chloro-4-[(2,4-difluorobenzyl)oxy]-2-methyl-6-oxopyrimidin-1(6H)-yl]-N-(2-hydroxyethyl)-4-methylbenzamide using glycine amide HCl (1.2 g, 10.95 mmol) as the amine and with an addition of a second equivalent of N-methylmorpholine. After reverse phase HPLC purification, the organic extracts were concentrated under reduced pressure and dried in vacuo to afford the desired product (1.79 g, 52%) as white solid. $^1$H-NMR (CD$_3$OD, 400 MHz) δ 7.97 (dd, 1H, J=1.6 Hz), 7.73 (d, 1H, J=1.6 Hz), 7.62 (m, 1H), 7.53 (d, 1H, J=8 Hz), 7.01 (m, 2H), 5.59 (q, 2H, J=12.4 Hz), 4.01 (d, 2H, J=1.6 Hz), 2.18 (s, 3H), 2.13 (s, 3H); ES-HRMS m/z 477.1128 (M+H C$_{22}$H$_{20}$ClF$_2$N$_4$O$_4$ requires 477.1136).

Preparation of (−) 3-[5-chloro-4-[(2,4-difluorobenzyl)oxy]-2-methyl-6-oxopyrimidin-1(6H)-yl]-4-methyl-N-{1-[aminocarbonyl]methyl}benzamide

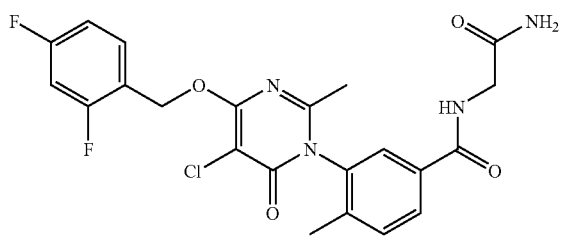

Racemic compound, (±) 3-[5-chloro-4-[(2,4-difluorobenzyl)oxy]-2-methyl-6-oxopyrimidin-1(6H)-yl]-4-methyl-N-{1-[aminocarbonyl]methyl}benzamide (1.7 g), was resolved using a Chiralpak AD-H column, 21×250 mm. The sample was dissolved in MeOH (10 mg/mL). The injection volume was 4 mL and the material was eluted using EtOH/hexane (80/20 v/v) with a flow rate of 8 mL/min. The fractions with (−) rotation were combined and reduced in vacuo to obtain the desired product (0.50 g) as beige solid. $^1$H-NMR (CD$_3$OD, 400 MHz) δ 7.97 (dd, 1H, J=1.6 Hz), 7.73 (d, 1H, J=1.6 Hz), 7.62 (m, 1H), 7.57 (d, 1H, J=8 Hz), 7.01 (m, 2H), 5.59 (q, 2H, J=12.4 Hz), 4.01 (d, 2H, J=1.6 Hz), 2.18 (s, 3H), 2.13 (s, 3H); ES-HRMS m/z 477.1141 (M+H C$_{22}$H$_{20}$ClF$_2$N$_4$O$_4$ requires 477.1136).

Preparation of (+) 3-[5-chloro-4-[(2,4-difluorobenzyl)oxy]-2-methyl-6-oxopyrimidin-1(6H)-yl]-4-methyl-N-{1-[aminocarbonyl]methyl}benzamide

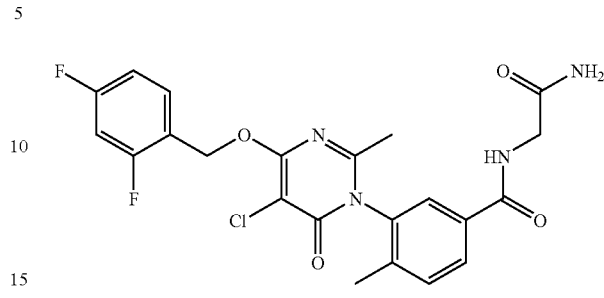

The title compound was isolated from racemic material, (±) 3-[5-chloro-4-[(2,4-difluorobenzyl)oxy]-2-methyl-6-oxopyrimidin-1(6H)-yl]-4-methyl-N-{1-[aminocarbonyl]methyl}benzamide (1.7 g) according to resolution procedure for 3-(4-(2,4-difluorobenzyloxy)-5-chloro-2-methyl-6-oxopyrimidin-1(6H)-yl)-N-(carbamoylmethyl)-4-methylbenzamide. The fractions with (+) rotation were combined and reduced in vacuo to obtain the desired product (0.57 g) as beige solid. $^1$H-NMR (CD$_3$OD, 400 MHz) δ 7.97 (dd, 1H, J=1.6 Hz), 7.73 (d, 1H, J=1.6 Hz), 7.62 (m, 1H), 7.57 (d, 1H, J=8 Hz), 7.01 (m, 2H), 5.59 (q, 2H, J=12.4 Hz), 4.01 (d, 2H, J=1.6 Hz), 2.18 (s, 3H), 2.13 (s, 0.3H), ES-HRMS m/z 477.1125 (M+H C$_{22}$H$_{20}$ClF$_2$N$_4$O$_4$ requires 477.1136).

Preparation of (±) 3-[5-chloro-4-[(2,4-difluorobenzyl)oxy]-2-methyl-6-oxopyrimidin-1(6H)-yl]-4-methyl-N-{1-[(methylamino)carbonyl]methyl}benzamide

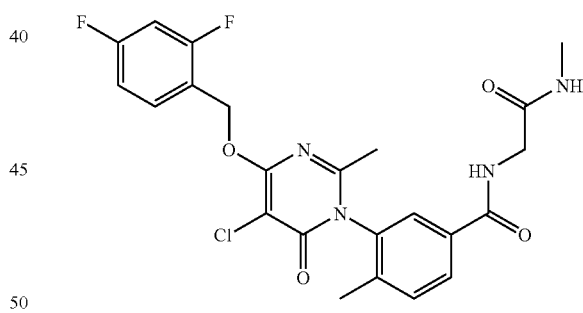

The title compound was prepared by a procedure similar to the one described for (±) 3-[5-chloro-4-[(2,4-difluorobenzyl)oxy]-2-methyl-6-oxopyrimidin-1(6H)-yl]-N-(2-hydroxyethyl)-4-methylbenzamide using glycine methyl amide HCl (1.77 g, 14.25 mmol) as the amine and with an addition of a second equivalent of N-methylmorpholine. After reverse phase HPLC purification, the organic extracts were concentrated under reduced pressure and dried in vacuo to afford the desired product (1.55 g, 33%) as white solid. $^1$H-NMR (CD$_3$OD, 400 MHz) δ 7.97 (dd, 1H, J=1.6 Hz), 7.73 (d, 1H, J=1.6 Hz), 7.62 (m, 1H), 7.57 (d, 1H, J=8 Hz), 7.01 (m, 2H), 5.59 (q, 2H, J=12.4 Hz), 3.98 (s, 2H), 2.74 (s, 3H), 2.18 (s, 3H), 2.14 (s, 3H); ES-HRMS m/z 491.1262 (M+H C$_{23}$H$_{22}$ClF$_2$N$_4$O$_4$ requires 491.1292). Both (+) and (−) atropomers will be resolved and characterized.

Preparation of +3-[5-chloro-4-[(2,4-difluorobenzyl)oxy]-2-methyl-6-oxopyrimidin-1(6H)-yl]-N-[(2S)-2-hydroxypropyl]-4-methylbenzamide

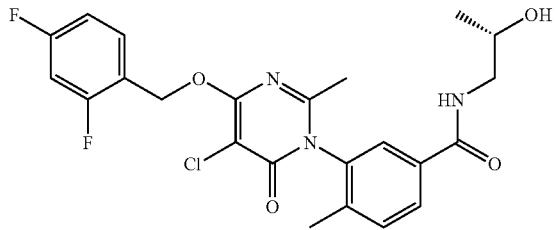

The title compound was prepared by a procedure similar to the one described for (±) 3-[5-chloro-4-[(2,4-difluorobenzyl)oxy]-2-methyl-6-oxopyrimidin-1(6H)-yl]-N-(2-hydroxyethyl)-4-methylbenzamide using (S)-(+)-1-amino-2-propanol (0.98 mL, 12.45 mmol) as the amine. After reverse phase HPLC purification, the organic extracts were concentrated under reduced pressure and dried in vacuo to afford the desired product (2.13 g, 53%) as white solid. $^1$H-NMR (CD$_3$OD, 400 MHz) δ 7.93 (dd, 1H, J=1.6 Hz), 7.69 (d, 1H, J=1.6 Hz), 7.62 (m, 1H), 7.56 (d, 1H, J=8 Hz), 7.01 (m, 2H), 5.59 (q, 2H, J=12.4 Hz), 3.94 (m, 1H), 3.39 (m, 2H), 2.18 (s, 3H), 2.13 (s, 3H), 1.9 (d, 3H, J=6.4 Hz); ES-HRMS m/z 478.1308 (M+H C$_{23}$H$_{23}$ClF$_2$N$_3$O$_4$ requires 478.1340). Both (+) and (−) atropomers will be resolved and characterized.

Preparation of ±3-[5-chloro-4-[(2,4-difluorobenzyl)oxy]-2-methyl-6-oxopyrimidin-1(6H)-yl]-N-[(2R)-2-hydroxypropyl]-4-methylbenzamide

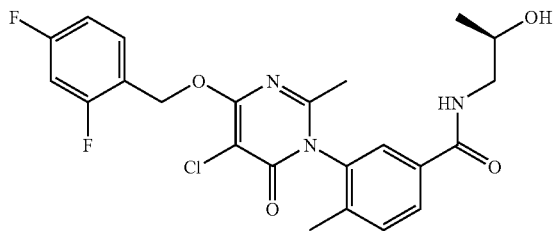

The title compound was prepared by a procedure similar to the one described for (±) 3-[5-chloro-4-[(2,4-difluorobenzyl)oxy]-2-methyl-6-oxopyrimidin-1(6H)-yl]-N-(2-hydroxyethyl)-4-methylbenzamide using (R)-(−)-1-amino-2-propanol (0.98 mL, 12.45 mmol) as the amine. After reverse phase HPLC purification, the organic extracts were concentrated under reduced pressure and dried in vacuo to afford the desired product (2.70 g, 58%) as beige solid. $^1$H-NMR (CD$_3$OD, 400 MHz) δ 7.93 (dd, 1H, J=1.6 Hz), 7.69 (d, 1H, J=1.6 Hz), 7.62 (m, 1H), 7.56 (d, 1H, J=8 Hz), 7.01 (m, 2H), 5.59 (q, 2H, J=12.4 Hz), 3.94 (m, 1H), 3.39 (m, 2H), 2.18 (s, 3H), 2.13 (s, 3H), 1.9 (d, 3H, J=6.4 Hz); ES-HRMS m/z 478.1322 (M+H C$_{23}$H$_{23}$ClF$_2$N$_3$O$_4$ requires 478.1340). Both (+) and (−) atropomers will be resolved and characterized.

Biological Evaluation p38 Kinase Assay

Cloning of Human p38a:

The coding region of the human p38a cDNA is obtained by PCR-amplification from RNA isolated from the human monocyte cell line THP.1. First strand cDNA is synthesized from total RNA as follows: 2 μg of RNA is annealed to 100 ng of random hexamer primers in a 10 μl reaction by heating to 70° C. for 10 minutes followed by 2 minutes on ice. cDNA is then synthesized by adding 1 μl of RNAsin (Promega, Madison Wis.), 2 μl of 50 mM dNTP's, 4 μl of 5× buffer, 2 μl of 100 mM DTT and 1 μl (200 U) of Superscript II™ AMV reverse transcriptase. Random primer, dNTP's and Superscript II™ reagents are all purchased from Life-Technologies, Gaithersburg, Mass. The reaction is incubated at 42° C. for 1 hour. Amplification of p38 cDNA is performed by aliquoting 5 μl of the reverse transcriptase reaction into a 100 μl PCR reaction containing the following: 80 μl dH.sub.2 O, 2. μl 50 mM dNTP's, 1 μl each of forward and reverse primers (50 μmol/μl), 10 μl of 10× buffer and 1 μl Expand™ polymerase (Boehringer Mannheim). The PCR primers incorporated Bam HI sites onto the 5' and 3' end of the amplified fragment, and are purchased from Genosys. The sequences of the forward and reverse primers were 5'-GATCGAGGATTCATGTCTCAG-GAGAGGCCCA-3' and 5'GATCGAGGATTCTCAG-GACTCCATCTCTTC-3' respectively. The PCR amplification is carried out in a DNA Thermal Cycler (Perkin Elmer) by repeating 30 cycles of 94° C. for 1 minute, 60° C. for 1 minute and 68° C. for 2 minutes. After amplification, excess primers and unincorporated dNTP's is removed from the amplified fragment with a Wizard™ PCR prep (Promega) and digested with Bam HI (New England Biolabs). The Bam HI digested fragment is ligated into BamHI digested pGEX 2T plasmid DNA (PharmaciaBiotech) using T-4 DNA ligase (New England Biolabs) as described by T. Maniatis, Molecular Cloning: A Laboratory Manual, 2nd ed. (1989). The ligation reaction is transformed into chemically competent E. coli DH10B cells purchased from Life-Technologies following the manufacturer's instructions. Plasmid DNA is isolated from the resulting bacterial colonies using a Promega Wizard™ miniprep kit. Plasmids containing the appropriate Bam HI fragment are sequenced in a DNA Thermal Cycler (Perkin Elmer) with Prism™ (Applied Biosystems Inc.). cDNA clones are identified that coded for both human p38a isoforms (Lee et al. Nature 372, 739). One of the clones that contained the cDNA for p38a-2 (CSB-2) inserted in the cloning site of PGEX 2T, 3' of the GST coding region is designated pMON 35802. The sequence obtained for this clone is an exact match of the cDNA clone reported by Lee et al. This expression plasmid allows for the production of a GST-p38a fusion protein.

Expression of Human p38a

GST/p38a fusion protein is expressed from the plasmid pMON 35802 in E. coli, stain DH10B (Life Technologies, Gibco-BRL). Overnight cultures are grown in Luria Broth (LB) containing 100 mg/ml ampicillin. The next day, 500 ml of fresh LB is inoculated with 10 ml of overnight culture, and grown in a 2 liter flask at 37° C. with constant shaking until the culture reached an absorbance of 0.8 at 600 nm. Expression of the fusion protein is induced by addition of isopropyl b-D-thiogalactosidase (IPTG) to a final concentration of 0.05 mM. The cultures are shaken for three hours at room temperature, and the cells are harvested by centrifugation. The cell pellets are stored frozen until protein purification.

Purification of P38 Kinase-Alpha

All chemicals are from Sigma Chemical Co. unless noted. Twenty grams of E. coli cell pellet collected from five 1 L shake flask fermentations is resuspended in a volume of PBS (140 mM NaCl, 2.7 mM KCl, 10 mM Na.sub.2 HPO.sub.4, 1.8 mM KH.sub.2 PO.sub.4, pH 7.3) up to 200 ml. The cell suspension is adjusted to 5 mM DTT with 2 M DTT and then split equally into five 50 ml Falcon conical tubes. The cells are sonicated (Ultrasonics model W375) with a 1 cm probe for 3×1 minutes (pulsed) on ice. Lysed cell material is removed by centrifugation (12,000×g, 15 minutes) and the clarified supernatant applied to glutathione-sepharose resin (Pharmacia).

Glutathione-Sepharose Affinity Chromatography

Twelve ml of a 50% glutathione sepharose-PBS suspension is added to 200 ml clarified supernatant and incubated batchwise for 30 minutes at room temperature. The resin is collected by centrifugation (600×g, 5 min) and washed with 2×150 ml PBS/1% Triton X-100, followed by 4×40 ml PBS. To cleave the p38 kinase from the GST-p38 fusion protein, the glutathione-sepharose resin is resuspended in 6 ml PBS containing 250 units thrombin protease (Pharmacia, specific activity>7500 units/mg) and mixed gently for 4 hours at room temperature. The glutathione-sepharose resin is removed by centrifugation (600.times.g, 5 min) and washed 2×6 ml with PBS. The PBS wash fractions and digest supernatant containing p38 kinase protein are pooled and adjusted to 0.3 mM PMSF.

Mono Q Anion Exchange Chromatography

The thrombin-cleaved p38 kinase is further purified by FPLC-anion exchange chromatography. Thrombin-cleaved sample is diluted 2-fold with Buffer A (25 mM HEPES, pH 7.5, 25 mM beta-glycerophosphate, 2 mM DTT, 5% glycerol) and injected onto a Mono Q HR 10/10 (Pharmacia) anion exchange column equilibrated with Buffer A. The column is eluted with a 160 ml 0.1 M-0.6 M NaCl/Buffer A gradient (2 ml/minute flowrate). The p38 kinase peak eluting at 200 mM NaCl is collected and concentrated to 3-4 ml with a Filtron 10 concentrator. (Filtron Corp.).

Sephacryl S100 Gel Filtration Chromatography

The concentrated Mono Q-p38 kinase purified sample is purified by gel filtration chromatography (Pharmacia HiPrep 26/60 Sephacryl S100 column equilibrated with Buffer B (50 mM HEPES, pH 7.5, 50 mM NaCl, 2 mM DTT, 5% glycerol)). Protein is eluted from the column with Buffer B at a 0.5 ml/minute flowrate and protein is detected by absorbance at 280 nm. Fractions containing p38 kinase (detected by SDS-polyacrylamide gel electrophoresis) are pooled and frozen at −80° C. Typical purified protein yields from 5 L E. coli shake flasks fermentations are 35 mg p38 kinase.

In Vitro Assay

The ability of compounds to inhibit human p38 kinase alpha is evaluated using two in vitro assay methods. In the first method, activated human p38 kinase alpha phosphorylates a biotinylated substrate, PHAS-I (phosphorylated heat and acid stable protein-insulin inducible), in the presence of gamma $^{32}$P-ATP ($^{32}$P-ATP). PHAS-I is biotinylated prior to the assay and provides a means of capturing the substrate, which is phosphorylated during the assay. p38 Kinase is activated by MKK6. Compounds were tested in 10 fold serial dilutions over the range of 100 μM to 0.001 μM using 1% DMSO. Each concentration of inhibitor is tested in triplicate.

All reactions are carried out in 96 well polypropylene plates. Each reaction well contains 25 mM HEPES pH 7.5, 10 mM magnesium acetate and 50 μM unlabeled ATP. Activation of p38 is required to achieve sufficient signal in the assay. Biotinylated PHAS-I is used at 1-2 μg per 50 μl reaction volume, with a final concentration of 1.5 μM. Activated human p38 kinase alpha is used at 1 μg per 50 μl reaction volume representing a final concentration of 0.3 μM. Gamma $^{32}$P-ATP is used to follow the phosphorylation of PHAS-I. $^{32}$P-ATP has a specific activity of 3000 Ci/mmol and is used at 1.2 μCi per 50 μl reaction volume. The reaction proceeds either for one hour or overnight at 30° C.

Following incubation, 20 μl of reaction mixture is transferred to a high capacity streptavidin coated filter plate (SAM-streptavidin-matrix, Promega) prewetted with phosphate buffered saline. The transferred reaction mix is allowed to contact the streptavidin membrane of the Promega plate for 1-2 minutes. Following capture of biotinylated PHAS-I with $^{32}$P incorporated, each well is washed to remove unincorporated $^{32}$P-ATP three times with 2M NaCl, three washes of 2M NaCl with 1% phosphoric, three washes of distilled water and finally a single wash of 95% ethanol. Filter plates are air-dried and 20 μl of scintillant is added. The plates are sealed and counted.

A second assay format is also employed that is based on p38 kinase alpha induced phosphorylation of EGFRP (epidermal growth factor receptor peptide, a 21 mer) in the presence $^{33}$P-ATP. Compounds are tested in 10 fold serial dilutions over the range of 100 μM to 0.001 μM in 1% DMSO. Each concentration of inhibitor is tested in triplicate. Compounds were evaluated in 50 μl reaction volumes in the presence of 25 mM Hepes pH 7.5, 10 mM magnesium acetate, 4% glycerol, 0.4% bovine serum albumin, 0.4 mM DTT, 50 μM unlabeled ATP, 25 μg EGFRP (200 μM), and 0.05 μCi $^{33}$P-ATP. Reactions are initiated by addition of 0.09 μg of activated, purified human GST-p38 kinase alpha. Activation is carried out using GST-MKK6 (5:1, p38:MKK6) for one hour at 30° C. in the presence of 50 μM ATP. Following incubation for 60 minutes at room temperature, the reaction is stopped by addition of 150 μl of AG 1×8 resin in 900 mM sodium formate buffer, pH 3.0 (1 volume resin to 2 volumes buffer). The mixture is mixed three times with pipetting and the resin is allowed to settle. A total of 50 μl of clarified solution head volume is transferred from the reaction wells to Microlite-2 plates. 150 μl of Microscint 40 is then added to each well of the Microlite plate, and the plate is sealed, mixed, and counted.

Preferred compounds of the invention exhibit IC50 values of 25 micromolar or less. More preferred compounds of the invention exhibit IC50 values of 10 micromolar or less. Even more preferred compounds of the invention exhibit IC50 values of 5 micromolar or less. Especially preferred compounds of the invention exhibit IC50 values of 1 micromolar or less.

Some representative examples with IC50 values are shown below.

| Structure | p38 Alpha Avg. IC50 (uM) |
|---|---|
| [structure] | <5.00 |
| [structure] | <5.00 |

-continued

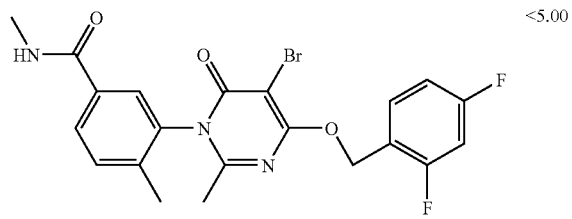

<5.00

TNF Cell Assays

Method of Isolation of Human Peripheral Blood Mononuclear Cells:

Human whole blood is collected in Vacutainer tubes containing EDTA as an anticoagulant. A blood sample (7 ml) is carefully layered over 5 ml PMN Cell Isolation Medium (Robbins Scientific) in a 15 ml round bottom centrifuge tube. The sample is centrifuged at 450-500×g for 30-35 minutes in a swing out rotor at room temperature. After centrifugation, the top band of cells are removed and washed 3 times with PBS w/o calcium or magnesium. The cells are centrifuged at 400 times gravity for 10 minutes at room temperature. The cells are resuspended in Macrophage Serum Free Medium (Gibco BRL) at a concentration of 2 million cells/ml.

LPS Stimulation of Human PBMs

PBM cells (0.1 ml, 2 million/ml) are co-incubated with 0.1 ml compound (10-0.41 µM, final concentration) for 1 hour in flat bottom 96 well microtiter plates. Compounds are dissolved in DMSO initially and diluted in TCM for a final concentration of 0.1% DMSO. LPS (Calbiochem, 20 ng/ml, final concentration) is then added at a volume of 0.010 ml. Cultures are incubated overnight at 37° C. Supernatants are then removed and tested by ELISA for TNF-a and IL1-b. Viability is analyzed using MTS. After 0.1 ml supernatant is collected, 0.020 ml MTS is added to remaining 0.1 ml cells. The cells are incubated at 37° C. for 2-4 hours, then the O.D. is measured at 490-650 nM.

Maintenance and Differentiation of the U937 Human Histiocytic Lymphoma Cell Line U937 cells (ATCC) are propagated in RPMI 1640 containing 10% fetal bovine serum, 100 IU/ml penicillin, 100 µg/ml streptomycin, and 2 mM glutamine (Gibco). Fifty million cells in 100 ml media are induced to terminal monocytic differentiation by 24 hour incubation with 20 ng/ml phorbol 12-myristate 13-acetate (Sigma). The cells are washed by centrifugation (200×g for 5 min) and resuspended in 100 ml fresh medium. After 24-48 hours, the cells are harvested, centrifuged, and resuspended in culture medium at 2 million cells/ml.

LPS Stimulation of TNF Production by U937 Cells

U937 cells (0.1 ml, 2 million/ml) are incubated with 0.1 ml compound (0.004-50 µM, final concentration) for 1 hour in 96 well microtiter plates. Compounds are prepared as 10 mM stock solutions in DMSO and diluted in culture medium to yield a final DMSO concentration of 0.1% in the cell assay. LPS (*E coli*, 100 ng/ml final concentration) is then added at a volume of 0.02 ml. After 4 hour incubation at 37° C., the amount of TNF-alpha released in the culture medium is quantitated by ELISA. Inhibitory potency is expressed as IC50 (µM).

Rat Assay

The efficacy of the novel compounds in blocking the production of TNF also is evaluated using a model based on rats challenged with LPS. Male Harlen Lewis rats [Sprague Dawley Co.] are used in this model. Each rat weighed approximately 300 g and is fasted overnight prior to testing. Compound administration is typically by oral gavage (although intraperitoneal, subcutaneous and intravenous administration are also used in a few instances) 1 to 24 hours prior to the LPS challenge. Rats are administered 30 µg/kg LPS [*salmonella typhosa*, Sigma Co.] intravenously via the tail vein. Blood is collected via heart puncture 1 hour after the LPS challenge. Serum samples are stored at −20° C. until quantitative analysis of TNF-alpha by Enzyme Linked-Immuno-Sorbent Assay ("ELISA") [Biosource]. Additional details of the assay are set forth in Perretti, M., et al., Br. J. Pharmacol. (1993), 110, 868-874, which is incorporated by reference in this application.

Mouse Assay

Mouse Model of LPS-Induced TNF Alpha Production

TNF alpha is induced in 10-12 week old BALB/c female mice by tail vein injection with 100 ng lipopolysaccharide (from *S. Typhosa*) in 0.2 ml saline. One hour later mice are bled from the retroorbital sinus and TNF concentrations in serum from clotted blood are quantified by ELISA. Typically, peak levels of serum TNF ranged from 2-6 ng/ml one hour after LPS injection.

The compounds tested are administered to fasted mice by oral gavage as a suspension in 0.2 ml of 0.5% methylcellulose and 0.025% Tween 20 in water at 1 hour or 6 hours prior to LPS injection. The 1 hour protocol allows evaluation of compound potency at Cmax plasma levels whereas the 6 hour protocol allows estimation of compound duration of action. Efficacy is determined at each time point as percent inhibition of serum TNF levels relative to LPS injected mice that received vehicle only.

Induction and Assessment of Collagen-Induced Arthritis in Mice

Arthritis is induced in mice according to the procedure set forth in J. M. Stuart, Collagen Autoimmune Arthritis, Annual Rev. Immunol. 2:199 (1984), which is incorporated herein by reference. Specifically, arthritis is induced in 8-12 week old DBA/1 male mice by injection of 50 µg of chick type II collagen (CII) (provided by Dr. Marie Griffiths, Univ. of Utah, Salt Lake City, Utah) in complete Freund's adjuvant (Sigma) on day 0 at the base of the tail. Injection volume is 100 µl. Animals are boosted on day 21 with 50 µg of CII in incomplete Freund's adjuvant (100 µl volume). Animals are evaluated several times each week for signs of arthritis. Any animal with paw redness or swelling is counted as arthritic. Scoring of arthritic paws is conducted in accordance with the procedure set forth in Wooley et al., Genetic Control of Type II Collagen Induced Arthritis in Mice: Factors Influencing Disease Suspectibility and Evidence for Multiple MHC Associated Gene Control., Trans. Proc., 15:180 (1983). Scoring of severity is carried out using a score of 1-3 for each paw (maximal score of 12/mouse). Animals displaying any redness or swelling of digits or the paw are scored as 1. Gross swelling of the whole paw or deformity is scored as 2. Ankylosis of joints is scored as 3. Animals are evaluated for 8 weeks. 8-10 animals per group are used.

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as invention, the following claims conclude this specification.

What is claimed is:

1. A method of treating neuropathic pain in a subject, the method comprising treating a subject in need thereof with a therapeutically effective amount of a compound of the formula

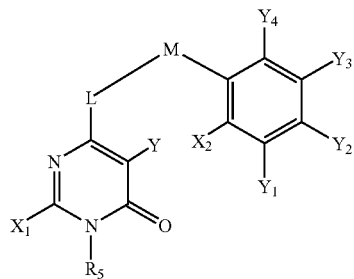

or a pharmaceutically acceptable salt thereof, wherein
L is —O—;
M is —$CH_2$—;
$R_5$ is

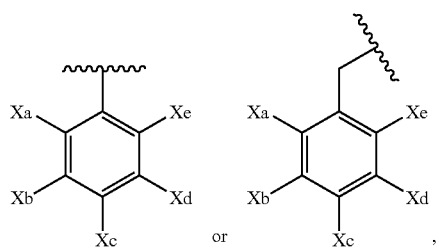

wherein
$X_1$, $X_2$, $X_a$, $X_b$, $X_c$, $X_d$, and $X_e$ at are independently selected from —C(O)$NR_6R_7$, —($C_1$-$C_4$ alkyl)-C(O)$NR_6R_7$, —$NR_6R_7$, hydroxy($C_1$-$C_4$)alkyl, $C_1$-$C_4$ dihydroxyalkyl, H, halogen, haloalkyl, alkyl, haloalkoxy, heteroaryl, heterocycloalkyl, $C_3$-$C_7$, cycloalkyl, $R_6R_7N$—($C_1$-$C_6$ alkyl)-, —$CO_2$—($C_1$-$C_6$) alkyl, —N(R)C(O)$NR_6R_7$, —N(R)C(O)—($C_1$-$C_6$)alkoxy, $CO_2R$—($C_1$-$C_6$ alkyl)-, or —$SO_2NR_6R_7$; wherein the heteroaryl and heterocycloalkyl groups are optionally substituted with —$NR_6R_7$, —C(O)$NR_6R_7$, $R_6R_7N$—($C_1$-$C_6$ alkyl)-, $C_1$-$C_6$ alkyl, $C_1$-$C_6$ alkoxy, or halogen; or $R_5$ is heteroaryl or heteroarylalkyl, wherein the heteroaryl and heteroaryl groups are optionally substituted with 1, 2, 3, or 4 groups that are independently —C(O)$NR_6R_7$, —($C_1$-$C_4$ alkyl)-C (O)$NR_6R_7$, —$NR_6R_7$, hydroxy($C_1$-$C_4$)alkyl, $C_1$-$C_4$ dihydroxyalkyl, H, OH, halogen, haloalkyl, alkyl, haloalkoxy, $R_6R_7N$—($C_1$-$C_6$ alkyl)-, —$CO_2$—($C_1$-$C_6$)alkyl, —N(R)C(O)$NR_6R_7$, or —N(R)C(O)—($C_1$-$C_6$) alkoxy; wherein $R_6$ and $R_7$ are independently at each occurrence H, $C_1$-$C_6$ alkyl, $C_1$-$C_6$ alkoxy, $C_1$-$C_6$ alkoxy $C_1$-$C_6$ alkyl, $C_1$-$C_6$ alkoxycarbonyl, OH, $C_1$-$C_6$ hydroxyalkyl, $C_1$-$C_4$ dihydroxyalkyl, $C_1$-$C_6$ thiohydroxyalkyl, —$C_1$-$C_4$)alkyl-$CO_2$-alkyl, pyridyl $C_1$-$C_6$ alkyl, $C_1$-$C_6$ alkanoyl, benzyl, phenyl $C_1$-$C_6$ alkoxy, or phenyl $C_1$-$C_6$ alkanoyl, wherein each of the above is unsubstituted or substituted with 1, 2, or 3 groups that are independently, halogen, $C_3$-$C_6$ cycloalkyl, $C_1$-$C_6$ alkoxy, piperidinyl $C_1$-$C_6$ alkyl, morpholinyl $C_1$-$C_6$alkyl, piperazinyl $C_1$-$C_6$ alkyl, OH, SH, $NH_2$, NH(alkyl), N(alkyl)(alkyl), —O—$C_1$-$C_4$ alkanoyl, $C_1$-$C_4$ alkyl, $CF_3$, or $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$-$C_4$ alkyl, $C_1$-$C_4$ alkoxy, hydroxy, hydroxy $C_1$-$C_4$ alkyl, $C_1$-$C_4$ dihydroxyalkyl, or halogen;

R at each occurrence is independently H or $C_1$-$C_6$ alkyl; and

Y, $Y_1$, $Y_2$, $Y_3$, and $Y_4$ are independently selected from H, halogen, alkyl, carboxaldehyde, hydroxyalkyl, dihydroxyalkyl, alkenyl, alkynyl, CN, alkanoyl, alkoxy, alkoxyalkyl, haloalkyl, and carboxyl.

2. A method according to claim 1, wherein

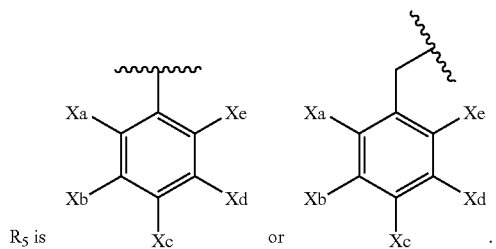

R$_5$ is

3. The method according to claim 2, wherein
X$_a$ is hydrogen;
two of X$_b$, X$_c$, and X$_d$ are hydrogen and the other is —C(O)NR$_6$R$_7$, —(C$_1$-C$_4$ alkyl)-C (O)NR$_6$R$_7$, —NR$_6$R$_7$, R$_6$R$_7$N—(C$_1$-C$_6$ alkyl)- or —CO$_2$—(C$_1$-C$_6$)alkyl; wherein
R$_6$ and R$_7$ are independently at each occurrence H, C$_1$-C$_6$ alkyl, C$_1$-C$_6$ alkoxy, C$_1$-C$_6$ alkoxy C$_1$-C$_6$ alkyl, C$_1$-C$_6$ alkoxycarbonyl, OH, C$_1$-C$_6$ hydroxyalkyl, C$_1$-C$_4$ dihydroxyalkyl, -(C$_1$-C$_4$)alkyl-CO$_2$-alkyl, pyridyl C$_1$-C$_6$ alkyl, C$_1$-C$_6$ alkanoyl, benzyl, phenyl C$_1$-C$_6$ alkoxy, or phenyl C$_1$-C$_6$ alkanoyl, wherein each of the above is unsubstituted or substituted with 1, 2, or 3 groups that are independently, halogen, C$_3$-C$_6$ cycloalkyl, C$_1$-C$_6$ alkoxy, piperidinyl C$_1$-C$_6$ alkyl, morpholinyl C$_1$-C$_6$ alkyl, piperazinyl C$_1$-C$_6$ alkyl, OH, NH$_2$, NH(alkyl), N(alkyl)(alkyl), —O—C$_1$-C$_4$ alkanoyl, C$_1$-C$_4$ alkyl, CF$_3$, or OCF$_3$; or
R$_6$, R$_7$, and the nitrogen to which they are attached form a morpholinyl, piperidinyl, pyrrolidinyl, or piperazinyl ring which is optionally substituted with 1 or 2 groups that are independently C$_1$-C$_4$ alkyl, C$_1$-C$_4$ alkoxy, hydroxy, hydroxy C$_1$-C$_4$ alkyl, C$_1$-C$_4$ dihydroxyalkyl, or halogen; and
X$_e$ is hydrogen, methyl, C$_1$-C$_2$ alkoxy, or halogen.

4. The method according to claim 3, wherein
X$_b$ is —C(O)NR$_6$R$_7$, —(C$_1$-C$_4$ alkyl)-C(O)NR$_6$R$_7$, —NR$_6$R$_7$, or R$_6$R$_7$N—(C$_1$-C$_6$ alkyl)- wherein
R$_6$ is hydrogen or C$_1$-C$_4$ alkyl;
R$_7$ is OH, C$_1$-C$_6$ alkyl or C$_1$-C$_6$ alkanoyl, wherein the alkyl and alkanoyl groups are substituted with 1, 2, or 3 groups that are independently NH$_2$, NH(C$_1$-C$_6$ alkyl), N(C$_1$-C$_6$ alkyl)(C$_1$-C$_6$ alkyl), C$_3$-C$_6$ cycloalkyl, OH, or C$_1$-C$_4$ alkoxy.

5. The method according to claim 2, wherein
X$_a$ is halogen or methyl;
X$_b$ is H, —NR$_6$R$_7$, R$_6$R$_7$N—(C$_1$-C$_6$ alkyl)-, —C(O)NR$_6$R$_7$, or —CO$_2$—(C$_1$-C$_6$)alkyl;
X$_c$ is —NR$_6$R$_7$, R$_6$R$_7$N—(C$_1$-C$_6$ alkyl)-, —C(O)NR$_6$R$_7$, halogen, —CO$_2$—(C$_1$-C$_6$)alkyl, NH$_2$, NH(C$_1$-C$_6$ alkyl), N(C$_1$-C$_6$ alkyl)(C$_1$-C$_6$ alkyl), —SO$_2$NH$_2$, —SO$_2$NH(C$_1$-C$_6$ alkyl), —SO$_2$N(C$_1$-C$_6$ alkyl)(C$_1$-C$_6$ alkyl), or piperazinyl, wherein the piperazinyl group is optionally substituted with 1 or 2 groups that are independently C$_1$-C$_4$ alkyl, C$_1$-C$_4$ alkoxy, or halogen;
X$_d$ is hydrogen; and
X$_e$ is H, methyl, NH$_2$, NH(C$_1$-C$_6$ alkyl) or N(C$_1$-C$_6$ alkyl)(C$_1$-C$_6$ alkyl).

6. The method according to claim 2, wherein
X$_1$, X$_2$, X$_a$, X$_b$, X$_c$, X$_d$, and X$_e$ are independently selected from H, halogen, CF$_3$, alkyl, OCF$_3$, pyridyl, pyridazinyl, pyrimidyl, pyrazinyl, thienyl, furyl, pyrrolyl, piperidinyl, piperazinyl, or C$_3$-C$_7$ cycloalkyl, wherein any heteroaryl or the heterocycloalkyl group is optionally substituted with —NR$_6$R$_7$, —C(O)NR$_6$R$_7$, R$_6$R$_7$N—(C$_1$-C$_6$ alkyl)-, C$_1$-C$_6$ alkyl, C$_1$-C$_6$ alkoxy, or halogen.

7. The method according to claim 1, wherein
R$_5$ is a heteroaryl or heteroarylalkyl group, where each heteroaryl is pyrazolyl, imidazolyl, furanyl, pyridyl, pyridazinyl, pyrimidinyl, pyrazinyl, pyrazolyl, imidazolyl, dihydroindolyl, dihydroisoindolyl, indolon-2-yl, quinolinyl, isoquinolinyl, tetrahydroisoquinolinyl, dihydroisoquinolinyl, or indolyl, each of which is optionally substituted with 1, 2, 3, or 4 groups that are independently —C(O)NR$_6$R$_7$, —(C$_1$-C$_4$ alkyl)-C(O)NR$_6$R$_7$, —NR$_6$R$_7$, hydroxy(C$_1$-C$_4$)alkyl, C$_1$-C$_4$ dihydroxyalkyl, hydrogen, hydroxy, halogen, haloalkyl, alkyl, haloalkoxy, R$_6$R$_7$N—(C$_1$-C$_6$ alkyl)-, —CO$_2$—(C$_1$-C$_6$)alkyl, —N(R)C(O)NR$_6$R$_7$, or —N(R)C(O)—(C$_1$-C$_6$)alkoxy; wherein
R$_6$ and R$_7$ are independently at each occurrence H, C$_1$-C$_6$ alkyl, C$_1$-C$_6$ alkoxy, C$_1$-C$_6$ alkoxy C$_1$-C$_6$ alkyl, C$_1$-C$_6$ alkoxycarbonyl, OH, C$_1$-C$_6$ hydroxyalkyl, C$_1$-C$_6$ dihydroxyalkyl, C$_1$-C$_6$ thiohydroxyalkyl, —(C$_1$-C$_4$)alkyl-CO$_2$-alkyl, pyridyl C$_1$-C$_6$ alkyl, C$_1$-C$_6$ alkanoyl, benzyl, phenyl C$_1$-C$_6$ alkoxy, or phenyl C$_1$-C$_6$ alkanoyl, wherein each of the above is unsubstituted or substituted with 1, 2, or 3 groups that are independently, halogen, C$_3$-C$_6$ cycloalkyl, C$_1$-C$_6$ alkoxy, piperidinyl C$_1$-C$_6$alkyl, morpholinyl C$_1$-C$_6$alkyl, piperazinyl C$_1$-C$_6$ alkyl, OH, SH, NH$_2$, NH(alkyl), N(alkyl)(alkyl), —O—-C$_1$-C$_4$ alkanoyl, C$_1$-C$_4$ alkyl, CF$_3$, or OCF$_3$.

8. The method according to claim 7, wherein
Y$_2$, Y$_4$, and Y are independently halogen; and
Y$_1$ and Y$_3$ are both hydrogen.

9. The method according to claim 8, wherein
X$_1$ and X$_2$ are independently H, methyl, —NR$_6$R$_7$, R$_6$R$_7$N—(C$_1$-C$_6$ alkyl)-, —C(O)NR$_6$R$_7$, —(C$_1$-C$_4$ alkyl)-C(O)NR$_6$R$_7$, hydroxy(C$_1$-C$_4$)alkyl, C$_1$-C$_4$ dihydroxyalkyl, or —(C$_1$-C$_4$ alkyl)-morpholinyl.

10. The method according to claim 9, wherein
R$_5$ is pyridyl C$_1$-C$_6$ alkyl, pyrimidinyl C$_1$-C$_6$ alkyl, or pyrazinyl C$_1$-C$_6$ alkyl, each of which is optionally substituted with 1, 2, or 3 groups that are independently hydroxy(C$_1$-C$_4$)alkyl, C$_1$-C$_4$ dihydroxyalkyl, OH, halogen, CF$_3$, (C$_1$-C$_4$)alkyl, OCF$_3$, —NR$_6$R$_7$, —(C$_1$-C$_4$ alkyl)-C(O)NR$_6$R$_7$, R$_6$R$_7$N—(C$_1$-C$_6$ alkyl)-, or —C(O)NR$_6$R$_7$.

11. The method according to claim 3 wherein the compound is selected from the group consisting of:
3-[5-Bromo-4-[(2,4-difluorobenzyl)oxy]-2-methyl-6-oxopyrimidin-1(6H)-yl]-N,4-dimethylbenzamide; Methyl 3-[4-[(2,4-difluorobenzy)oxy]-2-methyl-6-oxopyrimidin-1(6H)-yl]-4-methylbenzoate ; Methyl 3-[5-bromo-4-[(2,4-difluorobenzyl)oxy]-2-methyl-6-oxopyrimidin-1(6H)-yl ]-4-methylbenzoate; 3-[5-Bromo-4-[(2,4-difluorobenzyl)oxy]-2-methyl-6-oxopyrimidin-1(6H)-yl]-4-methylbenzamide; 3-[5-chloro-4-[(2,4-difluorobenzyl)oxy]-2-(methylthio)-6-oxopyrimidin-1 (6H)-yl]-4-methylbenzamide;

3-[5-chloro-4-[(2,4-difluorobenzyl)oxy]-6-oxopyrimidin-1(6H)-yl]-4-methylbenzamide;

(±) 3-[5-bromo-4-[(2,4-difluorobenzyl)oxy]-2-methyl-6-oxopyrimidin-1(6H)-yl]-4-methyl-N -{1-[(methylamino)carbonyl]methyl}benzamide;

(−) 3-[5-bromo-4-[(2,4-difluorobenzyl)oxy]-2-methyl-6-oxopyrimidin-1(6H)-yl]-4-methyl-N-{1-[(methylamino)carbonyl]methyl}benzamide;

(+) 3-[5-bromo-4-[(2,4-difluorobenzyl)oxy]-2-methyl-6-oxopyrimidin-1(6H)-yl]-4-methyl-N -{1-[(methylamino)carbonyl]methyl}benzamide;

(+)3-[5-bromo-4-[(2,4-difluorobenzyl)oxy]-2-methyl-6-oxopyrimidin-1(6H)-yl]-4-methylbenzamide;

(+) 3-[5-Bromo-4-[(2,4-difluorobenzyl)oxy]-2-methyl-6-oxopyrimidin-1(6H)-yl]-N,4-dimethylbenzamide;

(+) 3-[5-bromo-4-[(2,4-difluorobenzyl)oxy]-2-methyl-6-oxopyrimidin-1(6H)-yl]-4-methyl-N -{1-[aminocarbonyl]methyl}benzamide;

(−) 3-[5-bromo-4-[(2,4-difluorobenzyl)oxy]-2-methyl-6-oxopyrimidin-1(6H)-yl]-N-[(2S)-2,3-dihydroxpropyl]-4-methylbenzamide;

(±) 3-[5-bromo-4-[(2,4-difluorobenzyl)oxy]-2-methyl-6-oxopyrimidin-1(6H)-yl]-N-[(2R)-2,3-dihydroxypropyl]-4-methylbenzamide;

(+) 3-[5-bromo-4-[(2,4-difluorobenzyl)oxy]-2-methyl-6-oxopyrimidin-1(6H)-yl]-N-[(2R)-2,3-dihydroxypropyl]-4-methylbenzamide;

(+) N-[(1S)-1-(aminocarbony)ethyl]-3-[5-bromo-4-[(2,4-difluorobenzyl)oxy]-2-methyl-6-oxopyrimidin -1(6H)-yl]-4-methylbenzamide;

(±) 3-[5-bromo-4-[(2,4-difluorobenzyl)oxy]-2-methyl-6-oxopyrimidin-1(6H)-yl]-N-[(1R)-2-hydroxy -1-methylethyl]-4-methylbenzamide;

(±) 3[5-bromo-4-[(2,4-difluorobenzyl)oxy]-2-methyl-6-oxopyrimidin-1(6H)-yl]-N-[(1S)-2-hydroxy -1-methylethyl]-4-methylbenzamide;

(±)3[5-bromo-4-[(2,4-difluorobenzyl)oxy]-2-methyl-6-oxopyrimidin-1(6H)-yl]-N-[(2S)-2-hydroxypropyl ]-4-methylbenzamide;

(−)3-[5-bromo-4-[(2,4-difluorobenzyl)oxy]-2-methyl-6-oxopyrimidin-1(6H)-yl]-N-[(2S)-2-hydroxypropyl ]-4-methylbenzamide;

(+)3-[5-bromo-4-[(2,4-difluorobenzyl)oxy]-2-methyl-6-oxopyrimidin-1(6H)-yl]-N-[(2S)-2-hydroxypropyl ]-4-methylbenzamide;

(±)3-[5-bromo-4-[(2,4-difluorobenzyl)oxy]-2-methyl-6-oxopyrimidin-1(6H)-yl]-N-[(2R)-2-hydroxypropyl ]-4-methylbenzamide;

(+)3-[5-bromo-4-[(2,4-difluorobenzyl)oxy]-2-methyl-6-oxopyrimidin-1(6H)-yl]-N-[(2R)-2-hydroxypropyl ]-4-methylbenzamide;

(±) 3-[5-bromo-4-[(2,4-difluorobenzyl)oxy]-2-methyl-6-oxopyrimidin-1(6H)-yl]-N-(2-hydroxyethyl )-4-methylbenzamide;

(−) 3-[5-bromo-4-[(2,4-difluorobenzyl)oxy]-2-methyl-6-oxopyrimidin-1(6H)-yl]-N-(2-hydroxyethyl )-4-methylbenzamide;

(+) 3-[5-bromo-4-[(2,4-difluorobenzyl)oxy]-2-methyl-6-oxopyrimidin-1(6H)-yl]-N-(2-hydroxyethyl) -4-methylbenzamide;

(±) N-[(1S)-1-(aminocarbonyl)propyl]-3-[5-bromo-4-[(2,4-difluorobenzyl)oxy]-2-methyl-6-oxopyrimidin-1(6H)-yl]-4-methylbenzamide;

3-[5-chloro-4-[(2,4-difluorobenzyl)oxy]-6-oxopyrimidin-1(6H)-yl]-N-[1-(aminocarbonyl)methyl]-4-methylbenzamide;

3-[4[(2,4-difluorobenzyl)oxy]-6-oxopyrimidin-1(6H)-yl]-4-methylbenzoate;

3-[5-chloro-4-[(2,4-difluorobenzyl)oxy]-6-oxopyrimidin-1(6H)-yl]-4-methyl-N-{1-[(methylamino)carbonyl]methyl}benzamide;

3-[5-chloro-4-[(2,4-difluorobenzyl)oxy]-6-oxopyrimidin-1(6H)-yl]-N-[(2S)-2,3-dihydroxpropyl]-4-methylbenzamide;

N-[(1S)-1-(aminocarbonyl)ethyl]-3-[5-chloro-4-[(2,4-difluorobenzyl)oxy]-6-oxopyrimidin-1(6H)-yl]-4-methylbenzamide;

3-[5-chloro-4-[(2,4-difluorobenzyl)oxy]-6-oxopyrimidin-1(6H)-yl]-N-[(1S)-2-hydroxy-1-methylethyl ]-4-methylbenzamide;

3-[5-choro-4-[(2,4-difluorobenzyl)oxy]-6-oxopyrimidin-1(6H)-yl]-N-(2-hydroxyethyl)-4-methylbenzamide;

3-[5-chloro-4-[(2,4-difluorobenzyl)oxy]-6-oxopyrimidin-1(6H)-yl]-N-[(1R)-2-hydroxy-1-methylethyl ]-4-methylbenzamide;

3-[5-bromo-4-[(2,4-difluorobenzyl)oxy]-6-oxopyrimidin-1(6H)-yl]-N-[1-(aminocarbonyl )methyl]-N,4-dimethylbenzamide;

3-[5-chloro-4-[(2,4-difluorobenzyl)oxy]-6-oxopyrimidin-1(6H)-yl]-N-[(2R)-2,3-dihydroxypropyl]-4-methylbenzamide;

N-[(1R)-1-(aminocarbonyl)-2-hydroxyethyl]-3-[5-chloro-4-[(2,4-difluorobenzyl)oxy]-6-oxopyrimidin -1(6H)-yl]-4-methylbenzamide;

N-[(1R)-1-(aminocarbonyl)ethyl]-3-[5-chloro-4-[(2,4-difluorobenzyl)oxy]-6-oxopyrimidin-1(6H)-yl]-4-methylbenzamide;

3-[5-bromo-4-[(2,4-difluorobenzyl)oxy]-6-oxopyrimidin-1(6H)-yl]-N-[(1S)-2-hydroxy-1-methylethyl ]-4-methylbenzamide;

3-[5-bromo-4-[(2,4-difluorobenzyl)oxy]-6-oxopyrimidin-1(6H)-yl]-N-[(1R)-2-hydroxy-1-methylethyl ]-4-methylbenzamide;

3-[5-bromo-4-[(2,4-difluorobenzyl)oxy]-6-oxopyrimidin-1(6H)-yl]-N,4-dimethylbenzamide;

N-[1-(aminocarbonyl)methyl]-3-[5-bromo-4-[(2,4-difluorobenzyl)oxy]-6-oxopyrimidin-1(6H)-yl]-4-methylbenzamide;

N-[(1R)-1-(aminocarbonyl)ethyl]-3-[5-bromo-4-[(2,4-difluorobenzyl)oxy]-6-oxopyrimidin-1(6H)-yl]-4-methylbenzamide;

N-[(1S)-1-(aminocarbonyl)propyl]-3-[5-chloro-4-[(2,4-difluorobenzyl)oxy]-6-oxopyrimidin-1(6H)-yl]-4-methylbenzamide;

3-[5-chloro-4-[(2,4-difluorobenzyl)oxy]-6-oxopyrimidin-1(6H)-yl]-N-[(2S)-2-hydroxypropyl ]-4-methylbenzamide;

3-[5-chloro-4-[(2,4-difluorobenzyl)oxy]-6-oxopyrimidin-1(6H)-yl]-N-[(2R)-2-hydroxypropyl ]-4-methylbenzamide;

5-chloro-6-[(2,4-difluorobenzyl)oxy]-3-(5-{[(3S)-3-hydroxypyrrolidin-1-yl]carbonyl}-2-methylphenyl)pyrimidin-4(3H)-one;

3-[5-chloro-4-[(2,4-difluorobenzyl)oxy]-6-oxopyrimidin-1(6H)-yl]-N-(2-methoxyethyl)-4-methylbenzamide;

5-chloro-6-[(2,4-difluorobenzyl)oxy]-3-(5-{[(3R)-3-hydroxypyrrolidin-1-yl]carbonyl}-2-methylphenyl)pyrimidin-4(3H)-one;

3-[4-[(2,4-difluorobenzyl)oxy]-5-ethyl-6-oxopyrimidin-1(6H)-yl]-N-[(1R)-2-hydroxy-1-methylethyl]-4-methylbenzamide;

methyl 3[4-[(2,4-difluorobenzyl)oxy]-5-iodo-6-oxopyrimidin-1(6H)-yl]-4-methylbenzoate;

methyl 3-[4-[(2,4-difluorobenzyl)oxy]-5-ethyl-6-oxopyrimidin-1(6H)-yl]-4-methylbenzoate;

3-[4-[(2,4-difluorobenzyl)oxy]-5-ethyl-6-oxopyrimidin-1(6H)-yl]-N-(2-hydroxyethyl)-4-methylbenzamide;

3-[5-bromo-4-[(2,4-difluorobenzyl)oxy]-2-(methylamino)-6-oxopyrimidin-1(6H)-yl]-N,4dimethylbenzamide;

methyl 3-[5-bromo-4-[(2,4-difluorobenzyl)oxy]-2-(methylamino)-6-oxopyrimidin-1(6H)-yl]-4-methylbenzoate;
N-[1-(aminocarbonyl)methyl]-3-[5-bromo-4-[(2,4-difluorobenzyl)oxy]-2-(methylamino)-6-oxopyrimidin-1(6H)-yl]-4-methylbenzamide;
3-[5-bromo-4-[(2,4-difluorobenzyl)oxy]-2-(methylamino)-6-oxopyrimidin-1(6H)-yl]-N-[(2S)-2,3-dihydroxypropyl]-4-methylbenzamide;
3-[5-bromo-4-[(2,4-difluorobenzyl)oxy]-6-oxopyrimidin-1(6H)-yl]-4-methyl-N-{1-[(methylamino)carbonyl]methyl}benzamide;
3-[5-bromo-4-[(2,4-difluorobenzyl)oxy]-6-oxopyrimidin-1(6H)-yl]-N-[(2S)-2,3-dihydroxypropyl]-4-methylbenzamide;
3-[5-bromo-4-[(2,4-difluorobenzyl)oxy]-6-oxopyrimidin-1(6H)-yl]-N-[(2R)-2,3-dihydroxypropyl]-4-methylbenzamide;
3-[5-bromo-4-[(2,4-difluorobenzyl)oxy]-6-oxopyrimidin-1(6H)-yl]-N-(2-hydroxyethyl)-4-methylbenzamide;
N-[(1S)-1-(aminocarbonyl)ethyl]-3-[5-bromo-4-[(2,4-difluorobenzyl)oxy]-6-oxopyrimidin-1(6H)-yl]-4-methylbenzamide;
3-[5-bromo-4-[(2,4-difluorobenzyl)oxy]-6-oxopyrimidin-1(6H)-yl]-N-[(2S)-2-hydroxypropyl]-4-methylbenzamide;
3-[5-bromo-4-[(2,4-difluorobenzyl)oxy]-6-oxopyrimidin1(6H)-yl]-N-[(2R)-2-hydroxypropyl]-4-methylbenzamide;
(±) 3-[5-chloro-4-[(2,4-difluorobenzyl)oxy]-2-methyl-6-oxopyrimidin-1(6H)-yl]-N-(2-hydroxyethyl)-4-methylbenzamide;
(−) 3-[5-chloro-4-[(2,4-difluorobenzyl)oxy]-2-methyl-6-oxopyrimidin-1(6H)-yl]-N-(2-hydroxyethyl)-4-methylbenzamide;
(+) 3-[5-chloro-4-[(2,4-difluorobenzyl)oxy]-2-methyl-6-oxopyrimidin-1(6H)-yl]-N-(2-hydroxyethyl)-4-methylbenzamide;
(±) 3-[5-chloro-4-[(2,4-difluorobenzyl)oxy]-2-methyl-6-oxopyrimidin-1(6H)-yl]-4-methyl-N-{1-[aminocarbonyl]methyl}benzamide;
(−)3-[5-chloro-4-[(2,4-difluorobenzyl)oxy]-2-methyl-6-oxopyrimidin-1(6H)-yl]-4-methyl-N-{1-[aminocarbonyl]methyl}benzamide;
(±) 3-[5-chloro-4-[(2,4-difluorobenzyl)oxy]-2-methyl-6-oxopyrimidin-1(6H)-yl]-4-methyl-N-{1-[(methylamino)carbonyl]methyl}benzamide;
(±) 3-[5-chloro-4-[(2,4-difluorobenzyl)oxy]-2-methyl-6-oxopyrimidin-1(6H)-yl]-4-methyl-N-{1-[(methylamino)carbonyl]methyl}benzamide;
±3-[5-chloro-4-[(2,4-difluorobenzyl)oxy]-2-methyl-6-oxopyrimidin-1(6H)-yl]-N-[(2S)-2-hydroxypropyl]-4-methylbenzamide;
±3-[5-chloro-4-[(2,4-difluorobenzyl)oxy]-2-methyl-6-oxopyrimidin-1(6H)-yl]-N-[(2R)-2-hydroxypropyl]-4-methylbenzamide;
3-benzyl-6-(benzyloxy)-5-bromopyrimidin-4(3H)-one;
3-benzyl-6-(benzyloxy)-pyrimidin-4(3H)-one; 4-{[5-bromo-4-[(2,4-difluorobenzyl)oxy]-2-methyl-6-oxopyrimidin-1(6H)-yl]methyl}-N-methylbenzamide; and methyl 4-{[4-[(2,4-difluorobenzyl)oxy]-2-methyl-6-oxopyrimidin-1(6H)-yl]methyl}benzoate;
or a pharmaceutically acceptable salt thereof.

12. A method according to claim 11 wherein the compound is 3-[5-chloro-4-[(2,4-difluorobenzyl)oxy]-6-oxopyrimidin-1(6H)-yl]-N-(2-hydroxyethyl)-4-methylbenzamide or a pharmaceutically acceptable salt thereof.

\* \* \* \* \*

SEQUENCE LISTING

```
<160> NUMBER OF SEQ ID NOS: 2

<210> SEQ ID NO 1
<211> LENGTH: 30
<212> TYPE: DNA
<213> ORGANISM: Homo sapiens

<400> SEQUENCE: 1
gatcgaggat tcatgtctca ggagaggcca                                    30

<210> SEQ ID NO 2
<211> LENGTH: 30
<212> TYPE: DNA
<213> ORGANISM: Homo sapiens

<400> SEQUENCE: 2
gatcgaggat tctcaggact ccatctcttc                                    30
```